US012617796B2

(12) United States Patent
McCarthy et al.

(10) Patent No.: US 12,617,796 B2
(45) Date of Patent: May 5, 2026

(54) ANTAGONISTS OF THE ADENOSINE A2a RECEPTOR

(71) Applicant: JANSSEN PHARMACEUTICA NV, Beerse (BE)

(72) Inventors: Clive McCarthy, Edinburgh (GB); Benjamin Moulton, Alderley Edge (GB)

(73) Assignee: Janssen Pharmaceutica NV, Beerse (BE)

(*) Notice: Subject to any disclaimer, the term of this patent is extended or adjusted under 35 U.S.C. 154(b) by 696 days.

(21) Appl. No.: 17/923,374

(22) PCT Filed: May 6, 2021

(86) PCT No.: PCT/GB2021/051106

§ 371 (c)(1), (2) Date: Nov. 4, 2022

(87) PCT Pub. No.: WO2021/224636

PCT Pub. Date: Nov. 11, 2021

(65) Prior Publication Data

US 2023/0203041 A1 Jun. 29, 2023

(30) Foreign Application Priority Data

May 7, 2020 (GB) ..................................... 2006823
Dec. 16, 2020 (GB) ..................................... 2019922

(51) Int. Cl.
*C07D 487/04* (2006.01)

(52) U.S. Cl.
CPC .................................. *C07D 487/04* (2013.01)

(58) Field of Classification Search
CPC ..... C07D 487/04; C07D 519/00; A61P 35/00; A61K 31/519; A61K 31/5377; A61K 31/5383; A61K 31/5386; A61K 31/541; A61K 31/55
See application file for complete search history.

(56) References Cited

U.S. PATENT DOCUMENTS

| | | | |
|---|---|---|---|
| 3,910,907 | A | 10/1975 | O'Brien et al. |
| 5,624,931 | A | 4/1997 | Oku et al. |
| 6,525,069 | B1 | 2/2003 | Ko et al. |
| 6,605,623 | B1 | 8/2003 | Ko et al. |
| 2004/0044203 | A1 | 3/2004 | Wittman et al. |
| 2004/0127508 | A1 | 7/2004 | Gerlach et al. |
| 2005/0080113 | A1 | 4/2005 | Ohkawa et al. |
| 2008/0167314 | A1 | 7/2008 | Uchikawa et al. |
| 2017/0121409 | A1 | 5/2017 | Verona et al. |
| 2019/0225689 | A1 | 7/2019 | Attiyeh et al. |
| 2023/0293517 | A1 | 9/2023 | McCarthy et al. |
| 2024/0083904 | A1 | 3/2024 | McCarthy et al. |

FOREIGN PATENT DOCUMENTS

| | | | |
|---|---|---|---|
| CN | 104418821 | A | 3/2015 |
| EP | 1205478 | A1 | 5/2002 |
| EP | 1505068 | A1 | 2/2005 |
| EP | 1368355 | B1 | 6/2006 |
| EP | 1700856 | A1 | 9/2006 |
| EP | 2217601 | A1 | 8/2010 |
| EP | 2402337 | A1 | 1/2012 |
| EP | 2402343 | A1 | 1/2012 |
| EP | 2402344 | A1 | 1/2012 |
| EP | 2402345 | A1 | 1/2012 |
| EP | 2635578 | A1 | 9/2013 |
| JP | 2000302680 | A | 10/2000 |
| WO | WO-99/21555 | A2 | 5/1999 |
| WO | WO-2000/035449 | A1 | 6/2000 |
| WO | WO-2000/035451 | A1 | 6/2000 |
| WO | WO-2000/035452 | A1 | 6/2000 |
| WO | WO-2000/035453 | A1 | 6/2000 |
| WO | WO-2000/035454 | A1 | 6/2000 |
| WO | WO-2001/010865 | A1 | 2/2001 |
| WO | WO-01/74811 | A2 | 10/2001 |

(Continued)

OTHER PUBLICATIONS

"From bench to clinic and back: perspective on the 1st IQPC translational research conference" H Hörig and W Pullman J. Translational Med. vol. 2 Article No. 44. (Year: 2004).*
"Targeting A2 adenosine receptors in cancer" Allard et al. Immun Cell Bio, vol. 95, p. 333-339 (Year: 2017).*
"Breakthroughs in modern cancer therapy and elusive cardiotoxicity: Critical research-practice gaps, challenges, and insights" Zheng et al. Med Res Rev, vol. 38 p. 325-376 (Year: 2017).*
U.S. Appl. No. 18/018,741, Published.
U.S. Appl. No. 18/266,428, Published.
U.S. Appl. No. 18/018,741, Pending.
U.S. Appl. No. 18/266,428, Pending.
U.S. Appl. No. 18/869,980, Pending.
International Search Report and Written Opinion for Application No. PCT/GB2021/053252 dated Feb. 18, 2022.
Manuel De Lera Ruiz et al: "Adenosine A 2A Receptor as a Drug Discovery Target", Journal of Medicinal Chemistry, vol. 57, No. 9, pp. 3623-3650. (2013).

(Continued)

*Primary Examiner* — Adam C Milligan
*Assistant Examiner* — Sophia P Hirakis
(74) *Attorney, Agent, or Firm* — BakerHostetler

(57) ABSTRACT

The present invention relates to compounds of formula I shown below:

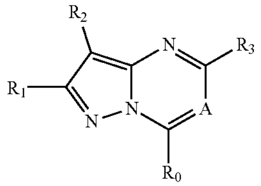

wherein $R_0$, $R_1$, $R_2$, $R_3$ and A are each as defined in the application. The present invention also relates to processes for the preparation of these compounds, to pharmaceutical compositions comprising them, and to their use in the treatment of diseases or conditions in which adenosine A2*a* receptor activity is implicated, such as, for example, cancer.

12 Claims, 18 Drawing Sheets

(56) References Cited

FOREIGN PATENT DOCUMENTS

| | | | |
|---|---|---|---|
| WO | WO-2001/098269 | A2 | 12/2001 |
| WO | WO-2001/098270 | A2 | 12/2001 |
| WO | WO-2002/051442 | A1 | 7/2002 |
| WO | WO-2002/062792 | A1 | 8/2002 |
| WO | WO-02/079192 | A1 | 10/2002 |
| WO | WO-2003/039451 | A2 | 5/2003 |
| WO | WO-2005/021510 | A2 | 3/2005 |
| WO | WO-2005/066177 | A1 | 7/2005 |
| WO | WO-2005/070926 | A1 | 8/2005 |
| WO | WO-2008/157751 | A2 | 12/2008 |
| WO | WO-2009/027733 | A1 | 3/2009 |
| WO | WO-2009/059162 | A1 | 5/2009 |
| WO | WO-2009/108838 | A1 | 9/2009 |
| WO | WO-2009/115321 | A1 | 9/2009 |
| WO | WO-2010/063487 | A1 | 6/2010 |
| WO | WO-2010/084425 | A1 | 7/2010 |
| WO | 2011/006074 | A1 | 1/2011 |
| WO | WO-2012/100342 | A1 | 8/2012 |
| WO | WO-2012/113774 | A1 | 8/2012 |
| WO | 2013/055577 | A1 | 4/2013 |
| WO | WO-2013/050437 | A1 | 4/2013 |
| WO | WO-2015/106158 | A1 | 7/2015 |
| WO | WO-2016/087342 | A1 | 6/2016 |
| WO | 2016/160617 | A2 | 10/2016 |
| WO | WO-2017/178844 | A1 | 10/2017 |
| WO | WO-2019/115711 | A1 | 6/2019 |
| WO | WO-2020/010197 | A1 | 1/2020 |
| WO | WO-2020/261156 | A1 | 12/2020 |
| WO | WO-2021/096849 | A1 | 5/2021 |
| WO | WO-2021/174164 | A1 | 9/2021 |
| WO | WO-2021/174165 | A1 | 9/2021 |
| WO | WO-2021/207550 | A1 | 10/2021 |
| WO | WO-2021/207554 | A1 | 10/2021 |
| WO | WO-2021/225878 | A1 | 11/2021 |
| WO | WO-2022/023772 | A1 | 2/2022 |
| WO | WO-2022/130288 | A1 | 6/2022 |
| WO | WO-2022/130290 | A1 | 6/2022 |
| WO | WO-2022/132914 | A1 | 6/2022 |

OTHER PUBLICATIONS

Moine et al: "Development of new highly potent imidazo[I,2-b]pyridazines targeting Toxoplasma gondiicalcium-dependent protein kinase 1", European Journal of Medicinal Chemistry, vol. 105, pp. 80-105. (2015).
Moine et al, "A small-molecule cell-based screen led to the identification of biphenylimidazoazines with highly potent and broad-spectrum anti-apicomplexan activity", . Eur. J. Med. Chem., vol. 89 ,pp. 386-400 (2015).
United Kingdom Search Report for Application No. GB2019622.6 dated Mar. 25, 2021.
Aurora Building Blocks 4, Publication Date Apr. 4, 2022, Order No. Cat. 136.020.400. See CHEMCATS Accession No. 1683518024 for the compound having the CAS Reg. No. 2474059-00-0, i.e. 5-(5-chloro-4-methyl-IH-I,3-benzodiazol-2-yl)pyrimidine-2,4-diol.
Aurora Building Blocks 4, Publication Date Apr. 4, 2022, Order No. Cat. 136.455.713. See CHEMCATS Accession No. 2068351744 for the compound having the CAS Reg. No. 2498620-70-3, i.e. 5-{ 4 methoxy-3H-imidazo[ 4,5-c ]pyridin-2-yl }pyrimidine-2,4-diol.
Aurora Building Blocks 4, Publication Date Apr. 4, 2022, Order No. Cat. 138.870.867. See CHEMCATS Accession No. 1832943298 for the compound having the CAS Reg. No. 2517926-64-4, i.e. 5-(5-fluoro-4-methyl-IH-I,3-benzodiazol-2-yl)pyrimidine-2,4-diol.
Aurora Building Blocks 4, Publication Date Apr. 4, 2022, Order No. Cat. 139.280.408. See CHEMCATS Accession No. 1280872530 for the compound having the CAS Reg. No. 2548028-06-2, i.e. 5-{7-amino-3H-imidazo[4,5-b ]pyridin-2-yl }pyrimidine-2,4-diol.
Aurora Building Blocks 5, Publication Date Apr. 4, 2022, Order No. Cat. 146.088.372. See CHEMCATS Accession No. 0314102230 for the compound having the CAS Reg. No. 2623032-74-4, i.e. 5-(7-tert-butyl-IH-I,3-benzodiazol-2-yl)pyrimidine-2,4-diol.
Aurora Building Blocks 5, Publication Date Apr. 4, 2022, Order No. Cat. 147.558.184. See CHEMCATS Accession No. 1932560991 for the compound having the CAS Reg. No. 2601819-92-3, i.e. 5-(5-fluoro-7-methyl-IH-I,3-benzodiazol-2-yl)pyrimidine-2,4-diol.
Aurora Building Blocks 5, Publication Date Apr. 4, 2022, Order No. Cat. 148.973.677. See CHEMCATS Accession No. 1914190390 for the compound having the CAS Reg. No. 2572655-77-5, i.e. 5-[4-(trifluoromethyl)-IH-1,3-benzodiazol-2-yl]pyrimidine-2,4-diol.
United Kingdom Search Report for UK Application No. GB2207972.7 dated Nov. 29, 2022.
Compton et al., "Pyrazolo [1, 5-a] pyrimidines: estrogen receptor ligands possessing estrogen receptor [beta] antagonist activity." Journal of Medicinal Chemistry 47 (2004): 5872-5893.
Database Registry CAS, Accession No. RN 1368112-92-8, Entered STN: Apr. 15, 2012.
Database Registry CAS, Accession No. RN 1368284-95-0, Entered STN: Apr. 15, 2012.
Database Registry CAS, Accession No. RN 1369098-70-3, Entered STN: Apr. 16, 2012.
Database Registry CAS, Accession No. RN 1369203-40-6, Entered STN: Apr. 16, 2012.
Database Registry CAS, Accession No. RN 1369203-45-1, Entered STN: Apr. 16, 2012.
Database Registry CAS, Accession No. RN 1369219-38-4, Entered STN: Apr. 16, 2012.
Database Registry CAS, Accession No. RN 1369297-07-3, Entered STN: Apr. 16, 2012.
Database Registry CAS, Accession No. RN 1369297-16-4, Entered STN: Apr. 16, 2012.
Database Registry CAS, Accession No. RN 1464135-21-4, Entered STN: Oct. 25, 2013.
Database Registry CAS, Accession No. RN 1465940-39-9, Entered STN: Oct. 29, 2013.
Database Registry CAS, Accession No. RN 1466840-94-7, Entered STN: Oct. 31, 2013.
Database Registry CAS, Accession No. RN 1466953-30-9, Entered STN: Oct. 31, 2013.
Database Registry CAS, Accession No. RN 1478515-11-5, Entered STN: Nov. 22, 2013.
Database Registry CAS, Accession No. RN 1479542-11-4, Entered STN: Nov. 24, 2013.
Database Registry CAS, Accession No. RN 1485910-48-2, Entered STN: Dec. 3, 2013.
Database Registry CAS, Accession No. RN 1486930-92-0, Entered STN: Dec. 4, 2013.
Database Registry CAS, Accession No. RN 1491086-05-5, Entered STN: Dec. 9, 2013.
Database Registry CAS, Accession No. RN 1494055-01-4, Entered STN: Dec. 13, 2013.
Database Registry CAS, Accession No. RN 1494438-74-2, Entered STN: Dec. 13, 2013.
Database Registry CAS, Accession No. RN 1495955-16-2, Entered STN: Dec. 16, 2013.
Database Registry CAS, Accession No. RN 1498457-36-5, Entered STN: Dec. 19, 2013.
Database Registry CAS, Accession No. RN 1498531-01-3, Entered STN: Dec. 19, 2013.
Database Registry CAS, Accession No. RN 2112683-44-8, Entered STN: Aug. 11, 2017.
Database Registry CAS, Accession No. RN 2112994-98-4, Entered STN: Aug. 13, 2017.
Database Registry, Database accession No. 1367863-71 -5, 1367833-85-9, 1367824-67-6, 1367817-15-9, 1367753-06-7, Apr. 13, 2012, XP05581.
Database Registry, Database accession No. 1782806-38-5, Jun. 17, 2015, XP055814410.
Database Registry, Database accession Nos. 1368113-54-5, 1368112-99-5, Apr. 15, 2012, XP055814515.
Database Registry, Database accession Nos. 1496345-00-6, 1496301-75-7, 1495849-63-2, Dec. 16, 2013, XP055814512.
Database registry, Database accession Nos. 924984-28-1, 924984-25-8, 924984-19-0, 924984-16-7, Mar. 6, 2007, XP055814519.

(56) References Cited

OTHER PUBLICATIONS

International Search Report and Written Opinion for Application No. PCT/GB2021/051106 dated Jun. 25, 2021.
Kaping et al., "A facile, regioselective synthesis of pyrazolo [I,5-a]pyrimidine analogs in the presence of KHS04 in aqueous media assisted by ultrasound and their anti-inflammatory and anti-cancer activities" Monatshefte fur Chemie, 147,(7): 1257-1276 (2016).
Neustadt et al.: "Potent and selective adenosine A"2"A recept or antagonists: 1, 2, 4-Triazo Io [I, 5-c] pyrimidines", Biorg . Med. Chem. Lett., 19(3):967-971 (2009).
Norman et al., "11 N,N-Dialkyl-N 1 -Chlorosulfonyl Chloroformamidines in Heterocyclic Synthesis. Part XIII. Cleavage and Rearrangement Reactions of Pyrazolo[I,5-b] [1,2,4,6]thiatriazinel, I-Dioxides 11" Australian Journal of Chemistry, 69 (1): 61-75 (2015).
Ruiz et al. "Adenosine A 2A Receptor as a Drug Discovery Target", J. Med. Chem, 57(9): 3623-3650 (2013).
United Kingdom Search Report for GB Application No. 2006823.5 dated Oct. 16, 2020.
Chilean Search Report for CL Application No. 202203055 dated Jun. 17, 2024.
International Preliminary Report on Patentability for International Application No. PCT/GB2021/051984 dated Jan. 31, 2023.
PubChem Compound Summary for CID 49761307, (5-Chloro-2-hydroxyphenyl)-[2-(furan-2-yl)pyrazolo[1,5-a]pyrimidin-5-yl]methanone Accessed Feb. 20, 2024.
PubChem Compound Summary for CID 49761369, (5-Chloro-2-hydroxy-4-methylphenyl)-[2-(furan-2-yl)pyrazolo[1,5-a]pyrimidin-5-yl]methanone Accessed Feb. 20, 2024.
PubChem Compound Summary for CID 49761462, (5-Ethyl-2-hydroxyphenyl)-[2-(furan-2-yl)pyrazolo[1,5-a]pyrimidin-5-yl]methanone Accessed Feb. 20, 2024.
PubChem Compound Summary for CID 49761485, [2-(Furan-2-yl)pyrazolo[1,5-a]pyrimidin-5-yl]-(2-hydroxy-5-methylphenyl)methanone Accessed Feb. 20, 2024.
PubChem Compound Summary for CID 82271949, [2-(Furan-2-yl)pyrazolo[1,5-a]pyrimidin-3-yl]methanol Accessed Feb. 20, 2024.
PubChem Compound Summary for CID 82271968, 2-(4-Chlorophenyl)pyrazolo[1,5-a]pyrimidine-3-carbonitrile Accessed Feb. 20, 2024.
PubChem Compound Summary for CID 82271974, 2-(3-Ethoxyphenyl)pyrazolo[1,5-a]pyrimidine-3-carbonitrile Accessed Feb. 20, 2024.
PubChem Compound Summary for CID 82271978, 2-(3,4-Dimethoxyphenyl)pyrazolo[1,5-a]pyrimidine-3-carbonitrile Accessed Feb. 20, 2024.
PubChem Compound Summary for CID 82271982, 2-Pyridin-2-ylpyrazolo[1,5-a]pyrimidine-3-carbonitrile Accessed Feb. 20, 2024.
PubChem Compound Summary for CID 82271984, 2-Pyridin-4-ylpyrazolo[1,5-a]pyrimidine-3-carbonitrile Accessed Feb. 20, 2024.
PubChem Compound Summary for CID 82271985, 2-(Furan-2-yl)pyrazolo[1,5-a]pyrimidine-3-carbonitrile Accessed Feb. 20, 2024.
PubChem Compound Summary for CID 82271986, 2-(5-Bromofuran-2-yl)pyrazolo[1,5-a]pyrimidine-3-carbonitrile Accessed Feb. 20, 2024.
PubChem Compound Summary for CID 82272027, [2-(Furan-2-yl)pyrazolo[1,5-a]pyrimidin-3-yl]methanamine Accessed Feb. 20, 2024.
PubChem Compound Summary for CID 82272147, 2-[2-(5-Bromofuran-2-yl)pyrazolo[1,5-a]pyrimidin-3-yl]acetonitrile Accessed Feb. 20, 2024.
PubChem Compound Summary for CID 84685611, 3-Pyrazolo[1,5-a]pyrimidin-2-ylbenzonitrile Accessed Feb. 20, 2024.
Beavis et al., "Adenosine Receptor 2A Blockade Increases the Efficacy of Anti-PD-1 through Enhanced Antitumor T-cell Responses", Cancer Immunol Res., May 2015, 3(5), 506-517.
Beavis et al., "Blockade of A2A receptors potently suppresses the metastasis of CD73+ tumors", PNAS, Sep. 3, 2013, vol. 110, No. 36, 14711-14716.
Bundgaard, "(C) Means to Enhance Penetration, (1) Prodrugs as a means to improve the delivery of peptide drugs", Advanced Drug Delivery Reviews, 1992, 8, 1-38.
Bundgaard, "Design of Pro-drugs: Bioreversible derivatives for various functional groups and chemical entities", 1985, Chapter 1, 1-91.
Cekic et al., "Adenosine A2A receptors intrinsically regulate CD8+ T cells in the tumor microenvironment", Cancer Res., Dec. 15, 2014, 74(24), 7239-7249.
Deady, "Ring Nitrogen Oxidation of Amino substituted Nitrogen Heterocycles with m-Chmroperbenzoic Acid", Syn. Comm., 1977, 7, 509-514.
Deaglio et al., "Adenosine generation catalyzed by CD39 and CD73 expressed on regulatory T cells mediates immune suppression", J. Exp. Med., Jun. 11, 2007, 204, No. 6, 1257-1265.
Gao et al., "The roles of CD73 in cancer", Biomed Res Int., 2014, 460654.
Higuchi et al., "Pro-Drugs as Novel Delivery Systems", A.C.S. Symposium Series, 1975, vol. 14.
Houthuys et al., SITC 2017, "A novel non-competitive and non-brain penetrant adenosine A2A receptor antagonist designed to reverse adenosine-mediated suppression of anti-tumor immunity", Conference, Maryland, 2016, poster, 1pp.
Houthuys et al., SITC 2017, "A novel non-competitive and non-brain penetrant adenosine A2A receptor antagonist designed to reverse adenosine-mediated suppression of anti-tumor immunity", Conference, Maryland, Nov. 2017, SITC 2017, Annual Meeting Abstracts Book, 545-546.
Iannone et al., "Adenosine limits the therapeutic effectiveness of anti-CTLA4 mAb in a mouse melanoma model", Am J Cancer Res., 2014, 4(2), 172-181.
Kakeya et al., "Studies on Prodrugs of Cephalosporins. I. 1 > Synthesis and Biological Properties, of Glycyloxybenzoyloxymethyl and Glycylaminobenzoyloxymethyl Esters of 7 /J-[2-(2-Aminothiazol-4-yl)-(Z)-2-methoxyiminoacetamido ]-3- methyl-3-cephem-4-carboxylic Acid", Chem. Pharm. Bull., 1984, 32, (2), 692-698.
Krogsgaard-Larsen et al., "A Textbook of Drug Design and Development", Chapter 5, Design and Application of Pro- drugs, 1991, 113-191.
Loi et al., "CD73 promotes anthracycline resistance and poor prognosis in triple negative breast cancer", Proc Natl Acad Sci USA, 2013, 110(27), 11091-11096.
March, Advanced Organic Chemistry, 4th Edition, Wiley Interscience, 1992, pp. 131-133.
Mittal et al., "Antimetastatic Effects of Blocking PD-1 and the Adenosine A2A Receptor", Cancer Res., Jul. 15, 2014, 74(14), 3652-3658.
Ohta et al., "A2A adenosine receptor protects tumors from antitumor T cells", PNAS, Aug. 29, 2006, vol. 103, No. 35, 13132-13137.
Reinhardt et al., "MAPK Signaling and Inflammation Link Melanoma Phenotype Switching to Induction of CD73 during Immunotherapy", Cancer Res., Sep. 1, 2017, 77(17), 4697-4709.
Rutkowski et al., Journal of Clinical Oncology, 2019, 37(8), 31.
Sukari et al., "Cancer Immunology and Immunotherapy", Anticancer Res., 2016, 36(11), 5593-5606.
Suryakiran et al., "An expeditious synthesis of 3-amino 2H-pyrazoles promoted by methanesulphonic acid under solvent and solvent free conditions", Journal of Molecular Catalysis A: Chemical 258, 2006, 371-375.
Vijayan et al., "Targeting immunosuppressive adenosine in cancer", Nat. Rev Cancer, 2017, 17(12), 709-724.
Waickman et al., "Enhancement of tumor immunotherapy by deletion of the A2A adenosine receptor", Cancer Immunol Immunother, 2012, 61, 917-926.
Widder et al., "Methods in Enzymology, Drug and Enzyme Targeting", Part A, Academic Press, 1985, vol. 112, 309-396.

* cited by examiner

Intermediate A5

Intermediate B1

Intermediate B

Intermediate C2

Intermediate C3 - iodo
Intermediate E1 - bromo

Intermediate D - iodo
Intermediate E - bromo

Intermediate O

Example 36

Example 35

A1
A2
A3
A4
A5

Intermediate Y

Intermediate Z

Intermediate AB

Same conditions as used towards Intermediate A

ANTAGONISTS OF THE ADENOSINE A2a RECEPTOR

CROSS-REFERENCE TO RELATED APPLICATION

This application is the § 371 National Stage of PCT/GB2021/051106, filed May 6, 2021, which claims the benefit of GB 2019922.0, filed Dec. 16, 2020, and GB 2006823.5, filed May 7, 2020. The contents of PCT/GB2021/051106 are hereby incorporated by reference in their entirety.

INTRODUCTION

The present invention relates to certain compounds that function as antagonists of the adenosine A2a receptor. Additionally, some of the compounds are also antagonists of the A2b receptor. The present invention also relates to processes for the preparation of these compounds, to pharmaceutical compositions comprising them, and to their use in the treatment of diseases or conditions in which adenosine A2a receptor activity is implicated, such as, for example, cancer.

BACKGROUND OF THE INVENTION

A number of immunosuppressive pathways are active in the tumour microenvironment which enable tumour cells to evade elimination by cytotoxic T cells and can diminish the clinical response of patients to immunotherapy with anti-checkpoint antibodies. The anti-PD-1 antibodies pembrolizumab and nivolumab and anti-PD-L1 antibodies durvalumab, avelumab and atezolizumab are approved for the treatment of number of solid tumours including non-small cell lung cancer, head and neck squamous cancer and urothelial cancer.

However, only 20-30% of patients respond to checkpoint blockade and the side effects of such treatments are significant (Sukari et al, 2016). Consequently, other approaches to enhance the cytotoxic potential of the tumour microenvironment are actively being investigated. This includes agents that could be used as monotherapies or, more likely, used in combination with checkpoint inhibitors and cytotoxic agents to enhance their efficacy.

One approach that has attracted attention is to interfere with the production and/or action of adenosine in the tumour microenvironment (Vijayan et al, 2017). Adenosine has immunosuppressive properties and is present in the tumour microenvironment at high concentrations. Recent studies estimate the concentration of adenosine to be about 10 μM in human tumours compared to <1 μM in normal tissue (Houthuys et al 2017). Adenosine is formed at both intracellular and extracellular sites by two distinct pathways that involve two different substrates. Intracellular adenosine is derived from AMP and S-adenosyl homocysteine whilst the high extracellular adenosine concentrations observed during metabolic stress are associated with the release and degradation of precursor adenine nucleotides (ATP, ADP and AMP) by the concerted action of CD39 and CD73 (Vijayan et al, 2017).

CD39 and CD73 are upregulated in the tumour microenvironment in response to hypoxia. CD73 represents a putative patient stratification method for adenosine antagonists as its expression on tumour cells is also associated with poor overall prognosis in many different cancer types suggesting that adenosine production contributes to the undesirable immunosuppressive phenotype of the tumour microenvironment (Gao et al 2014; Loi et al, 2013;). CD73 expression by tumour-infiltrating immune cells is also important in promoting tumour immune suppression as CD73 negative Treg cells fail to suppress effector T cell functions (Deaglio et al, 2007; Reinhardt et al, (2017). Furthermore, patients resistant to anti-PD1 treatment have elevated levels of CD73 (Reinhardt et al, 2017).

Adenosine regulates cell function via occupancy of specific GPCRs on the cell surface of the P1 purinoceptor subtypes. The P1 receptor family is further subdivided into A1, A2a, A2b and A3.

A2 receptors are subdivided into A2a and A2b, based on high and low affinity for adenosine, respectively. A2a is expressed by lymphocytes and activation of A2a leads to suppression of cytokine production and other effector functions. Tumour growth is inhibited by genetic ablation of A2a in syngeneic mouse models and this effect has been demonstrated to be due to enhanced lymphocyte activation and cytotoxic function (Ohta et al, 2006; Waickman et al 2012; Beavis et al, 2013; Mittal et al, 2014; Cekic et al, 2014). A2a–/– mice show an increased response to inhibition of checkpoint pathways such as PD-1, with an improvement in both tumourfree survival and overall survival. Adenosine-mediated A2a activation also limits the efficacy of ant-CTLA4 treatment (lannone et al, 2014).

The effects of genetic deficiency of A2a in mouse models is mimicked by pharmacological blockade of A2a. A2a antagonists have been shown to enhance the cytotoxic CD8+ T cells and to enhance the ability of NK cells prevent metastasis of CD73-expressing tumours (Beavis et al, 2013). Importantly, A2a antagonists enhance the efficacy of anti-PD1 antibodies (Beavis et al, 2015).

These findings have prompted the development of selective A2a antagonists for use in cancer immunotherapy and clinical trials are ongoing with CPI-444, the first selective A2a antagonist to be evaluated in cancer, being used as both as a monotherapy and in combination with the anti-PDL1 antibody atezolizumab. The preliminary data indicated that the compound was well tolerated and showed early indications of reducing tumour size and enhancing CD8+ T infiltration into tumour tissue.

However, there remains a need for second generation compounds that are potent adenosine A2a antagonists. In particular, there is a need for compounds that are potent and selective adenosine A2a antagonists and, in some cases, potent and selective adenosine A2a and A2b antagonists. There is also a need for compounds that are potent adenosine A2a antagonists or adenosine A2a and A2b antagonists that retain activity in the presence of the high concentrations of adenosine that are present in the tumour microenvironment.

SUMMARY OF THE INVENTION

According to a first aspect of the present invention, there is provided a compound, or a pharmaceutically acceptable salt, hydrate or solvate thereof, as defined herein.

According to a further aspect of the present invention, there is provided a pharmaceutical composition comprising a compound as defined herein, or a pharmaceutically acceptable salt, hydrate or solvate thereof, in admixture with a pharmaceutically acceptable diluent or carrier.

According to a further aspect of the present invention, there is provided a method of antagonising adenosine A2a receptors (and in some cases A2b receptors) in vitro or in vivo, said method comprising contacting a cell with an effective amount of a compound or a pharmaceutically acceptable salt, hydrate or solvate thereof as defined herein.

According to a further aspect of the present invention, there is provided a method of selectively antagonising adenosine A2a receptors (and in some cases A2b receptors) in vitro or in vivo, said method comprising contacting a cell with an effective amount of a compound, or a pharmaceutically acceptable salt, hydrate or solvate thereof, as defined herein.

According to a further aspect of the present invention, there is provided a method of inhibiting cell proliferation, in vitro or in vivo, said method comprising contacting a cell with an effective amount of a compound or a pharmaceutically acceptable salt, hydrate or solvate thereof as defined herein, or a pharmaceutical composition as defined herein. Suitably, the compound or pharmaceutical composition is administered in combination with one or more additional antiproliferative agents (e.g. checkpoint inhibitors and/or cytotoxic agents).

According to a further aspect of the present invention, there is provided a method of treating a disease or disorder associated with adenosine A2a receptor activity in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating a proliferative disorder in a patient in need of such treatment, said method comprising administering to said patient a therapeutically effective amount of a compound or a pharmaceutically acceptable salt, hydrate or solvate thereof as defined herein, or a pharmaceutical composition as defined herein. Suitably, the compound or pharmaceutical composition is administered in combination with one or more additional antiproliferative agents (e.g. checkpoint inhibitors and/or cytotoxic agents).

According to a further aspect of the present invention, there is provided a method of treating cancer in a patient in need of such treatment, said method comprising administering to said patient a therapeutically effective amount of a compound or a pharmaceutically acceptable salt, hydrate or solvate thereof as defined herein, or a pharmaceutical composition as defined herein. Suitably, the compound or pharmaceutical composition is administered in combination with one or more additional anticancer agents (e.g. checkpoint inhibitors and/or cytotoxic agents).

According to a further aspect of the present invention, there is provided a compound, or a pharmaceutically acceptable salt, hydrate or solvate thereof, or a pharmaceutical composition as defined herein for use in therapy.

According to a further aspect of the present invention, there is provided a compound or a pharmaceutically acceptable salt, hydrate or solvate thereof as defined herein, or a pharmaceutical composition as defined herein, for use in the treatment of a proliferative condition. Suitably, the compound or pharmaceutical composition is administered in combination with one or more additional antiproliferative agents (e.g. checkpoint inhibitors and/or cytotoxic agents).

According to a further aspect of the present invention, there is provided a compound, or a pharmaceutically acceptable salt, hydrate or solvate thereof, or a pharmaceutical composition as defined herein for use in the treatment of cancer. In a particular embodiment, the cancer is human cancer. Suitably, the compound or pharmaceutical composition is administered in combination with one or more additional anticancer agents (e.g. checkpoint inhibitors and/or cytotoxic agents).

According to a further aspect of the present invention, there is provided a compound, or a pharmaceutically acceptable salt, hydrate or solvate thereof, as defined herein for use as an adenosine A2a antagonist. In an embodiment, the compounds of the invention are selective adenosine A2a antagonists. In an alternative embodiment, certain compounds of the invention are selective adenosine A2a and adenosine A2b antagonists.

According to a further aspect of the present invention, there is provided a compound, or a pharmaceutically acceptable salt, hydrate or solvate thereof, as defined herein for use in the treatment of a disease or disorder in which adenosine A2a is implicated.

According to a further aspect of the present invention, there is provided the use of a compound, or a pharmaceutically acceptable salt, hydrate or solvate thereof, as defined herein in the manufacture of a medicament for the treatment of a proliferative condition. Suitably, the compound or pharmaceutical composition is administered in combination with one or more additional antiproliferative agents (e.g. checkpoint inhibitors and/or cytotoxic agents).

According to a further aspect of the present invention, there is provide the use of a compound, or a pharmaceutically acceptable salt, hydrate or solvate thereof, as defined herein in the manufacture of a medicament for the treatment of cancer. Suitably, the cancer is a human cancer. Suitably, the compound or pharmaceutical composition is administered in combination with one or more additional anticancer agents (e.g. checkpoint inhibitors and/or cytotoxic agents).

According to a further aspect of the present invention, there is provided a use of a compound, or a pharmaceutically acceptable salt, hydrate or solvate thereof, as defined herein in the manufacture of a medicament for use as an adenosine A2a antagonist.

According to a further aspect of the present invention, there is provided a use of a compound, or a pharmaceutically acceptable salt, hydrate or solvate thereof, as defined herein in the manufacture of a medicament for the treatment of a disease or disorder in which adenosine A2a is implicated.

According to a further aspect of the present invention, there is provided a process for preparing a compound, or a pharmaceutically acceptable salt, hydrate or solvate thereof, as defined herein.

According to a further aspect of the present invention, there is provided a compound, or a pharmaceutically acceptable salt, hydrate or solvate thereof, obtainable by, or obtained by, or directly obtained by a process of preparing a compound as defined herein.

According to a further aspect of the present invention, there are provided novel intermediates as defined herein which are suitable for use in any one of the synthetic methods set out herein.

Features, including optional, suitable, and preferred features in relation to one aspect of the invention may also be features, including optional, suitable and preferred features in relation to any other aspect of the invention.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For Example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like. [0037]"(2-6C) alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like. [0038]"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

The term "(m-nC)cycloalkyl" means a hydrocarbon ring containing from m to n carbon atoms, for example "(3-6C) cycloalkyl" means a hydrocarbon ring containing from 3 to 6 carbon atoms, for example, cyclopropyl, cyclobutyl, cyclopentyl, cyclohexyl. The term "(m-nC). cycloalkyl" also encompasses non-aromatic saturated or partially saturated monocyclic, fused, bridged, or spiro bicyclic carbocyclic ring system(s). The term "(m-nC)cycloalkyl" includes both monovalent species and divalent species. Monocyclic "(m-nC)cycloalkyl" rings contain from about 3 to 12 (suitably from 3 to 8, most suitably from 5 to 6) ring carbon atoms. Bicyclic "(m-nC)cycloalkyl" contain from 7 to 17 ring carbon atoms, suitably 7 to 12 ring carbon atoms.

Bicyclic "$C_{m-n}$ cycloalkyl" rings may be fused, spiro, or bridged ring systems.

(3-8C)cycloalkyl" means a hydrocarbon ring or bridged system containing from 3 to 8 carbon atoms, for example, cyclopropyl, cyclobutyl, cyclopentyl, cyclohexyl, cycloheptyl or bicyclo[2.2.1 heptyl.

(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydrooxathiolyl, tetrahydrooxazolyl, tetrahydro-oxadiazolyl, tetrahydrodioxazolyl, tetrahydrooxathiazolyl, hexahydrotriazinyl, tetrahydrooxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

A "carbon-linked heterocyclyl" means a heterocycle group as defined above that is connected via a carbon atom, rather than a heteroatom such as nitrogen.

By "spirocyclic ring systems" it is meant a compound which at least two rings which have only one atom in common and are not linked by a bridge.

By "fused ring systems" it is meant a compound in which two rings share two adjacent atoms. In otherwords, the rings share one covalent bond.

By "bridged ring systems" is meant ring systems in which two rings share more than two atoms, see for example Advanced Organic Chemistry, by Jerry March, 4* Edition, Wiley Interscience, pages 131-133, 1992. Examples of bridged heterocyclyl ring systems include, aza-bicyclo [2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4] octane, 2-oxa-6-azaspiro[3.4]octane, 2-azaspiro[3.3]heptanes, 2-oxa-6-azaspiro[3.3]heptanes, 7-oxa-2-azaspiro[3.5] nonane, 6-oxa-2-azaspiro[3.4]octane, 2-oxa-7-azaspiro[3.5] nonane and 2-oxa-6-azaspiro[3.5]nonane.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 14, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members.

The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of heteroaryl include fury), pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3b]-furanyl-, 2H-furo[3,2b]-pyranyl-, 5H-pyrido[2,3-d]-ooxazinyl-, 1H-pyrazolo[4,3-d]-oxazolyl, 4H-imidazo[4,5d]thiazolyl, pyrazino[2,3d]pyridazinyl, -imidazo[2,1b]thiazolyl, -imidazo[1,2b][1,2,4]-triazinyl. "Heteroaryl" also covers partially aromatic bi- or polycyclic ring systems wherein at least one ring is an aromatic ring and one or more of the other ring(s) is a nonaromatic, saturated or partially saturated ring, provided at least one ring contains one or more heteroatoms selected from nitrogen, oxygen or -sulfur-. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl, 3,4-dihydro-2H-pyrido[3,2-b][1,4]oxazinyl and 6,8-dihydro-5H-[1,2,4]triazolo[4,3-a]pyrazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

- a benzene ring fused to a 5- or 6-membered ring containing 1, 2 or 3 ring heteroatoms;
- a pyridine ring fused to a 5- or 6-membered ring containing 1, 2 or 3 ring heteroatoms;
- a pyrimidine ring fused to a 5- or 6-membered ring containing 1 or 2 ring heteroatoms;
- a pyrrole ring fused to a 5- or 6-membered ring containing 1, 2 or 3 ring heteroatoms;
- a pyrazole ring fused to a 5- or 6-membered ring containing 1 or 2 ring heteroatoms;
- a pyrazine ring fused to a 5- or 6-membered ring containing 1 or 2 ring heteroatoms;
- an imidazole ring fused to a 5- or 6-membered ring containing 1 or 2 ring heteroatoms;
- an oxazole ring fused to a 5- or 6-membered ring containing 1 or 2 ring heteroatoms;
- an isoxazole ring fused to a 5- or 6-membered ring containing 1 or 2 ring heteroatoms;
- a thiazole ring fused to a 5- or 6-membered ring containing 1 or 2 ring heteroatoms;
- an isothiazole ring fused to a 5- or 6-membered ring containing 1 or 2 ring heteroatoms;
- a thiophene ring fused to a 5- or 6-membered ring containing 1, 2 or 3 ring heteroatoms;
- a furan ring fused to a 5- or 6-membered ring containing 1, 2 or 3 ring heteroatoms;
- a cyclohexyl ring fused to a 5- or 6-membered heteroaromatic ring containing 1, 2 or 3 ring heteroatoms; and
- a cyclopentyl ring fused to a 5- or 6-membered heteroaromatic ring containing 1, 2 or 3 ring heteroatoms.

Particular Examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular Examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For Example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In a first aspect, the present invention relates to compounds, or pharmaceutically acceptable salts, hydrates or solvates thereof, having the structural formula I shown below:

I

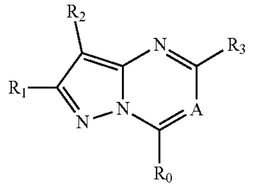

wherein:

$R_c$ is hydrogen or deuterium;

$R_1$ is selected from aryl or heteroaryl, wherein $R_1$ is optionally substituted by one or more $R_{1z}$ substituents independently selected from (1-4C)alkyl, halo, (1-4C)haloalkyl, (1-4C)haloalkoxy, cyano, $(CH_2)_{q1}NR_{1B}R_{1C}$, $(CH_2)_{q1}R_{1B}$, $(CH_2)_{q1}C(O)R_{1B}$, $(CH_2)_{q1}C(O)OR_{1B}$, $(CH_2)_{q1}OC(O)R_{1B}$, $(CH_2)_{q1}C(O)N(R_{1C})R_{1B}$, $(CH_2)_{q1}N(R_{1C})C(O)R_{1B}$, $(CH_2)_{q1}S(O)_pR_{1B}$ (where p is 0, 1 or 2), $(CH_2)_{q1}SO_2N(R_{1C})R_{1B}$, or $(CH_2)_{q1}N(R_{1C})SO_2R_{1B}$, and wherein q1 is 0, 1, 2 or 3 and $R_{1B}$ and $R_{1C}$ are each independently selected from hydrogen, (1-4C)alkyl, (3-6C)cycloalkyl or (3-6C)cycloalkyl(1-2C)alkyl;

$R_2$ is selected from hydrogen,cyano, halo, (1-4C)alkyl, (1-4C)haloalkyl, $C(O)OR_{2A}$, $C(O)NR_{2A}R_{2B}$, aryl, heteroaryl, (2-6C)alkenyl, (2-6C)alkynyl or (1-4C)alkanoyl;

wherein $R_{2A}$ and $R_{2B}$ are each independently selected from hydrogen, (1-4C)alkyl, (1-4C)alkoxy, (3-6C)cycloalkyl or (3-6C)cycloalkyl(1-2C)alkyl, or, in the $CONR_{2A}R_{2B}$ group, $R_{2A}$ and $R_{2B}$ are linked such that, together with the nitrogen atom to which they are attached, they form a heterocyclic ring, and wherein any alkyl, alkenyl, alkynyl, alkanoyl, aryl, heteroaryl or heterocyclyl group (formed by $R_{2A}$ and $R_{2B}$) is optionally substituted by one or more substituents independently selected from (1-4C)alkyl, halo, (1-4C)haloalkyl, (1-4C)haloalkoxy, amino, (1-4C)aminoalkyl, cyano, $(CH_2)_{q2}NR_{2D}R_{2E}$, $(CH_2)_{q2}OR_{2D}$, $(CH_2)_{q2}C(O)R_{2D}$, $(CH_2)_{q2}C(O)OR_{2D}$, $(CH_2)_{q2}OC(O)R_{2D}$, $(CH_2)_{q2}C(O)N(R_{2E})R_{2D}$, $(CH_2)_{q2}N(R_{2E})C(O)R_{2D}$, $(CH_2)_{q2}S(O)_pR_{2D}$ (where p is 0, 1 or 2), $(CH_2)_{q2}SO_2N(R_{2E})R_{2D}$, or $(CH_2)_{q2}N(R_{2E})SO_2R_{2D}$, wherein q2 is 0, 1, 2 or 3; and wherein $R_{2o}$ and $R_{2E}$ are each independently selected from hydrogen, (1-4C)alkyl, (3-6C)cycloalkyl or (3-6C)cycloalkyl(1-2C)alkyl;

$R_3$ is selected from hydrogen, halo, cyano or a group of the formula:

$$-L-Y-L_q-Q$$

wherein:

L is absent or (1-4C)alkylene optionally substituted by one or more substituents selected from (1-2C)alkyl or oxo;

Y is absent or O, S, SO, $SO_2$, $N(R_a)$, C(O), C(O)O, OC(O), $C(O)N(R_a)$, $C(O)N(R_a)O$, $N(R_a)C(O)$, $N(R_a)C(O)N(R_b)$, $N(R_a)C(O)O$, $OC(O)N(R_a)$, $C(=NR_y)N(R_a)$, $N(R_a)C(=NR_y)$, $N(R_a)C(=NR_y)N(R_b)$, $S(O)_2N(R_a)$, $N(R_a)SO_2$, $N(R_a)SO_2N(R_b)$ or $C(O)N(R_a)SO_2$, wherein $R_a$ and $R_b$ are each independently selected from hydrogen or (1-4C)alkyl and Ry is selected from hydrogen, (1-4C)alkyl, nitro or cyano;

$L_q$ is absent or (1-4C)alkylene optionally substituted by one or more substituents selected from (1-2C)alkoxy, halo, cyano, amino or oxo; and Q is hydrogen, (1-6C)alkyl, (2-6C)alkenyl, (2-6C)alkynyl, aryl, (3-8)cycloalkyl, (3-8C)cycloalkenyl, heteroaryl or heterocyclyl;

wherein Q is optionally further substituted by one or more substituent groups independently selected from oxo, (1-4C)alkyl, halo, (1-4C)haloalkyl, (1-4C)haloalkoxy, (1-4C)aminoalkyl, (1-4C)hydroxyalkyl, cyano, $NR_cR_d$, $OR_c$, $C(O)R_e$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, or $(CH_2)_qNR_cR_d$ (where q is 1, 2 or 3); wherein $R_c$, $R_d$ and $R_e$ are each independently selected from hydrogen, (1-6C)alkyl, (3-6C)cycloalkyl or (3-6C)cycloalkyl(1-2C)alkyl; or $R_c$ and $R_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, di-[(1-4C)alkyl]amino, amino, cyano or hydroxy; and/or Q is optionally substituted by one or more group(s) of the formula:

$$-L_1-L_{Q1}-W_1$$

wherein:

$L_1$ is absent or (1-3C)alkylene optionally substituted by one or more substituents selected from (1-2C)alkyl or oxo;

$L_{Q1}$ is absent or selected from or O, S, SO, $SO_2$, $N(R_f)$, C(O), C(O)O, OC(O), $C(O)N(R_f)$, $N(R_f)C(O)$, $N(R_f)C(O)N(R_g)$, $N(R_f)C(O)O$, $OC(O)N(R_f)$, $S(O)_2N(R_f)$, $N(R_f)SO_2$ wherein $R_f$ and $R_g$ are each independently selected from hydrogen or (1-2C)alkyl; and $W_1$ is hydrogen, (1-6C)alkyl, aryl, aryl(1-2C)alkyl, (3-8C)cycloalkyl, (3-8C)cycloalkenyl, heteroaryl or heterocyclyl; wherein $W_1$ is optionally substituted by one or more substituents selected from oxo, (1-4C) alkyl, halo, (1-4C)haloalkyl, (1-4C)haloalkoxy, (1-4C)alkoxy, (1-4C)alkylamino, cyano, aryl, heteroaryl, heterocycyl, (3-6C)cycloalkyl, $NR_hR_i$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), $SO_2N(R_i)R_h$, $N(R_i)SO_2R_h$ or $(CH_2)_SNR_iR_h$ (where s is 1, 2 or 3); wherein $R_h$ and $R_1$ are each independently selected from hydrogen, (1-4C)alkyl, (3-6C)cycloalkyl or (3-6C)cycloalkyl(1-2C)alkyl;

and wherein any alkyl, alkoxy, aryl, hereoaryl, heterocyclyl or cycloalkyl moiety in a substituent group present on $W_1$ is optionally further substituted by one or more halo, (1-4C)alkyl, (1-4C)haloalkyl, (1-4C) haloalkoxy, (1-4C)alkoxy, (1-4C)alkylamino, di-[(1-4C)alkyl]amino, amino, cyano or hydroxy groups; or $R_h$ and $R_1$ are linked such that, together with the nitrogen atom to which they are attached, they form a 4-7 membered heterocyclic ring which is optionally substituted by one or more substituents selected from oxo, (1-4C)alkyl, halo, (1-4C)haloalkyl, (1-4C) haloalkoxy, (1-4C)alkoxy, (1-4C)alkylamino, di-[(1-4C)alkyl]amino, amino, cyano or hydroxy;

A is selected from $CR_4$ and N, wherein $R_4$ is hydrogen, halo or (1-4C)alkyl optionally substituted by one or more substituents selected from halo, (1-4C)haloalkyl, (1-4C)haloalkoxy; (1-4C)aminoalkyl, cyano, $(CH_2)qaNR_{4A}R_{4B}$, $(CH_2)_{qa}OR_{4A}$, $(CH_2)_{qa}C(O)R_{c4A}$, $(CH_2)_{qa}C(O)OR_{4A}$, $(CH_2)_{qa}OC(O)R_{4A}$, $(CH_2)_{qa}C(O)N(R_{4B})R_{4A}$, $(CH_2)_{qa}N(R_{4B})C(O)R_{4A}$, $(CH_2)_{qa}S(O)_pR_{4A}$ (where p is 0, 1 or 2), $(CH_2)_{qa}SO_2N(R_{4B})R_{4A}$, or $(CH_2)_{qa}N(R_{4B})SO_2R_{4A}$, wherein qa is 0, 1, 2 or 3 and $R_{4A}$ and $R_{4B}$ are each independently selected from hydrogen, (1-6C)alkyl, (3-6C)cycloalkyl or (3-6C)cycloalkyl(1-2C)alkyl;

and wherein any tertiary amine in a compound of formula I is optionally in the form of a N-oxide and the nitrogen atom in a pyridine ring is optionally in the form of an N-oxide; and wherein any S atoms present in the heterocyclic ring may optionally be present as S(=O), $S(=O)_2$ or $S(=O)(=NR_z)$ wherein Rz is selected from hydrogen, (1-3C)alkyl or (2-3C)alkanoyl.

Particular compounds of the invention include, for example, compounds of the formula I, or pharmaceutically acceptable salts, hydrates and/or solvates thereof, wherein, unless otherwise stated, each of $R_0$, $R_1$, $R_2$, $R_3$ and A have any of the meanings defined hereinbefore or in any of paragraphs (1) to (55) hereinafter:-

(1) $R_c$ is hydrogen;

(2) $R_c$ is deuterium;

(3) $R_1$ is selected from aryl or heteroaryl, wherein $R_1$ is optionally substituted by one or more $R_1$, substituents independently selected from (1-4C)alkyl, halo, (1-4C)haloalkyl, (1-4C)haloalkoxy, cyano, $(CH_2)_{q1}NR_{1B}R_{1C}$, $(CH_2)_{q1}OR_{1B}$, $(CH_2)_{q1}C(O)R_{1B}$, $(CH_2)_{q1}C(O)OR_{1B}$, $(CH_2)_{q1}OC(O)R_{1B}$, $(CH_2)_{q1}C(O)N(R_{1C})R_{1B}$, $(CH_2)_{q1}N(R_{1C})C(O)R_{1B}$, $(CH_2)_{q1}S(O)_pR_{1B}$(where p is 0, 1 or 2), $(CH_2)_{q1}SO_2N(R_{1C})R_{1B}$, or $(CH_2)_{q1}N(R_{1C})SO_2R_{1B}$, and wherein q1 is 0, 1, 2 or 3 and $R_{1B}$ and $R_{1C}$ are each independently selected from hydrogen, (1-2C)alkyl, (3-4C)cycloalkyl or (3-4C)cycloalkyl(1-2C)alkyl;

(4) $R_1$ is selected from aryl or heteroaryl, wherein $R_1$ is optionally substituted by one or more $R_1$ substituents independently selected from (1-4C)alkyl, halo, (1-4C)haloalkyl, (1-4C)haloalkoxy, cyano, $(CH_2)_{q1}NR_{1B}R_{1C}$, $OR_{1B}$, $C(O)R_{1B}$, $C(O)OR_{1B}$, $OC(O)R_{1B}$, $C(O)N(R_{1C})R_{1B}$, $N(R_{1C})C(O)R_{1B}$, $S(O)_pR_{1B}$ (where p is 0, 1 or 2), $SO_2N(R_{1C})R_{1B}$, or $N(R_{1C})SO_2R_{1B}$ and wherein:

q1 is 0, 1 or 2; and $R_{1B}$ and $R_{1C}$ are each independently selected from hydrogen, (1-4C)alkyl, (3-6C)cycloalkyl or (3-6C)cycloalkyl(1-2C)alkyl;

(5) $R_1$ is selected from aryl or heteroaryl, wherein $R_1$ is optionally substituted by one or more $R_1$, substituents independently selected from (1-2C)alkyl, halo, (1-2C)haloalkyl, (1-2C)haloalkoxy, cyano, $(CH_2)_{q1}NR_{1B}R_{1C}$, $OR_{1B}$, $C(O)R_{1B}$, $C(O)OR_{1B}$, $OC(O)R_{1B}$, $C(O)N(R_{1C})R_{1B}$, $N(R_{1C})C(O)R_{1B}$, $S(O)_pR_{1B}$(where p is 0, 1 or 2), $SO_2N(R_{1C})R_{1B}$, or $N(R_{1C})SO_2R_{1B}$ and wherein:

q1 is 0, 1 or 2; and $R_{1B}$ and $R_{1C}$ are each independently selected from hydrogen, (1-2C)alkyl or (3-4C)cycloalkyl;

(5) $R_1$ is selected from aryl or heteroaryl, wherein $R_1$ is optionally substituted by one or more $R_{11}$ substituents independently selected from (1-4C)alkyl, halo, (1-4C)haloalkyl, (1-4C)haloalkoxy, cyano, $(CH_2)_{q1}NR_{1B}R_{1C}$, $(CH_2)_{q1}OR_{1B}$, $(CH_2)_{q1}C(O)R_{1B}$, $(CH_2)_{q1}C(O)OR_{1B}$, $(CH_2)_{q1}OC(O)R_{1B}$, $(CH_2)_{q1}C(O)N(R_{1C})R_{1B}$, $(CH_2)_{q1}N(R_{1C})C(O)R_{1B}$, $(CH_2)_{q1}S(O)_pR_{1B}$ (where p is 0, 1 or 2), $(CH_2)_{q1}SO_2N(R_{1C})R_{1B}$, or $(CH_2)_{q1}N(R_{1C})SO_2R_{1B}$ and wherein:

q1 is 0, 1 or 2; and $R_{1B}$ and $R_{1C}$ are each independently selected from hydrogen, (1-4C)alkyl, (3-6C)cycloalkyl or (3-6C)cycloalkyl(1-2C)alkyl;

(6) $R_1$ is selected from phenyl or a 5 or 6 membered heteroaryl, wherein $R_1$ is optionally substituted by one or more $R_1$, substituents independently selected from (1-4C)alkyl, halo, (1-4C)haloalkyl, (1-4C)haloalkoxy, cyano, $(CH_2)_{q1}NR_{1B}R_{1C}$, $OR_{1B}$, $C(O)R_{1B}$, $C(O)OR_{1C}$, $OC(O)R_{1B}$, $C(O)N(R_{1C})R_{1B}$, $N(R_{1C})C(O)R_{1B}$, $S(O)$, $R_{1B}$ (where p is 0, 1 or 2), $SO_2N(R_{1C})R_{1B}$, or $N(R_{1C})SO_2R_{1B}$ and wherein:

q1 is 0, 1 or 2; and $R_{1B}$ and $R_{1C}$ are each independently selected from hydrogen, (1-4C)alkyl, (3-6C)cycloalkyl or (3-6C)cycloalkyl(1-2C)alkyl;

(7) $R_1$ is selected from aryl or heteroaryl, wherein $R_1$ is optionally substituted by one or more $R_{1z}$ substituents independently selected from (1-2C)alkyl, halo, (1-2C)haloalkyl, (1-2C)haloalkoxy, cyano, $(CH_2)_{q1}NR_{1B}R_{1C}$, $OR_{1B}$, $C(O)R_{1B}$, $C(O)OR_{1B}$, $OC(O)R_{1B}$, $C(O)N(R_{1C})R_{1B}$, $N(R_{1C})C(O)R_{1B}$, $S(O)_pR_{1B}$ (where p is 0, 1 or 2), $SO_2N(R_{1C})R_{1B}$, or $N(R_{1C})SO_2R_{1B}$ and wherein:

q1 is 0, 1 or 2; and $R_{1B}$ and $R_{1C}$ are each independently selected from hydrogen, (1-2C)alkyl or (3-4C)cycloalkyl;

(8) $R_1$ is selected from aryl or heteroaryl, wherein $R_1$ is optionally substituted by one or more $R_{1z}$ substituents independently selected from (1-2C)alkyl, halo, (1-2C)haloalkyl, (1-2C)haloalkoxy, cyano, $(CH_2)_{q1}NR_{1B}R_{1C}$, $(CH_2)_{q1}OR_{1B}$, $(CH_2)_{q1}C(O)R_{1B}$, $(CH_2)_{q1}C(O)OR_{1B}$, $(CH_2)_{q1}OC(O)R_{1B}$, $(CH_2)_{q1}C(O)N(R_{1C})R_{1B}$, or $(CH_2)_{q1}N(R_{1C})C(O)R_{1B}$, and wherein q1 is 0, 1, 2 or 3 and $R_{1B}$ and $R_{1C}$ are each independently selected from hydrogen or (1-2C) alkyl;

(9) $R_1$ is selected from aryl or heteroaryl, wherein $R_1$ is optionally substituted by one or more $R_{1z}$ substituents independently selected from (1-2C)alkyl, halo, (1-2C)haloalkyl, (1-2C)haloalkoxy, cyano, $(CH_2)_{q1}NR_{1B}R_{1C}$, $(CH_2)_{q1}OR_{1B}$, or $(CH_2)_{q1}C(O)R_{1B}$, and wherein q1 is 0, 1, 2 or 3 and $R_{1B}$ and $R_{1C}$ are each independently selected from hydrogen or (1-2C) alkyl;

(10) $R_1$ is selected from phenyl or a 5- or 6-membered heteroaryl, wherein $R_1$ is optionally substituted by one or more $R_1$, substituents independently selected from (1-2C)alkyl, halo, (1-2C)haloalkyl, (1-2C)haloalkoxy, cyano, $(CH_2)_{q1}NR_{1B}R_{1C}$, $OR_{1B}$, $C(O)R_{1B}$, $C(O)OR_{1B}$, $OC(O)R_{1B}$, $C(O)N(R_{1C})R_{1B}$, $N(R_{1C})C(O)R_{1B}$, $S(O)_pR_{1B}$ (where p is 0, 1 or 2), $SO_2N(R_{1C})R_{1B}$, or $N(R_{1C})SO_2R_{1B}$ and wherein:

q1 is 0, 1 or 2; and $R_{1B}$ and $R_{1C}$ are each independently selected from hydrogen or (1-2C)alkyl;

(11) $R_1$ is phenyl, which is optionally substituted by one or more $R_{1z}$ substituents defined in any one of paragraphs (1) to (10) above.

(12) $R_1$ is a 5 or 6-membered heteroaryl, which is optionally substituted by one or more $R_1$, substituents defined in any one of paragraphs (1) to (10) above.

(13) $R_1$ is selected from phenyl, furyl, pyridyl, oxazolyl, thiazolyl, isoxazolyl or oxazolin-2-yl, wherein a phenyl, furyl, pyridyl or oxazolyl ring is optionally substituted by halo, (1-2C)alkyl, (1-2C)alkoxy or cyano.

(14) $R_1$ is selected from phenyl, furyl, pyridyl or oxazolyl, wherein a phenyl, furyl, pyridyl or oxazolyl ring is optionally substituted by one or more of halo, $C_{1-2}$alkoxy or cyano.

(15) $R_1$ is selected from phenyl, furyl, pyridyl or oxazolyl, wherein a phenyl, furyl, pyridyl or oxazolyl ring is optionally substituted by halo or cyano.

(16) $R_1$ is selected from 3-cyanophenyl, furyl, or oxazolyl, thiazolyl, isoxazolyl or oxazolin-2-yl.

(17) $R_1$ is 3-cyanophenyl.

(18) $R_2$ is selected from hydrogen, cyano, halo, (1-4C) alkyl, (1-4C)haloalkyl, $C(O)OR_{2A}$, $C(O)NR_{2A}R_{2B}$, aryl, heteroaryl, (2-6C)alkenyl, (2-6C)alkynyl or (1-4C)alkanoyl;

wherein $R_{2A}$ and $R_{2B}$ are each independently selected from hydrogen, (1-4C)alkyl, (1-4C)alkoxy, (3-6C) cycloalkyl or (3-6C)cycloalkyl(1-2C)alkyl, or, in the $CONR_{2A}R_{2B}$ group, $R_{2A}$ and $R_{2B}$ are linked such that, together with the nitrogen atom to which they are attached, they form a 4-7 membered heterocyclic ring, and wherein any alkyl, alkenyl, alkynyl, alkanoyl, aryl, heteroaryl or heterocyclyl group (formed by $R_{2A}$ and $R_{2B}$) is optionally substituted by one or more substituents independently selected from (1-4C)alkyl, halo, (1-2C)haloalkyl, (1-2C)haloalkoxy, cyano, $(CH_2)_{q2}NR_{2D}R_{2E}$, $(CH_2)_{q2}OR_{2D}$, $(CH_2)_{q2}C(O)R_{2D}$, $(CH_2)_{q2}C(O)OR_{2D}$, $(CH_2)_{q2}OC(O)R_{2D}$, $(CH_2)_{q2}C(O)N(R_{2E})R_{2D}$, $(CH_2)_{q2}N(R_{2E})C(O)R_{1D}$, $(CH_2)_{q2}S(O)_pR_{2D}$ (where p is 0, 1 or 2), $(CH_2)_{q2}SO_2N(R_2E)R_{2D}$, or $(CH_2)_{q2}N(R_{2E})SO_2R_{2D}$, wherein q2 is 0, 1, or 2; and wherein $R_{2D}$ and $R_{2E}$ are each independently selected from hydrogen, (1-2C)alkyl, (3-4C)cycloalkyl or (3-4C)cycloalkyl(1-2C)alkyl;

and wherein when $R_2$ is pyridiyl, the ring nitrogen atom is optionally in the form of a N-oxide;

(19) $R_2$ is selected from hydrogen, cyano, halo, (1-4C) alkyl, (1-4C)haloalkyl, $C(O)OR_{2A}$, $C(O)NR_{2A}R_{2B}$, phenyl, a 5 or 6-membered heteroaryl, (2-4C)alkenyl or (1-4C)alkanoyl, wherein $R_{2A}$ and $R_{2B}$ are each independently selected from hydrogen, (1-4C)alkyl or (3-6C)cycloalkyl or (3-6C)cycloalkyl(1-2C)alkyl, and wherein any alkyl, alkenyl, alkanoyl, phenyl or heteroaryl group is optionally substituted by one or more substituents independently selected from (1-4C)alkyl, halo, (1-2C)haloalkyl, (1-2C)haloalkoxy, cyano, $(CH_2)_{q2}NR_{2D}R_{2E}$, $(CH_2)_{q2}OR_{2D}$, $(CH_2)_{q2}C(O)R_{2D}$, $(CH_2)_{q2}C(O)OR_{2D}$, $(CH_2)_{q2}OC(O)R_{2D}$, $(CH_2)_{q2}C(O)N(R_{2E})R_{2D}$, $(CH_2)_{q2}N(R_{2E})C(O)R_{2D}$, $(CH_2)_{q2}S(O)_pR_{2D}$ (where p is 0, 1 or 2), $(CH_2)_{q2}SO_2N(R_2E)R_{2D}$, or $(CH_2)_{q2}N(R_{2E})SO_2R_{2D}$, wherein q2 is 0, 1, or 2;

and wherein $R_{2D}$ and $R_{2E}$ are each independently selected from hydrogen, (1-2C)alkyl, (3-4C)cycloalkyl or (3-4C)cycloalkyl(1-2C)alkyl;

and wherein when $R_2$ is pyridiyl, the ring nitrogen atom is optionally in the form of a N-oxide;

(20) $R_2$ is selected from hydrogen, cyano, halo, (1-2C) alkyl, (1-2C)haloalkyl, $C(O)OR_ZA$, $C(O)NR_{2A}R_{2B}$, phenyl, a 5 or 6-membered heteroaryl or (1-4C)alkanoyl, wherein $R_{2A}$ and $R_2$s are each independently selected from hydrogen or (1-4C)alkyl, and wherein any alkyl, alkenyl, alkanoyl, phenyl or heteroaryl group is optionally substituted by one or more substituents independently selected from (1-4C)alkyl, halo, (1-2C)haloalkyl, (1-2C)haloalkoxy, cyano, $(CH_2)_{q2}NR_{2D}R_{2E}$, $(CH_2)_{q2}OR_{2D}$, $(CH_2)_{q2}C(O)R_{2D}$, $(CH_2)_{q2}C(O)OR_{2D}$, $(CH_2)_{q2}OC(O)R_{2D}$, $(CH_2)_{q2}C(O)N(R_{2E})R_{2D}$, $(CH_2)_{q2}N(R_{2E})C(O)R_{2D}$, $(CH_2)_{q2}S(O)_pR_{2D}$ (where p is 0, 1 or 2), $(CH_2)_{q2}SO_2N(R_{2E})R_{2D}$, or $(CH_2)_{q2}N(R_{2E})SO_2R_{2D}$, wherein q2 is 0, 1, or 2; and wherein $R_{2D}$ and $R_{2E}$ are each independently selected from hydrogen, (1-2C)alkyl, (3-4C)cycloalkyl or (3-4C)cycloalkyl(1-2C)alkyl;

and wherein when $R_2$ is pyridiyl, the ring nitrogen atom is optionally in the form of a N-oxide;

(21) $R_2$ is selected from cyano, halo, methyl, $CF_3$, $C(O)OR_{2A}$, $C(O)NR_{2A}R_{2B}$, a 5 or 6-membered heteroaryl or (2-4C)alkanoyl, wherein $R_{2A}$ and $R_{2B}$ are each independently selected from hydrogen or (1-4C)alkyl, wherein any phenyl or heteroaryl group is optionally substituted by one or more substituents independently selected from (1-2C)alkyl, halo, (1-2C)haloalkyl, (1-2C)haloalkoxy, cyano, $(CH_2)_{q2}NR_{2D}R_{2E}$, $OR_{2D}$, $C(O)R_{2D}$, $C(O)OR_{2D}$, $OC(O)R_{2D}$, $C(O)N(R_{2E})R_{2D}$, $N(R_{2E})C(O)R_{2D}$, $S(O)R_{2D}$ (where p is 0, 1 or 2), $SO_2N(R_2E)R_{2D}$, or $N(R_2E)SO_2R_{2D}$, wherein q2 is 0 or 1; and wherein $R_{2D}$ and $R_{2E}$ are each independently selected from hydrogen or (1-2C) alkyl;

and wherein when $R_2$ is pyridiyl, the ring nitrogen atom is optionally in the form of a N-oxide;

(22) $R_2$ is selected from cyano or a 5 or 6-membered heteroaryl which is optionally substituted as defined above in any one of paragraphs (18) to (21); and wherein when $R_2$ is pyridiyl, the ring nitrogen atom is optionally in the form of a N-oxide;

(23) $R_2$ is selected from cyano or a 5 or 6-membered heteroaryl which is optionally substituted by one or more substituents independently selected from (1-2C) alkyl, halo, (1-2C)haloalkyl, (1-2C)alkoxy, (1-2C)haloalkoxy or cyano; and wherein when $R_2$ is pyridiyl, the ring nitrogen atom is optionally in the form of a N-oxide;

(24) $R_2$ is a 5 or 6-membered heteroaryl which is optionally substituted by one or more substituents-independently selected from (1-2C)alkyl, halo, (1-2C)haloalkyl, (1-2C)alkoxy, (1-2C)haloalkoxy or cyano; and wherein when $R_2$ is pyridiyl, the ring nitrogen atom is optionally in the form of a N-oxide;

(25) $R_2$ is a 5 or 6-membered heteroaryl which is optionally substituted by one or more substituents independently selected from (1-2C)alkyl or halo; and wherein when $R_2$ is pyridiyl, the ring nitrogen atom is optionally in the form of a N-oxide;

(26) $R_2$ is a 6-membered heteroaryl which is optionally substituted by one or more substituents independently selected from(1-2C)alkyl, halo, (1-2C)haloalkyl, (1-2C)alkoxy, (1-2C)haloalkoxy or cyano; and wherein when $R_2$ is pyridiyl, the ring nitrogen atom is optionally in the form of a N-oxide;

(27) $R_2$ is a 6-membered nitrogen containing heteroaryl which is optionally substituted by one or more substituents independently selected from (1-2C)alkyl or halo; and wherein when $R_2$ is pyridiyl, the ring nitrogen atom is optionally in the form of a N-oxide;

(28) $R_2$ is a 6-membered nitrogen containing heteroaryl which is optionally substituted by one or more substituents independently selected from methyl or chloro; and wherein when $R_2$ is pyridiyl, the ring nitrogen atom is optionally in the form of a N-oxide;

(29) $R_2$ is:

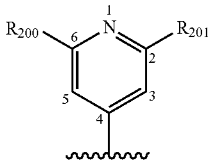

wherein:

(i) $R_{200}$ and $R_{201}$ are each independently selected from (1-2C)alkyl, hydroxy(1-2C)alkyl, amino halo, (1-2C)haloalkyl, (1-2C)alkoxy, (1-2C)haloalkoxy, (1-2C)alkanoyl or cyano;

(ii) $R_{200}$ and $R_{201}$ are each independently selected from methyl, hydroxymethyl, halo, di-fluoromethyl, trifluoromethyl, methoxy, acetyl or cyano;

(iii) $R_{200}$ is methyl or chloro and $R_{201}$ is selected from methyl, hydroxymethyl, halo, di-fluoromethyl, trifluoromethyl, methoxy, acetyl or cyano;

or

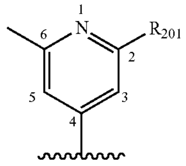

wherein:

(i) $R_{201}$ is (1-2C)alkyl, halo, (1-2C)haloalkyl, hydroxy (1-2C)alkyl, (1-2C)alkoxy, (1-2C)haloalkoxy, (1-2C)alkanoyl or cyano;

(ii) $R_{201}$ is methyl, hydroxymethyl, halo, di-fluoromethyl, trifluoromethyl, methoxy, acetyl or cyano;

(iii) $R_{201}$ is methyl, hydroxymethyl or chloro;

(iv) $R_{201}$ is methyl;

(v) $R_{201}$ is chloro;

(30) $R_2$ is pyridinyl (e.g. pyridine-4-yl) which is optionally substituted by one or more substituents independently selected from methyl or chloro;

(31) $R_2$ is 2-chloro-6-methylpyridin-4-yl or 2,6-dimethylpyridin-4-yl, i.e.

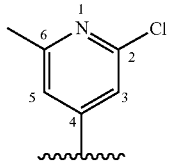 or 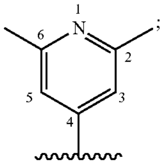;

(32) $R_a$ is selected from hydrogen, halo, cyano or a group of the formula:

-L-Y-$L_q$-Q wherein:

L is absent or (1-4C)alkylene;

Y is absent or O, S, SO, $SO_2$, $N(R_a)$, C(O), C(O)O, OC(O), $C(O)N(R_a)$, $C(O)N(R_a)O$, $N(R_a)C(O)$, $N(R_a)C(O)N(R_b)$, $N(R_a)C(O)O$, $OC(O)N(R_a)$, $C({=}NR_y)N(R_a)$, $N(R_a)C({=}NR_y)$, $N(R_a)C({=}NR_y)N(R_b)$, $S(O)_2N(R_a)$, $N(R_a)SO_2$, $N(R_a)SO_2N(R_b)$ or $C(O)N(R_a)SO_2$, wherein $R_a$ and $R_b$ are each independently selected from hydrogen or (1-4C)alkyl and Ry is selected from hydrogen, (1-4C)alkyl, nitro or cyano;

$L_q$ is absent or (1-4C)alkylene optionally substituted by one or more substituents selected from (1-2C)alkoxy, halo, cyano, amino or oxo; and Q is hydrogen, (1-6C)alkyl, (2-6C)alkenyl, (2-6C)alkynyl, aryl, (3-8)cycloalkyl, (3-8C)cycloalkenyl, heteroaryl or heterocyclyl;

wherein Q is optionally further substituted by one or more substituent groups independently selected from oxo, (1-4C)alkyl, halo, (1-4C)haloalkyl, (1-4C)haloalkoxy, (1-4C)aminoalkyl, (1-4C)hydroxyalkyl, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, or $(CH_2)_qNR_cR_d$ (where q is 1, 2 or 3); wherein $R_c$ and $R_d$ are each independently selected from hydrogen, (1-6C)alkyl, (3-6C)cycloalkyl or (3-6C)cycloalkyl(1-2C)alkyl; or $R_c$ and $R_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, di-[(1-4C)alkyl]amino, amino, cyano or hydroxy; and/or Q is optionally substituted by one or more group(s) of the formula:

$-L_1-L_{Q1}-W_1$ wherein:

$L_1$ is absent or (1-3C)alkylene;

$L_{Q1}$ is absent or selected from or O, S, SO, $SO_2$, $N(R_f)$, C(O), C(O)O, OC(O), $C(O)N(R_f)$, $N(R_f)C(O)$, $N(R_f)C(O)N(R_g)$, $N(R_f)C(O)O$, $OC(O)N(R_f)$, $S(O)_2N(R_f)$, $N(R_f)SO_2$ wherein $R_f$ and $R_g$ are each independently selected from hydrogen or (1-2C)alkyl; and $W_1$ is hydrogen, (1-6C)alkyl, aryl, aryl(1-2C)alkyl, (3-8C)cycloalkyl, (3-8C)cycloalkenyl, heteroaryl or heterocyclyl; wherein $W_1$ is optionally substituted by one or more substituents selected from oxo, (1-4C)alkyl, halo, (1-4C)haloalkyl, (1-4C)haloalkoxy, (1-4C)alkoxy, (1-4C)alkylamino, cyano, aryl, heteroaryl, heterocycyl, (3-6C)cycloalkyl, $NR_hR_i$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), $SO_2N(R_i)R_h$, $N(R_i)SO_2R_h$ or $(CH_2)SNR_iR_h$ (where s is 1, 2 or 3); wherein $R_h$ and $R_i$ are each independently selected from hydrogen, (1-4C)alkyl, (3-6C)cycloalkyl or (3-6C)cycloalkyl(1-2C)alkyl;

and wherein any alkyl, alkoxy, aryl, hereoaryl, heterocyclyl or cycloalkyl moiety in a substituent group present on $W_1$ is optionally further substituted by one or more halo, (1-4C)alkyl, (1-4C)haloalkyl, (1-4C)haloalkoxy, (1-4C)alkoxy, (1-4C)alkylamino, di-[(1-4C)alkyl]amino, amino, cyano or hydroxy groups; or $R_h$ and $R_i$ are linked such that, together with the nitrogen atom to which they are attached, they form a 4-7 membered heterocyclic ring which is optionally substituted by one or more substituents selected from oxo, (1-4C)alkyl, halo, (1-4C)haloalkyl, (1-4C)haloalkoxy, (1-4C)alkoxy, (1-4C)alkylamino, di-[(1-4C)alkyl]amino, amino, cyano or hydroxy; and wherein any tertiary amine or nitrogen atom in a pyridyl ring in a $R_3$ group is optionally in the form of a N-oxide;

(33) $R_3$ is selected from hydrogen, halo, cyano or a group of the formula:

$-L-Y-L_q-Q$ wherein:

L is absent or (1-4C)alkylene;

Y is absent or O, S, SO, $SO_2$, $N(R_a)$, C(O), C(O)O, OC(O), $C(O)N(R_a)$, $C(O)N(R_a)O$, $N(R_a)C(O)$, $N(R_a)C(O)N(R_b)$, $N(R_a)C(O)O$, $OC(O)N(R_a)$, $C(=NR_y)N(R_a)$, $N(R_a)C(=NR_y)$, $N(R_a)C(=NR_y)N(R_b)$, $S(O)_2N(R_a)$, $N(R_a)SO_2$, $N(R_a)SO_2N(R_b)$ or $C(O)N(R_a)SO_2$, wherein $R_a$ and $R_b$ are each independently selected from hydrogen or (1-4C)alkyl and Ry is selected from hydrogen, (1-4C)alkyl, nitro or cyano;

$L_q$ is absent or (1-4C)alkylene optionally substituted by one or more substituents selected from (1-2C)alkoxy, halo, cyano, amino or oxo; and Q is hydrogen, (1-6C)alkyl, (2-6C)alkenyl, (2-6C)alkynyl, aryl, (3-8)cycloalkyl, (3-8C)cycloalkenyl, heteroaryl or heterocyclyl;

wherein Q is optionally further substituted by one or more substituent groups independently selected from oxo, (1-4C)alkyl, halo, (1-4C)haloalkyl, (1-4C)haloalkoxy, (1-4C)aminoalkyl, (1-4C)hydroxyalkyl, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_a$ (where p is 0, 1 or 2), $SO_2N(R_d)R_c$, $N(R_d)SO_2R_c$, or $(CH_2)_qNR_cR_d$ (where q is 1, 2 or 3); wherein $R_c$ and $R_d$ are each independently selected from hydrogen, (1-6C)alkyl, (3-6C)cycloalkyl or (3-6C)cycloalkyl(1-2C)alkyl; and/or Q is optionally substituted by one or more group(s) of the formula:

$-L_1-L_{Q1}-W_1$ wherein:

$L_1$ is absent or (1-3C)alkylene;

$L_{Q1}$ is absent or selected from or O, S, SO, $SO_2$, $N(R_f)$, C(O), C(O)O, OC(O), $C(O)N(R_f)$, $N(R_f)C(O)$, $N(R_f)C(O)N(R_g)$, $N(R_i)C(O)O$, $OC(O)N(R_f)$, $S(O)_2N(R_f)$, $N(R_i)SO_2$ wherein $R_f$ and $R_g$ are each independently selected from hydrogen or (1-2C)alkyl; and $W_1$ is hydrogen, (1-6C)alkyl, aryl, aryl(1-2C)alkyl, (3-8C)cycloalkyl, (3-8C)cycloalkenyl, heteroaryl or heterocyclyl; wherein $W_1$ is optionally substituted by one or more substituents selected from oxo, (1-4C)alkyl, halo, (1-4C)haloalkyl, (1-4C)haloalkoxy, (1-4C)alkoxy, (1-4C)alkylamino, cyano, aryl, heteroaryl, heterocycyl, (3-6C)cycloalkyl, $NR_hR_i$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), $SO_2N(R_i)R_h$, $N(R_i)SO_2R_h$ or $(CH_2)_sNR_iR_h$ (where s is 1, 2 or 3); wherein $R_h$ and $R_i$ are each independently selected from hydrogen, (1-4C)alkyl, (3-6C)cycloalkyl or (3-6C)cycloalkyl(1-2C)alkyl;

and wherein any tertiary amine or nitrogen atom in a pyridyl ring in a $R_3$ group is optionally in the form of a N-oxide;

(34) $R_3$ is selected from hydrogen, halo, cyano or a group of the formula:

$-L-Y-L_q-Q$ wherein:

L is absent or (1-2C)alkylene;

Y is absent or O, S, SO, $SO_2$, $N(R_a)$, C(O), C(O)O, OC(O), $C(O)N(R_a)$, $C(O)N(R_a)O$, $N(R_a)C(O)$, $N(R_a)C(O)N(R_b)$, $N(R_a)C(O)O$, $OC(O)N(R_a)$, $C(=NR_y)N(R_a)$, $N(R_a)C(=NR_y)$, $N(R_a)C(=NR_y)N(R_b)$, $S(O)_2N(R_a)$, $N(R_a)SO_2$, $N(R_a)SO_2N(R_b)$ or $C(O)N(R_a)SO_2$, wherein $R_a$ and $R_b$ are each independently selected from hydrogen or (1-4C)alkyl and Ry is selected from hydrogen, (1-4C)alkyl, nitro or cyano;

$L_q$ is absent or (1-4C)alkylene optionally substituted by one or more substituents selected from (1-2C)alkoxy, halo, cyano, amino or oxo; and Q is hydrogen, (1-6C)alkyl, aryl, (3-8)cycloalkyl, heteroaryl or heterocyclyl; wherein Q is optionally further substituted by one or more substituent groups independently selected from oxo, (1-4C)alkyl, halo, (1-4C)haloalkyl, (1-4C)haloalkoxy, (1-4C)aminoalkyl, (1-4C)hydroxyalkyl, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_f$, or $(CH_2)_qNR_cR_d$ (where q is 1, 2 or 3); wherein $R_c$ and $R_d$ are each independently selected from hydrogen, (1-6C)alkyl, (3-6C)cycloalkyl or (3-6C)cycloalkyl(1-2C)alkyl; and/or Q is optionally substituted by one or more group(s) of the formula:

$-L_1-L_{Q1}-W_1$ wherein:

$L_1$ is absent or (1-2C)alkylene;

$L_{Q1}$ is absent or selected from or O, S, SO, $SO_2$, $N(R_f)$, C(O), C(O)O, OC(O), $C(O)N(R_f)$, $N(R_f)C(O)$, $N(R_f)C(O)N(R_g)$, $N(R_f)C(O)O$, $OC(O)N(R_f)$, $S(O)_2N(R_f)$, $N(R_f)SO_2$ wherein $R_f$ and $R_g$ are each independently selected from hydrogen or (1-2C)alkyl; and $W_1$ is hydrogen, (1-6C)alkyl, aryl, aryl(1-2C)alkyl, (3-8C)cycloalkyl, heteroaryl or heterocyclyl; wherein $W_1$ is optionally substituted by one or more substituents selected from oxo, (1-4C)alkyl, halo, (1-4C)haloalkyl, (1-4C)haloalkoxy, (1-4C)alkoxy, (1-4C)alkylamino, cyano, $NR_hR_c$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), $SO_2N(R_i)R_h$, $N(R_j)SO_2R_h$ or $(CH_2)_sNR_iR_h$ (where s is 1, 2 or 3); wherein $R_h$ and $R_j$ are each independently selected from hydrogen or (1-4C)alkyl;

and wherein any tertiary amine or nitrogen atom in a pyridyl ring in a $R_3$ group is optionally in the form of a N-oxide;

(35) $R_3$ is selected from hydrogen, halo, cyano or a group of the formula:

$$-L-Y-L_q-Q$$

wherein:

L is absent or (1-2C)alkylene;

Y is absent or 0, $N(R_a)$, C(O), C(O)O, $C(O)N(R_a)$, $N(R_a)C(O)$, $C(O)N(R_a)O$, $N(R_a)C(O)N(R_b)$, $N(R_a)C(O)O$, $OC(O)N(R_a)$, $C({=}NR_y)N(R_a)$, $N(R_a)C({=}NR_y)$, $N(R_a)C({=}NR_y)N(R_b)$, $S(O)_2N(R_a)$, $N(R_a)SO_2$, $N(R_a)SO_2N(R_b)$ or $C(O)N(R_a)SO_2$, wherein $R_a$ and $R_b$ are each independently selected from hydrogen or (1-4C)alkyl and $R_y$ is selected from hydrogen, (1-4C)alkyl, nitro or cyano; $L_q$ is absent or (1-4C)alkylene optionally substituted by one or more substituents selected from (1-2C)alkoxy, halo, cyano, amino or oxo; and Q is hydrogen, (1-6C)alkyl, aryl, (3-8)cycloalkyl, heteroaryl or heterocyclyl; wherein Q is optionally further substituted by one or more substituent groups independently selected from oxo, (1-4C)alkyl, halo, (1-4C)haloalkyl, (1-4C)haloalkoxy, (1-4C)aminoalkyl, (1-4C)hydroxyalkyl, cyano, $NR_cR_d$, $OR_C$, $C(O)R_c$, $C(O)OR_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, or $(CH_2)_qNR_cR_d$ (where q is 1, 2 or 3); wherein R, and $R_d$ are each independently selected from hydrogen or (1-6C)alkyl; and/or Q is optionally substituted by one or more group(s) of the formula:

$$-L-L_{Q1}-W_1$$

wherein:

$L_1$ is absent or (1-2C)alkylene;

$L_{Q1}$ is absent; and

W, is hydrogen, (1-6C)alkyl, aryl, aryl(1-2C)alkyl, (3-8C)cycloalkyl, heteroaryl or heterocyclyl; wherein $W_1$ is optionally substituted by one or more substituents selected from oxo, (1-4C)alkyl, halo, (1-4C)haloalkyl, (1-4C)haloalkoxy, (1-4C)alkoxy, (1-4C)alkylamino, cyano, $NR_hR_i$, $OR_h$, $C(O)R_h$, $C(O)OR_h$, $OC(O)R_h$, $C(O)N(R_i)R_h$, $N(R_j)C(O)R_h$, $S(O),R_h$ (where r is 0, 1 or 2), wherein $R_h$ and $R_i$ are each independently selected from hydrogen or (1-4C)alkyl;

and wherein any tertiary amine or nitrogen atom in a pyridyl ring in a $R_3$ group is optionally in the form of a N-oxide;

(35a) $R_3$ is selected from hydrogen, halo, cyano or a group of the formula:

$$-L-Y-L_q-Q$$

wherein:

L is absent or (1-2C)alkylene;

Y is absent or $N(R_a)$, C(O), $C(O)N(R_a)$, $N(R_a)C({=}NR_y)N(R_b)$, $C(O)N(R_a)O$, or $N(R_a)C(O)N(R_b)$; wherein $R_a$ and $R_b$ are each independently selected from hydrogen or (1-4C)alkyl and $R_y$ is selected from hydrogen, (1-4C)alkyl or cyano; $L_q$ is absent or (1-4C)alkylene optionally substituted by one or more substituents selected from (1-2C)alkoxy, halo, cyano, amino or oxo; and Q is hydrogen, (1-6C)alkyl, (2-6C)alkenyl, (3-8)cycloalkyl, or heterocyclyl; wherein Q is optionally further substituted by one or more substituent groups independently selected from oxo, (1-4C)alkyl, halo, (1-4C)haloalkyl, (1-4C)haloalkoxy, (1-4C)aminoalkyl, (1-4C)hydroxyalkyl, cyano, $NR_cR_d$, ORC, $C(O)R_c$, $C(O)OR_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, or $(CH_2)_qNR_cR_d$ (where q is 1, 2 or 3); wherein $R_e$ and $R_d$ are each independently selected from hydrogen or (1-6C)alkyl; and/or Q is optionally substituted by one or more group(s) of the formula:

$$—Li-L_{Q1}-W_1$$

wherein:

$L_1$ is absent or (1-2C)alkylene;

$L_{Q1}$ is absent; and $W_1$ is hydrogen, (1-6C)alkyl, aryl, aryl(1-2C)alkyl, (3-8C)cycloalkyl, heteroaryl or heterocyclyl; wherein $W_1$ is optionally substituted by one or more substituents selected from oxo, (1-4C)alkyl, halo, (1-4C)haloalkyl, (1-4C)haloalkoxy, (1-4C)alkoxy, (1-4C)alkylamino, cyano, $NR_hR_i$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), wherein $R_h$ and $R_i$ are each independently selected from hydrogen or (1-4C)alkyl;

and wherein any tertiary amine or nitrogen atom in a pyridyl ring in a $R_3$ group is optionally in the form of a N-oxide;

(36) $R_a$ is a group of the formula:

$$-L-Y-L_q-Q$$

wherein:

L is absent;

Y is $N(R_a)$ or $C(O)N(R_a)$;

$L_q$ is absent; and

Q is (1-6C)alkyl or (3-8)cycloalkyl;

wherein Q is optionally further substituted by one or more substituent groups independently selected from halo, cyano, $NR_cR_d$, $OR_c$, $C(O)R_c$, $C(O)OR_c$, $C(O)N(R_d)R_c$, $N(R_d)C(O)R_c$, $S(O)PR_c$ (where p is 0, 1 or 2), $SO_2N(R_d)R_c$, $N(R_d)SO_2R_c$, or $(CH_2)_qNR_cR_d$ (where q is 1, 2 or 3); wherein $R_c$ and $R_d$ are each independently selected from hydrogen or (1-6C) alkyl;

(37) $R_3$ is a group of the formula:

$$-L-Y-L_q-Q$$

wherein:

L is absent;

Y is $N(R_a)$ or $C(O)N(R_a)$;

$L_q$ is absent; and

Q is (1-6C)alkyl;

wherein Q is optionally further substituted by one or more substituent groups independently selected from halo, cyano, $NR_cR_d$, $OR_c$, $C(O)OR_c$, $S(O)_pR_c$ (where p is 0, 1 or 2), $SO_2N(R_d)R$.; wherein $R_c$ and $R_d$ are each independently selected from hydrogen or (1-6C)alkyl;

(38) $R_3$ is a group of the formula:

-L-Y-$L_q$-Q wherein:

L is absent;

Y is $N(R_a)$ or $C(O)N(R_a)$;

$L_q$ is absent; and

Q is (1-6C)alkyl;

wherein Q is optionally further substituted by one or more $OR_c$; wherein $R_c$ is selected from hydrogen or (1-4C)alkyl;

(39) $R_3$ is a group of the formula:

-L-Y-$L_q$-Q wherein:

L is absent;

Y is $N(R_a)$ or $C(O)N(R_a)$;

$L_q$ is absent; and

Q is (1-6C)alkyl;

wherein Q is optionally further substituted by one or more OH;

(40) $R_3$ is a group of the formula:

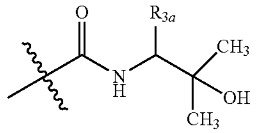

wherein $R_3a$ is hydrogen or methyl;

(41) $R_3$ is selected from halo or a group of the formula:

-L-Y-Q wherein:

L is absent;

Y is absent or O, S, SO, $SO_2$, $N(R_a)$, C(O), C(O)O, OC(O), $C(O)N(R_a)$, $C(O)N(R_a)O$, $N(R_a)C(O)$, $S(O)_2N(R_a)$, $N(R_a)SO_2$ or $N(R_a)SO_2N(R_b)$, wherein $R_a$ and $R_b$ are each independently selected from hydrogen or (1-2C)alkyl; and Q is (1-4C)alkyl, heteroaryl or heterocyclyl;

wherein Q is optionally further substituted by one or more substituent groups independently selected from oxo, (1-4C)alkyl, halo, (1-4C)haloalkyl, (1-4C)haloalkoxy, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, or $(CH_2)_qNR_cR_d$ (where q is 1, 2 or 3); wherein $R_c$, $R_d$ and $R_e$ are each independently selected from hydrogen, (1-4C)alkyl or (3-6C)cycloalkyl; or $R_c$ and $R_d$ are linked such that, together with the nitrogen atom to which they are attached, they form a 4-6 membered heterocyclic ring which is optionally substituted by one or more substituents selected from (1-2C)alkyl, halo, (1-2C)haloalkyl, (1-2C)haloalkoxy, (1-2C)alkoxy, (1-2C)alkylamino, di-[(1-2C)alkyl]amino, amino, cyano or hydroxy; and/or Q is optionally substituted by a group of the formula:

-$L_1$-$L_{Q1}$-$W_1$ wherein:

$L_1$ is absent or (1-3C)alkylene optionally substituted by one or more substituents selected from (1-2C)alkyl or oxo;

$L_{Q1}$ is absent or selected from or O, S, SO, $SO_2$, $N(R_f)$, C(O), C(O)O, OC(O), $C(O)N(R_f)$, $N(R_f)C(O)$, $N(R_f)C(O)O$, $OC(O)N(R_f)$, $S(O)_2N(R_f)$, or $N(R_f)SO_2$, wherein $R_f$ and $R_g$ are each independently selected from hydrogen or (1-2C)alkyl; and $W_1$ is hydrogen, (1-4C)alkyl, aryl, heteroaryl or heterocyclyl; wherein $W_1$ is optionally substituted by one or more substituents selected from oxo, (1-4C)alkyl, halo, (1-4C)haloalkyl, (1-4C)haloalkoxy, (1-4C)alkoxy, cyano, $NR_hR_i$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), $SO_2N(R_i)R_h$, $N(R_i)SO_2R_h$ or $(CH_2)_sNR_1R_h$ (where s is 1, 2 or 3); wherein $R_h$ and $R_i$ are each independently selected from hydrogen, (1-4C)alkyl or (3-6C)cycloalkyl; and wherein any alkyl, alkoxy, aryl, hereoaryl, heterocyclyl or cycloalkyl moiety in a substituent group present on $W_1$ is optionally further substituted by one or more halo, (1-4C)alkyl, (1-4C)haloalkyl, (1-4C)haloalkoxy, (1-4C)alkoxy, (1-4C)alkylamino, di-[(1-4C)alkyl]amino, amino, cyano or hydroxy groups;

and wherein any tertiary amine or nitrogen atom in a pyridyl ring present in a $R_3$ group is optionally in the form of a N-oxide;

(42) $R_3$ is selected from halo or a group of the formula:

-Q wherein:

Q is heteroaryl or heterocyclyl;

wherein Q is optionally further substituted by one or more substituent groups independently selected from oxo, (1-4C)alkyl, halo, (1-4C)haloalkyl, (1-4C)haloalkoxy, cyano, $NR_cR_d$, ORE, $C(O)R_c$, $C(O)OR_c$, $OC(O)R_c$, $C(O)N(R_d)R_c$, $N(R_d)C(O)R_c$, $S(O)_rR_c$ (where p is 0, 1 or 2), $SO_2N(R_d)R_c$, $N(R_d)SO_2R_c$, or $(CH_2)_qNR_cR_d$ (where q is 1, 2 or 3); wherein $R_D$, $R_d$ and $R_B$ are each independently selected from hydrogen, (1-4C)alkyl or (3-6C)cycloalkyl; or $R_c$ and $R_d$ are linked such that, together with the nitrogen atom to which they are attached, they form a 4-6 membered heterocyclic ring which is optionally substituted by one or more substituents selected from (1-2C)alkyl, halo, (1-2C)haloalkyl, (1-2C)haloalkoxy, (1-2C)alkoxy, (1-2C)alkylamino, di-[(1-2C)alkyl]amino, amino, cyano or hydroxy; and/or Q is optionally substituted by a group of the formula:

-$L_1$-$L_{Q1}$-$W_1$ wherein:

$L_1$ is absent or (1-3C)alkylene optionally substituted by one or more substituents selected from (1-2C)alkyl or oxo;

$L_{Q1}$ is absent or selected from or O, S, SO, $SO_2$, $N(R_f)$, C(O), C(O)O, OC(O), $C(O)N(R_f)$, $N(R_f)C(O)$, $N(R_f)C(O)O$, $OC(O)N(R_f)$, $S(O)_2N(R_f)$, or $N(R_f)SO_2$, wherein $R_f$ and $R_g$ are each independently selected from hydrogen or (1-2C)alkyl; and $W_1$ is hydrogen, (1-4C)alkyl, aryl, heteroaryl or heterocyclyl;

wherein $W_1$ is optionally substituted by one or more substituents selected from oxo, (1-4C)alkyl, halo, (1-4C)haloalkyl, (1-4C)haloalkoxy, (1-4C)alkoxy, cyano, $NR_hR_i$, $OR_h$, $C(O)R_h$, $C(O)OR_h$, $OC(O)R_h$, $C(O)N(R_i)R_h$, $N(R_a)C(O)R_h$, $S(O)_rR_h$ (where r is 0, 1 or 2), $SO_2N(R_i)R_h$, $N(R_i)SO_2R_h$ or $(CH_2)_sNR_iR_h$ (where s is 1, 2 or 3); wherein $R_h$ and $R_i$ are each independently selected from hydrogen, (1-4C)alkyl or (3-6C)cycloalkyl;

or $R_h$ and $R_i$ are linked such that, together with the nitrogen atom to which they are attached, they form a 4-7 membered heterocyclic ring which is optionally substituted by one or more substituents selected from oxo, (1-4C)alkyl, halo, (1-4C)haloalkyl, (1-4C) haloalkoxy, (1-4C)alkoxy, (1-4C)alkylamino, di-[(1-4C)alkyl]amino, amino, cyano or hydroxy;

and wherein any alkyl, alkoxy, aryl, hereoaryl, heterocyclyl or cycloalkyl moiety in a substituent group present on $W_1$ is optionally further substituted by one or more halo, (1-4C)alkyl, (1-4C)haloalkyl, (1-4C) haloalkoxy, (1-4C)alkoxy, (1-4C)alkylamino, di-[(1-4C)alkyl]amino, amino, cyano or hydroxy groups;

and wherein any tertiary amine or nitrogen atom in a pyridyl ring present in a $R_3$ group is optionally in the form of a N-oxide;

(43) $R_3$ is a heterocyclyl which is optionally further substituted by one or more substituent groups independently selected from oxo, (1-4C)alkyl, halo, (1-4C) haloalkyl, (1-. 4C)haloalkoxy, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, or $(CH_2)_qNR_cR_d$ (where q is 1, 2 or 3); wherein $R_c$, $R_d$ and $R_e$ are each independently selected from hydrogen, (1-4C)alkyl or (3-6C)cycloalkyl; or $R_c$ and $R_d$ are linked such that, together with the nitrogen atom to which they are attached, they form a 4-6 membered heterocyclic ring which is optionally substituted by one or more substituents selected from (1-2C)alkyl, halo, (1-2C)haloalkyl, (1-2C)haloalkoxy, (1-2C)alkoxy, (1-2C)alkylamino, di-[(1-2C)alkyl]amino, amino, cyano or hydroxy; and/or $R_3$ is. optionally substituted by a group of the formula:

$-L_1-L_{Q1}-W_1$ wherein:

$L_1$ is absent or (1-3C)alkylene optionally substituted by one or more substituents selected from (1-2C)alkyl or oxo;

$L_{Q1}$ is absent or selected from or O, S, SO, $SO_2$, $N(R_f)$, C(O), C(O)O, OC(O), $C(O)N(R_f)$, $N(R_f)C(O)$, $N(R_f)C(O)O$, $OC(O)N(R_f)$, $S(O)_2N(R_f)$, or $N(R_f)SO_2$, wherein $R_f$ and $R_9$ are each independently selected from hydrogen or (1-2C)alkyl; and $W_1$ is hydrogen, (1-4C)alkyl, aryl, heteroaryl or heterocyclyl; wherein $W_1$ is optionally substituted by one or more substituents selected from oxo, (1-4C) alkyl, halo, (1-4C)haloalkyl, (1-4C)haloalkoxy, (1-4C)alkoxy, cyano, $NR_hR_i$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), $SO_2N(R_i)R_h$, $N(R_i)SO_2R_h$ or $(CH_2)_sNR_iR_h$ (where s is 1, 2 or 3); wherein $R_h$ and $R_i$ are each independently selected from hydrogen, (1-4C)alkyl or (3-6C)cycloalkyl; or $R_h$ and R; are linked such that, together with the nitrogen atom to which they are attached, they form a 4-7 membered heterocyclic ring which is optionally substituted by one or more substituents selected from oxo, (1-4C)alkyl, halo, (1-4C)haloalkyl, (1-4C) haloalkoxy, (1-4C)alkoxy, (1-4C)alkylamino, di-[(1-4C)alkyl]amino, amino, cyano or hydroxy;

and wherein any alkyl, alkoxy, aryl, hereoaryl, heterocyclyl or cycloalkyl moiety in a substutent group present on $W_1$ is optionally further substituted by one or more halo, (1-4C)alkyl, (1-4C)haloalkyl, (1-4C) haloalkoxy, (1-4C)alkoxy, (1-4C)alkylamino, di-[(1-4C)alkyl]amino, amino, cyano or hydroxy groups;

and wherein any tertiary amine or nitrogen atom in a pyridyl ring present in a $R_3$ group is optionally in the form of a N-oxide;

(44) $R_3$ is a nitrogen-linked heterocycle selected from a 4-7 membered heterocylic ring system, a 9-15 membered bicyclic ring system or a 9-15 membered spirocyclic ring system;

wherein $R_3$ optionally further substituted by one or more substituent groups independently selected from oxo, (1-4C)alkyl, halo, (1-4C)haloalkyl, (1-4C)haloalkoxy, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, or $(CH_2)_qNR_cR_d$ (where q is 1, 2 or 3); wherein $R_c$, $R_d$ and $R_e$ are each independently selected from hydrogen, (1-4C)alkyl or (3-6C)cycloalkyl; or $R_c$ and $R_d$ are linked such that, together with the nitrogen atom to which they are attached, they form a 4-6 membered heterocyclic ring which is optionally substituted by one or more substituents selected from (1-2C)alkyl, halo, (1-2C)haloalkyl, (1-2C)haloalkoxy, (1-2C)alkoxy, (1-2C)alkylamino, di-[(1-2C)alkyl]amino, amino, cyano or hydroxy; and/or $R_3$ is optionally substituted by a group of the formula:

$-L_1-L_{Q1}-W_1$ wherein:

$L_1$ is absent or (1-3C)alkylene optionally substituted by one or more substituents selected from (1-2C)alkyl or oxo;

$L_{Q1}$ is absent or selected from or O, S, SO, $SO_2$, $N(R_t)$, C(O), C(O)O, OC(O), $C(O)N(R_f)$, $N(R_f)C(O)$, $N(R_f)C(O)O$, $OC(O)N(R_f)$, $S(O)_2N(R_f)$, or $N(R_f)SO_2$, wherein $R_f$ and $R_g$ are each independently selected from hydrogen or (1-2C)alkyl; and $W_1$ is hydrogen, (1-4C)alkyl, aryl, heteroaryl or heterocyclyl; wherein $W_1$ is optionally substituted by one or more substituents selected from oxo, (1-4C) alkyl, halo, (1-4C)haloalkyl, (1-4C)haloalkoxy, (1-4C)alkoxy, cyano, $NR_hR_i$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), $SO_2N(R_i)R_h$, $N(R_i)SO_2R_h$ or $(CH_2)_sNR_iR_h$ (where s is 1, 2 or 3); wherein $R_h$ and $R_i$ are each independently selected from hydrogen, (1-4C)alkyl or (3-6C)cycloalkyl; or $R_h$ and $R_i$ are linked such that, together with the nitrogen atom to which they are attached, they form a 4-7 membered heterocyclic ring which is optionally substituted by one or more substituents selected from oxo, (1-4C)alkyl, halo, (1-4C)haloalkyl, (1-4C) haloalkoxy, (1-4C)alkoxy, (1-4C)alkylamino, di-[(1-4C)alkyl]amino, amino, cyano or hydroxy;

and wherein any alkyl, alkoxy, aryl, hereoaryl, heterocyclyl or cycloalkyl moiety in a substutent group present on $W_1$ is optionally further substituted by one or more halo, (1-4C)alkyl, (1-4C)haloalkyl, (1-4C) haloalkoxy, (1-4C)alkoxy, (1-4C)alkylamino, di-[(1-4C)alkyl]amino, amino, cyano or hydroxy groups;

and wherein any tertiary amine or nitrogen atom in a pyridyl ring present in a $R_3$ group is optionally in the form of a N-oxide.

(45) $R_3$ is a heterocyclyl selected from piperazinyl, piperidinyl, pyrrolidinyl, oxetanyl, morpholinyl, diazepanyl, azetidinyl, each of which may be optionally further substituted by one or more $R_e$ groups; or $R_3$ has one of the following structures:

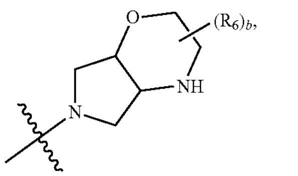
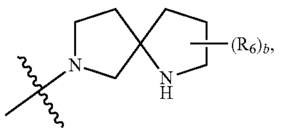
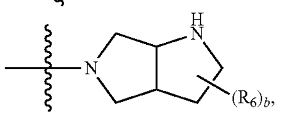
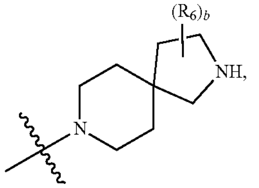
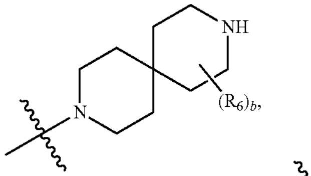
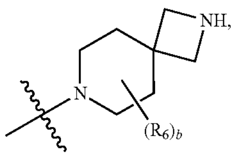
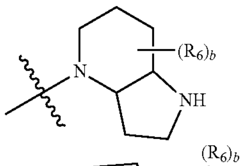
or
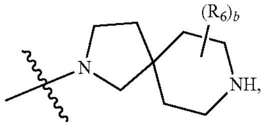

wherein b is an integer selected from 0, 1, 2, 3 or 4;

wherein each $R_5$ group is independently selected from (1-4C)alkyl, halo, (1-4C)haloalkyl, (1-4C)haloalkoxy, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, or $(CH_2)_qNR_cR_d$ (where q is 1, 2 or 3) or a group of the formula:

$-L_1-L_{Q1}-W_1$ wherein $R_c$, $R_d$ and $R_e$ are each independently selected from hydrogen, (1-4C)alkyl or (3-6C)cycloalkyl; or $R_e$ and $R_d$ are linked such that, together with the nitrogen atom to which they are attached, they form a 4-6 membered heterocyclic ring which is optionally substituted by one or more substituents selected from (1-2C)alkyl, halo, (1-2C)haloalkyl, (1-2C)haloalkoxy, (1-2C)alkoxy, (1-2C)alkylamino, di-[(1-2C)alkyl]amino, amino, cyano or hydroxy; and wherein:

$L_1$ is absent or (1-3C)alkylene optionally substituted by one or more substituents selected from (1-2C)alkyl or oxo; $L_{Q1}$ is absent or selected from or O, S, SO, $SO_2$, $N(R_f)$, C(O), C(O)O, OC(O), C(O)N(R), $N(R_f)C(O)$, $N(R_f)C(O)O$, $OC(O)N(R_f)$, $S(O)_2N(R_f)$, or $N(R_f)SO_2$, wherein $R_f$ and $R_g$ are each independently selected from hydrogen or (1-2C)alkyl; and $W_1$ is hydrogen, (1-4C)alkyl, aryl, heteroaryl or heterocyclyl; wherein $W_1$ is optionally substituted by one or more substituents selected from oxo, (1-4C)alkyl, halo, (1-4C)haloalkyl, (1-4C)haloalkoxy, (1-4C)alkoxy, cyano, $NR_hR_i$, $OR_h$, $C(O)R_h$, $C(O)OR_h$, $OC(O)R_h$, $C(O)N(R_i)R_h$, $N(R_j)C(O)R_h$, $S(O)_rRh$ (where r is 0, 1 or 2), $SO_2N(R_i)R_h$, $N(R_j)SO_2R_h$, or $(CH_2)_sNR_iR_h$ (where s is 1, 2 or 3); wherein $R_h$ and $R_i$ are each independently selected from hydrogen, (1-4C)alkyl or (3-6C)cycloalkyl; or $R_h$ and $R_i$ are linked such that, together with the nitrogen atom to which they are attached, they form a 4-7 membered heterocyclic ring which is optionally substituted by one or more substituents selected from oxo, (1-4C)alkyl, halo, (1-4C)haloalkyl, (1-4C)haloalkoxy, (1-4C)alkoxy, (1-4C)alkylamino, di-[(1-4C)alkyl]amino, amino, cyano or hydroxy;

and wherein any alkyl, alkoxy, aryl, hereoaryl, heterocyclyl or cycloalkyl moiety in a substutent group present on $W_1$ is optionally further substituted by one or more halo, (1-4C)alkyl, (1-4C)haloalkyl, (1-4C)haloalkoxy, (1-4C)alkoxy, (1-4C)alkylamino, di-[(1-4C)alkyl)amino, amino, cyano or hydroxy groups;

and wherein any tertiary amine or nitrogen atom in a pyridyl ring present in a $R_s$ group is optionally in the form of a N-oxide.

(46) $R_a$ is a heterocyclyl selected from piperazinyl, piperidinyl, pyrrolidinyl, oxetanyl, morpholinyl, diazepanyl, azetidinyl, or one of the following structures:

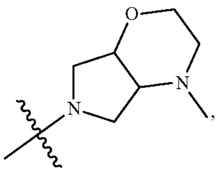
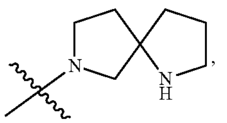
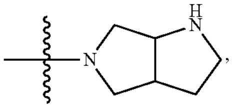
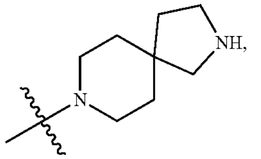
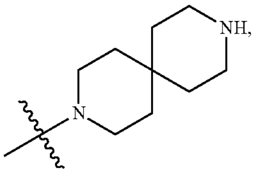

-continued

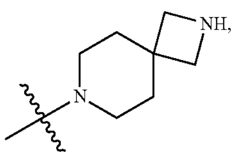

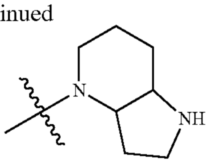

or

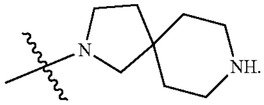

(47) $R_3$ is a nitrogen-linked heterocycle selected from a 4-7 membered heterocylic ring system, a 9-15 membered bicyclic ring system or a 9-15 membered spirocyclic ring system;

wherein $R_3$ optionally further substituted by one or more substituent groups independently selected from oxo, (1-4C)alkyl, halo, (1-4C)haloalkyl, (1-4C)haloalkoxy, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$(where p is 0, 1 or 2), $SO_2N(R_d)R_c$, $N(R_d)SO_2R_c$, or $(CH_2)_qNR_cR_d$ (where q is 1, 2 or 3);

wherein $R_c$, $R_d$ and $R_e$ are each independently selected from hydrogen, (1-4C)alkyl or (3-6C)cycloalkyl; or $R_c$ and $R_d$ are linked such that, together with the nitrogen atom to which they are attached, they form a 4-6 membered heterocyclic ring which is optionally substituted by one or more substituents selected from (1-2C)alkyl, halo, (1-2C)haloalkyl, (1-2C)haloalkoxy, (1-2C)alkoxy, (1-2C)alkylamino, di-[(1-2C)alkyl]amino, amino, cyano or hydroxy.

(48) $R_3$ is a heterocyclyl selected from piperazinyl, piperidinyl, pyrrolidinyl, oxetanyl, morpholinyl, diazepanyl, azetidinyl, each of which may be optionally further substituted by one or more $R_e$ groups; or $R_3$ has one of the following structures:

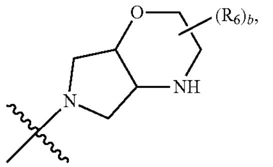

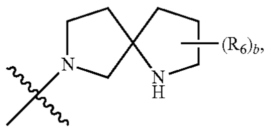

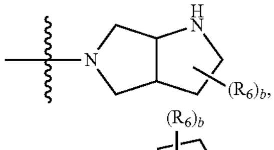

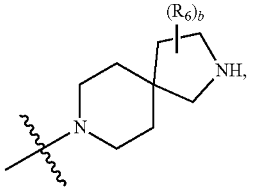

-continued

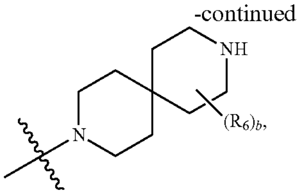

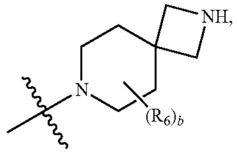

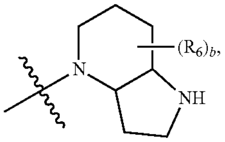

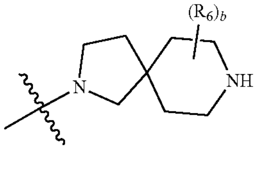

or

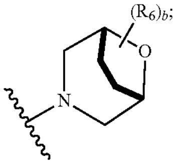

wherein b is an integer selected from 0, 1, 2, 3 or 4;

wherein each $R_6$ group is independently selected from (1-4C)alkyl, halo, (1-4C)haloalkyl, (1-4C)haloalkoxy, cyano, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$(where p is 0, 1 or 2), $SO_2N(R_d)R_c$, $N(R_d)SO_2R_c$, or $(CH_2)_qNR_eR_d$ (where q is 1, 2 or 3);

wherein $R_c$ and $R_d$ are each independently selected from hydrogen, (1-4C)alkyl or (3-6C)cycloalkyl; or $R_c$ and $R_d$ are linked such that, together with the nitrogen atom to which they are attached, they form a 4-6 membered heterocyclic ring which is optionally substituted by one or more substituents selected from (1-2C)alkyl, halo, (1-2C)haloalkyl, (1-2C)haloalkoxy, (1-2C)alkoxy, (1-2C)alkylamino, di-[(1-2C)alkyl]amino, amino, cyano or hydroxy;

and wherein any tertiary amine present in a $R_3$ group is optionally in the form of a N-oxide.

(49) $R_3$ is a heterocyclyl selected from piperazinyl, piperidinyl, pyrrolidinyl, oxetanyl, morpholinyl, diazepanyl, azetidinyl, or one of the following structures:

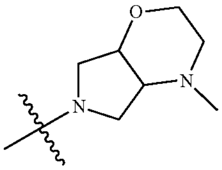

,

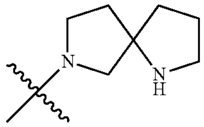

,

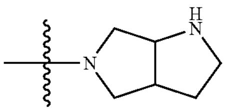

,

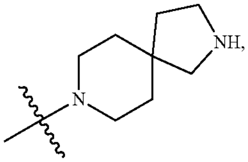

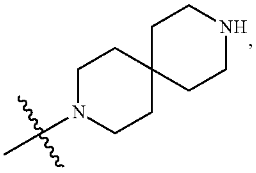

,

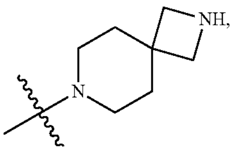

-continued

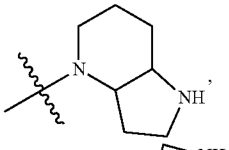 , 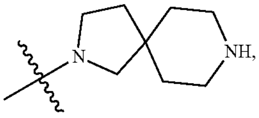

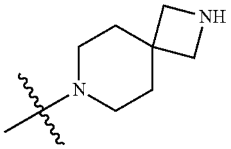 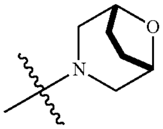 or

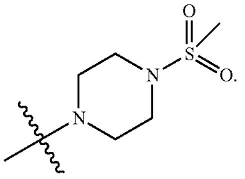

(50) A is selected from $CR_4$ and N, wherein $R_4$ is hydrogen, halo or (1-2C)alkyl optionally substituted by one or more substituents selected from halo, (1-2C)haloalkyl, (1-2C)haloalkoxy, amino, cyano, $(CH_2)_{qa}NR_{4A}R_{4B}$, $(CH_2)_{qa}OR_{4A}$, $(CH_2)_{qa}C(O)R_{c4A}$, $(CH_2)_{qa}C(O)OR_{4A}$, $(CH_2)_{qa}OC(O)R_{4A}$, $(CH_2)_{qa}C(O)N(R_{4B})R_{4A}$, $(CH_2)_{qa}N(R_{4B})C(O)R_{4A}$, $(CH_2)_{qa}S(O)_pR_{4A}$(where p is 0, 1 or 2), $(CH_2)_{qa}SO_2N(R_{4B})R_{4A}$, or $(CH_2)_{qa}N(R_{4B})SO_2R_{4A}$, wherein qa is 0, 1, 2 or 3 and wherein $R_{4A}$ and $R_{4B}$ are each independently selected from hydrogen, (1-4C)alkyl, (3-4C)cycloalkyl or (3-4C)cycloalkyl(1-2C)alkyl;

(51) A is selected from $CR_4$ and N, wherein $R_4$ is hydrogen, halo or (1-2C)alkyl optionally substituted by one or more substituents selected from halo;

(52) A is selected from $CR_4$ and N, wherein $R_4$ is hydrogen, methyl or halo;

(53) A is from $CR_4$ and $R_4$ is hydrogen, methyl, fluoro or chloro;

(54) A is CH;

(55) A is N.

Suitably, a heteroaryl or heterocyclyl group as defined herein is a monocyclic heteroaryl or mono, bicyclic or bridged heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5-, 6-, 7- or 8-membered heterocyclyl ring comprising one, two or three heteroatoms selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably, an aryl group is phenyl.

Suitably, $R_0$ is as defined in paragraphs (1) or (2) above. In an embodiment, $R_0$ is hydrogen. In another embodiment, $R_0$ is deuterium.

Suitably, $R_1$ is as defined in any one of paragraphs (3) to (17) above. More suitably, $R_1$ is as defined in any one of paragraphs (13) to (17) above. Most suitably, $R_1$ is as defined in paragraph (13) or (17) above.

Suitably, $R_2$ is as defined in any one of paragraphs (18) to (31). More suitably, $R_2$ is cyano or is as defined in any one of paragraphs (25) to (31). Most suitably, $R_2$ is as defined in paragraph (25) or (31).

Suitably, $R_3$ is as defined in any one of paragraphs (32) to (49). More suitably, $R_3$ is as defined in any one of paragraphs (35) to (40) (e.g. any one of paragraphs (35) to (39)).

Most suitably, $R_2$ is as defined in paragraph (39) or (40).

Suitably, A is as defined in any one of paragraphs (50) to (55). Most suitably, A is as defined in paragraph (51), (54) or (55).

In a particular group of compounds of Formula I above, $R_1$ is as defined in any one of paragraphs (3), (4), (5), (10), (13) or (17) and $R_0$, $R_2$, $R_3$ and A each have any one of the definitions herein.

In a particular group of compounds of Formula I above, $R_2$ is as defined in any one of paragraphs (18), (19), (20), (25), (29), (30) or (31) and $R_0$, $R_1$, $R_3$ and A each have any one of the definitions herein.

In a particular group of compounds of Formula I above, $R_3$ is as defined in any one of paragraphs (32), (33), (34), (35), (35a), (38), (39) or (40) and $R_0$, $R_1$, $R_2$ and A each have any one of the definitions herein.

In a particular group of compounds of Formula I above, A is as defined in any one of paragraphs (50), (51), (54) or (55) and $R_0$, $R_1$, $R_2$ and $R_3$ each have any one of the definitions herein.

In an embodiment of the compounds of formula I above:

$R_0$ is as defined in either paragraph (1) or (2);

$R_1$ is as defined in paragraph (3) to (17) above;

$R_2$ is as defined in any one of paragraphs (18) to (31) above;

$R_3$ is as defined in any one of paragraphs (32) to (49) above; and

A is as defined in any one of paragraphs (50) to (55) above.

In a particular group of compounds of Formula I above:

$R_0$ is as defined in either paragraph (1) or (2);

$R_1$ is as defined in paragraph (13) to (17) above;

$R_2$ is as defined in any one of paragraphs (25) to (31) above;

$R_3$ is as defined in any one of paragraphs (35) to (40) above; and

A is as defined in any one of paragraphs (51), (54) or (55) above.

In a particular group of compounds of Formula I above:

$R_0$ is as defined paragraph (1) or (2);

$R_1$ is as defined in paragraph (5) above;

$R_2$ is as defined in paragraph (19) above;

$R_3$ is as defined in paragraph (33) above; and

A is as defined in paragraph (51) above.

In a particular group of compounds of Formula I above:

$R_0$ is as defined paragraph (1);

$R_1$ is as defined in paragraph (10) above;

$R_2$ is as defined in paragraph (20) above;

$R_3$ is as defined in paragraph (34) above; and

A is as defined in paragraph (51) above.

In a particular group of compounds of Formula I above:

$R_0$ is as defined paragraph (1);

$R_1$ is as defined in paragraph (13) above;

$R_2$ is as defined in paragraph (25) above;

$R_3$ is as defined in paragraph (35) or (35a) above; and

A is as defined in paragraph (53) above.

In a particular group of compounds of Formula I above:

$R_0$ is as defined paragraph (1);

$R_1$ is as defined in paragraph (17) above;

$R_2$ is as defined in paragraph (29) above;

$R_3$ is as defined in paragraph (38) above; and

A is as defined in paragraph (54) above.

In a particular group of compounds of the invention, the compounds have the structural formula Ib [a sub-definition of formula (I)] shown below, or a pharmaceutically acceptable salt, hydrate and/or solvate thereof:

Ib

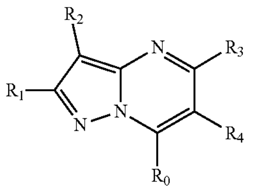

wherein $R_0$, $R_1$, $R_2$ and $R_3$ are each as defined hereinbefore and $R_4$ is hydrogen, methyl, fluoro or chloro.

In an embodiment of the compounds of formula Ib:

$R_0$ is as defined in either paragraph (1) or (2);

$R_1$ is as defined in any one of paragraphs (3) to (17) above;

$R_2$ is as defined in any one of paragraphs (18) to (31) above;

$R_3$ is as defined in any one of paragraphs (32) to (40) above; and $R_4$ is hydrogen, methyl, fluoro or chloro.

In an embodiment of the compounds of formula Ib:

$R_0$ is as defined in either paragraph (1) or (2);

$R_1$ is as defined in any one of paragraphs (3) to (17) above;

$R_2$ is as defined in any one of paragraphs (18) to (31) above;

$R_3$ is as defined in any one of paragraphs (32) to (49) above; and $R_4$ is hydrogen, methyl, fluoro or chloro.

In another embodiment of the compounds of formula Ib:

$R_0$ is as defined in paragraph (1) above;

$R_1$ is as defined in paragraph (13) above;

$R_2$ is as defined in paragraph (25) above;

$R_3$ is as defined in paragraph (35) above; and $R_4$ is hydrogen.

In another embodiment of the compounds of formula Ib:

$R_0$ is as defined in paragraph (1) above;

$R_1$ is as defined in paragraph (17) above;

$R_2$ is as defined in paragraph (31) above;

$R_3$ is as defined in paragraph (38), (39) or (40) above; and $R_4$ is hydrogen.

In another embodiment of the compounds of formula Ib:

$R_0$ is as defined in paragraph (1) above;

$R_1$ is as defined in paragraph (17) above;

$R_2$ is as defined in paragraph (31) above;

$R_3$ is as defined in paragraph (40) above; and $R_4$ is hydrogen.

In a particular group of compounds of the invention, the compounds have the structural formula Ic [a sub-definition of formula (I)] shown below, or a pharmaceutically acceptable salt, hydrate and/or solvate thereof:

Ic

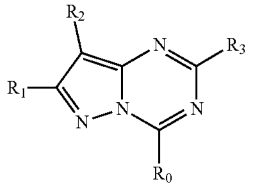

wherein $R_0$, $R_1$, $R_2$ and $R_3$ are each as defined hereinbefore.

In an embodiment of the compounds of formula Ic:

$R_0$ is as defined in either paragraph (1) or (2);

$R_1$ is as defined in any one of paragraphs (3) to (17) above;

$R_2$ is as defined in any one of paragraphs (18) to (31) above; and $R_3$ is as defined in any one of paragraphs (32) to (40) above.

In another embodiment of the compounds of formula Ic:

$R_0$ is as defined in either paragraph (1) or (2);

$R_1$ is as defined in any one of paragraphs (3) to (17) above;

$R_1$ is as defined in any one of paragraphs (18) to (31) above; and $R_3$ is as defined in any one of paragraphs (32) to (49) above.

In another embodiment of the compounds of formula Ic:

$R_0$ is as defined in paragraph (1) above;

$R_1$ is as defined in paragraph (13) above;

$R_2$ is as defined in paragraph (25) above; and $R_3$ is as defined in paragraph (35) above.

In another embodiment of the compounds of formula Ic:

$R_0$ is as defined in paragraph (1) above;

$R_1$ is as defined in paragraph (17) above;

$R_2$ is as defined in paragraph (31) above; and $R_3$ is as defined in paragraph (38), (39) or (40) above.

In another embodiment of the compounds of formula Ic:

$R_0$ is as defined in paragraph (1) above;

$R_1$ is as defined in paragraph (17) above;

$R_2$ is as defined in paragraph (30) above; and $R_3$ is as defined in paragraph (40) above.

In a particular group of compounds of the invention, the compounds have the structural formula Id [a sub-definition of formula (I)] shown below, or a pharmaceutically acceptable salt, hydrate and/or solvate thereof:

Id

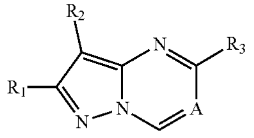

wherein A, $R_1$, $R_2$ and $R_3$ are each as defined hereinbefore.

In an embodiment of the compounds of formula Id:

$R_1$ is as defined in any one of paragraphs (3) to (17) above;

$R_2$ is as defined in any one of paragraphs (18) to (31) above;

$R_3$ is as defined in any one of paragraphs (32) to (40) above; and

A is as defined in any one of paragraphs (50) to (55) above.

In an embodiment of the compounds of formula Id:

$R_1$ is as defined in any one of paragraphs (3) to (17) above;

$R_2$ is as defined in any one of paragraphs (18) to (31) above;

$R_3$ is as defined in any one of paragraphs (32) to (49) above; and

A is as defined in any one of paragraphs (50) to (55) above.

In another embodiment of the compounds of formula Id:

$R_1$ is as defined in paragraph (13) above;

$R_2$ is as defined in paragraph (25) above;

$R_3$ is as defined in paragraph (35) above; and

A is as defined in paragraph (51) above.

In another embodiment of the compounds of formula Id:

$R_1$ is as defined in paragraph (17) above;

$R_2$ is as defined in paragraph (31) above; and $R_3$ is as defined in paragraph (38), (39) or (40) above; and A is as defined in paragraph (54) or (55) above.

In another embodiment of the compounds of formula Id:

$R_1$ is as defined in paragraph (17) above;

$R_2$ is as defined in paragraph (31) above; and $R_3$ is as defined in paragraph (40) above; and A is as defined in paragraph (54) or (55) above.

In a particular group of compounds of the invention, the compounds have the structural formula Ie [a sub-definition of formula (I)] shown below, or a pharmaceutically acceptable salt, hydrate and/or solvate thereof:

Ie

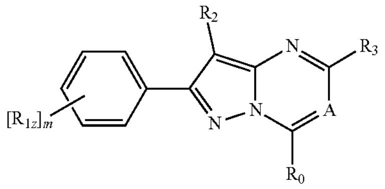

wherein A, $R_0$, $R_2$, $R_3$ and $R_{1z}$ are each as defined hereinbefore and m is 0, 1 or 2.

In an embodiment of the compounds of formula Ie:

$R_0$ is as defined in either paragraph (1) or (2) above;

$R_{1z}$ is as defined in any one of paragraphs (3) to (10) above;

m is 0, 1 or 2;

$R_2$ is as defined in any one of paragraphs (18) to (31) above;

$R_3$ is as defined in any one of paragraphs (32) to (40) above; and

A is as defined in any one of paragraphs (50) to (55) above.

In an embodiment of the compounds of formula Ie:

$R_0$ is as defined in either paragraph (1) or (2) above;

$R_{1z}$ is as defined in any one of paragraphs (3) to (10) above;

m is 0, 1 or 2;

$R_2$ is as defined in any one of paragraphs (18) to (31) above;

$R_3$ is as defined in any one of paragraphs (31) to (49) above; and

A is as defined in any one of paragraphs (50) to (55) above.

In another embodiment of the compounds of formula Ie:

$R_0$ is as defined in paragraph (1) above;

$R_{1z}$ is halo or cyano;

m is 0 or 1;

$R_2$ is as defined in paragraph (25) above;

$R_3$ is as defined in paragraph (35) above; and

A is as defined in paragraph (51) above.

In another embodiment of the compounds of formula Ie:

$R_0$ is as defined in paragraph (1) above;

$R_1Z$ is cyano;

m is 1;

$R_1$ is as defined in paragraph (17) above;

$R_2$ is as defined in paragraph (31) above;

$R_3$ is as defined in paragraph (38), (39) or (40) above; and

A is as defined in paragraph (54) or (55) above.

In another embodiment of the compounds of formula Ie:

$R_0$ is as defined in paragraph (1) above;

$R_{1z}$ is cyano;

m is 1;

$R_2$ is as defined in paragraph (31) above;

$R_3$ is as defined in paragraph (40) above; and

A is as defined in paragraph (54) or (55) above.

In a particular group of compounds of the invention, the compounds have the structural formula If [a sub-definition of formula (I)] shown below, or a pharmaceutically acceptable salt, hydrate and/or solvate thereof:

If

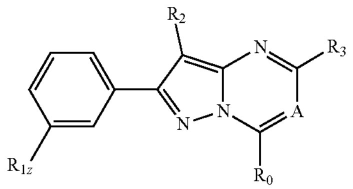

wherein A, $R_0$, $R_2$, $R_3$ and $R_{1z}$ are each as defined hereinbefore.

In an embodiment of the compounds of formula If:

$R_0$ is as defined in either paragraph (1) or (2) above;

$R_{1z}$ is as defined in any one of paragraphs (3) to (10) above;

$R_2$ is as defined in any one of paragraphs (18) to (31) above;

$R_3$ is as defined in any one of paragraphs (32) to (40) above; and

A is as defined in any one of paragraphs (50) to (55) above.

In an embodiment of the compounds of formula If:

$R_0$ is as defined in either paragraph (1) or (2) above;

$R_{1z}$ is as defined in any one of paragraphs (3) to (10) above;

$R_2$ is as defined in any one of paragraphs (18) to (31) above;

$R_3$ is as defined in any one of paragraphs (32) to (49) above; and

A is as defined in any one of paragraphs (50) to (55) above.

In another embodiment of the compounds of formula If:

$R_0$ is as defined in paragraph (1) above;

$R_{1z}$ is halo or cyano;

$R_2$ is as defined in paragraph (25) above;

$R_3$ is as defined in paragraph (35) above; and

A is as defined in paragraph (51).

In another embodiment of the compounds of formula If:

$R_0$ is as defined in paragraph (1) above;

$R_{1z}$ is cyano;

$R_2$ is as defined in paragraph (31) above;

$R_3$ is as defined in paragraph (38), (39) or (40) above; and

A is as defined in paragraph (54) or (55) above.

In another embodiment of the compounds of formula If:

$R_0$ is as defined in paragraph (1) above;

$R_{1z}$ is cyano;

$R_2$ is as defined in paragraph (31) above;

$R_3$ is as defined in paragraph (40) above; and

A is as defined in paragraph (54) or (55) above.

In a particular group of compounds of the invention, the compounds have the structural formula Ig [a sub-definition of formula (I)] shown below, or a pharmaceutically acceptable salt, hydrate and/or solvate thereof:

Ig

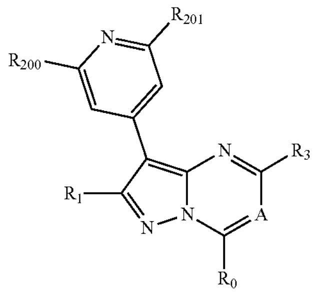

wherein A, $R_0$, $R_1$ and $R_3$ are each as defined hereinbefore; and $R_{200}$ and $R_{201}$ are each independently selected from hydrogen, methyl, hyroxymethyl, halo, trifluoromethyl, difluoromethyl, methoxy or acetyl. Suitably, $R_{200}$ and $R_{201}$ are each independently selected from hydrogen, methyl or halo.

In an embodiment of the compounds of formula Ig:

$R_0$ is as defined in either paragraph (1) or (2) above;

$R_1$ is as defined in any one of paragraphs (3) to (17) above;

$R_3$ is as defined in any one of paragraphs (32) to (49) above;

A is as defined in any one of paragraphs (50) to (55); and $R_{200}$ and $R_{201}$ are each independently selected from hydrogen, methyl, hydroxymethyl or halo.

In an embodiment of the compounds of formula Ig:

$R_0$ is as defined in either paragraph (1) or (2) above;

$R_1$ is as defined in any one of paragraphs (3) to (17) above;

$R_3$ is as defined in any one of paragraphs (32) to (40) above;

A is as defined in any one of paragraphs (50) to (55); and $R_{200}$ and $R_{201}$ are each independently selected from hydrogen, methyl, hydroxymethyl or halo.

In another embodiment of the compounds of formula Ig:

$R_0$ is as defined in paragraph (1) above;

$R_1$ is as defined in paragraph (13) above;

$R_2$ is as defined in paragraph (25) above;

$R_3$ is as defined in paragraph (35) above;

A is as defined in paragraph (51); and $R_{200}$ and $R_{201}$ are each independently selected from methyl or chloro.

In another embodiment of the compounds of formula Ig:

$R_0$ is as defined in paragraph (1) above;

$R_1$ is as defined in paragraph (17) above;

$R_2$ is as defined in paragraph (31) above;

$R_3$ is as defined in paragraph (38), (39) or (40) above;

A is as defined in paragraph (54) or (55); and $R_{200}$ is methyl and $R_{201}$ is chloro or methyl.

In another embodiment of the compounds of formula Ig:

$R_0$ is as defined in paragraph (1) above;

$R_1$ is as defined in paragraph (17) above;

$R_2$ is as defined in paragraph (31) above;

$R_3$ is as defined in paragraph (40) above;

A is as defined in paragraph (54) or (55) above; and $R_{200}$ is methyl and $R_{201}$ is chloro or methyl.

In a particular group of compounds of the invention, the compounds have the structural formula Ig2 [a sub-definition of formula (I)] shown below, or a pharmaceutically acceptable salt, hydrate and/or solvate thereof:

Ig2

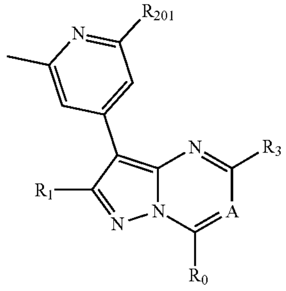

wherein A, $R_0$, $R_1$ and $R_3$ are each as defined hereinbefore and $R_{201}$ is selected from hydrogen, methyl, halo, trifluoromethyl, difluoromethyl, methoxy or acetyl.

In an embodiment of the compounds of formula Ig2:

In an embodiment of the compounds of formula Ig2:

$R_0$ is as defined in either paragraph (1) or (2) above;

$R_1$ is as defined in any one of paragraphs (3) to (17) above;

$R_3$ is as defined in any one of paragraphs (32) to (40) above;

A is as defined in any one of paragraphs (50) to (55); and $R_{201}$ is selected from hydrogen, methyl or halo.

In an embodiment of the compounds of formula Ig2:

$R_0$ is as defined in either paragraph (1) or (2) above;

$R_1$ is as defined in any one of paragraphs (3) to (17) above;

$R_3$ is as defined in any one of paragraphs (32) to (49) above;

A is as defined in any one of paragraphs (50) to (55) above; and $R_{201}$ is selected from methyl, methoxy or halo.

In another embodiment of the compounds of formula Ig2:

$R_0$ is as defined in paragraph (1) above;

$R_1$ is as defined in paragraph (13) above;

$R_3$ is as defined in paragraph (35) above;

A is as defined in paragraph (51) above; and $R_{201}$ is selected from methyl or halo.

In another embodiment of the compounds of formula Ig2:

$R_0$ is as defined in paragraph (1) above;

$R_1$ is as defined in paragraph (17) above;

$R_2$ is as defined in paragraph (31) above;

$R_3$ is as defined in paragraph (38), (39) or (40) above;

A is as defined in paragraph (54) or (55) above; and $R_{201}$ is selected from methyl or chloro.

In another embodiment of the compounds of formula Ig2:

$R_0$ is as defined in paragraph (1) above;

$R_1$ is as defined in paragraph (17) above;

$R_2$ is as defined in paragraph (31) above;

$R_3$ is as defined in paragraph (40) above;

A is as defined in paragraph (54) or (55) above; and $R_{201}$ is selected from methyl or chloro.

In a particular group of compounds of the invention, the compounds have the structural formula Ih [a sub-definition of formula (I)] shown below, or a pharmaceutically acceptable salt, hydrate and/or solvate thereof:

Ih

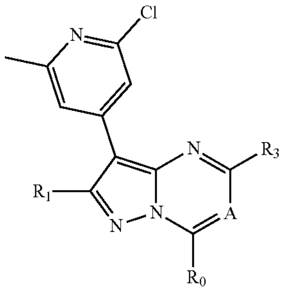

wherein A, $R_0$, $R_1$ and $R_3$ are each as defined hereinbefore.

In an embodiment of the compounds of formula Ih:

$R_0$ is as defined in either paragraph (1) or (2) above;

$R_1$ is as defined in any one of paragraphs (3) to (17) above;

$R_3$ is as defined in any one of paragraphs (32) to (40) above; and

A is as defined in any one of paragraphs (50) to (55).

In an embodiment of the compounds of formula Ih:

$R_0$ is as defined in either paragraph (1) or (2) above;

$R_1$ is as defined in any one of paragraphs (3) to (17) above;

$R_3$ is as defined in any one of paragraphs (32) to (49) above; and

A is as defined in any one of paragraphs (50) to (55).

In another embodiment of the compounds of formula Ih:

$R_0$ is as defined in paragraph (1) above;

$R_1$ is as defined in paragraph (13) above;

$R_2$ is as defined in paragraph (25) above;

$R_3$ is as defined in paragraph (35) above; and

A is as defined in paragraph (51).

In another embodiment of the compounds of formula Ih:

$R_0$ is as defined in paragraph (1) above;

$R_1$ is as defined in paragraph (17) above;

$R_2$ is as defined in paragraph (31) above;

$R_3$ is as defined in paragraph (38), (39) or (40) above; and

A is as defined in paragraph (54) or (55).

In another embodiment of the compounds of formula Ih:

$R_0$ is as defined in paragraph (1) above;

$R_1$ is as defined in paragraph (17) above;

$R_2$ is as defined in paragraph (30) above;

$R_3$ is as defined in paragraph (39) or (40) above; and

A is as defined in paragraph (52) or (53).

In a particular group of compounds of the invention, the compounds have the structural formula Ih [a sub-definition of formula (I)] shown below, or a pharmaceutically acceptable salt, hydrate and/or solvate thereof:

Ih2

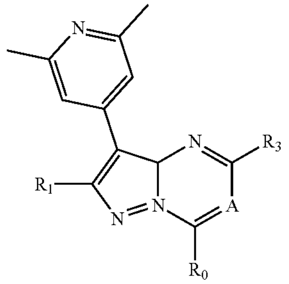

wherein A, $R_c$, $R_1$ and $R_3$ are each as defined hereinbefore.

In an embodiment of the compounds of formula Ih2:

$R_0$ is as defined in either paragraph (1) or (2) above;

$R_1$ is as defined in any one of paragraphs (3) to (17) above;

$R_3$ is as defined in any one of paragraphs (32) to (40) above; and

A is as defined in any one of paragraphs (50) to (55) above.

In an embodiment of the compounds of formula Ih2:

$R_0$ is as defined in either paragraph (1) or (2) above;

$R_1$ is as defined in any one of paragraphs (3) to (17) above;

$R_3$ is as defined in any one of paragraphs (32) to (49) above; and

A is as defined in any one of paragraphs (50) to (55).

In another embodiment of the compounds of formula Ih2:

$R_0$ is as defined in paragraph (1) above;

$R_1$ is as defined in paragraph (13) above;

$R_3$ is as defined in paragraph (35) above; and

A is as defined in paragraph (51) above.

In another embodiment of the compounds of formula Ih2:

$R_0$ is as defined in paragraph (1) above;

$R_1$ is as defined in any one of paragraphs (14) to (17) above;

$R_3$ is as defined in paragraph (38), (39) or (40) above; and

A is as defined in paragraph (52) or (53) above.

In another embodiment of the compounds of formula Ih2:

$R_0$ is as defined in paragraph (1) above;

$R_1$ is as defined in paragraph (17) above;

$R_3$ is as defined in paragraph (38), (39) or (40) above; and

A is as defined in paragraph (52) or (53) above.

In another embodiment of the compounds of formula Ih2:

$R_0$ is as defined in paragraph (1) above;

$R_1$ is as defined in paragraph (17) above;

$R_2$ is as defined in paragraph (31) above;

$R_3$ is as defined in paragraph (40) above; and

A is as defined in paragraph (52) or (53).

In a particular group of compounds of the invention, the compounds have the structural formula II [a sub-definition of formula (I)] shown below, or a pharmaceutically acceptable salt, hydrate and/or solvate thereof:

Ii

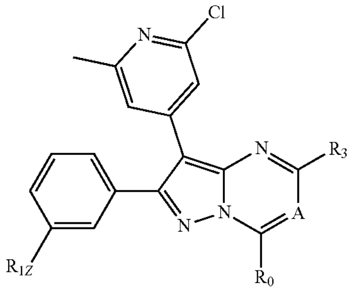

wherein A, $R_0$, $R_3$ and $R_{1z}$ are each as defined hereinbefore.

In an embodiment of the compounds of formula Ii:

$R_0$ is as defined in either paragraph (1) or (2) above;

$R_{1z}$ is as defined in any one of paragraphs (3) to (10) above;

$R_3$ is as defined in any one of paragraphs (32) to (49) above; and

A is as defined in any one of paragraphs (50) to (55).

In an embodiment of the compounds of formula II:

$R_0$ is as defined in either paragraph (1) or (2) above;

$R_{1z}$ is as defined in any one of paragraphs (3) to (10) above;

$R_3$ is as defined in any one of paragraphs (32) to (40) above; and

A is as defined in any one of paragraphs (50) to (55).

In another embodiment of the compounds of formula Ii:

$R_0$ is as defined in paragraph (1) above;

$R_{1z}$ is halo or cyano;

$R_3$ is as defined in paragraph (35) above; and

A is as defined in paragraph (51) above.

In another embodiment of the compounds of formula Ii:

$R_0$ is as defined in paragraph (1) above;

$R_1Z$ is cyano;

$R_3$ is as defined in paragraph (38), (39) or (40) above; and

A is as defined in paragraph (54) or (55) above.

In another embodiment of the compounds of formula Ii:

$R_0$ is as defined in paragraph (1) above;

$R_{1z}$ is cyano;

$R_3$ is as defined in paragraph (40) above;

A is as defined in paragraph (54) or (55) above

In a particular group of compounds of the invention, the compounds have the structural formula Ii2 [a sub-definition of formula (I)] shown below, or a pharmaceutically acceptable salt, hydrate and/or solvate thereof:

Ii2

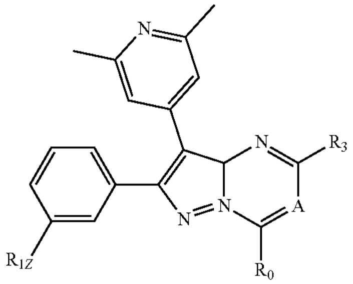

wherein A, $R_0$, $R_3$ and $R_{1z}$ are each as defined hereinbefore.

In an embodiment of the compounds of formula Ii2:

$R_0$ is as defined in either paragraph (1) or (2) above;

$R_{1z}$ is as defined in any one of paragraphs (3) to (10) above;

$R_3$ is as defined in any one of paragraphs (32) to (40) above; and

A is as defined in any one of paragraphs (50) to (55).

In an embodiment of the compounds of formula Ii2:

$R_0$ is as defined in either paragraph (1) or (2) above;

$R_{1z}$ is as defined in any one of paragraphs (3) to (10) above;

$R_3$ is as defined in any one of paragraphs (32) to (49) above; and

A is as defined in any one of paragraphs (50) to (55).

In another embodiment of the compounds of formula Ii2:

$R_0$ is as defined in paragraph (1) above;

$R_{1z}$ is halo or cyano;

$R_3$ is as defined in paragraph (35) above; and

A is as defined in paragraph (51) above.

In another embodiment of the compounds of formula Ii2:

$R_0$ is as defined in paragraph (1) above;

$R_{1z}$ is cyano;

$R_3$ is as defined in paragraph (38), (39) or (40) above; and

A is as defined in paragraph (54) or (55) above.

In another embodiment of the compounds of formula 112:

$R_0$ is as defined in paragraph (1) above;

$R_{1z}$ is cyano;

$R_3$ is as defined in paragraph (40) above; and

A is as defined in paragraph (54) or (55) above.

In a particular group of compounds of the invention, the compounds have the structural formula Ii3 [a sub-definition of formula (I)] shown below, or a pharmaceutically acceptable salt, hydrate and/or solvate thereof:

Ii3

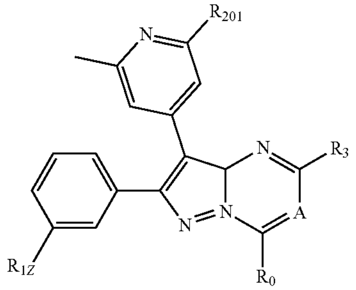

wherein A, $R_0$, $R_3$ and $R_{1z}$ are each as defined hereinbefore and $R_{201}$ is selected from hydrogen, methyl, hydroxymethyl, halo, trifluoromethyl, difluoromethyl, methoxy or acetyl.

In an embodiment of the compounds of formula Ii2:

$R_0$ is as defined in either paragraph (1) or (2) above;

$R_{1z}$ is as defined in any one of paragraphs (3) to (10) above;

$R_3$ is as defined in any one of paragraphs (32) to (40) above;

A is as defined in any one of paragraphs (50) to (55) above; and $R_{201}$ is selected from methyl, hydroxymethyl, halo, trifluoromethyl, difluoromethyl, methoxy or acetyl.

In an embodiment of the compounds of formula Ii3:

$R_0$ is as defined in either paragraph (1) or (2) above;

$R_{1z}$ is as defined in any one of paragraphs (3) to (10) above;

$R_3$ is as defined in any one of paragraphs (32) to (49) above;

A is as defined in any one of paragraphs (50) to (55) above; and $R_{201}$ is selected from methyl, hydroxymethyl, halo, trifluoromethyl, difluoromethyl, methoxy or acetyl.

In another embodiment of the compounds of formula Ii3:

$R_0$ is as defined in paragraph (1) above;

$R_{1z}$ is halo or cyano;

$R_3$ is as defined in paragraph (35) above;

A is as defined in paragraph (50) above; and $R_{201}$ is selected from methyl, hydroxymethyl, halo or methoxy.

In another embodiment of the compounds of formula Ii3:

$R_0$ is as defined in paragraph (1) above;

$R_{1z}$ is cyano;

$R_3$ is as defined in paragraph (38), (39) or (40) above;

A is as defined in paragraph (54) or (55) above; and $R_{201}$ is selected from methyl or chloro.

In another embodiment of the compounds of formula Ii3:

$R_0$ is as defined in paragraph (1) above;

$R_{1z}$ is cyano;

$R_3$ is as defined in paragraph (40) above;

A is as defined in paragraph (54) or (55) above; and $R_{201}$ is selected from methyl or chloro.

Particular compounds of the present invention include any of the compounds described in the example section of the present application, or a pharmaceutically acceptable salt or solvate thereof, and, in particular, any of the following:

3-[5-Amino-3-(4-pyridyl)pyrazolo[1,5-a]pyrimidin-2-yl]benzonitrile;

3-15-Amino-3-(1H-pyrazol-4-yl)pyrazolo[1,5-a]pyrimidin-2-yl]benzonitrile;

3-(5-Amino-3-pyridazin-4-yl-pyrazolo[1,5-a]pyrimidin-2-yl)benzonitrile;

3-[5-Amino-3-(2-ethylpyrazol-3-yl)pyrazolo[1,5-a]pyrimidin-2-yl]benzonitrile;

3-[5-Amino-3-(2-chloro-6-methyl-4-pyridyl)pyrazolo[1,5-a]pyrimidin-2-yl]benzonitrile;

3-[5-Amino-3-(2,6-dimethyl-4-pyridyl)pyrazolo[1,5-a]pyrimidin-2-yl]benzonitrile;

3-[3-(2-Chloro-6-methyl-4-pyridyl)-5-[(2-hydroxy-2-methyl-propyl)amino]pyrazolo[1,5-a]pyrimidin-2-yl]benzonitrile;

3-[3-(2-Chloro-6-methyl-4-pyridyl)-5-[(3-hydroxy-1-bicyclo[1.1.1]pentanyl)amino]pyrazolo[1,5-a]pyrimidin-2-yl]benzonitrile;

3-[3-(2-Chloro-6-methyl-4-pyridyl)-5-(8-methyl-3,8-diazabicyclo[3.2.1]octan-3-yl)pyrazolo[1,5-a]pyrimidin-2-yl]benzonitrile;

(3S)-4-[3-(2-Chloro-6-methyl-4-pyridyl)-2-(3-cyanophenyl)pyrazolo[1,5-a]pyrimidin-5-yl]morpholine-3-carboxylic acid;

3-[3-(2-Chloro-6-methyl-4-pyridyl)-5-[(1-ethyl-4-piperidyl)amino]pyrazolo[1,5-a]pyrimidin-2-yl]benzonitrile;

3-[3-(2-Chloro-6-methyl-4-pyridyl)-5-[[(3S,4S)-4-methoxy-1-methyl-pyrrolidin-3-yl]amino]pyrazolo[1,5-a]pyrimidin-2-yl]benzonitrile;

3-[3-(2-Chloro-6-methyl-4-pyridyl)-5-[[(3R)-tetrahydrofuran-3-yl]amino]pyrazolo[1,5-a]pyrimidin-2-yl]benzonitrile;

3-[3-(2-Chloro-6-methyl-4-pyridyl)-5-[3-(hydroxymethyl)-4-methyl-piperazin-1-yl]pyrazolo[1,5-a]pyrimidin-2-yl]benzonitrile;

3-[3-(2-Chloro-6-methyl-4-pyridyl)-5-[(3-hydroxyoxetan-3-yl)methylamino]pyrazolo [1,5-a]pyrimidin-2-yl]benzonitrile;

3-[3-(2-Chloro-6-methyl-4-pyridyl)-5-[(3-hydroxy-3-methyl-butyl)amino]pyrazolo [1,5-a]pyrimidin-2-yl]benzonitrile;

3-[3-(2-Chloro-6-methyl-4-pyridyl)-5-[(3-hydroxycyclobutyl)amino]pyrazolo[1,5-a]pyrimidin-2-yl]benzonitrile;

3-[3-(2-Chloro-6-methyl-4-pyridyl)-5-[(1-methylsulfonyl-4-piperidyl)amino]pyrazolo[1,5-a]pyrimidin-2-yl]benzonitrile;

3-[3-(2-Chloro-6-methyl-4-pyridyl)-5-(8-oxa-3-azabicyclo[3.2.1]octan-3-yl)pyrazolo[1,5-a]pyrimidin-2-yl]benzonitrile;

3-[[3-(2-Chloro-6-methyl-4-pyridyl)-2-(3-cyanophenyl)pyrazolo[1,5-a]pyrimidin-5-yl]amino]-2,2-dimethyl-propanoic acid;

3-[3-(2-Chloro-6-methyl-4-pyridyl)-5-[(5-oxopyrrolidin-3-yl)methylamino]pyrazolo[1,5-a]pyrimidin-2-yl]benzonitrile;

3-[3-(2-Chloro-6-methyl-4-pyridyl)-5-[[(1S)-2-hydroxy-1,2-dimethyl-propyl]amino]pyrazolo[1,5-a]pyrimidin-2-yl]benzonitrile;

3-[3-(2-Chloro-6-methyl-4-pyridyl)-5-[[rac-(3R,4R)-4-hydroxytetrahydrofuran-3-yl]amino]pyrazolo[1,5-a]pyrimidin-2-yl]benzonitrile;

3-[3-(2-Chloro-6-methyl-4-pyridyl)-5-(quinuclidin-3-ylamino)pyrazolo[1,5-a]pyrimidin-2-yl]benzonitrile;

3-[3-(2-Chloro-6-methyl-4-pyridyl)-5-[(3-hydroxycyclobutyl)amino]pyrazolo[1,5-a]pyrimidin-2-yl]benzonitrile;

3-[3-(2-Chloro-6-methyl-4-pyridyl)-5-(2-morpholinoethylamino)pyrazolo[1.5-a]pyrimidin-2-yl]benzonitrile;

3-[3-(2-Chloro-6-methyl-4-pyridyl)-5-[[(1R)-2-hydroxy-1,2-dimethyl-propyl]amino]pyrazolo[1,5-a]pyrimidin-2-yl]benzonitrile;

3-[3-(2-Chloro-6-methyl-4-pyridyl)-5-[2-[2-(dimethylamino)ethyl]morpholin-4-yl]pyrazolo[1,5-a]pyrimidin-2-yl]benzonitrile;

3-[3-(2-Chloro-6-methyl-4-pyridyl)-5-[[(1R,2S)-2-hydroxycyclobutyl]amino]pyrazolo[1,5-a]pyrimidin-2-yl]benzonitrile;

3-[3-(2-Chloro-6-methyl-4-pyridyl)-5-(4H-1,2,4-triazol-3-ylmethylamino)pyrazolo[1,5-a]pyrimidin-2-yl]benzonitrile;

(2R)-4-[3-(2-Chloro-6-methyl-4-pyridyl)-2-(3-cyanophenyl)pyrazolo[1,5-a]pyrimidin-5-yl]morpholine-2-carboxylic acid;

3-[3-(2-Chloro-6-methyl-4-pyridyl)-5-[[(3S)-tetrahydrofuran-3-yl]amino]pyrazolo[1,5-a]pyrimidin-2-yl]benzonitrile;

3-[3-(2-Chloro-6-methyl-4-pyridyl)-5-(1-imino-1-oxo-1,4-thiazinan-4-yl)pyrazolo [1,5-a]pyrimidin-2-yl]benzonitrile;

3-[3-(2-Chloro-6-methyl-4-pyridyl)-5-[(1,1-dioxothian-4-yl)amino]pyrazolo[1,5-a]pyrimidin-2-yl]benzonitrile;

2-[[3-(2-Chloro-6-methyl-4-pyridyl)-2-(3-cyanophenyl)pyrazolo[1,5-a]pyrimidin-5-yl]amino]acetamide;

3-[3-(2-Chloro-6-methyl-4-pyridyl)-5-piperazin-1-yl-pyrazolo[1,5-a]pyrimidin-2-yl]benzonitrile;

3-[3-(2-Chloro-6-methyl-4-pyridyl)-5-[[2-(dimethylamino)-1-methyl-ethyl]amino]pyrazolo[1,5-a]pyrimidin-2-yl]benzonitrile;

3-[3-(2-Chloro-6-methyl-4-pyridyl)-5-hydroxy-pyrazolo[1,5-a]pyrimidin-2-ylbenzonitrile;

3-[3-(2-Chloro-6-methyl-4-pyridyl)-5-(1H-imidazol-2-ylmethylamino)pyrazolo[1,5-a]pyrimidin-2-yl]benzonitrile;

3-[3-(2-Chloro-6-methyl-4-pyridyl)-5-morpholino-pyrazolo[1,5-a]pyrimidin-2-yl]benzonitrile;

1-[3-(2-Chloro-6-methyl-4-pyridyl)-2-(3-cyanophenyl)pyrazolo[1,5-a]pyrimidin-5-yl]azetidine-2-carboxylic acid;

1-[3-(2-Chloro-6-methyl-4-pyridyl)-2-(3-cyanophenyl)pyrazolo[1,5-a]pyrimidin-5-yl]azetidine-3-carboxylic acid;

(3R)-1-[3-(2-Chloro-6-methyl-4-pyridyl)-2-(3-cyanophenyl)pyrazolo[1,5-a]pyrimidin-5-yl]pyrrolidine-3-carboxylic acid;

4-[3-(2-Chloro-6-methyl-4-pyridyl)-2-(3-cyanophenyl)pyrazolo[1,5-a]pyrimidin-5-yl]piperazine-1-sulfonamide;

3-[[3-(2-Chloro-6-methyl-4-pyridyl)-2-(3-cyanophenyl)pyrazolo[1,5-a]pyrimidin-5-yl]amino]bicyclo[1.1.1]pentane-1-carboxylic acid;

3-[3-(2-Chloro-6-methyl-4-pyridyl)-5-[[(2R)-2-hydroxypropyl]amino]pyrazolo[1,5-a]pyrimidin-2-yl]benzonitrile;

3-[3-(2-Chloro-6-methyl-4-pyridyl)-5-[[(2S)-2-hydroxypropyl]amino]pyrazolo[1,5-a]pyrimidin-2-yl]benzonitrile;

3-[5-(tert-Butylamino)-3-(2-chloro-6-methyl-4-pyridyl)pyrazolo[1,5-a]pyrimidin-2-yl]benzonitrile;

3-[3-(2-Chloro-6-methyl-4-pyridyl)-5-[[(1R)-2-hydroxy-1-methyl-ethyl]amino]pyrazolo [1,5-a]pyrimidin-2-yl]benzonitrile;

3-[3-(2-Chloro-6-methyl-4-pyridyl)-5-[(1-hydroxycyclopropyl)methylamino]pyrazoo[1,5-a]pyrimidin-2-yl]benzonitrile;

3-[3-(2-Chloro-6-methyl-4-pyridyl)-5-(4-piperidylamino)pyrazolo[1,5-a]pyrimidin-2-yl]benzonitrile;

3-[3-(2-Chloro-6-methyl-4-pyridyl)-5-[[(3R)-morpholin-3-yl]methylamino]pyrazolo[1,5-a]pyrimidin-2-yl]benzonitrile;

tert-Butyl(3R)-3-[[[3-(2-chloro-6-methyl-4-pyridyl)-2-(3-cyanophenyl)pyrazolo[1,5-a]pyrimidin-5-yl]amino]methyl]morpholine-4-carboxylate;

3-[3-(2-Chloro-6-methyl-4-pyridyl)-5-[[(3R)-3-piperidyl]amino]pyrazolo[1,5-a]pyrimidin-2-yl]benzonitrile;

tert-Butyl(3R)-3-[[3-(2-chloro-6-methyl-4-pyridyl)-2-(3-cyanophenyl)pyrazolo[1,5-a]pyrimidin-5-yl]amino]piperidine-1-carboxylate;

3-[3-(2-Chloro-6-methyl-4-pyridyl)-5-[[(3R)-pyrrolidin-3-yl]amino]pyrazolo[1,5-a]pyrimidin-2-yl]benzonitrile;

tert-Butyl(3R)-3-[[3-(2-chloro-6-methyl-4-pyridyl)-2-(3-cyanophenyl)pyrazolo[1,5-a]pyrimidin-5-yl]amino]pyrrolidine-1-carboxylate;

3-[3-(2-Chloro-6-methyl-4-pyridyl)-5-[rac-(4aS,7aS)-3,4,4a,5,7,7a-hexahydro-2H-pyrrolo[3,4-b][1,4]oxazin-6-yl]pyrazolo[1,5-a]pyrimidin-2-yl]benzonitrile;

tert-Butyl rac-(4aS,7aS)-6-[3-(2-chloro-6-methyl-4-pyridyl)-2-(3-cyanophenyl)pyrazolo[1,5-a]pyrimidin-5-yl]-2,3,4a,5,7,7a-hexahydropyrrolo[3,4-b][1,4]oxazine-4-carboxylate;

3-[3-(2-Chloro-6-methyl-4-pyridyl)-5-[[(3S)-morpholin-3-yl]methylamino]pyrazolo[1,5-a]pyrimidin-2-yl]benzonitrile;

tert-Butyl(3S)-3-[[[3-(2-chloro-6-methyl-4-pyridyl)-2-(3-cyanophenyl)pyrazolo[1,5-a]pyrimidin-5-yl]amino]methyl]morpholine-4-carboxylate;

3-[3-(2-Chloro-6-methyl-4-pyridyl)-5-[[(3S)-pyrrolidin-3-yl]amino]pyrazolo[1,5-a]pyrimidin-2-yl]benzonitrile;

tert-Butyl(3S)-3-[[3-(2-chloro-6-methyl-4-pyridyl)-2-(3-cyanophenyl)pyrazolo[1,5-a]pyrimidin-5-yl]amino]pyrrolidine-1-carboxylate;

3-[3-(2-Chloro-6-methyl-4-pyridyl)-5-[[(3S)-3-piperidyl]amino]pyrazolo[1,5-a]pyrimidin-2-yl]benzonitrile;

tert-Butyl(3S)-3-[[3-(2-chloro-6-methyl-4-pyridyl)-2-(3-cyanophenyl)pyrazolo[1,5-a]pyrimidin-5-yl]amino]piperidine-1-carboxylate;

3-(2-Chloro-6-methyl-4-pyridyl)-2-(3-cyanophenyl)-N-(3-hydroxy-1-bicyclo[1.1.1]penta nyl)pyrazolo[1,5-a]pyrimidine-5-carboxamide;

N-tert-Butyl-3-(2-chloro-6-methyl-4-pyridyl)-2-(3-cyanophenyl)pyrazolo[1,5-a]pyrimidine-5-carboxamide;

3-(2-Chloro-6-methyl-4-pyridyl)-2-(3-cyanophenyl)-N-(2-hydroxy-2-methyl-propyl)pyrazolo[1,5-a]pyrimidine-5-carboxamide;

3-(2-Chloro-6-methyl-4-pyridyl)-2-(3-cyanophenyl)-N-(3-hydroxy-3-methyl-butyl)pyrazolo[1,5-a]pyrimidine-5-carboxamide;

3-(2-Chloro-6-methyl-4-pyridyl)-2-(3-cyanophenyl)-N-[2-(4-phenylpiperazin-1-yl)ethyl]pyrazolo[1,5-a]pyrimidine-5-carboxamide;

3-(2-Chloro-6-methyl-4-pyridyl)-2-(3-cyanophenyl)-N-(oxetan-3-yl)pyrazolo[1,5-a]pyrimidine-5-carboxamide;

3-(2-Chloro-6-methyl-4-pyridyl)-2-(3-cyanophenyl)pyrazolo[1,5-a]pyrimidine-5-carboxamide;

3-[3-(2-Chloro-6-methyl-4-pyridyl)-5-(morpholine-4-carbonyl)pyrazolo[1,5-a]pyrimidin-2-yl]benzonitrile;

3-(2-Chloro-6-methyl-4-pyridyl)-2-(3-cyanophenyl)-N-[(1S)-2-hydroxy-1,2-dimethyl-propyl]pyrazolo[1,5-a]pyrimidine-5-carboxamide;

N-(2-Amino-2-methyl-propyl)-3-(2-chloro-6-methyl-4-pyridyl)-2-(3-cyanophenyl)pyrazolo[1,5-a]pyrimidine-5-carboxamide;

3-(2-Chloro-6-methyl-4-pyridyl)-2-(3-cyanophenyl)-N-[(1-hydroxycyclopropyl)methyl]pyrazolo[1,5-a]pyrimidine-5-carboxamide;

3-(2-Chloro-6-methyl-4-pyridyl)-2-(3-cyanophenyl)-N-[(1-hydroxycyclobutyl)methyl]pyrazolo[1,5-a]pyrimidine-5-carboxamide;

3-(2-Chloro-6-methyl-4-pyridyl)-2-(3-cyanophenyl)-N-[(1R)-2-hydroxy-1,2-dimethyl-propyl]pyrazolo[1,5-a]pyrimidine-5-carboxamide;

3-(2-Chloro-6-methyl-4-pyridyl)-2-(3-cyanophenyl)-N-[(2R)-2-hydroxypropyl]pyrazolo[1,5-a]pyrimidine-5-carboxamide;

3-(2-Chloro-6-methyl-4-pyridyl)-2-(3-cyanophenyl)-N-[(1R)-2-hydroxy-1-methyl-ethyl]pyrazolo[1,5-a]pyrimidine-5-carboxamide;

3-(2-Chloro-6-methyl-4-pyridyl)-2-(3-cyanophenyl)-N-[(3-hydroxyoxetan-3-yl)methyl]pyrazolo[1,5-a]pyrimidine-5-carboxamide;

3-(2-Chloro-6-methyl-4-pyridyl)-2-(3-cyanophenyl)-N-methylsulfonyl-pyrazolo[1,5-a]pyrimidine-5-carboxamide;

3-(2-Chloro-6-methyl-4-pyridyl)-2-(3-cyanophenyl)-N-(2,3-dihydroxy-2-methyl-propyl)pyrazolo(1,5-a]pyrimidine-5-carboxamide;

3-(2-Chloro-6-methyl-4-pyridyl)-2-(3-cyanophenyl)-N-[(3-hydroxycyclobutyl)methyl]pyrazolo[1,5-a]pyrimidine-5-carboxamide;

3-(2-Chloro-6-methyl-4-pyridyl)-N-(1-cyano-2-methoxy-1-methyl-ethyl)-2-(3-cyanophenyl)pyrazolo[1,5-a]pyrimidine-5-carboxamide;

N-(4-Aminonorbornan-1-yl)-3-(2-chloro-6-methyl-4-pyridyl)-2-(3-cyanophenyl)pyrazolo[1,5-a]pyrimidine-5-carboxamide;

3-(2-Chloro-6-methyl-4-pyridyl)-2-(3-cyanophenyl)-N-[(2S)-2,3-dihydroxypropyl]pyrazolo[1,5-a]pyrimidine-5-carboxamide;

3-(2-Chloro-6-methyl-4-pyridyl)-2-(3-cyanophenyl)-N-[(3S,4S)-4-methoxy-1-methyl-pyrrolidin-3-yl]pyrazolo[1,5-a]pyrimidine-5-carboxamide;

3-(2-Chloro-6-methyl-4-pyridyl)-2-(3-cyanophenyl)-N-[(2R)-2,3-dihydroxypropyl]pyrazolo[1,5-a]pyrimidine-5-carboxamide;

3-(2-Chloro-6-methyl-4-pyridyl)-2-(3-cyanophenyl)-N-(1-methylazetidin-3-yl)pyrazolo[1,5-a]pyrimidine-5-carboxamide;

3-(2-Chloro-6-methyl-4-pyridyl)-2-(3-cyanophenyl)-N-[(3S,4S)-4-hydroxytetrahydrofuran-3-yl]pyrazolo[1,5-a]pyrimidine-5-carboxamide;

3-(2-Chloro-6-methyl-4-pyridyl)-2-(3-cyanophenyl)-N-(2-hydroxy-2-methyl-propyl)-N-methyl-pyrazolo[1,5-a]pyrimidine-5-carboxamide;

N-(3-Amino-3-methyl-butyl)-3-(2-chloro-6-methyl-4-pyridyl)-2-(3-cyanophenyl)pyrazolo [1,5-a]pyrimidine-5-carboxamide;

N-(3-Amino-1-bicyclo[1.1.1]pentanyl)-3-(2-chloro-6-methyl-4-pyridyl)-2-(3-cyanophenyl)pyrazolo[1,5-a]pyrimidine-5-carboxamide;

tert-Butyl N-[3-[[3-(2-chloro-6-methyl-4-pyridyl)-2-(3-cyanophenyl)pyrazolo[1,5-a]pyrimidine-5-carbonyl]amino]-1-bicyclo[1.1.1]pentanyl]carbamate;

3-(2-Chloro-6-methyl-4-pyridyl)-2-(3-cyanophenyl)-N-[cis-(3S,4R)-4-hydroxypyrrolidin-3-yl]pyrazolo[1,5-a]pyrimidine-5-carboxamide;

tert-Butyl(3S,4R)-3-[[3-(2-chloro-6-methyl-4-pyridyl)-2-(3-cyanophenyl)pyrazolo[1,5-a]pyrimidine-5-carbonyl]amino]-4-hydroxy-pyrrolidine-1-carboxylate;

N-(2-Amino-1,1-dimethyl-ethyl)-3-(2-chloro-6-methyl-4-pyridyl)-2-(3-cyanophenyl)pyrazolo[1,5-a]pyrimidine-5-carboxamide;

tert-Butyl N-[2-[[3-(2-chloro-6-methyl-4-pyridyl)-2-(3-cyanophenyl)pyrazolo[1,5-a]pyrimidine-5-carbonyl]amino]-2-methyl-propyl]carbamate;

3-(2-Chloro-6-methyl-4-pyridyl)-2-(3-cyanophenyl)-N-[(3S)-3-piperidyl]pyrazolo[1,5-a]pyrimidine-5-carboxamide;

tert-Butyl(3S)-3-[[3-(2-chloro-6-methyl-4-pyridyl)-2-(3-cyanophenyl)pyrazolo[1,5-a]pyrimidine-5-carbonyl]amino]piperidine-1-carboxylate;

3-(2-Chloro-6-methyl-4-pyridyl)-2-(3-cyanophenyl)-N-[trans-(3S,4S)-4-hydroxypyrrolidin-3-yl]pyrazolo[1,5-a]pyrimidine-5-carboxamide:

tert-Butyl trans-(3S,4S)-3-[[3-(2-chloro-6-methyl-4-pyridyl)-2-(3-cyanophenyl) pyrazolo[1,5-a]pyrimidine-5-carbonyl]amino]-4-hydroxy-pyrrolidine-1-carboxylate;

3-(2-Chloro-6-methyl-4-pyridyl)-2-(3-cyanophenyl)-N-[(3-hydroxypyrrolidin-3-yl)methyl]pyrazolo[1,5-a]pyrimidine-5-carboxamide;

tert-Butyl 3-[[[3-(2-chloro-6-methyl-4-pyridyl)-2-(3-cyanophenyl)pyrazolo[1,5-a]pyrimidine-5-carbonyl]amino]methyl]-3-hydroxy-pyrrolidine-1-carboxylate;

3-(2-Chloro-6-methyl-4-pyridyl)-2-(3-cyanophenyl)-N-[(3R)-3-piperidyl]pyrazolo[1,5-a]pyrimidine-5-carboxamide;

tert-Butyl(3R)-3-[[3-(2-chloro-6-methyl-4-pyridyl)-2-(3-cyanophenyl)pyrazolo[1,5-a]pyrimidine-5-carbonyl]amino]piperidine-1-carboxylate;

3-(2-Chloro-6-methyl-4-pyridyl)-2-(3-cyanophenyl)-N-(3-methylpyrrolidin-3-yl)pyrazolo[1,5-a]pyrimidine-5-carboxamide;

Tert-butyl 3-[[3-(2-chloro-6-methyl-4-pyridyl)-2-(3-cyanophenyl)pyrazolo[1,5-a]pyrimidine-5-carbonyl]amino]-3-methyl-pyrrolidine-1-carboxylate;

3-(2-Chloro-6-methyl-4-pyridyl)-2-(3-cyanophenyl)-N-[(1R,2S)-2,3-dihydroxy-1-methyl-propyl]pyrazolo[1,5-a]pyrimidine-5-carboxamide;

3-(2-Chloro-6-methyl-4-pyridyl)-2-(3-cyanophenyl)-N-[(1R)-1-[(4S)-2,2-dimethyl-1,3-dioxolan-4-yl]ethyl]pyrazolo [1,5-a]pyrimidine-5-carboxamide;

N-[(1-Amino-3,3-difluoro-cyclobutyl)methyl]-3-(2-chloro-6-methyl-4-pyridyl)-2-(3-cyanophenyl)pyrazolo[1,5-a]pyrimidine-5-carboxamide;

tert-Butyl N-[1-[[[3-(2-chloro-6-methyl-4-pyridyl)-2-(3-cyanophenyl)pyrazolo[1,5-a]pyrimidine-5-carbonyl]amino]methyl]-3,3-difluoro-cyclobutyl]carbamate;

3-(2-Chloro-6-methyl-4-pyridyl)-2-(3-cyanophenyl)-N-(morpholin-2-ylmethyl)pyrazolo[1,5-a]pyrimidine-5-carboxamide;

tert-Butyl 2-[[[3-(2-chloro-6-methyl-4-pyridyl)-2-(3-cyanophenyl)pyrazolo(1,5-a]pyrimidine-5-carbonyl]amino]methyl]morpholine-4-carboxylate;

3-[3-(2-Chloro-6-methyl-4-pyridyl)-5-(piperazine-1-carbonyl)pyrazolo[1,5-a]pyrimidin-2-yl]benzonitrile;

Tert-butyl 4-[3-(2-chloro-6-methyl-4-pyridyl)-2-(3-cyanophenyl)pyrazolo[1,5-a]pyrimidine-5-carbonyl]piperazine-1-carboxylate;

3-(2-Chloro-6-methyl-4-pyridyl)-2-(3-cyanophenyl)-N-[(3R)-pyrrolidin-3-yl]pyrazolo[1,5-a]pyrimidine-5-carboxamide;

Tert-butyl(3R)-3-[[3-(2-chloro-6-methyl-4-pyridyl)-2-(3-cyanophenyl)pyrazolo[1,5-a]pyrimidine-5-carbonyl]amino]pyrrolidine-1-carboxylate;

3-[3-(2-Chloro-6-methyl-4-pyridyl)-5-(1-hydroxy-1-methyl-ethyl)pyrazolo[1,5-a]pyrimidin-2-yl]benzonitrile;

3-(2-Chloro-6-methyl-4-pyridyl)-2-(3-cyanophenyl)pyrazolo[1,5-a]pyrimidine-5-carboxylic acid;

2-(3-Cyanophenyl)-3-(2,6-dimethyl-4-pyridyl)-N-(2-hydroxy-2-methyl-propyl)pyrazolo[1,5-a]pyrimidine-5-carboxamide;

2-(3-Cyanophenyl)-3-(2-ethylpyrazol-3-yl)-N-(2-hydroxy-2-methyl-propyl)pyrazolo[1,5-a]pyrimidine-5-carboxamide;

2-(3-Cyanophenyl)-3-(2-ethyl-5-methyl-pyrazol-3-yl)-N-(2-hydroxy-2-methyl-propyl)pyrazolo[1,5-a]pyrimidine-5-carboxamide;

2-(3-Cyanophenyl)-N-(2-hydroxy-2-methyl-propyl)-3-(2-methyl-4-pyridyl)pyrazolo[1,5-a]pyrimidine-5-carboxamide;

2-(3-Cyanophenyl)-3-(2-ethyl-4-methyl-pyrazol-3-yl)-N-(2-hydroxy-2-methyl-propyl)pyrazolo[1,5-a]pyrimidine-5-carboxamide;

2-(3-Cyanophenyl)-3-[2-(difluoromethyl)-6-methyl-4-pyridyl]-N-(2-hydroxy-2-methyl-propyl)pyrazolo[1,5-a]pyrimidine-5-carboxamide;

2-(3-Cyanophenyl)-N-(2-hydroxy-2-methyl-propyl)-3-(2-methylpyrazol-3-yl)pyrazolo[1,5-a]pyrimidine-5-carboxamide;

2-(3-Cyanophenyl)-N-(2-hydroxy-2-methyl-propyl)-3-pyrimidin-4-yl-pyrazolo[1,5-a]pyrimidine-5-carboxamide;

3-Cyano-2-(3-cyanophenyl)-N-(2-hydroxy-2-methyl-propyl)pyrazolo[1,5-a]pyrimidine-5-carboxamide;

3-[3-(2-Chloro-6-methyl-4-pyridyl)-5-(2-hydroxy-2-methyl-propoxy)pyrazolo[1,5-a]pyrimidin-2-yl]benzonitrile;

N-[3-(2-Chloro-6-methyl-4-pyridyl)-2-(3-cyanophenyl)pyrazolo[1,5-a]pyrimidin-5-yl]methanesulfonamide;

(2S)-2-[[3-(2-Chloro-6-methyl-4-pyridyl)-2-(3-cyanophenyl)pyrazolo[1,5-a]pyrimidin-5-yl]amino]propanoic acid;

3-[3-(2-Chloro-6-methyl-4-pyridyl)-5-[(3R)-pyrrolidin-3-yl]oxy-pyrazolo[1,5-a]pyrmidin-2-yl]benzonitrile formate;
3-[3-(2-Chloro-6-methyl-4-pyridyl)-5-(2-hydroxyethylamino)pyrazolo[1,5-a]pyrimidin-2-yl]benzonitrile;
3-[3-(2-Chloro-6-methyl-4-pyridyl)-5-(morpholinomethyl)pyrazolo[1,5-a]pyrimidin-2-yl]benzonitrile;
3-[5-(Aminomethyl)-3-(2-chloro-6-methyl-4-pyridyl)pyrazoo[1,5-a]pyrinidin-2-yl]benzonitrile;
3-[3-(2-Chloro-6-methyl-4-pyridyl)-5-(3-hydroxy-3-methyl-butyl)pyrazolo[1,5-a]pyrimidin-2-yl]benzonitrile;
3-[3-[2-(Difluoromethyl)-6-methyl-4-pyridyl]-5-[(2-hydroxy-2-methyl-propyl)amino]pyrazolo[1,5-a]pyrimidin-2-yl]benzonitrile;
3-[5-[(2-Hydroxy-2-methyl-propyl)amino]-3-(2-methoxy-6-methyl-4-pyridyl)pyrazolo[1,5-a]pyrimidin-2-yl]benzonitrile;
3-[3-(2,6-Dimethyl-4-pyridyl)-5-[(2-hydroxy-2-methyl-propyl)amino]pyrazolo[1,5-a]pyrimidin-2-yl]benzonitrile;
3-[3-(2-Chloro-6-methyl-4-pyridyl)-5-[[(1S)-2-hydroxy-1-methyl-ethyl]amino]pyrazolo[1,5-a]pyrimidin-2-yl]benzonitrile;
3-[3-(2-Chloro-6-methyl-4-pyridyl)-5-(dimethylamino)pyrazolo[1,5-a]pyrimidin-2-yl]benzonitrile;
3-[3-(2-Chloro-6-methyl-4-pyridyl)-5-(4-piperidyloxy)pyrazolo[1,5-a]pyrimidin-2-yl]benzonitrile;
3-[3-(2-Chloro-6-methyl-4-pyridyl)-5-[[(3R)-3-piperidyl]oxy]pyrazolo[1,5-a]pyrimidin-2-yl]benzonitrile;
tert-Butyl(3R)-3-[3-(2-chloro-6-methyl-4-pyridyl)-2-(3-cyanophenyl)pyrazolo[1,5-a]pyrimidin-5-yl]oxypiperidine-1-carboxylate;
3-[3-(2-Chloro-6-methyl-4-pyridyl)-5-[(3S)-pyrrolidin-3-yl]oxy-pyrazolo[1,5-a]pyrimidin-2-yl]benzonitrile;
tert-Butyl(3S)-3-[3-(2-chloro-6-methyl-4-pyridyl)-2-(3-cyanophenyl)pyrazolo[1,5-a]pyrimidin-5-yl]oxypyrrolidine-1-carboxylate;
3-[3-(2-Chloro-6-methyl-4-pyridyl)-5-[[(3S)-3-piperidyl]oxy]pyrazolo[1,5-a]pyrimidin-2-yl]benzonitrile;
tert-Butyl(3S)-3-[3-(2-chloro-6-methyl-4-pyridyl)-2-(3-cyanophenyl)pyrazolo[1,5-a]pyrimidin-5-yl]oxypiperidine-1-carboxylate;
3-[5-Amino-3-(6-amino-5-methyl-3-pyridyl)pyrazolo[1,5-a]pyrimidin-2-yl]benzonitrile;
3-[5-Amino-3-[2-(difluoromethyl)-6-methyl-4-pyridyl]pyrazolo[1,5-a]pyrimidin-2-yl]benzonitrile;
3-[5-Amino-3-(2-methoxy-6-methyl-4-pyridyl)pyrazolo[1,5-a]pyrimidin-2-yl]benzonitrile;
4-[5-Amino-2-(3-cyanophenyl)pyrazolo [1,5-a]pyrimidin-3-yl]-6-methyl-pyridine-2-carbonitrile;
3-[5-Amino-3-(2-fluoro-6-methyl-4-pyridyl)pyrazolo[1,5-a]pyrimidin-2-yl]benzonitrile;
3-[5-Amino-3-(1-methylpyrazol-4-yl)pyrazolo[1,5-a]pyrimidin-2-yl]benzonitrile;
3-[5-Amino-3-(2,6-dimethyl-1-oxido-pyridin-1-ium-4-yl)pyrazolo[1,5-a]pyrimidin-2-yl]benzonitrile;
3-[5-Amino-3-(2-amino-6-methyl-4-pyridyl)pyrazolo[1,5-a]pyrimidin-2-yl]benzonitrile;
4-[5-Amino-2-(3-cyanophenyl)pyrazolo[1,5-a]pyrimidin-3-yl]-6-methyl-pyridine-2-carboxamide;
N-[4-[5-Amino-2-(3-cyanophenyl)pyrazolo[1,5-a]pyrimidin-3-yl]-6-methyl-2-pyridyl]acetamide;
3-[5-Amino-3-(5-methyl-[1,2,4]triazolo[1,5-a]pyridin-7-yl)pyrazolo[1,5-a]pyrimidin-2-yl]benzonitrile;
4-[5-Amino-2-(3-cyanophenyl)pyrazolo[1,5-a]pyrimidin-3-yl]-6-methyl-pyridine-2-carboxylic acid;
3-[5-Amino-3-[2-(dimethylamino)-6-methyl-4-pyridyl]pyrazolo[1,5-a]pyrimidin-2-yl]benzonitrile;
[3-(2-Chloro-6-methyl-4-pyridyl)-2-(3-cyanophenyl)pyrazolo[1,5-a]pyrimidin-5-yl]urea;
1-[3-(2-Chloro-6-methyl-4-pyridyl)-2-(3-cyanophenyl)pyrazolo[1,5-a]pyrimidin-5-yl]-3-(2-hydroxy-2-methyl-propyl)urea;
1-[3-(2-Chloro-6-methyl-4-pyridyl)-2-(3-cyanophenyl)pyrazolo[1,5-a]pyrimidin-5-yl]-3-(1-ethyl-4-piperidyl)urea;
N-[3-(2-Chloro-6-methyl-4-pyridyl)-2-(3-cyanophenyl)pyrazolo[1,5-a]pyrimidin-5-yl]piperazine-1-carboxamide;
1-[3-(2-Chloro-6-methyl-4-pyridyl)-2-(3-cyanophenyl)pyrazolo[1,5-a]pyrimidin-5-y]-3-[(3S)-pyrrolidin-3-yl]urea;
1-(2-Aminoethyl)-3-[3-(2-chloro-6-methyl-4-pyridyl)-2-(3-cyanophenyl)pyrazolo[1,5-a]pyrimidin-5-yl]urea;
1-[3-(2-Chloro-6-methyl-4-pyridyl)-2-(3-cyanophenyl)pyrazolo[1,5-a]pyrimidin-5-yl]-3-[(3R)-pyrrolidin-3-yl)urea;
1-[3-(2-Chloro-6-methyl-4-pyridyl)-2-(3-cyanophenyl)pyrazolo[1,5-a]pyrimidin-5-yl]-2-cyano-guanidine;
3-[3-(2-Ethylpyrazol-3-yl)-5-[(2-hydroxy-2-methyl-propyl)amino]pyrazolo[1,5-a]pyrimidin-2-yl]benzonitrile;
3-[3-(2-Ethylpyrazol-3-yl)-5-[3-(hydroxymethyl)-4-methyl-piperazin-1-yl]pyrazolo[1,5-a]pyrimidin-2-yl]benzonitrile;
3-[3-(2-Ethylpyrazol-3-yl)-5-(8-oxa-3-azabicyclo[3.2.1]octan-3-yl)pyrazolo[1,5-a]pyrimidin-2-yl]benzonitrile;
3-[3-(2-Ethylpyrazol-3-yl)-5-(8-methyl-3,8-diazabicyclo[3.2.1]octan-3-yl)pyrazolo[1,5-a]pyrimidin-2-yl]benzonitrile;
3-[3-(2-Ethylpyrazol-3-yl)-5-(4-methylsulfonylpiperazin-1-yl)pyrazolo[1,5-a]pyrimidin-2-yl]benzonitrile;
3-[3-(2-Ethylpyrazol-3-yl)-5-(4H-1,2,4-triazol-3-ylmethyl-amino)pyrazolo[1,5-a]pyrimidin-2-yl]benzonitrile;
3-[3-(2-Ethylpyrazol-3-yl)-5-piperazin-1-yl-pyrazolo[1,5-a]pyrimidin-2-yl]benzonitrile;
3-[3-(2-Ethylpyrazol-3-yl)-5-(1-imino-1-oxo-1,4-thiazinan-4-yl)pyrazolo[1,5-a]pyrimidin-2-yl]benzonitrile;
5-(Benzylamino)-2-(2-fluorophenyl)pyrazolo[1,5-a]pyrimidine-3-carbonitrile;
N-Benzyl-2-(2-fluorophenyl)pyrazolo[1,5-a]pyrimidin-5-amine;
2-(2-Furyl)-5-[(3-methyl-2-pyridyl)methylamino]pyrazolo[1,5-a]pyrimidine-3-carbonitrile;
tert-Butyl(2S)-2-[[[3-cyano-2-(2-furyl)pyrazolo[1,5-a]pyrimidin-5-yl]amino]methyl]morpholine-4-carboxylate;
tert-Butyl(2R)-2-[[[3-cyano-2-(2-furyl)pyrazolo[1,5-a]pyrimidin-5-yl]amino]methyl]pyrrolidine-1-carboxylate;
5-[4-(2-Fluoroethyl)piperazin-1-yl]-2-(2-furyl)pyrazolo[1,5-a]pyrimidine-3-carbonitrile;
tert-Butyl(2S)-2-[[[3-cyano-2-(2-furyl)pyrazolo[1,5-a]pyrimidin-5-yl]amino]methyl]pyrrolidine-1-carboxylate;
tert-Butyl(2R)-2-[[[3-cyano-2-(2-furyl)pyrazolo[1,5-a]pyrimidin-5-yl]amino]methyl]morpholine-4-carboxylate;
2-(2-Furyl)-5-[4-(2-phenylethyl)piperazin-1-yl]pyrazolo[1,5-a]pyrimidine-3-carbonitrile;
2-(2-Furyl)-5-[4-(2-pyridylmethyl) piperazin-1-yl]pyrazolo[1,5-a]pyrimidine-3-carbonitrile;
2-(2-Furyl)-5-(4-methylpiperazin-1-yl)pyrazolo[1,5-a]pyrimidine-3-carbonitrile;
5-[(1-Benzyl-4-piperidyl)methylamino]-2-(2-furyl)pyrazolo[1,5-a]pyrimidine-3-carbonitrile;
Tert-butyl(2R)-4-[3-cyano-2-(2-furyl)pyrazolo[1,5-a]pyrimidin-5-yl]-2-methyl-piperazine-1-carboxylate;

Tert-butyl(2S)-4-[3-cyano-2-(2-furyl)pyrazolo[1,5-a]pyrimidin-5-yl]-2-methyl-piperazine-1-carboxylate;
5-[2-(4-Benzylpiperazin-1-yl)ethylamino]-2-(2-furyl)pyrazolo[1,5-a]pyrimidine-3-carbonitrile;
2-(2-Furyl)-5-[(3-methyl-2-pyridyl)methylamino]pyrazolo[1,5-a]pyrimidine-3-carboxamide;
5-[4-(2-Fluoroethyl)piperazin-1-yl]-2-(2-furyl)pyrazolo[1,5-a]pyrimidine-3-carboxamide;
5-[3-(Dimethylamino)azetidin-1-yl]-2-(2-furyl)pyrazolo[1,5-a]pyrimidine-3-carboxamide;
tert-Butyl 4-[3-cyano-2-(2-furyl)pyrazolo[1,5-a]pyrimidin-5-yl]-3,6-dihydro-2H-pyridine-1-carboxylate;
2-(2-Furyl)-5-piperazin-1-yl-pyrazolo[1,5-a]pyrimidine-3-carbonitrile;
2-(2-Furyl)-5-[[(2S)-morpholin-2-yl]methylamino]pyrazolo[1,5-a]pyrimidine-3-carbonitrile;
2-(2-Furyl)-5-[[(2R)-morpholin-2-yl]methylamino]pyrazolo[1,5-a]pyrimidine-3-carbonitrile;
5-(4-Benzylpiperazin-1-yl)-2-(2-furyl)pyrazolo[1,5-a]pyrimidine-3-carbonitrile;
N-Benzyl-3-bromo-2-(2-furyl)pyrazolo[1,5-a]pyrimidin-5-amine;
5-(Benzylamino)-2-(2-furyl)pyrazolo[1,5-a]pyrimidine-3-carbonitrile;
5-(Benzylamino)-2-(2-furyl)pyrazolo[1,5-a]pyrimidine-3-carboxamide;
5-(Benzylamino)-2-(2-furyl)pyrazolo[1,5-a]pyrimidine-3-carbaldehyde;
N-Benzyl-2-(2-furyl)pyrazolo[1,5-a]pyrimidin-5-amine;
5-Amino-2-(2-furyl)pyrazolo[1,5-a]pyrimidine-3-carbonitrile;
3-Bromo-2-(2-furyl)pyrazolo[1,5-a]pyrimidin-5-amine;
2-(2-Furyl)-5-[4-[(3-methyl-2-pyridyl)methyl]piperazin-1-yl]pyrazolo[1,5-a]pyrimidine-3-carbonitrile;
2-(2-Furyl)-5-[4-[(2,4,6-trifluorophenyl)methyl]piperazin-1-yl]pyrazolo[1,5-a]pyrimidine-3-carbonitrile;
2-(2-Furyl)-5-[4-[(1-methylimidazol-2-yl)methyl]piperazin-1-yl]pyrazolo[1,5-a]pyrimidine-3-carbonitrile;
2-(2-Furyl)-5-[4-(2-hydroxyethyl)piperazin-1-yl]pyrazolo[1,5-a]pyrimidine-3-carbonitrile;
N-benzyl-2-(2-furyl)-3-(1-methylpyrazol-4-yl)pyrazolo[1,5-a]pyrimidin-5-amine;
N-benzyl-2-(2-furyl)-3-(2-methylpyrazol-3-yl)pyrazolo[1,5-a]pyrimidin-5-amine;
Methyl(E)-3-[5-(benzylamino)-2-(2-furyl)pyrazolo[1,5-a]pyrimidin-3-yl]prop-2-enoate;
(E)-3-[5-(Benzylamino)-2-(2-furyl)pyrazolo[1,5-a]pyrimidin-3-yl]prop-2-enoic acid;
2-(2-Furyl)-5-(4-phenylpiperazin-1-yl)pyrazolo[1,5-a]pyrimidine-3-carbonitrile;
2-(2-Furyl)-5-(3-hydroxypropylamino)pyrazolo[1,5-a]pyrimidine-3-carbonitrile;
2-(2-furyl)-5-(2-hydroxyethylamino)pyrazolo[1,5-a]pyrimidine-3-carbonitrile;
2-(2-Furyl)-5-(3-piperidylmethylamino)pyrazolo[1,5-a]pyrimidine-3-carbonitrile hydrochloride;
5-(Benzylamino)-2-oxazol-2-yl-pyrazolo[1,5-a]pyrimidine-3-carbonitrile;
5-(Benzylamino)-2-(3-cyanophenyl)pyrazolo[1,5-a]pyrimidine-3-carbonitrile;
2-(3-Cyanophenyl)-5-[4-[(3-methyl-2-pyridyl)methyl]piperazin-1-yl]pyrazolo[1,5-a]pyrimidine-3-carbonitrile;
2-(3-Fluorophenyl)-5-[4-[(3-methyl-2-pyridyl)methyl]piperazin-1-yl]pyrazolo[1,5-a]pyrimidine-3-carbonitrile;
5-[4-(2-Fluoroethyl)piperazin-1-yl]-2-(3-fluorophenyl)pyrazolo[1,5-a]pyrimidine-3-carbonitrile;
5-[4-(2-Fluoroethyl)piperazin-1-yl]-2-oxazol-5-yl-pyrazolo[1,5-a]pyrimidine-3-carbonitrile;
5-(Benzylamino)-2-(4-fluorophenyl)pyrazolo[1,5-a]pyrimidine-3-carbonitrile;
5-(benzylamino)-2-(5-methyl-2-furyl)pyrazolo[1,5-a]pyrimidine-3-carbonitrile;
5-[4-[(3-Methyl-2-pyridyl)methyl]piperazin-1-yl]-2-oxazol-5-yl-pyrazolo[1,5-a]pyrimidine-3-carbonitrile;
N-benzyl-2-(3-fluorophenyl)pyrazolo[1,5-a]pyrimidin-5-amine;
2-(3-Fluorophenyl)-N-[(3-methyl-2-pyridyl)methyl]pyrazolo[1,5-a]pyrimidin-5-amine;
2-(3-Fluorophenyl)-N-(2-phenylethyl)pyrazolo[1,5-a]pyrimidin-5-amine;
N-(1H-Benzimidazol-2-ylmethyl)-2-(3-fluorophenyl)pyrazolo[1,5-a]pyrimidin-5-amine;
2-(3-Fluorophenyl)-N-(2-isoindolin-2-ylethyl)pyrazolo[1,5-a]pyrimidin-5-amine;
N-Benzyl-3-chloro-2-(3-fluorophenyl)pyrazolo[1,5-a]pyrimidin-5-amine;
3-Bromo-5-chloro-2-(3-fluorophenyl)pyrazolo[1,5-a]pyrimidine;
N-Benzyl-3-bromo-2-(3-fluorophenyl)pyrazolo[1,5-a]pyrimidin-5-amine;
5-(Benzylamino)-2-(3-fluorophenyl)pyrazolo[1,5-a]pyrimidine-3-carbonitrile;
3-Bromo-2-(3-fluorophenyl)pyrazolo[1,5-a]pyrimidin-5-amine;
5-Amino-2-(3-fluorophenyl)pyrazolo[1,5-a]pyrimidine-3-carbonitrile;
2-(2-Furyl)-N-(thiazol-2-ylmethyl)pyrazolo[1,5-a]pyrimidin-5-amine;
[5-(Benzylamino)-2-(2-furyl)pyrazolo[1,5-a]pyrimidin-3-yl]methanol;
5-(Benzylamino)-2-(2-furyl)pyrazolo[1,5-a]pyrimidine-3-carboxylic acid;
N-Benzyl-2-(2-furyl)-3-iodo-pyrazolo[1,5-a]pyrimidin-5-amine;
2-(2-Furyl)-3-(4-pyridyl)pyrazolo[1,5-a]pyrimidin-5-amine;
2-(2-Furyl)-5-[[(2R)-pyrrolidin-2-yl]methylamino]pyrazolo[1,5-a]pyrimidine-3-carbonitrile;
2-(2-Furyl)-5-[[(2R)-1-methylpyrrolidin-2-yl]methylamino]pyrazolo[1,5-a]pyrimidine-3-carbonitrile;
2-(2-Furyl)-5-[(3R)-3-methylpiperazin-1-yl]pyrazolo[1,5-a]pyrimidine-3-carbonitrile hydrochloride;
Tert-butyl 4-[3-cyano-2-(2-furyl)pyrazolo[1,5-a]pyrimidin-5-yl]piperidine-1-carboxylate;
N-Benzyl-7-(2-furyl)pyrazolo[1,5-a][1,3,5]triazin-2-amine;
N-Benzyl-2-(2-furyl)pyrazolo[1,5-a]pyrimidine-5-carboxamide;
2-(3-Cyanophenyl)-5-[4-(2-fluoroethyl)piperazin-1-yl]pyrazolo[1,5-a]pyrimidine-3-carbonitrile;
2-(3-Cyanophenyl)-5-[2-(4-phenylpiperazin-1-yl)ethylamino]pyrazolo[1,5-a]pyrimidine-3-carbonitrile;
3-(2-Chloro-6-methyl-4-pyridyl)-2-(4-fluorophenyl)pyrazolo[1,5-a]pyrimidin-5-amine;
N-tert-Butyl-3-(2-chloro-6-methyl-4-pyridyl)-2-(3-cyanophenyl)pyrazolo[1,5-a]pyrimidine-5-carboxamidine;
3-(2-Amino-6-methyl-4-pyridyl)-N-tert-butyl-2-(3-cyanophenyl)pyrazolo[1,5-a]pyrimidine-5-carboxamide;
2-(3-Cyanophenyl)-3-(2,6-dimethyl-4-pyridyl)-N-[(1S)-2-hydroxy-1,2-dimethyl-propyl]pyrazolo[1,5-a]pyrimidine-5-carboxamide;
2-(3-Cyanophenyl)-N-(2,3-dihydroxy-2-methyl-propyl)-3-(2,6-dimethyl-4-pyridyl)pyrazolo[1,5-a]pyrimidine-5-carboxamide;

2-(3-Cyanophenyl)-3-(2,6-dimethyl-4-pyridyl)-N-(3-hydroxy-1-bicyclo[1.1.1]pentanyl)pyrazolo[1,5-a]pyrimidine-5-carboxamide;

3-(2-chloro-6-methyl-4-pyridyl)-2-(3-cyanophenyl)-5-(sulfamoylamino)pyrazolo[1,5-a]pyrimidine;

N-[3-(2-Chloro-6-methyl-4-pyridyl)-2-(3-cyanophenyl)pyrazolo[1,5-a]pyrimidin-5-yl]-2-hydroxy-2-methyl-propanamide;

N-{3-(2-Chloro-6-methyl-4-pyridyl)-2-(3-cyanophenyl)pyrazolo[1,5-a]pyrimidin-5-yl]-2,2-dimethyl-propanamide;

N-(3-Amino-3-methyl-butyl)-2-(3-cyanophenyl)-3-(2,6-dimethyl-4-pyridyl)pyrazolo[1,5-a]pyrimidine-5-carboxamide.

Further compounds of the invention, or pharmaceutical salts thereof, include:

3-(2-chloro-6-methyl-4-pyridyl)-2-(3-cyanophenyl)-N-(2-hydroxy-1,1-dimethyl-ethyl)pyrazolo[1,5-a]pyrimidine-5-carboxamide;

2-(3-cyanophenyl)-N-(2-hydroxy-2-methyl-propyl)-3-[2-methyl-6-(trifluoromethyl)-4-pyridyl]pyrazolo[1,5-a]pyrimidine-5-carboxamide;

3-(2-chloro-6-methyl-4-pyridyl)-N-(1-cyano-1-methyl-ethyl)-2-(3-cyanophenyl)pyrazolo[1,5-a]pyrimidine-5-carboxamide;

3-(2-chloro-6-methyl-4-pyridyl)-2-(3-cyanophenyl)-N-[(1S,2S)-2,3-dihydroxy-1-methyl-propyl]pyrazolo[1,5-a]pyrimidine-5-carboxamide;

1-[3-(2-chloro-6-methyl-4-pyridyl)-2-(3-cyanophenyl)pyrazolo[1,5-a]pyrimidin-5-yl]-2-cyano-3-isopropyl-guanidine;

3-[3-(2-chloro-6-methyl-4-pyridyl)-5-[[(1R)-2-hydroxy-1-methyl-ethyl]amino]pyrazolo[1,5-a]pyrimidin-2-yl]benzonitrile;

2-(3-cyano-2-methyl-phenyl)-3-(2,6-dimethyl-4-pyridyl)-N-(2-hydroxy-2-methyl-propyl)pyrazolo[1,5-a]pyrimidine-5-carboxamide;

3-(2-chloro-6-methyl-4-pyridyl)-2-(3-cyanophenyl)-N-(3-hydroxycyclobutyl)pyrazolo[1,5-a]pyrimidine-5-carboxamide;

2-(3-cyanophenyl)-3-(2,6-dimethyl-4-pyridyl)-N-[(2-oxo-3-piperidyl)methyl]pyrazolo[1,5-a]pyrimidine-5-carboxamide;

3-(2-chloro-6-methyl-4-pyridyl)-2-(3-cyanophenyl)-N-(2-hydroxy-1,1,2-trimethyl-propyl)pyrazolo[1,5-a]pyrimidine-5-carboxamide;

2-(3-cyanophenyl)-3-(2,6-dimethyl-4-pyridyl)-N-[(1-methyl-2-oxo-3-piperidyl)methyl]pyrazolo[1,5-a]pyrimidine-5-carboxamide;

2-(3-cyanophenyl)-N-[(1S)-1,2-dimethylallyl]-3-(2,6-dimethyl-4-pyridyl)pyrazolo[1,5-a]pyrimidine-5-carboxamide;

N-(2-acetamido-2-methyl-propyl)-3-(2-chloro-6-methyl-4-pyridyl)-2-(3-cyanophenyl)pyrazolo[1,5-a]pyrimidine-5-carboxamide:

N-(3-amino-3-methyl-butyl)-3-(2-chloro-6-methyl-4-pyridyl)-2-(3-cyanophenyl)pyrazolo[1,5-a]pyrimidine-5-carboxamide;

3-[3-(2-chloro-6-methyl-4-pyridyl)-5-[(1-methyl-4-piperidyl)amino]pyrazolo[1,5-a]pyrimidin-2-yl]benzonitrile;

2-(3-cyanophenyl)-3-(2,6-dimethyl-4-pyridyl)-N-[(1R)-2-hydroxy-1,2-dimethyl-propyl]pyrazolo[1,5-a]pyrimidine-5-carboxamide;

3-(2-chloro-6-methyl-4-pyridyl)-2-(3-cyano-2-methyl-phenyl)-N-(2-hydroxy-2-methyl-propyl)pyrazolo[1,5-a]pyrimidine-5-carboxamide;

3-[3-(2-chloro-6-methyl-4-pyridyl)-5-[[(1R,2S)-2,3-dihydroxy-1-methyl-propyl]amino]pyrazolo[1,5-a]pyrimidin-2-yl]benzonitrile;

2-(3-cyanophenyl)-3-(2,6-dimethyl-4-pyridyl)-N-(4-hydroxy-4-methyl-cyclohexyl)pyrazolo[1,5-a]pyrimidine-5-carboxamide;

3-[3-[2-(difluoromethyl)-6-methyl-4-pyridyl]-5-[(2-hydroxy-2-methyl-propyl)amino]pyrazolo[1,5-a]pyrimidin-2-yl]benzonitrile;

2-(3-cyanophenyl)-3-(2,6-dimethyl-4-pyridyl)-N-[(4-methyl-2-oxo-oxazolidin-4-yl)methyl]pyrazolo[1,5-a]pyrimidine-5-carboxamide;

2-(3-cyanophenyl)-3-(2,6-dimethyl-4-pyridyl)-N-[(2-methyl-5-oxo-pyrrolidin-2-yl)methyl]pyrazolo[1,5-a]pyimidine-5-carboxamide;

2-(3-cyanophenyl)-3-(2,6-dimethyl-4-pyridyl)-N-[1-(3-hydroxyoxetan-3-yl)ethyl]pyrazolo[1,5-a]pyrimidine-5-carboxamide;

2-(3-cyanophenyl)-3-(2,6-dimethyl-4-pyridyl)-N-[(3-methyl-6-oxo-3-piperidyl)methyl]pyrazolo[1,5-a]pyrimidine-5-carboxamide;

1-[3-(2-chloro-6-methyl-4-pyridyl)-2-(3-cyanophenyl)pyrazolo[1,5-a]pyrimidin-5-yl]-2-cyano-3-(2-hydroxy-2-methyl-propyl)guanidine;

3-(2-chloro-6-methyl-4-pyridyl)-2-(3-cyanophenyl)-N-(3-hydroxy-1-bicyclo[1.1.1]pentanyl)pyrazolo[1,5-a]pyrimidine-5-carboxamide;

3-(2-chloro-6-methyl-4-pyridyl)-2-(3-cyanophenyl)-N-[rac-(2R)-2-hydroxypropyl]pyrazolo[1,5-a]pyrimidine-5-carboxamide;

2-(3-cyano-2-methyl-phenyl)-3-(2,6-dimethyl-4-pyridyl)-N-[(1R)-2-hydroxy-1,2-dimethyl-propyl]pyrazolo[1,5-a]pyrimidine-5-carboxamide;

3-[3-(2-chloro-6-methyl-4-pyridyl)-5-[[rac-(3S,4S)-4-methoxy-1-methyl-pyrrolidin-3-yl]amino]pyrazolo[1,5-a]pyrimidin-2-yl]benzonitrile;

3-(2-chloro-6-methyl-4-pyridyl)-2-(3-cyanophenyl)-N-[(3-methyl-3-piperidyl)methyl]pyrazolo[1,5-a]pyrimidine-5-carboxamide;

2-(3-cyanophenyl)-N-(2-hydroxy-2-methyl-propyl)-3-(2-methoxy-6-methyl-4-pyridyl)pyrazolo[1,5-a]pyrimidine-5-carboxamide;

2-(3-cyanophenyl)-3-(2,6-dimethyl-4-pyridyl)-N-[(4-methyl-2,5-dioxo-imidazolidin-4-yl)methyl]pyrazolo[1,5-a]pyrimidine-5-carboxamide;

3-[3-(2-chloro-6-methyl-4-pyridyl)-5-[[(1S,2S)-2,3-dihydroxy-1-methyl-propyl]amino]pyrazolo[1,5-a]pyrimidin-2-yl]benzonitrile;

2-(3-cyanophenyl)-3-(2,6-dimethyl-4-pyridyl)-N-(3-hydroxy-3-methyl-cyclobutyl)pyrazolo[1,5-a]pyrimidine-5-carboxamide;

3-[3-(2-chloro-6-methyl-4-pyridyl)-5-[[rac-(3R)-3-piperidyl]amino]pyrazolo[1,5-a]pyrimidin-2-yl]benzonitrile;

2-(3-cyano-2-methyl-phenyl)-3-(2,6-dimethyl-4-pyridyl)-N-[(1S)-2-hydroxy-1,2-dimethyl-propyl]pyrazolo[1,5-a]pyrimidine-5-carboxamide;

N-[3-(2-chloro-6-methyl-4-pyridyl)-2-(3-cyanophenyl)pyrazolo[1,5-a]pyrimidin-5-yl]-3-hydroxy-3-methyl-butanamide;

3-[3-(2-chloro-6-methyl-4-pyridyl)-5-[(3-hydroxyoxetan-3-yl)methylamino]pyrazolo[1,5-a]pyrimidin-2-yl]benzonitrile;

3-[3-(2-chloro-6-methyl-4-pyridyl)-5-[[1-(2-hydroxyethyl)-4-piperidyl]amino]pyrazolo[1,5-a]pyrimidin-2-yl]benzonitrile;

3-[3-(2-chloro-6-methyl-4-pyridyl)-5-[(3-hydroxy-3-methyl-butyl)amino]pyrazolo[1,5-a]pyrimidin-2-yl]benzonitrile;

1-[3-(2-chloro-6-methyl-4-pyridyl)-2-(3-cyanophenyl)pyrazolo[1,5-a]pyrimidin-5-yl]guanidine;

2-(3-cyanophenyl)-3-(2,6-dimethyl-4-pyridyl)pyrazolo[1,5-a]pyrimidine-5-carboxamidine;

2-(3-cyanophenyl)-3-(2,6-dimethyl-4-pyridyl)-N-(2-hydroxy-2-methyl-propoxy)pyrazolo[1,5-a]pyrimidine-5-carboxamide;

3-[3-(2-chloro-6-methyl-4-pyridyl)-5-[(5-oxopyrrolidin-3-yl)methylamino]pyrazolo[1,5-a]pyrimidin-2-yl]benzonitrile;

3-[3-(2-chloro-6-methyl-4-pyridyl)-5-[(3S)-3-(1-hydroxy-1-methyl-ethyl)piperazin-1-yl]pyrazolo[1,5-a]pyrimidin-2-yl]benzonitrile;

3-[3-(2,6-dimethyl-4-pyridyl)-5-[(1-methyl-2-oxo-4-piperidyl)amino]pyrazolo[1,5-a]pyrimidin-2-yl]benzonitrile;

N-[2-(3-cyanophenyl)-3-(2,6-dimethyl-4-pyridyl)pyrazolo[1,5-a]pyrimidin-5-yl]-3-hydroxy-3-methyl-butanamide;

N-[3-(2-chloro-6-methyl-4-pyridyl)-2-(3-cyanophenyl)pyrazolo[1,5-a]pyrimidin-5-yl]acetamide

[2-(3-cyanophenyl)-3-(2,6-dimethyl-4-pyridyl)pyrazolo[1,5-a]pyrimidin-5-yl]urea;

2-(3-cyanophenyl)-3-(2,6-dimethyl-4-pyridyl)-N-[(3-hydroxyoxetan-3-yl)methyl]pyrazolo[1,5-a]pyrimidine-5-carboxamide;

3-[3-(2-chloro-6-methyl-4-pyridyl)-5-[[(1S)-2-hydroxy-1,2-dimethyl-propyl]amino]pyrazolo[1,5-a]pyrimidin-2-yl]benzonitrile;

3-[3-(2-chloro-6-methyl-4-pyridyl)-5-[[rac-(2S)-2-hydroxypropyl]amino]pyrazolo{1,5-a]pyrimidin-2-yl]benzonitrile;

3-(2-chloro-6-methyl-4-pyridyl)-2-(3-cyanophenyl)-N-[(1S,3S)-3-aminocyclopentyl]pyrazolo[1,5-a]pyrimidine-5-carboxamide;

m-{4-[({[(3S)-5-Oxo-3-pyrrolidinyl]methyl}amino)carbonyl]-7-(2,6-dimethyl-4-pyridyl)-1.5,9-triazabicyclo[4.3.0]nona-2,4,6,8-tetraen-8-yl}benzonitrile;

3-[5-[(2-amino-2-methyl-propyl)amino]-3-(2-chloro-6-methyl-4-pyridyl)pyrazolo[1,5-a]pyrimidin-2-yl]benzonitrile;

3-(2-cyano-6-methyl-4-pyridyl)-2-(3-cyanophenyl)-N-(2-hydroxy-2-methyl-propyl)pyrazolo[1,5-a]pyrimidine-5-carboxamide;

3-[3-(2-chloro-6-methyl-4-pyridyl)-5-[[rac-(1R)-2-hydroxy-1,2-dimethyl-propyl]amino]pyrazolo[1,5-a]pyrimidin-2-yl]benzonitrile;

N-[2-(3-cyanophenyl)-3-(2,6-dimethyl-4-pyridyl)pyrazolo[1,5-a]pyrimidin-5-yl]-2-hydroxy-2-methyl-propanamide;

3-(2-chloro-6-methyl-4-pyridyl)-2-(3-cyanophenyl)-N-[rac-(3S)-3-piperidyl]pyrazolo[1,5-a]pyrimidine-5-carboxamide;

2-(3-cyanophenyl)-3-(3-fluoro-2,6-dimethyl-4-pyridyl)-N-(2-hydroxy-2-methyl-propyl)pyrazolo[1,5-a]pyrimidine-5-carboxamide;

2-(3-cyanophenyl)-3-(2,6-dimethyl-4-pyridyl)-N-[(2-oxo-4-piperidyl)methyl]pyrazolo[1,5-a]pyrimidine-5-carboxamide;

2-(3-cyanophenyl)-3-(3-fluoro-2,6-dimethyl-4-pyridyl)-N-[(4-methyl-2,5-dioxo-imidazolidin-4-yl)methyl]pyrazolo[1,5-a]pyrimidine-5-carboxamide;

2-(3-cyanophenyl)-3-(2,6-dimethyl-4-pyridyl)-N-(5-oxopyrrolidin-3-yl)pyrazolo[1,5-a]pyrimidine-5-carboxamide;

2-(3-cyanophenyl)-3-(2,6-dimethyl-4-pyridyl)pyrazolo[1,5-a]pyrimidine-5-carboxamide;

3-[3-(2-chloro-6-methyl-4-pyridyl)-5-[(3R)-3-(1-hydroxy-1-methyl-ethyl)piperazin-1-yl]pyrazolo[1,5-a]pyrimidin-2-yl]benzonitrile;

m-[7-(2,6-Dimethyl-4-pyridyl)-4-({[(5-oxo-3-pyrrolidinyl)methyl]amino}carbonyl)-1.5.9-triazabicyclo[4.3.0]nona-2,4,6,8-tetraen-8-yl]benzonitrile;

3-[3-(2-chloro-6-methyl-4-pyridyl)-5-[[(1R,2S)-2-hydroxycyclobutyl]amino]pyrazolo[1,5-a]pyrimidin-2-yl]benzonitrile;

m-{4-[({[(3R)-5-Oxo-3-pyrrolidinyl]methyl}amino)carbonyl]-7-(2,6-dimethyl-4-pyridyl)-1.5.9-triazabicyclo[4.3.0]nona-2,4,6,8-tetraen-8-yl}benzonitrile;

3-[3-(2-chloro-6-methyl-4-pyridyl)-5-[(3-hydroxyazetidin-3-yl)methylamino]pyrazolo[1,5-a]pyrimidin-2-yl]benzonitrile;;

4-[5-amino-2-(3-cyanophenyl)pyrazolo[1,5-a]pyrimidin-3-yl]-6-methyl-pyridine-2-carbonitrile;

3-[3-(2-chloro-6-methyl-4-pyridyl)-5-(1-imino-1-oxo-1,4-thiazinan-4-yl)pyrazolo[1,5-a]pyrimidin-2-yl]benzonitrile;

3-[5-[(1-acetyl-4-piperidyl)amino]-3-(2,6-dimethyl-4-pyridyl)pyrazolo[1,5-a]pyrimidin-2-yl]benzonitrile;

2-(3-cyanophenyl)-3-(2,6-dimethyl-4-pyridyl)-N-[(5-oxomorpholin-2-yl)methyl]pyrazolo[1,5-a]pyrimidine-5-carboxamide;

3-[3-(2-chloro-6-methyl-4-pyridyl)-5-[(3R)-pyrrolidin-3-yl]oxy-pyrazolo[1,5-a]pyrimidin-2-yl]benzonitrile;

1-(2-amino-2-methyl-propyl)-3-[3-(2-chloro-6-methyl-4-pyridyl)-2-(3-cyanophenyl)pyrazolo[1,5-a]pyrimidin-5-yl]urea.

Particular compounds of the present invention include any of the compounds described in the example section of the present application, or a pharmaceutically acceptable salt or solvate thereof, and, in particular, any of the following:

3-[5-Amino-3-(4-pyridyl)pyrazolo[1,5-a]pyrimidin-2-yl]benzonitrile;

3-[5-Amino-3-(1H-pyrazol-4-yl)pyrazolo[1,5-a]pyrimidin-2-yl]benzonitrile;

3-(5-Amino-3-pyridazin-4-yl-pyrazolo[1,5-a]pyrimidin-2-yl)benzonitrile;

3-[5-Amino-3-(2-ethylpyrazol-3-yl)pyrazolo[1,5-a]pyrimidin-2-yl]benzonitrile;

3-[5-Amino-3-(2-chloro-6-methyl-4-pyridyl)pyrazolo[1,5-a]pyrimidin-2-yl]benzonitrile;

3-[5-Amino-3-(2,6-dimethyl-4-pyridyl)pyrazolo[1,5-a]pyrimidin-2-yl]benzonitrile;

3-[3-(2-Chloro-6-methyl-4-pyridyl)-5-[(2-hydroxy-2-methyl-propyl)amino]pyrazolo[1,5-a]pyrimidin-2-yl]benzonitrile;

3-[3-(2-Chloro-6-methyl-4-pyridyl)-5-[(3-hydroxy-1-bicyclo[1.1.1]pentanyl)amino]pyrazolo[1,5-a]pyrimidin-2-yl]benzonitrile;

3-[3-(2-Chloro-6-methyl-4-pyridyl)-5-(8-methyl-3,8-diazabicyclo[3.2.1]octan-3-yl)pyrazolo[1,5-a]pyrimidin-2-yl]benzonitrile;

(3S)-4-[3-(2-Chloro-6-methyl-4-pyridyl)-2-(3-cyanophenyl)pyrazolo[1,5-a]pyrimidin-5-yl]morpholine-3-carboxylic acid;

3-[3-(2-Chloro-6-methyl-4-pyridyl)-5-[(1-ethyl-4-piperidyl)amino]pyrazolo[1,5-a]pyrimidin-2-yl]benzonitrile;

3-[3-(2-Chloro-6-methyl-4-pyridyl)-5-[[(3S,4S)-4-methoxy-1-methyl-pyrrolidin-3-yl]amino]pyrazolo[1,5-a]pyrimidin-2-yl]benzonitrile;

3-[3-(2-Chloro-6-methyl-4-pyridyl)-5-[[(3R)-tetrahydrofuran-3-yl]amino]pyrazolo[1,5-a]pyrimidin-2-yl]benzonitrile;

3-[3-(2-Chloro-6-methyl-4-pyridyl)-5-[3-(hydroxymethyl)-4-methyl-piperazin-1-yl]pyrazolo[1,5-a]pyrimidin-2-yl]benzonitrile;

3-[3-(2-Chloro-6-methyl-4-pyridyl)-5-[(3-hydroxyoxetan-3-yl)methylamino]pyrazolo [1,5-a]pyrimidin-2-yl]benzonitrile;

3-[3-(2-Chloro-6-methyl-4-pyridyl)-5-[(3-hydroxy-3-methyl-butyl)amino]pyrazolo [1,5-a]pyrimidin-2-yl]benzonitrile;

3-[3-(2-Chloro-6-methyl-4-pyridyl)-5-[(3-hydroxycyclobutyl)amino]pyrazolo[1,5-a]pyrimidin-2-yl]benzonitrile;

3-[3-(2-Chloro-6-methyl-4-pyridyl)-5-[(1-methylsulfonyl-4-piperidyl)amino]pyrazolo[1,5-a]pyrimidin-2-yl]benzonitrile;

3-[3-(2-Chloro-6-methyl-4-pyridyl)-5-(8-oxa-3-azabicyclo[3.2.1]octan-3-yl)pyrazolo[1,5-a]pyrimidin-2-yl]benzonitrile;

3-[[3-(2-Chloro-6-methyl-4-pyridyl)-2-(3-cyanophenyl)pyrazolo[1,5-a]pyrimidin-5-yl]amino]-2,2-dimethyl-propanoic acid;

3-[3-(2-Chloro-6-methyl-4-pyridyl)-5-[(5-oxopyrrolidin-3-yl)methylamino]pyrazolo[1,5-a]pyrimidin-2-yl]benzonitrile;

3-[3-(2-Chloro-6-methyl-4-pyridyl)-5-[[(1S)-2-hydroxy-1,2-dimethyl-propyl]amino]pyrazolo[1,5-a]pyrimidin-2-yl]benzonitrile;

3-[3-(2-Chloro-6-methyl-4-pyridyl)-5-[[rac-(3R,4R)-4-hydroxytetrahydrofuran-3-yl]amino]pyrazolo[1,5-a]pyrimidin-2-yl]benzonitrile;

3-[3-(2-Chloro-6-methyl-4-pyridyl)-5-(quinuclidin-3-ylamino)pyrazolo[1,5-a]pyrimidin-2-yl]benzonitrile;

3-[3-(2-Chloro-6-methyl-4-pyridyl)-5-[(3-hydroxycyclobutyl)amino]pyrazolo[1,5-a]pyrimidin-2-yl]benzonitrile;

3-[3-(2-Chloro-6-methyl-4-pyridyl)-5-(2-morpholinoethylamino)pyrazolo[1,5-a]pyrimidin-2-yl]benzonitrile;

3-[3-(2-Chloro-6-methyl-4-pyridyl)-5-[[(1R)-2-hydroxy-1,2-dimethyl-propyl]amino]pyrazolo[1,5-a]pyrimidin-2-yl]benzonitrile;

3-[3-(2-Chloro-6-methyl-4-pyridyl)-5-[2-[2-(dimethylamino)ethyl]morpholin-4-yl]pyrazolo[1,5-a]pyrimidin-2-yl]benzonitrile;

3-[3-(2-Chloro-6-methyl-4-pyridyl)-5-[[(1R,2S)-2-hydroxycyclobutyl]amino]pyrazolo[1,5-a]pyrimidin-2-yl]benzonitrile;

3-[3-(2-Chloro-6-methyl-4-pyridyl)-5-(4H-1,2,4-triazol-3-ylmethylamino)pyrazolo[1,5-a]pyrimidin-2-yl]benzonitrite;

(2R)-4-[3-(2-Chloro-6-methyl-4-pyridyl)-2-(3-cyanophenyl)pyrazolo[1,5-a]pyrimidin-5-yl]morpholine-2-carboxylic acid;

3-[3-(2-Chloro-6-methyl-4-pyridyl)-5-[[(3S)-tetrahydrofuran-3-yl]amino]pyrazolo[1,5-a]pyrimidin-2-yl]benzonitrile;

3-[3-(2-Chloro-6-methyl-4-pyridyl)-5-(1-imino-1-oxo-1,4-thiazinan-4-yl)pyrazolo [1,5-a]pyrimidin-2-yl]benzonitrile;

3-[3-(2-Chloro-6-methyl-4-pyridyl)-5-[(1,1-dioxothian-4-yl)amino]pyrazolo[1,5-a]pyrimidin-2-yl]benzonitrile;

2-[[3-(2-Chloro-6-methyl-4-pyridyl)-2-(3-cyanophenyl)pyrazolo[1,5-a]pyrimidin-5-yl]amino]acetamide;

3-[3-(2-Chloro-6-methyl-4-pyridyl)-5-piperazin-1-yl-pyrazolo[1,5-a]pyrimidin-2-yl]benzonitrile;

3-[3-(2-Chloro-6-methyl-4-pyridyl)-5-[[2-(dimethylamino)-1-methyl-ethyl]amino]pyrazolo[1,5-a]pyrimidin-2-yl]benzonitrile;

3-[3-(2-Chloro-6-methyl-4-pyridyl)-5-hydroxy-pyrazolo[1,5-a]pyrimidin-2-yl]benzonitrile;

3-[3-(2-Chloro-6-methyl-4-pyridyl)-5-(1H-imidazol-2-ylmethylamino)pyrazolo[1,5-a]pyrimidin-2-yl]benzonitrile;

3-[3-(2-Chloro-6-methyl-4-pyridyl)-5-morpholino-pyrazolo[1,5-a]pyrimidin-2-yl]benzonitrile;

1-[3-(2-Chloro-6-methyl-4-pyridyl)-2-(3-cyanophenyl)pyrazolo[1,5-a]pyrimidin-5-yl]azetidine-2-carboxylic acid;

1-[3-(2-Chloro-6-methyl-4-pyridyl)-2-(3-cyanophenyl)pyrazolo[1,5-a]pyrimidin-5-yl]azetidine-3-carboxylic acid;

(3R)-1-[3-(2-Chloro-6-methyl-4-pyridyl)-2-(3-cyanophenyl)pyrazolo[1,5-a]pyrimidin-5-yl]pyrrolidine-3-carboxylic acid;

4-[3-(2-Chloro-6-methyl-4-pyridyl)-2-(3-cyanophenyl)pyrazolo[1,5-a]pyrimidin-5-yl]piperazine-1-sulfonamide;

3-[[3-(2-Chloro-6-methyl-4-pyridyl)-2-(3-cyanophenyl)pyrazolo[1,5-a]pyrimidin-5-yl]amino]bicyclo[1.1.1]pentane-1-carboxylic acid;

3-[3-(2-Chloro-6-methyl-4-pyridyl)-5-[[(2R)-2-hydroxypropyl]amino]pyrazolo[1,5-a]pyrimidin-2-yl]benzonitrile;

3-[3-(2-Chloro-6-methyl-4-pyridyl)-5-[[(2S)-2-hydroxypropyl]amino]pyrazolo[1,5-a]pyrimidin-2-yl]benzonitrile;

3-[5-(tert-Butylamino)-3-(2-chloro-6-methyl-4-pyridyl)pyrazolo[1,5-a]pyrimidin-2-yl]benzonitrile;

3-[3-(2-Chloro-6-methyl-4-pyridyl)-5-[[(1R)-2-hydroxy-1-methyl-ethyl]amino]pyrazolo [1,5-a]pyrimidin-2-yl]benzonitrile;

3-[3-(2-Chloro-6-methyl-4-pyridyl)-5-[(1-hydroxycyclopropyl)methylamino]pyrazoo[1,5-a]pyrimidin-2-yl]benzonitrile;

3-[3-(2-Chloro-6-methyl-4-pyridyl)-5-(4-piperidylamino)pyrazolo[1,5-a]pyrimidin-2-yl]benzonitrile;

3-[3-(2-Chloro-6-methyl-4-pyridyl)-5-[[(3R)-morpholin-3-yl]methylamino]pyrazolo[1,5-a]pyrimidin-2-yl]benzonitrile;

tert-Butyl(3R)-3-[[[3-(2-chloro-6-methyl-4-pyridyl)-2-(3-cyanophenyl)pyrazolo[1,5-a]pyrimidin-5-yl]amino]methyl]morpholine-4-carboxylate;

3-[3-(2-Chloro-6-methyl-4-pyridyl)-5-[[(3R)-3-piperidyl]amino]pyrazolo[1,5-a]pyrimidin-2-yl]benzonitrile;

tert-Butyl(3R)-3-[[3-(2-chloro-6-methyl-4-pyridyl)-2-(3-cyanophenyl)pyrazolo[1,5-a]pyrimidin-5-yl]amino]piperidine-1-carboxylate;

3-[3-(2-Chloro-6-methyl-4-pyridyl)-5-[[(3R)-pyrrolidin-3-yl]amino]pyrazolo[1,5-a]pyrimidin-2-yl}benzonitrile;

tert-Butyl(3R)-3-[[3-(2-chloro-6-methyl-4-pyridyl)-2-(3-cyanophenyl)pyrazolo[1,5-a]pyrimidin-5-yl]amino]pyrrolidine-1-carboxylate;

3-[3-(2-Chloro-6-methyl-4-pyridyl)-5-[rac-(4aS,7aS)-3,4,4a,5,7,7a-hexahydro-2H-pyrrolo[3,4-b][1,4]oxazin-6-yl]pyrazolo[1,5-a]pyrimidin-2-yl]benzonitrile;

tert-Butyl rac-(4aS,7aS)-6-[3-(2-chloro-6-methyl-4-pyridyl)-2-(3-cyanophenyl)pyrazolo[1,5-a]pyrimidin-5-yl]-2,3,4a,5,7,7a-hexahydropyrrolo[3,4-b][1,4]oxazine-4-carboxylate;

3-[3-(2-Chloro-6-methyl-4-pyridyl)-5-[[(3S)-morpholin-3-yl]methylamino]pyrazolo[1,5-a]pyrimidin-2-yl]benzonitrile;

tert-Butyl(3S)-3-[[[3-(2-chloro-6-methyl-4-pyridyl)-2-(3-cyanophenyl)pyrazolo[1,5-a]pyrimidin-5-yl]amino]methyl]morpholine-4-carboxylate;

3-[3-(2-Chloro-6-methyl-4-pyridyl)-5-[[(3S)-pyrrolidin-3-yl]amino]pyrazolo[1,5-a]pyrimidin-2-yl]benzonitrile;

tert-Butyl(3S)-3-[[3-(2-chloro-6-methyl-4-pyridyl)-2-(3-cyanophenyl)pyrazolo[1,5-a]pyrimidin-5-yl]amino]pyrrolidine-1-carboxylate;

3-[3-(2-Chloro-6-methyl-4-pyridyl)-5-[[(3S)-3-piperidyl]amino]pyrazolo[1,5-a]pyrimidin-2-yl]benzonitrile;

tert-Butyl(3S)-3-[[3-(2-chloro-6-methyl-4-pyridyl)-2-(3-cyanophenyl)pyrazolo[1,5-a]pyrimidin-5-yl]amino]piperidine-1-carboxylate;

3-(2-Chloro-6-methyl-4-pyridyl)-2-(3-cyanophenyl)-N-(3-hydroxy-1-bicyclo[1.1.1]penta nyl)pyrazolo[1,5-a]pyrimidine-5-carboxamide;

N-tert-Butyl-3-(2-chloro-6-methyl-4-pyridyl)-2-(3-cyanophenyl)pyrazolo[1,5-a]pyrimidine-5-carboxamide;

3-(2-Chloro-6-methyl-4-pyridyl)-2-(3-cyanophenyl)-N-(2-hydroxy-2-methyl-propyl)pyrazolo[1,5-a]pyrimidine-5-carboxamide;

3-(2-Chloro-6-methyl-4-pyridyl)-2-(3-cyanophenyl)-N-(3-hydroxy-3-methyl-butyl)pyrazolo[1,5-a]pyrimidine-5-carboxamide;

3-(2-Chloro-6-methyl-4-pyridyl)-2-(3-cyanophenyl)-N-[2-(4-phenylpiperazin-1-yl)ethyl]pyrazolo[1,5-a]pyrimidine-5-carboxamide;

3-(2-Chloro-6-methyl-4-pyridyl)-2-(3-cyanophenyl)-N-(oxetan-3-yl)pyrazolo[1,5-a]pyrimidine-5-carboxamide;

3-(2-Chloro-6-methyl-4-pyridyl)-2-(3-cyanophenyl)pyrazolo[1,5-a]pyrimidine-5-carboxamide;

3-[3-(2-Chloro-6-methyl-4-pyridyl)-5-(morpholine-4-carbonyl)pyrazoo[1,5-a]pyrimidin-2-yl]benzonitrile;

3-(2-Chloro-6-methyl-4-pyridyl)-2-(3-cyanophenyl)-N-[(1S)-2-hydroxy-1,2-dimethyl-propyl]pyrazolo{1,5-a]pyrimidine-5-carboxamide;

N-(2-Amino-2-methyl-propyl)-3-(2-chloro-6-methyl-4-pyridyl)-2-(3-cyanophenyl)pyrazolo[1,5-a]pyrimidine-5-carboxamide;

3-(2-Chloro-6-methyl-4-pyridyl)-2-(3-cyanophenyl)-N-[(1-hydroxycyclopropyl)methyl]pyrazolo[1,5-a]pyrimidine-5-carboxamide;

3-(2-Chloro-6-methyl-4-pyridyl)-2-(3-cyanophenyl)-N-[(1-hydroxycyclobutyl)methyl]pyrazolo[1,5-a]pyrimidine-5-carboxamide;

3-(2-Chloro-6-methyl-4-pyridyl)-2-(3-cyanophenyl)-N-[(1R)-2-hydroxy-1,2-dimethyl-propyl]pyrazolo[1,5-a]pyrimidine-5-carboxamide;

3-(2-Chloro-6-methyl-4-pyridyl)-2-(3-cyanophenyl)-N-[(2R)-2-hydroxypropyl]pyrazolo[1,5-a]pyrimidine-5-carboxamide;

3-(2-Chloro-6-methyl-4-pyridyl)-2-(3-cyanophenyl)-N-[(1R)-2-hydroxy-1-methyl-ethyl]pyrazolo[1,5-a]pyrimidine-5-carboxamide;

3-(2-Chloro-6-methyl-4-pyridyl)-2-(3-cyanophenyl)-N-[(3-hydroxyoxetan-3-yl)methyl]pyrazolo[1,5-a]pyrimidine-5-carboxamide;

3-(2-Chloro-6-methyl-4-pyridyl)-2-(3-cyanophenyl)-N-methylsulfonyl-pyrazolo[1,5-a]pyrimidine-5-carboxamide;

3-(2-Chloro-6-methyl-4-pyridyl)-2-(3-cyanophenyl)-N-(2,3-dihydroxy-2-methyl-propyl)pyrazolo[1,5-a]pyrimidine-5-carboxamide;

3-(2-Chloro-6-methyl-4-pyridyl)-2-(3-cyanophenyl)-N-[(3-hydroxycyclobutyl)methyl]pyrazolo[1,5-a]pyrimidine-5-carboxamide;

3-(2-Chloro-6-methyl-4-pyridyl)-N-(1-cyano-2-methoxy-1-methyl-ethyl)-2-(3-cyanophenyl)pyrazolo[1,5-a]pyrimidine-5-carboxamide;

N-(4-Aminonorbornan-1-yl)-3-(2-chloro-6-methyl-4-pyridyl)-2-(3-cyanophenyl)pyrazolo(1,5-a]pyrimidine-5-carboxamide;

3-(2-Chloro-6-methyl-4-pyridyl)-2-(3-cyanophenyl)-N-[(2S)-2,3-dihydroxypropyl]pyrazolo[1,5-a]pyrimidine-5-carboxamide;

3-(2-Chloro-6-methyl-4-pyridyl)-2-(3-cyanophenyl)-N-[(3S,4S)-4-methoxy-1-methyl-pyrrolidin-3-yl]pyrazolo[1,5-a]pyrimidine-5-carboxamide;

3-(2-Chloro-6-methyl-4-pyridyl)-2-(3-cyanophenyl)-N-[(2R)-2,3-dihydroxypropyl]pyrazolo[1,5-a]pyrimidine-5-carboxamide;

3-(2-Chloro-6-methyl-4-pyridyl)-2-(3-cyanophenyl)-N-(1-methylazetidin-3-yl)pyrazolo[1,5-a]pyrimidine-5-carboxamide;

3-(2-Chloro-6-methyl-4-pyridyl)-2-(3-cyanophenyl)-N-[(3S,4S)-4-hydroxytetrahydrofuran-3-yl]pyrazolo[1,5-a]pyrimidine-5-carboxamide;

3-(2-Chloro-6-methyl-4-pyridyl)-2-(3-cyanophenyl)-N-(2-hydroxy-2-methyl-propyl)-N-methyl-pyrazolo[1,5-a]pyrimidine-5-carboxamide;

N-(3-Amino-3-methyl-butyl)-3-(2-chloro-6-methyl-4-pyridyl)-2-(3-cyanophenyl)pyrazolo [1,5-a]pyrimidine-5-carboxamide;

N-(3-Amino-1-bicyclo[1.1.1]pentanyl)-3-(2-chloro-6-methyl-4-pyridyl)-2-(3-cyanophenyl)pyrazolo[1,5-a]pyrimidine-5-carboxamide;

tert-Butyl N-[3-[[3-(2-chloro-6-methyl-4-pyridyl)-2-(3-cyanophenyl)pyrazolo[1,5-a]pyrimidine-5-carbonyl]amino]-1-bicyclo[1.1.1]pentanyl]carbamate;

3-(2-Chloro-6-methyl-4-pyridyl)-2-(3-cyanophenyl)-N-[cis-(3S,4R)-4-hydroxypyrrolidin-3-yl]pyrazolo[1,5-a]pyrimidine-5-carboxamide;

tert-Butyl(3S,4R)-3-[[3-(2-chloro-6-methyl-4-pyridyl)-2-(3-cyanophenyl)pyrazolo[1,5-a]pyrimidine-5-carbonyl]amino]-4-hydroxy-pyrrolidine-1-carboxylate;

N-(2-Amino-1,1-dimethyl-ethyl)-3-(2-chloro-6-methyl-4-pyridyl)-2-(3-cyanophenyl)pyrazolo[1,5-a]pyrimidine-5-carboxamide;

tert-Butyl N-[2-[[3-(2-chloro-6-methyl-4-pyridyl)-2-(3-cyanophenyl)pyrazolo[1,5-a]pyrimidine-5-carbonyl]amino]-2-methyl-propyl]carbamate;

3-(2-Chloro-6-methyl-4-pyridyl)-2-(3-cyanophenyl)-N-[(3S)-3-piperidyl]pyrazolo[1,5-a]pyrimidine-5-carboxamide;

tert-Butyl(3S)-3-[[3-(2-chloro-6-methyl-4-pyridyl)-2-(3-cyanophenyl)pyrazolo[1,5-a]pyrimidine-5-carbonyl]amino]piperidine-1-carboxylate;

3-(2-Chloro-6-methyl-4-pyridyl)-2-(3-cyanophenyl)-N-[trans-(3S,4S)-4-hydroxypyrrolidin-3-yl]pyrazolo[1,5-a]pyrimidine-5-carboxamide;

tert-Butyl trans-(3S,4S)-3-[[3-(2-chloro-6-methyl-4-pyridyl)-2-(3-cyanophenyl) pyrazolo[1,5-a]pyrimidine-5-carbonyl]amino]-4-hydroxy-pyrrolidine-1-carboxylate;

3-(2-Chloro-6-methyl-4-pyridyl)-2-(3-cyanophenyl)-N-[(3-hydroxypyrrolidin-3-yl)methyl]pyrazolo[1,5-a]pyrimidine-5-carboxamide;

tert-Butyl 3-[[[3-(2-chloro-6-methyl-4-pyridyl)-2-(3-cyanophenyl) pyrazolo[1,5-a]pyrimidine-5-carbonyl]amino]methyl]-3-hydroxy-pyrrolidine-1-carboxylate;

3-(2-Chloro-6-methyl-4-pyridyl)-2-(3-cyanophenyl)-N-[(3R)-3-piperidyl]pyrazolo[1,5-a]pyrimidine-5-carboxamide;

tert-Butyl(3R)-3-[[3-(2-chloro-6-methyl-4-pyridyl)-2-(3-cyanophenyl)pyrazolo[1,5-a]pyrimidine-5-carbonyl]amino]piperidine-1-carboxylate;

3-(2-Chloro-6-methyl-4-pyridyl)-2-(3-cyanophenyl)-N-(3-methylpyrrolidin-3-yl)pyrazolo[1,5-a]pyrimidine-5-carboxamide;

Tert-butyl 3-[[3-(2-chloro-6-methyl-4-pyridyl)-2-(3-cyanophenyl)pyrazolo[1,5-a]pyrimidine-5-carbonyl]amino]-3-methyl-pyrrolidine-1-carboxylate;

3-(2-Chloro-6-methyl-4-pyridyl)-2-(3-cyanophenyl)-N-[(1R,2S)-2,3-dihydroxy-1-methyl-propyl]pyrazolo[1,5-a]pyrimidine-5-carboxamide;

3-(2-Chloro-6-methyl-4-pyridyl)-2-(3-cyanophenyl)-N-[(1R)-1-[(4S)-2,2-dimethyl-1,3-dioxolan-4-yl]ethyl]pyrazolo [1,5-a]pyrimidine-5-carboxamide;

N-[(1-Amino-3,3-difluoro-cyclobutyl)methyl]-3-(2-chloro-6-methyl-4-pyridyl)-2-(3-cyanophenyl)pyrazolo[1,5-a]pyrimidine-5-carboxamide;

tert-Butyl N-[1-[[[3-(2-chloro-6-methyl-4-pyridyl)-2-(3-cyanophenyl)pyrazolo[1,5-a]pyrimidine-5-carbonyl]amino]methyl]-3,3-difluoro-cyclobutyl]carbamate;

3-(2-Chloro-6-methyl-4-pyridyl)-2-(3-cyanophenyl)-N-(morpholin-2-ylmethyl)pyrazolo[1,5-a]pyrimidine-5-carboxamide;

tert-Butyl 2-[[[3-(2-chloro-6-methyl-4-pyridyl)-2-(3-cyanophenyl)pyrazolo[1,5-a]pyrimidine-5-carbonyl]amino]methyl]morpholine-4-carboxylate;

3-[3-(2-Chloro-6-methyl-4-pyridyl)-5-(piperazine-1-carbonyl)pyrazolo[1,5-a]pyrimidin-2-yl]benzonitrile;

Tert-butyl 4-[3-(2-chloro-6-methyl-4-pyridyl)-2-(3-cyanophenyl)pyrazolo[1,5-a]pyrimidine-5-carbonyl]piperazine-1-carboxylate;

3-(2-Chloro-6-methyl-4-pyridyl)-2-(3-cyanophenyl)-N-[(3R)-pyrrolidin-3-yl]pyrazolo[1,5-a]pyrimidine-5-carboxamide;

Tert-butyl(3R)-3-[[3-(2-chloro-6-methyl-4-pyridyl)-2-(3-cyanophenyl)pyrazolo[1,5-a]pyrimidine-5-carbonyl]amino]pyrrolidine-1-carboxylate;

3-[3-(2-Chloro-6-methyl-4-pyridyl)-5-(1-hydroxy-1-methyl-ethyl)pyrazolo[1,5-a]pyrimidin-2-yl]benzonitrile;

3-(2-Chloro-6-methyl-4-pyridyl)-2-(3-cyanophenyl)pyrazolo[1,5-a]pyrimidine-5-carboxylic acid;

2-(3-Cyanophenyl)-3-(2,6-dimethyl-4-pyridyl)-N-(2-hydroxy-2-methyl-propyl)pyrazoo[1,5-a]pyrimidine-5-carboxamide;

2-(3-Cyanophenyl)-3-(2-ethylpyrazol-3-yl)-N-(2-hydroxy-2-methyl-propyl)pyrazolo[1,5-a]pyrimidine-5-carboxamide;

2-(3-Cyanophenyl)-3-(2-ethyl-5-methyl-pyrazol-3-yl)-N-(2-hydroxy-2-methyl-propyl)pyrazolo[1,5-a]pyrimidine-5-carboxamide;

2-(3-Cyanophenyl)-N-(2-hydroxy-2-methyl-propyl)-3-(2-methyl-4-pyridyl)pyrazolo[1,5-a]pyrimidine-5-carboxamide;

2-(3-Cyanophenyl)-3-(2-ethyl-4-methyl-pyrazol-3-yl)-N-(2-hydroxy-2-methyl-propyl)pyrazolo[1,5-a]pyrimidine-5-carboxamide;

2-(3-Cyanophenyl)-3-[2-(difluoromethyl)-6-methyl-4-pyridyl]-N-(2-hydroxy-2-methyl-propyl)pyrazolo[1,5-a]pyrimidine-5-carboxamide;

2-(3-Cyanophenyl)-N-(2-hydroxy-2-methyl-propyl)-3-(2-methylpyrazol-3-yl)pyrazolo[1,5-a]pyrimidine-5-carboxamide;

2-(3-Cyanophenyl)-N-(2-hydroxy-2-methyl-propyl)-3-pyrimidin-4-yl-pyrazolo[1,5-a]pyrimidine-5-carboxamide;

3-Cyano-2-(3-cyanophenyl)-N-(2-hydroxy-2-methyl-propyl)pyrazolo[1,5-a]pyrimidine-5-carboxamide;

3-[3-(2-Chloro-6-methyl-4-pyridyl)-5-(2-hydroxy-2-methyl-propoxy)pyrazolo[1,5-a]pyrimidin-2-yl]benzonitrile;

N-[3-(2-Chloro-6-methyl-4-pyridyl)-2-(3-cyanophenyl)pyrazolo[1,5-a]pyrimidin-5-yl]methanesulfonamide;

(2S)-2-[[3-(2-Chloro-6-methyl-4-pyridyl)-2-(3-cyanophenyl)pyrazolo[1,5-a]pyrimidin-5-yl]amino]propanoic acid;

3-{3-(2-Chloro-6-methyl-4-pyridyl)-5-[(3R)-pyrrolidin-3-yl]oxy-pyrazolo[1,5-a]pyrimidin-2-yl]benzonitrile formate;

3-[3-(2-Chloro-6-methyl-4-pyridyl)-5-(2-hydroxyethylamino)pyrazolo[1,5-a]pyrimidin-2-yl]benzonitrile;

3-[3-(2-Chloro-6-methyl-4-pyridyl)-5-(morpholinomethyl)pyrazolo[1,5-a]pyrimidin-2-yl]benzonitrile;

3-[5-(Aminomethyl)-3-(2-chloro-6-methyl-4-pyridyl)pyrazolo[1,5-a]pyrimidin-2-yl]benzonitrile;

3-[3-(2-Chloro-6-methyl-4-pyridyl)-5-(3-hydroxy-3-methyl-butyl)pyrazolo[1,5-a]pyrimidin-2-yl]benzonitrile;

3-[3-[2-(Difluoromethyl)-6-methyl-4-pyridyl]-5-[(2-hydroxy-2-methyl-propyl)amino]pyrazolo[1,5-a]pyrimidin-2-yl]benzonitrile;

3-[5-[(2-Hydroxy-2-methyl-propyl)amino]-3-(2-methoxy-6-methyl-4-pyridyl)pyrazolo[1,5-a]pyrimidin-2-yl]benzonitrile;

3-[3-(2,6-Dimethyl-4-pyridyl)-5-[(2-hydroxy-2-methyl-propyl)amino]pyrazolo[1,5-a]pyrimidin-2-yl]benzonitrile;

3-[3-(2-Chloro-6-methyl-4-pyridyl)-5-[[(1S)-2-hydroxy-1-methyl-ethyl]amino]pyrazolo[1,5-a]pyrimidin-2-yl]benzonitrile;

3-[3-(2-Chloro-6-methyl-4-pyridyl)-5-(dimethylamino)pyrazolo[1,5-a]pyrimidin-2-yl]benzonitrile;

3-[3-(2-Chloro-6-methyl-4-pyridyl)-5-(4-piperidyloxy)pyrazolo[1,5-a]pyrimidin-2-yl]benzonitrile;

3-[3-(2-Chloro-6-methyl-4-pyridyl)-5-[[(3R)-3-piperidyl]oxy]pyrazclo[1,5-a]pyrimidin-2-yl]benzonitrile;

tert-Butyl(3R)-3-[3-(2-chloro-6-methyl-4-pyridyl)-2-(3-cyanophenyl)pyrazolo[1,5-a]pyrimidin-5-yl]oxypiperidine-1-carboxylate;

3-[3-(2-Chloro-6-methyl-4-pyridyl)-5-[(3S)-pyrrolidin-3-yl]oxy-pyrazolo[1,5-a]pyrimidin-2-yl]benzonitrile;

tert-Butyl(3S)-3-[3-(2-chloro-6-methyl-4-pyridyl)-2-(3-cyanophenyl)pyrazolo[1,5-a]pyrimidin-5-yl]oxypyrrolidine-1-carboxylate;

3-[3-(2-Chloro-6-methyl-4-pyridyl)-5-[[(3S)-3-piperidyl]oxy]pyrazolo[1,5-a]pyrimidin-2-yl]benzonitrile;

tert-Butyl(3S)-3-[3-(2-chloro-6-methyl-4-pyridyl)-2-(3-cyanophenyl)pyrazolo[1,5-a]pyrimidin-5-yl]oxypiperidine-1-carboxylate;

3-[5-Amino-3-(6-amino-5-methyl-3-pyridyl)pyrazolo[1,5-a]pyrimidin-2-yl]benzonitrile;

3-[5-Amino-3-[2-(difluoromethyl)-6-methyl-4-pyridyl]pyrazolo[1,5-a]pyrimidin-2-yl]benzonitrile;

3-[5-Amino-3-(2-methoxy-6-methyl-4-pyridyl)pyrazolo[1,5-a]pyrimidin-2-yl]benzonitrile;

4-[5-Amino-2-(3-cyanophenyl)pyrazolo [1,5-a]pyrimidin-3-yl]-6-methyl-pyridine-2-carbonitrile;

3-[5-Amino-3-(2-fluoro-6-methyl-4-pyridyl)pyrazolo[1,5-a]pyrimidin-2-yl]benzonitrile;

3-[5-Amino-3-(1-methylpyrazol-4-yl)pyrazolo[1,5-a]pyrimidin-2-yl]benzonitrile;

3-[5-Amino-3-(2,6-dimethyl-1-oxido-pyridin-1-ium-4-yl)pyrazolo[1,5-a]pyrimidin-2-yl]benzonitrile;

3-[5-Amino-3-(2-amino-6-methyl-4-pyridyl)pyrazolo[1,5-a]pyrimidin-2-yl]benzonitrile;

4-[5-Amino-2-(3-cyanophenyl)pyrazolo[1,5-a]pyrimidin-3-yl]-6-methyl-pyridine-2-carboxamide;

N-[4-[5-Amino-2-(3-cyanophenyl)pyrazolo[1,5-a]pyrimidin-3-yl]-6-methyl-2-pyridyl]acetamide;

3-[5-Amino-3-(5-methyl-[1,2,4]triazolo[1,5-a]pyridin-7-yl)pyrazolo[1,5-a]pyrimidin-2-yl]benzonitrile;

4-[5-Amino-2-(3-cyanophenyl)pyrazolo[1,5-a]pyrimidin-3-yl]-6-methyl-pyridine-2-carboxylic acid;
3-[5-Amino-3-[2-(dimethylamino)-6-methyl-4-pyridyl]pyrazolo[1,5-a]pyrimidin-2-yl]benzonitrile;
[3-(2-Chloro-6-methyl-4-pyridyl)-2-(3-cyanophenyl)pyrazolo[1,5-a]pyrimidin-5-yl]urea;
1-[3-(2-Chloro-6-methyl-4-pyridyl)-2-(3-cyanophenyl)pyrazolo[1,5-a]pyrimidin-5-yl]-3-(2-hydroxy-2-methyl-propyl)urea;
1-[3-(2-Chloro-6-methyl-4-pyridyl)-2-(3-cyanophenyl)pyrazolo[1,5-a]pyrimidin-5-yl]-3-(1-ethyl-4-piperidyl)urea;
N-[3-(2-Chloro-6-methyl-4-pyridyl)-2-(3-cyanophenyl)pyrazolo[1,5-a]pyrimidin-5-yl]piperazine-1-carboxamide;
1-[3-(2-Chloro-6-methyl-4-pyridyl)-2-(3-cyanophenyl)pyrazolo[1,5-a]pyrimidin-5-yl]-3-[(3S)-pyrrolidin-3-yl]urea;
1-(2-Aminoethyl)-3-[3-(2-chloro-6-methyl-4-pyridyl)-2-(3-cyanophenyl)pyrazolo[1,5-a]pyrimidin-5-yl]urea;
1-[3-(2-Chloro-6-methyl-4-pyridyl)-2-(3-cyanophenyl)pyrazolo[1,5-a]pyrimidin-5-yl]-3-[(3R)-pyrrolidin-3-yl]urea;
1-[3-(2-Chloro-6-methyl-4-pyridyl)-2-(3-cyanophenyl)pyrazolo[1,5-a]pyrimidin-5-yl]-2-cyano-guanidine;
3-[3-(2-Ethylpyrazol-3-yl)-5-[(2-hydroxy-2-methyl-propyl)amino]pyrazolo[1,5-a]pyrimidin-2-yl]benzonitrile;
3-[3-(2-Ethylpyrazol-3-yl)-5-[3-(hydroxymethyl)-4-methyl-piperazin-1-yl]pyrazolo[1,5-a]pyrimidin-2-yl]benzonitrile;
3-[3-(2-Ethylpyrazol-3-yl)-5-(8-oxa-3-azabicyclo[3.2.1]octan-3-yl)pyrazolo[1,5-a]pyrimidin-2-yl]benzonitrile;
3-[3-(2-Ethylpyrazol-3-yl)-5-(8-methyl-3,8-diazabicyclo[3.2.1]octan-3-yl)pyrazolo[1,5-a]pyrimidin-2-yl]benzonitrile;
3-[3-(2-Ethylpyrazol-3-yl)-5-(4-methylsulfonylpiperazin-1-yl)pyrazolo[1,5-a]pyrimidin-2-yl]benzonitrile;
3-[3-(2-Ethylpyrazol-3-yl)-5-(4H-1,2,4-triazol-3-ylmethyl-amino)pyrazolo[1,5-a]pyrimidin-2-yl]benzonitrile;
3-[3-(2-Ethylpyrazol-3-yl)-5-piperazin-1-yl-pyrazolo[1,5-a]pyrimidin-2-yl]benzonitrile;
3-[3-(2-Ethylpyrazol-3-yl)-5-(1-imino-1-oxo-1,4-thiazinan-4-yl)pyrazolo[1,5-a]pyrimidin-2-yl]benzonitrile;
5-(Benzylamino)-2-(2-fluorophenyl)pyrazolo[1,5-a]pyrimidine-3-carbonitrile;
N-Benzyl-2-(2-fluorophenyl)pyrazolo[1,5-a]pyrimidin-5-amine;
2-(2-Furyl)-5-[(3-methyl-2-pyridyl)methylamino]pyrazolo[1,5-a]pyrimidine-3-carbonitrile;
tert-Butyl(2S)-2-[[[3-cyano-2-(2-furyl)pyrazolo[1,5-a]pyrimidin-5-yl]amino]methyl]morpholine-4-carboxylate;
tert-Butyl(2R)-2-[[[3-cyano-2-(2-furyl)pyrazolo[1,5-a]pyrimidin-5-yl]amino]methyl]pyrrolidine-1-carboxylate;
5-[4-(2-Fluoroethyl)piperazin-1-yl]-2-(2-furyl)pyrazolo[1,5-a]pyrimidine-3-carbonitrile;
tert-Butyl(2S)-2-[[3-cyano-2-(2-furyl)pyrazolo[1,5-a]pyrimidin-5-yl]amino]methyl]pyrrolidine-1-carboxylate;
tert-Butyl(2R)-2-[[[3-cyano-2-(2-furyl)pyrazolo[1,5-a]pyrimidin-5-yl]amino]methyl]morpholine-4-carboxylate;
2-(2-Furyl)-5-[4-(2-phenylethyl)piperazin-1-yl]pyrazolo[1,5-a]pyrimidine-3-carbonitrile;
2-(2-Furyl)-5-[4-(2-pyridylmethyl) piperazin-1-yl]pyrazolo[1,5-a]pyrimidine-3-carbonitrile;
2-(2-Furyl)-5-(4-methylpiperazin-1-yl)pyrazolo[1,5-a]pyrimidine-3-carbonitrile;
5-[(1-Benzyl-4-piperidyl)methylamino]-2-(2-furyl)pyrazolo[1,5-a]pyrimidine-3-carbonitrile;
Ted-butyl(2R)-4-[3-cyano-2-(2-furyl)pyrazolo[1,5-a]pyrimidin-5-yl]-2-methyl-piperazine-1-carboxylate;
Tert-butyl(2S)-4-[3-cyano-2-(2-furyl)pyrazolo[1,5-a]pyrimidin-5-yl]-2-methyl-piperazine-1-carboxylate;
5-[2-(4-Benzylpiperazin-1-yl)ethylamino]-2-(2-furyl)pyrazolo[1,5-a]pyrimidine-3-carbonitrile;
2-(2-Furyl)-5-[(3-methyl-2-pyridyl)methylamino]pyrazolo[1,5-a]pyrimidine-3-carboxamide;
5-[4-(2-Fluoroethyl)piperazin-1-yl]-2-(2-furyl)pyrazolo[1,5-a]pyrimidine-3-carboxamide;
5-[3-(Dimethylamino)azetidin-1-yl]-2-(2-furyl)pyrazolo[1,5-a]pyrimidine-3-carboxamide; tert-Butyl 4-[3-cyano-2-(2-furyl)pyrazolo[1,5-a]pyrimidin-5-yl]-3,6-dihydro-2H-pyridine-1-carboxylate;
2-(2-Furyl)-5-piperazin-1-yl-pyrazolo[1,5-a]pyrimidine-3-carbonitrile;
2-(2-Furyl)-5-[[(2S)-morpholin-2-yl]methylamino]pyrazolo[1,5-a]pyrimidine-3-carbonitrile;
2-(2-Furyl)-5-[[(2R)-morpholin-2-yl]methylamino]pyrazolo[1,5-a]pyrimidine-3-carbonitrile;
5-(4-Benzylpiperazin-1-yl)-2-(2-furyl)pyrazolo[1,5-a]pyrimidine-3-carbonitrile;
N-Benzyl-3-bromo-2-(2-furyl)pyrazolo[1,5-a]pyrimidin-5-amine;
5-(Benzylamino)-2-(2-furyl)pyrazolo[1,5-a]pyrimidine-3-carbonitrile;
5-(Benzylamino)-2-(2-furyl)pyrazolo[1,5-a]pyrimidine-3-carboxamide;
5-(Benzylamino)-2-(2-furyl)pyrazolo[1,5-a]pyrimidine-3-carbaldehyde;
N-Benzyl-2-(2-furyl)pyrazolo[1,5-a]pyrimidin-5-amine;
5-Amino-2-(2-furyl)pyrazolo[1,5-a]pyrimidine-3-carbonitrile;
3-Bromo-2-(2-furyl)pyrazolo[1,5-a]pyrimidin-5-amine;
2-(2-Furyl)-5-[4-[(3-methyl-2-pyridyl)methyl]piperazin-1-yl]pyrazolo[1,5-a]pyrimidine-3-carbonitrile;
2-(2-Furyl)-5-[4-[(2,4,6-trifluorophenyl)methyl]piperazin-1-yl]pyrazolo[1,5-a]pyrimidine-3-carbonitrile;
2-(2-Furyl)-5-[4-[(1-methylimidazol-2-yl)methyl]piperazin-1-yl]pyrazolo[1,5-a]pyrimidine-3-carbonitrile;
2-(2-Furyl)-5-[4-(2-hydroxyethyl)piperazin-1-yl]pyrazolo[1,5-a]pyrimidine-3-carbonitrile;
N-benzyl-2-(2-furyl)-3-(1-methylpyrazol-4-yl)pyrazolo[1,5-a]pyrimidin-5-amine;
N-benzyl-2-(2-furyl)-3-(2-methylpyrazol-3-yl)pyrazolo[1,5-a]pyrimidin-5-amine;
Methyl(E)-3-[5-(benzylamino)-2-(2-furyl)pyrazolo[1,5-a]pyrimidin-3-yl]prop-2-enoate;
(E)-3-[5-(Benzylamino)-2-(2-furyl)pyrazolo[1,5-a]pyrimidin-3-yl]prop-2-enoic acid;
2-(2-Furyl)-5-(4-phenylpiperazin-1-yl)pyrazolo[1,5-a]pyrimidine-3-carbonitrile;
2-(2-Furyl)-5-(3-hydroxypropylamino)pyrazolo[1,5-a]pyrimidine-3-carbonitrile;
2-(2-furyl)-5-(2-hydroxyethylamino)pyrazolo[1,5-a]pyrimidine-3-carbonitrile;
2-(2-Furyl)-5-(3-piperidylmethylamino)pyrazolo[1,5-a]pyrimidine-3-carbonitrile hydrochloride;
5-(Benzylamino)-2-oxazol-2-yl-pyrazolo[1,5-a]pyrimidine-3-carbonitrile;
5-(Benzylamino)-2-(3-cyanophenyl)pyrazolo[1,5-a]pyrimidine-3-carbonitrile;
2-(3-Cyanophenyl)-5-[4-[(3-methyl-2-pyridyl)methyl]piperazin-1-yl]pyrazolo[1,5-a]pyrimidine-3-carbonitrile;
2-(3-Fluorophenyl)-5-[4-[(3-methyl-2-pyridyl)methyl]piperazin-1-yl]pyrazolo[1,5-a]pyrimidine-3-carbonitrile;

5-[4-(2-Fluoroethyl)piperazin-1-yl]-2-(3-fluorophenyl) pyrazolo[1,5-a]pyrimidine-3-carbonitrile;

5-[4-(2-Fluoroethyl)piperazin-1-yl]-2-oxazol-5-yl-pyrazolo [1,5-a]pyrimidine-3-carbonitrile;

5-(Benzylamino)-2-(4-fluorophenyl)pyrazolo[1,5-a]pyrimidine-3-carbonitrile;

5-(benzylamino)-2-(5-methyl-2-furyl)pyrazolo[1,5-a]pyrimidine-3-carbonitrile;

5-[4-[(3-Methyl-2-pyridyl)methyl]piperazin-1-yl]-2-oxazol-5-yl-pyrazolo[1,5-a]pyrimidine-3-carbonitrile;

N-benzyl-2-(3-fluorophenyl)pyrazolo[1,5-a]pyrimidin-5-amine;

2-(3-Fluorophenyl)-N-[(3-methyl-2-pyridyl)methyl]pyrazolo[1,5-a]pyrimidin-5-amine;

2-(3-Fluorophenyl)-N-(2-phenylethyl)pyrazolo[1,5-a]pyrimidin-5-amine;

N-(1H-Benzimidazol-2-ylmethyl)-2-(3-fluorophenyl)pyrazolo[1,5-a]pyrimidin-5-amine;

2-(3-Fluorophenyl)-N-(2-isoindolin-2-ylethyl)pyrazolo[1,5-a]pyrimidin-5-amine;

N-Benzyl-3-chloro-2-(3-fluorophenyl)pyrazolo[1,5-a]pyrimidin-5-amine;

3-Bromo-5-chloro-2-(3-fluorophenyl)pyrazolo[1,5-a]pyrimidine;

N-Benzyl-3-bromo-2-(3-fluorophenyl)pyrazolo[1,5-a]pyrimidin-5-amine;

5-(Benzylamino)-2-(3-fluorophenyl)pyrazolo[1,5-a]pyrimidine-3-carbonitrile;

3-Bromo-2-(3-fluorophenyl)pyrazolo[1,5-a]pyrimidin-5-amine;

5-Amino-2-(3-fluorophenyl)pyrazolo[1,5-a]pyrimidine-3-carbonitrile;

2-(2-Furyl)-N-(thiazol-2-ylmethyl)pyrazolo[1,5-a]pyrimidin-5-amine;

[5-(Benzylamino)-2-(2-furyl)pyrazolo[1,5-a]pyrimidin-3-yl]methanol;

5-(Benzylamino)-2-(2-furyl)pyrazolo[1,5-a]pyrimidine-3-carboxylic acid;

N-Benzyl-2-(2-furyl)-3-iodo-pyrazolo[1,5-a]pyrimidin-5-amine;

2-(2-Furyl)-3-(4-pyridyl)pyrazolo[1,5-a]pyrimidin-5-amine;

2-(2-Furyl)-5-[[(2R)-pyrrolidin-2-yl]methylamino]pyrazolo [1,5-a]pyrimidine-3-carbonitrile;

2-(2-Furyl)-5-[[(2R)-1-methylpyrrolidin-2-yl]methylamino] pyrazolo[1,5-a]pyrimidine-3-carbonitrile;

2-(2-Furyl)-5-[(3R)-3-methylpiperazin-1-yl]pyrazolo[1,5-a] pyrimidine-3-carbonitrile hydrochloride;

Tert-butyl 4-[3-cyano-2-(2-furyl)pyrazolo[1,5-a]pyrimidin-5-yl]piperidine-1-carboxylate;

N-Benzyl-7-(2-furyl)pyrazolo[1,5-a][1,3,5]triazin-2-amine;

N-Benzyl-2-(2-furyl)pyrazolo[1,5-a]pyrimidine-5-carboxamide;

2-(3-Cyanophenyl)-5-[4-(2-fluoroethyl)piperazin-1-yl] pyrazolo[1,5-a]pyrimidine-3-carbonitrile;

2-(3-Cyanophenyl)-5-[2-(4-phenylpiperazin-1-yl)ethylamino]pyrazolo[1,5-a]pyrimidine-3-carbonitrile;

3-(2-Chloro-6-methyl-4-pyridyl)-2-(4-fluorophenyl)pyrazolo[1,5-a]pyrimidin-5-amine;

N-tert-Butyl-3-(2-chloro-6-methyl-4-pyridyl)-2-(3-cyanophenyl)pyrazolo[1,5-a]pyrimidine-5-carboxamidine;

3-(2-Amino-6-methyl-4-pyridyl)-N-tert-butyl-2-(3-cyanophenyl)pyrazolo[1,5-a]pyrimidine-5-carboxamide;

2-(3-Cyanophenyl)-3-(2,6-dimethyl-4-pyridyl)-N-[(1S)-2-hydroxy-1,2-dimethyl-propyl]pyrazolo[1,5-a]pyrimidine-5-carboxamide;

2-(3-Cyanophenyl)-N-(2,3-dihydroxy-2-methyl-propyl)-3-(2,6-dimethyl-4-pyridyl)pyrazolo[1,5-a]pyrimidine-5-carboxamide;

2-(3-Cyanophenyl)-3-(2,6-dimethyl-4-pyridyl)-N-(3-hydroxy-1-bicyclo[1.1.1]pentanyl)pyrazolo[1,5-a]pyrimidine-5-carboxamide;

3-(2-chloro-6-methyl-4-pyridyl)-2-(3-cyanophenyl)-5-(sulfamoylamino)pyrazolo[1,5-a]pyrimidine;

N-[3-(2-Chloro-6-methyl-4-pyridyl)-2-(3-cyanophenyl) pyrazolo[1,5-a]pyrimidin-5-yl]-2-hydroxy-2-methyl-propanamide;

N-[3-(2-Chloro-6-methyl-4-pyridyl)-2-(3-cyanophenyl) pyrazolo[1,5-a]pyrimidin-5-yl]-2,2-dimethyl-propanamide;

N-(3-Amino-3-methyl-butyl)-2-(3-cyanophenyl)-3-(2,6-dimethyl-4-pyridyl)pyrazolo[1,5-a]pyrimidine-5-carboxamide;

3-(2-chloro-6-methyl-4-pyridyl)-2-(3-cyanophenyl)-N-(2-hydroxy-1,1-dimethyl-ethyl)pyrazolo[1,5-a]pyrimidine-5-carboxamide;

2-(3-cyanophenyl)-N-(2-hydroxy-2-methyl-propyl)-3-[2-methyl-6-(trifluoromethyl)-4-pyridyl]pyrazolo[1,5-a]pyrimidine-5-carboxamide;

3-(2-chloro-6-methyl-4-pyridyl)-N-(1-cyano-1-methyl-ethyl)-2-(3-cyanophenyl)pyrazolo[1,5-a]pyrimidine-5-carboxamide;

3-(2-chloro-6-methyl-4-pyridyl)-2-(3-cyanophenyl)-N-[(1S,2S)-2,3-dihydroxy-1-methyl-propyl]pyrazolo[1,5-a] pyrimidine-5-carboxamide;

1-[3-(2-chloro-6-methyl-4-pyridyl)-2-(3-cyanophenyl)pyrazolo[1,5-a]pyrimidin-5-yl]-2-cyano-3-isopropyl-guanidine;

3-[3-(2-chloro-6-methyl-4-pyridyl)-5-[[(1R)-2-hydroxy-1-methyl-ethyl]amino]pyrazolo[1,5-a]pyrimidin-2-yl]benzonitrile;

2-(3-cyano-2-methyl-phenyl)-3-(2,6-dimethyl-4-pyridyl)-N-(2-hydroxy-2-methyl-propyl)pyrazolo[1,5-a]pyrimidine-5-carboxamide;

3-(2-chloro-6-methyl-4-pyridyl)-2-(3-cyanophenyl)-N-(3-hydroxycyclobutyl)pyrazolo[1,5-a]pyrimidine-5-carboxamide;

2-(3-cyanophenyl)-3-(2,6-dimethyl-4-pyridyl)-N-[(2-oxo-3-piperidyl)methyl]pyrazolo[1,5-a]pyrimidine-5-carboxamide;

3-(2-chloro-6-methyl-4-pyridyl)-2-(3-cyanophenyl)-N-(2-hydroxy-1,1,2-trimethyl-propyl)pyrazolo[1,5-a]pyrimidine-5-carboxamide;

2-(3-cyanophenyl)-3-(2,6-dimethyl-4-pyridyl)-N-[(1-methyl-2-oxo-3-piperidyl)methyl]pyrazolo[1,5-a]pyrimidine-5-carboxamide;

2-(3-cyanophenyl)-N-[(1S)-1,2-dimethylallyl]-3-(2,6-dimethyl-4-pyridyl)pyrazolo[1,5-a]pyrimidine-5-carboxamide;

N-(2-acetamido-2-methyl-propyl)-3-(2-chloro-6-methyl-4-pyridyl)-2-(3-cyanophenyl)pyrazolo[1,5-a]pyrimidine-5-carboxamide;

N-(3-amino-3-methyl-butyl)-3-(2-chloro-6-methyl-4-pyridyl)-2-(3-cyanophenyl)pyrazolo[1,5-a]pyrimidine-5-carboxamide;

3-[3-(2-chloro-6-methyl-4-pyridyl)-5-[(1-methyl-4-piperidyl)amino]pyrazolo[1,5-a]pyrimidin-2-yl]benzonitrile;

2-(3-cyanophenyl)-3-(2,6-dimethyl-4-pyridyl)-N-[(1R)-2-hydroxy-1,2-dimethyl-propyl]pyrazolo[1,5-a]pyrimidine-5-carboxamide;

3-(2-chloro-6-methyl-4-pyridyl)-2-(3-cyano-2-methyl-phenyl)-N-(2-hydroxy-2-methyl-propyl)pyrazolo[1,5-a]pyrimidine-5-carboxamide;

3-[3-(2-chloro-6-methyl-4-pyridyl)-5-[[(1R,2S)-2,3-dihydroxy-1-methyl-propyl]amino]pyrazolo[1,5-a]pyrimidin-2-yl]benzonitrile;

2-(3-cyanophenyl)-3-(2,6-dimethyl-4-pyridyl)-N-(4-hydroxy-4-methyl-cyclohexyl)pyrazolo[1,5-a]pyrimidine-5-carboxamide;

3-[3-[2-(difluoromethyl)-6-methyl-4-pyridyl]-5-[(2-hydroxy-2-methyl-propyl)amino]pyrazolo[1,5-a]pyrimidin-2-yl]benzonitrile;

2-(3-cyanophenyl)-3-(2,6-dimethyl-4-pyridyl)-N-[(4-methyl-2-oxo-oxazolidin-4-yl)methyl]pyrazolo[1,5-a]pyrimidine-5-carboxamide;

2-(3-cyanophenyl)-3-(2,6-dimethyl-4-pyridyl)-N-[(2-methyl-5-oxo-pyrrolidin-2-yl)methyl]pyrazolo[1,5-a]pyrimidine-5-carboxamide;

2-(3-cyanophenyl)-3-(2,6-dimethyl-4-pyridyl)-N-[1-(3-hydroxyoxetan-3-yl)ethyl pyrazolo[1,5-a]pyrimidine-5-carboxamide;

2-(3-cyanophenyl)-3-(2,6-dimethyl-4-pyridyl)-N-[(3-methyl-6-oxo-3-piperidyl)methyl]pyrazolo[1,5-a]pyrimidine-5-carboxamide;

1-[3-(2-chloro-6-methyl-4-pyridyl)-2-(3-cyanophenyl)pyrazolo[1,5-a]pyrimidin-5-yl]-2-cyano-3-(2-hydroxy-2-methyl-propyl)guanidine;

3-(2-chloro-6-methyl-4-pyridyl)-2-(3-cyanophenyl)-N-(3-hydroxy-1-bicyclo[1.1.1]pentanyl)pyrazolo[1,5-a]pyrimidine-5-carboxamide;

3-(2-chloro-6-methyl-4-pyridyl)-2-(3-cyanophenyl)-N-[rac-(2R)-2-hydroxypropyl]pyrazolo[1,5-a]pyrimidine-5-carboxamide;

2-(3-cyano-2-methyl-phenyl)-3-(2,6-dimethyl-4-pyridyl)-N-[(1R)-2-hydroxy-1,2-dimethyl-propyl]pyrazolo[1,5-a]pyrimidine-5-carboxamide;

3-[3-(2-chloro-6-methyl-4-pyridyl)-5-[[rac-(3S,4S)-4-methoxy-1-methyl-pyrrolidin-3-yl]amino]pyrazolo[1,5-a]pyrimidin-2-yl]benzonitrile;

3-(2-chloro-6-methyl-4-pyridyl)-2-(3-cyanophenyl)-N-[(3-methyl-3-piperidyl)methyl]pyrazolo[1,5-a]pyrimidine-5-carboxamide;

2-(3-cyanophenyl)-N-(2-hydroxy-2-methyl-propyl)-3-(2-methoxy-6-methyl-4-pyridyl)pyrazolo[1,5-a]pyrimidine-5-carboxamide;

2-(3-cyanophenyl)-3-(2,6-dimethyl-4-pyridyl)-N-[(4-methyl-2,5-dioxo-imidazolidin-4-yl)methyl]pyrazolo[1,5-a]pyrimidine-5-carboxamide;

3-[3-(2-chloro-6-methyl-4-pyridyl)-5-[[(1S,2S)-2,3-dihydroxy-1-methyl-propyl]amino]pyrazolo[1,5-a]pyrimidin-2-yl]benzonitrile;

2-(3-cyanophenyl)-3-(2,6-dimethyl-4-pyridyl)-N-(3-hydroxy-3-methyl-cyclobutyl)pyrazolo[1,5-a]pyrimidine-5-carboxamide;

3-[3-(2-chloro-6-methyl-4-pyridyl)-5-[[rac-(3R)-3-piperidyl]amino]pyrazolo[1,5-a]pyrimidin-2-yl]benzonitrile;

2-(3-cyano-2-methyl-phenyl)-3-(2,6-dimethyl-4-pyridyl)-N-[(1S)-2-hydroxy-1,2-dimethyl-propyl]pyrazolo[1,5-a]pyrimidine-5-carboxamide;

N-[3-(2-chloro-6-methyl-4-pyridyl)-2-(3-cyanophenyl)pyrazolo[1,5-a]pyrimidin-5-yl]-3-hydroxy-3-methyl-butanamide:

3-[3-(2-chloro-6-methyl-4-pyridyl)-5-[(3-hydroxyoxetan-3-yl)methylamino]pyrazolo[1,5-a]pyrimidin-2-yl]benzonitrile;

3-[3-(2-chloro-6-methyl-4-pyridyl)-5-[[1-(2-hydroxyethyl)-4-piperidyl]amino]pyrazolo[1,5-a]pyrimidin-2-yl]benzonitrile;

3-[3-(2-chloro-6-methyl-4-pyridyl)-5-[(3-hydroxy-3-methyl-butyl)amino]pyrazolo[1,5-a]pyrimidin-2-yl]benzonitrile;

1-[3-(2-chloro-6-methyl-4-pyridyl)-2-(3-cyanophenyl)pyrazolo[1,5-a]pyrimidin-5-yl]guanidine;

2-(3-cyanophenyl)-3-(2,6-dimethyl-4-pyridyl)pyrazolo[1,5-a]pyrimidine-5-carboxamidine;

2-(3-cyanophenyl)-3-(2,6-dimethyl-4-pyridyl)-N-(2-hydroxy-2-methyl-propoxy)pyrazolo[1,5-a]pyrimidine-5-carboxamide;

3-[3-(2-chloro-6-methyl-4-pyridyl)-5-[(5-oxopyrrolidin-3-yl)methylamino]pyrazolo[1,5-a]pyrimidin-2-yl]benzonitrile;

3-[3-(2-chloro-6-methyl-4-pyridyl)-5-[(3S)-3-(1-hydroxy-1-methyl-ethyl)piperazin-1-yl]pyrazolo[1,5-a]pyrimidin-2-yl]benzonitrile;

3-[3-(2,6-dimethyl-4-pyridyl)-5-[(1-methyl-2-oxo-4-piperidyl)amino]pyrazolo[1,5-a]pyrimidin-2-yl]benzonitrile;

N-[2-(3-cyanophenyl)-3-(2,6-dimethyl-4-pyridyl)pyrazolo[1,5-a]pyrimidin-5-yl]-3-hydroxy-3-methyl-butanamide;

N-[3-(2-chloro-6-methyl-4-pyridyl)-2-(3-cyanophenyl)pyrazolo[1,5-a]pyrimidin-5-yl]acetamide

[2-(3-cyanophenyl)-3-(2,6-dimethyl-4-pyridyl)pyrazolo[1,5-a]pyrimidin-5-yl]urea;

2-(3-cyanophenyl)-3-(2,6-dimethyl-4-pyridyl)-N-[(3-hydroxyoxetan-3-yl)methyl]pyrazolo[1,5-a]pyrimidine-5-carboxamide;

3-[3-(2-chloro-6-methyl-4-pyridyl)-5-[[(1S)-2-hydroxy-1,2-dimethyl-propyl]amino]pyrazolo[1,5-a]pyrimidin-2-yl]benzonitrile;

3-[3-(2-chloro-6-methyl-4-pyridyl)-5-[[rac-(2S)-2-hydroxypropyl]amino]pyrazolo[1,5-a]pyrimidin-2-yl]benzonitrile;

3-(2-chloro-6-methyl-4-pyridyl)-2-(3-cyanophenyl)-N-[(1S,3S)-3-aminocyclopentyl]pyrazolo[1,5-a]pyrimidine-5-carboxamide;

m-{4-[({[(3S)-5-Oxo-3-pyrrolidinyl]methyl}amino)carbonyl]-7-(2,6-dimethyl-4-pyridyl)-1.5.9-triazabicyclo[4.3.0]nona-2,4,6,8-tetraen-8-yl}benzonitrile;

3-[5-[(2-amino-2-methyl-propyl)amino]-3-(2-chloro-6-methyl-4-pyridyl)pyrazolo[1,5-a]pyrimidin-2-yl]benzonitrile;

3-(2-cyano-6-methyl-4-pyridyl)-2-(3-cyanophenyl)-N-(2-hydroxy-2-methyl-propyl)pyrazolo[1,5-a]pyrimidine-5-carboxamide;

3-[3-(2-chloro-6-methyl-4-pyridyl)-5-[[rac-(1R)-2-hydroxy-1,2-dimethyl-propyl]amino]pyrazolo[1.5-a]pyrimidin-2-y]benzonitrile;

N-[2-(3-cyanophenyl)-3-(2,6-dimethyl-4-pyridyl)pyrazolo[1,5-a]pyrimidin-5-yl]-2-hydroxy-2-methyl-propanamide;

3-(2-chloro-6-methyl-4-pyridyl)-2-(3-cyanophenyl)-N-[rac-(3S)-3-piperidyl]pyrazolo[1,5-a]pyrimidine-5-carboxamide;

2-(3-cyanophenyl)-3-(3-fluoro-2,6-dimethyl-4-pyridyl)-N-(2-hydroxy-2-methyl-propyl)pyrazolo[1,5-a]pyrimidine-5-carboxamide;

2-(3-cyanophenyl)-3-(2,6-dimethyl-4-pyridyl)-N-[(2-oxo-4-piperidyl)methyl]pyrazolo[1,5-a]pyrimidine-5-carboxamide;

2-(3-cyanophenyl)-3-(3-fluoro-2,6-dimethyl-4-pyridyl)-N-[(4-methyl-2,5-dioxo-imidazolidin-4-yl)methyl]pyrazolo[1,5-a]pyrimidine-5-carboxamide;

2-(3-cyanophenyl)-3-(2,6-dimethyl-4-pyridyl)-N-(5-oxopyrrolidin-3-yl)pyrazolo[1,5-a]pyrimidine-5-carboxamide;

2-(3-cyanophenyl)-3-(2,6-dimethyl-4-pyridyl)pyrazolo[1,5-a]pyrimidine-5-carboxamide;

3-[3-(2-chloro-6-methyl-4-pyridyl)-5-[(3R)-3-(1-hydroxy-1-methyl-ethyl)piperazin-1-yl]pyrazolo[1,5-a]pyrimidin-2-yl]benzonitrile;

m-[7-(2,6-Dimethyl-4-pyridyl)-4-({[(5-oxo-3-pyrrolidinyl)methyl]amino}carbonyl)-1.5.9-triazabicyclo[4.3.0]nona-2,4,6,8-tetraen-8-yl]benzonitrile;

3-[3-(2-chloro-6-methyl-4-pyridyl)-5-[[(1R,2S)-2-hydroxycyclobutyl]amino]pyrazolo[1,5-a]pyrimidin-2-yl]benzonitrile;

m-{4-[({{(3R)-5-Oxo-3-pyrrolidinyl]methyl}amino)carbonyl]-7-(2,6-dimethyl-4-pyridyl)-1.5.9-triazabicyclo[4.3.0]nona-2,4,6,8-tetraen-8-yl}benzonitrile;

3-[3-(2-chloro-6-methyl-4-pyridyl)-5-[(3-hydroxyazetidin-3-yl)methylamino]pyrazolo[1,5-a]pyrimidin-2-yl]benzonitrile;;

4-[5-amino-2-(3-cyanophenyl)pyrazolo[1,5-a]pyrimidin-3-yl]-6-methyl-pyridine-2-carbonitrile;

3-[3-(2-chloro-6-methyl-4-pyridyl)-5-(1-imino-1-oxo-1,4-thiazinan-4-yl)pyrazolo[1,5-a]pyrimidin-2-yl]benzonitrile;

3-[5-[(1-acetyl-4-piperidyl)amino]-3-(2,6-dimethyl-4-pyridyl)pyrazolo[1,5-a]pyrimidin-2-yl]benzonitrile;

2-(3-cyanophenyl)-3-(2,6-dimethyl-4-pyridyl)-N-[(5-oxomorpholin-2-yf)methyl]pyrazolo[1,5-a]pyrimidine-5-carboxamide;

3-[3-(2-chloro-6-methyl-4-pyridyl)-5-[(3R)-pyrrolidin-3-yl]oxy-pyrazolo[1,5-a]pyrimidin-2-yl]benzonitrile;

1-(2-amino-2-methyl-propyl)-3-[3-(2-chloro-6-methyl-4-pyridyl)-2-(3-cyanophenyl)pyrazolo[1,5-a]pyrimidin-5-yl]urea;

3-[3-(2,6-dimethyl-4-pyridyl)-5-(2,4-dioxo-1,3,8-triazaspiro[4.5]decane-8-carbonyl)pyrazolo[1,5-a]pyrimidin-2-yl]benzonitrile;

2-(3-cyanophenyl)-3-(2,6-dimethyl-4-pyridyl)-N-[(3S,4S)-4-hydroxytetrahydrofuran-3-yl]pyrazolo[1,5-a]pyrimidine-5-carboxamide;

2-(3-cyanophenyl)-3-(2,6-dimethyl-4-pyridyl)-N-[[(2R)-5-oxopyrrolidin-2-yl]methyl]pyrazolo[1,5-a]pyrimidine-5-carboxamide;

2-(3-cyanophenyl)-3-(2,6-dimethyl-4-pyridyl)-N-[(3R,4R)-4-hydroxy-4-methyl-tetrahydrofuran-3-yl]pyrazolo[1,5-a]pyrimidine-5-carboxamide 2-(3-cyanophenyl)-3-(2,6-dimethyl-4-pyridyl)-N-[(3R,4S)-4-hydroxy-4-methyl-tetrahydrofuran-3-yl]pyrazolo[1,5-a]pyrimidine-5-carboxamide;

2-(3-cyanophenyl)-3-(2,6-dimethyl-4-pyridyl)-N-[(6-oxo-3-piperidy)methyl]pyrazolo[1,5-a]pyrimidine-5-carboxamide;

2-(3-cyanophenyl)-3-(2,6-dimethyl-4-pyridyl)-N-[(38,4R)-4-hydroxytetrahydrofuran-3-yl]pyrazolo[1,5-a]pyrimidine-5-carboxamide;

2-(3-cyanophenyl)-3-(2,6-dimethyl-4-pyridyl)-N-[(3R,4R)-4-hydroxytetrahydrofuran-3-yg]pyrazolo[1,5-a]pyrimidine-5-carboxamide;

2-(3-cyanophenyl)-3-(2,6-dimethyl-4-pyridyl)-N-[(3R,4S)-4-hydroxytetrahydrofuran-3-yl]pyrazolo[1,5-a]pyrimidine-5-carboxamide;

2-(3-cyanophenyl)-3-(2,6-dimethyl-4-pyridyl)-N-[(3R,4R)-4-hydroxy-1-methyl-pyrrolidin-3-yl]pyrazolo[1,5-a]pyrimidine-5-carboxamide;

2-(3-cyanophenyl)-3-(2,6-dimethyl-4-pyridyl)-N-[[(2S)-5-oxopyrrolidin-2-yl]methyl]pyrazolo[1,5-a]pyrimidine-5-carboxamide;

2-(3-cyanophenyl)-3-(2,6-dimethyl-4-pyridyl)-N-[(3S,4R)-4-hydroxy-1-methyl-pyrrolidin-3-yl]pyrazolo[1,5-a]pyrimidine-5-carboxamide;

2-(3-cyanophenyl)-N-(2-hydroxy-2-methyl-propyl)-3-thiazol-5-yl-pyrazolo[1,5-a]pyrimidine-5-carboxamide;

3-[5-[(2-amino-2-methyl-propyl)amino]-3-(2-chloro-6-methyl-4-pyridyl)pyrazolo[1,5-a]pyrimidin-2-yl]benzonitrile;;

3-(2-chloro-6-methyl-4-pyridyl)-2-(3-cyanophenyl)-N-(4-piperidyl)pyrazolo[1,5-a]pyrimidine-5-carboxamide;

3-(2-chloro-6-methyl-4-pyridyl)-2-(3-cyanophenyl)-N-(4-cyano-4-piperidyl)pyrazolo[1,5-a]pyrimidine-5-carboxamide;

N-(4-carbamoyl-4-piperidyl)-3-(2-chloro-6-methyl-4-pyridyl)-2-(3-cyanophenyl)pyrazolo[1,5-a]pyrimidine-5-carboxamide;

3-[3-(2,6-dimethyl-4-pyridyl)-5-(piperazin-1-ylmethy)pyrazolo[1,5-a]pyrimidin-2-yl]benzonitrile;;

2-(3-cyanophenyl)-N-[(1S)-2-hydroxy-1,2-dimethyl-propyl]-3-[2-(hydroxymethyl)-6-methyl-4-pyridyl]pyrazolo[1,5-a]pyrimidine-5-carboxamide;

3-[3-(2,6-dimethyl-4-pyridyl)-5-(3-oxo-2,8-diazaspiro[4.5]decan-8-yl)pyrazolo[1,5-a]pyrimidin-2-yl]benzonitrile;

3-[3-(2,6-dimethyl-4-pyridyl)-5-[[1-(2-hydroxy-2-methyl-propyl)-4-piperidyl]amino]pyrazolo[1,5-a]pyrimidin-2-yl]benzonitrie;

(2S)-N-[2-(3-cyanophenyl)-3-(2,6-dimethyl-4-pyridyl)pyrazolo[1,5-a]pyrimidin-5-yl]-3,3,3-trifluoro-2-hydroxy-2-methyl-propanamide;

N-[2-(3-cyanophenyl)-3-(2,6-dimethyl-4-pyridyl)pyrazolo[1,5-a]pyrimidin-5-yl]-2-oxa-6-azaspiro[3.3]heptane-6-carboxamide; and 4-cyano-N-[2-(3-cyanophenyl)-3-(2,6-dimethyl-4-pyridyl)pyrazolo[1,5-a]pyrimidin-5-yl]-4-methyl-piperidine-1-carboxamide.

The various functional groups and substituents making up the compounds of the formula (I) are typically chosen such that the molecular weight of the compound of the formula (1) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acidaddition- salt of a compound of the invention which is sufficiently basic, for example, an acidaddition- salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are nonsuperimposable mirror images of each other are termed "enantiomers". When a compound has an asymmetric center-, for example, it is bonded to four different groups, a pair of enantiomers is possible. An enantiomer can be characterized by the absolute configuration of its asymmetric center and is described by the R and S sequencing rules of Cahn and Prelog, or by the manner in which the molecule rotates the plane of polarized light and designated as dextrorotatory or -levorotatory-(i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R) or (S)stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E and Z isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For Example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain compounds of the formula (I) may exist in solvated as well as unsolvated forms such as, for example, hydrated forms. It is to be understood that the invention encompasses all such solvated forms that possess antiproliferative activity.

It is also to be understood that certain compounds of the formula I may exhibit polymorphism, and that the invention encompasses all such forms that possess antiproliferative activity.

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

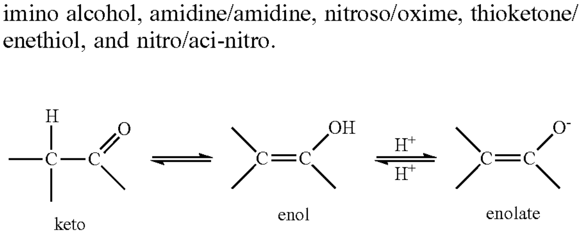

keto enol enolate

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular Examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of formula (I) may be administered in the form of a prodrug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula (I) and in-vivo cleavable amide derivatives that may be formed at a carboxy group or an amino group in a compound of the formula (I).

Accordingly, the present invention includes those compounds of the formula (I) as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically acceptable pro-drug of a compound of the formula (I) is one that is based on reasonable medical judgement as being suitable for administration to the human or animal body without undesirable pharmacological activities and without undue toxicity.

Various forms of pro-drug have been described, for example in the following documents:- a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include C1-6alkyl esters such as methyl, ethyl and tert-butyl, C1-6alkoxymethyl esters such as methoxymethyl esters, C1-6alkanoyloxymethyl esters such as pivaloyloxymethyl esters, 3-phthalidyl esters, C3-8cycloalkylcarbonyloxy- C1-6alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and C1-6alkoxycarbonyloxy- C1-6alkyl esters such as methoxycarbonyloxymethyl and 1-methoxycarbonyloxyethyl esters.

A suitable pharmaceutically acceptable pro-drug of a compound of the Formula (I) that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include C1-10alkanoyl groups such as acetyl, benzoyl, phenylacetyl and substituted benzoyl and phenylacetyl groups, C1-10alkoxycarbonyl groups such as ethoxycarbonyl, N,N -$(C1-6)_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula (I) that possesses a carboxy group is, for example, an in vivo cleavable amide thereof, for example an amide formed with an amine such as ammonia, a C1-4alkylamine such as methylamine, a $(C1-4alkyl)_2$amine such as dimethylamine, N-ethyl-N-methylamine or diethylamine, a C1-4alkoxy- C2-4alkylamine such as 2-methoxyethylamine, a phenyl-C1-4alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof.

Suitable pharmaceutically acceptable amides from an amino group include, for example an amide formed with C1-10alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl.

The in vivo effects of a compound of the formula (I) may be exerted in part by one or more metabolites that are formed within the human or animal body after administration of a compound of the formula (I). As stated hereinbefore, the in vivo effects of a compound of the formula (I) may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

SYNTHESIS

The compounds of the present invention can be prepared by any suitable technique known in the art. Particular processes for the preparation of the compounds of the invention are described in the Example section below and in the reaction schemes for preparing such compounds are shown in FIGS. 1 to 18. In reference to the accompanying Figures.

Figure 1:
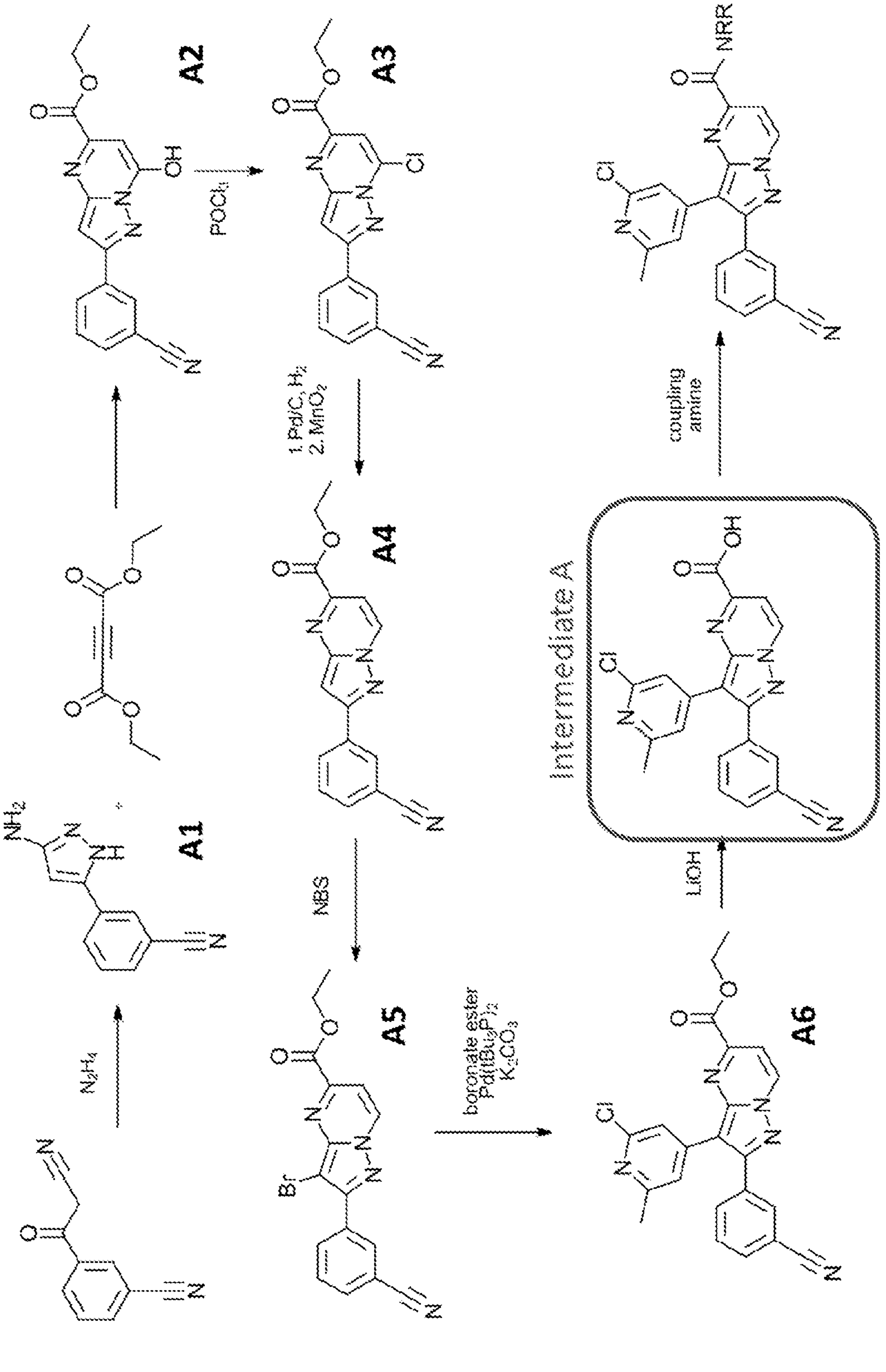
FIG. 1 shows a reaction scheme for the preparation of compounds of formula i in which A is CH, $R_1$ is 3-cyanophenyl; $R_2$ is 2-chloro-6-methylpyridin-4-yl and $R_3$ is an amide linked substituent group, denoted by the formula —C(O)NRR, where each R is hydrogen or a substituent group.
Figure 2:
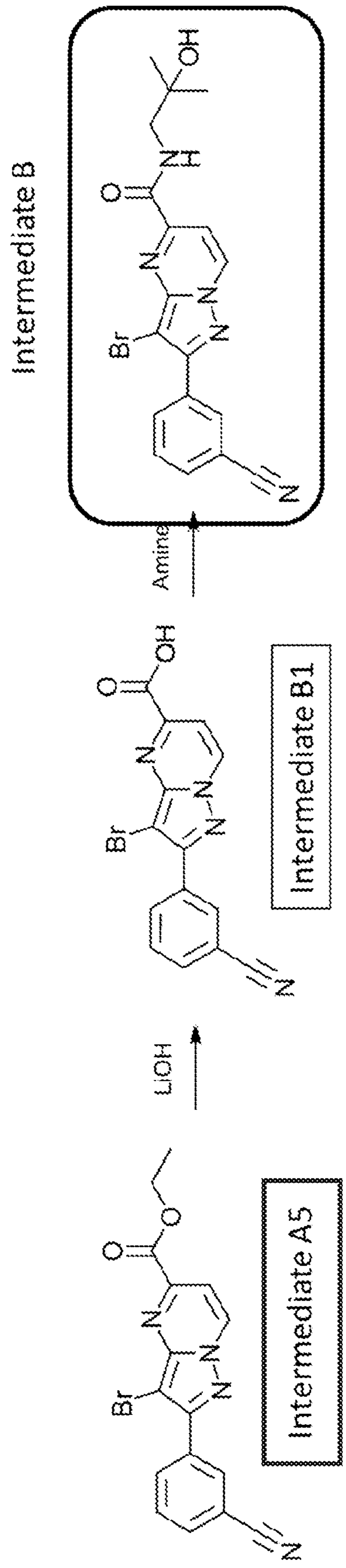
FIG. 2 shows a reaction scheme for the preparation of intermediate B (described in the accompanying example section).
Figure 3:
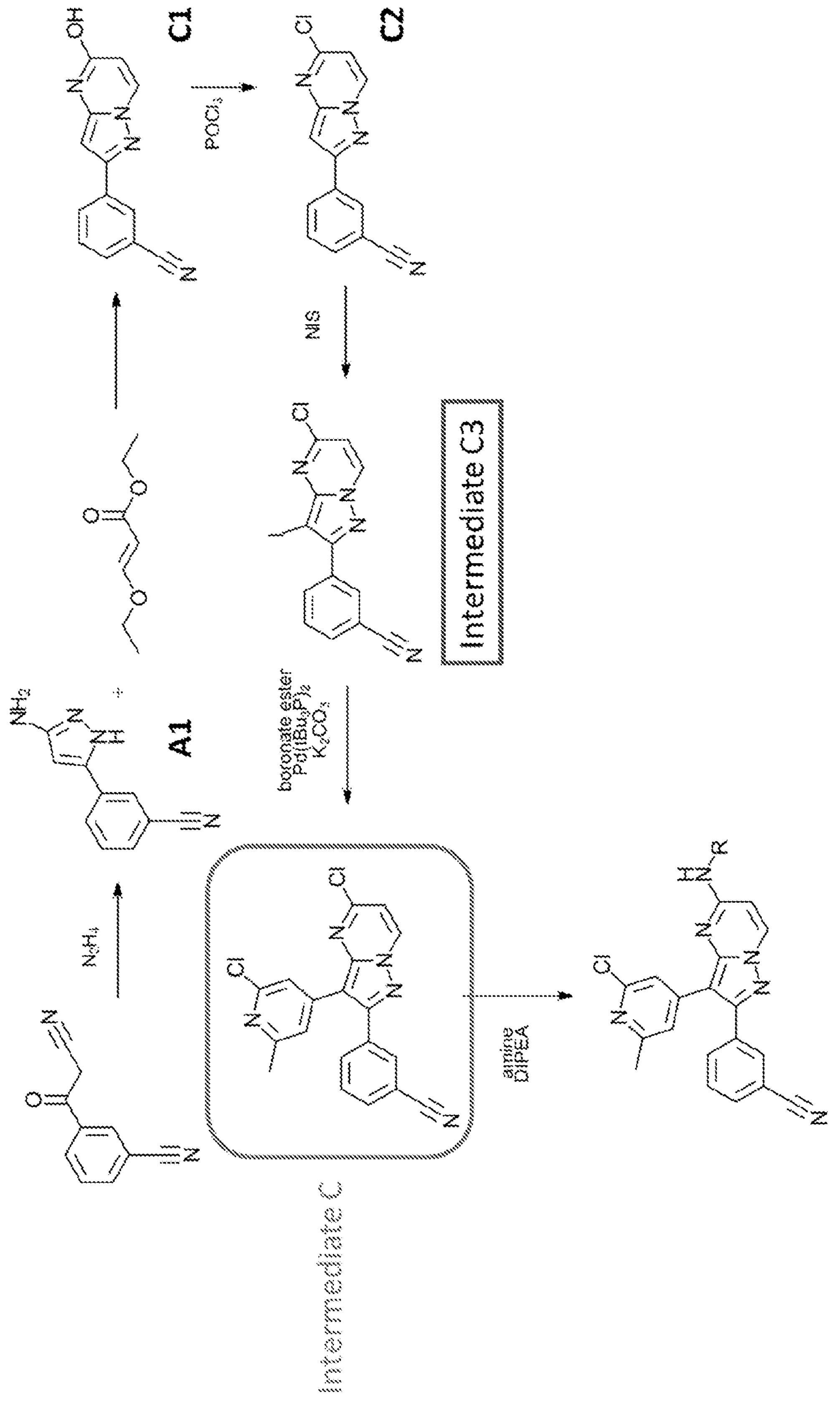
FIG. 3 shows a reaction scheme for the preparation of compounds of formula I in which A is CH, $R_1$ is 3-cyanophenyl; $R_2$ is 2-chloro-6-methylpyridin-4-yl and $R_3$ is an amine linked substituent group, denoted by the formula —NH-R.
Figure 4:
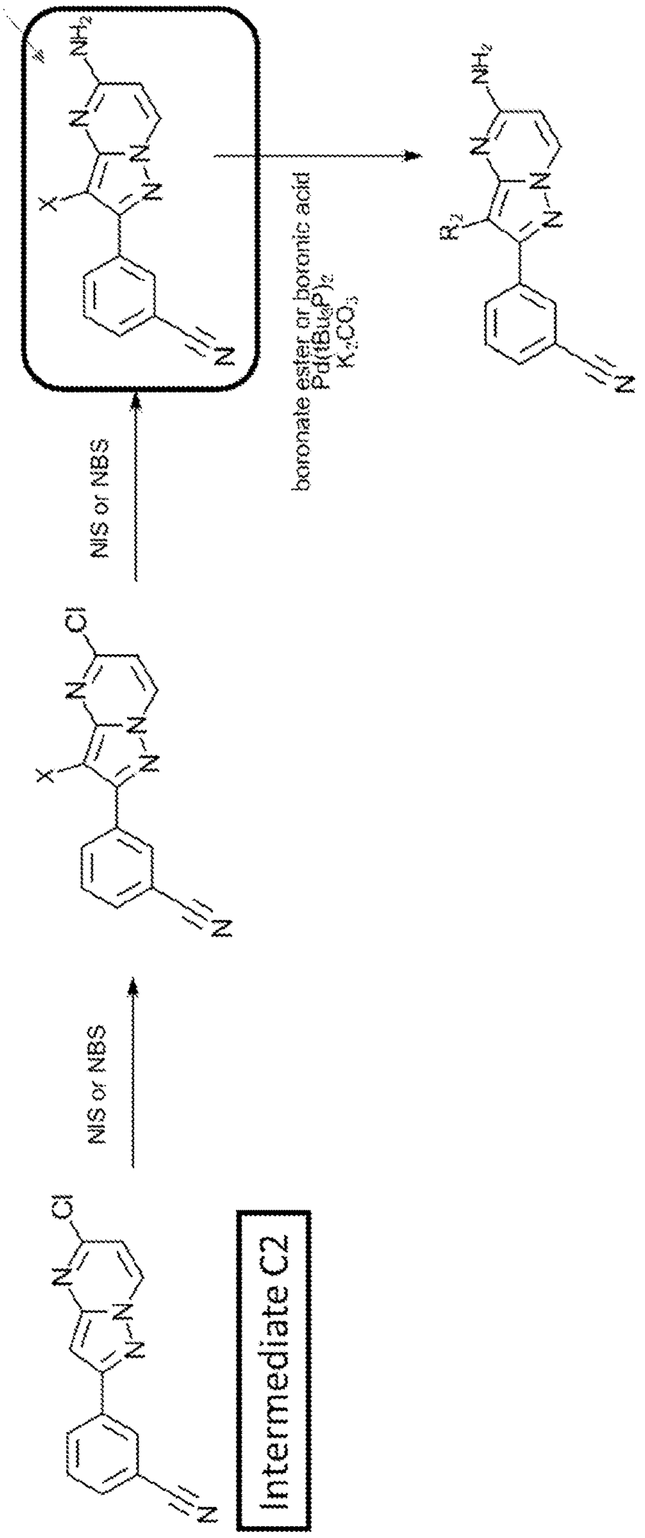
FIG. 4 shows a reaction scheme for the preparation of compounds of formula I in which A is CH, $R_1$ is 3-cyanophenyl; $R_2$ is a group as defined herein, and $R_3$ is an amine group (which is capable of further reaction to form an amine-linked substituent group).
Figure 5:
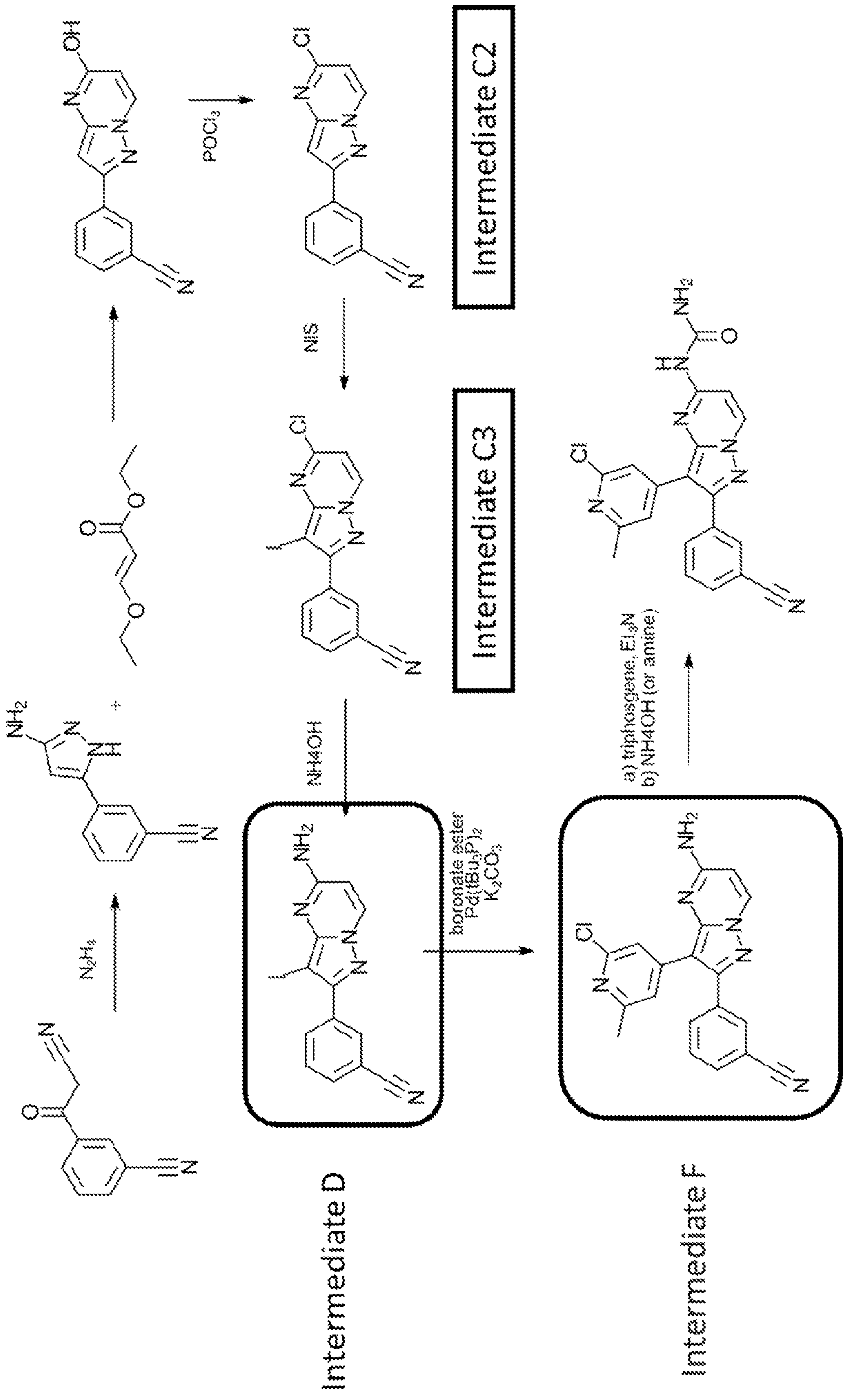
FIG. 5 shows a reaction scheme for the preparation of compounds of formula I in which A is CH, $R_1$ is 3-cyanophenyl; $R_2$ is 2-chloro-6-methylpyridin-4-yl and $R_3$ is a urea moiety of the formula —NH—C(O)—$NH_2$.
Figure 6:
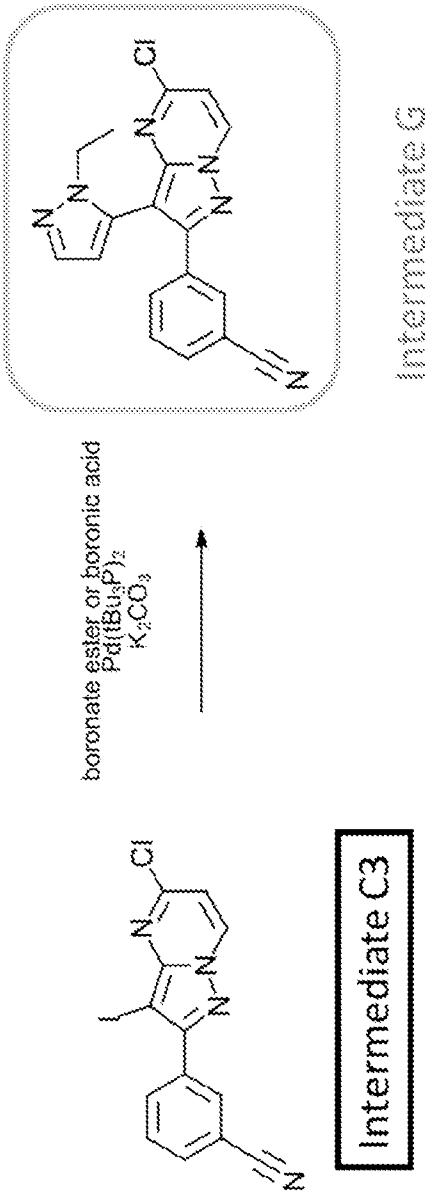
FIG. 6 shows a reaction scheme for the preparation of intermediate G (described in the accompanying example section).
Figure 7:
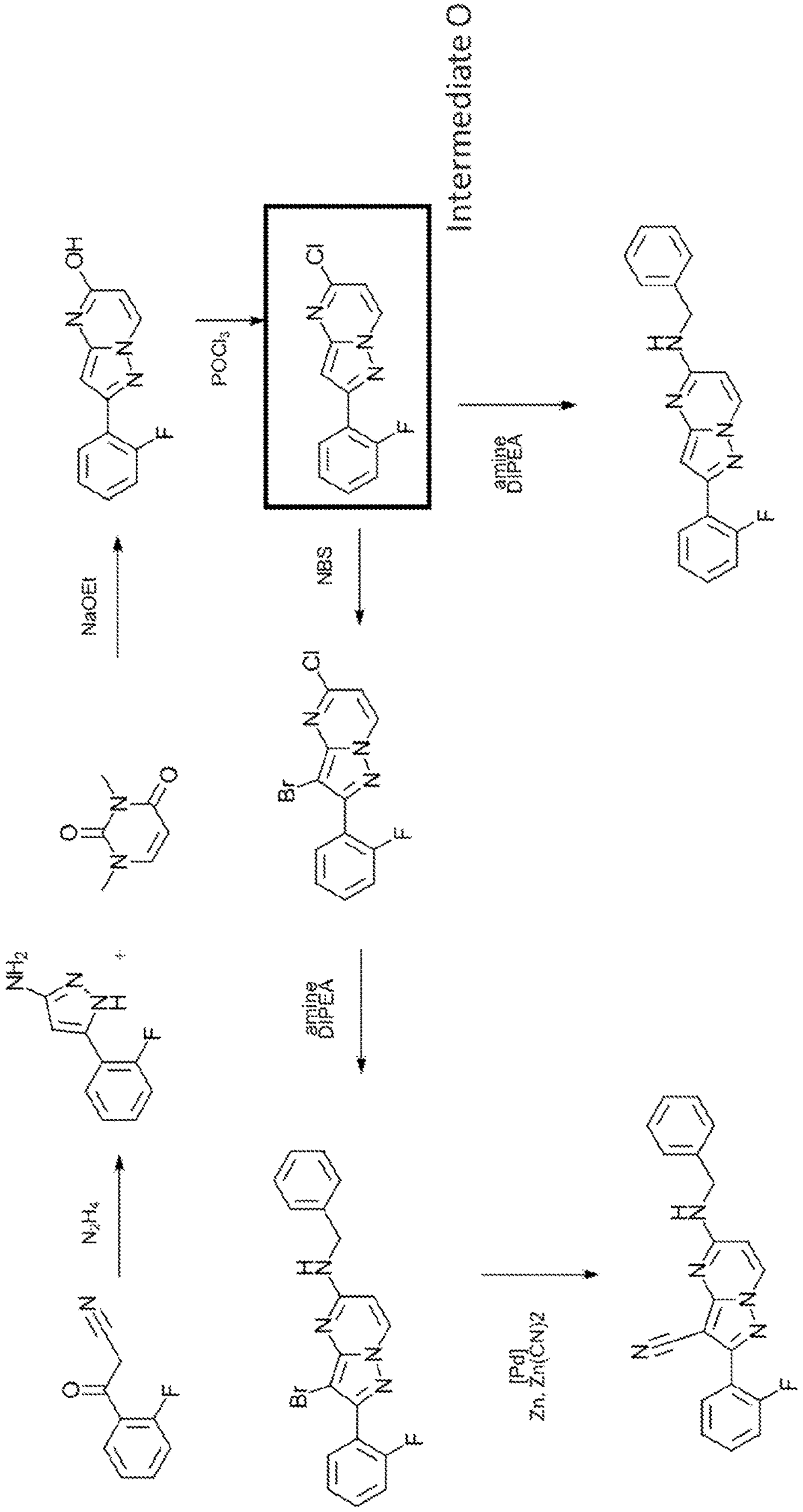
FIG. 7 shows a reaction scheme for the preparation of the compounds of Examples 35 and 36 herein.
Figure 8:
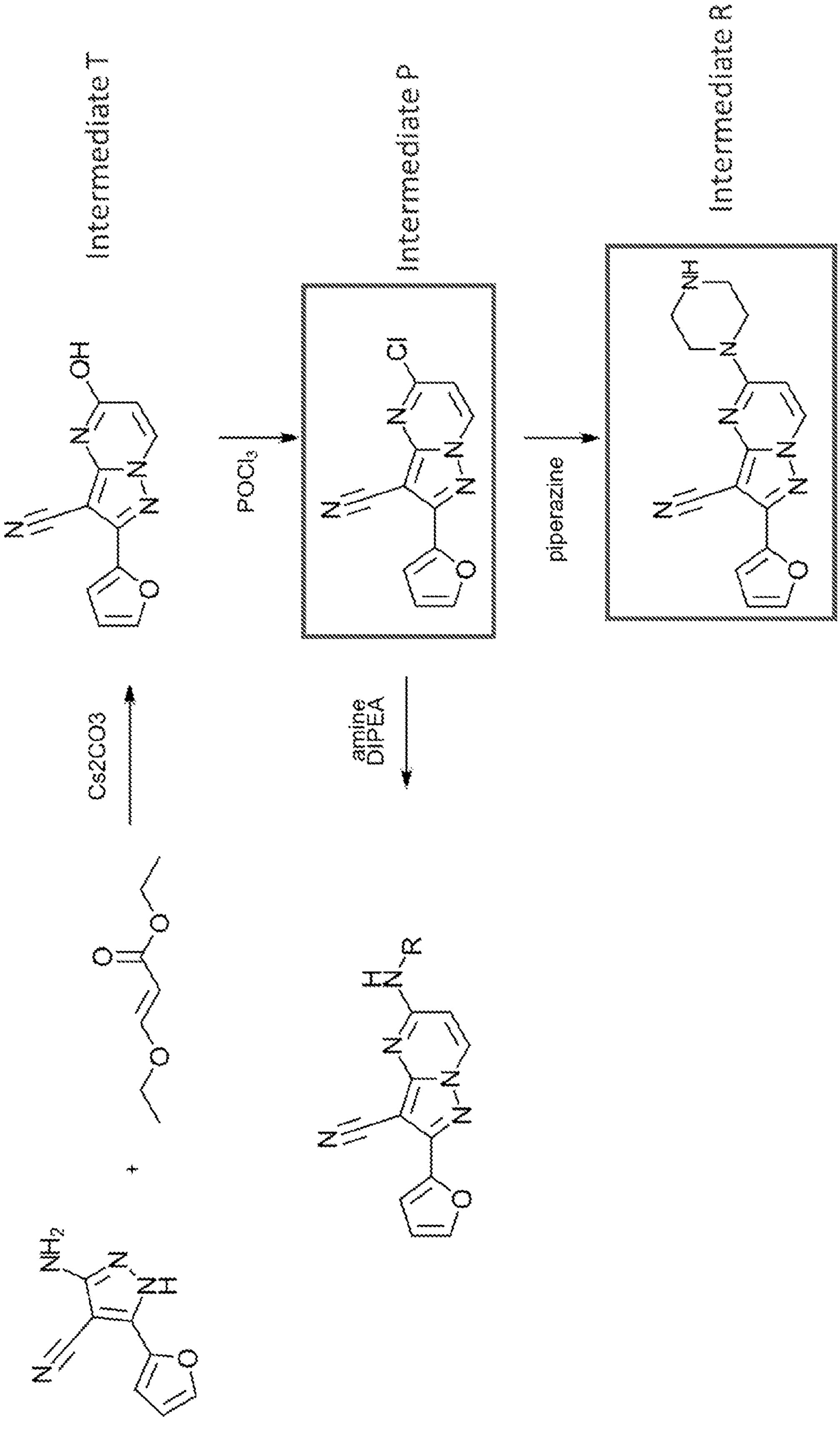
FIG. 8 shows a reaction scheme for the preparation of intermediate compounds T, P and R, as well as compounds of formula I in which A is CH, $R_1$ is furan-2-yl; $R_2$ is cyano and $R_3$ is an amine linked substituent group, denoted by the formula —NH-R.
Figure 9:
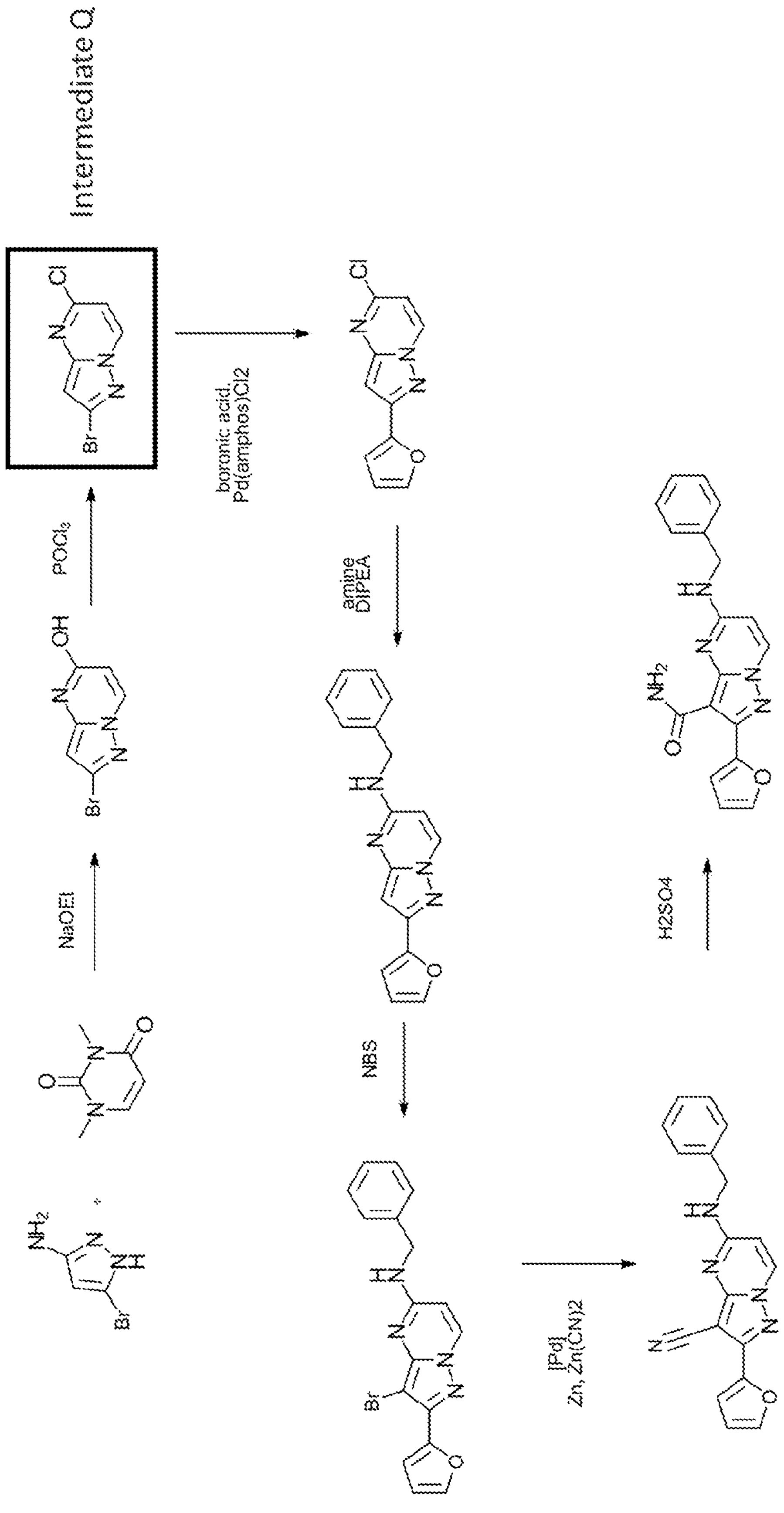
FIG. 9 shows a reaction scheme for the preparation of intermediate Q as well as compounds of formula I in which A is CH, $R_1$ is furan-2-yl; $R_2$ is Br, cyano or —C(O)$NH_2$, and $R_3$ is benzylamino.
Figure 10:
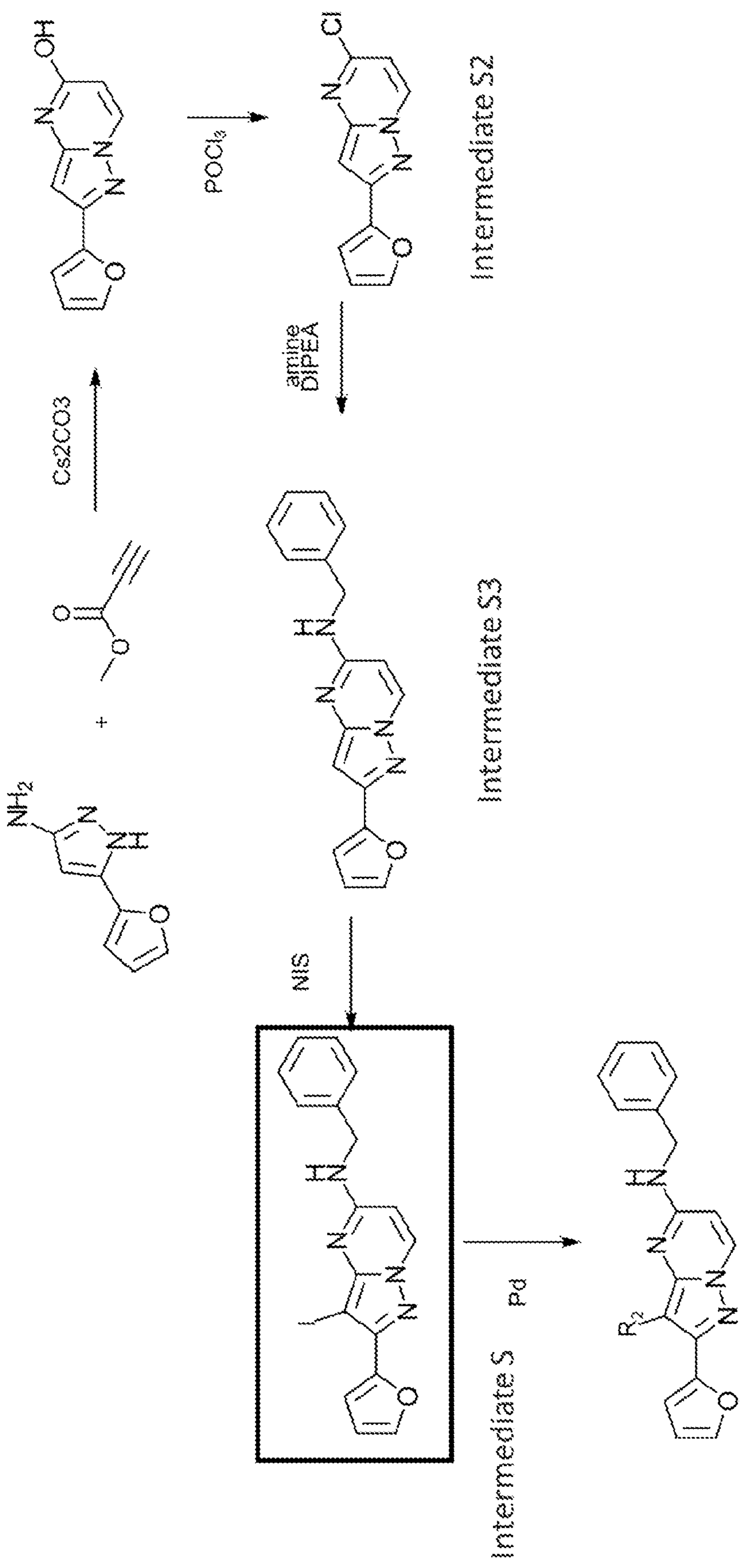
FIG. 10 shows a reaction scheme for the preparation of intermediate S as well as compounds of formula I in which A is CH, $R_1$ is furan-2-yl; $R_2$ is a group as defined herein, and $R_3$ is benzylamino.
Figure 11:
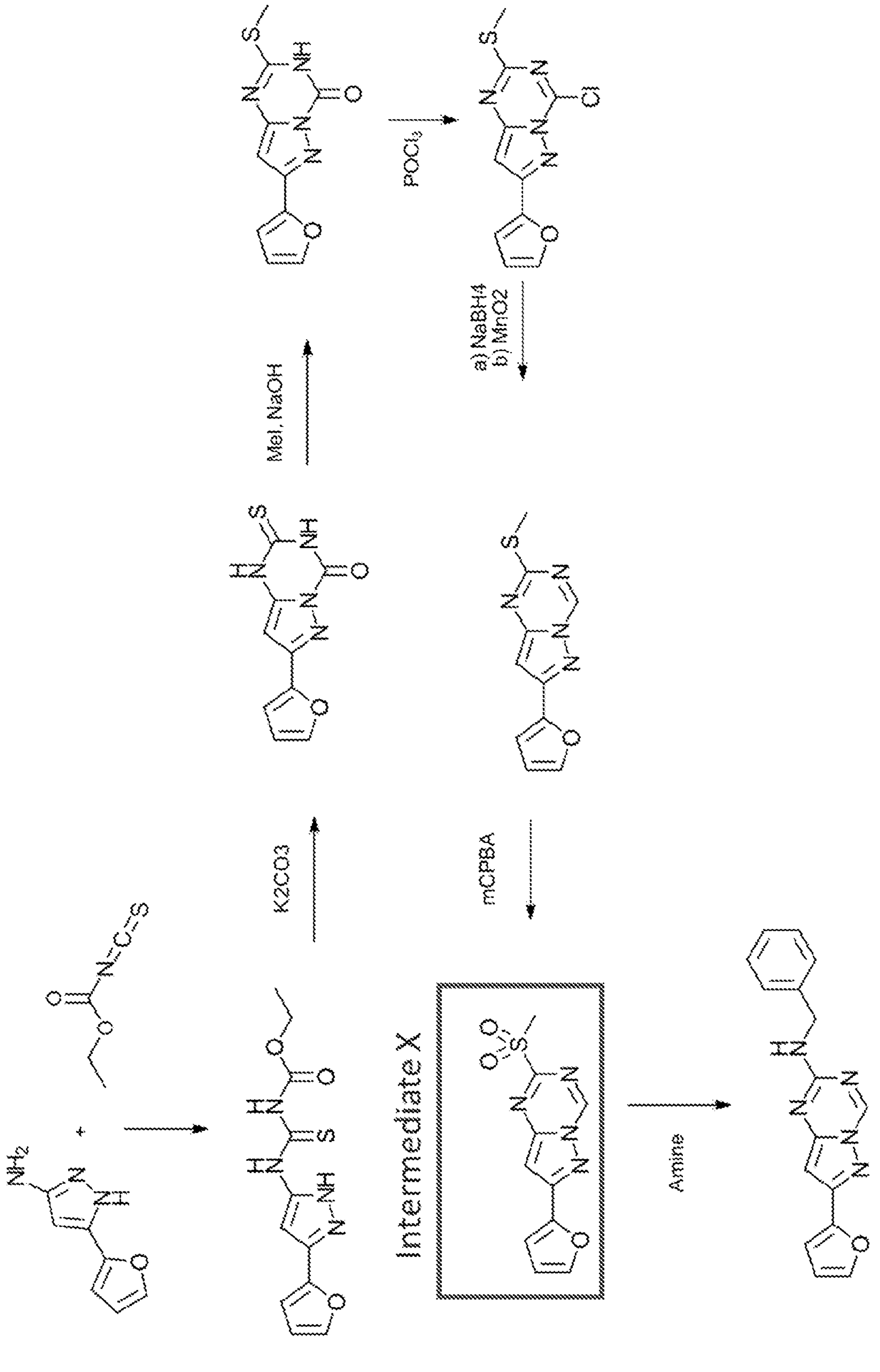
FIG. 11 shows a reaction scheme for the preparation of a compound, via intermediate X, of formula I in which A is CH, $R_1$ is furan-2-yl; $R_2$ is hydrogen, and $R_3$ is benzylamino.
Figure 12:
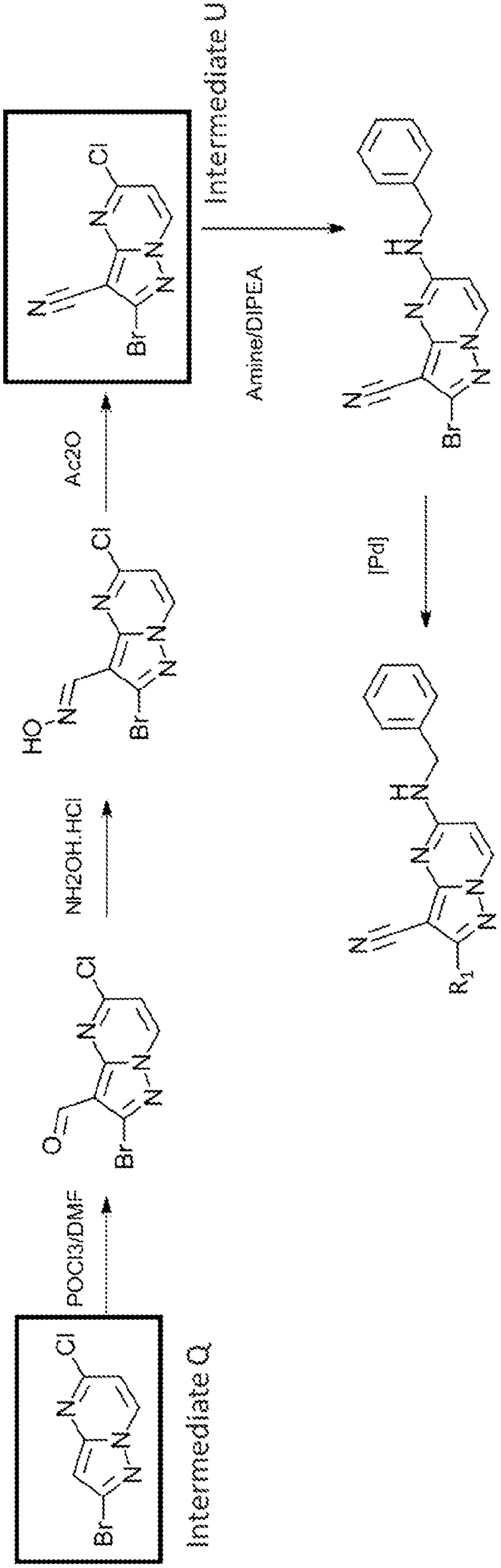
FIG. 12 shows a reaction scheme for the preparation of intermediate U as well as compounds of formula I in which A is CH, $R_1$ is a group as defined herein; $R_2$ is cyano, and $R_3$ is benzylamino.
Figure 13:
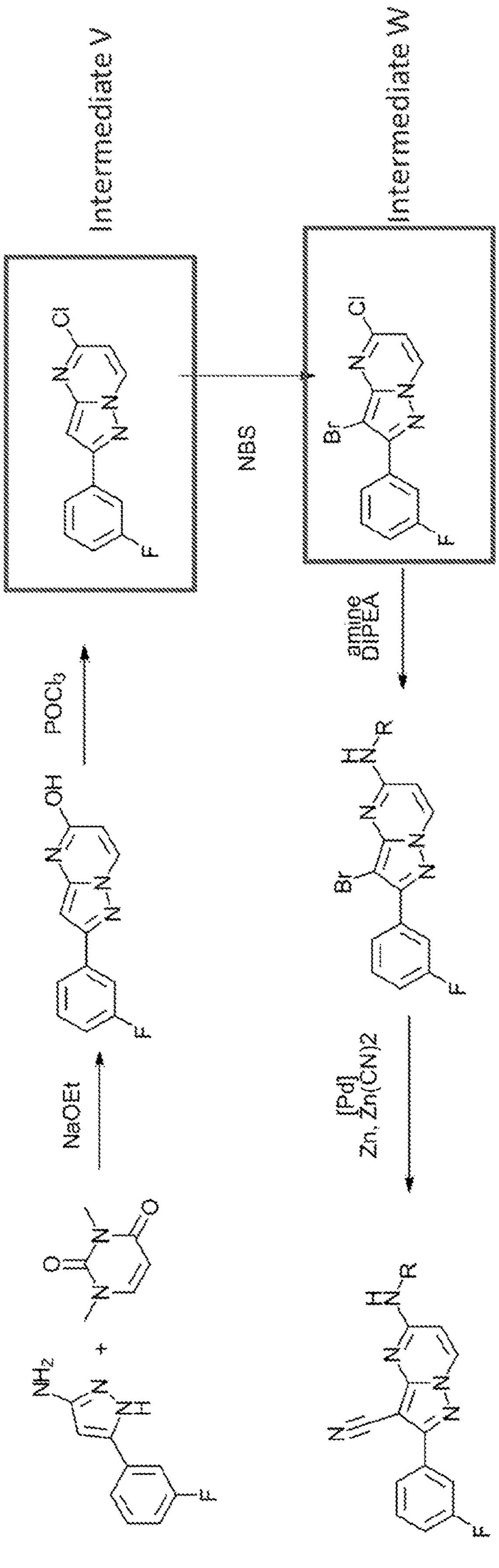
FIG. 13 shows a reaction scheme for the preparation of intermediate compounds V and W, as well as compounds of formula I in which A is CH, $R_1$ is 3-fluorophenyl, $R_2$ is cyano or bromo, and $R_a$ is an amine linked substituent group, denoted by the formula —NHR.
Figure 14:
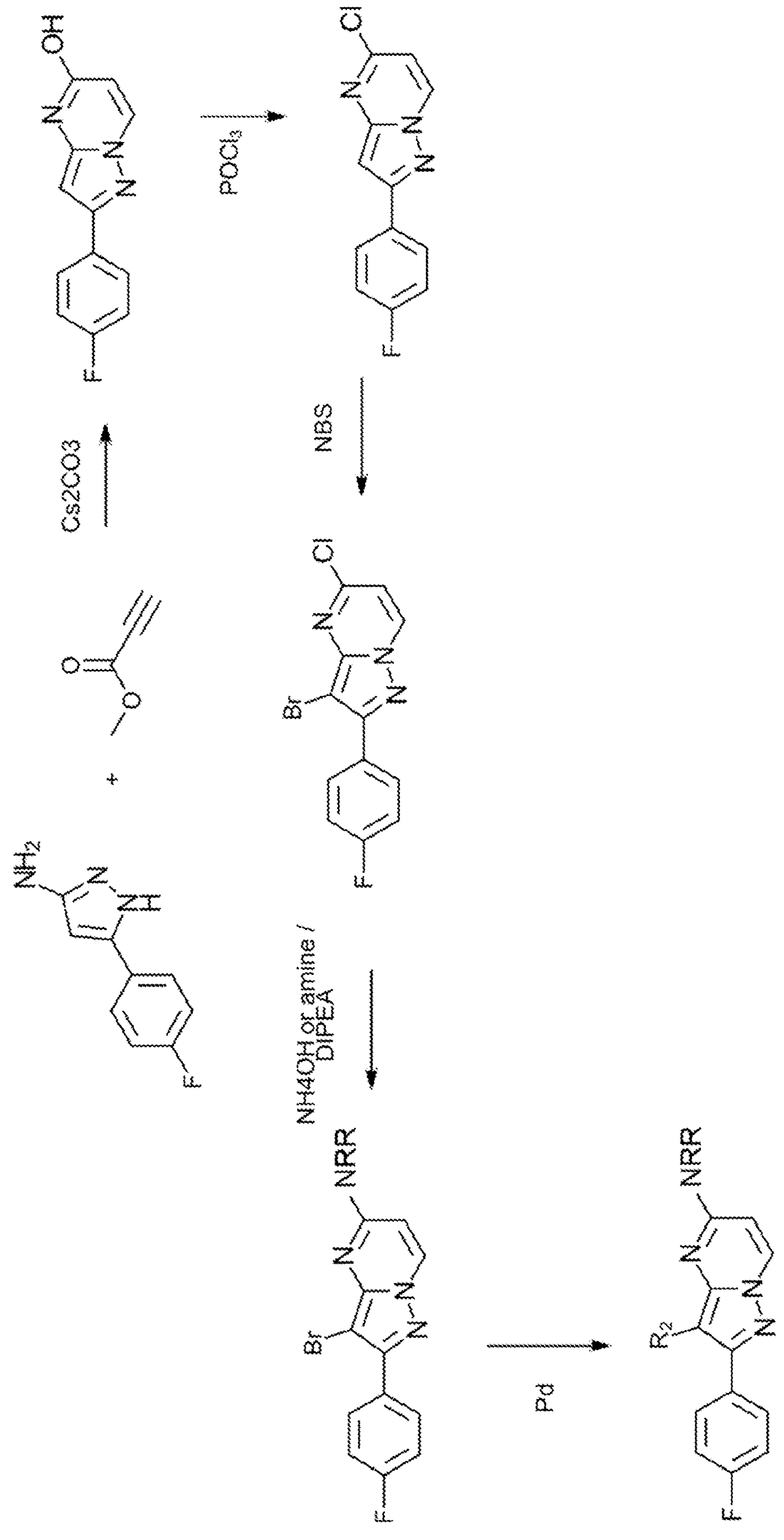
FIG. 14 shows a reaction scheme for the preparation of compounds of formula I in which A is CH, $R_1$ is 4-fluorophenyl, $R_2$ is a group as defined herein, $R_s$ is an amine linked substituent group, denoted by the formula "—NRR", where each R is hydrogen or a substituent group.
Figure 15:
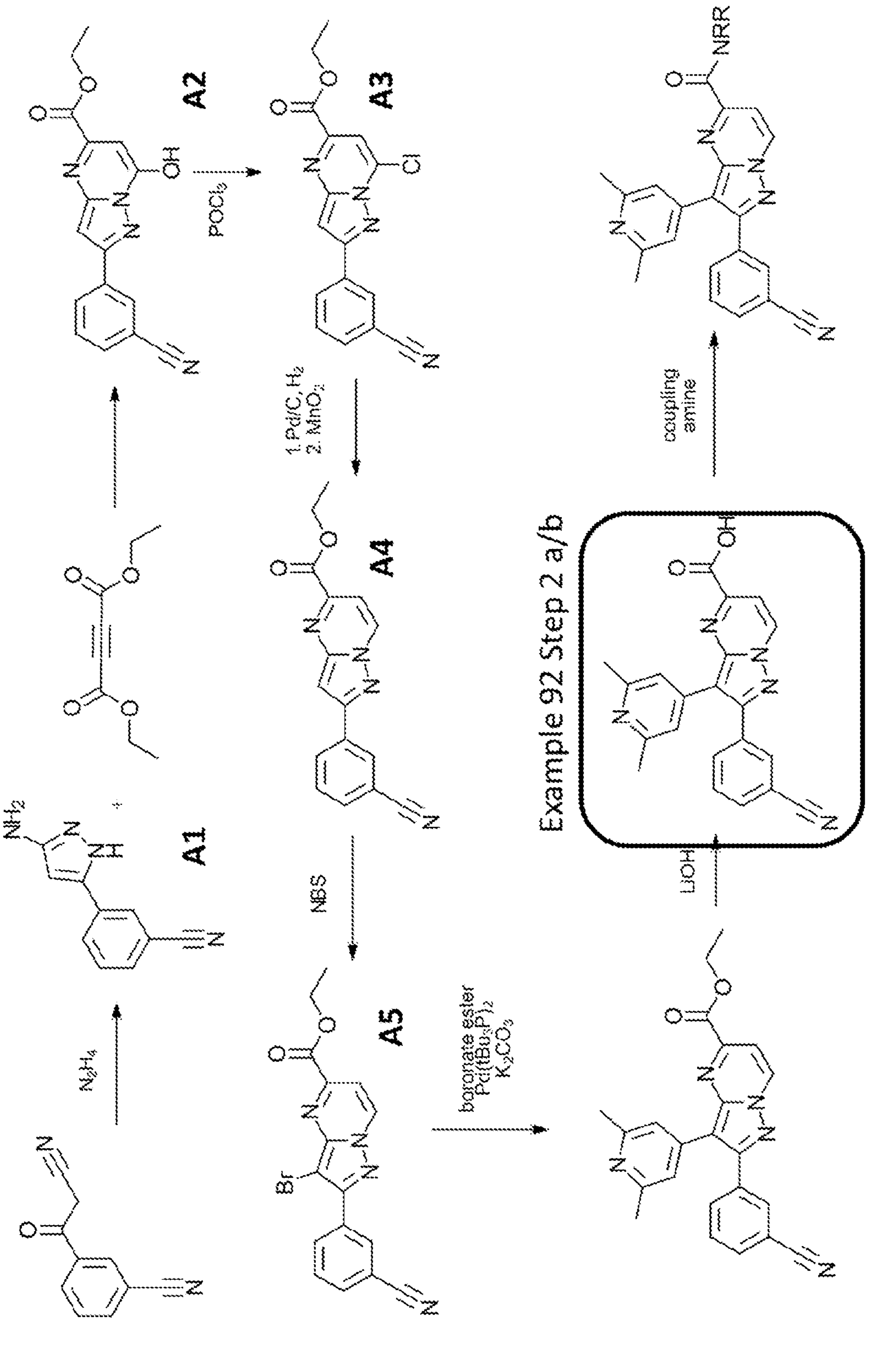
FIG. 15 shows a reaction scheme for the preparation of intermediate compound shown in Example 92 step 2a and 2b, as well as compounds of formula I in which A is CH, $R_1$ is 3-cyanophenyl, $R_2$ is 2,6-dimethylpyridin-4-yl, and $R_3$ is an amide linked substituent group, denoted by the formula —C(O)—NRR, where each R is hydrogen or a substituent group.
Figure 16:
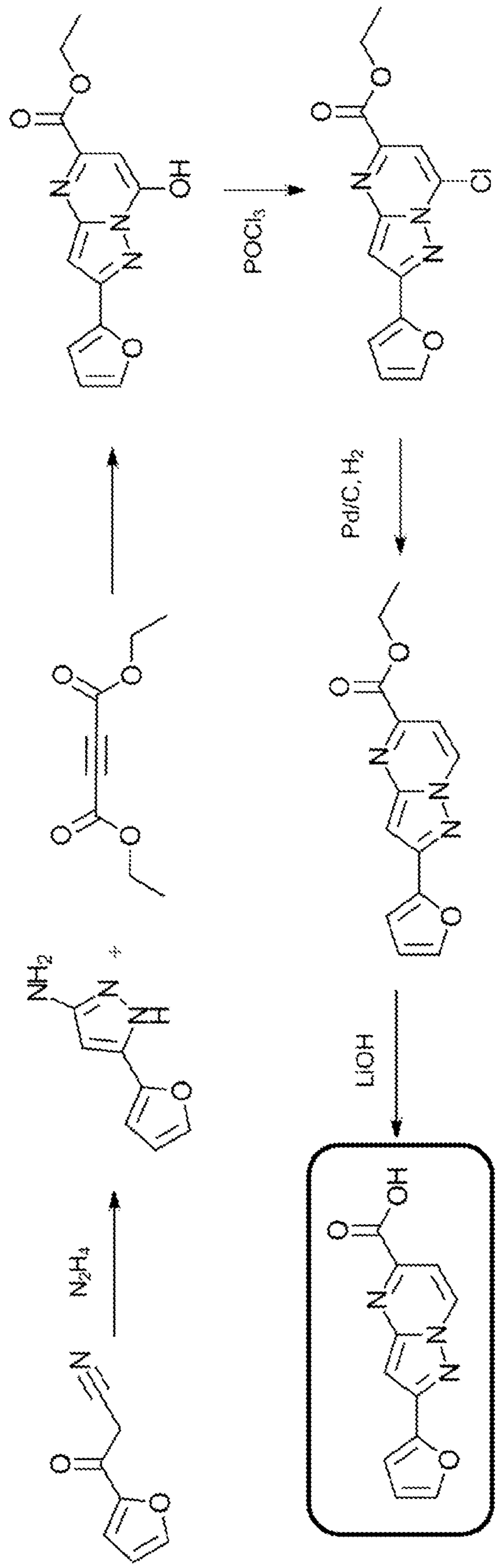
FIG. 16 shows a reaction scheme for the preparation of intermediate compound Y.
Figure 17:
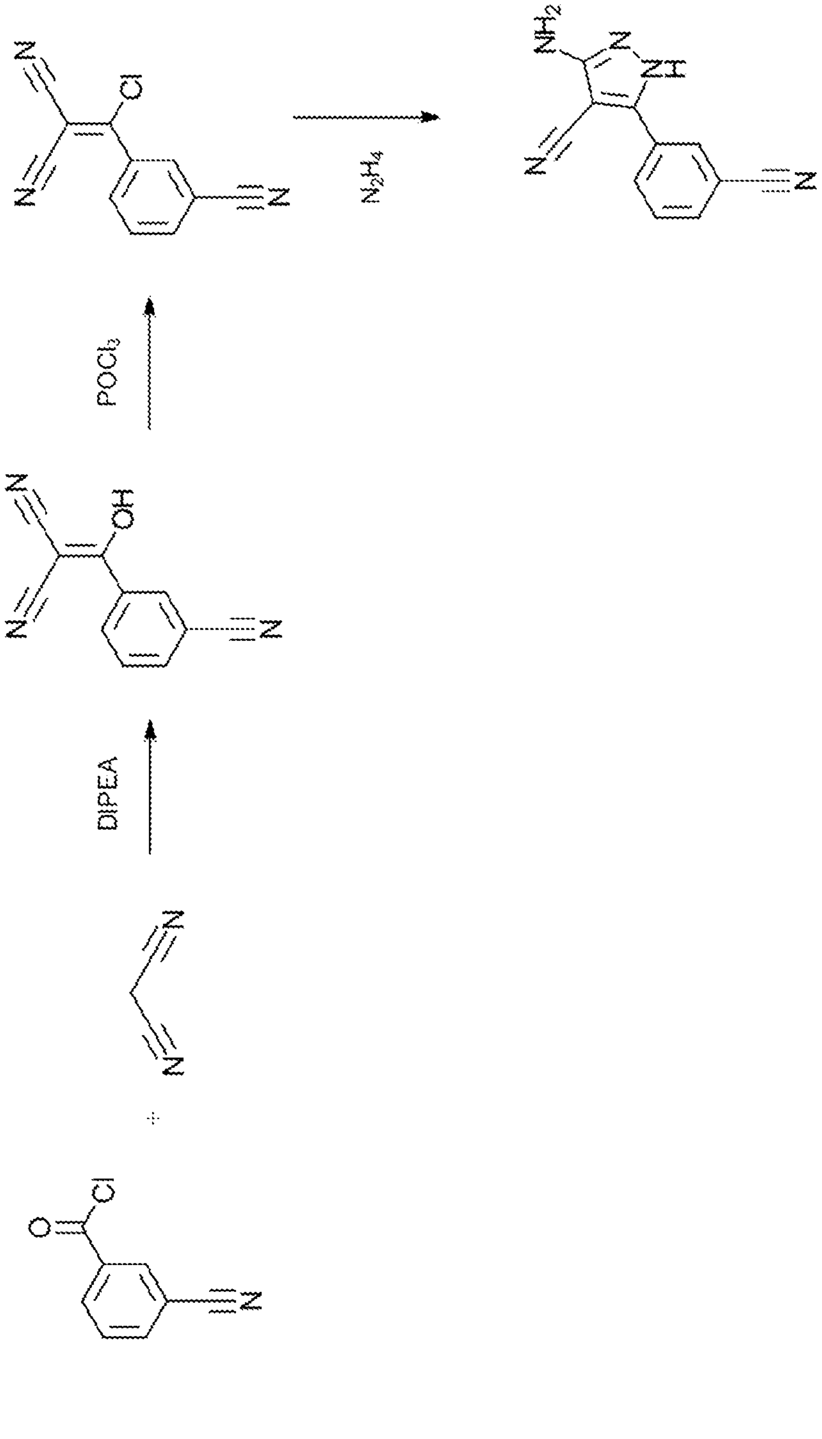
FIG. 17 shows a reaction scheme for the preparation of intermediate compound Z.
Figure 18:
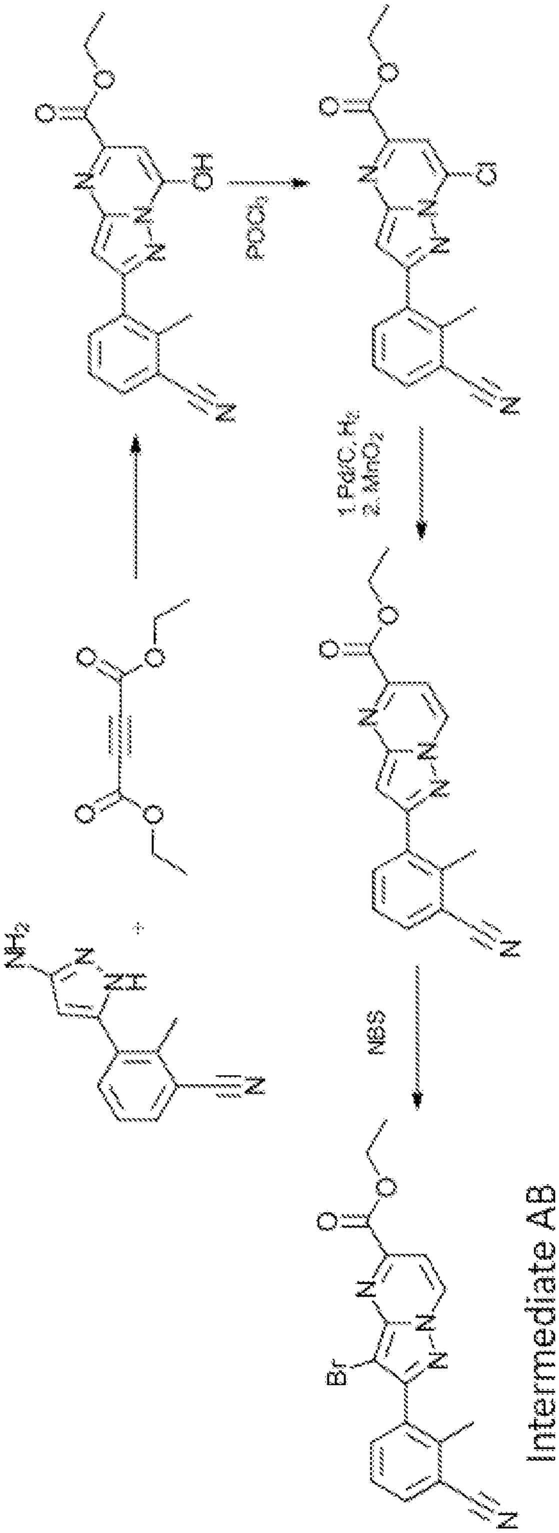
FIG. 18 shows a reaction scheme for the preparation of intermediate compound AB.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction.

The skilled chemist will-appreciate when such protection is required, and how such protecting groups may be put in place, and later removed.

For Examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of Example, a suitable protecting group for an amino or alkylamino group is, for example, an acyl group, for example an alkanoyl group such as acetyl, an alkoxycarbonyl group, for example -a methoxycarbonyl, ethoxycarbonyl or tbutoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide.

Alternatively an acyl group such as a tertbutoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladiumoncarbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively, an arylmethyl group such as a benzyl group may be removed, for example, by hydrogenation over a catalyst such as palladiumoncarbon.

A suitable protecting group for a carboxy group is, for example, an esterifying group, for example a methyl or an ethyl group which may be removed, for example, by hydrolysis with a base such as sodium hydroxide, or for example a tbutyl group which may be removed, for example, by treatment with an acid, for example an organic acid such as trifluoroacetic acid, or for example a benzyl group which may be removed, for example, by hydrogenation over a catalyst such as palladiumoncarbon.

Resins may also be used as a protecting group.

The methodology employed to synthesise a compound of formula (I) will vary depending on the nature of A, $R_1$, $R_2$ and $R_3$ and any substituent groups associated therewith. Suitable processes for their preparation are described further in the accompanying Examples.

Once a compound of formula (I) has been synthesised by any one of the processes defined herein, the processes may then further comprise one or more of the additional steps of:

(i) removing any protecting groups present;

(ii) converting the compound formula (I) into another compound of formula (I);

(iii) forming a pharmaceutically acceptable salt, hydrate or solvate of the compound of formula I; and/or (iv) forming a prodrug of the compound of formula I.

An Example of (ii) above is when a compound of formula (I) is synthesised and then one or more of the groups of A, $R_1$, $R_2$ or $R_3$, may be further reacted to change the nature of the group and provide an alternative compound of formula (I).

The resultant compounds of formula (I) can be isolated and purified using techniques well known in the art.

Certain compounds of formula I defined herein may be prepared by:

(i) reacting a compound of formula IIa

IIa

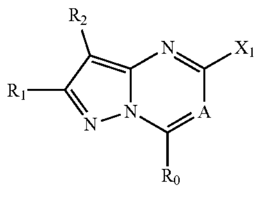

wherein A, $R_0$, $R_1$ and $R_2$ are each as defined hereinbefore, and $X_1$ is a suitable leaving group (e.g. bromo, chloro, iodo, —SMe, —S(O)Me or —$S(O)_2Me$);

with a group $[R_3-X_2]$—H, wherein $X_2$ is N, S or O and $[R_3-X_2]$together represent a group $R_3$ as defined hereinbefore that is linked through a $X_2$ atom; and optionally thereafter, the process may further comprise one or more of the additional steps of:

(i) removing any protecting groups that may be present;

(ii) converting the compound formula (I) into another compound of formula (I) (e.g. converting a $R_3$ substituent into another $R_3$ substituent group as defined herein);

(iii) forming a pharmaceutically acceptable salt, hydrate or solvate of the compound of formula I; and/or (iv) forming a prodrug of the compound of formula I.

For the avoidance of any doubt, the $X_2$ atom is a heteroatom present in a group $R_3$, i.e. $[R_3-X_2]$is a $R_3$ group comprising a $X_2$ heteroatom.

It will be appreciated that, in the above reaction, if a compound of formula il is reacted with a $[R_3-X_2]$—H group, the $X_1$ group is displaced along with the H atom of the $[R_3-X_2]$-H group and the $R_3$ substituent group is bound to the compound of formula II via the $X_2$ atom.

A person skilled in the art, will be able to readily select suitable reaction conditions for the reaction between a compound of formula II and a $[R_a-X_2]$—H group. Examples of suitable reaction conditions are described in the accompanying example section herein.

Compounds of formula II can be prepared by suitable techniques known in the art, as will be evident from the accompanying example section. Particular examples of the preparation of compounds of formula II are described in the accompanying example section herein.

Compounds of formula I may also be prepared by Suzuki-Miyaura or Stille coupling reactions. For example, certain compounds of formula I defined herein may also be prepared by:

(i) reacting a compound of formula III:

III

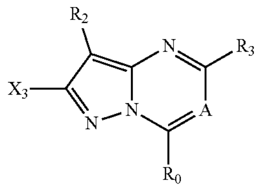

wherein A, $R_0$, $R_2$ and $R_3$ are each as defined hereinbefore and $X_3$ is a halo atom (e.g. bromo, chloro or iodo);

with a group of the formula:

$R_1$-M wherein M is a coupling reagent (e.g. a boron coupling agent or a tin coupling agent as defined herein) and $R_1$ is as defined hereinbefore; or (ii) reacting a compound of formula IV:

IV

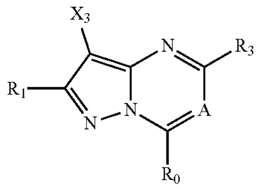

wherein A, $R_0$, $R_1$ and $R_3$ are each as defined hereinbefore and $X_3$ is a halo atom (e.g. bromo, chloro or iodo);

with a group of the formula:

$R_2$-M wherein M is a coupling reagent (e.g. a boron coupling agent or a tin coupling agent as defined herein) and $R_2$ is as defined hereinbefore; or (iii) reacting a compound of formula V:

V

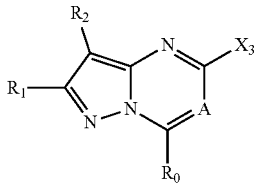

wherein A, $R_0$, $R_1$ and $R_2$ are each as defined hereinbefore and $X_3$ is a halo atom (e.g. bromo, chloro or iodo);

with a group of the formula:

$R_3$-M wherein M is a coupling reagent (e.g. a boron coupling agent or a tin coupling agent as defined herein) and $R_3$ is as defined hereinbefore; or and optionally thereafter, the process may further comprise one or more of the additional steps of:

(i) removing any protecting groups that may be present;

(ii) converting the compound formula (I) into another compound of formula (I);

(iii) forming a pharmaceutically acceptable salt, hydrate or solvate of the compound of formula I; and/or (iv) forming a prodrug of the compound of formula I.

The group M may be a suitable boron coupling reagent known in the art for Suzuki-Miyaura coupling reactions. Examples of suitable boron agents include: boronic acid, boronic esters (e.g. catechol boronic acid ester, pinacol boronic acid ester, triisopropyl boronate, MIDA boronate, cycictriol boronate), boranes (e.g. 9-BBN borane), organotrifluoroborate or boronamides (e.g. 1,8-diaminonaphthyl boronamide). Particular examples are —$B(OH)_2$ or -$B(OCH_3)_2$.

Suzuki-Miyaura coupling reactions are well known and a person skilled in the art will be able to readily select suitable reaction conditions for this reaction.

In Stille coupling reactions, M is a tin coupling agent, suitably a tin coupling agent of the formula —Sn[(1-6C) alkyl]$_3$, for example —Sn(butyl)$_3$.

Stille coupling reactions are well known and a person skilled in the art will be ale to readily select suitable reaction conditions for this reaction. Such reactions are typically carried out in the presence of a palladium catalyst.

BIOLOGICAL ACTIVITY

The biological assays described in the example section (Biological Examples 1 to 3) may be used to measure the pharmacological effects of the compounds of the present invention.

Although the pharmacological properties of the compounds of formula I vary with structural change, as expected, the compounds of the invention were found to be active in the assays described in Biological Examples 1, 2 and 3.

In general, in terms of adenosine A2a antagonism, the compounds of the invention demonstrate an $IC_{50}$ of 1 μM or less in the assay described in Biological Example 1, with preferred compounds of the invention demonstrating an $IC_{50}$ of 200 nM or less and the most preferred compounds of the invention demonstrating an $IC_{50}$ of 50 nM or less.

Suitably the $IC_{50}$ at the adenosine A1, A2b or A3 receptors of the compounds of the invention in the assay described in Biological Example 1 is at least two-fold higher than the $IC_{50}$ at the adenosine A2a receptor, and more suitably it is at least 5-fold higher, and even more suitably it is at least 10-fold higher.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For Example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as antagonists of adenosine A2 receptors, especially adenosine A2a receptors.

According to a further aspect of the present invention, there is provided a method of antagonising adenosine A2a receptors in vitro or in vivo, said method comprising contacting a cell with an effective amount of a compound or a pharmaceutically acceptable salt, hydrate or solvate thereof as defined herein.

According to a further aspect of the present invention, there is provided a method of selectively antagonising adenosine A2a receptors in vitro or in vivo, said method comprising contacting a cell with an effective amount of a compound, or a pharmaceutically acceptable salt, hydrate or solvate thereof, as defined herein.

According to a further aspect of the present invention, there is provided a method of inhibiting cell proliferation, in vitro or in vivo, said method comprising contacting a cell with an effective amount of a compound or a pharmaceutically acceptable salt, hydrate or solvate thereof as defined herein, or a pharmaceutical composition as defined herein. Suitably, the compound or pharmaceutical composition is administered in combination with one or more additional antiproliferative agents (e.g. checkpoint inhibitors and/or cytotoxic agents).

According to a further aspect of the present invention, there is provided a method of treating a disease or disorder in which adenosine A2a receptor activity is implicated in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating a proliferative disorder in a patient in need of such treatment, said method comprising administering to said patient a therapeutically effective amount of a compound or a pharmaceutically acceptable salt, hydrate or solvate thereof as defined herein, or a pharmaceutical composition as defined herein. Suitably, the compound or pharmaceutical composition is administered in combination with one or more additional antiproliferative agents (e.g. checkpoint inhibitors and/or cytotoxic agents).

According to a further aspect of the present invention, there is provided a method of treating cancer in a patient in need of such treatment, said method comprising administering to said patient a therapeutically effective amount of a compound or a pharmaceutically acceptable salt, hydrate or solvate thereof as defined herein, or a pharmaceutical composition as defined herein. Suitably, the compound or pharmaceutical composition is administered in combination with one or more additional anticancer agents (e.g. checkpoint inhibitors and/or cytotoxic agents).

According to a further aspect of the present invention, there is provided a compound, or a pharmaceutically acceptable salt, hydrate or solvate thereof, or a pharmaceutical composition as defined herein for use in therapy.

According to a further aspect of the present invention, there is provided a compound or a pharmaceutically acceptable salt, hydrate or solvate thereof as defined herein, or a pharmaceutical composition as defined herein, for use in the treatment of a proliferative condition. Suitably, the compound or pharmaceutical composition is administered in combination with one or more additional antiproliferative agents (e.g. checkpoint inhibitors and/or cytotoxic agents).

According to a further aspect of the present invention, there is provided a compound, or a pharmaceutically acceptable salt, hydrate or solvate thereof, or a pharmaceutical composition as defined herein for use in the treatment of cancer. In a particular embodiment, the cancer is human cancer. Suitably, the compound or pharmaceutical composition is administered in combination with one or more additional anticancer agents (e.g. checkpoint inhibitors and/or cytotoxic agents).

According to a further aspect of the present invention, there is provided a compound, or a pharmaceutically acceptable salt, hydrate or solvate thereof, as defined herein for use as an adenosine A2a antagonist. In an embodiment, the compounds of the invention are selective adenosine A2a antagonists. In an alternative embodiment, certain compounds of the invention are selective adenosine A2a and adenosine A2b antagonists.

According to a further aspect of the present invention, there is provided a compound, or a pharmaceutically acceptable salt, hydrate or solvate thereof, as defined herein for use in the treatment of a disease or disorder in which adenosine A2a is implicated.

According to a further aspect of the present invention, there is provided the use of a compound, or a pharmaceutically acceptable salt, hydrate or solvate thereof, as defined herein in the manufacture of a medicament for the treatment of a proliferative condition.

Suitably, the compound or pharmaceutical composition is administered in combination with one or more additional antiproliferative agents (e.g. checkpoint inhibitors and/or cytotoxic agents).

According to a further aspect of the present invention, there is provide the use of a compound, or a pharmaceutically acceptable salt, hydrate or solvate thereof, as defined herein in the manufacture of a medicament for the treatment of cancer. Suitably, the cancer is a human cancer. Suitably, the compound or pharmaceutical composition is administered in combination with one or more additional anticancer agents (e.g. checkpoint inhibitors and/or cytotoxic agents).

According to a further aspect of the present invention, there is provided a use of a compound, or a pharmaceutically acceptable salt, hydrate or solvate thereof, as defined herein in the manufacture of a medicament for use as an adenosine A2a antagonist.

According to a further aspect of the present invention, there is provided a use of a compound, or a pharmaceutically acceptable salt, hydrate or solvate thereof, as defined herein in the manufacture of a medicament for use as an adenosine A2a antagonist.

According to a further aspect of the present invention, there is provided a use of a compound, or a pharmaceutically acceptable salt, hydrate or solvate thereof, as defined herein in the manufacture of a medicament for the treatment of a disease or disorder in which adenosine A2a receptor activity is implicated.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers (by virtue of their adenosine A2a antagonist activity).

More specifically, there is provided a compound of general formula (I) for use in the treatment of cancer, particularly solid tumours, for example non-small cell or small cell lung cancer, head and neck squamous cancer and urothelial cancer.

More specifically, there is provided a compound of general formula (I) for use in the treatment of cancer, for example, lung cancer, such as small cell lung cancer or non-small cell lung cancer.

There is also provided the use of a compound of general formula (I) in the manufacture of a medicament for the treatment of cancer, particularly solid tumours, for example non-small cell or small cell lung cancer, head and neck squamous cancer and urothelial cancer.

The invention further provides a method for the treatment of cancer, particularly solid tumours, for example non-small cell or small cell lung cancer, head and neck squamous cancer and urothelial cancer, the method comprising administering to a patient in need of such treatment an effective amount of a compound of general formula (I).

The patient to be treated is suitably a mammal and more suitably a human.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, intrasternal, and intratumoural; by implant of a depot or reservoir, for example, subcutaneously or intramuscularly.

The compounds of the invention or pharmaceutical compositions comprising these compounds may be administered by intratumoural delivery.

Combination Therapies

The compounds of formula I are useful for the treatment and/or prophylaxis of proliferative disorders, such as, for example, cancer. A compound of formula I defined herein may be used in combination with one or more additional antiproliferative/anticancer therapies, such as, for example, chemotherapy with one or more additional antiproliferative/anticancer agents, radiotherapy and/or conventional surgery.

An additional antiproliferative/anticancer agent may be included in the pharmaceutical composition with a compound of formula (I) as defined herein or, alternatively, it may be administered separately, either at the same time as the compound of formula (I) or at an earlier or later time.

Therefore, in a further aspect of the present invention there is provided a product comprising a compound of general formula (I) and an additional agent useful in the treatment or prevention of cancer as a combined preparation for simultaneous, sequential or separate use in the treatment of cancer.

The present invention also provides a compound of general formula (I) in combination with one or more additional antiproliferative/anticancer agents for use in the treatment of cancer as a combined preparation for simultaneous, sequential or separate use in the treatment of treatment of cancer, In particular, the combination therapy defined herein is suitable for the treatment of solid tumours for example non-small cell or small cell lung cancer, head and neck squamous cancer and urothelial cancer.

Suitable additional antiproliferative/anti-cancer agents that may be used in combination with a compound of formula I defined herein [either separately or as part of a combined pharmaceutical composition or a combined preparation with the compounds of general formula (I)]include:

1) other forms of cancer immunotherapy and anti-cancer chemotherapeutic agents;
2) adenosine pathway modulators, including, but not limited to A2b antagonists, CD73 inhibitors and CD39 inhibitors;
3) anti-PD-1 and PDL-1 antibodies including, but not limited to, cetrelimab pembrolizumab, nivolumab, durvalumab, avelumab and atezolizumab; and
4) anti-CTLA4 antibodies including, but not limited to, ipilimumab.

The compounds of formula I defined herein are particularly suited to use in combination with anti-PD-1 and PDL-1 antibodies including, but not limited to, Cetrelimab, pembrolizumab, nivolumab, durvalumab, avelumab and atezolizumab.

Suitably, the anti-PD1 antibody is one of the antibodies disclosed in U.S.

Publication No. 2019/0225689 or U.S. Publication No. 2017/0121409 (incorporated herein by reference in their entireties), such as cetrelimab. Cetrelimab (JNJ-63723283, CET) is a fully human immunoglobulin (Ig) G4 kappa monoclonal antibody that binds to programmed death receptor-1 (PD-1) with high affinity and specificity. Cetrelimab has shown activity in solid tumors. Rutkowski P, et al. Journal of Clinical Oncology. 2019;37(8):31.

The compounds of formula I defined herein are particularly suited to use in combination with adenosine pathway modulators, including, but not limited to A2b antagonists, CD73 inhibitors and CD39 inhibitors.

The A2a antagonists of general formula (I) can also be used in combination with cell-based immunotherapy and cancer vaccines that include, but are not limited to CAR-T cell therapy.

Examples of the additional antiproliferative/anticancer chemotherapeutic agents include, but are not limited to, any one or more of the following: MEK (e.g. MEK1, MEK2, or MEK1 and MEK2) inhibitors (e.g. XL518, C1-1040, PD035901,selumetinib/AZD6244, GSK1 120212/trametinib, GDC-0973, ARRY-162, ARRY-300, AZD8330, PD0325901, U0126, PD98059, TAK-733, PD3 18088, AS703026, BAY 869766), alkylating agents (e.g., cyclophosphamide, ifosfamide, chlorambucil, busulfan, meiphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, arboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec.RTM.), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-l, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin II1 derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine;

bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fiudarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatinA; marimastat; masoprocol; maspin; matrilysin inhibitors; matrix metalloproteinase inhibitors; menogaril; merbarone; meterelin; methioninase; metoclopramide; MIF inhibitor; mifepristone;miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzyl guanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-basedimmune modulator; protein kinase C inhibitor; protein kinase C inhibitors, microalgal; proteintyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAPinhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichioride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride;

hydroxyurea; idarubicin hydrochloride; ifosfamide; iimofosine; interleukin 2 (including recombinant interleukin 2, or rlL.sub.2), interferon alfa-2a; interferon alfa-2b; interferon alfa-ni; interferon alfa-n3; interferon beta- la; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol.TM (i.e. paclitaxel), Taxotere.TM, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-3 10705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DF E), Fijianolide B, Laulimalide, Narcosine (also known as NSC-5366), Nascapine, Hemiasterlin, Vanadocene acetylacetonate, Monsatrol, Inanocine (i.e. NSC-698666), Eleutherobins (such as Desmethyleleutherobin, Desaetyleleutherobin, Isoeleutherobin A, and ZEleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-F£ER2, anti-CD52, anti- ULA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to In, OY, or I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035,BMS-599626), sorafenib, imatinib, sunitinib, dasatinib, hormonal therapies, or the like.

As indicated above, the combination therapy of the present invention may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and one or more additional antiproliferative/anticancer agents.

According to this aspect of the invention there is also provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and one or more additional antiproliferative/anticancer agents selected from those listed above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

General Conditions:

Mass spectra were run on LC-MS systems using electrospray ionization. These were run using either a Waters Acquity H-Class UPLC with PDA and QDa mass detection, an Acquity UPLC (binary pump/PDA detector)+ZQ Mass Spectrometer or Acquity i-Class (quaternary pump/PDA detector)+Quattro Micro Mass Spectrometer, a Waters Acquity uPLC system with Waters PDA and ELS detectors or a Shimadzu LC-MS-2010EV system. [M+H]+refers to mono-isotopic molecular weights.

NMR spectra were run on either a Bruker Ultrashield 500 MHz NMR spectrometer, a Bruker Avance Ill HD 400 MHz NMR spectrometer, a Bruker Avance DPX 300 MHz NMR spectrometer, a BrukerAvance III HD 500 MHz or a BrukerAvance Ill HD 250 MHz. Spectra were recorded at 298K and were referenced using the solvent peak.

The following examples are intended to illustrate the invention and are not to be construed as being limitations thereon. Temperatures are given in degrees centigrade. If not mentioned otherwise, all evaporations are performed in vacuo, preferably between about 15 mm Hg and 100 mm Hg (=20-133 mbar). The structure of final products, intermediates and starting materials is confirmed by standard analytical methods e.g., MS and NMR.

Abbreviations used are those conventional in the art. If not defined, the terms have their generally accepted meanings.

Abbreviations app apparent
br broad
d doublet
dd doublet of doublets
DABCO (1,4-diazabicyclo [2.2.2]octane)
DBU 1,8-diazabicyclo[5.4.0]undec-7-ene
DCM dichloromethane
DIPEA diisopropylethylamine
DMA dimethylacetamide
DMF N,N-dimethylformamide
EtOAc ethyl acetate
HPLC high performance liquid chromatography
HBTU hexafluorophosphate benzotriazole tetramethyl uranium
IMS industrial methylated spirit
LC-MS liquid chromatography and mass spectrometry
mCPBA 3-chloroperbenzoic acid
MeOH methanol
MeCN acetonitrile
MS mass spectrometry
m multiplet
min(s) minute(s)
mL millilitre(s)
m/z mass to charge ratio
NBS N-bromosuccinimide
NMR nuclear magnetic resonance
$Pd(amphos)_2Cl_2$ bis(di-tert-butyl(4-dimethylaminophenyl)phosphine)dichloropalladium(II) $Pd(tBu_3P)_2$ bis(tri-tert-butylphosphine)palladium(0)
ppm parts per million
PS polymer supported
$R_t$ retention time
s singlet
t triplet
T3P propanephosphonic acid anhydride
TFA trifluoroacetic acid
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompass any tautomeric form of the drawn structure.

If not indicated otherwise, the analytical HPLC conditions are as follows:

Method 2A
- Column: Kinetex Core-Shell C18 2.1×50 mm 5 μm
- Column Temp 40° C.
- Eluents: A: $H_2O$+0.1% formic acid, B: MeCN+0.1% formic acid
- Flow Rate: 1.2 mL/min
- Gradient: 0-1.83 min 5-100 B, 1.83-2.25 min 100% B, 2.25-2.26 min 100-5% B Method 2.5B
- Column: Phenomenex Gemini-NX C18 2×50 mm 3 μm
- Column Temp: 40° C.
- Eluents: A: 2 mM ammonium bicarbonate, buffered to pH10, B: MeCN
- Flow Rate: 1 mL/mins
- Gradient: 0-1.80 min 1-100% B, 1.80-2.10 min 100% B, 2.10-2.30 min 100-1% B Method 3A
- Column: Acquity UPLC CSH C18 2.1×50 mm, 1.7 μm
- Column Temp: 50° C.
- Eluents: A: $H_2O$, B: MeCN, 0.1% formic acid
- Flow Rate: 1 mL/min
- Gradient: 0.2-2.5 min 2-98% B, 2.5-3.0 min 98% B Method 3B
- Column: Acquity UPLC BEH C18 2.1×50 mm, 1.7 μm
- Column Temp: 50° C.
- Eluents: A: H2O, B: MeCN, 0.1% ammonia
- Flow Rate: 1 mL/min
- Gradient: 0.2-2.5 min 2-98% B, 2.5-3.0 min 98% B Method 5A
- Column: YMC-Triart C18 2×50 mm, 5 μm.
- Flow rate: 0.8 mL/min.
- Eluents: A: H2O, B: MeCN, C: 50% H2O/50% MeCN+1.0% formic acid
- Gradient: 0.0-4.0 min 0-95% B, 5% C; 4.0-4.4 min 95% B, 5% C; 4.4-4.5 min 95% A, 5% B Method 5B
- Column: YMC-Triart C18 2×50 mm, 5 μm.
- Flow rate: 0.8 mL/min.

Eluents: A: $H_2O$, B: MeCN, C: 50% $H_2O$/50% MeCN+ 1.0% ammonia (aq.)

Gradient: 0.0-4.0 min 0-95% B, 5% C; 4.0-4.4 min 95% B, 5% C; 4.4-4.5 min 95% A, 5% B Method 7A Column: Phenomenex Kinetix-XB C18 2.1×100 mm, 1.7 μm Column Temp: 40° C.

Eluents: A: $H_2O$ 0.1% formic acid, B: MeCN, 0.1% formic acid

Flow Rate: 0.6 mL/min

Gradient: 0-5.3.0 min 5-100% B, 5.3-5.8 min 100% B, 5.8-5.82 min 100-5% B, 5.82-7.00 min 5% B Method 7B Column: Waters UPLC® BEH™ C18, 2.1 mm×100 mm, 1.7 μm column Column Temp: 40° C.

Eluents: A: 2 mM ammonium bicarbonate buffered to pH10, B: MeCN

Flow Rate: 0.6 mL/min

Gradient: 0-5.3.0 min 5-100% B, 5.3-5.8 min 100% B, 5.8-5.82 min 100-5% B, 5.82-7.00 min 5% B Method 8A Column: Acquity UPLC CSH C18 2.1×100 mm, 1.7 μm Column Temp: 50° C.

Eluents: A: $H_2O$, B: MeCN, 0.1% formic acid

Flow Rate: 0.6 mL/min

Gradient: 0.5-6.5 min 2-98% B 6.5-7.5 min 98% B

Method 8B

Column: Acquity UPLC BEH C18 2.1×100 mm, 1.7 μm

Column Temp: 50° C.

Eluents: A: $H_2O$, B: MeCN, 0.1% ammonia

Flow Rate: 0.6 mL/min

Gradient: 0.5-6.5 min 2-98% B 6.5-7.5 min 98% B

Method 15A

Column: YMC-Triart C18 2×50 mm, 5 μm.

Flow rate: 0.8 mL/min.

Eluents: A: $H_2O$, B: MeCN, C: 50% $H_2O$/50% MeCN+ 1.0% formic acid

Gradient: 0.0-12.0 min 0-95% B, 5% C; 12.0-14.0 min 95% B, 5% C; 14.0-14.2 min 95% A, 5% B

Method 15B

Column: YMC-Triart C18 50×2 mm, 5 μm.

Flow rate: 0.8 mL/min.

Eluents: A: $H_2O$, B: MeCN, C: 50% $H_2O$/50% MeCN+ 1.0% ammonia (aq.)

Gradient: 0.0-12.0 min 0-95% B, 5% C; 12.0-14.0 min 95% B, 5% C; 14.0-14.2 min 95% A, 5% B Example 1-3-[5-Amino-3-(4-pyridyl)pyrazolo[1,5-a]pyrimidin-2-yl]benzonitrile

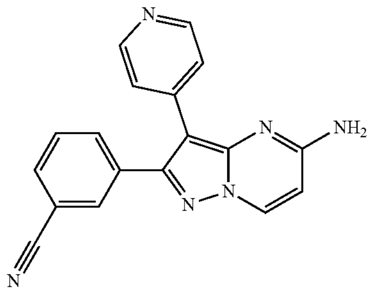 [SMILES: N#Cc1cccc(-c2nn3ccc(N)nc3c2-c2ccncc2)c1]

A mixture of 3-(5-amino-3-bromo-pyrazolo[1,5-a]pyrimidin-2-yl)benzonitrile (Intermediate E) (89 mg, 0.28 mmol), 4-pyridylboronic acid (52 mg, 0.42 mmol) and $K_2CO_3$ (78 mg, 0.57 mmol) in 1,4-dioxane (5 mL) and water (1 mL) was degassed under a flow of $N_2$. $Pd(tBu_3P)_2$ (14 mg, 0.03 mmol) was added and the reaction mixture heated to 120° C. (pre-heated bath) for 1 h. The resulting mixture was cooled to room temperature and added dropwise to stirring water (50 mL). The precipitate was collected by filtration and purification was carried out by chromatography on silica eluting with a gradient of 5 to 10% MeOH in DCM. The resulting material was triturated with MeOH (3 mL) followed by EtOAc (5 mL) to afford the title compound as a beige solid.

LC-MS (Method 15A): Rt 5.14 mins; MS m/z 313.2=[M+H]+

$^1$H NMR (500 MHz, DMSO-d6) δ 8.62 (d, J=7.5 Hz, 1H), 8.44 (d, J=5.5 Hz, 2H), 7.91 (t, J=3.3 Hz, 2H), 7.78 (d, J=7.9 Hz, 1H), 7.65 (t, J=8.0 Hz, 1H), 7.40 (d, J=5.2 Hz, 2H), 7.25 (s, 2H), 6.39 (d, J=7.5 Hz, 1H).

The compounds of the following tabulated Examples (Table Ex1) were prepared analogously to Example 1 from 3-(5-amino-3-bromo-pyrazolo[1,5-a]pyrimidin-2-yl)benzonitrile (Intermediate E) and the appropriate boronic acid or boronate ester.

TABLE Ex1

| Ex. | Structure and Name | Retention Time, [M + H]+, 1H NMR |
|---|---|---|
| 1.1 | 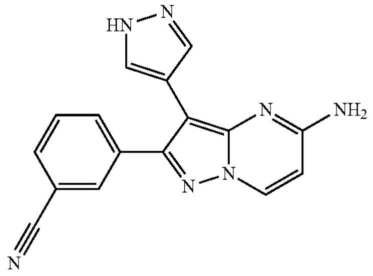 3-[5-Amino-3-(1H-pyrazol-4-yl)pyrazolo[1,5-a]pyrimidin-2-yl]benzonitrile | LC-MS (Method 15A): Rt 5.43 mins; MS m/z 302.2 = [M + H]+ $^1$H NMR (500 MHz, DMSO-d6) δ 12.81 (s, 1H), 8.54 (d, J = 7.4 Hz, 1H), 8.00-7.95 (m, 1H), 7.93 (d, J = 7.9 Hz, 1H), 7.85 (d, J = 7.7 Hz, 1H), 7.81-7.57 (m, 2H), 7.51 (br s, 1H), 6.98 (s, 2H), 6.30 (d, J = 7.5 Hz, 1H). |

TABLE Ex1-continued

| Ex. | Structure and Name | Retention Time, [M + H]+, 1H NMR |
|---|---|---|
| 1.2 | 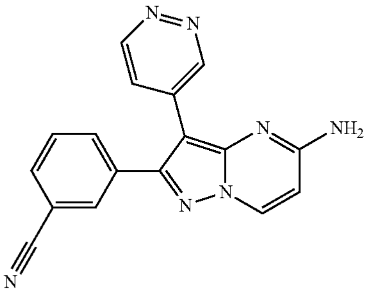<br>3-(5-Amino-3-pyridazin-4-yl-pyrazolo[1,5-a]pyrimidin-2-yl)benzonitrile | LC-MS (Method 8B): Rt 3.20 mins; MS m/z 314.1 = [M + H]+<br>$^1$H NMR (500 MHz, DMSO-d6) δ 9.34 (s, 1H), 9.02 (d, J = 4.2 Hz, 1H), 8.66 (d, J = 7.0 Hz, 1H), 8.06-7.89 (m, 2H), 7.82 (d, J = 7.3 Hz, 1H), 7.69 (d, J = 7.3 Hz, 1H), 7.55 (s, 1H), 7.41 (s, 2H), 6.44 (d, J = 7.0 Hz, 1H). |
| 1.3 | 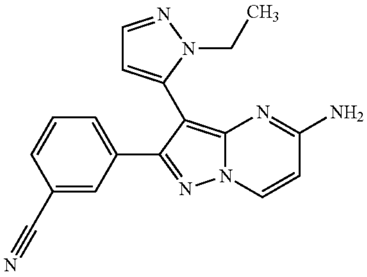<br>3-[5-Amino-3-(2-ethylpyrazol-3-yl)pyrazolo[1,5-a]pyrimidin-2-yl]benzonitrile | LC-MS (Method 8B): Rt 3.70 mins; MS m/z 330.1 = [M + H]+<br>$^1$H NMR (500 MHz, DMSO-d6) δ 8.62 (d, J = 7.5 Hz, 1H), 7.82-7.79 (m, 2H), 7.76 (dt, J = 8.0, 1.5 Hz, 1H), 7.57 (t, J = 8.2 Hz, 1H), 7.53 (d, J = 1.7 Hz, 1H), 7.19 (s, 2H), 6.36 (d, J = 7.5 Hz, 1H), 6.21 (d, J = 1.8 Hz, 1H), 3.86 (q, J = 7.2 Hz, 2H), 1.12 (t, J = 7.2 Hz, 3H). |
| 1.4 | 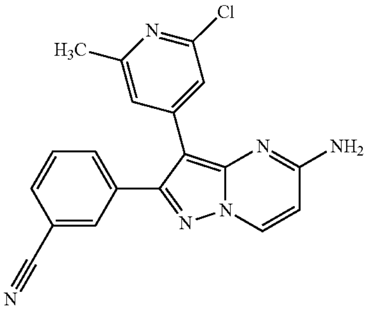<br>3-[5-Amino-3-(2-chloro-6-methyl-4-pyridyl)pyrazolo[1,5-a]pyrimidin-2-yl]benzonitrile<br>(Full preparation described in Intermediate F) | LC-MS (Method 8B): Rt 4.19 mins; MS m/z 361.1/363.1 = [M + H]+<br>$^1$H NMR (500 MHz, DMSO-d6) δ 8.62 (d, J = 7.5 Hz, 1H), 7.96-7.90 (m, 2H), 7.78 (dt, J = 7.9, 1.5 Hz, 1H), 7.69-7.62 (m, 1H), 7.35-7.28 (m, 3H), 7.19 (d, J = 1.3 Hz, 1H), 6.41 (d, J = 7.5 Hz, 1H), 2.33 (s, 3H). |
| 1.6 | 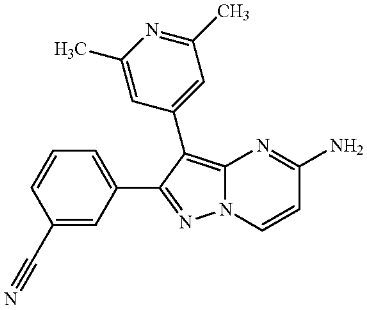<br>3-[5-Amino-3-(2,6-dimethyl-4-pyridyl)pyrazolo[1,5-a]pyrimidin-2-yl]benzonitrile | LC-MS (Method 8B): Rt 3.78 mins; MS m/z 341.1 = [M + H]+<br>$^1$H NMR (500 MHz, DMSO-$d_6$) δ 8.61 (d, J = 7.5 Hz, 1H), 8.05-7.81 (m, 2H), 7.79-7.72 (m, 1H), 7.63 (t, J = 8.1 Hz, 1H), 7.18 (s, 2H), 7.04 (s, 2H), 6.38 (d, J = 7.5 Hz, 1H), 2.34 (s, 6H). |

Example 2-3-[3-(2-Chloro-6-methyl-4-pyridyl)-5-[(2-hydroxy-2-methyl-propyl)amino]pyrazolo[1,5-a]pyrimidin-2-yl]benzonitrile

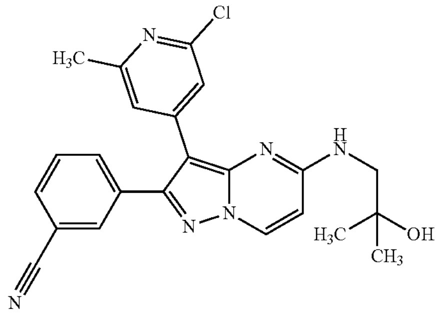 [SMILES: Cc1cc(-c2c(-c3cccc(C#N)c3)nn3ccc(NCC(C)(C)O)nc23)cc(Cl)n1]

A suspension of 3-[5-chloro-3-(2-chloro-6-methyl-4-pyridyl)pyrazolo[1,5-a]pyrimidin-2-yl]benzonitrile (Intermediate C) (900 mg, 2.37 mmol), 1-amino-2-methyl-propan-2-ol (316 mg, 3.55 mmol) and DIPEA (2.06 mL, 11.83 mmol) in NMP (15 mL) was heated to 50° C. for 3 h. After cooling to room temperature, the mixture was partitioned between 90% brine solution (100 mL) and EtOAc (100 mL). The organic layer was washed with 50% brine solution (3x50 mL), dried over $MgSO_4$ and concentrated in vacuo. Purification of the crude material by chromatography on silica eluting with a gradient of 0 to 5% MeOH in DCM afforded the title compound as a colourless solid.

LC-MS (Method 8B): Rt 4.24 mins; MS m/z 431.2/433.2=[M−H]−

$^1$H NMR (500 MHz, DMSO-$d_6$) δ 8.57 (d, J=7.6 Hz, 1H), 8.01-7.90 (m, 3H), 7.83 (d, J=7.8 Hz, 1H), 7.68 (t, J=7.8 Hz, 1H), 7.41 (s, 1H), 7.27 (s, 1H), 6.61 (d, J=7.6 Hz, 1H), 4.63 (s, 1H), 3.44 (d, J=5.8 Hz, 2H), 2.33 (s, 3H), 1.19 (s, 6H).

The compounds of the following tabulated Examples (Table Ex2) were prepared analogously to Example 2 from 3-[5-chloro-3-(2-chloro-6-methyl-4-pyridyl)pyrazolo[1,5-a]pyrimidin-2-yl]benzonitrile (Intermediate C) and the appropriate amine.

TABLE Ex2

| Ex. | Structure and Name | Retention Time, [M+H]+, 1H NMR |
|---|---|---|
| 2.1 | 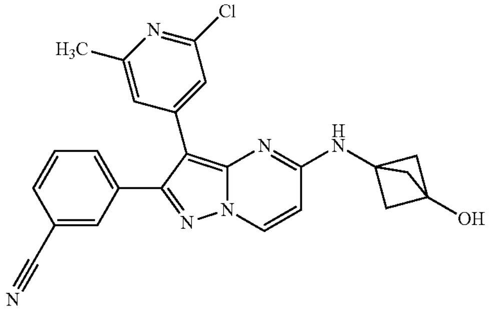 3-[3-(2-Chloro-6-methyl-4-pyridyl)-5-[(3-hydroxy-1-bicyclo[1.1.1]pentanyl)amino]pyrazolo[1,5-a]pyrimidin-2-yl]benzonitrile | LC-MS (Method 15B): Rt 7.32 mins; MS m/z 443.1/445.0 = [M + H]+. $^1$H NMR (500 MHz, DMSO-d6) δ 8.63 (d, J = 7.6 Hz, 1H), 8.49 (s, 1H), 8.02-7.93 (m, 2H), 7.87-7.82 (m, 1H), 7.70 (t, J = 7.8 Hz, 1H), 7.39 (s, 1H), 7.36 (s, 1H), 6.41 (d, J = 7.6 Hz, 1H), 6.32 (s, 1H), 2.37 (s, 3H), 2.23 (s, 6H) |
| 2.2 | 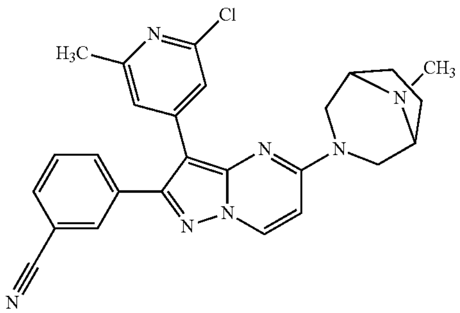 3-[3-(2-Chloro-6-methyl-4-pyridyl)-5-(8-methyl-3,8-diazabicyclo[3.2.1]octan-3-yl)pyrazolo[1,5-a]pyrimidin-2-yl]benzonitrile | LC-MS (Method 8B): Rt 5.05 mins; MS m/z 470.3/472.2 = [M + H]+. $^1$H NMR (500 MHz, DMSO-d6) δ 8.78 (d, J = 7.8 Hz, 1H), 8.02-7.93 (m, 2H), 7.84 (dt, J = 7.8, 1.5 Hz, 1H), 7.70 (t, J = 7.8 Hz, 1H), 7.33 (s, 1H), 7.29 (s, 1H), 6.85 (d, J = 7.9 Hz, 1H), 4.04 (s, 2H), 3.31-3.25 (m, 2H), 3.20 (s, 2H), 2.35 (s, 3H), 2.27 (s, 3H), 2.03-1.93 (m, 2H), 1.61-1.47 (m, 2H). |

TABLE Ex2-continued

| Ex. | Structure and Name | Retention Time, [M+H]+, 1H NMR |
|---|---|---|
| 2.3 | 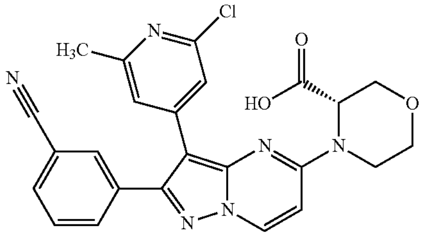 (3S)-4-[3-(2-Chloro-6-methyl-4-pyridyl)-2-(3-cyanophenyl)pyrazolo[1,5-a]pyrimidin-5-yl]morpholine-3-carboxylic acid | LC-MS (Method 7A): Rt 3.06 mins; MS m/z 475.2/477.2 = [M + H]+. $^1$H NMR (400 MHz, DMSO-d6) δ 8.89 (s, 1H), 8.00-7.98 (m, 1H), 7.97 (dt, J = 7.7, 1.3 Hz, 1H), 7.84 (dt, J = 7.8, 1.2 Hz, 1H), 7.70 (t, J = 7.8 Hz, 1H), 7.39 (s, 1H), 7.09 (s, 1H), 6.98 (s, 1H), 5.02 (s, 1H), 4.36 (d, J = 12.0 Hz, 1H), 4.07-3.96 (m, 2H), 3.79 (d, J = 10.0 Hz, 1H), 3.65-3.54 (m, 2H), 2.37 (s, 3H). Carboxylic acid proton not observed. |
| 2.4 | 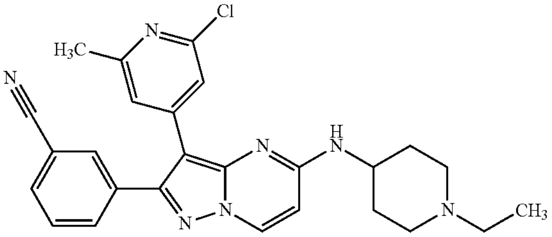 3-[3-(2-Chloro-6-methyl-4-pyridyl)-5-[(1-ethyl-4-piperidyl)amino]pyrazolo[1,5-a]pyrimidin-2-yl]benzonitrile | LC-MS (Method 7B): Rt 3.75 mins; MS m/z 472.4/474.3 = [M + H]+. $^1$H NMR (500 MHz, DMSO-d6) δ 8.58 (d, J = 7.6 Hz, 1H), 7.98 (t, J = 1.4 Hz, 1H), 7.96 (dt, J = 7.7, 1.3 Hz, 1H), 7.93 (d, J = 6.6 Hz, 1H), 7.84 (dt, J = 7.9, 1.4 Hz, 1H), 7.69 (t, J = 7.8 Hz, 1H), 7.44 (s, 1H), 7.27 (s, 1H), 6.42 (d, J = 7.6 Hz, 1H), 3.86-3.76 (m, 1H), 2.91 (d, J = 11.8 Hz, 2H), 2.35 (q, J = 7.0 Hz, 2H), 2.32 (s, 3H), 2.08-1.99 (m, 4H), 1.49 (dq, J = 12.3, 6.7, 3.9 Hz, 2H), 1.01 (t, J = 7.2 Hz, 3H). |
| 2.5 | 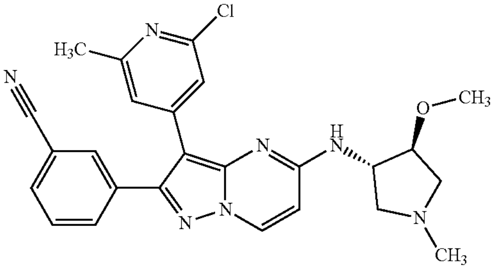 3-[3-(2-Chloro-6-methyl-4-pyridyl)-5-[[(3S,4S)-4-methoxy-1-methyl-pyrrolidin-3-yl]amino]pyrazolo[1,5-a]pyrimidin-2-yl]benzonitrile | LC-MS (Method 2A): Rt 2.32 mins; MS m/z 474.3/476.2 = [M + H]+. $^1$H NMR (400 MHz, DMSO-d6) δ 8.60 (d, J = 7.5 Hz, 1H), 8.19 (d, J = 7.0 Hz, 1H), 7.98-7.92 (m, 2H), 7.81 (dt, J = 7.9, 1.4 Hz, 1H), 7.68 (t, J = 7.8 Hz, 1H), 7.34 (s, 1H), 7.30 (s, 1H), 6.51 (d, J = 7.6 Hz, 1H), 4.34-4.27 (m, 1H), 3.79-3.74 (m, 1H), 3.27 (s, 3H), 2.99 (dd, J = 9.9, 6.7 Hz, 1H), 2.85 (dd, J = 9.5, 6.5 Hz, 1H), 2.56 (dd, J = 9.7, 3.6 Hz, 1H), 2.34 (s, 3H), 2.33-2.30 (m, 1H), 2.28 (s, 3H). |
| 2.6 | 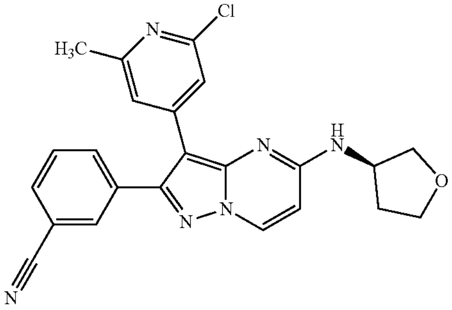 3-[3-(2-Chloro-6-methyl-4-pyridyl)-5-[[(3R)-tetrahydrofuran-3-yl]amino]pyrazolo[1,5-a]pyrimidin-2-yl]benzonitrile | LC-MS (Method 15B): Rt 7.88 mins; MS m/z 431.1/433.0 = [M + H]+. $^1$H NMR (500 MHz, DMSO-d6) δ 8.62 (d, J = 7.5 Hz, 1H), 8.19 (d, J = 5.3 Hz, 1H), 8.01-7.93 (m, 2H), 7.84 (d, J = 7.9 Hz, 1H), 7.70 (t, J = 7.8 Hz, 1H), 7.40 (s, 1H), 7.29 (s, 1H), 6.46 (d, J = 7.6 Hz, 1H), 4.44 (s, 1H), 3.97 (dd, J = 9.1, 5.9 Hz, 1H), 3.88 (q, J = 7.6 Hz, 1H), 3.81-3.73 (m, 2H), 2.34 (s, 3H), 2.32-2.24 (m, 1H), 2.01-1.91 (m, 1H). |

TABLE Ex2-continued

| Ex. | Structure and Name | Retention Time, [M+H]+, 1H NMR |
|---|---|---|
| 2.7 | 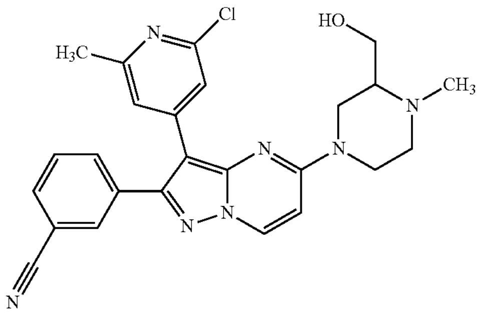 3-[3-(2-Chloro-6-methyl-4-pyridyl)-5-[3-(hydroxymethyl)-4-methyl-piperazin-1-yl]pyrazolo[1,5-a]pyrimidin-2-yl]benzonitrile | LC-MS (Method 8B): Rt 4.38 mins; MS m/z 474.2/476.2 = [M + H]+. $^1$H NMR (500 MHz, DMSO-d6) δ 8.78 (d, J = 7.9 Hz, 1H), 7.99 (t, J = 1.8 Hz, 1H), 7.97 (dt, J = 7.8, 1.5 Hz, 1H), 7.84 (dt, J = 7.8, 1.5 Hz, 1H), 7.70 (t, J = 7.8 Hz, 1H), 7.42 (s, 1H), 7.21 (s, 1H), 6.91 (d, J = 7.9 Hz, 1H), 4.68 (t, J = 5.3 Hz, 1H), 4.55 (s, 1H), 4.24 (s, 1H), 3.73-3.66 (m, 1H), 3.43-3.37 (m, 1H), 3.28-3.21 (m, 1H), 3.03-2.95 (m, 1H), 2.85 (dd, J = 12.0, 3.0 Hz, 1H), 2.36 (s, 3H), 2.27 (s, 3H), 2.21 (td, J = 11.5, 3.2 Hz, 1H), 2.12-2.07 (m, 1H). |
| 2.8 | 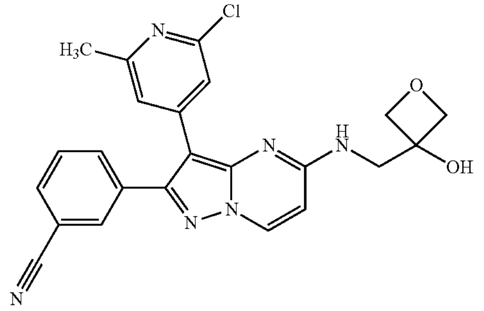 3-[3-(2-Chloro-6-methyl-4-pyridyl)-5-[(3-hydroxyoxetan-3-yl)methylamino]pyrazolo[1,5-a]pyrimidin-2-yl]benzonitrile | LC-MS (Method 15B): Rt 6.87 mins; MS m/z 447.1/449.1 = [M + H]+. $^1$H NMR (500 MHz, DMSO-d6) δ 8.62 (d, J = 7.5 Hz, 1H), 8.10 (br s, 1H), 8.01-7.94 (m, 2H), 7.83 (dd, J = 8.0, 1.6 Hz, 1H), 7.69 (t, J = 7.8 Hz, 1H), 7.47 (s, 1H), 7.21 (s, 1H), 6.58 (d, J = 7.6 Hz, 1H), 6.10 (s, 1H), 4.52-4.46 (m, 4H), 3.83 (d, J = 5.7 Hz, 2H), 2.37 (s, 3H). |
| 2.9 | 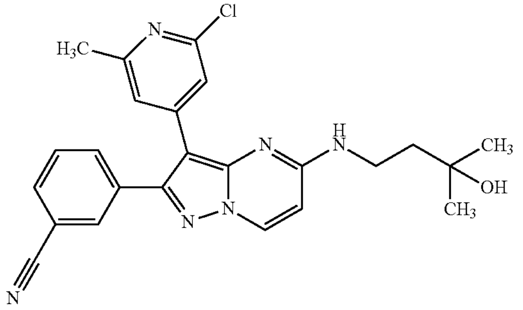 3-[3-(2-Chloro-6-methyl-4-pyridyl)-5-[(3-hydroxy-3-methyl-butyl)amino]pyrazolo[1,5-a]pyrimidin-2-yl]benzonitrile | LC-MS (Method 8A): Rt 4.63 mins; MS m/z 447.3/449.3 = [M + H]+. $^1$H NMR (500 MHz, DMSO-d6) δ 8.56 (d, J = 7.6 Hz, 1H), 7.99-7.91 (m, 3H), 7.83 (dt, J = 7.9, 1.5 Hz, 1H), 7.69 (t, J = 7.7 Hz, 1H), 7.36 (s, 1H), 7.31 (s, 1H), 6.41 (d, J = 7.6 Hz, 1H), 4.35 (s, 1H), 3.55-3.47 (m, 2H), 2.33 (s, 3H), 1.80-1.66 (m, 2H), 1.18 (s, 6H). |
| 2.10 | 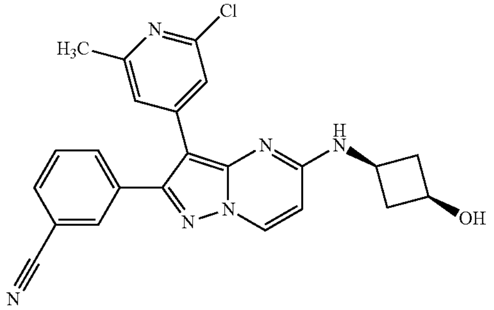 3-[3-(2-Chloro-6-methyl-4-pyridyl)-5-[(cis-3-hydroxycyclobutyl)amino]pyrazolo[1,5-a]pyrimidin-2-yl]benzonitrile | LC-MS (Method 15B): Rt 7.20 mins; MS m/z 431.1/433.0 = [M + H]+. $^1$H NMR (500 MHz, DMSO-d6) δ 8.59 (d, J = 7.6 Hz, 1H), 8.20 (d, J = 5.4 Hz, 1H), 7.99-7.94 (m, 2H), 7.83 (dt, J = 7.9, 1.4 Hz, 1H), 7.70 (t, J = 7.7 Hz, 1H), 7.44 (s, 1H), 7.28 (s, 1H), 6.41 (d, J = 7.6 Hz, 1H), 5.21 (br s, 1H), 4.02-3.90 (m, 1H), 3.88-3.74 (m, 1H), 2.85-2.73 (m, 2H), 2.34 (s, 3H), 1.89-1.77 (m, 2H). |

TABLE Ex2-continued

| Ex. | Structure and Name | Retention Time, [M+H]+, 1H NMR |
|---|---|---|
| 2.11 | 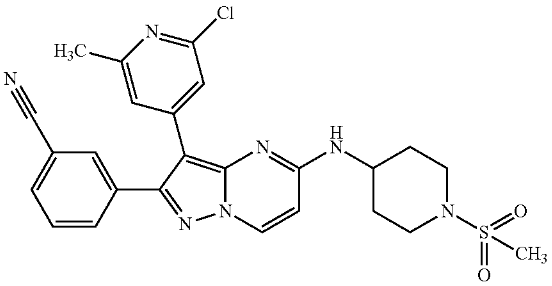<br>3-[3-(2-Chloro-6-methyl-4-pyridyl)-5-[(1-methylsulfonyl-4-piperidyl)amino]pyrazolo[1,5-a]pyrimidin-2-yl]benzonitrile | LC-MS (Method 7A): Rt 3.38 mins; MS m/z 522.2/524.1 = [M + H]+.<br>$^1$H NMR (400 MHz, DMSO-d6) δ 8.61 (d, J = 7.5 Hz, 1H), 8.01 (d, J = 6.1 Hz, 1H), 7.99-7.97 (m, 1H), 7.96 (dt, J = 7.7, 1.4 Hz, 1H), 7.83 (dt, J = 7.8, 1.3 Hz, 1H), 7.69 (t, J = 7.8 Hz, 1H), 7.38 (s, 1H), 7.27 (s, 1H), 6.45 (d, J = 7.6 Hz, 1H), 3.99-3.88 (m, 1H), 3.62 (dt, J = 12.3, 3.3 Hz, 2H), 3.01-2.91 (m, 2H), 2.90 (s, 3H), 2.34 (s, 3H), 2.19 (d, J = 10.5 Hz, 2H), 1.65-1.52 (m, 2H). |
| 2.12 | 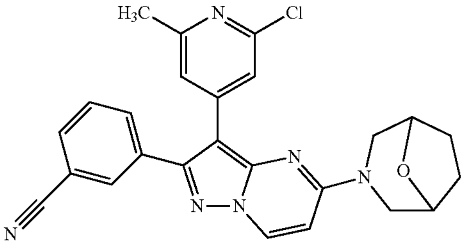<br>3-[3-(2-Chloro-6-methyl-4-pyridyl)-5-(8-oxa-3-azabicyclo[3.2.1]octan-3-yl)pyrazolo[1,5-a]pyrimidin-2-yl]benzonitrile | LC-MS (Method 8B): Rt 5.07 mins; MS m/z 457.2/459.2 = [M + H]+.<br>$^1$H NMR (500 MHz, DMSO-d6) δ 8.81 (d, J = 7.9 Hz, 1H), 8.03-7.90 (m, 2H), 7.83 (d, J = 7.8 Hz, 1H), 7.69 (t, J = 7.8 Hz, 1H), 7.29 (s, 2H), 6.86 (d, J = 7.9 Hz, 1H), 4.54-4.45 (m, 2H), 4.16-4.01 (m, 2H), 3.21 (d, J = 11.9 Hz, 2H), 2.35 (s, 3H), 1.90-1.82 (m, 2H), 1.77-1.69 (m, 2H). |
| 2.13 | 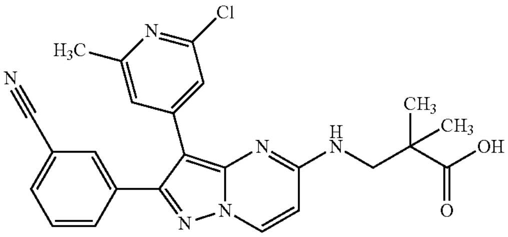<br>3-[[3-(2-Chloro-6-methyl-4-pyridyl)-2-(3-cyanophenyl)pyrazolo[1,5-a]pyrimidin-5-yl]amino]-2,2-dimethyl-propanoic acid | LC-MS (Method 7A): Rt 3.33 mins; MS m/z 461.2/463.2 = [M + H]+.<br>$^1$H NMR (500 MHz, DMSO-d6) δ 8.58 (d, J = 7.6 Hz, 1H), 7.98 (t, J = 1.4 Hz, 1H), 7.96 (dt, J = 7.7, 1.3 Hz, 1H), 7.92 (t, J = 5.9 Hz, 1H), 7.85-7.82 (m, 1H), 7.69 (t, J = 7.8 Hz, 1H), 7.37 (d, J = 4.7 Hz, 2H), 6.58 (d, J = 7.6 Hz, 1H), 3.67 (d, J = 6.1 Hz, 2H), 2.34 (s, 3H), 1.20 (s, 6H). Carboxylic acid proton not observed. |
| 2.14 | 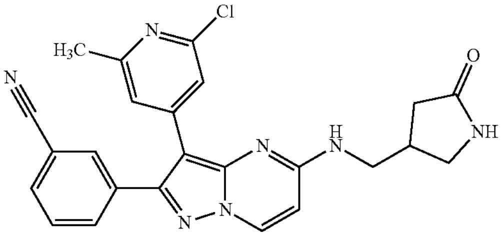<br>3-[3-(2-Chloro-6-methyl-4-pyridyl)-5-[(5-oxopyrrolidin-3-yl)methylamino]pyrazolo[1,5-a]pyrimidin-2-yl]benzonitrile | LC-MS (Method 7A): Rt 2.93 mins; MS m/z 458.2/460.2 = [M + H]+.<br>$^1$H NMR (400 MHz, DMSO-d6) δ 8.60 (d, J = 7.5 Hz, 1H), 8.15 (t, J = 5.2 Hz, 1H), 8.00-7.92 (m, 2H), 7.83 (d, J = 7.9 Hz, 1H), 7.69 (t, J = 7.8 Hz, 1H), 7.54 (s, 1H), 7.37 (s, 1H), 7.29 (s, 1H), 6.43 (d, J = 7.6 Hz, 1H), 3.45 (t, J = 6.3 Hz, 2H), 3.39 (dd, J = 9.6, 8.2 Hz, 1H), 3.06 (dd, J = 9.6, 5.2 Hz, 1H), 2.85 (dt, J = 13.8, 6.9 Hz, 1H), 2.36-2.28 (m, 4H), 2.01 (dd, J = 16.6, 6.2 Hz, 1H). |

TABLE Ex2-continued

| Ex. | Structure and Name | Retention Time, [M+H]+, 1H NMR |
|---|---|---|
| 2.15 | 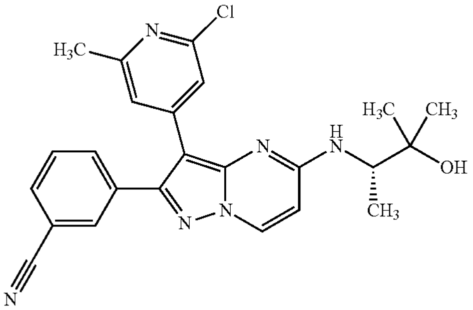 3-[3-(2-Chloro-6-methyl-4-pyridyl)-5-[[(1S)-2-hydroxy-1,2-dimethyl-propyl]amino]pyrazolo[1,5-a]pyrimidin-2-yl]benzonitrile | LC-MS (Method 15B): Rt 7.95 mins; MS m/z 447.3/449.1 = [M + H]+. $^1$H NMR (500 MHz, DMSO-d6) δ 8.56 (d, J = 7.6 Hz, 1H), 8.00-7.92 (m, 2H), 7.83 (d, J = 7.9 Hz, 1H), 7.73-7.64 (m, 2H), 7.40 (s, 1H), 7.30 (s, 1H), 6.60 (d, J = 7.6 Hz, 1H), 4.57 (s, 1H), 4.21-4.09 (m, 1H), 2.33 (s, 3H), 1.23-1.19 (m, 6H), 1.18 (s, 3H). |
| 2.16 | 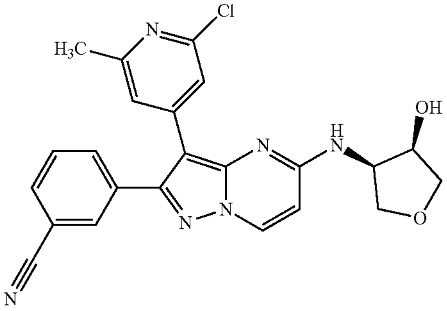 3-[3-(2-Chloro-6-methyl-4-pyridyl)-5-[[rac-(3R,4R)-4-hydroxytetrahydrofuran-3-yl]amino]pyrazolo[1,5-a]pyrimidin-2-yl]benzonitrile | LC-MS (Method 8B): Rt 4.12 mins; MS m/z 447.2/449.1 = [M + H]+. $^1$H NMR (400 MHz, DMSO-d6) δ 8.64 (d, J = 7.6 Hz, 1H), 8.01-7.94 (m, 2H), 7.92 (d, J = 6.2 Hz, 1H), 7.84 (dt, J = 7.9, 1.4 Hz, 1H), 7.70 (t, J = 7.8 Hz, 1H), 7.40 (s, 1H), 7.29 (s, 1H), 6.71 (d, J = 7.6 Hz, 1H), 5.45 (d, J = 4.2 Hz, 1H), 4.46 (s, 1H), 4.39 (p, J = 6.9 Hz, 1H), 4.12 (t, J = 7.7 Hz, 1H), 3.98 (dd, J = 9.5, 4.5 Hz, 1H), 3.70 (dd, J = 9.5, 2.4 Hz, 1H), 3.63 (t, J = 8.2 Hz, 1H), 2.34 (s, 3H). |
| 2.17 | 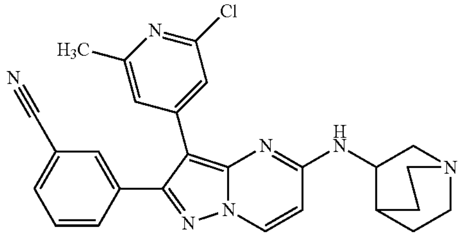 3-[3-(2-Chloro-6-methyl-4-pyridyl)-5-(quinuclidin-3-ylamino)pyrazolo[1,5-a]pyrimidin-2-yl]benzonitrile | LC-MS (Method 2A): Rt 2.37 mins; MS m/z 470.3/472.3 = [M + H]+. $^1$H NMR (400 MHz, DMSO-d6) δ 8.75 (d, J = 7.9 Hz, 0.6H), 8.70 (d, J = 7.9 Hz, 0.4H), 8.00-7.92 (m, 2H), 7.83 (dt, J = 7.9, 1.3 Hz, 1H), 7.69 (t, J = 7.8 Hz, 1H), 7.35-7.27 (m, 2H), 6.96 (d, J = 8.0 Hz, 0.6H), 6.83 (d, J = 8.0 Hz, 0.4H), 4.84-4.56 (m, 1H), 4.02-3.87 (m, 1H), 3.84-3.68 (m, 1H), 3.23-3.18 (m, 1H), 2.99-2.85 (m, 2H), 2.81-2.71 (m, 1H), 2.34 (d, J = 4.5 Hz, 2H), 2.29-2.18 (m, 1H), 2.05-1.72 (m, 2H), 1.70-1.57 (m, 1H), 1.54-1.44 (m, 1H), 1.41-1.26 (m, 1H). 1 proton not observed. |
| 2.18 | 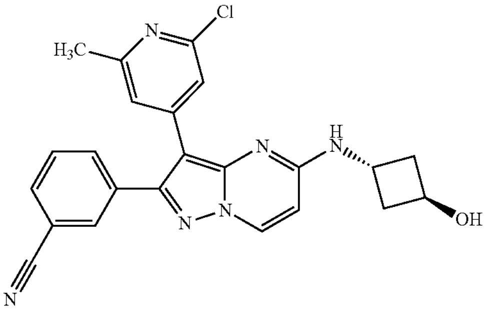 3-[3-(2-Chloro-6-methyl-4-pyridyl)-5-[(trans-3-hydroxycyclobutyl)amino]pyrazolo[1,5-a]pyrimidin-2-yl]benzonitrile | LC-MS (Method 8B): Rt 3.93 mins; MS m/z 431.5/433.1 = [M + H]+. $^1$H NMR (500 MHz, DMSO-d6) δ 8.59 (d, J = 7.6 Hz, 1H), 8.20 (d, J = 5.0 Hz, 1H), 8.01-7.93 (m, 2H), 7.83 (d, J = 7.8 Hz, 1H), 7.69 (t, J = 7.8 Hz, 1H), 7.39 (s, 1H), 7.31 (s, 1H), 6.41 (d, J = 7.6 Hz, 1H), 5.13 (d, J = 5.6 Hz, 1H), 4.36 (apr h, J = 6.1 Hz, 1H), 4.33-4.27 (m, 1H), 2.34 (s, 3H), 2.30 (apr t, J = 6.2 Hz, 4H). |

TABLE Ex2-continued

| Ex. | Structure and Name | Retention Time, [M+H]+, 1H NMR |
| --- | --- | --- |
| 2.19 | 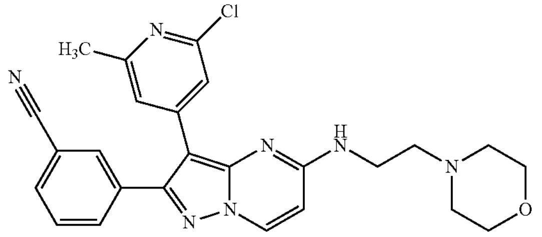 3-[3-(2-Chloro-6-methyl-4-pyridyl)-5-(2-morpholinoethylamino)pyrazolo[1,5-a]pyrimidin-2-yl]benzonitrile | LC-MS (Method 7A): Rt 2.12 mins; MS m/z 474.3/476.3 = [M + H]+. $^1$H NMR (400 MHz, DMSO-d6) δ 8.58 (d, J = 7.6 Hz, 1H), 7.99-7.90 (m, 3H), 7.82 (dt, J = 7.9, 1.3 Hz, 1H), 7.68 (t, J = 7.8 Hz, 1H), 7.38 (s, 1H), 7.24 (s, 1H), 6.47 (d, J = 7.5 Hz, 1H), 3.59-3.51 (m, 6H), 2.56 (t, J = 6.7 Hz, 2H), 2.47-2.43 (m, 4H), 2.32 (s, 3H). |
| 2.20 | 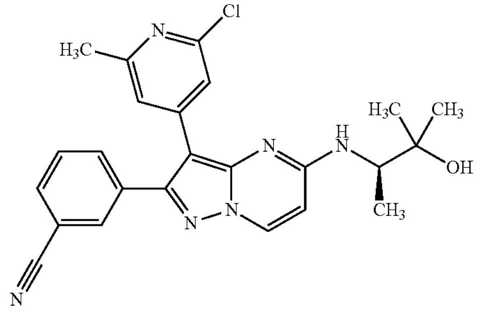 3-[3-(2-Chloro-6-methyl-4-pyridyl)-5-[[(1R)-2-hydroxy-1,2-dimethyl-propyl]amino] pyrazolo[1,5-a]pyrimidin-2-yl]benzonitrile | LC-MS (Method 8B): Rt 4.67 mins; MS m/z 447.2/449.2 = [M + H]+. $^1$H NMR (500 MHz, DMSO-d6) δ 8.56 (d, J = 7.6 Hz, 1H), 8.00-7.93 (m, 2H), 7.83 (d, J = 7.9 Hz, 1H), 7.69 (t, J = 8.0 Hz, 2H), 7.40 (s, 1H), 7.30 (s, 1H), 6.60 (d, J = 7.6 Hz, 1H), 4.57 (s, 1H), 4.20-4.11 (m, 1H), 2.33 (s, 3H), 1.22-1.19 (m, 6H), 1.18 (s, 3H). |
| 2.21 | 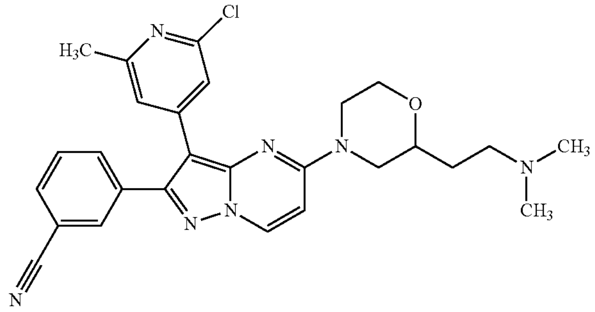 3-[3-(2-Chloro-6-methyl-4-pyridyl)-5-[2-[2-(dimethylamino)ethyl]morpholin-4-yl]pyrazolo[1,5-a]pyrimidin-2-yl]benzonitrile | LC-MS (Method 15B): Rt 9.38 mins; MS m/z 502.3/504.1 = [M + H]+. $^1$H NMR (500 MHz, DMSO-d6) δ 8.86 (d, J = 7.9 Hz, 1H), 8.03-8.01 (m, 1H), 7.99 (dt, J = 7.8, 1.4 Hz, 1H), 7.87 (dt, J = 7.9, 1.4 Hz, 1H), 7.72 (t, J = 7.8 Hz, 1H), 7.38 (s, 1H), 7.27 (s, 1H), 6.98 (d, J = 8.0 Hz, 1H), 4.47 (br s, 1H), 4.30 (br s, 1H), 4.00 (d, J = 11.3 Hz, 1H), 3.56 (td, J = 11.7, 2.9 Hz, 2H), 3.25-3.11 (m, 1H), 2.88 (t, J = 11.8 Hz, 1H), 2.40-2.32 (m, 5H), 2.15 (s, 6H), 1.67 (q, J = 7.1 Hz, 2H). |
| 2.22 | 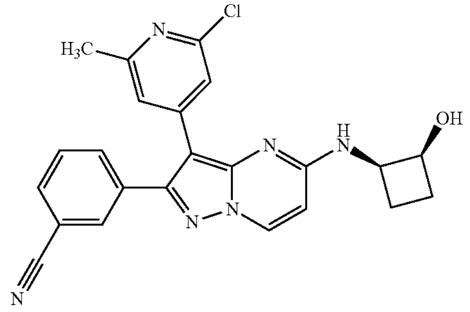 3-[3-(2-Chloro-6-methyl-4-pyridyl)-5-[[(1R,2S)-2-hydroxycyclobutyl] amino]pyrazolo[1,5-a]pyrimidin-2-yl]benzonitrile | LC-MS (Method 15B): Rt 7.68 mins; MS m/z 431.1/433.0 = [M + H]+. $^1$H NMR (500 MHz, DMSO-d6) δ 8.59 (d, J = 7.6 Hz, 1H), 8.02-7.93 (m, 3H), 7.83 (dt, J = 7.9, 1.5 Hz, 1H), 7.70 (td, J = 7.7, 0.7 Hz, 1H), 7.43 (s, 1H), 7.31-7.28 (m, 1H), 6.67 (d, J = 7.6 Hz, 1H), 5.28 (dd, J = 4.8, 1.3 Hz, 1H), 4.53-4.46 (m, 1H), 4.43-4.35 (m, 1H), 2.34 (s, 3H), 2.25-2.12 (m, 2H), 2.09-2.00 (m, 1H), 1.90-1.78 (m, 1H). |

TABLE Ex2-continued

| Ex. | Structure and Name | Retention Time, [M+H]+, 1H NMR |
|---|---|---|
| 2.23 | 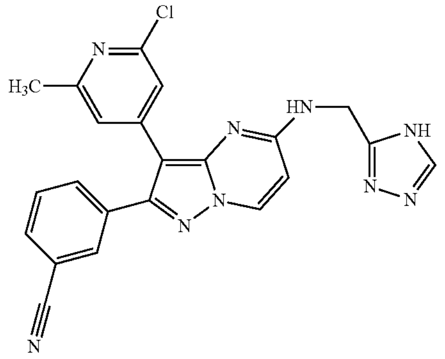<br>3-[3-(2-Chloro-6-methyl-4-pyridyl)-5-(4H-1,2,4-triazol-3-ylmethylamino)pyrazolo[1,5-a]pyrimidin-2-yl]benzonitrile | LC-MS (Method 8B): Rt 3.85 mins; MS m/z 442.2/444.2 = [M + H]+.<br>$^{1}$H NMR (500 MHz, DMSO-d6) δ 13.80 (s, 1H), 8.64 (d, J = 7.6 Hz, 1H), 8.49 (s, 1H), 8.29 (s, 1H), 7.99-7.89 (m, 2H), 7.81 (d, J = 7.9 Hz, 1H), 7.68 (t, J = 7.9 Hz, 1H), 7.36 (s, 1H), 7.09 (s, 1H), 6.57 (d, J = 7.6 Hz, 1H), 4.68 (d, J = 3.7 Hz, 2H), 2.37 (s, 3H). |
| 2.24 | 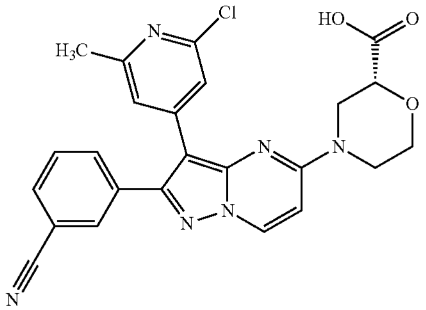<br>(2R)-4-[3-(2-Chloro-6-methyl-4-pyridyl)-2-(3-cyanophenyl)pyrazolo[1,5-a]pyrimidin-5-yl]morpholine-2-carboxylic acid | LC-MS (Method 8A): Rt 4.51 mins; MS m/z 475.3/477.3 = [M + H]+.<br>$^{1}$H NMR (500 MHz, DMSO-d6) δ 13.20 (br s, 1H), 8.84 (d, J = 7.8 Hz, 1H), 8.01-7.93 (m, 2H), 7.84 (d, J = 7.8 Hz, 1H), 7.70 (t, J = 7.8 Hz, 1H), 7.41 (s, 1H), 7.22 (s, 1H), 6.96 (d, J = 7.9 Hz, 1H), 4.43 (br s, 1H), 4.21 (br s, 1H), 4.03 (t, J = 14.6 Hz, 2H), 3.66 (t, J = 9.8 Hz, 1H), 3.57-3.45 (m, 2H), 2.37 (s, 3H). |
| 2.25 | 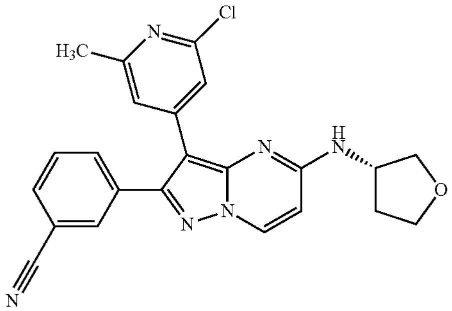<br>3-[3-(2-Chloro-6-methyl-4-pyridyl)-5-[[(3S)-tetrahydrofuran-3-yl]amino]pyrazolo[1,5-a]pyrimidin-2-yl]benzonitrile | LC-MS (Method 15B): Rt 7.84 mins; MS m/z 431.1/433.0 = [M + H]+.<br>$^{1}$H NMR (500 MHz, DMSO-d6) δ 8.62 (d, J = 7.5 Hz, 1H), 8.20 (d, J = 5.3 Hz, 1H), 8.00-7.94 (m, 2H), 7.84 (d, J = 7.8 Hz, 1H), 7.70 (t, J = 7.8 Hz, 1H), 7.40 (s, 1H), 7.29 (s, 1H), 6.46 (d, J = 7.5 Hz, 1H), 4.49-4.38 (m, 1H), 3.97 (dd, J = 9.1, 5.8 Hz, 1H), 3.92-3.84 (m, 1H), 3.82-3.72 (m, 2H), 2.34 (s, 3H), 2.33-2.25 (m, 1H), 2.01-1.91 (m, 1H). |

TABLE Ex2-continued

| Ex. | Structure and Name | Retention Time, [M+H]+, 1H NMR |
|---|---|---|
| 2.26 | 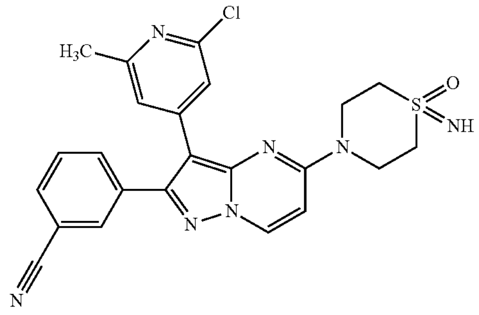 3-[3-(2-Chloro-6-methyl-4-pyridyl)-5-(1-imino-1-oxo-1,4-thiazinan-4-yl)pyrazolo[1,5-a]pyrimidin-2-yl]benzonitrile | LC-MS (Method 8B): Rt 3.94 mins; MS m/z 478.1/480.1 = [M + H]+. $^{1}$H NMR (400 MHz, DMSO-d6) δ 8.91 (d, J = 7.8 Hz, 1H), 8.03-7.96 (m, 2H), 7.84 (dt, J = 7.9, 1.4 Hz, 1H), 7.71 (t, J = 7.8 Hz, 1H), 7.39-7.30 (m, 1H), 7.26 (t, J = 1.0 Hz, 1H), 7.08 (d, J = 7.9 Hz, 1H), 4.44-4.33 (m, 2H), 4.04-3.91 (m, 2H), 3.88 (s, 1H), 3.21-3.12 (m, 4H), 2.38 (s, 3H). |
| 2.27 | 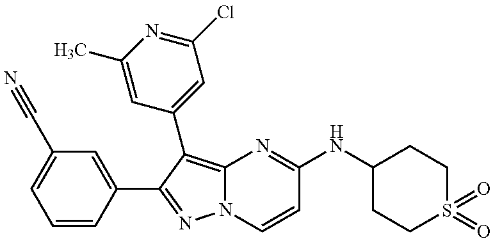 3-[3-(2-Chloro-6-methyl-4-pyridyl)-5-[(1,1-dioxothian-4-yl)amino]pyrazolo[1,5-a]pyrimidin-2-yl]benzonitrile | LC-MS (Method 7B): Rt 3.13 mins; MS m/z 493.3/495.3 = [M + H]+. $^{1}$H NMR (400 MHz, DMSO-d6) δ 8.64 (d, J = 7.6 Hz, 1H), 8.03 (d, J = 6.3 Hz, 1H), 7.98 (d, J = 1.4 Hz, 1H), 7.96 (dt, J = 7.7, 1.4 Hz, 1H), 7.83 (dt, J = 8.0, 1.2 Hz, 1H), 7.69 (t, J = 7.8 Hz, 1H), 7.31 (s, 1H), 7.30 (s, 1H), 6.45 (d, J = 7.5 Hz, 1H), 4.23-4.11 (m, 1H), 3.49-3.34 (m, 2H), 3.21 (d, J = 14.7 Hz, 2H), 2.45-2.37 (m, 2H), 2.36 (s, 3H), 2.11-1.99 (m, 2H). |
| 2.28 | 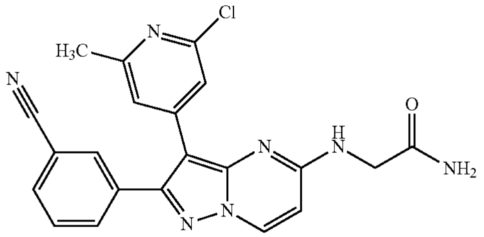 2-[[3-(2-Chloro-6-methyl-4-pyridyl)-2-(3-cyanophenyl)pyrazolo[1,5-a]pyrimidin-5-yl]amino]acetamide | LC-MS (Method 7B): Rt 2.52 mins; MS m/z 418.4/420.3 = [M + H]+. $^{1}$H NMR (500 MHz, DMSO-d6) δ 8.63 (d, J = 7.5 Hz, 1H), 8.17 (s, 1H), 7.95 (dt, J = 6.8, 1.5 Hz, 2H), 7.81 (dt, J = 7.8, 1.4 Hz, 1H), 7.72-7.66 (m, 1H), 7.50 (s, 1H), 7.48 (s, 1H), 7.13 (s, 1H), 7.09 (s, 1H), 6.58 (d, J = 7.6 Hz, 1H), 3.95 (d, J = 5.5 Hz, 2H), 2.39 (s, 3H). |
| 2.29 | 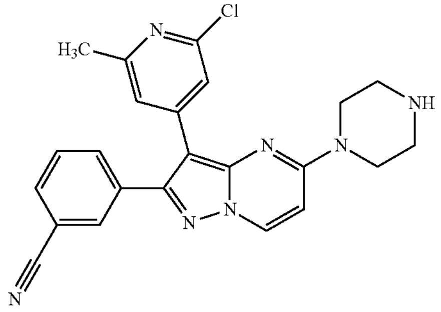 3-[3-(2-Chloro-6-methyl-4-pyridyl)-5-piperazin-1-yl-pyrazolo[1,5-a]pyrimidin-2-yl]benzonitrile | LC-MS (Method 8B): Rt 4.49 mins; MS m/z 430.3/432.3 = [M + H]+. $^{1}$H NMR (500 MHz, DMSO-d6) δ 8.77 (d, J = 7.9 Hz, 1H), 8.01-7.92 (m, 2H), 7.83 (d, J = 7.9 Hz, 1H), 7.69 (t, J = 7.9 Hz, 1H), 7.32 (s, 1H), 7.27 (s, 1H), 6.92 (d, J = 7.9 Hz, 1H), 3.74-3.64 (m, 4H), 2.85-2.76 (m, 4H), 2.34 (s, 3H). NH proton not observed. |

TABLE Ex2-continued

| Ex. | Structure and Name | Retention Time, [M+H]+, 1H NMR |
|---|---|---|
| 2.30 | 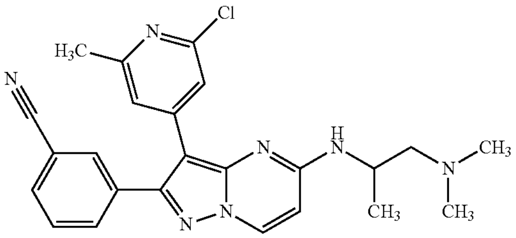 3-[3-(2-Chloro-6-methyl-4-pyridyl)-5-[[2-(dimethylamino)-1-methyl-ethyl]amino]pyrazolo[1,5-a]pyrimidin-2-yl]benzonitrile | LC-MS (Method 7B): Rt 3.68 mins; MS m/z 446.4/448.3 = [M + H]+. $^1$H NMR (500 MHz, DMSO-d6) δ 8.57 (d, J = 7.6 Hz, 1H), 7.98-7.93 (m, 2H), 7.81 (dt, J = 7.9, 1.4 Hz, 1H), 7.76 (d, J = 7.3 Hz, 1H), 7.68 (t, J = 7.7 Hz, 1H), 7.38 (s, 1H), 7.22 (s, 1H), 6.43 (d, J = 7.5 Hz, 1H), 4.27 (dt, J = 13.4, 6.9 Hz, 1H), 2.40 (dd, J = 11.9, 6.5 Hz, 1H), 2.30 (s, 3H), 2.23 (dd, J = 11.9, 7.8 Hz, 1H), 2.19 (s, 6H), 1.23 (d, J = 6.5 Hz, 3H). |
| 2.31 | 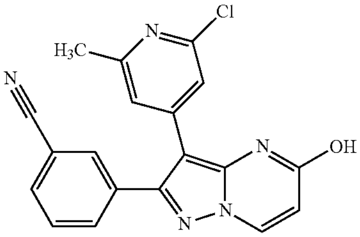 3-[3-(2-Chloro-6-methyl-4-pyridyl)-5-hydroxy-pyrazolo[1,5-a]pyrimidin-2-yl]benzonitrile (by-product of reaction) | LC-MS (Method 7A): Rt 2.62 mins; MS m/z 362.1/364.1 = [M + H]+. $^1$H NMR (400 MHz, DMSO-d6) δ 12.40 (s, 1H), 8.65 (d, J = 6.6 Hz, 1H), 7.90 (dt, J = 7.5, 1.5 Hz, 1H), 7.87 (s, 1H), 7.68 (d, J = 8.0 Hz, 1H), 7.62 (t, J = 7.7 Hz, 1H), 7.16 (s, 1H), 7.14 (s, 1H), 6.20 (s, 1H), 2.39 (s, 3H). |
| 2.32 | 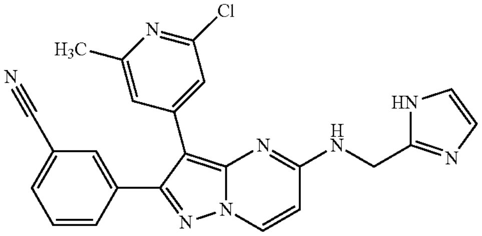 3-[3-(2-Chloro-6-methyl-4-pyridyl)-5-(1 H-imidazol-2-ylmethylamino)pyrazolo[1,5-a]pyrimidin-2-yl]benzonitrile | LC-MS (Method 7A): Rt 2.11 mins; MS m/z 441.2/443.2 = [M + H]+. $^1$H NMR (400 MHz, DMSO-d6) δ 11.93 (s, 1H), 8.64 (d, J = 7.6 Hz, 1H), 8.36 (br. s, 1H), 7.98-7.92 (m, 2H), 7.81 (dt, J = 7.9, 1.4 Hz, 1H), 7.71-7.65 (m, 1H), 7.33 (s, 1H), 7.18 (s, 1H), 7.07 (br. s, 1H), 6.87 (br. s, 1H), 6.57 (d, J = 7.6 Hz, 1H), 4.61 (s, 2H), 2.35 (s, 3H). |
| 2.33 | 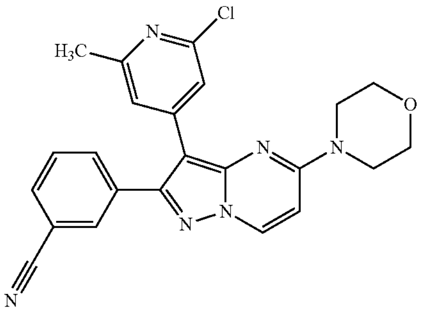 3-[3-(2-Chloro-6-methyl-4-pyridyl)-5-morpholino-pyrazolo[1,5-a]pyrimidin-2-yl]benzonitrile | LC-MS (Method 8A): Rt 4.97 mins; MS m/z 431.3/433.3 = [M + H]+. $^1$H NMR (500 MHz, DMSO-d6) δ 8.84 (d, J = 7.9 Hz, 1H), 8.03-7.93 (m, 2H), 7.84 (dt, J = 7.9, 1.5 Hz, 1H), 7.70 (t, J = 7.8 Hz, 1H), 7.33-7.24 (m, 2H), 6.95 (d, J = 7.9 Hz, 1H), 3.77-3.72 (m, 8H), 2.36 (s, 3H). |

TABLE Ex2-continued

| Ex. | Structure and Name | Retention Time, [M+H]+, 1H NMR |
|---|---|---|
| 2.34 | 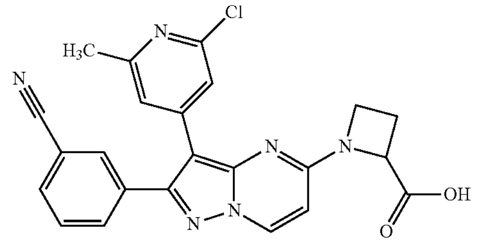 1-[3-(2-Chloro-6-methyl-4-pyridyl)-2-(3-cyanophenyl)pyrazolo[1,5-a]pyrimidin-5-yl]azetidine-2-carboxylic acid | LC-MS (Method 7A): Rt 2.99 mins; MS m/z 445.2/447.2 = [M + H]+. $^1$H NMR (400 MHz, DMSO-d6) δ 8.84-8.74 (m, 1H), 8.00-7.93 (m, 2H), 7.84 (dt, J = 7.9, 1.3 Hz, 1H), 7.69 (t, J = 7.8 Hz, 1H), 7.45 (s, 1H), 7.08 (s, 1H), 6.48 (d, J = 7.4 Hz, 1H), 5.00-4.78 (m, 1H), 4.26-4.07 (m, 2H), 2.78-2.69 (m, 1H), 2.39-2.31 (m, 4H). Carboxylic acid proton not observed. |
| 2.35 | 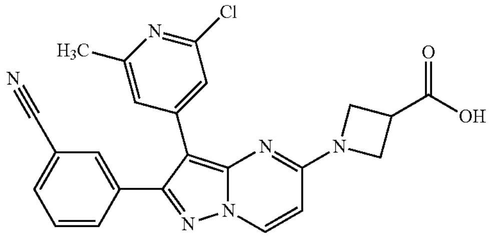 1-[3-(2-Chloro-6-methyl-4-pyridyl)-2-(3-cyanophenyl)pyrazolo[1,5-a]pyrimidin-5-yl]azetidine-3-carboxylic acid | LC-MS (Method 7A): Rt 3.03 mins; MS m/z 445.1/447.1 = [M + H]+. $^1$H NMR (500 MHz, DMSO-d6) δ 8.79 (d, J = 7.6 Hz, 1H), 7.98-7.94 (m, 2H), 7.82 (dt, J = 7.9, 1.4 Hz, 1H), 7.69 (t, J = 7.7 Hz, 1H), 7.33 (s, 1H), 7.30 (s, 1H), 6.48 (d, J = 7.6 Hz, 1H), 4.37 (t, J = 8.9 Hz, 2H), 4.24 (t, J = 6.5 Hz, 2H), 3.61 (tt, J = 8.9, 5.8 Hz, 1H), 2.34 (s, 3H). Carboxylic acid proton not observed. |
| 2.36 | 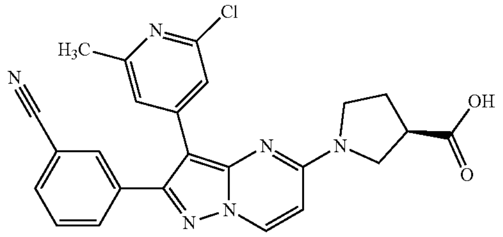 (3R)-1-[3-(2-Chloro-6-methyl-4-pyridyl)-2-(3-cyanophenyl)pyrazolo[1,5-a]pyrimidin-5-yl]pyrrolidine-3-carboxylic acid | LC-MS (Method 7A): Rt 3.18 mins; MS m/z 459.2/461.1 = [M + H]+. $^1$H NMR (500 MHz, DMSO-d6) δ 8.76 (d, J = 7.7 Hz, 1H), 7.98 (t, J = 1.4 Hz, 1H), 7.96 (dt, J = 7.7, 1.4 Hz, 1H), 7.83 (dt, J = 7.9, 1.3 Hz, 1H), 7.69 (t, J = 7.8 Hz, 1H), 7.39 (s, 1H), 7.30 (s, 1H), 6.67-6.58 (m, 1H), 3.87-3.58 (m, 5H), 2.33 (s, 3H), 2.31-2.14 (m, 2H) Carboxylic acid proton not observed. |
| 2.37 | 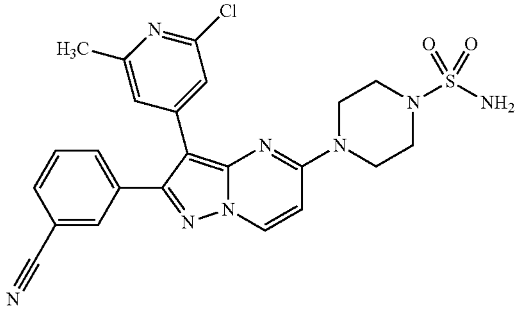 4-[3-(2-Chloro-6-methyl-4-pyridyl)-2-(3-cyanophenyl)pyrazolo[1,5-a]pyrimidin-5-yl]piperazine-1-sulfonamide | LC-MS (Method 15B): Rt 7.62 mins; MS m/z 509.1/511.1 = [M + H]+. $^1$H NMR (500 MHz, DMSO-d6) δ 8.87 (d, J = 7.8 Hz, 1H), 8.01-7.95 (m, 2H), 7.84 (dt, J = 7.9, 1.4 Hz, 1H), 7.70 (t, J = 7.8 Hz, 1H), 7.33 (d, J = 1.3 Hz, 1H), 7.27 (d, J = 1.2 Hz, 1H), 7.00 (d, J = 7.9 Hz, 1H), 6.89 (br s, 2H), 3.92-3.86 (m, 4H), 3.13-3.08 (m, 4H), 2.38 (s, 3H). |

TABLE Ex2-continued

| Ex. | Structure and Name | Retention Time, [M+H]+, 1H NMR |
|---|---|---|
| 2.38 | 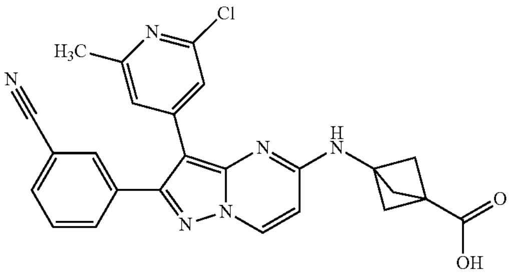 3-[[3-(2-Chloro-6-methyl-4-pyridyl)-2-(3-cyanophenyl)pyrazolo[1,5-a]pyrimidin-5-yl]amino]bicyclo[1.1.1]pentane-1-carboxylic acid (Prepared using Intermediate I) | LC-MS (Method 7A): Rt 3.06 mins; MS m/z 471.2/473.1 = [M + H]+. $^{1}$H NMR (500 MHz, DMSO-d6) δ 8.65 (d, J = 7.5 Hz, 1H), 8.62 (s, 1H), 7.99 (t, J = 1.4 Hz, 1H), 7.96 (dt, J = 7.7, 1.3 Hz, 1H), 7.85 (dt, J = 7.9, 1.3 Hz, 1H), 7.70 (t, J = 7.8 Hz, 1H), 7.39 (s, 1H), 7.34 (s, 1H), 6.39 (d, J = 7.4 Hz, 1H), 2.41 (s, 6H), 2.36 (s, 3H). Carboxylic acid proton not observed. |
| 2.39 | 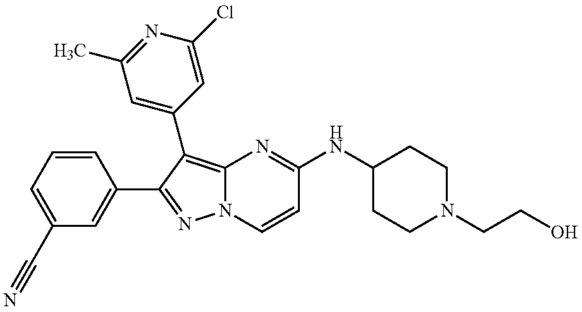 3-[3-(2-chloro-6-methyl-4-pyridyl)-5-[[1-(2-hydroxyethyl)-4-piperidyl]amino]pyrazolo[1,5-a]pyrimidin-2-yl]benzonitrile | LC-MS (Method 8B): Rt 3.72 mins; MS m/z 488.3 = [M + H]+ 1H NMR (500 MHz, DMSO-d6) δ 8.59 (d, J = 7.4 Hz, 1H), 8.02-7.91 (m, 3H), 7.84 (d, J = 7.9 Hz, 1H), 7.69 (t, J = 7.7 Hz, 1H), 7.42 (s, 1H), 7.27 (s, 1H), 6.43 (d, J = 7.5 Hz, 1H), 4.40 (s, 1H), 3.83 (s, 1H), 3.54 (s, 2H), 2.95 (s, 2H), 2.43 (s, 2H), 2.33 (s, 3H), 2.12 (d, J = 42.4 Hz, 4H), 1.54 (s, 2H). |
| 2.40 | 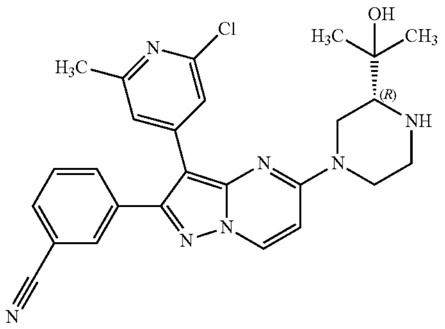 3-[3-(2-chloro-6-methyl-4-pyridyl)-5-[(3R)-3-(1-hydroxy-1-methyl-ethyl)piperazin-1-yl]pyrazolo[1,5-a]pyrimidin-2-yl]benzonitrile (Prepared using Intermediate ZH) | LC-MS (Method 8B): Rt 3.71 mins; MS m/z 488.2 = [M + H]+ $^{1}$H NMR (500 MHz, DMSO-$d_6$) δ 8.76 (d, J = 7.8 Hz, 1H), 8.02-7.95 (m, 2H), 7.84 (d, J = 7.8 Hz, 1H), 7.70 (t, J = 7.8 Hz, 1H), 7.30 (d, J = 9.0 Hz, 2H), 6.92 (d, J = 7.8 Hz, 1H), 4.79 (br s, 1H), 4.49 (s, 1H), 4.25 (br s, 1H), 3.09 (d, J = 11.9 Hz, 1H), 3.06-2.95 (m, 1H), 2.73-2.62 (m, 2H), 2.44 (s, 2H), 2.33 (s, 3H), 1.21 (s, 3H), 1.18 (s, 3H). |

TABLE Ex2-continued

| Ex. | Structure and Name | Retention Time, [M+H]+, 1H NMR |
|---|---|---|
| 2.41 | 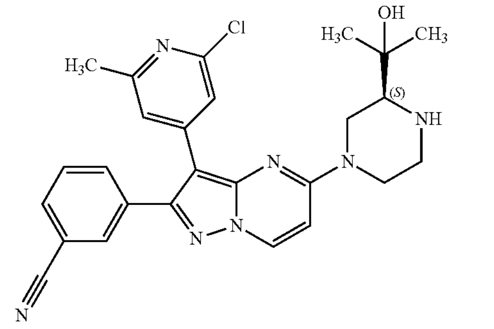 3-[3-(2-chloro-6-methyl-4-pyridyl)-5-[(3S)-3-(1-hydroxy-1-methyl-ethyl)piperazin-1-yl]pyrazolo[1,5-a]pyrimidin-2-yl]benzonitrile (Prepared using Intermediate ZI) | LC-MS (Method 8B): Rt 4.39 mins; MS m/z 488.2 = [M + H]+ $^1$H NMR (500 MHz, DMSO) δ 8.76 (d, J = 7.9 Hz, 1H), 7.98 (s, 1H), 7.98-7.95 (m, 1H), 7.85-7.82 (m, 1H), 7.69 (apr t, J = 7.8 Hz, 1H), 7.30 (s, 1H), 7.29 (s, 1H), 6.91 (d, J = 7.9 Hz, 1H), 4.79 (br s, 1H), 4.47 (s, 1H), 4.19 (br s, 1H), 3.08 (br d, J = 11.9 Hz, 1H), 3.04-2.95 (m, 1H), 2.70-2.63 (m, 2H), 2.49-2.40 (m, 2H), 2.33 (s, 3H), 1.21 (s, 3H), 1.17 (s, 3H) |
| 2.42 | 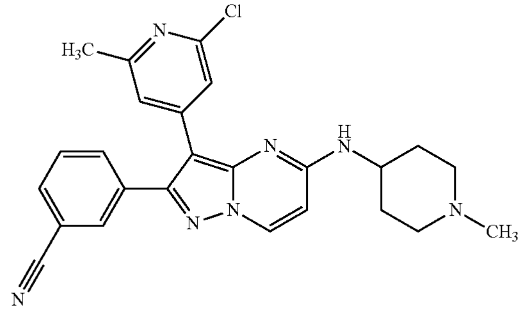 3-[3-(2-chloro-6-methyl-4-pyridyl)-5-[(1-methyl-4-piperidyl)amino]pyrazolo[1,5-a]pyrimidin-2-yl]benzonitrile | LC-MS (Method 8B): Rt 4.49 mins; MS m/z 458.3 = [M + H]+ $^1$H NMR (500 MHz, DMSO-$d_6$) δ 8.58 (d, J = 7.6 Hz, 1H), 7.99 (s, 1H), 7.96 (d, J = 7.8 Hz, 1H), 7.92 (d, J = 6.6 Hz, 1H), 7.84 (d, J = 7.8 Hz, 1H), 7.69 (t, J = 7.8 Hz, 1H), 7.44 (s, 1H), 7.28 (s, 1H), 6.42 (d, J = 7.6 Hz, 1H), 3.78 (s, 1H), 2.81 (d, J = 9.6 Hz, 2H), 2.33 (s, 3H), 2.19 (s, 3H), 2.09-1.97 (m, 4H), 1.59-1.46 (m, 2H). |

Example 3-3-[3-(2-Chloro-6-methyl-4-pyridyl)-5-[[(2R)-2-hydroxypropyl]amino]pyrazolo[1,5-a]pyrimidin-2-yl]benzonitrile

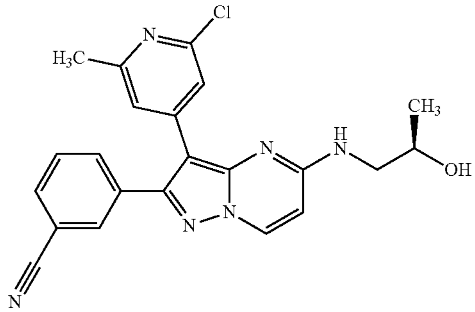 [SMILES: Cc1cc(-c2c(-c3cccc(C#N)c3)nn3ccc(NC[C@@H](C)O)nc23)cc(Cl)n1]

(2R)-1-Aminopropan-2-ol (0.08 mL, 1.05 mmol) was added to 3-[5-chloro-3-(2-chloro-6-methyl-4-pyridyl)pyrazolo[1,5-a]pyrimidin-2-yl]benzonitrile (Intermediate C), (100 mg, 0.26 mmol) in DMF (1 mL) and stirred at 60° C. for 45 mins. The resulting mixture was allowed to cool to room temperature and added dropwise to stirring water (20 mL). EtOAc (50 mL) was added and the aqueous layer was separated. The organic layer was washed with brine (50 mL), dried over $Na_2SO_4$ and concentrated in vacuo. Purification of the crude material by reverse phase chromatography eluting with 40 to 50% MeCN in water (+0.1 wt % $NH_4OH$) followed by purification by chromatography on silica eluting with a gradient of 0 to 8% MeOH in DCM afforded the title compound as a colourless solid.

LC-MS (Method 15B): Rt 7.23 mins; MS m/z 419.2/421.1=[M+H]+ 1H NMR (500 MHz, DMSO-$d_6$) δ 8.59 (d, J=7.5 Hz, 1H), 8.05 (s, 1H), 8.00-7.94 (m, 2H), 7.84 (dt, J=7.9, 1.4 Hz, 1H), 7.70 (t, J=7.7 Hz, 1H), 7.38 (s, 1H), 7.29 (s, 1H), 6.53 (d, J=7.6 Hz, 1H), 4.83 (d, J=4.8 Hz, 1H), 4.01-3.92 (m, 1H), 3.56-3.45 (m, 1H), 3.22 (dt, J=13.0, 6.1 Hz, 1H), 2.34 (s, 3H), 1.16 (d, J=6.2 Hz, 3H).

The compounds of the following tabulated Examples (Table Ex3) were prepared analogously to Example 3 from 3-[5-chloro-3-(2-chloro-6-methyl-4-pyridyl)pyrazolo[1,5-a]pyrimidin-2-yl]benzonitrile (Intermediate C) and the appropriate amine.

TABLE Ex3

| Ex. | Structure and Name | Retention Time, [M + H]+, 1H NMR |
| --- | --- | --- |
| 3.1 | 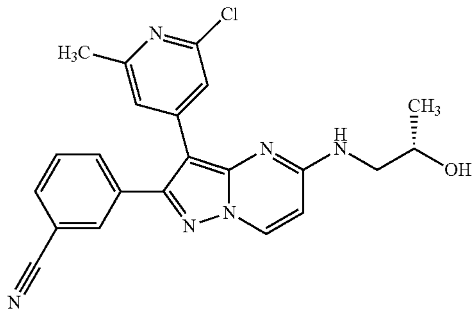 3-[3-(2-Chloro-6-methyl-4-pyridyl)-5-[[(2S)-2-hydroxypropyl]amino]pyrazolo[1,5-a]pyrimidin-2-yl]benzonitrile | LC-MS (Method 15B): Rt 7.28 mins; MS m/z 419.1/421.0 = [M + H]+ $^{1}$H NMR (500 MHz, DMSO-d6) δ 8.58 (d, J = 7.5 Hz, 1H), 8.11-8.01 (m, 1H), 8.01-7.95 (m, 2H), 7.83 (dt, J = 7.9, 1.4 Hz, 1H), 7.74-7.65 (m, 1H), 7.38 (s, 1H), 7.29 (s, 1H), 6.53 (d, J = 7.6 Hz, 1H), 4.83 (d, J = 4.8 Hz, 1H), 4.00-3.92 (m, 1H), 3.56-3.45 (m, 1H), 3.27-3.17 (m, 1H), 2.34 (s, 3H), 1.16 (d, J = 6.3 Hz, 3H). |
| 3.2 | 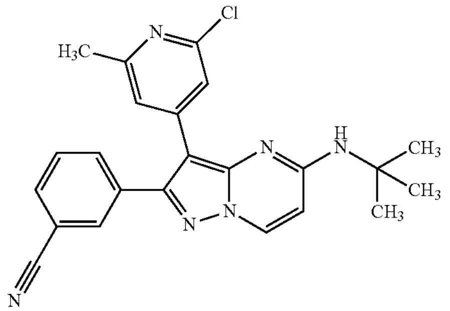 3-[5-(tert-Butylamino)-3-(2-chloro-6-methyl-4-pyridyl)pyrazolo[1,5-a]pyrimidin-2-yl]benzonitrile | LC-MS (Method 15B): Rt 9.42 mins; MS m/z 417.2/419.0 = [M + H]+ $^{1}$H NMR (500 MHz, DMSO-$d_6$) δ 8.56 (d, J = 7.5 Hz, 1H), 8.00-7.94 (m, 2H), 7.84 (d, J = 7.9 Hz, 1H), 7.70 (t, J = 7.8 Hz, 1H), 7.61 (s, 1H), 7.41 (s, 1H), 7.31 (s, 1H), 6.47 (d, J = 7.6 Hz, 1H), 2.33 (s, 3H), 1.50 (s, 9H). |
| 3.3 | 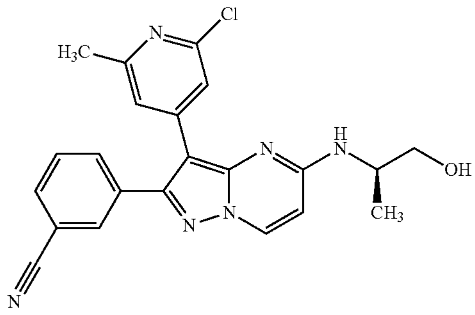 3-[3-(2-Chloro-6-methyl-4-pyridyl)-5-[[(1R)-2-hydroxy-1-methyl-ethyl]amino]pyrazolo[1,5-a]pyrimidin-2-yl]benzonitrile | LC-MS (Method 15B): Rt 7.30 mins; MS m/z 419.1/421.0 = [M + H]+ $^{1}$H NMR (500 MHz, DMSO-$d_6$) δ 8.58 (d, J = 7.6 Hz, 1H), 8.01-7.93 (m, 2H), 7.87-7.81 (m, 2H), 7.69 (t, J = 7.7 Hz, 1H), 7.34 (s, 2H), 6.50 (d, J = 7.6 Hz, 1H), 4.87 (s, 1H), 4.09 (s, 1H), 3.55 (d, J = 5.2 Hz, 2H), 2.34 (s, 3H), 1.24 (d, J = 6.6 Hz, 3H). |

TABLE Ex3-continued

| Ex. | Structure and Name | Retention Time, [M + H]+, 1H NMR |
| --- | --- | --- |
| 3.4 | 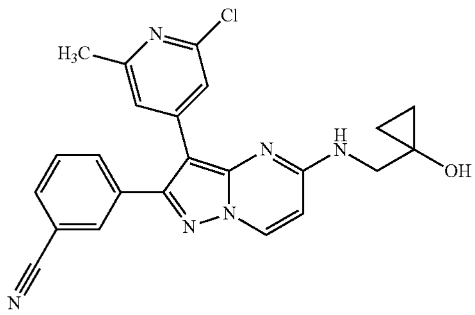 3-[3-(2-Chloro-6-methyl-4-pyridyl)-5-[(1-hydroxycyclopropyl)methylamino]pyrazolo[1,5-a]pyrimidin-2-yl]benzonitrile | LC-MS (Method 15B): Rt 7.44 mins; MS m/z 431.1/433.1 = [M + H]+ $^1$H NMR (500 MHz, DMSO-d6) δ 8.58 (d, J = 7.6 Hz, 1H), 8.18-8.10 (m, 1H), 8.00-7.92 (m, 2H), 7.82 (dt, J = 7.8, 1.5 Hz, 1H), 7.68 (t, J = 7.8 Hz, 1H), 7.34 (s, 1H), 7.26 (s, 1H), 6.57 (d, J = 7.6 Hz, 1H), 5.49 (s, 1H), 3.57 (d, J = 5.4 Hz, 2H), 2.32 (s, 3H), 0.65 (s, 4H). |

Example 4-3-[3-(2-Chloro-6-methyl-4-pyridyl)-5-(4-piperidylamino)pyrazolo[1,5-a]pyrimidin-2-yl]benzonitrile

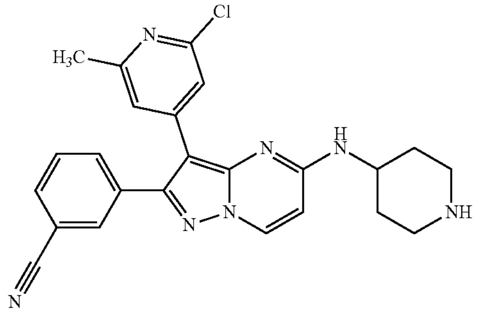 [SMILES: Cc1cc(-c2c(-c3cccc(C#N)c3)nn3ccc(NC4CCNCC4)nc23)cc(Cl)n1]

Step 1: tert-Butyl 4-[[3-(2-chloro-6-methyl-4-pyridyl)-2-(3-cyanophenyl)pyrazolo[1,5-a]pyrimidin-5-yl]amino]piperidine-1-carboxylate

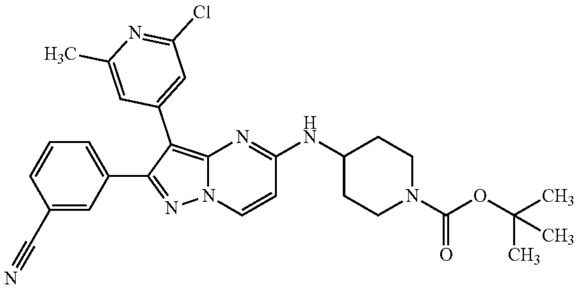 [SMILES: Cc1cc(-c2c(-c3cccc(C#N)c3)nn3ccc(NC4CCN(C(=O)OC(C)(C)C)CC4)nc23)cc(Cl)n1]

tert-Butyl 4-aminopiperidine-1-carboxylate (69 mg, 0.34 mmol) was added to a suspension of DIPEA (0.06 mL, 0.34 mmol) and 3-[5-chloro-3-(2-chloro-6-methyl-4-pyridyl)pyrazolo[1,5-a]pyrimidin-2-yl]benzonitrile (Intermediate C) (100 mg, 0.26 mmol) in DMF (1 mL) and allowed stir at 60° C. overnight. After cooling to room temperature, the mixture was added dropwise to stirring water (20 mL) and the resulting precipitate was collected by filtration, washing with water (2×5 mL). The solid was azeotroped from acetone (20 ml) and purification by reverse phase eluting with a gradient of 40 to 65% MeCN in water (+0.1 wt % $NH_4OH$) afforded the title compound as a colourless solid.

LC-MS (Method 5B): Rt 3.89 mins; MS m/z 544.2=[M+H]+

$^1$H NMR (500 MHz, DMSO-$d_6$) δ 8.63 (d, J=7.6 Hz, 1H), 8.03-7.93 (m, 3H), 7.86 (dt, J=8.0, 1.5 Hz, 1H), 7.72 (t, J=7.8 Hz, 1H), 7.43 (s, 1H), 7.30 (s, 1H), 6.45 (d, J=7.6 Hz, 1H), 4.06-3.94 (m, 3H), 2.97 (br s, 2H), 2.36 (s, 3H), 2.15-2.03 (m, 2H), 1.48-1.34 (m, 11H).

Step 2: 3-[3-(2-Chloro-6-methyl-4-pyridyl)-5-(4-piperidylamino)pyrazolo[1,5-a]pyrimidin-2-yl]benzonitrile 4M HCl in 1,4-dioxane (0.55 mL, 2.19 mmol) was added to a suspension of tert-butyl 4-[[3-(2-chloro-6-methyl-4-pyridyl)-2-(3-cyanophenyl)pyrazolo[1,5-a]pyrimidin-5-yl]amino]piperidine-1-carboxylate (step 1)(119 mg, 0.22 mmol) in MeOH (0.50 mL) and allowed to stir at room temperature for 1 h. The resulting mixture was concentrated in vacuo and purification by reverse phase eluting with a gradient of 5-60% MeCN in water (+0.1 wt % $NH_4OH$) afforded the title compound as a colourless solid.

LC-MS (Method 8B): Rt 4.78 mins; MS m/z 444.2/446.2=[M+H]+

$^1$H NMR (500 MHz, DMSO-$d_6$) b 8.58 (d, J=7.6 Hz, 1H), 8.02-7.94 (m, 2H), 7.92 (d, J=6.8 Hz, 1H), 7.85 (dt, J=7.9, 1.5 Hz, 1H), 7.70 (t, J=7.8 Hz, 1H), 7.45 (s, 1H), 7.28 (s, 1H), 6.43 (d, J=7.6 Hz, 1H), 3.94-3.82 (m, 1H), 3.07-2.97 (m, 2H), 2.64-2.55 (m, 2H), 2.33 (s, 3H), 2.06-1.96 (m, 2H), 1.45-1.29 (m, 2H). NH proton not observed.

The compounds of the following tabulated Examples (Table Ex4) were prepared analogously to Example 4 from 3-{5-Chloro-3-(2-chloro-6-methyl-4-pyridyl)pyrazolo[1,5-a]pyrimidin-2-yl]benzonitrile (Intermediate C) and the appropriate amine (step 1) followed by deprotection using 4M HCl/dioxane (step 2).

TABLE Ex4

| Ex. | Structure and Name | Retention Time, [M + H]+, 1H NMR |
|---|---|---|
| 4.1 | 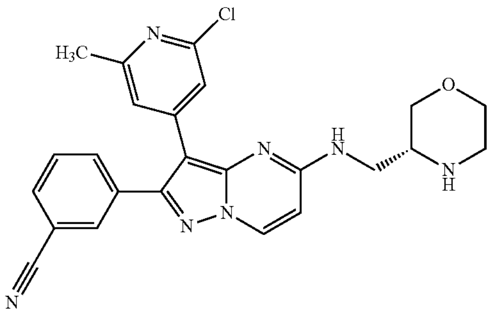 3-[3-(2-Chloro-6-methyl-4-pyridyl)-5-[[(3R)-morpholin-3-yl]methylamino]pyrazolo[1,5-a]pyrimidin-2-yl]benzonitrile | LC-MS (Method 15B): Rt 6.98 mins; MS m/z 460.2/462.1 = [M + H]+. $^1$H NMR (500 MHz, DMSO-d6) δ 8.60 (d, J = 7.6 Hz, 1H), 8.05-7.93 (m, 3H), 7.83 (dt, J = 7.9, 1.5 Hz, 1H), 7.70 (t, J = 7.8 Hz, 1H), 7.37 (s, 1H), 7.32 (s, 1H), 6.47 (d, J = 7.5 Hz, 1H), 3.78 (dd, J = 10.8, 3.0 Hz, 1H), 3.65 (dt, J = 10.9, 2.8 Hz, 1H), 3.43-3.35 (m, 2H), 3.27 (dd, J = 13.3, 6.2 Hz, 1H), 3.23-3.17 (m, 1H), 3.07-2.98 (m, 1H), 2.81 (dt, J = 12.1, 2.7 Hz, 1H), 2.73 (ddd, J = 12.3, 10.3, 3.2 Hz, 1H), 2.35 (s, 3H). NH proton not observed. |
| | Prepared via: 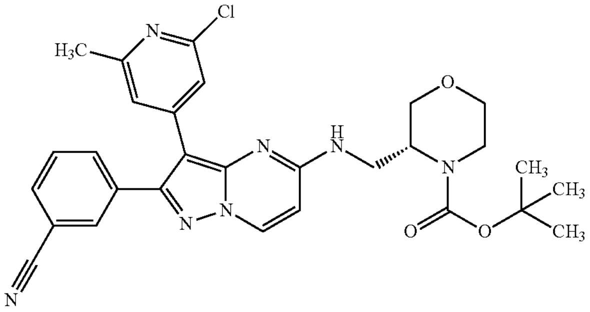 tert-Butyl (3R)-3-[[[3-(2-chloro-6-methyl-4-pyridyl)-2-(3-cyanophenyl)pyrazolo[1,5-a]pyrimidin-5-yl]amino]methyl]morpholine-4-carboxylate | Intermediate Data: LC-MS (Method 5B): Rt 3.39 mins; MS m/z 560.3 = [M + H]+ $^1$H NMR (500 MHz, DMSO-d6) δ 8.63 (s, 1H), 8.14 (s, 1H), 8.00-7.94 (m, 2H), 7.86-7.80 (m, 1H), 7.69 (t, J = 7.8 Hz, 1H), 7.48-7.36 (m, 1H), 7.26 (s, 1H), 6.45 (s, 1H), 4.51-4.23 (m, 2H), 3.89-3.75 (m, 3H), 3.73-3.50 (m, 3H), 3.27-3.11 (m, 1H), 2.33 (s, 3H), 1.39-0.96 (m, 9H). |
| 4.2 | 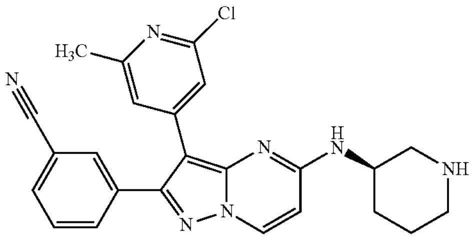 3-[3-(2-Chloro-6-methyl-4-pyridyl)-5-[[(3R)-3-piperidyl]amino]pyrazolo[1,5-a]pyrimidin-2-yl]benzonitrile Prepared via: | LC-MS (Method 7A): Rt 2.29 mins; MS m/z 444.3/446.3 = [M + H]+ $^1$H NMR (500 MHz, DMSO-d6) δ 8.56 (d, J = 7.5 Hz, 1H), 7.98-7.92 (m, 2H), 7.85-7.78 (m, 2H), 7.68 (t, J = 7.7 Hz, 1H), 7.34 (s, 2H), 6.46 (d, J = 7.6 Hz, 1H), 3.92-3.84 (m, 1H), 3.17-3.11 (m, 1H), 2.81 (dd, J = 12.1, 3.8 Hz, 1H, 2.34 (s, 3H), 2.10-2.05 (m, 1H), 1.72-1.63 (m, 1H), 1.53-1.40 (m, 2H). 2 alkyl protons under DMSO peak as shown in HSQC, 1 NH proton not observed. |

TABLE Ex4-continued

| Ex. | Structure and Name | Retention Time, [M + H]+, 1H NMR |
|---|---|---|
| | 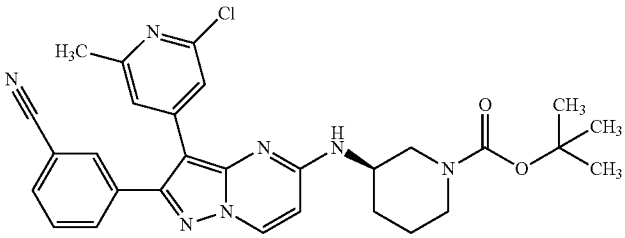<br>tert-Butyl (3R)-3-[[3-(2-chloro-6-methyl-4-pyridyl)-2-(3-cyanophenyl)pyrazolo[1,5-a]pyrimidin-5-yl]amino]piperidine-1-carboxylate | Intermediate Data:<br>LC-MS (Method 7A): Rt 4.30 mins; MS m/z 544.3/546.3 = [M + H]+<br>$^{1}$H NMR (400 MHz, Chloroform-d) δ 8.26 (d, J = 7.5 Hz, 1H), 7.96 (s, 1H), 7.76 (d, J = 7.8 Hz, 1H), 7.72 (d, J = 7.8 Hz, 1H), 7.52 (t, J = 7.8 Hz, 1H), 7.44 (s, 1H), 7.15 (s, 1H), 6.18 (d, J = 7.1 Hz, 1H), 5.31-5.18 (m, 1H), 3.69-3.47 (m, 4H), 3.40-3.30 (m, 1H), 2.44 (s, 3H), 2.03-1.91 (m, 2H), 1.79-1.71 (m, 1H), 1.67-1.60 (m, 1H), 1.43 (s, 9H). |
| 4.3 | 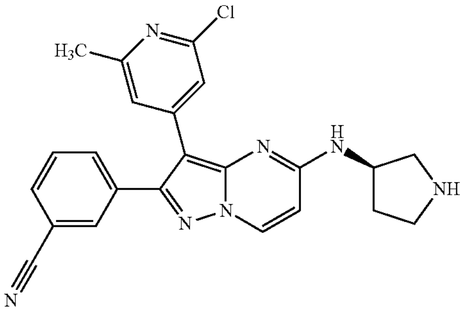<br>3-[3-(2-Chloro-6-methyl-4-pyridyl)-5-[[(3R)-pyrrolidin-3-yl]amino]pyrazolo[1,5-a]pyrimidin-2-yl]benzonitrile | LC-MS (Method 15A): Rt 6.61 mins; MS m/z 430.2/432.1 = [M + H]+<br>$^{1}$H NMR (500 MHz, DMSO-d6) δ 8.58 (d, J = 7.5 Hz, 1H), 8.02 (d, J = 5.6 Hz, 1H), 8.00-7.94 (m, 2H), 7.84 (d, J = 7.8 Hz, 1H), 7.70 (t, J = 7.8 Hz, 1H), 7.43 (s, 1H), 7.31 (s, 1H), 6.44 (d, J = 7.6 Hz, 1H), 4.27 (br s, 1H), 3.15 (dd, J = 11.5, 6.8 Hz, 1H), 2.97-2.87 (m, 1H), 2.86-2.75 (m, 2H), 2.34 (s, 3H), 2.16-2.06 (m, 1H), 1.77-1.65 (m, 1H). NH proton not observed. |
| | Prepared via:<br>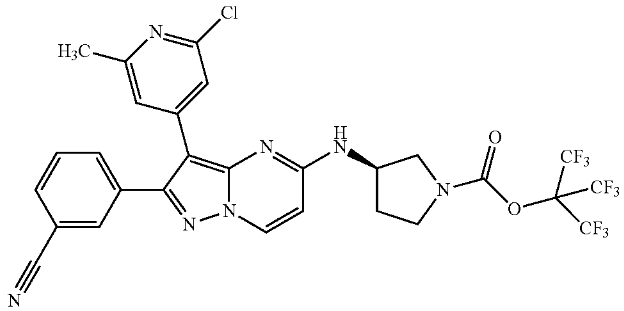<br>tert-Butyl (3R)-3-[[3-(2-chloro-6-methyl-4-pyridyl)-2-(3-cyanophenyl)pyrazolo[1,5-a]pyrimidin-5-yl]amino]pyrrolidine-1-carboxylate | Intermediate Data:<br>LC-MS (Method 3B): Rt 2.80 mins; MS m/z 530.2 = [M + H]+<br>$^{1}$H NMR (400 MHz, DMSO-d6) δ 8.64 (d, J = 7.5 Hz, 1H), 8.18 (d, J = 5.3 Hz, 1H), 8.01-7.94 (m, 2H), 7.87-7.82 (m, 1H), 7.70 (t, J = 7.8 Hz, 1H), 7.39-7.26 (m, 2H), 6.47 (d, J = 7.6 Hz, 1H), 4.47-4.31 (m, 1H), 3.82-3.63 (m, 1H), 3.46-3.38 (m, 2H), 3.37-3.25 (m, 1H), 2.35 (s, 3H), 2.30-2.17 (m, 1H), 2.06-1.96 (m, 1H), 1.47-1.36 (m, 9H). |

TABLE Ex4-continued

| Ex. | Structure and Name | Retention Time, [M + H]+, 1H NMR |
|---|---|---|
| 4.4 | 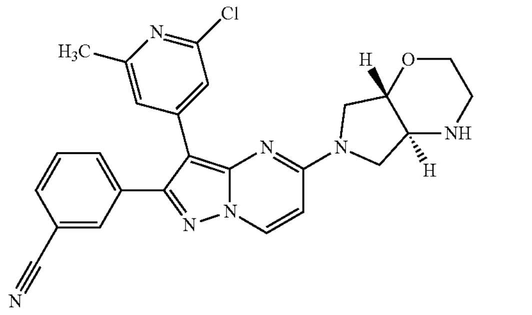 3-[3-(2-Chloro-6-methyl-4-pyridyl)-5-[rac-(4aS,7aS)-3,4,4a,5,7,7a-hexahydro-2H-pyrrolo[3,4-b][1,4]oxazin-6-yl]pyrazolo[1,5-a]pyrimidin-2-yl]benzonitrile | LC-MS (Method 15B): Rt 7.31 mins; MS m/z 472.1/474.0 = [M + H]+ $^1$H NMR (500 MHz, DMSO-d6) δ 8.90 (d, J = 7.9 Hz, 1H), 8.00-7.93 (m, 2H), 7.82 (dt, J = 7.9, 1.5 Hz, 1H), 7.69 (t, J = 7.8 Hz, 1H), 7.27 (s, 1H), 7.16 (s, 1H), 6.98 (d, J = 7.9 Hz, 1H), 4.18-4.09 (m, 2H), 4.06 (dd, J = 10.5, 6.7 Hz, 1H), 3.87-3.79 (m, 1H), 3.76-3.65 (m, 1H), 3.25-3.02 (m, 4H), 2.77 (t, J = 9.9 Hz, 1H), 2.41 (s, 3H). NH proton not observed. |
| | Prepared via: 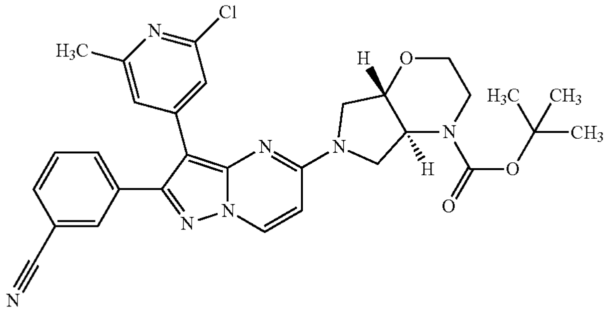 tert-Butyl rac-(4aS,7aS)-6-[3-(2-chloro-6-methyl-4-pyridyl)-2-(3-cyanophenyl)pyrazolo[1,5-a]pyrimidin-5-yl]-2,3,4,a,5,7,7a-hexahydropyrrolo[3,4-b][1,4]oxazine-4-carboxylate | Intermediate Data: LC-MS (Method 5A): Rt 3.53 mins; MS m/z 572.3 = [M + H]+ $^1$H NMR (500 MHz, DMSO-$d_6$) δ 8.94 (d, J = 7.8 Hz, 1H), 8.00-7.93 (m, 2H), 7.84-7.79 (m, 1H), 7.69 (t, J = 7.9 Hz, 1H), 7.29-7.24 (m, 2H), 7.04 (d, J = 7.9 Hz, 1H), 4.54-4.43 (m, 1H), 4.23-4.11 (m, 2H), 3.95-3.82 (m, 2H), 3.82-3.74 (m, 1H), 3.67-3.55 (m, 1H), 3.26-3.19 (m, 1H), 3.14-3.02 (m, 2H), 2.38 (s, 3H), 1.23 (s, 9H). |
| 4.5 | 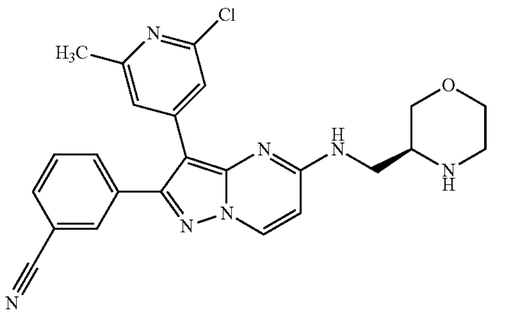 3-[3-(2-Chloro-6-methyl-4-pyridyl)-5-[[(3S)-morpholin-3-yl]methylamino]pyrazolo[1,5-a]pyrimidin-2-yl]benzonitrile | LC-MS (Method 15B): Rt 7.01 mins; MS m/z 460.1/462.1 = [M + H]+ $^1$H NMR (500 MHz, DMSO-d6) δ 9.42 (br s, 1H), 8.67 (d, J = 7.6 Hz, 1H), 8.39 (s, 1H), 8.01-7.93 (m, 2H), 7.82 (dt, J = 7.9, 1.5 Hz, 1H), 7.69 (t, J = 7.7 Hz, 1H), 7.32 (s, 1H), 7.27 (s, 1H), 6.55 (d, J = 7.6 Hz, 1H), 4.06-3.97 (m, 1H), 3.88 (dt, J = 12.3, 3.3 Hz, 1H), 3.81-3.52 (m, 5H), 3.28-3.19 (m, 1H), 3.04 (ddd, J = 13.4, 10.4, 3.7 Hz, 1H), 2.38 (s, 3H). |

TABLE Ex4-continued

| Ex. | Structure and Name | Retention Time, [M + H]+, 1H NMR |
|---|---|---|
| | Prepared via:<br>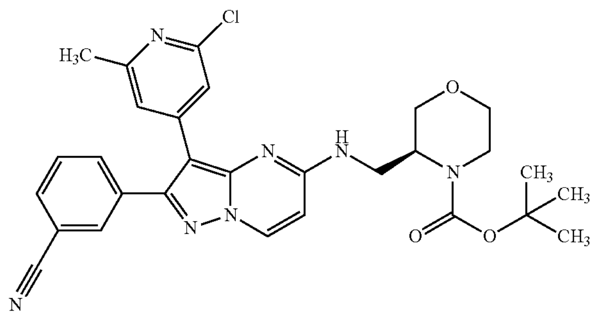<br>tert-Butyl (3S)-3-[[[3-(2-chloro-6-methyl-4-pyridyl)-2-(3-cyanophenyl)pyrazolo[1,5-a]pyrimidin-5-yl]amino]methyl]morpholine-4-carboxylate | Intermediate Data:<br>LC-MS (Method 5B): Rt 3.37 mins; MS m/z 560.3 = [M + H]+<br>$^{1}$H NMR (500 MHz, DMSO-d6) δ 8.62 (br s, 1H), 8.14 (br s, 1H), 8.02-7.94 (m, 2H), 7.83 (d, J = 7.9 Hz, 1H), 7.69 (t, J = 7.8 Hz, 1H), 7.41 (br s, 1H), 7.26 (br s, 1H), 6.45 (br s, 1H), 4.45-4.27 (m, 2H), 3.89-3.76 (m, 3H), 3.75-3.51 (m, 4H), 2.33 (s, 3H), 1.42-0.90 (m, 9H). |
| 4.6 | 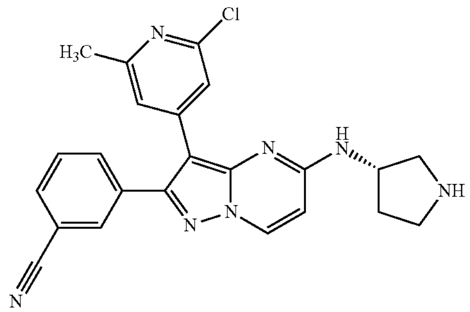<br>3-[3-(2-Chloro-6-methyl-4-pyridyl)-5-[[(3S)-pyrrolidin-3-yl]amino]pyrazolo[1,5-a]pyrimidin-2-yl]benzonitrile | LC-MS (Method 15B): Rt 9.60 mins; MS m/z 430.1/432.0 = [M + H]+<br>$^{1}$H NMR (500 MHz, DMSO-d6) δ 8.61 (d, J = 7.5 Hz, 1H), 8.12-8.06 (m, 1H), 8.02-7.93 (m, 2H), 7.84 (d, J = 7.8 Hz, 1H), 7.70 (t, J = 7.8 Hz, 1H), 7.41 (s, 1H), 7.31 (s, 1H), 6.45 (d, J = 7.6 Hz, 1H), 4.36-4.27 (m, 1H), 3.21 (dd, J = 11.4, 6.5 Hz, 1H), 3.07-2.96 (m, 1H), 2.95-2.85 (m, 2H), 2.34 (s, 3H), 2.23-2.10 (m, 1H), 1.85-1.71 (m, 1H). NH proton not observed. |
| | Prepared via:<br>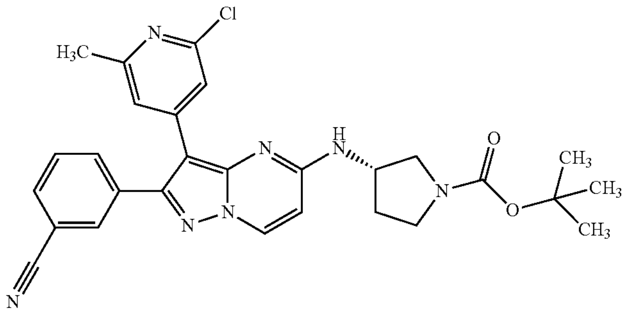<br>tert-Butyl (3S)-3-[[3-(2-chloro-6-methyl-4-pyridyl)-2-(3-cyanophenyl)pyrazolo[1,5-a]pyrimidin-5-yl]amino]pyrrolidine-1-carboxylate | Intermediate Data:<br>LC-MS (Method 5B): Rt 3.72 mins; MS m/z 530.3 = [M + H]+<br>$^{1}$H NMR (500 MHz, DMSO-d6) δ 8.64 (d, J = 7.5 Hz, 1H), 8.21-8.17 (m, 1H), 8.01-7.95 (m, 2H), 7.85 (d, J = 7.9 Hz, 1H), 7.70 (t, J = 7.7 Hz, 1H), 7.38-7.29 (m, 2H), 6.46 (d, J = 7.6 Hz, 1H), 4.48-4.33 (m, 1H), 3.81-3.63 (m, 1H), 3.48-3.38 (m, 2H), 3.37-3.27 (m, 1H), 2.35 (s, 3H), 2.30-2.21 (m, 1H), 2.07-1.95 (m, 1H), 1.47-1.35 (m, 9H). |

TABLE Ex4-continued

| Ex. | Structure and Name | Retention Time, [M + H]+, 1H NMR |
| --- | --- | --- |
| 4.7 | 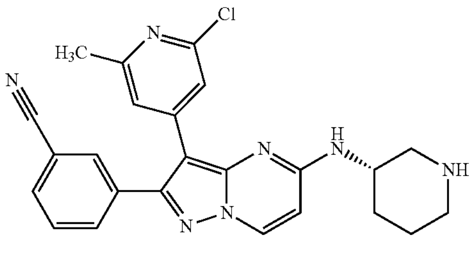 3-[3-(2-Chloro-6-methyl-4-pyridyl)-5-[[(3S)-3-piperidyl]amino]pyrazolo[1,5-a]pyrimidin-2-yl]benzonitrile | LC-MS (Method 7A): Rt 2.28 mins; MS m/z 444.3/446.3 = [M + H]+ $^1$H NMR (500 MHz, DMSO-d6) δ 8.57 (d, J = 7.5 Hz, 1H), 8.00-7.94 (m, 2H), 7.83 (d, J = 7.8 Hz, 2H), 7.69 (t, J = 7.8 Hz, 1H), 7.34 (s, 2H), 6.46 (d, J = 7.6 Hz, 1H), 3.92-3.83 (m, 1H), 3.17-3.11 (m, 1H), 2.85-2.78 (m, 1H), 2.34 (s, 3H), 2.11-2.05 (m, 1H), 1.71-1.64 (m, 1H), 1.53-1.41 (m, 2H). 2 alkyl protons under DMSO peak as shown in HSQC, 1 NH proton not observed |
| | Prepared via: 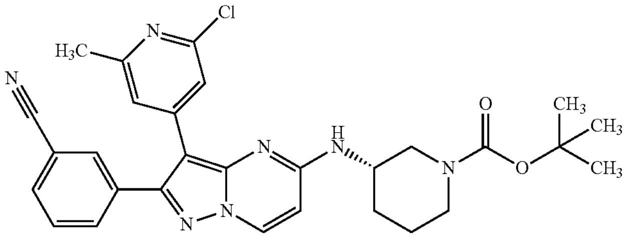 tert-Butyl (3S)-3-[[3-(2-chloro-6-methyl-4-pyridyl)-2-(3-cyanophenyl)pyrazolo[1,5-a]pyrimidin-5-yl]amino]piperidine-1-carboxylate | Intermediate Data: LC-MS (Method 7A): Rt 4.30 mins; MS m/z 544.3/546.3 = [M + H]+ $^1$H NMR (400 MHz, Chloroform-d) δ 8.26 (d, J = 7.6 Hz, 1H), 7.96 (t, J = 1.4 Hz, 1H), 7.80-7.74 (m, 1H), 7.72 (dt, J = 7.7, 1.3 Hz, 1H), 7.52 (t, J = 7.8 Hz, 1H), 7.44 (s, 1H), 7.15 (s, 1H), 6.18 (d, J = 7.1 Hz, 1H), 5.30 (br.s, 1H), 3.73-3.44 (m, 4H), 3.40-3.30 (m, 1H), 2.44 (s, 3H), 2.03-1.87 (m, 2H), 1.82-1.72 (m, 1H), 1.66-1.58 (m, 1H), 1.43 (s, 9H). |

Example 4.8-3-[3-(2-Chloro-6-methyl-4-pyridyl)-5-[[(1R,2S)-2,3-dihydroxy-1-methyl-propyl]amino]pyrazolo[1,5-a]pyrimidin-2-yl]benzonitrile

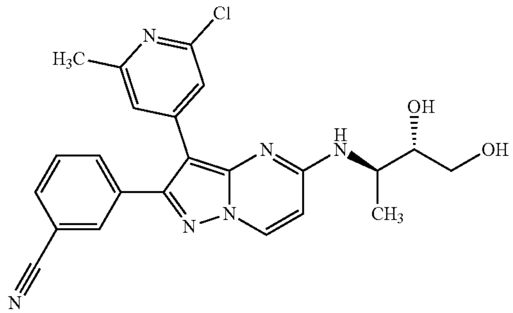 [SMILES: Cc1cc(-c2c(-c3cccc(C#N)c3)nn3ccc(N[C@H](C)[C@H](O)CO)nc23)cc(Cl)n1]

Step 1-3-[3-(2-Chloro-6-methyl-4-pyridyl)-5-[[(1R)-1-[(4S)-2,2-dimethyl-1,3-dioxolan-4-yl]ethyl}amino]pyrazolo[1,5-a]pyrimidin-2-yl]benzonitrile

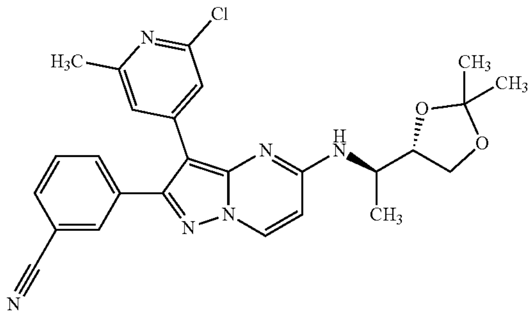 [SMILES: Cc1cc(-c2c(-c3cccc(C#N)c3)nn3ccc(N[C@H](C)[C@H]4COC(C)(C)O4)nc23)cc(Cl)n1]

The title compound was prepared analogously to Example 4 step 1 from 3-[5-chloro-3-(2-chloro-6-methyl-4-pyridyl)

pyrazolo[1,5-a]pyrimidin-2-yl]benzonitrile (Intermediate C) and (1R)-1-[(4S)-2,2-dimethyl-1,3-dioxolan-4-yl] ethanamine.

LC-MS (Method 58): Rt 3.84 mins; MS m/z 489.2/491.1=[M+H]+

1H NMR (500 MHz, DMSO-d6) b 8.60 (d, J=7.6 Hz, 1H), 8.02-7.93 (m, 2H), 7.89-7.80 (m, 2H), 7.69 (t, J=7.8 Hz, 1H), 7.34 (s, 1H), 7.31 (s, 1H), 6.50 (d, J=7.6 Hz, 1H), 4.29 (s, 2H), 4.03 (dd, J=8.2, 6.2 Hz, 1H), 3.72 (dd, J=8.2, 6.2 Hz, 1H), 2.35 (s, 3H), 1.36 (s, 3H), 1.30 (s, 3H), 1.21 (d, J=6.0 Hz, 3H).

Step 2-3-[3-(2-Chloro-6-methyl-4-pyridyl)-5-[[(1R, 2S)-2,3-dihydroxy-1-methyl-propyl]amino]pyrazolo [1,5-a]pyrimidin-2-yl]benzonitrile To a suspension of 3-[3-(2-chloro-6-methyl-4-pyridyl)-5-[[(1R)-1-[(4S)-2,2-dimethyl-1,3-dioxolan-4-yl]ethyl] amino]pyrazolo[1,5-a]pyrimidin-2-ylbenzonitrile (step 1) (49.1 mg, 0.1000 mmol) in THE (1 mL) was added 2M aqueous HCl (0.5 mL, 1 mmol) and the reaction mixture was stirred at room temperature for 16 h. The resulting mixture was partitioned between ethyl acetate (15 mL) and water (15 mL). The organic layer was separated and the aqueous layer was further extracted with ethyl acetate (2×10 mL). The combined organic layers were washed with brine (15 mL), dried over $Na_2SO_4$, filtered and concentrated in vacuo. Purification by chromatography on silica eluting with a gradient of 2 to 10% MeOH in DCM afforded the title compound as a white solid.

LC-MS (Method 8B): Rt 4.06 mins; MS m/z 449.2/451.2=[M+H]+

1H NMR (500 MHz, DMSO-d6) δ 8.56 (d, J=7.6 Hz, 1H), 7.99-7.93 (m, 2H), 7.83 (d, J=8.1, 1.5 Hz, 1H), 7.73-7.62 (m, 2H), 7.38 (s, 1H), 7.31 (s, 1H), 6.62 (d, J=7.6 Hz, 1H), 5.03 (d, J=4.7 Hz, 1H), 4.56 (t, J=5.5 Hz, 1H), 4.40-4.26 (m, 1H), 3.65-3.54 (m, 1H), 3.38 (t, J=6.0 Hz, 2H), 2.34 (s, 3H), 1.26 (d, J=6.7 Hz, 3H).

Example 4.9-3-[3-(2-Chloro-6-methyl-4-pyridyl)-5-[[(1S,2S)-2,3-dihydroxy-1-methyl-propyl]amino] pyrazolo[1,5-a]pyrimidin-2-yl]benzonitrile

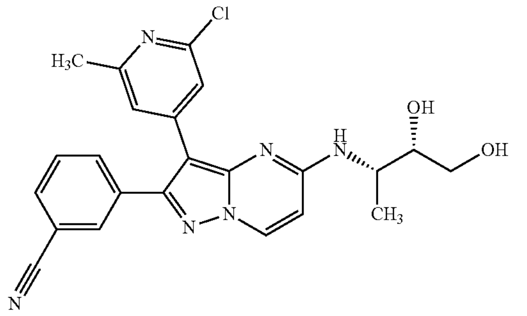 [SMILES: Cc1cc(-c2c(-c3cccc(C#N)c3)nn3ccc(N[C@@H](C)[C@H](O)CO)nc23)cc(Cl)n1]

Step 1-3-[3-(2-Chloro-6-methyl-4-pyridyl)-5-[[(1S)-1-[(4S)-2,2-dimethyl-1,3-dioxolan-4-yl]ethyl]amino] pyrazolo[1,5-a]pyrimidin-2-yl]benzonitrile

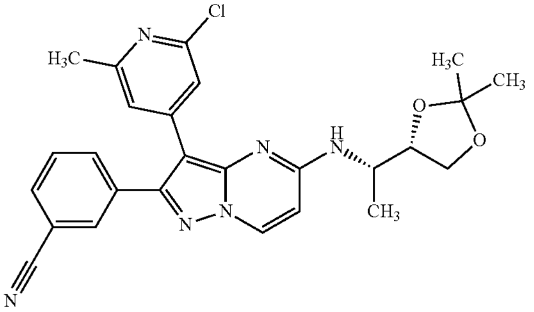 [SMILES: Cc1cc(-c2c(-c3cccc(C#N)c3)nn3ccc(N[C@@H](C)[C@H]4COC(C)(C)O4)nc23)cc(Cl)n1]

The title compound was prepared analogously to Example 4 step 1 from 3-[5-chloro-3-(2-chloro-6-methyl-4-pyridyl) pyrazolo[1,5-a]pyrimidin-2-yl]benzonitrile (Intermediate C) and (1S)-1-[(4S)-2,2-dimethyl-1,3-dioxolan-4-yl] ethanamine.

LC-MS (Method 5B): Rt 2.29 mins; MS m/z 489.4/491.1=[M+H]+

1H NMR (500 MHz, DMSO-d6) δ 8.61 (d, J=7.5 Hz, 1H), 8.00-7.93 (m, 2H), 7.92 (d, J=8.0 Hz, 1H), 7.83 (d, J=8.0 Hz, 1H), 7.69 (t, J=7.8 Hz, 1H), 7.34 (s, 1H), 7.28 (s, 1H), 6.45 (d, J=7.6 Hz, 1H), 4.25 (q,J=7.1 Hz, 1H), 4.15 (q,J=6.2 Hz, 1H), 4.04 (dd, J=8.4, 6.5 Hz, 1H), 3.85 (dd, J=8.4, 5.5 Hz, 1H), 2.34 (s, 3H), 1.40 (s, 3H), 1.30 (s, 3H), 1.24 (d, J=6.6 Hz, 3H).

Step 2-3-[3-(2-Chloro-6-methyl-4-pyridyl)-5-[[(1S, 2S)-2,3-dihydroxy-1-methyl-propyl]amino]pyrazolo [1,5-a]pyrimidin-2-yl]benzonitrile The title compound was prepared analogously to Example 4.8 step 2 from 3-[3-(2-Chloro-6-methyl-4-pyridyl)-5-[[(1S)-1-[(4S)-2,2-dimethyl-1,3-dioxolan-4-yl]ethyl]amino] pyrazolo[1,5-a]pyrimidin-2-yl]benzonitrile (step 1) and 2M aqueous HCl.

LC-MS (Method 8B): Rt 4.01 mins; MS m/z 449.2/451.2=[M+H]+

1H NMR (500 MHz, DMSO-d6) δ 8.57 (d, J=7.5 Hz, 1H), 8.00-7.93 (m, 2H), 7.88-7.79 (m, 2H), 7.70 (t, J=7.7 Hz, 1H), 7.44 (s, 1H), 7.22 (s, 1H), 6.52 (d, J=7.6 Hz, 1H), 4.86 (d, J=5.3 Hz, 1H), 4.60 (t, J=5.4 Hz, 1H), 4.30-4.17 (m, 1H), 3.75-3.66 (m, 1H), 3.43 (t, J=5.9 Hz, 2H), 2.36 (s, 3H), 1.18 (d, J=6.7 Hz, 3H).

Example 4.10-[5-[(2-Amino-2-methyl-propyl) amino]-3-(2-chloro-6-methyl-4-pyridyl)pyrazolo[1,5-a]pyrimidin-2-yl]benzonitrile trifluoroacetate

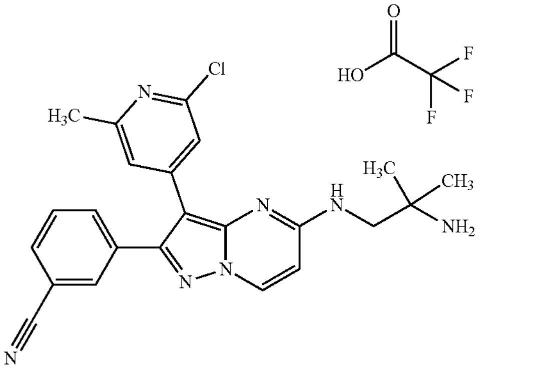 [SMILES: Cc1cc(-c2c(-c3cccc(C#N)c3)nn3ccc(NCC(C)(C)N)nc23)cc(Cl)n1 ; O=C(O)C(F)(F)F]

Step 1—tert-Butyl N-[2-[[3-(2-chloro-6-methyl-4-pyridyl)-2-(3-cyanophenyl)pyrazolo[1,5-a]pyrimidin-5-yl]amino]-1,1-dimethyl-ethyl]carbamate

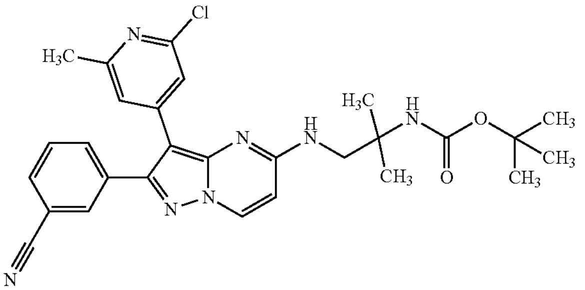 [SMILES: Cc1cc(-c2c(-c3cccc(C#N)c3)nn3ccc(NCC(C)(C)NC(=O)OC(C)(C)C)nc23)cc(Cl)n1]

The title compound was prepared analogously to Example 4 step 1 from 3-[5-chloro-3-(2-chloro-6-methyl-4-pyridyl) pyrazolo[1,5-a]pyrimidin-2-yl]benzonitrile (Intermediate C) and tert-butyl N-(2-amino-1,1-dimethyl-ethyl)carbamate.

LC-MS (Method 5B): Rt 3.34 mins; MS m/z 530.3/532.3=[M−H]−

1H NMR (500 MHz, DMSO-d6) δ 8.61 (d, J=7.6 Hz, 1H), 8.02-7.92 (m, 3H), 7.83 (d, J=7.8 Hz, 1H), 7.70 (t, J=7.8 Hz, 1H), 7.41 (s, 1H), 7.32 (s, 1H), 6.67 (s, 1H), 6.57 (d, J=7.6 Hz, 1H), 3.65 (d, J=6.1 Hz, 2H), 2.37 (s, 3H), 1.32-1.24 (m, 15H).

Step 2-[5-[(2-Amino-2-methyl-propyl)amino]-3-(2-chloro-6-methyl-4-pyridyl)pyrazolo[1,5-a]pyrimidin-2-yl]benzonitrile trifluoroacetate Trifluoroacetic acid (0.14 mL, 1.84 mmol) was added to a suspension of tert-butyl N-[2-[[3-(2-chloro-6-methyl-4-pyridyl)-2-(3-cyanophenyl)pyrazolo[1,5-a]pyrimidin-5-yl] amino]-1,1-dimethyl-ethyl]carbamate (step 1)(65.4 mg, 0.1200 mmol) in DCM (1 mL) and the reaction mixture stirred at room temperature for 16 h. The mixture was concentrated in vacuo and the solid residue was then triturated with diethyl ether (2 mL) and acetonitrile (2 mL) to afford the title compound as an off-white solid.

LC-MS (Method 8B): Rt 4.51 mins; MS m/z 432.2/434.2=[MH]+

1H NMR (500 MHz, DMSO-d6) δ 8.69 (d, J=7.6 Hz, 1H), 8.03 (s, 1H), 7.99-7.94 (m, 2H), 7.90 (br s, 3H), 7.84-7.78 (m, 1H), 7.69 (t, J=8.0 Hz, 1H), 7.34 (s, 1H), 7.27 (s, 1H), 6.55 (d, J=7.7 Hz, 1H), 3.62 (d, J=6.2 Hz, 2H), 2.37 (s, 3H), 1.33 (s, 6H),

Example 4.11-3-[3-(2-chloro-6-methyl-4-pyridyl)-5-[(3-hydroxyazetidin-3-yl)methylamino]pyrazolo[1,5-a]pyrimidin-2-yl]benzonitrile trifluoroacetate

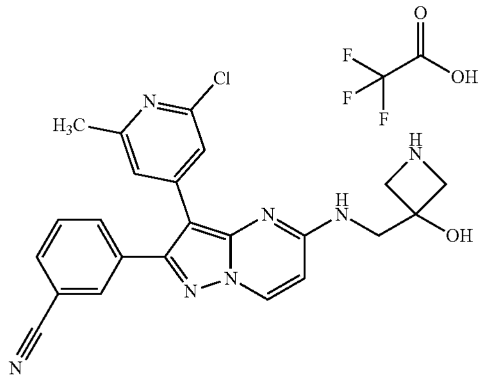

Step 1—tert-butyl 3-[[[3-(2-chloro-6-methyl-4-pyridyl)-2-(3-cyanophenyl)pyrazolo[1,5-a]pyrimidin-5-yl]amino]methyl]-3-hydroxy-azetidine-1-carboxylate

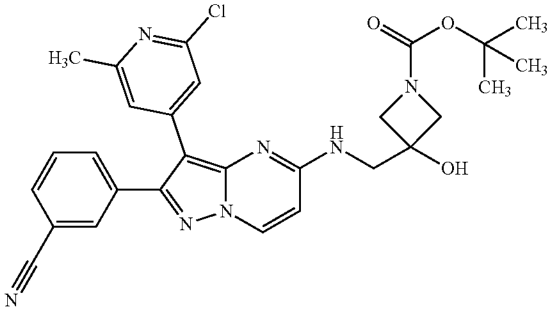 [SMILES: Cc1cc(-c2c(-c3cccc(C#N)c3)nn3ccc(NCC4(O)CN(C(=O)OC(C)(C)C)C4)nc23)cc(Cl)n1]

The title compound was prepared analogously to Example 4 step 1 from 3-[5-chloro-3-(2-chloro-6-methyl-4-pyridyl) pyrazolo[1,5-a]pyrimidin-2-yl]benzonitrile (Intermediate C) and tert-butyl 3-(aminomethyl)-3-hydroxy-azetidine-1-carboxylate.

LC-MS (Method 5B): Rt 3.15 mins; MS m/z 546.2=[M+H]+

$^1$H NMR (500 MHz, DMSO-$d_6$) δ 8.62 (d, J=7.5 Hz, 1H), 8.16-8.06 (m, 1H), 8.01-7.92 (m, 2H), 7.84 (d,J=7.9 Hz, IH), 7.70 (t, J=7.8 Hz, 1H), 7.41 (s, 1H), 7.24 (s, IH), 6.57 (d, J=7.6 Hz, 1H), 6.07 (s, 1H), 3.91 (s, 2H), 3.81-3.66 (m, 4H), 2.35 (s, 3H), 1.34 (s, 9H).

Step 2-3-[3-(2-chloro-6-methyl-4-pyridyl)-5-[(3-hydroxyazetidin-3-yl)methylamino]pyrazolo[1,5-a] pyrimidin-2-yl]benzonitrile trifluoroacetate The title compound was prepared analogously to Example 4.10 step 2 from tert-butyl 3-[[[3-(2-chloro-6-methyl-4-pyridyl)-2-(3-cyanophenyl)pyrazolo[1,5-a]pyrimidin-5-yl] amino]methyl]-3-hydroxy-azetidine-1-carboxylate (step 1) and TFA.

LC-MS (Method 15B): Rt 8.34 mins; MS m/z 446.1=[M+H]+

$^1$H NMR (500 MHz, DMSO-$d_6$) δ 8.84 (s, 1H), 8.75-8.60 (m, 2H), 8.11 (s, 1H), 8.02-7.91 (m, 2H), 7.81 (d, J=7.9 Hz, 1H), 7.69 (t, J=7.9 Hz, 1H), 7.33 (s, 1H), 7.26 (s, 1H), 6.58 (d, J=7.6 Hz, 1H), 6.47 (s, 1H), 4.12-4.00 (m, 2H), 3.86 (dd, J=11.4, 5.8 Hz, 2H), 3.68 (d, J=5.5 Hz, 2H), 2.38 (s, 3H).

Example 5-3-(2-Chloro-6-methyl-4-pyridyl)-2-(3-cyanophenyl)-N-(3-hydroxy-1-bicyclo[1.1.1]pentanyl)pyrazolo[1,5-a]pyrimidine-5-carboxamide

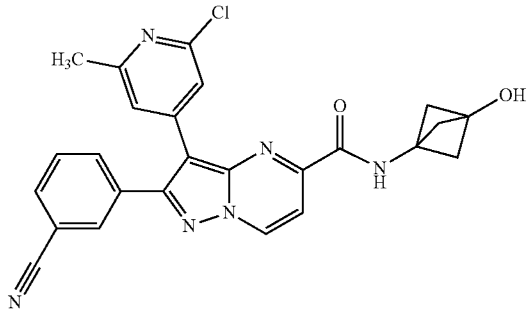 [SMILES: Cc1cc(-c2c(-c3cccc(C#N)c3)nn3ccc(C(=O)NC45CC(O)(C4)C5)nc23)cc(Cl)n1]

To a suspension of 3-(2-chloro-6-methyl-4-pyridyl)-2-(3-cyanophenyl)pyrazolo[1,5-a]pyrimidine-5-carboxylic acid (Intermediate A) (50 mg, 0.13 mmol) in DCM (1 mL) was added DMF (1 drop) followed by oxalyl chloride (33 μL, 0.38 mmol) dropwise and the mixture stirred at room temperature for 5 min. Additional DCM (1 mL) and oxalyl chloride (0.02 mL, 0.26 mmol) were added and the mixture stirred for a further 5 mins before the resulting mixture was concentrated in vacuo to afford the acid chloride.

To a solution of 3-aminobicyclo[1.1.1]pentan-1-ol hydrochloride (26 mg, 0.19 mmol) and DIPEA (89 μL, 0.51 mmol) in DCM (1 mL) was added dropwise a suspension of the acid chloride in DCM (1 mL) and the mixture stirred for 45 min. Further 3-aminobicyclo[1.1.1]pentan-1-ol hydrochloride (9 mg, 0.06 mmol) was added and the reaction mixture was stirred at room temperature overnight. The resulting mixture was partitioned between $H_2O$ (10 mL) and DCM (10 mL) and the organic portion was separated. The aqueous was further extracted with DCM (2×10 mL) and the combined organic extracts were washed with brine (10 mL), dried over $MgSO_4$ and the solvent removed in vacuo. Purification by chromatography on silica eluting with a gradient of 0 to 2% MeOH in DCM afforded the title compound as a yellow solid.

LC-MS (Method 88): Rt 4.32 mins; MS m/z 471.2/473.1=[M+H]+

$^1$H NMR (500 MHz, DMSO-d6) δ 9.41 (d, J=7.2 Hz, 1H), 9.24 (s, 1H), 8.05 (s, 1H), 7.99 (d, J=7.8 Hz, 1H), 7.87 (d, J=7.8 Hz, 1H), 7.71 (t, J=7.8 Hz, 1H), 7.65 (d, J=7.2 Hz, 1H), 7.52 (s, 1H), 7.33 (s, 1H), 6.30 (s, 1H), 2.46 (s, 3H), 2.18 (s, 6H).

The compounds of the following tabulated Examples (Table Ex5) were prepared analogously to Example 5 from 3-(2-chloro-6-methyl-4-pyridyl)-2-(3-cyanophenyl)pyrazolo[1,5-a]pyrimidine-5-carboxylic acid (Intermediate A), oxalyl chloride and the appropriate amine.

TABLE Ex5

| Ex. | Structure and Name | Retention Time, [M + H]+, 1H NMR |
|---|---|---|
| 5.1 | 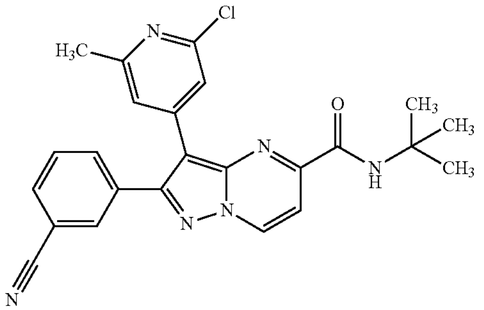 N-tert-Butyl-3-(2-chloro-6-methyl-4-pyridyl)-2-(3-cyanophenyl)pyrazolo[1,5-a]pyrimidine-5-carboxamide | LC-MS (Method 8B): Rt 5.33 mins; MS m/z 445.2/447.2 = [M + H]+ $^1$H NMR (500 MHz, DMSO-d6) δ 9.43 (d, J = 6.5 Hz, 1H), 8.15-7.88 (m, 4H), 7.79-7.64 (m, 2H), 7.51 (s, 1H), 7.41 (s, 1H), 2.44 (s, 3H), 1.45 (s, 9H). |

TABLE Ex5-continued

| Ex. | Structure and Name | Retention Time, [M + H]+, 1H NMR |
|---|---|---|
| 5.2 | 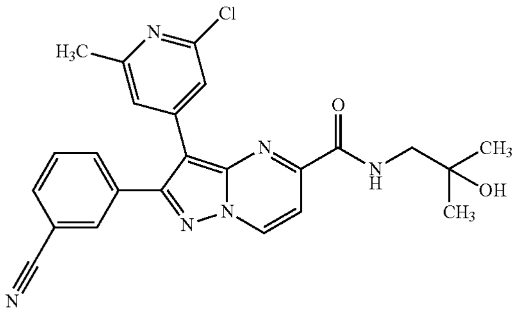 3-(2-Chloro-6-methyl-4-pyridyl)-2-(3-cyanophenyl)-N-(2-hydroxy-2-methyl-propyl)pyrazolo[1,5-a]pyrimidine-5-carboxamide | LC-MS (Method 8B): Rt 4.33 mins; MS m/z 461.2/463.2 = [M + H]+ $^1$H NMR (400 MHz, DMSO-$d_6$) δ 9.45 (d, J = 7.2 Hz, 1H), 8.42 (t, J = 6.0 Hz, 1H), 8.10 (t, J = 1.5 Hz, 1H), 8.02 (dt, J = 7.9, 1.5 Hz, 1H), 7.92 (dt, J = 7.9, 1.5 Hz, 1H), 7.74 (t, J = 7.9 Hz, 1H), 7.73 (d, J = 7.2 Hz, 1H), 7.58-7.53 (m, 1H), 7.33-7.28 (m, 1H), 4.73 (s, 1H), 2.45 (s, 3H), 1.17 (s, 6H). CH2 signal not observed. $^1$H NMR (400 MHz, Chloroform-d) δ 8.88 (d, J = 7.2 Hz, 1H), 8.18 (t, J = 5.8 Hz, 1H), 8.05 (t, J = 1.6 Hz, 1H), 7.89 (d, J = 7.2 Hz, 1H), 7.82 (dt, J = 7.7, 1.6 Hz, 1H), 7.77 (dt, J = 7.7, 1.6 Hz, 1H), 7.57 (t, J = 7.7 Hz, 1H), 7.41 (s, 1H), 7.23 (s, 1H), 3.52 (d, J = 5.8 Hz, 2H), 2.53 (s, 3H), 1.34 (s, 6H). OH proton not observed. |
| 5.3 | 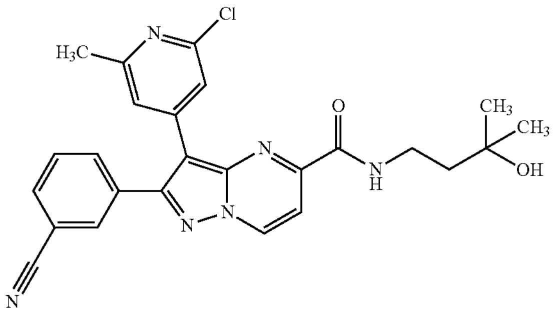 3-(2-Chloro-6-methyl-4-pyridyl)-2-(3-cyanophenyl)-N-(3-hydroxy-3-methyl-butyl)pyrazolo[1,5-a]pyrimidine-5-carboxamide | LC-MS (Method 8B): Rt 4.54 mins; MS m/z 475.2/477.2 = [M + H]+ $^1$H NMR (500 MHz, DMSO-d6) δ 9.42 (d, J = 7.1 Hz, 1H), 8.94 (t, J = 5.4 Hz, 1H), 8.06 (s, 1H), 8.00 (d, J = 7.7 Hz, 1H), 7.88 (d, J = 7.7 Hz, 1H), 7.75-7.69 (m, 2H), 7.54 (s, 1H), 7.24 (s, 1H), 4.46 (s, 1H), 3.45 (q, J = 6.7 Hz, 2H), 3.29 (s, 3H), 1.69 (t, J = 7.2 Hz, 2H), 1.18 (s, 6H). |
| 5.4 | 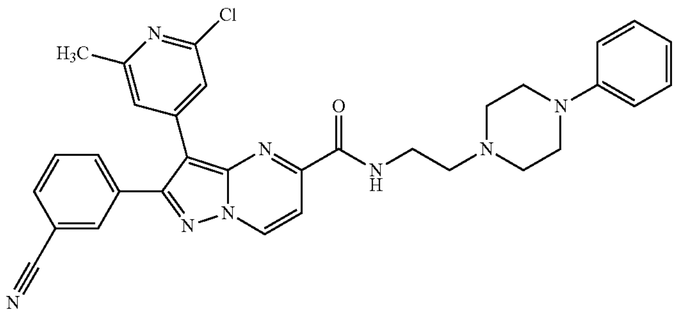 3-(2-Chloro-6-methyl-4-pyridyl)-2-(3-cyanophenyl)-N-[2-(4-phenylpiperazin-1-yl)ethyl]pyrazolo[1,5-a]pyrimidine-5-carboxamide | LC-MS (Method 5B): Rt 5.32 mins; MS m/z 577.2/579.2 = [M + H]+ $^1$H NMR (500 MHz, DMSO-d6) δ 9.42 (d, J = 7.1 Hz, 1H), 8.65 (t, J = 5.8 Hz, 1H), 8.05 (s, 1H), 7.99 (d, J = 7.9 Hz, 1H), 7.86 (d, J = 7.9 Hz, 1H), 7.75-7.68 (m, 2H), 7.41 (s, 1H), 7.34 (s, 1H), 7.24-7.16 (m, 2H), 6.90 (d, J = 8.1 Hz, 2H), 6.76 (t, J = 7.3 Hz, 1H), 3.53-3.49 (m, 2H), 3.12-3.07 (m, 4H), 2.62-2.57 (m, 6H), 2.41 (s, 3H). |

TABLE Ex5-continued

| Ex. | Structure and Name | Retention Time, [M + H]+, 1H NMR |
|---|---|---|
| 5.5 | 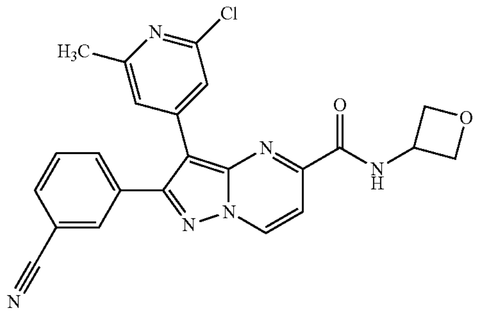 3-(2-Chloro-6-methyl-4-pyridyl)-2-(3-cyanophenyl)-N-(oxetan-3-yl)pyrazolo[1,5-a]pyrimidine-5-carboxamide | LC-MS (Method 8B): Rt 4.25 mins; MS m/z 445.1/447.1 = [M + H]+ $^{1}$H NMR (500 MHz, DMSO-d6) δ 9.49 (d, J = 6.7 Hz, 1H), 9.43 (d, J = 7.2 Hz, 1H), 8.08 (s, 1H), 8.01 (d, J = 7.8 Hz, 1H), 7.90 (d, J = 7.8 Hz, 1H), 7.73 (t, J = 7.8 Hz, 1H), 7.67 (d, J = 7.2 Hz, 1H), 7.57 (s, 1H), 7.37 (s, 1H), 5.09-5.00 (m, 1H), 4.80 (apr t, J = 7.0 Hz, 2H), 4.69 (apr t, J = 6.4 Hz, 2H), 3.29 (s, 3H). |
| 5.6 | 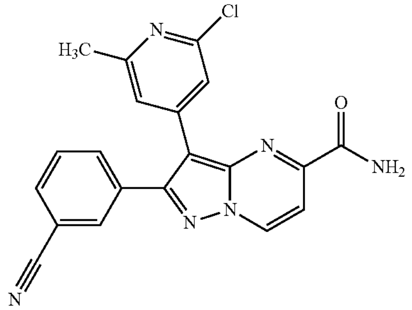 3-(2-Chloro-6-methyl-4-pyridyl)-2-(3-cyanophenyl)pyrazolo[1,5-a]pyrimidine-5-carboxamide | LC-MS (Method 8B): Rt 4.09 mins; MS m/z 389.2/391.1 = [M + H]+ $^{1}$H NMR (500 MHz, DMSO-d6) δ 9.42 (d, J = 7.2 Hz, 1H), 8.26 (s, 1H), 8.07 (s, 1H), 8.04-7.95 (m, 2H), 7.88 (apr d, J = 7.9 Hz, 1H), 7.77-7.67 (m, 2H), 7.52 (s, 1H), 7.32 (s, 1H), 2.47 (s, 3H). |
| 5.7 | 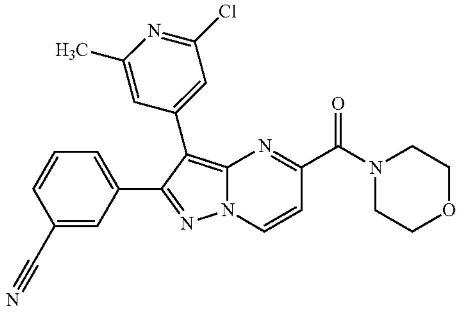 3-[3-(2-Chloro-6-methyl-4-pyridyl)-5-(morpholine-4-carbonyl)pyrazolo[1,5-a]pyrimidin-2-yl]benzonitrile | LC-MS (Method 8B): Rt 4.29 mins; MS m/z 459.2/461.2 = [M + H]+ $^{1}$H NMR (400 MHz, Chloroform-d) δ 8.82 (d, J = 7.2 Hz, 1H), 8.02 (t, J = 1.6 Hz, 1H), 7.80 (dt, J = 7.8, 1.6 Hz, 1H), 7.76 (dt, J = 7.8, 1.6 Hz, 1H), 7.56 (t, J = 7.8 Hz, 1H), 7.47 (d, J = 7.2 Hz, 1H), 7.38 (s, 1H), 7.12 (s, 1H), 3.94-3.90 (m, 2H), 3.85 (s, 4H), 3.82-3.78 (m, 2H), 2.50 (s, 3H). |

Example 5.8-2-(3-Cyanophenyl)-3-(2,6-dimethyl-4-pyridyl)pyrazolo[1,5-a}pyrimidine-5-carboxamide

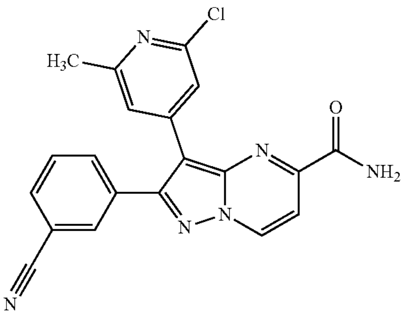 [SMILES: Cc1cc(-c2c(-c3cccc(C#N)c3)nn3ccc(C(N)=O)nc23)cc(Cl)n1]

The title compound was prepared from 2-(3-cyanophenyl)-3-(2,6-dimethyl-4-pyridyl)pyrazolo[1,5-a]pyrimidine-5-carboxylic acid (Example 92 step 2b), oxalyl chloride and ammonium hydroxide analogously to Example 5.

LC-MS (Method 8B): Rt 3.74 mins; MS m/z 369.2=[M+H]+

1H NMR (500 MHz, DMSO-d6) δ 9.37 (d, J=7.2 Hz, 1H), 8.12 (s, 1H), 8.04-8.00 (m, 1H), 7.99-7.94 (m, 2H), 7.86 (d, J=7.9 Hz, 1H), 7.71-7.65 (m, 2H), 7.18 (s, 2H), 2.41 (s, 6H).

Example 6-3-(2-Chloro-6-methyl-4-pyridyl)-2-(3-cyanophenyl)-N-[(1S)-2-hydroxy-1,2-dimethyl-propyl]pyrazolo[1,5-a]pyrimidine-5-carboxamide

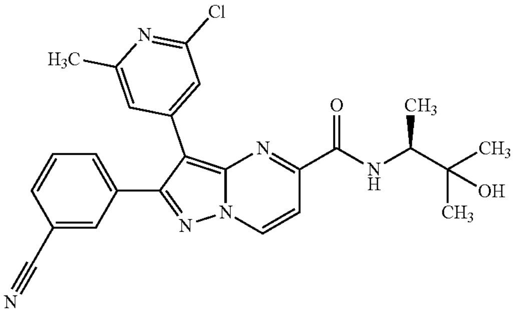 [SMILES: Cc1cc(-c2c(-c3cccc(C#N)c3)nn3ccc(C(=O)N[C@@H](C)C(C)(C)O)nc23)cc(Cl)n1]

To a mixture of 3-(2-chloro-6-methyl-4-pyridyl)-2-(3-cyanophenyl)pyrazolo[1,5-a]pyrimidine-5-carboxylic acid (Intermediate A) (40 mg, 0.10 mmol) and (3S)-3-amino-2-methyl-butan-2-ol hydrochloride (21 mg, 0.15 mmol) in DMF (2 mL) was added DIPEA (89 μL, 0.51 mmol) followed by T3P® (50% in DMF) (0.14 mL, 0.21 mmol) dropwise and the reaction mixture was stirred at room temperature for 1 h. The resulting mixture was diluted in EtOAc (10 mL) and water (10 mL). The layers were separated and the aqueous layer was extracted with EtOAc (2×10 mL). The combined organic layers were washed with 50% brine (3×10 mL), dried over $MgSO_4$, filtered and concentrated in vacuo. Purification by chromatography on silica eluting with a gradient of 0 to 3% MeOH in DCM afforded the title compound as a yellow solid.

LC-MS (Method 88): Rt 4.57 mins; MS m/z 475.2/477.2=[M+H]+

$^1$H NMR (500 MHz, DMSO-$d_6$) δ 9.45 (d, J=7.1 Hz, 1H), 8.27 (d, J=9.0 Hz, 1H), 8.10 (s, 1H), 8.02 (d, J=7.8 Hz, 1H), 7.93 (d, J=8.0 Hz, 1H), 7.77-7.69 (m, 2H), 7.55 (s, 1H), 7.30 (s, 1H), 4.73 (s, 1H), 3.95-3.83 (m, 1H), 2.45 (s, 3H), 1.22-1.13 (m, 9H).

The compounds of the following tabulated Examples (Table Ex6) were prepared analogously to Example 6 from 3-(2-chloro-6-methyl-4-pyridyl)-2-(3-cyanophenyl)pyrazolo[1,5-a]pyrimidine-5-carboxylic acid (Intermediate A), T3P®, DIPEA and the appropriate amine.

TABLE EX6

| Ex. | Structure and Name | Retention Time, [M + H]+, 1H NMR |
|---|---|---|
| 6.1 | 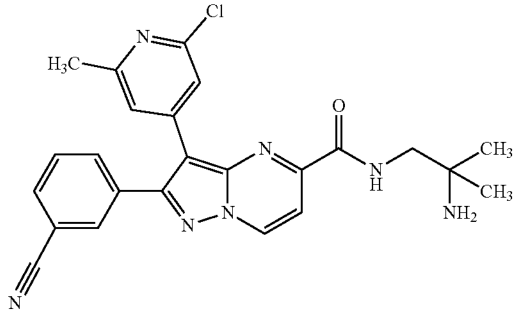 [SMILES: Cc1cc(-c2c(-c3cccc(C#N)c3)nn3ccc(C(=O)NCC(C)(C)N)nc23)cc(Cl)n1] N-(2-Amino-2-methyl-propyl)-3-(2-chloro-6-methyl-4-pyridyl)-2-(3-cyanophenyl)pyrazolo[1,5-a]pyrimidine-5-carboxamide | LC-MS (Method 8B): Rt 4.38 mins; MS m/z 460.2/462.1 = [M + H]+ $^1$H NMR (500 MHz, DMSO-d6) δ 9.44 (d, J = 7.1 Hz, 1H), 8.63 (t, J = 5.8 Hz, 1H), 8.10 (s, 1H), 8.02 (d, J = 7.7 Hz, 1H), 7.93 (d, J = 7.7 Hz, 1H), 7.78 – 7.69 (m, 2H), 7.56 (s, 1H), 7.34 (s, 1H), 3.22 (d, J = 5.4 Hz, 2H), 2.44 (s, 3H), 1.72 (s, 2H), 1.09 (s, 6H). |

TABLE EX6-continued

| Ex. | Structure and Name | Retention Time, [M + H]+, 1H NMR |
| --- | --- | --- |
| 6.2 | 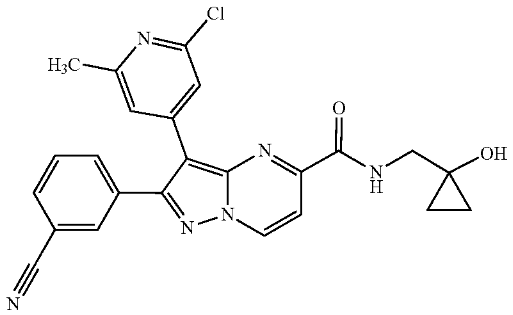 [SMILES: Cc1cc(-c2c(-c3cccc(C#N)c3)nn3ccc(C(=O)NCC4(O)CC4)nc23)cc(Cl)n1] 3-(2-Chloro-6-methyl-4-pyridyl)-2-(3-cyanophenyl)-N-[(1-hydroxycyclopropyl)methyl]pyrazolo[1,5-a]pyrimidine-5-carboxamide | LC-MS (Method 8B): Rt 4.31 mins; MS m/z 459.1 / 461.1 = [M + H]+ $^{1}$H NMR (500 MHz, DMSO-$d_6$) δ 9.45 (d, J = 7.1 Hz, 1H), 8.58 (t, J = 5.9 Hz, 1H), 8.09 (s, 1H), 8.01 (d, J = 7.8 Hz, 1H), 7.91 (d, J = 7.8 Hz, 1H), 7.76 - 7.70 (m, 2H), 7.56 (s, 1H), 7.33 (s, 1H), 5.57 (s, 1H), 3.50 (d, J = 5.9 Hz, 2H), 2.47 (s, 3H), 0.62 (s, 4H). |
| 6.3 | 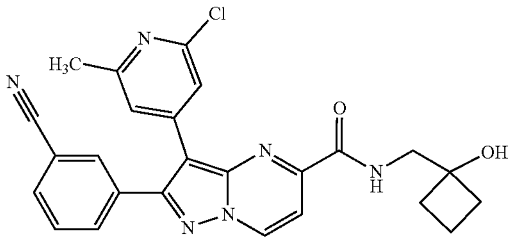 [SMILES: Cc1cc(-c2c(-c3cccc(C#N)c3)nn3ccc(C(=O)NCC4(O)CCC4)nc23)cc(Cl)n1] 3-(2-Chloro-6-methyl-4-pyridyl)-2-(3-cyanophenyl)-N-[(1-hydroxycyclobutyl)methyl]pyrazolo[1,5-a]pyrimidine-5-carboxamide | LC-MS (Method 7A): Rt 3.22 mins; MS m/z 473.2/475.1 = [M + H]+ $^{1}$H NMR (400 MHz, DMSO-d6) δ 9.45 (d, J = 7.2 Hz, 1H), 8.40 (t, J = 5.8 Hz, 1H), 8.09 (t, J = 1.4 Hz, 1H), 8.01 (dt, J = 7.7, 1.4 Hz, 1H), 7.91 (dt, J = 7.9, 1.2 Hz, 1H), 7.77 - 7.70 (m, 2H), 7.53 (s, 1H), 7.29 (s, 1H), 5.41 (s, 1H), 3.48 (d, J = 5.9 Hz, 2H), 2.45 (s, 3H), 2.10 - 1.93 (m, 4H), 1.71 - 1.61 (m, 1H), 1.60 - 1.49 (m, 1H). |
| 6.4 | 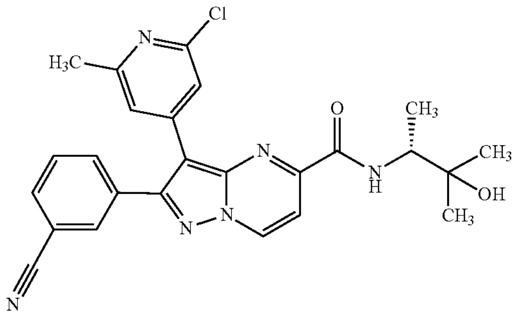 [SMILES: Cc1cc(-c2c(-c3cccc(C#N)c3)nn3ccc(C(=O)N[C@H](C)C(C)(C)O)nc23)cc(Cl)n1] 3-(2-Chloro-6-methyl-4-pyridyl)-2-(3-cyanophenyl)-N-[(1 R)-2-hydroxy-1,2-dimethyl-propyl]pyrazolo[1,5-a]pyrimidine-5-carboxamide | LC-MS (Method 8B): Rt 4.56 mins; MS m/z 475.2/477.1 = [M + H]+ $^{1}$H NMR (500 MHz, DMSO-d6) δ 9.44 (d, J = 7.2 Hz, 1H), 8.27 (d, J = 9.0 Hz, 1H), 8.10 (s, 1H), 8.02 (d, J = 7.8 Hz, 1H), 7.93 (d, J = 7.8 Hz, 1H), 7.81 - 7.67 (m, 2H), 7.55 (s, 1H), 7.30 (s, 1H), 4.73 (s, 1H), 3.93 - 3.85 (m, 1H), 2.45 (s, 3H), 1.26 - 1.11 (m, 9H). |
| 6.5 | 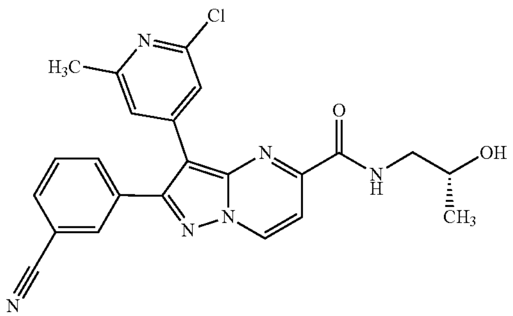 [SMILES: Cc1cc(-c2c(-c3cccc(C#N)c3)nn3ccc(C(=O)NC[C@@H](C)O)nc23)cc(Cl)n1] 3-(2-Chloro-6-methyl-4-pyridyl)-2-(3-cyanophenyl)-N-[(2R)-2-hydroxypropyl]pyrazolo[1,5-a]pyrimidine-5-carboxamide | LC-MS (Method 8B): Rt 4.18 mins; MS m/z 447.2/449.1 = [M + H]+ $^{1}$H NMR (500 MHz, DMSO-d6) δ 9.44 (d, J = 7.2 Hz, 1H), 8.59 (t, J = 5.5 Hz, 1H), 8.08 (s, 1H), 8.01 (d, J = 7.8 Hz, 1H), 7.90 (d, J = 7.8 Hz, 1H), 7.77 - 7.68 (m, 2H), 7.54 (s, 1H), 7.30 (s, 1H), 4.95 - 4.87 (m, 1H), 3.87 - 3.80 (m, 1H), 3.29 - 3.19 (m, 2H), 2.46 (s, 3H), 1.12 (d, J = 6.2 Hz, 3H). |

TABLE EX6-continued

| Ex. | Structure and Name | Retention Time, [M + H]+, 1H NMR |
|---|---|---|
| 6.6 | 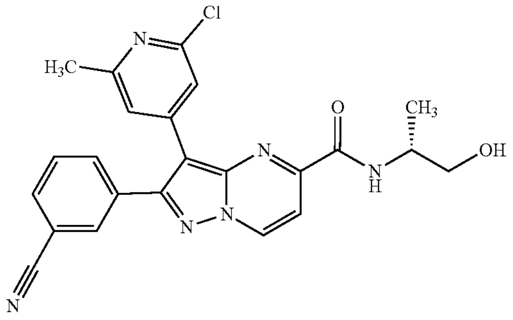 [SMILES: Cc1cc(-c2c(-c3cccc(C#N)c3)nn3ccc(C(=O)N[C@H](C)CO)nc23)cc(Cl)n1] 3-(2-Chloro-6-methyl-4-pyridyl)-2-(3-cyanophenyl)-N-[(1R)-2-hydroxy-1-methyl-ethyl]pyrazolo[1,5-a]pyrimidine-5-carboxamide | LC-MS (Method 8B): Rt 4.24 mins; MS m/z 447.2/449.1 = [M + H]+ $^1$H NMR (500 MHz, DMSO-d6) δ 9.44 (d, J = 7.2 Hz, 1H), 8.39 (d, J = 8.2 Hz, 1H), 8.10 (s, 1H), 8.02 (d, J = 7.8 Hz, 1H), 7.92 (d, J = 7.8 Hz, 1H), 7.78 - 7.68 (m, 2H), 7.57 (s, 1H), 7.32 (s, 1H), 4.94 (t, J = 5.0 Hz, 1H), 4.07 - 4.00 (m, 1H), 3.52 - 3.49 (m, 2H), 2.47 (s, 3H), 1.21 (d, J = 6.7 Hz, 3H). |
| 6.7 | 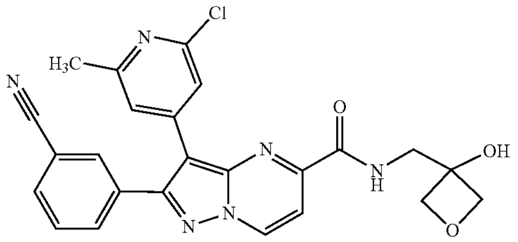 [SMILES: Cc1cc(-c2c(-c3cccc(C#N)c3)nn3ccc(C(=O)NCC4(O)COC4)nc23)cc(Cl)n1] 3-(2-Chloro-6-methyl-4-pyridyl)-2-(3-cyanophenyl)-N-[(3-hydroxyoxetan-3-yl)methyl]pyrazolo[1,5-a]pyrimidine-5-carboxamide | LC-MS (Method 7A): Rt 2.73 mins; MS m/z 475.1/477.1 = [M + H]+ 1H NMR (400 MHz, DMSO-d6) δ 9.45 (d, J = 7.2 Hz, 1H), 8.69 (t, J = 6.1 Hz, 1H), 8.08 (t, J = 1.4 Hz, 1H), 8.01 (dt, J = 7.7, 1.4 Hz, 1H), 7.91 (dt, J = 7.9, 1.3 Hz, 1H), 7.76 - 7.70 (m, 2H), 7.53 (s, 1H), 7.31 (s, 1H), 6.06 (s, 1H), 4.50 (d, J = 6.8 Hz, 2H), 4.45 (d, J = 6.7 Hz, 2H), 3.68 (d, J = 6.2 Hz, 2H), 2.46 (s, 3H). |
| 6.8 | 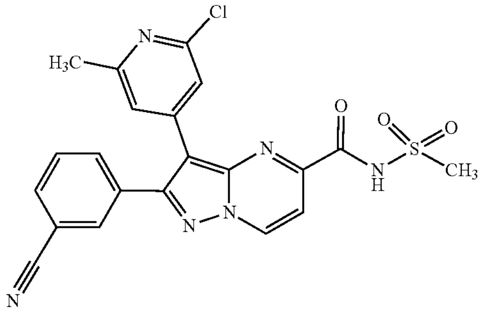 [SMILES: Cc1cc(-c2c(-c3cccc(C#N)c3)nn3ccc(C(=O)NS(C)(=O)=O)nc23)cc(Cl)n1] 3-(2-Chloro-6-methyl-4-pyridyl)-2-(3-cyanophenyl)-N-methylsulfonyl-pyrazolo[1,5-a]pyrimidine-5-carboxamide | LC-MS (Method 8A): Rt 4.50/4.54 (split peak)mins; MS m/z 467.1/469.0 = [M + H]+ $^1$H NMR (500 MHz, DMSO-d6) δ 12.35 (s, 1H), 9.41 (d, J = 6.8 Hz, 1H), 8.07 (s, 1H), 8.00 (d, J = 7.7 Hz, 1H), 7.89 (d, J = 7.9 Hz, 1H), 7.76 - 7.66 (m, 2H), 7.50 (s, 1H), 7.45 (s, 1H), 2.43 (s, 3H). 1 × CH3 signal not observed. |
| 6.9 | 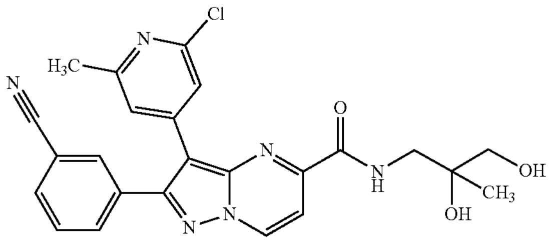 [SMILES: Cc1cc(-c2c(-c3cccc(C#N)c3)nn3ccc(C(=O)NCC(C)(O)CO)nc23)cc(Cl)n1] 3-(2-Chloro-6-methyl-4-pyridyl)-2-(3-cyanophenyl)-N-(2,3-dihydroxy-2-methyl-propyl)pyrazolo[1,5-a]pyrimidine-5-carboxamide | LC-MS (Method 7A): Rt 2.67 mins; MS m/z 477.2/479.2 = [M + H]+ 1H NMR (500 MHz, DMSO-d6) δ 9.45 (d, J = 7.1 Hz, 1H), 8.48 (t, J = 5.8 Hz, 1H), 8.09 (t, J = 1.5 Hz, 1H), 8.02 (dt, J = 7.8, 1.4 Hz, 1H), 7.91 (dt, J = 7.9, 1.2 Hz, 1H), 7.76 - 7.72 (m, 2H), 7.57 (s, 1H), 7.25 (s, 1H), 4.81 (t, J = 5.6 Hz, 1H), 4.71 (s, 1H), 3.38 (dq, J = 13.4, 6.4, 5.6 Hz, 2H), 3.34 - 3.26 (m, 2H), 2.47 (s, 3H), 1.10 (s, 3H). 1 × CH2 signal underneath water peak as shown in HSQC. |

TABLE EX6-continued

| Ex. | Structure and Name | Retention Time, [M + H]+, 1H NMR |
|---|---|---|
| 6.10 | 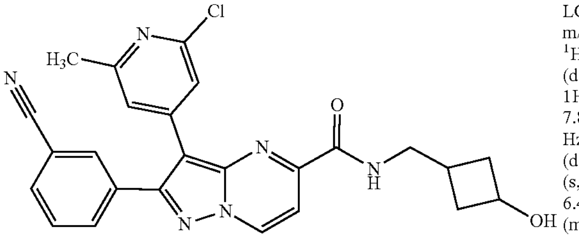 3-(2-Chloro-6-methyl-4-pyridyl)-2-(3-cyanophenyl)-N-[(3-hydroxycyclobutyl)methyl]pyrazolo[1,5-a]pyrimidine-5-carboxamide | LC-MS (Method 7A): Rt 3.02 mins; MS m/z 473.3/475.2 = [M + H]+ $^1$H NMR (500 MHz, DMSO-d6) δ 9.42 (d, J = 7.2 Hz, 1H), 8.72 (t, J = 6.1 Hz, 1H), 8.08 (t, J = 1.4 Hz, 1H), 8.01 (dt, J = 7.8, 1.4 Hz, 1H), 7.90 (dt, J = 7.9, 1.2 Hz, 1H), 7.73 (t, J = 7.8 Hz, 1H), 7.69 (d, J = 7.2 Hz, 1H), 7.54 (s, 1H), 7.33 (s, 1H), 3.95 - 3.87 (m, 1H), 3.35 (t, J = 6.4 Hz, 2H), 2.47 (s, 3H), 2.32 - 2.23 (m, 2H), 2.01 - 1.94 (m, 1H), 1.64 - 1.54 (m, 2H). OH proton not observed. |
| 6.11 | 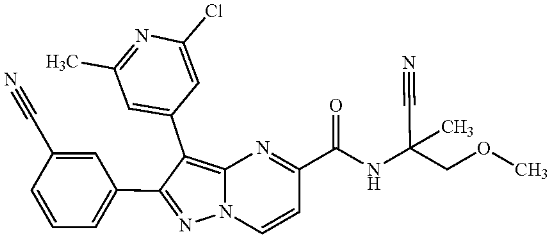 [SMILES: COCC(C)(C#N)NC(=O)c1ccn2nc(-c3cccc(C#N)c3)c(-c3cc(C)nc(Cl)c3)c2n1] 3-(2-Chloro-6-methyl-4-pyridyl)-N-(1-cyano-2-methoxy-1-methyl-ethyl)-2-(3-cyanophenyl)pyrazolo[1,5-a]pyrimidine-5-carboxamide | LC-MS (Method 7A): Rt 3.60 mins; MS m/z 486.2/488.2 = [M + H]+ $^1$H NMR (400 MHz, Methanol-d4) δ 8.43 (d, J = 7.2 Hz, 1H), 7.25 (d, J = 1.5 Hz, 1H), 7.12 - 7.04 (m, 2H), 7.01 (d, J = 7.2 Hz, 1H), 6.86 (t, J = 7.8 Hz, 1H), 6.69 (s, 1H), 6.59 (s, 1H), 3.04 (d, J = 9.6 Hz, 1H), 2.99 (d, J = 9.6 Hz, 1H), 2.74 (s, 3H), 1.68 (s, 3H), 1.01 (s, 3H). NH proton not observed. |
| 6.12 | 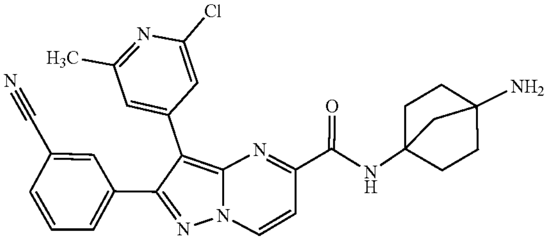 [SMILES: Cc1cc(-c2c(-c3cccc(C#N)c3)nn3ccc(C(=O)NC45CCC(N)(CC4)C5)nc23)cc(Cl)n1] N-(4-Aminonorbornan-1-yl)-3-(2-chloro-6-methyl-4-pyridyl)-2-(3-cyanophenyl)pyrazolo[1,5-a]pyrimidine-5-carboxamide | LC-MS (Method 7A): Rt 1.99 mins; MS m/z 498.3/500.3 = [M + H]+ $^1$H NMR (400 MHz, Methanol-d4) δ 9.19 (d, J = 7.2 Hz, 1H), 8.06 (s, 1H), 7.90 (dt, J = 8.0, 1.4 Hz, 1H), 7.87 (dt, J = 7.8, 1.3 Hz, 1H), 7.75 (d, J = 7.2 Hz, 1H), 7.67 (t, J = 7.8 Hz, 1H), 7.51 (s, 1H), 7.42 (s, 1H), 2.48 (s, 3H), 2.24 - 2.13 (m, 2H), 2.06 - 1.97 (m, 4H), 1.86 1.77 (m, 2H), 1.75 - 1.66 (m, 2H). 3 NH protons not observed |
| 6.13 | 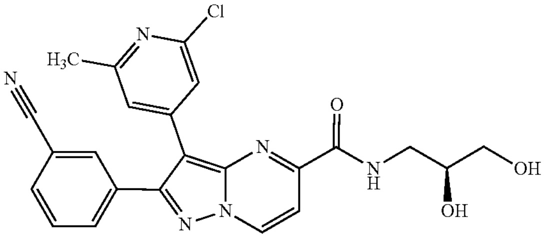 [SMILES: Cc1cc(-c2c(-c3cccc(C#N)c3)nn3ccc(C(=O)NC[C@H](O)CO)nc23)cc(Cl)n1] 3-(2-Chloro-6-methyl-4-pyridyl)-2-(3-cyanophenyl)-N-[(2S)-2,3-dihydroxypropyl]pyrazolo[1,5-a]pyrimidine-5-carboxamide | LC-MS (Method 7A): Rt 2.51 mins; MS m/z 463.2/465.2 = [M + H]+ $^1$H NMR (400 MHz, Methanol-d4) δ 9.20 (d, J = 7.2 Hz, 1H), 8.05 (t, J = 1.4 Hz, 1H), 7.90 - 7.85 (m, 2H), 7.81 (d, J = 7.2 Hz, 1H), 7.66 (t, J = 7.8 Hz, 1H), 7.51 (s, 1H), 7.36 (s, 1H), 3.85 (dq, J = 6.8, 5.4 Hz, 1H), 3.69 (dd, J = 13.7, 4.6 Hz, 1H), 3.60 (dd, J = 5.5, 2.0 Hz, 2H), 3.48 (dd, J = 13.7, 6.9 Hz, 1H), 2.52 (s, 3H). Exchangeable protons not observed |

TABLE EX6-continued

| Ex. | Structure and Name | Retention Time, [M + H]+, 1H NMR |
| --- | --- | --- |
| 6.14 | 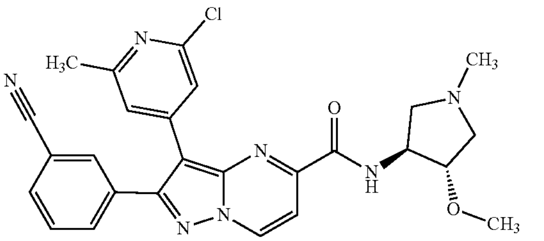 [SMILES: CO[C@H]1CN(C)C[C@@H]1NC(=O)c1ccn2nc(-c3cccc(C#N)c3)c(-c3cc(C)nc(Cl)c3)c2n1] 3-(2-Chloro-6-methyl-4-pyridyl)-2-(3-cyanophenyl)-N-[(3S,4S)-4-methoxy-1-methyl-pyrrolidin-3-yl]pyrazolo[1,5-a]pyrimidine-5-carboxamide | LC-MS (Method 7A): Rt 1.90 mins; MS m/z 502.3/504.3 = [M + H]+ $^1$H NMR (400 MHz, Methanol-d4) δ 9.23 (d, J = 7.2 Hz, 1H), 8.08 (t, J = 1.4 Hz, 1H), 7.93 - 7.87 (m, 2H), 7.80 (d, J = 7.2 Hz, 1H), 7.68 (t, J = 7.8 Hz, 1H), 7.50 (s, 1H), 7.47 (s, 1H), 4.47 (ddd, J = 6.7, 4.5, 2.3 Hz, 1H), 3.92 (ddd, J = 6.3, 3.8, 2.4 Hz, 1H), 3.44 (s, 3H), 3.11 (dd, J = 10.5, 6.5 Hz, 1H), 2.98 (dd, J = 10.0, 6.7 Hz, 1H), 2.65 (dd, J = 10.0, 4.5 Hz, 1H), 2.55 (dd, J = 10.4, 3.9 Hz, 1H), 2.52 (s, 3H), 2.41 (s, 3H). NH proton not observed |
| 6.15 | 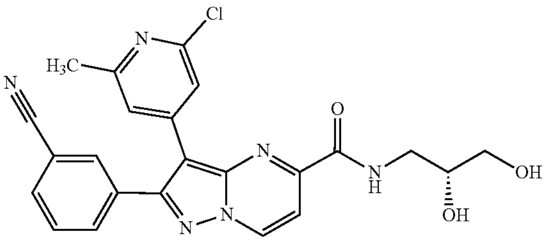 [SMILES: Cc1cc(-c2c(-c3cccc(C#N)c3)nn3ccc(C(=O)NC[C@@H](O)CO)nc23)cc(Cl)n1] 3-(2-Chloro-6-methyl-4-pyridyl)-2-(3-cyanophenyl)-N-[(2R)-2,3-dihydroxypropyl]pyrazolo[1,5-a]pyrimidine-5-carboxamide | LC-MS (Method 7A): Rt 2.51 mins; MS m/z 463.3/465.2 = [M + H]+ $^1$H NMR (400 MHz, DMSO-d6) δ 9.43 (d, J = 7.2 Hz, 1H), 8.59 (t, J = 5.8 Hz, 1H), 8.07 (t, J = 1.5 Hz, 1H), 8.01 (dt, J = 7.7, 1.4 Hz, 1H), 7.90 (dt, J = 7.9, 1.3 Hz, 1H), 7.76 - 7.69 (m, 2H), 7.54 (s, 1H), 7.26 (s, 1H), 5.00 (s, 1H), 4.70 (s, 1H), 3.71 - 3.64 (m, 1H), 3.58 - 3.50 (m, 1H), 3.45 (dd, J = 10.9, 5.1 Hz, 1H), 3.41 - 3.36 (m, 2H), 2.47 (s, 3H). |
| 6.16 | 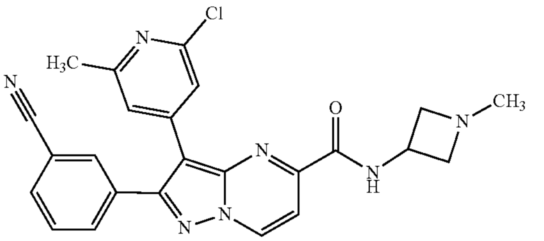 [SMILES: Cc1cc(-c2c(-c3cccc(C#N)c3)nn3ccc(C(=O)NC4CN(C)C4)nc23)cc(Cl)n1] 3-(2-Chloro-6-methyl-4-pyridyl)-2-(3-cyanophenyl)-N-(1-methylazetidin-3-yl)pyrazolo[1,5-a]pyrimidine-5-carboxamide | LC-MS (Method 7A): Rt 1.79 mins; MS m/z 458.3/460.3 = [M + H]+ $^1$H NMR (400 MHz, DMSO-d6) δ 9.42 (d, J = 7.2 Hz, 1H), 9.09 (d, J = 7.3 Hz, 1H), 8.08 (t, J = 1.4 Hz, 1H), 8.01 (dt, J = 7.7, 1.3 Hz, 1H), 7.90 (dt, J = 7.9, 1.2 Hz, 1H), 7.73 (t, J = 7.9 Hz, 1H), 7.66 (d, J = 7.2 Hz, 1H), 7.59 - 7.56 (m, 1H), 7.39 - 7.36 (m, 1H), 4.46 (h, J = 7.0 Hz, 1H), 3.63 (t, J = 7.3 Hz, 2H), 3.11 (t, J = 7.2 Hz, 2H), 2.47 (s, 3H), 2.29 (s, 3H). |
| 6.17 | 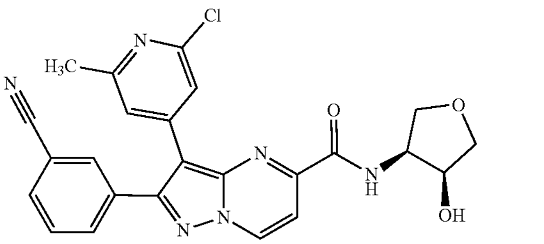 [SMILES: Cc1cc(-c2c(-c3cccc(C#N)c3)nn3ccc(C(=O)N[C@H]4COC[C@H]4O)nc23)cc(Cl)n1] 3-(2-Chloro-6-methyl-4-pyridyl)-2-(3-cyanophenyl)-N-[(3S,4S)-4-hydroxytetrahydrofuran-3-yl]pyrazolo[1,5-a]pyrimidine-5-carboxamide | LC-MS (Method 7A): Rt 2.82 mins; MS m/z 475.2/477.2 = [M + H]+ $^1$H NMR (500 MHz, Methanol-d4) δ 9.22 (d, J = 7.2 Hz, 1H), 8.07 (t, J = 1.4 Hz, 1H), 7.92 (dt, J = 7.9, 1.4 Hz, 1H), 7.88 (dt, J = 7.8, 1.3 Hz, 1H), 7.83 (d, J = 7.2 Hz, 1H), 7.68 (t, J = 7.8 Hz, 1H), 7.58 (s, 1H), 7.33 (s, 1H), 4.49 - 4.44 (m, 2H), 4.17 - 4.11 (m, 1H), 4.09-4.04 (m, 1H), 3.82 (dd, J = 9.9, 2.0 Hz, 1H), 3.71-3.65 (m, 1H), 2.52 (s, 3H). Exchangeable protons not observed |

TABLE EX6-continued

| Ex. | Structure and Name | Retention Time, [M + H]+, 1H NMR |
|---|---|---|
| 6.18 | 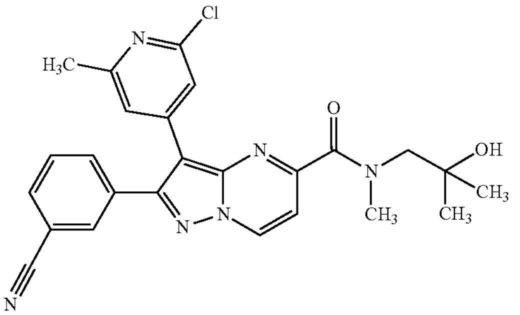 [SMILES: Cc1cc(-c2c(-c3cccc(C#N)c3)nn3ccc(C(=O)N(C)CC(C)(C)O)nc23)cc(Cl)n1]<br>3-(2-Chloro-6-methyl-4-pyridyl)-2-(3-cyanophenyl)-N-(2-hydroxy-2-methyl-propyl)-N-methyl-pyrazolo[1,5-a]pyrimidine-5-carboxamide | LC-MS (Method 8B): Rt 4.28 mins; MS m/z 475.2/477.2 = [M + H]+ $^1$H NMR (500 MHz, DMSO-d6) δ 9.40 (d, J = 7.2 Hz, 0.5H), 9.33 (d, J = 7.2 Hz, 0.5H), 8.08 (s, 0.5H), 8.05 (s, 0.5H) 8.03 - 7.96 (m, 1H), 7.90 (d, J = 8.0 Hz, 0.5H), 7.87 (d, J = 8.0 Hz, 0.5H), 7.75 - 7.68 (m, 1H), 7.41 - 7.25 (m, 3H), 4.62 (s, 0.5H), 4.46 (s, 0.5H), 3.61 (s, 1H), 3.51 (s, 1H), 3.18 (s, 1.5H), 3.15 (s, 1.5H), 2.41 (m, 3H), 1.19 (s, 3H), 1.01 (s, 3H). |
| 6.19 | 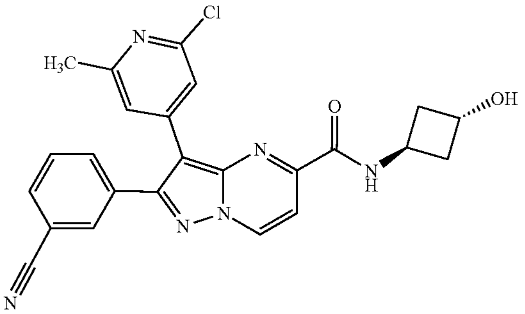 [SMILES: Cc1cc(-c2c(-c3cccc(C#N)c3)nn3ccc(C(=O)N[C@H]4C[C@H](O)C4)nc23)cc(Cl)n1]<br>3-(2-Chloro-6-methyl-4-pyridyl)-2-(3-cyanophenyl)-N-(trans-3-hydroxycyclobutyl)pyrazolo[1,5-a]pyrimidine-5-carboxamide | LC-MS (Method 8B): Rt 4.10 mins; MS m/z 459.2/461.2 = [M + H]+ $^1$H NMR (500 MHz, DMSO-d6) δ 9.41 (d, J = 7.2 Hz, 1H), 8.90 (d, J = 7.2 Hz, 1H), 8.09 (s, 1H), 8.01 (d, J = 7.9 Hz, 1H), 7.91 (d, J = 7.9 Hz, 1H), 7.73 (t, J = 7.9 Hz, 1H), 7.66 (d, J = 7.2 Hz, 1H), 7.57 (s, 1H), 7.40 (s, 1H), 5.08 (d, J = 5.2 Hz, 1H), 4.54 - 4.46 (m, 1H), 4.39 - 4.32 (m, 1H), 2.46 (s, 3H), 2.41 - 2.35 (m, 2H), 2.24 - 2.18 (m, 2H). |
| 6.20 | 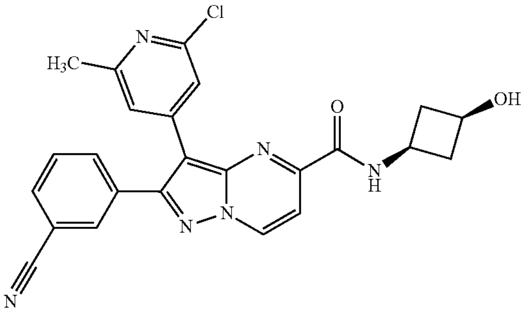 [SMILES: Cc1cc(-c2c(-c3cccc(C#N)c3)nn3ccc(C(=O)N[C@H]4C[C@@H](O)C4)nc23)cc(Cl)n1]<br>3-(2-Chloro-6-methyl-4-pyridyl)-2-(3-cyanophenyl)-N-(cis-3-hydroxycyclobutyl)pyrazolo[1,5-a]pyrimidine-5-carboxamide | LC-MS (Method 15B): Rt 7.05 mins; MS m/z 459.1/461.0 = [M + H]+ 1H NMR (500 MHz, DMSO-d6) δ 9.42 (d, J = 7.2 Hz, 1H), 8.86 (d, J = 7.8 Hz, 1H), 8.09 (s, 1H), 8.01 (d, J = 7.8 Hz, 1H), 7.91 (d, J = 7.8 Hz, 1H), 7.73 (t, J = 7.8 Hz, 1H), 7.66 (d, J = 7.2 Hz, 1H), 7.56 (s, 1H), 7.40 (s, 1H), 5.15 (d, J = 5.6 Hz, 1H), 3.98 - 3.87 (m, 2H), 2.65 - 2.58 (m, 2H), 2.48 (s, 3H), 2.06 - 1.98 (m, 2H). |

TABLE EX6-continued

| Ex. | Structure and Name | Retention Time, [M + H]+, 1H NMR |
|---|---|---|
| 6.21 | 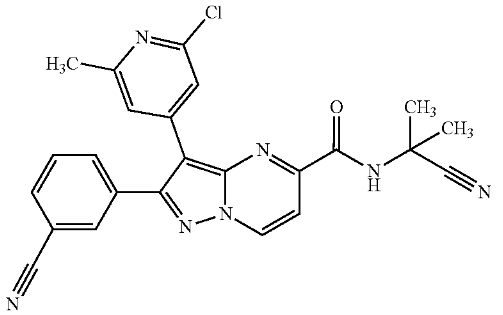 [SMILES: Cc1cc(-c2c(-c3cccc(C#N)c3)nn3ccc(C(=O)NC(C)(C)C#N)nc23)cc(Cl)n1]<br>3-(2-Chloro-6-methyl-4-pyridyl)-N-(1-cyano-1-methyl-ethyl)-2-(3-cyanophenyl)pyrazolo[1,5-a]pyrimidine-5-carboxamide | LC-MS (Method 8B): Rt 4.72 mins; MS m/z 456.2 / 458.2 = [M + H]+<br>1H NMR (500 MHz, DMSO-d6) δ 9.48 (d, J = 7.2 Hz, 1H), 8.93 (s, 1H), 8.11 (s, 1H), 8.02 (d, J = 7.7 Hz, 1H), 7.93 (dt, J = 8.0, 1.5 Hz, 1H), 7.78 - 7.70 (m, 2H), 7.63 (s, 1H), 7.39 (s, 1H), 2.46 (s, 3H), 1.78 (s, 6H). |
| 6.22 | 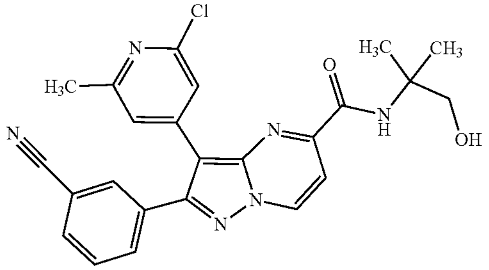 [SMILES: Cc1cc(-c2c(-c3cccc(C#N)c3)nn3ccc(C(=O)NC(C)(C)CO)nc23)cc(Cl)n1]<br>3-(2-Chloro-6-methyl-4-pyridyl)-2-(3-cyanophenyl)-N-(2-hydroxy-1,1-dimethyl-ethyl)pyrazolo[1,5-a]pyrimidine-5-carboxamide | LC-MS (Method 7B): Rt 3.36 mins; MS m/z 461.3/463.3 = [M + H]+<br>1H NMR (500 MHz, DMSO-d6) δ 9.45 (d, J = 7.2 Hz, 1H), 8.24 (s, 1H), 8.10 (t, J = 1.5 Hz, 1H), 8.02 (dt, J = 7.8, 1.4 Hz, 1H), 7.93 (dt, J = 7.9, 1.2 Hz, 1H), 7.77 - 7.71 (m, 2H), 7.57 - 7.54 (m, 1H), 7.28 - 7.25 (m, 1H), 5.19 (t, J = 5.3 Hz, 1H), 3.49 (d, J = 4.8 Hz, 2H), 2.48 (s, 3H), 1.39 (s, 6H). |
| 6.23 | 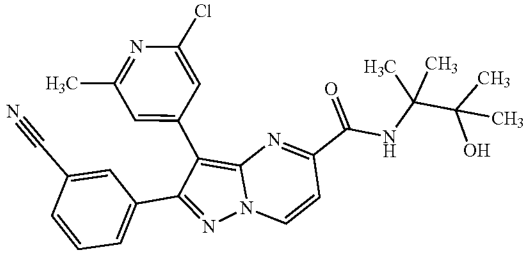 [SMILES: Cc1cc(-c2c(-c3cccc(C#N)c3)nn3ccc(C(=O)NC(C)(C)C(C)(C)O)nc23)cc(Cl)n1]<br>3-(2-Chloro-6-methyl-4-pyridyl)-2-(3-cyanophenyl)-N-(2-hydroxy-1,1,2-trimethyl-propyl)pyrazolo[1,5-a]pyrimidine-5-carboxamide | LC-MS (Method 7A): Rt 3.77 mins; MS m/z 489.4/491.3 = [M + H]+<br>1H NMR (500 MHz, DMSO-d6) δ 9.45 (d, J = 7.2 Hz, 1H), 8.64 (s, 1H), 8.10 (t, J = 1.5 Hz, 1H), 8.03 (dt, J = 7.8, 1.4 Hz, 1H), 7.93 (dt, J = 7.9, 1.3 Hz, 1H), 7.77 - 7.72 (m, 2H), 7.57 (s, 1H), 7.19 (s, 1H), 4.96 (s, 1H), 2.50 (s, 3H), 1.44 (s, 6H), 1.24 (s, 6H).—CH3 under DMSO peak, as shown in HSQC. |

Example 7—N-(3-Amino-3-methyl-butyl)-3-(2-chloro-6-methyl-4-pyridyl)-2-(3-cyanophenyl)pyrazolo[1,5-a]pyrimidine-5-carboxamide

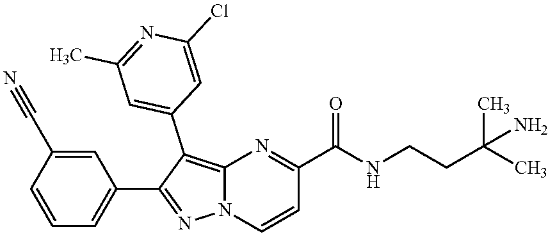 [SMILES: Cc1cc(-c2c(-c3cccc(C#N)c3)nn3ccc(C(=O)NCCC(C)(C)N)nc23)cc(Cl)n1]

Step 1: tert-Butyl N-[3-[[3-(2-Chloro-6-methyl-4-pyridyl)-2-(3-cyanophenyl)pyrazolo[1,5-a]pyrimidine-5-carbonyl]amino]-1,1-dimethyl-propyl]carbamate

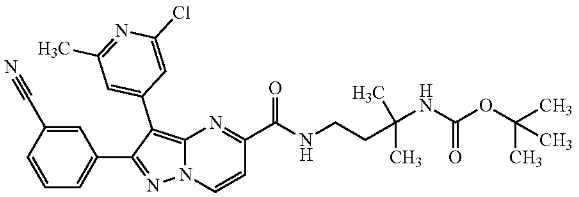 [SMILES: Cc1cc(-c2c(-c3cccc(C#N)c3)nn3ccc(C(=O)NCCC(C)(C)NC(=O)OC(C)(C)C)nc23)cc(Cl)n1]

A solution of 3-(2-chloro-6-methyl-4-pyridyl)-2-(3-cyanophenyl)pyrazolo[1,5-a]pyrimidine-5-carboxylic acid (intermediate A) (50 mg, 0.13 mmol), T3P® (50 wt % in EtOAc) (91 μL, 0.26 mmol), DIPEA (112 μL, 0.64 mmol) and tert-butyl N-(3-amino-1,1-dimethyl-propyl)carbamate (38.92 mg, 0.19 mmol) in DMF (1 mL) was stirred at 60° C. for 4 h. The mixture was diluted with water (5 ml) and the resulting precipitate was collected under vacuum filtration. The solid was dissolved in DCM (20 ml), filtered through a phase separating cartridge and concentrated in vacuo to afford the title compound as a yellow solid.

LC-MS (Method 2A): Rt 1.37 mins; MS m/z 574.3/576.3=[M+H]+

$^1$H NMR (400 MHz, DMSO-d6) δ 9.41 (d, J=7.2 Hz, 1), 8.70 (t, J=5.8 Hz, 1H), 8.06 (t, J=1.4 Hz, 1H), 8.00 (dt, J=7.7, 1.3 Hz, 1H), 7.88 (dt, J=7.9, 1.3 Hz, 1H), 7.73 (t, J=7.8 Hz, 1H), 7.69 (d, J=7.2 Hz, 1H), 7.51 (s, 1H), 7.32 (s, 1H), 6.43 (s, 1H), 2.47 (s, 3H), 1.91 (t, J=7.5 Hz, 2H), 1.35 (s, 9H), 1.24 (s, 6H). 1× $CH_2$ signal underwater peak as shown in HSQC.

Step 2: N-(3-Amino-3-methyl-butyl)-3-(2-chloro-6-methyl-4-pyridyl)-2-(3-cyanophenyl)pyrazolo[1,5-a]pyrimidine-5-carboxamide A solution of tert-butyl N-[3-[[3-(2-chloro-6-methyl-4-pyridyl)-2-(3-cyanophenyl)pyrazolo[1,5-a]pyrimidine-5-carbonyl]amino]-1,1-dimethyl-propyl]carbamate (step 1) (62 mg, 0.10 mmol) in DCM (2 mL) and 4M HCl in 1,4-dioxane (251 μL, 1 mmol) was stirred at room temperature for 18 h. The resulting mixture was concentrated in vacuo then purified using a 1 g Isolute® SCX cartridge eluting with 7M $NH_3$ in MeOH. The filtrate was concentrated in vacuo and freeze dried to afford the title compound as a yellow powder.

LC-MS (Method 7A): Rt 2.09 mins; MS m/z 474.2/476.2=[M+H]+

$^1$H NMR (500 MHz, DMSO-d6) δ 9.57-9.51 (m, 1H), 9.41 (d, J=7.2 Hz, 1H), 8.06 (t, J=1.4 Hz, 1H), 8.00 (dt, J=7.8, 1.3 Hz, 1H), 7.87 (dt, J=7.9, 1.3 Hz, 1H), 7.75.-7.68 (m, 2H), 7.38 (d, J=12.1 Hz, 2H), 3.45 (q, J=6.4 Hz, 2H), 2.44 (s, 3H), 1.61 (t, J=6.8 Hz, 2H), 1.12 (s, 6H). NH2 protons not observed.

The compounds of the following tabulated Examples (Table Ex 7) were prepared analogously to Example 7 from 3-(2-chloro-6-methyl-4-pyridyl)-2-(3-cyanophenyl)pyrazolo[1,5-a)pyrimidine-5-carboxylic acid (Intermediate A), T3P®, DIPEA and the appropriate amine. (step 1) followed by deprotection using 4M HCl in 1,4-dioxane (step 2).

TABLE EX7

| Ex. | Structure and Name | Retention Time, [M + H]+, 1H NMR |
|---|---|---|
| 7.1 | 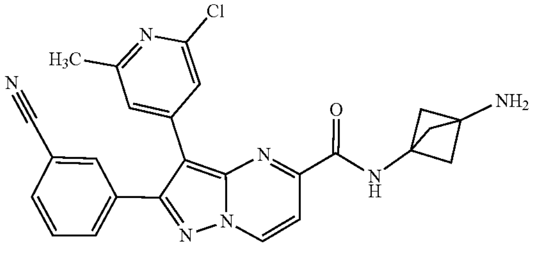 [SMILES: Cc1cc(-c2c(-c3cccc(C#N)c3)nn3ccc(C(=O)NC45CC(N)(C4)C5)nc23)cc(Cl)n1]<br>N-(3-Amino-1-bicyclo[1.1.1]pentanyl)-3-(2-chloro-6-methyl-4-pyridyl)-2-(3-cyanophenyl)pyrazolo[1,5-a]pyrimidine-5-carboxamide | LC-MS (Method 7A): Rt 2.01 mins; MS m/z 470.2/472.1 = [M + H]+ $^1$H NMR (400 MHz, DMSO-d6) δ 9.40 (d, J = 7.2 Hz, 1H), 9.19 (s, 1H), 8.05 (t, J = 1.4 Hz, 1H), 7.99 (dt, J = 7.7, 1.4 Hz, 1H), 7.87 (dt, J = 7.9, 1.2 Hz, 1H), 7.71 (t, J = 7.6 Hz, 1H), 7.65 (d, J = 7.2 Hz, 1H), 7.51 (s, 1H), 7.34 (s, 1H), 2.46 (s, 3H), 2.10 (s, 6H). NH2 protons observed. |

TABLE EX7-continued

| Ex. | Structure and Name | Retention Time, [M + H]+, 1H NMR |
|---|---|---|
| | Prepared via: | Intermediate Data: |
| | 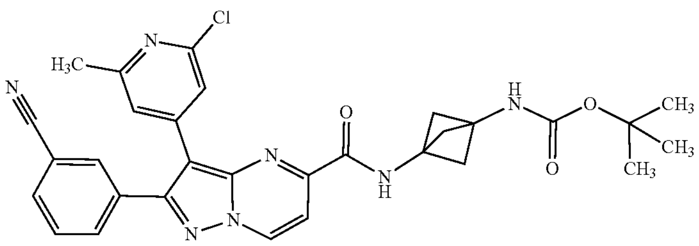 [SMILES: Cc1cc(-c2c(-c3cccc(C#N)c3)nn3ccc(C(=O)NC45CC(NC(=O)OC(C)(C)C)(C4)C5)nc23)cc(Cl)n1]<br>tert-Butyl N-[3-[[3-(2-chloro-6-methyl-4-pyridyl)-2-(3-cyanophenyl)pyrazolo[1,5-a]pyrimidine-5-carbonyl]amino]-1-bicyclo[1.1.1]pentanyl]carbamate | LC-MS (Method 2A): Rt 1.34 mins; MS m/z 570.3/572.2 = [M + H]+ $^{1}$H NMR (500 MHz, DMSO-d6) δ 9.41 (d, J = 7.2 Hz, 1H), 9.32 (s, 1H), 8.06 (t, J = 1.4 Hz, 1H), 8.00 (dt, J = 7.8, 1.4 Hz, 1H), 7.87 (dt, J = 7.9, 1.2 Hz, 1H), 7.71 (t, J = 7.9 Hz, 1H), 7.66 (d, J = 7.2 Hz, 1H), 7.59 (s, 1H), 7.53 (s, 1H), 7.33 (s, 1H), 2.46 (s, 3H), 2.27 (s, 6H), 1.39 (s, 9H). |
| 7.2 | 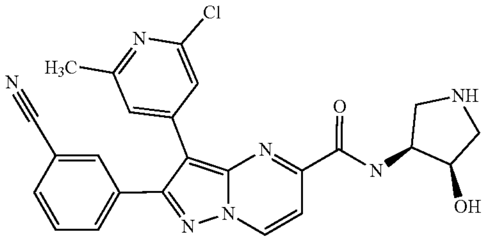<br>3-(2-Chloro-6-methyl-4-pyridyl)-2-(3-cyanophenyl)-N-[cis-(3S,4R)-4-hydroxypyrrolidin-3-yl]pyrazolo[1,5-a]pyrimidine-5-carboxamide | LC-MS (Method 7A): Rt 1.88 mins; MS m/z 474.2/476.4 = [M + H]+ $^{1}$H NMR (400 MHz, DMSO-d6) δ 9.46 (d, J = 7.2 Hz, 1H), 8.59 (d, J = 7.1 Hz, 1H), 8.27 (s, 1H), 8.09 (t, J = 1.4 Hz, 1H), 8.02 (dt, J = 7.8, 1.3 Hz, 1H), 7.92 (dt, J = 7.9, 1.2 Hz, 1H), 7.76 (d, J = 7.2 Hz, 1H), 7.73 (t, J = 7.9 Hz, 1H), 7.58 (s, 1H), 7.23 (s, 1H), 4.28 - 4.17 (m, 3H), 3.31 - 3.20 (m, 2H), 2.87 (d, J = 12.2 Hz, 1H), 2.80 - 2.74 (m, 1H), 2.47 (s, 3H). |
| | Prepared via: | Intermediate Data: |
| | 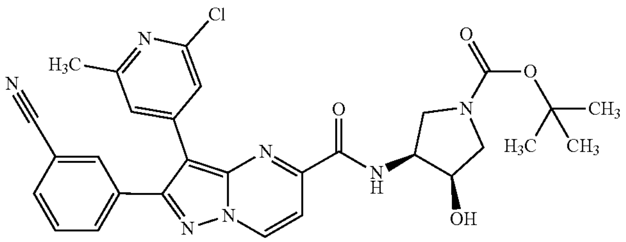 [SMILES: Cc1cc(-c2c(-c3cccc(C#N)c3)nn3ccc(C(=O)N[C@H]4CN(C(=O)OC(C)(C)C)C[C@H]4O)nc23)cc(Cl)n1]<br>tert-Butyl (3S,4R)-3-[[3-(2-chloro-6-methyl-a]pyrimidine-5-carbonyl]amino]-4-hydroxy-pyrrolidine-1-carboxylate | LC-MS (Method 2A): Rt 1.27 mins; MS m/z 518.2/520.2 = [M - tBu + 2H]+, 574.2/576.2 = [M + H]+. $^{1}$H NMR (400 MHz, DMSO-d6) δ 9.46 (d, J = 7.2 Hz, 1H), 8.50 (d, J = 7.6 Hz, 1H), 8.10 (t, J = 1.4 Hz, 1H), 8.02 (dt, J = 7.7, 1.4 Hz, 1H), 7.93 (dt, J = 7.9, 1.2 Hz, 1H), 7.77 - 7.71 (m, 2H), 7.56 (s, 1H), 7.27 (s, 1H), 4.43 - 4.36 (m, 1H), 4.31 - 4.25 (m, 1H), 3.72-3.64 (m, 2H), 3.53 - 3.45 (m, 2H), 3.22-3.16 (m, 1H), 2.46 (s, 3H), 1.40 (s, 9H). |
| 7.3 | 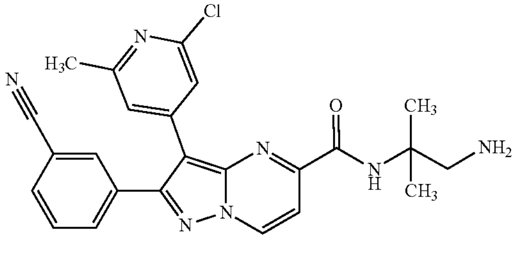 [SMILES: Cc1cc(-c2c(-c3cccc(C#N)c3)nn3ccc(C(=O)NC(C)(C)CN)nc23)cc(Cl)n1]<br>N-(2-Amino-1,1-dimethyl-ethyl)-3-(2-chloro-6-methyl-4-pyridyl)-2-(3-cyanophenyl)pyrazolo[1,5-a]pyrimidine-5-carboxamide | LC-MS (Method 7A): Rt 2.15 mins; MS m/z 460.2/462.2 = [M + H]+ $^{1}$H NMR (500 MHz, DMSO-d6) δ 9.44 (d, J = 7.2 Hz, 1H), 8.66 (s, 1H), 8.10 (t, J = 1.5 Hz, 1H), 8.02 (dt, J = 7.7, 1.3 Hz, 1H), 7.93 (dt, J = 7.9, 1.3 Hz, 1H), 7.77 - 7.71 (m, 2H), 7.50 (s, 1H), 7.36 (s, 1H), 2.83 (s, 2H), 2.44 (s, 3H), 1.40 (s, 6H). NH2 protons not observed. |

TABLE EX7-continued

| Ex. | Structure and Name | Retention Time, [M + H]+, 1H NMR |
|---|---|---|
| | Prepared via: | Intermediate Data: |
| | 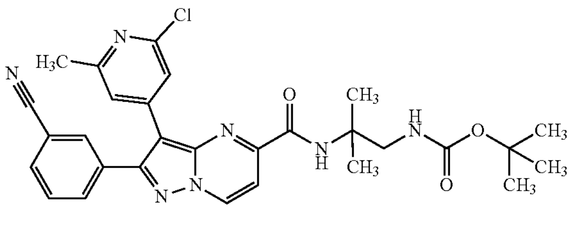 [SMILES: Cc1cc(-c2c(-c3cccc(C#N)c3)nn3ccc(C(=O)NC(C)(C)CNC(=O)OC(C)(C)C)nc23)cc(Cl)n1] tert-Butyl N-[2-[[3-(2-chloro-6-methyl-4-pyridyl)-2-(3-cyanophenyl)pyrazolo[1,5-a]pyrimidine-5-carbonyl]amino]-2-methyl-propyl]carbamate | LC-MS (Method 7A): Rt 4.08 mins; MS m/z 560.2/562.2 = [M + H]+ $^1$H NMR (500 MHz, DMSO-d6) δ 9.42 (d, J = 7.2 Hz, 1H), 8.44 (s, 1H), 8.10 (t, J = 1.7 Hz, 1H), 8.01 (dt, J = 7.8, 1.3 Hz, 1H), 7.91 (dt, J = 7.9, 1.4 Hz, 1H), 7.73 (t, J = 7.8 Hz, 1H), 7.70 (d, J = 7.2 Hz, 1H), 7.61 (s, 1H), 7.33 (s, 1H), 7.20 (t, J = 6.3 Hz, 1H), 3.24 (d, J = 6.3 Hz, 2H), 2.46 (s, 3H), 1.38 (s, 6H), 1.21 (s, 9H). |
| 7.4 | 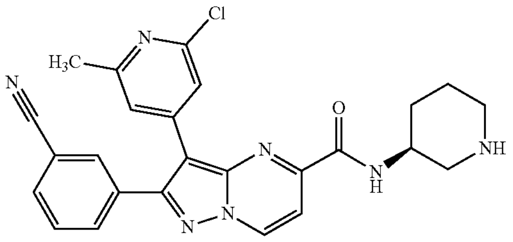 [SMILES: Cc1cc(-c2c(-c3cccc(C#N)c3)nn3ccc(C(=O)N[C@H]4CCCNC4)nc23)cc(Cl)n1] 3-(2-Chloro-6-methyl-4-pyridyl)-2-(3-cyanophenyl)-N-[(3S)-3-piperidyl]pyrazolo[1,5-a]pyrimidine-5-carboxamide | LC-MS (Method 7A): Rt 2.07 mins; MS m/z 472.2/474.6 = [M + H]+ $^1$H NMR (500 MHz, DMSO-d6) δ 9.44 (d, J = 7.1 Hz, 1H), 8.64 (d, J = 8.4 Hz, 1H), 8.10 (t, J = 1.5 Hz, 1H), 8.02 (dt, J = 7.7, 1.4 Hz, 1H), 7.92 (dt, J = 7.9, 1.2 Hz, 1H), 7.74 (t, J = 8.0 Hz, 1H), 7.71 (d, J = 7.2 Hz, 1H), 7.54 (s, 1H), 7.36 (s, 1H), 3.99 - 3.93 (m, 1H), 2.96 - 2.92 (m, 1H), 2.77 - 2.65 (m, 3H), 2.45 (s, 3H), 1.82 - 1.76 (m, 1H), 1.71 - 1.64 (m, 2H), 1.53 - 1.46 (m, 1H). NH proton not observed. |
| | Prepared via: | Intermediate Data: |
| | 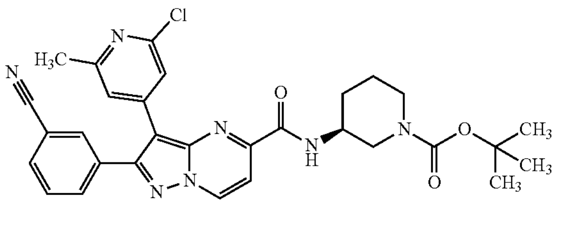 [SMILES: Cc1cc(-c2c(-c3cccc(C#N)c3)nn3ccc(C(=O)N[C@H]4CCCN(C(=O)OC(C)(C)C)C4)nc23)cc(Cl)n1] tert-Butyl (3S)-3-[[3-(2-chloro-6-methyl-4-pyridyl)-2-(3-cyanophenyl)pyrazolo[1,5-a]pyrimidine-5-carbonyl]amino]piperidine-1-carboxylate | LC-MS (Method 2A): Rt 1.40 mins; MS m/z 516.3/518.2 = [M-tBu+2H]+, 572.3/574.3 = [M + H]+ $^1$H NMR (400 MHz, DMSO-d6) δ 9.44 (d, J = 7.2 Hz, 1H), 8.47 (d, J = 8.0 Hz, 1H), 8.09 (t, J = 1.5 Hz, 1H), 8.01 (dt, J = 7.8, 1.4 Hz, 1H), 7.91 (dt, J = 7.9, 1.2 Hz, 1H), 7.73 (t, J = 8.1 Hz, 1H), 7.72 (d, J = 7.1 Hz, 1H), 7.53 (s, 1H), 7.34 (s, 1H), 3.89 (ddq, J = 11.5, 7.7, 4.1 Hz, 1H), 3.68 - 3.62 (m, 1H), 3.51 - 3.40 (m, 2H), 2.47 (s, 3H), 1.94 - 1.88 (m, 1H), 1.79 - 1.70 (m, 2H), 1.59 - 1.46 (m, 2H), 1.25 (d, J = 10.5 Hz, 9H). |
| 7.5 | 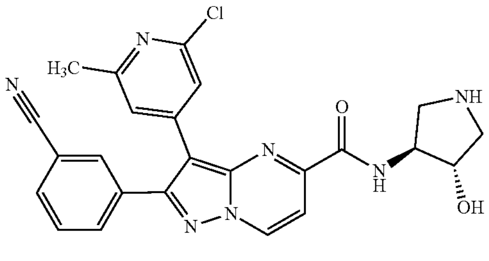 [SMILES: Cc1cc(-c2c(-c3cccc(C#N)c3)nn3ccc(C(=O)N[C@H]4CNC[C@@H]4O)nc23)cc(Cl)n1] 3-(2-Chloro-6-methyl-4-pyridyl)-2-(3-cyanophenyl)-N-[trans-(3S,4S)-4-hydroxypyrrolidin-3-yl]pyrazolo[1,5-a]pyrimidine-5-carboxamide | LC-MS (Method 7A): Rt 1.86 mins; MS m/z 474.2/476.1 = [M + H]+ $^1$H NMR (500 MHz, DMSO-d6) δ 9.43 (d, J = 7.2 Hz, 1H), 8.59 (d, J = 7.8 Hz, 1H), 8.09 (t, J = 1.4 Hz, 1H), 8.01 (dt, J = 7.8, 1.3 Hz, 1H), 7.91 (dt, J = 7.9, 1.3 Hz, 1H), 7.73 (t, J = 7.8 Hz, 1H), 7.68 (d, J = 7.2 Hz, 1H), 7.55 (s, 1H), 7.38 (s, 1H), 5.09 (d, J = 4.0 Hz, 1H), 4.15 - 4.07 (m, 2H), 3.18 (dd, J = 11.5, 6.3 Hz, 1H), 3.07 (dd, J = 11.7, 5.4 Hz, 1H), 2.71 (dd, J = 11.4, 3.9 Hz, 1H), 2.66 - 2.61 (m, 1H), 2.45 (s, 3H). NH proton not observed. |

TABLE EX7-continued

| Ex. | Structure and Name | Retention Time, [M + H]+, 1H NMR |
|---|---|---|
| | Prepared via: 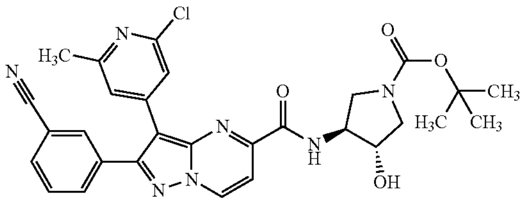 [SMILES: Cc1cc(-c2c(-c3cccc(C#N)c3)nn3ccc(C(=O)N[C@H]4CN(C(=O)OC(C)(C)C)C[C@@H]4O)nc23)cc(Cl)n1] tert-Butyl trans-(3S,4S)-3-[[3-(2-chloro-6-methyl-4-pyridyl)-2-(3-cyanophenyl) pyrazolo[1,5-a]pyrimidine-5-carbonyl]amino]-4-hydroxy-pyrrolidine-1-carboxylate | Intermediate Data: LC-MS (Method 2A): Rt 0.89 mins; MS m/z 574.2/576.2 = [M + H]+ 1H NMR (500 MHz, DMSO-d6) δ 9.43 (d, J = 7.2 Hz, 1H), 8.76 (d, J = 6.3 Hz, 1H), 8.10 (t, J = 1.4 Hz, 1H), 8.02 (dt, J = 7.8, 1.4 Hz, 1H), 7.92 (d, J = 8.1 Hz, 1H), 7.74 (t, J = 7.8 Hz, 1H), 7.67 (d, J = 7.2 Hz, 1H), 7.58 (d, J = 5.1 Hz, 1H), 7.39 (d, J = 8.1 Hz, 1H), 4.28 - 4.20 (m, 2H), 3.70 - 3.52 (m, 4H), 3.24 - 3.16 (m, 1H), 2.45 (s, 3H), 1.40 (s, 9H). |
| 7.6 | 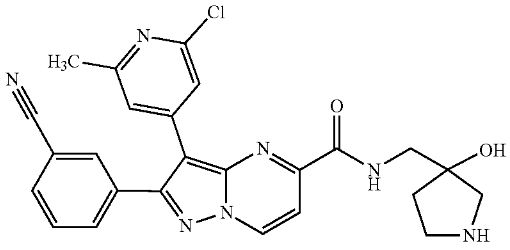 [SMILES: Cc1cc(-c2c(-c3cccc(C#N)c3)nn3ccc(C(=O)NCC4(O)CCNC4)nc23)cc(Cl)n1] 3-(2-Chloro-6-methyl-4-pyridyl)-2-(3-cyanophenyl)-N-[(3-hydroxypyrrolidin-3-yl)methyl]pyrazolo[1,5-a]pyrimidine-5-carboxamide | LC-MS (Method 7A): Rt 1.92 mins; MS m/z 488.2/490.2 = [M + H]+ $^1$H NMR (500 MHz, DMSO-d6) δ 9.45 (d, J = 7.2 Hz, 1H), 8.70 (t, J = 6.0 Hz, 1H), 8.35 (s, 1H), 8.09 (t, J = 1.5 Hz, 1H), 8.02 (dt, J = 7.8, 1.3 Hz, 1H), 7.91 (dt, J = 7.9, 1.3 Hz, 1H), 7.76-7.71 (m, 2H), 7.55 (s, 1H), 7.33 (s, 1H), 3.56 (ddt, J = 19.5, 13.3, 6.1 Hz, 2H), 3.17 - 3.01 (m, 2H), 2.97 (d, J = 11.8 Hz, 1H), 2.89 (d, J = 11.8 Hz, 1H), 2.46 (s, 3H), 1.93 - 1.86 (m, 1H), 1.80 (ddd, J = 12.6, 7.5, 4.0 Hz, 1H). OH proton not observed. |
| | Prepared via: 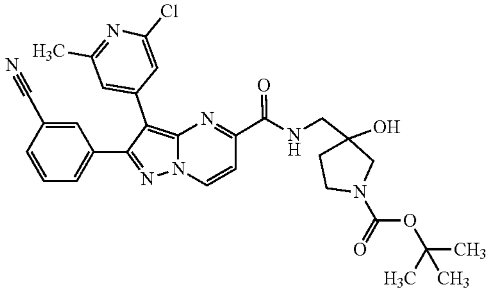 [SMILES: Cc1cc(-c2c(-c3cccc(C#N)c3)nn3ccc(C(=O)NCC4(O)CCN(C(=O)OC(C)(C)C)C4)nc23)cc(Cl)n1] tert-Butyl3-[[[3-(2-chloro-6-methyl-4-pyridyl)-2-(3-cyanophenyl)pyrazolo[1,5-a]pyrimidine-5-carbonyl]amino]methyl]-3-hydroxy-pyrrolidine-1-carboxylate | Intermediate Data: LC-MS (Method 2A): Rt 1.25 mins; MS m/z 532.22/534.2 = [M - tBu + 2H]+, 588.2/590.2 = [M + H]+ $^1$H NMR (500 MHz, DMSO-d6) δ 9.44 (d, J = 7.2 Hz, 1H), 8.66 (t, J = 5.9 Hz, 1H), 8.09 (t, J = 1.4 Hz, 1H), 8.01 (dt, J = 7.8, 1.3 Hz, 1H), 7.91 (dt, J = 8.0, 1.3 Hz, 1H), 7.76 - 7.70 (m, 2H), 7.55 (d, J = 10.2 Hz, 1H), 7.33 (d, J = 14.3 Hz, 1H), 5.22 (s, 1H), 3.56 - 3.49 (m, 2H), 3.23 (t, J = 12.9 Hz, 2H), 2.46 (s, 3H), 1.97 - 1.86 (m, 1H), 1.84 - 1.76 (m, 1H), 1.37 (s, 9H). 1 × CH2 signal under water peak as shown in HSQC. |
| 7.7 | 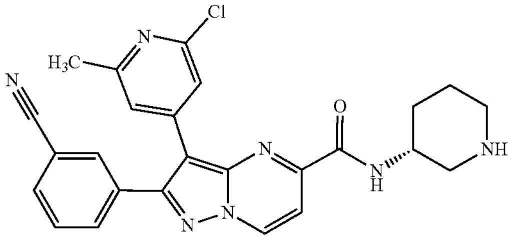 [SMILES: Cc1cc(-c2c(-c3cccc(C#N)c3)nn3ccc(C(=O)N[C@@H]4CCCNC4)nc23)cc(Cl)n1] 3-(2-Chloro-6-methyl-4-pyridyl)-2-(3-cyanophenyl)-N-[(3R)-3-piperidyl]pyrazolo[1,5-a]pyrimidine-5-carboxamide | LC-MS (Method 7A): Rt 2.07 mins; MS m/z 472.2/474.1 = [M + H]+ $^1$H NMR (500 MHz, DMSO-d6) δ 9.44 (d, J = 7.2 Hz, 1H), 8.62 (d, J = 8.5 Hz, 1H), 8.10 (t, J = 1.5 Hz, 1H), 8.02 (dt, J = 7.8, 1.4 Hz, 1H), 7.92 (dt, J = 7.9, 1.4 Hz, 1H), 7.74 (t, J = 8.0 Hz, 1H), 7.71 (d, J = 7.2 Hz, 1H), 7.54 (s, 1H), 7.36 (s, 1H), 3.99 - 3.90 (m, 1H), 2.91 (dd, J = 11.7, 3.0 Hz, 1H), 2.71 - 2.64 (m, 3H), 2.45 (s, 3H), 1.81 - 1.74 (m, 1H), 1.66 (dt, J = 11.4, 6.9 Hz, 2H), 1.51 - 1.43 (m, 1H). NH proton not observed. |

TABLE EX7-continued

| Ex. | Structure and Name | Retention Time, [M + H]+, 1H NMR |
|---|---|---|
| | Prepared via:<br>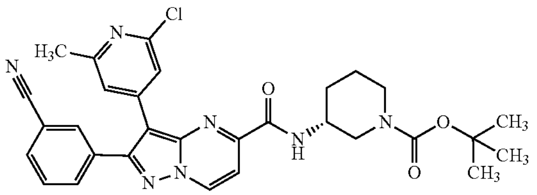 [SMILES: Cc1cc(-c2c(-c3cccc(C#N)c3)nn3ccc(C(=O)N[C@@H]4CCCN(C(=O)OC(C)(C)C)C4)nc23)cc(Cl)n1]<br>tert-Butyl (3R)-3-[[3-(2-chloro-6-methyl-4-pyridyl)-2-(3-cyanophenyl)pyrazolo[1,5-a]pyrimidine-5-carbonyl]amino]piperidine-1-carboxylate | Intermediate Data:<br>LC-MS (Method 2A): Rt 1.37 mins; MS m/z 572.1/574.1 = [M + H]+ $^{1}$H NMR (500 MHz, DMSO-d6) δ 9.45 (d, J = 7.1 Hz, 1H), 8.47 (d, J = 7.6 Hz, 1H), 8.09 (t, J = 1.5 Hz, 1H), 8.01 (dt, J = 7.8, 1.4 Hz, 1H), 7.91 (dt, J = 7.9, 1.3 Hz, 1H), 7.73 (t, J = 7.9 Hz, 1H), 7.72 (d, J = 7.2 Hz, 1H), 7.53 (s, 1H), 7.34 (s, 1H), 3.93 - 3.85 (m, 1H), 3.68 - 3.62 (m, 1H), 3.51 - 3.43 (m, 1H), 3.24 - 3.18 (m, 1H), 2.47 (s, 3H), 1.95 - 1.86 (m, 1H), 1.78 - 1.69 (m, 2H), 1.63 - 1.60 (m, 1H), 1.54 - 1.47 (m, 1H), 1.26 (s, 9H). |
| 7.8 | 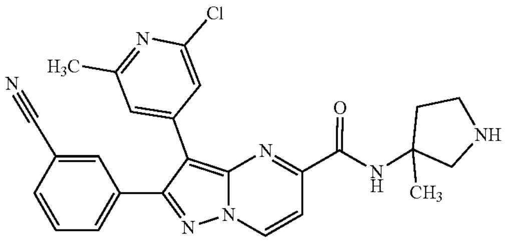 [SMILES: Cc1cc(-c2c(-c3cccc(C#N)c3)nn3ccc(C(=O)NC4(C)CCNC4)nc23)cc(Cl)n1]<br>3-(2-Chloro-6-methyl-4-pyridyl)-2-(3-cyanophenyl)-N-(3-methylpyrrolidin-3-yl)pyrazolo[1,5-a]pyrimidine-5-carboxamide | LC-MS (Method 7A): Rt 1.91 mins; MS m/z 472.3/474.2 = [M + H]+ $^{1}$H NMR (500 MHz, DMSO-d6) δ 9.44 (d, J = 7.2 Hz, 1H), 8.51 (s, 1H), 8.10 (t, J = 1.5 Hz, 1H), 8.02 (dt, J = 7.8, 1.3 Hz, 1H), 7.93 (dt, J = 7.9, 1.2 Hz, 1H), 7.74 (t, J = 8.0 Hz, 1H), 7.69 (d, J = 7.2 Hz, 1H), 7.58 (s, 1H), 7.42 (s, 1H), 3.52 (d, J = 11.7 Hz, 1H), 3.22 - 3.13 (m, 2H), 3.00 (d, J = 11.7 Hz, 1H), 2.45 (s, 3H), 2.40 (dd, J = 13.1, 5.6 Hz, 1H), 1.93 (dt, J = 13.2, 8.2 Hz, 1H), 1.55 (s, 3H). NH proton not observed |
| | Prepared via:<br>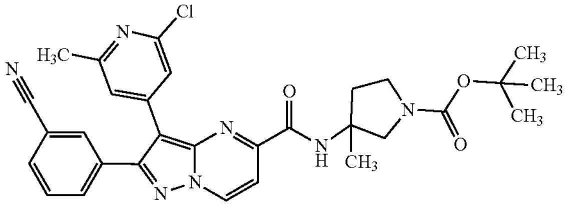 [SMILES: Cc1cc(-c2c(-c3cccc(C#N)c3)nn3ccc(C(=O)NC4(C)CCN(C(=O)OC(C)(C)C)C4)nc23)cc(Cl)n1]<br>Tert-butyl3-[[3-(2-chloro-6-methyl-4-pyridyl)-2-(3-cyanophenyl)pyrazolo[1,5-a]pyrimidine-5-carbonyl]amino]-3-methyl-pyrrolidine-1-carboxylate | Intermediate Data:<br>LC-MS (Method 2A): Rt 1.37 mins; MS m/z 572.2 = [M + H]+ $^{1}$H NMR (400 MHz, DMSO-d6) δ 9.44 (d, J = 7.2 Hz, 1H), 8.45 (s, 1H), 8.11 (t, J = 1.5 Hz, 1H), 8.02 (dt, J = 7.8, 1.3 Hz, 1H), 7.93 (dt, J = 7.9, 1.3 Hz, 1H), 7.74 (t, J = 7.9 Hz, 1H), 7.69 (d, J = 7.2 Hz, 1H), 7.56 (d, J = 4.8 Hz, 1H), 7.41 (d, J = 11.7 Hz, 1H), 3.81 (dd, J = 17.4, 10.9 Hz, 1H), 3.45 - 3.34 (m, 3H), 2.45 (s, 3H), 2.03 - 1.92 (m, 1H), 1.66 - 1.58 (m, 1H), 1.52 (s, 3H), 1.37 (s, 5H), 1.34 (s, 4H). |
| 7.9 | 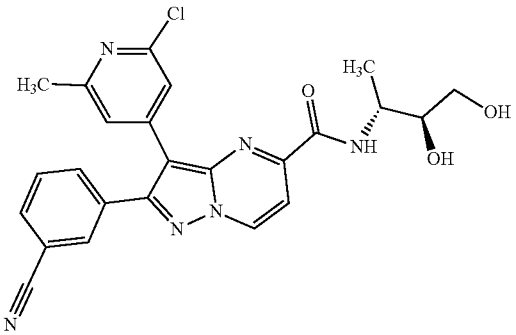 [SMILES: Cc1cc(-c2c(-c3cccc(C#N)c3)nn3ccc(C(=O)N[C@H](C)[C@H](O)CO)nc23)cc(Cl)n1]<br>3-(2-Chloro-6-methyl-4-pyridyl)-2-(3-cyanophenyl)-N-[(1 R,2S)-2,3-dihydroxy-1-methyl-propyl]pyrazolo[1,5-a]pyrimidine-5-carboxamide (Reaction carried out analogously to Example 4.8) | LC-MS (Method 8B): Rt 4.03 mins; MS m/z 477.2 / 479.1 = [M + H]+ $^{1}$H NMR (500 MHz, DMSO-d6) δ 9.45 (d, J = 7.2 Hz, 1H), 8.39 (d, J = 8.5 Hz, 1H), 8.09 (s, 1H), 8.02 (d, J = 7.6 Hz, 1H), 7.92 (d, J = 7.9 Hz, 1H), 7.77 - 7.69 (m, 2H), 7.57 (s, 1H), 7.21 (s, 1H), 5.24 (d, J = 4.6 Hz, 1H), 4.72 - 4.67 (m, 1H), 4.18 - 4.12 (m, 1H), 3.60 - 3.54 (m, 1H), 3.43 - 3.36 (m, 2H), 2.47 (s, 3H), 1.22 (d, J = 6.8 Hz, 3H). |

TABLE EX7-continued

| Ex. | Structure and Name | Retention Time, [M + H]+, 1H NMR |
|---|---|---|
| | Prepared via:<br>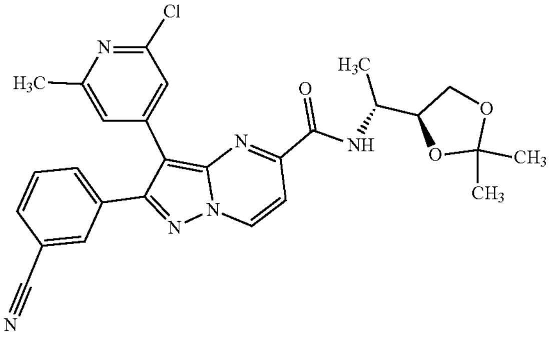 [SMILES: Cc1cc(-c2c(-c3cccc(C#N)c3)nn3ccc(C(=O)N[C@H](C)[C@H]4COC(C)(C)O4)nc23)cc(Cl)n1]<br>3-(2-Chloro-6-methyl-4-pyridyl)-2-(3-cyanophenyl)-N-[(1R)-1-[(4S)-2,2-dimethyl-1,3-dioxolan-4-yl]ethyl]pyrazolo[1,5-a]pyrimidine-5-carboxamide | Intermediate Data:<br>LC-MS (Method 5B): Rt 3.04 mins; MS m/z 517.2 = [M + H]+ $^{1}$H NMR (500 MHz, DMSO-d6) δ 9.45 (d, J = 7.2 Hz, 1H), 8.25 (d, J = 8.8 Hz, 1H), 8.07 (s, 1H), 7.99 (d, J = 7.8 Hz, 1H), 7.88 (d, J = 7.8 Hz, 1H), 7.75 - 7.68 (m, 2H), 7.44 (s, 1H), 7.36 (s, 1H), 4.25-4.21 (m, 1H), 4.16 - 4.11 (m, 1H), 4.03 - 3.98 (m, 1H), 3.64 - 3.58 (m, 1H), 2.45 (s, 3H), 1.34 - 1.13 (m, 9H). |
| 7.10 | 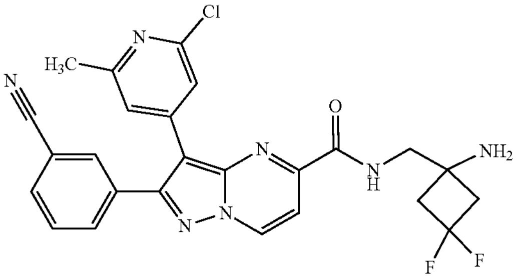 [SMILES: Cc1cc(-c2c(-c3cccc(C#N)c3)nn3ccc(C(=O)NCC4(N)CC(F)(F)C4)nc23)cc(Cl)n1]<br>N-[(1-Amino-3,3-difluoro-cyclobutyl)methyl]-3-(2-chloro-6-methyl-4-pyridyl)-2-(3-cyanophenyl)pyrazolo[1,5-a]pyrimidine-5-carboxamide | LC-MS (Method 7A): Rt 1.98 mins; MS m/z 508.2/510.2 = [M + H]+ $^{1}$H NMR (400 MHz, Methanol-d4) δ 9.21 (d, J = 7.2 Hz, 1H), 8.06 (t, J = 1.4 Hz, 1H), 7.93 - 7.85 (m, 2H), 7.80 (d, J = 7.2 Hz, 1H), 7.67 (t, J = 7.8 Hz, 1H), 7.47 (s, 2H), 3.64 (s, 2H), 2.86 - 2.73 (m, 2H), 2.59 - 2.45 (m, 2H), 2.49 (s, 3H). NH protons not observed. |
| | Prepared via:<br>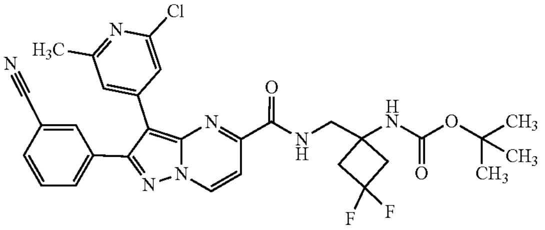 [SMILES: Cc1cc(-c2c(-c3cccc(C#N)c3)nn3ccc(C(=O)NCC4(NC(=O)OC(C)(C)C)CC(F)(F)C4)nc23)cc(Cl)n1]<br>tert-Butyl N-[1-[[[3-(2-chloro-6-methyl-4-pyridyl)-2-(3-cyanophenyl)pyrazolo[1,5-a]pyrimidine-5-carbonyl]amino]methyl]-3,3-difluoro-cyclobutyl]carbamate | Intermediate Data:<br>LC-MS (Method 2A): Rt 1.36 mins; MS m/z 608.2/610.2 = [M + H]+ $^{1}$H NMR (400 MHz, DMSO-d6) δ 9.43 (d, J = 7.2 Hz, 1H), 8.94 (t, J = 6.3 Hz, 1H), 8.08 (t, J = 1.4 Hz, 1H), 8.01 (dt, J = 7.7, 1.3 Hz, 1H), 7.91 (dt, J = 8.0, 1.3 Hz, 1H), 7.77 - 7.70 (m, 2H), 7.58 (s, 1H), 7.46 (s, 1H), 7.32 (s, 1H), 3.68 (d, J = 6.3 Hz, 2H), 2.97 - 2.76 (m,4H), 2.47 (s, 3H), 1.35 (s, 9H). |
| 7.11 | 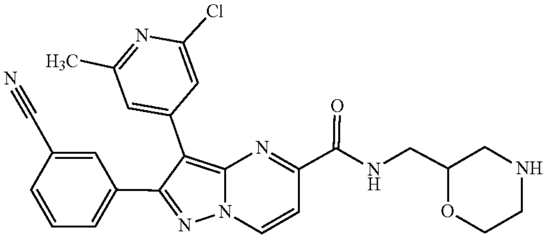 [SMILES: Cc1cc(-c2c(-c3cccc(C#N)c3)nn3ccc(C(=O)NCC4CNCCO4)nc23)cc(Cl)n1]<br>3-(2-Chloro-6-methyl-4-pyridyl)-2-(3-cyanophenyl)-N-(morpholin-2-ylmethyl)pyrazolo[1,5-a]pyrimidine-5-carboxamide | LC-MS (Method 7A): Rt 1.85 mins; MS m/z 488.2/490.2 = [M + H]+ $^{1}$H NMR (500 MHz, Methanol-d4) δ 9.21 (d, J = 7.2 Hz, 1H), 8.04 (t, J = 1.5 Hz, 1H), 7.92 - 7.84 (m, 2H), 7.79 (d, J = 7.2 Hz, 1H), 7.66 (t, J = 7.8 Hz, 1H), 7.46 (s, 1H), 7.41 (s, 1H), 3.99 (dt, J = 12.1, 1.9 Hz, 1H), 3.78 (dtt, J = 10.8, 4.4, 2.3 Hz, 1H), 3.70 (ddd, J = 12.0, 9.6, 4.7 Hz, 1H), 3.62 (dd, J = 13.9, 4.4 Hz, 1H), 3.47 (dd, J = 13.9, 7.0 Hz, 1H), 3.07 (dd, J = 12.6, 2.2 Hz, 1H), 2.95 - 2.90 (m, 2H), 2.72 (dd, J = 12.6, 10.7 Hz, 1H), 2.49 (s, 3H). Exchangeable protons not observed |

TABLE EX7-continued

| Ex. | Structure and Name | Retention Time, [M + H]+, 1H NMR |
|---|---|---|
| | Prepared via: 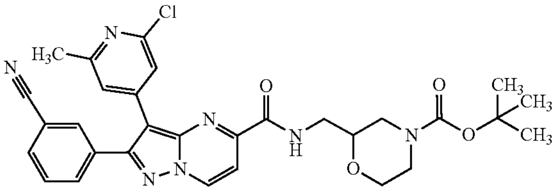 [SMILES: Cc1cc(-c2c(-c3cccc(C#N)c3)nn3ccc(C(=O)NCC4CN(C(=O)OC(C)(C)C)CCO4)nc23)cc(Cl)n1] tert-Butyl 2-[[[3-(2-chloro-6-methyl-4-pyridyl)-2-(3-cyanophenyl)pyrazolo[1,5-a]pyrimidine-5-carbonyl]amino]methyl]morpholine-4-carboxylate | Intermediate Data: LC-MS (Method 2A): Rt 1.33 mins; MS m/z 588.1/590.1 = [M + H]+ $^{1}$H NMR (400 MHz, DMSO-d6) δ 9.43 (d, J = 7.2 Hz, 1H), 8.74 (t, J = 6.0 Hz, 1H), 8.07 (t, J = 1.4 Hz, 1H), 8.00 (dt, J = 7.8, 1.3 Hz, 1H), 7.89 (dt, J = 7.9, 1.3 Hz, 1H), 7.72 (t, J = 8.0 Hz, 1H), 7.71 (d, J = 7.2 Hz, 1H), 7.50 (s, 1H), 7.34 (s, 1H), 3.91 - 3.81 (m, 2H), 3.71 (d, J = 13.3 Hz, 1H), 3.60 - 3.53 (m, 1H), 3.52 - 3.38 (m, 3H), 2.95 - 2.82 (m, 1H), 2.77 - 2.64 (m, 1H), 2.46 (s, 3H), 1.38 (s, 9H). |
| 7.12 | 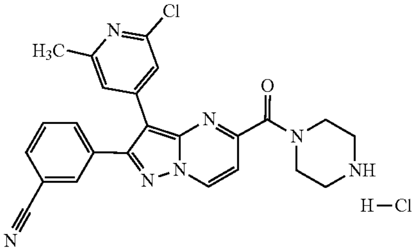 3-[3-(2-Chloro-6-methyl-4-pyridyl)-5-(piperazine-1-carbonyl)pyrazolo[1,5-a]pyrimidin-2-yl]benzonitrile hydrochloride | LC-MS (Method 8B): Rt 3.87 mins; MS m/z 458.3 / 460.3 = [M + H]+ $^{1}$H NMR (500 MHz, DMSO-d6) δ 9.44 (d, J = 7.2 Hz, 1H), 9.14 (s, 2H), 8.07 (s, 1H), 8.01 (d, J = 7.8 Hz, 1H), 7.88 (d, J = 7.8 Hz, 1H), 7.73 (t, J = 7.8 Hz, 1H), 7.47 (d, J = 7.2 Hz, 1H), 7.35 (s, 1H), 7.33 (s, 1H), 3.99 - 3.87 (m, 4H), 3.29 - 3.19 (m, 4H), 2.44 (s, 3H). |
| | Prepared via: 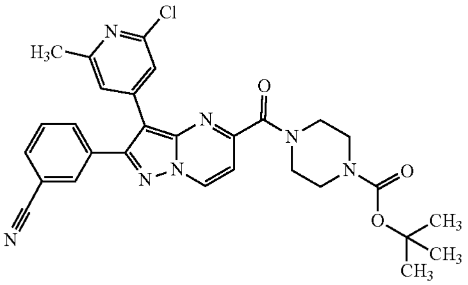 [SMILES: Cc1cc(-c2c(-c3cccc(C#N)c3)nn3ccc(C(=O)N4CCN(C(=O)OC(C)(C)C)CC4)nc23)cc(Cl)n1] tert-Butyl4-[3-(2-chloro-6-methyl-4-pyridyl)-2-(3-cyanophenyl)pyrazolo[1,5-a]pyrimidine-5-carbonyl]piperazine-1-carboxylate | Intermediate Data: LC-MS (Method 5B): Rt 3.41 mins; MS m/z 558.2 = [M + H]+ $^{1}$H NMR (500 MHz, Chloroform-d) δ 8.83 (d, J = 7.2 Hz, 1H), 8.03 (d, J = 9.2 Hz, 1H), 7.85 - 7.72 (m, 2H), 7.56 (t, J = 7.9 Hz, 1H), 7.450 - 7.44 (m, 1H), 7.40-7.33 (m, 1H), 7.13 (s, 1H), 3.90 - 3.78 (m, 4H), 3.66-5.55 (m, 4H), 2.52 (s, 3H), 1.49 (s, 9H). |
| 7.13 | 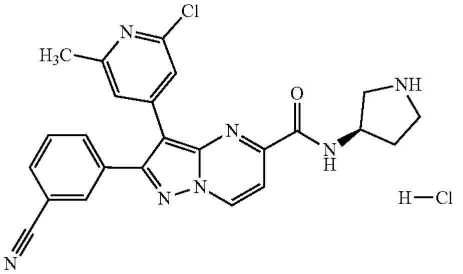 [SMILES: Cc1cc(-c2c(-c3cccc(C#N)c3)nn3ccc(C(=O)N[C@@H]4CCNC4)nc23)cc(Cl)n1 ; Cl] 3-(2-Chloro-6-methyl-4-pyridyl)-2-(3-cyanophenyl)-N-[(3R)-pyrrolidin-3-yl]pyrazolo[1,5-a]pyrimidine-5-carboxamide hydrochloride | LC-MS (Method 8B): Rt 3.66 mins; MS m/z 458.3 / 460.3 = [M + H]+ $^{1}$H NMR (500 MHz, DMSO-d6) δ 9.45 (d, J = 7.2 Hz, 1H), 9.17 - 8.98 (m, 3H), 8.08 (s, 1H), 8.01 (d, J = 7.9 Hz, 1H), 7.90 (d, J = 7.9 Hz, 1H), 7.76 - 7.68 (m, 2H), 7.61 (s, 1H), 7.35 (s, 1H), 4.66 - 4.58 (m, 1H), 3.31 - 3.21 (m, 2H), 2.48 (s, 3H), 2.33 - 2.20 (m, 2H), 2.15-2.01 (m, 2H). |

TABLE EX7-continued

| Ex. | Structure and Name | Retention Time, [M + H]+, 1H NMR |
|---|---|---|
| | Prepared via: 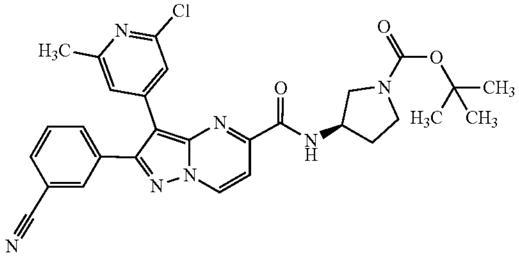 [SMILES: Cc1cc(-c2c(-c3cccc(C#N)c3)nn3ccc(C(=O)N[C@@H]4CCN(C(=O)OC(C)(C)C)C4)nc23)cc(Cl)n1] tert-Butyl (3R)-3-[[3-(2-chloro-6-methyl-4-pyridyl)-2-(3-cyanophenyl)pyrazolo[1,5-a]pyrimidine-5-carbonyl]amino]pyrrolidine-1-carboxylate | Intermediate Data: LC-MS (Method 5B): Rt 3.51 mins; MS m/z 558.2 = [M + H]+ $^{1}$H NMR (500 MHz, Chloroform-d) δ 8.88 (d, J = 7.1 Hz, 1H), 8.05 (s, 1H), 7.87 (d, J = 7.1 Hz, 1H), 7.82 (d, J = 8.0 Hz, 1H), 7.79 - 7.71 (m, 2H), 7.57 (t, J = 7.9 Hz, 1H), 7.43 (s, 1H), 7.14 (s, 1H), 4.71 - 4.61 (m, 1H), 3.80 - 3.73 (m, 1H), 3.55 (t, J = 7.0 Hz, 2H), 3.42-3.31 (m, 1H), 2.54 (s,3H), 2.35 - 2.25 (m, 1H), 2.03 - 1.97 (m, 1H), 1.47 (s, 9H). |
| 7.14 | 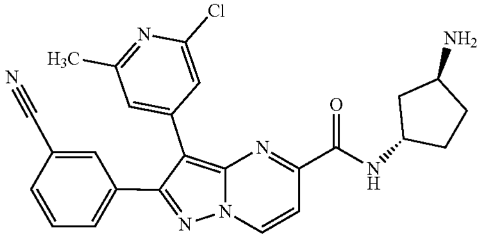 [SMILES: Cc1cc(-c2c(-c3cccc(C#N)c3)nn3ccc(C(=O)N[C@H]4CC[C@H](N)C4)nc23)cc(Cl)n1] 3-(2-Chloro-6-methyl-4-pyridyl)-2-(3-cyanophenyl)-N-[(1S,3S)-3-aminocyclopentyl]pyrazolo[1,5-a]pyrimidine-5-carboxamide | LC-MS (Method 7B): Rt 3.07 mins; MS m/z 472.3/474.2 = [M + H]+ 1H NMR (400 MHz, DMSO-d6) δ 9.41 (d, J = 7.2 Hz, 1H), 8.53 (d, J = 7.9 Hz, 1H), 8.09 (t, J = 1.4 Hz, 1H), 8.01 (dt, J = 7.7, 1.3 Hz, 1H), 7.91 (dt, J = 7.9, 1.2 Hz, 1H), 7.73 (t, J = 7.8 Hz, 1H), 7.67 (d, J = 7.2 Hz, 1H), 7.55 - 7.52 (m, 1H), 7.42 - 7.39 (m, 1H), 4.45 (dq, J = 14.4, 7.4 Hz, 1H), 3.47 (dt, J = 11.9, 6.1 Hz, 1H), 2.45 (s, 3H), 2.13 (dtd, J = 13.2, 8.0, 5.4 Hz, 1H), 2.01-1.91 (m, 1H), 1.82 (dt, J = 13.4, 6.8 Hz, 1H), 1.71 (ddd, J = 12.9, 7.8, 4.9 Hz, 1H), 1.58 (ddd, J = 15.1, 12.9, 8.0 Hz, 1H), 1.32 (dtd, J = 13.3, 8.1, 5.8 Hz, 1H).—NH2 protons not observed |
| | Prepared via: 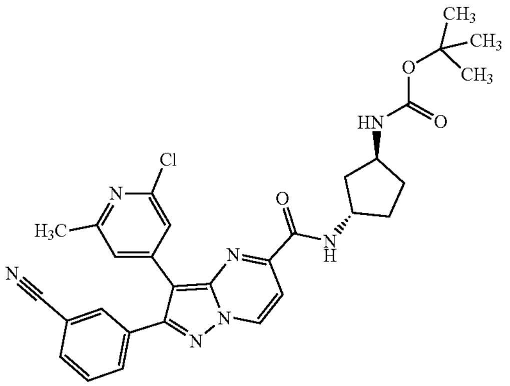 [SMILES: Cc1cc(-c2c(-c3cccc(C#N)c3)nn3ccc(C(=O)N[C@H]4CC[C@H](NC(=O)OC(C)(C)C)C4)nc23)cc(Cl)n1] tert-Butyl N-[(1S,3S)-3-[[3-(2-chloro-6-methyl-4-pyridyl)-2-(3-cyanophenyl)pyrazolo[1,5-a]pyrimidine-5-carbonyl]amino]cyclopentyl]carbamate | Intermediate Data: LC-MS (Method 2A): Rt 1.32 mins; MS m/z 572.2/574.3 = [M + H]+ 1H NMR (400 MHz, DMSO-d6) δ 9.41 (d, J = 7.2 Hz, 1H), 8.62 (d, J = 7.7 Hz, 1H), 8.09 (t, J = 1.4 Hz, 1H), 8.01 (dt, J = 7.7, 1.4 Hz, 1H), 7.91 (dt, J = 7.9, 1.2 Hz, 1H), 7.73 (t, J = 7.9 Hz, 1H), 7.67 (d, J = 7.2 Hz, 1H), 7.57 (s, 1H), 7.38 (s, 1H), 6.95 (d, J = 7.0 Hz, 1H), 4.38 (dq, J = 14.9, 7.3 Hz, 1H), 4.04 - 3.95 (m, 1H), 2.46 (s, 3H), 2.12 - 1.96 (m, 2H), 1.94 - 1.78 (m, 2H), 1.65 - 1.56 (m, 1H), 1.49 - 1.41 (m, 1H), 1.38 (s, 9H). |

TABLE EX7-continued

| Ex. | Structure and Name | Retention Time, [M + H]+, 1H NMR |
|---|---|---|
| 7.15 | 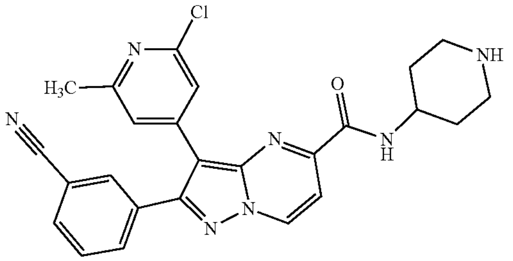 [SMILES: Cc1cc(-c2c(-c3cccc(C#N)c3)nn3ccc(C(=O)NC4CCNCC4)nc23)cc(Cl)n1] 3-(2-Chloro-6-methyl-4-pyridyl)-2-(3-cyanophenyl)-N-(4-piperidyl)pyrazolo[1,5-a]pyrimidine-5-carboxamide | LC-MS (Method 7B): Rt 3.04 mins; MS m/z 472.3/474.2 = [M + H]+ 1H NMR (400 MHz, DMSO-d6) δ 9.42 (d, J = 7.2 Hz, 1H), 8.51 (d, J = 8.0 Hz, 1H), 8.09 (t, J = 1.4 Hz, 1H), 8.03 - 7.99 (m, 1H), 7.93 - 7.90 (m, 1H), 7.73 (t, J = 7.8 Hz, 1H), 7.68 (d, J = 7.2 Hz, 1H), 7.54 (s, 1H), 7.40 (s, 1H), 3.94-3.85 (m, 1H), 3.01 (dt, J = 12.1, 3.4 Hz, 2H), 2.66 - 2.58 (m, 2H), 2.45 (s, 3H), 1.82 (dd, J = 12.5, 3.2 Hz, 2H), 1.55 (qd, J = 11.7, 3.8 Hz, 2H). NH proton not observed |
| | Prepared via: | Intermediate Data: |
| | 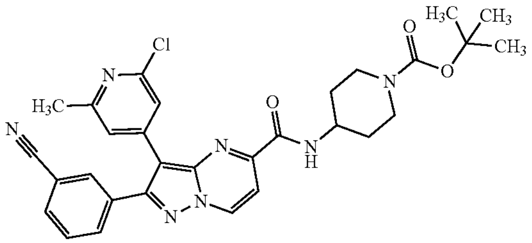 [SMILES: Cc1cc(-c2c(-c3cccc(C#N)c3)nn3ccc(C(=O)NC4CCN(C(=O)OC(C)(C)C)CC4)nc23)cc(Cl)n1] tert-Butyl 4-[[3-(2-chloro-6-methyl-4-pyridyl)-2-(3-cyanophenyl)pyrazolo[1,5-a]pyrimidine-5-carbonyl]amino]piperidine-1-carboxylate | LC-MS (Method 2A): Rt 1.37 mins; MS m/z 572.2/574.2 = [M + H]+ 1H NMR (400 MHz, DMSO-d6) δ 9.42 (d, J = 7.2 Hz, 1H), 8.60 (d, J = 8.2 Hz, 1H), 8.09 (s, 1H), 8.01 (d, J = 7.7 Hz, 1H), 7.91 (d, J = 7.9 Hz, 1H), 7.73 (t, J = 7.8 Hz, 1H), 7.68 (d, J = 7.2 Hz, 1H), 7.53 (s, 1H), 7.40 (s, 1H), 4.06-3.96 (m, 1H), 3.90 (d, J = 12.8 Hz, 2H), 3.02 - 2.88 (m, 2H), 2.44 (s, 3H), 1.87 - 1.79 (m, 2H), 1.61 - 1.50 (m, 2H), 1.41 (s, 9H). |
| 7.16 and 7.17: 7.16 | 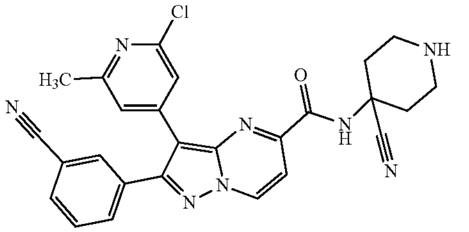 [SMILES: Cc1cc(-c2c(-c3cccc(C#N)c3)nn3ccc(C(=O)NC4(C#N)CCNCC4)nc23)cc(Cl)n1] 3-(2-Chloro-6-methyl-4-pyridyl)-2-(3-cyanophenyl)-N-(4-cyano-4-piperidyl)pyrazolo[1,5-a]pyrimidine-5-carboxamide (Second Eluted Peak) | LC-MS (Method 7B): Rt 3.00 mins; MS m/z 497.3/499.2 = [M + H]+ 1H NMR (500 MHz, DMSO-d6) δ 9.48 (d, J = 7.2 Hz, 1H), 8.94 (s, 1H), 8.12 (t, J = 1.5 Hz, 1H), 8.03 (dt, J = 7.8, 1.4 Hz, 1H), 7.94 (dt, J = 7.9, 1.2 Hz, 1H), 7.76 - 7.71 (m, 2H), 7.62 (s, 1H), 7.43 (s, 1H), 2.94 (dt, J = 12.7, 3.9 Hz, 2H), 2.75 (ddd, J = 12.6, 9.2, 2.7 Hz, 2H), 2.45 (s, 3H), 2.33 - 2.23 (m, 2H), 2.04 - 1.95 (m, 2H). NH proton not observed |
| 7.17 | 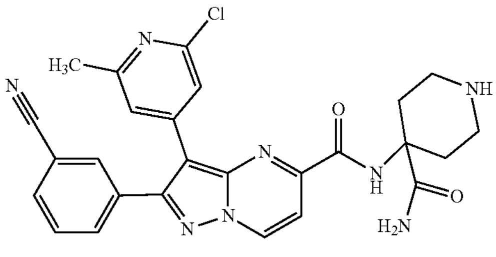 [SMILES: Cc1cc(-c2c(-c3cccc(C#N)c3)nn3ccc(C(=O)NC4(C(N)=O)CCNCC4)nc23)cc(Cl)n1] N-(4-Carbamoyl-4-piperidyl)-3-(2-chloro-6-methyl-4-pyridyl)-2-(3-cyanophenyl)pyrazolo[1,5-a]pyrimidine-5-carboxamide (First eluted peak) | LC-MS (Method 7B): Rt 2.52 mins; MS m/z 515.4/517.3 = [M + H]+ 1H NMR (500 MHz, DMSO-d6) δ 9.48 (d, J = 7.2 Hz, 1H), 8.35 (s, 1H), 8.15 (t, J = 1.5 Hz, 1H), 8.04 (dt, J = 7.8, 1.3 Hz, 1H), 7.98 (dt, J = 7.9, 1.2 Hz, 1H), 7.76 (t, J = 7.9 Hz, 1H), 7.72 (d, J = 7.1 Hz, 1H), 7.52 (d, J = 2.7 Hz, 2H), 7.30 (s, 1H), 6.95 (s, 1H), 2.87 - 2.81 (m, 2H), 2.71 - 2.65 (m, 2H), 2.44 (s, 3H), 2.16 - 2.09 (m, 2H), 1.87 (td, J = 13.1, 4.1 Hz, 2H). - NH proton not observed |

TABLE EX7-continued

| Ex. | Structure and Name | Retention Time, [M + H]+, 1H NMR |
|---|---|---|
| | Prepared via: | Intermediate Data: |
| | 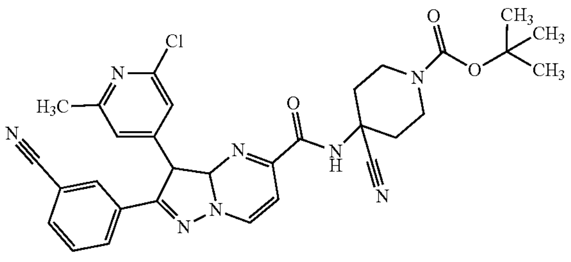 [SMILES: Cc1cc(C2C(c3cccc(C#N)c3)=NN3C=CC(C(=O)NC4(C#N)CCN(C(=O)OC(C)(C)C)CC4)=NC23)cc(Cl)n1] tert-Butyl4-[[3-(2-chloro-6-methyl-4-pyridyl)-2-(3-cyanophenyl)pyrazolo[1,5-a]pyrimidine-5-carbonyl]amino]-4-cyano-piperidine-1-carboxylate | LC-MS (Method 2A): Rt 1.37 mins; MS m/z 597.2/599.3 = [M + H]+ 1H NMR (400 MHz, DMSO-d6) δ 9.48 (d, J = 7.2 Hz, 1H), 9.09 (s, 1H), 8.12 (t, J = 1.5 Hz, 1H), 8.02 (dt, J = 7.8, 1.3 Hz, 1H), 7.94 (dt, J = 7.9, 1.3 Hz, 1H), 7.78 - 7.72 (m, 2H), 7.56 (s, Retention Time, [M + H]+, 1H NMR 1H), 7.46 (s, 1H), 3.66 - 3.60 (m, 2H), 3.38 (d, J = 10.4 Hz, 2H), 2.43 (s, 3H), 2.32 - 2.26 (m, 2H), 2.20 - 2.13 (m, 2H), 1.41 (s, 9H). |
| 7.18 | 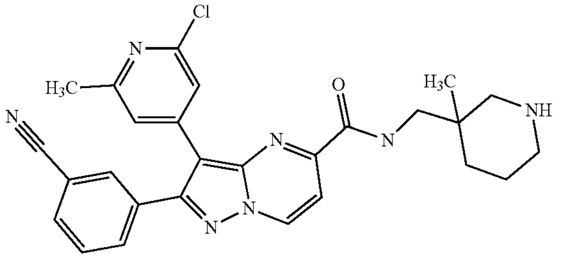 3-(2-Chloro-6-methyl-4-pyridyl)-2-(3-cyanophenyl)-N-[(3-methyl-3-piperidyl)methyl]pyrazolo[1,5-a]pyrimidine-5-carboxamide | LC-MS (Method 7A): Rt 2.15 mins; MS m/z 500.2/502.2 = [M + H]+ 1H NMR (500 MHz, DMSO-d6) δ 9.43 (d, J = 7.1 Hz, 1H), 8.79 (t, J = 6.1 Hz, 1H), 8.10 (t, J = 1.4 Hz, 1H), 8.02 (dt, J = 7.8, 1.3 Hz, 1H), 7.92 (dt, J = 7.9, 1.3 Hz, 1H), 7.74 (t, J = 7.9 Hz, 1H), 7.69 (d, J = 7.1 Hz, 1H), 7.54 (s, 1H), 7.40 (s, 1H), 3.40 (dd, J = 13.3, 6.7 Hz, 1H), 3.31 (dd, J = 13.3, 6.4 Hz, 1H), 2.82 - 2.69 (m, 3H), 2.60 - 2.54 (m, 1H), 2.43 (s, 3H), 1.70 - 1.61 (m, 1H), 1.57 - 1.48 (m, 2H), 1.39 - 1.29 (m, 1H), 0.97 (s, 3H).NH proton not observed |
| | Prepared via: | Intermediate Data: |
| | 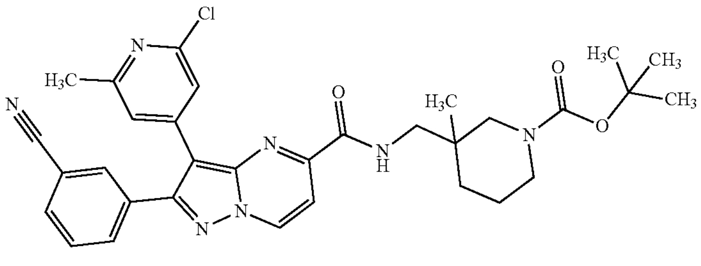 [SMILES: Cc1cc(-c2c(-c3cccc(C#N)c3)nn3ccc(C(=O)NCC4(C)CCCN(C(=O)OC(C)(C)C)C4)nc23)cc(Cl)n1] tert-Butyl3-[[[3-(2-chloro-6-methyl-4-pyridyl)-2-(3-cyanophenyl)pyrazolo[1,5-a]pyrimidine-5-carbonyl]amino]methyl]-3-methyl-piperidine-1-carboxylate | LC-MS (Method 2A): Rt 1.44 mins; MS m/z 600.3/602.3 = [M + H]+ 1H NMR (400 MHz, DMSO-d6) δ 9.44 (d, J = 7.2 Hz, 1H), 8.66 (s, 1H), 8.10 (s, 1H), 8.02 (dt, J = 7.8, 1.3 Hz, 1H), 7.93 (dt, J = 7.9, 1.2 Hz, 1H), 7.74 (t, J = 7.9 Hz, 1H), 7.69 (d, J = 7.2 Hz, 1H), 7.56 (s, 1H), 7.38 (s, 1H), 3.17-3.00 (m, 6H), 2.42 (s, 3H), 1.50 - 1.43 (m, 4H), 1.40 (s, 3H), 1.37 (d, J = 3.1 Hz, 9H). |

Example 7.19-3-(2-Chloro-6-methyl-4-pyridyl)-2-(3-cyanophenyl)-N-[(1S,2S)-2,3-dihydroxy-1-methyl-propyl]pyrazolo[1,5-a]pyrimidine-5-carboxamide

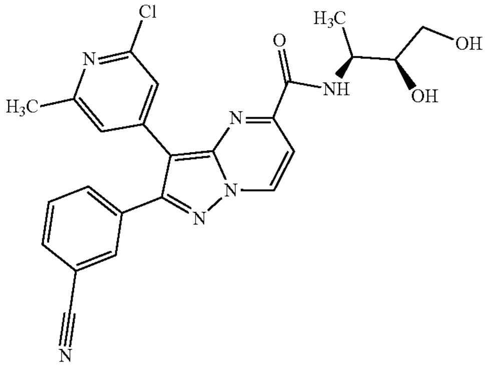 [SMILES: Cc1cc(-c2c(-c3cccc(C#N)c3)nn3ccc(C(=O)N[C@@H](C)[C@H](O)CO)nc23)cc(Cl)n1]

Step 1: 3-(2-Chloro-6-methyl-4-pyridyl)-2-(3-cyanophenyl)-N-[(1S)-1-[(4S)-2,2-dimethyl-1,3-dioxolan-4-yl]ethyl]pyrazolo[1,5-a]pyrimidine-5-carboxamide

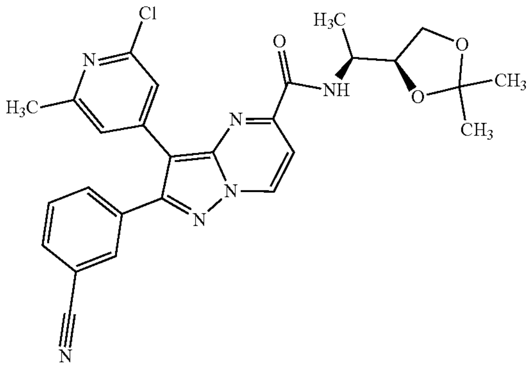

The title compound was prepared from 3-(2-chloro-6-methyl-4-pyridyl)-2-(3-cyanophenyl)pyrazolo[1,5-a]pyrimidine-5-carboxylic acid (Intermediate A) and (1S)-1-[(4S)-2,2-dimethyl-1,3-dioxolan-4-yl]ethanamine analogously to Example 7 step 1.

LC-MS (Method 5B): Rt 3.08 mins; MS m/z 517.2/519.2=[M+H]+

1H NMR (500 MHz, DMSO-d6) δ 9.44 (d, J=7.2 Hz, 1H), 8.50 (d, J=8.8 Hz, 1H), 8.09 (s, 1H), 8.01 (d, J=7.9 Hz, 1H), 7.91 (d, J=7.9 Hz, 1H), 7.73 (t, J=7.9 Hz, 1H), 7.70 (d, J=7.2 Hz, 1H), 7.54 (s, 1H), 7.33 (s, 1H), 4.23-4.17 (m, 1H), 4.14-4.08 (m, 1H), 4.03 (dd, J=8.7, 6.6 Hz, 1H), 3.90 (dd, J=8.7, 5.3 Hz, 1H), 2.46 (s, 3H), 1.33-1.20 (m, 9H)

Step 2: 3-(2-Chloro-6-methyl-4-pyridyl)-2-(3-cyanophenyl)-N-[(1S,2S)-2,3-dihydroxy-1-methyl-propyl]pyrazolo[1,5-a]pyrimidine-5-carboxamide The title compound was prepared from 3-(2-chloro-6-methyl-4-pyridyl)-2-(3-cyanophenyl)-N-[(1S)-1-[(4S)-2,2-dimethyl-1,3-dioxolan-4-yl]ethyl]pyrazolo[1,5-a]pyrimidine-5-carboxamide (step 1) and 2M aqueous HCl analogously to Example 4.8 step 2.

LC-MS (Method 8B): Rt 3.99 mins; MS m/z 477.2=[M+H]+

1H NMR (500 MHz, DMSO-d6) δ 9.44 (d, J=7.2 Hz, 1H), 8.57 (d, J=8.8 Hz, 1H), 8.09 (t, J=1.7 Hz, 1H), 8.01 (dt, J=7.8, 1.4 Hz, 1H), 7.91 (dt, J=8.1, 1.4 Hz, 1H), 7.77-7.71 (m, 2H), 7.58 (s, 1H), 7.25 (s, 1H), 5.02 (d, J=5.2 Hz, 1H), 4.73 (t, J=5.5 Hz, 1H), 4.20-4.10 (m, 1H), 3.65-3.57 (m, 1H), 3.53-3.47 (m, 1H), 3.44-3.39 (m, 1H), 2.47 (s, 3H), 1.15 (d, J=6.7 Hz, 3H).

Example 8-3-[3-(2-Chloro-6-methyl-4-pyridyl)-5-(1-hydroxy-1-methyl-ethyl)pyrazolo [1,5-a]pyrimidin-2-yl]benzonitrile

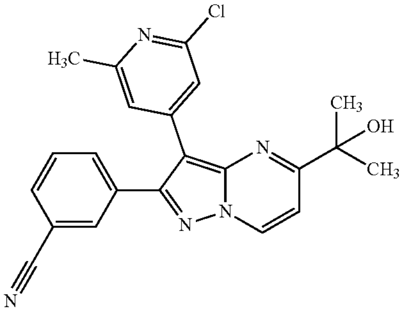 [SMILES: Cc1cc(-c2c(-c3cccc(C#N)c3)nn3ccc(C(C)(C)O)nc23)cc(Cl)n1]

Step 1: 3-[3-Bromo-5-(1-hydroxy-1-methyl-ethy) pyrazolo[1,5-a]pyrimidin-2-yl]benzonitrile

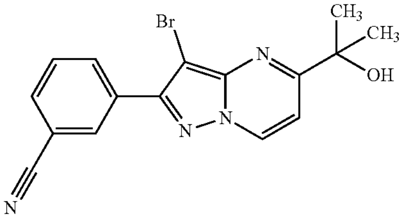 [SMILES: CC(C)(O)c1ccn2nc(-c3cccc(C#N)c3)c(Br)c2n1]

To a mixture of ethyl 3-bromo-2-(3-cyanophenyl)pyrazolo[1,5-a]pyrimidine-5-carboxylate (Intermediate A5) (96 mg, 0.26 mmol) at 0° C. in THF (5 mL) was added MeMgCl (3M in THF) (0.2 mL, 0.60 mmol) dropwise and the reaction mixture was stirred for 1.5 h. The resulting mixture was diluted with DCM (40 mL) and washed with NH4Cl (2×20 mL). The organic phase was dried over $MgSO_4$ and concentrated in vacuo. Purification by chromatography on silica eluting with a gradient of 0 to 2% MeOH in DCM to afforded the title compound as a colourless solid.

LC-MS (Method 5B): Rt 3.80 mins; MS m/z 357.0/359.0=[M+H]+

1H NMR (500 MHz, DMSO-d6) δ 9.16 (d, J=7.2 Hz, 1H), 8.39-8.36 (m, 1H), 8.35-8.30 (m, 1H), 8.01-7.98 (m, 1H), 7.79 (t, J=7.9 Hz, 1H), 7.46 (d, J=7.2 Hz, 1H), 5.61 (s, 1H), 1.52 (s, 6H).

Step 2: 3-[3-(2-Chloro-6-methyl-4-pyridyl)-5-(1-hydroxy-1-methyl-ethyl)pyrazolo[1,5-a]pyrimidin-2-yl]benzonitrile A mixture of 3-[3-bromo-5-(1-hydroxy-1-methyl-ethyl) pyrazolo[1,5-a]pyrimidin-2-yl]benzonitrile (step 1) (65 mg, 0.18 mmol), 2-chloro-6-methyl-4-(4,4,5,5-tetramethyl-1,3,2-dioxaborolan-2-yl)pyridine (62 mg, 0.24 mmol) and $K_2CO_3$ (75 mg, 0.55 mmol) in 1,4-dioxane (3 mL) and water (0.75 mL) was degassed under a flow of $N_2$. $Pd(tBu_3P)_2$ (9 mg, 0.02 mmol) was added and the reaction mixture heated to 80° C. for 15 mins. The resulting mixture was cooled to room temperature, added to water (30 mL) and extracted with DCM (2×30 mL).

The organic extracts were dried over $MgSO_4$ and concentrated in vacuo. Purification by chromatography on silica eluting with a gradient of 0 to 10% MeOH in DCM followed by C18 reverse phase chromatography eluting with a gradient of 40 to 80% MeCN in water (+0.1 wt % $NH_4OH$) and a final re-purification on silica eluting with a gradient of 0 to 10% MeOH in DCM afforded the title compound as a colourless solid.

LC-MS (Method 15B): Rt 7.79 mins; MS m/z 404.1/406.0=[M+H]+

1H NMR (500 MHz, DMSO-d6) δ 9.23 (d, J=7.3 Hz, 1H), 8.05 (s, 1H), 8.00 (d, J=7.7 Hz, 1H), 7.89 (d, J=7.8 Hz, 1H), 7.72 (t, J=7.8 Hz, 1H), 7.52 (d, J=7.3 Hz, 1H), 7.42 (s, 1H), 7.35 (s, 1H), 5.64 (s, 1H), 2.39 (s, 3H), 1.54 (s, 6H).

Example 9 (=Intermediate A)-3-(2-Chloro-6-methyl-4-pyridyl)-2-(3-cyanophenyl) pyrazolo[1,5-a]pyrimidine-5-carboxylic acid

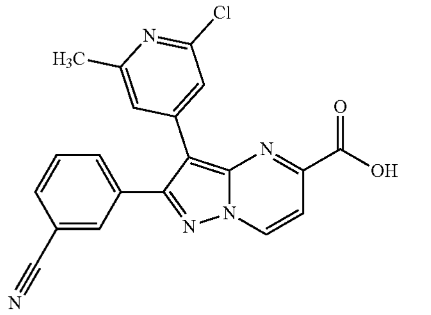

A solution of lithium hydroxide (273 mg, 11.42 mmol) in water (20 mL) was added to a stirred partial suspension of ethyl 3-(2-chloro-6-methyl-4-pyridyl)-2-(3-cyanophenyl) pyrazolo[1,5-a]pyrimidine-5-carboxylate (Intermediate A6) (1.59 g, 3.81 mmol) in 1,4-dioxane (50 mL) and the reaction mixture was stirred at room temperature for 1 h. The resulting mixture was partitioned between $H_2O$ (100 mL) and $Et_2O$ (100 mL). The organic fraction was removed and the aqueous portion was acidified with 2M HCl. The resulting solid was collected by filtration and azeotroped from MeOH (x2) to afford the title compound as a yellow solid.

LC-MS (Method 3B): Rt 1.09 mins; MS m/z 390.1=[M+H]+

1H NMR (500 MHz, DMSO-d6) δ 9.37 (d, J=7.2 Hz, 1H), 8.06 (s, 1H), 7.99 (d, J=7.8 Hz, 1H), 7.87 (d, J=7.8 Hz, 1H), 7.71 (t, J=7.8 Hz, 1H), 7.66 (d, J=7.2 Hz, 1H), 7.43 (s, 1H), 7.33 (s, 1H), 2.42 (s, 3H). OH proton not observed.

Example 10-2-(3-Cyanophenyl)-3-(2,6-dimethyl-4-pyridyl)-N-(2-hydroxy-2-methyl-propyl)pyrazolo[1,5-a]pyrimidine-5-carboxamide

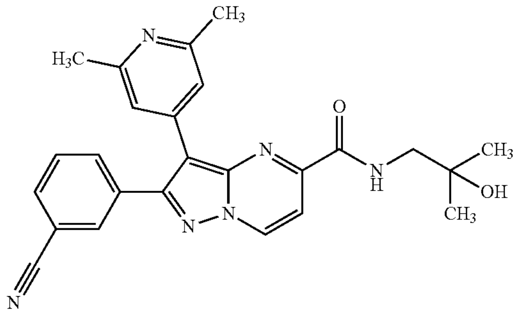 [SMILES: Cc1cc(-c2c(-c3cccc(C#N)c3)nn3ccc(C(=O)NCC(C)(C)O)nc23)cc(C)n1]

A solution of 3-bromo-2-(3-cyanophenyl)-N-(2-hydroxy-2-methyl-propyl)pyrazolo[1,5-a]pyrimidine-5-carboxamide (Intermediate B) (85 mg, 0.21 mmol) in 1,4-dioxane (2 mL) and water (0.40 mL) was degassed with $N_2$ and treated with (2,6-dimethyl-4-pyridyl)boronic acid (46 mg, 0.31 mmol), $K_2CO_3$ (57 mg, 0.41 mmol) and $Pd(tBusP)_2$ (5 mg, 0.01 mmol). The resulting mixture was heated to 50° C. for 1 h. Additional (2,6-dimethyl-4-pyridyl)boronic acid (46 mg, 0.31 mmol), $K_2CO_3$ (57 mg, 0.41 mmol) and $Pd(tBu_3P)_2$ (5 mg, 0.01 mmol) were added and the reaction mixture heated to 50° C. for a further 1 h.

Additional (2,6-dimethyl-4-pyridyl)boronic acid (46 mg, 0.31 mmol) was added in 2 portions at 30 min intervals and the reaction mixture heated to 50° C. for a further 30 min. Additional 2,6-dimethyl-4-(4,4,5,5-tetramethyl-1,3,2-dioxaborolan-2-yl)pyridine (48 mg, 0.21 mmol), $Pd(tBu_3P)_2$ (5 mg, 0.01 mmol) and $K_2CO_3$ (57 mg, 0.41 mmol) in water (0.2 mL) were added and the mixture heated to 50° C. for a further 1 h after which time the reaction was cooled to room temperature. The resulting mixture was partitioned between $H_2O$ (15 mL) and EtOAc (20 mL), the organic portion was separated and the aqueous further extracted with EtOAc (2×25 mL). The combined organic extracts were dried over $Na_2SO_4$ and concentrated in vacuo. Purification by chromatography on silica eluting with a gradient of 2 to 5% MeCOH in DCM afforded the title compound as a yellow solid.

LC-MS (Method 8B): Rt 4.06 mins; MS m/z 441.3=[M+H]+

$^1H$ NMR (500 MHz, DMSO-$d_6$) δ 9.42 (d, J=7.1 Hz, 1H), 8.37 (t, J=6.1 Hz, 1H), 8.06 (s, 1H), 7.99 (d, J=7.8 Hz, 1H), 7.91 (d, J=7.8 Hz, 1H), 7.71 (t, J=7.8 Hz, 1H), 7.70 (t, J=7.1 Hz, 1H), 7.22 (s, 2H), 4.75 (s, 1H), 2.40 (s, 6H), 1.16 (s, 6H). $CH_2$ signal not observed.

Example 12-2-(3-Cyanophenyl)-3-(2-ethylpyrazol-3-yl)-N-(2-hydroxy-2-methyl-propyl)pyrazolo[1,5-a]pyrimidine-5-carboxamide

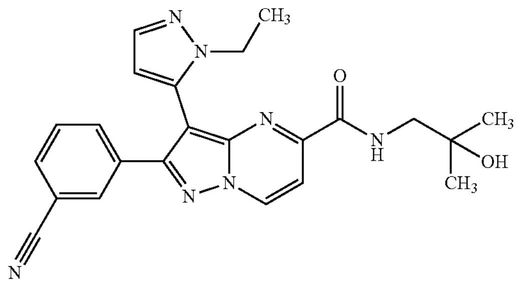 [SMILES: CCn1nccc1-c1c(-c2cccc(C#N)c2)nn2ccc(C(=O)NCC(C)(C)O)nc12]

A mixture of 3-bromo-2-(3-cyanophenyl)-N-(2-hydroxy-2-methyl-propyl)pyrazolo[1,5-a]pyrimidine-5-carboxamide (intermediate B) (60 mg, 0.14 mmol), (2-ethylpyrazol-3-yl) boronic acid (22 mg, 0.16 mmol) and $K_2CO_3$ (40 mg, 0.29 mmol) in 1,4-dioxane (1 mL) and water (0.20 mL-) was degassed under a flow of $N_2$. Pd(tBu$_3$P)2 (4 mg, 0.01 mmol) was added and the reaction mixture heated to 50° C. for 2 h. Additional (2-ethylpyrazol-3-yl)boronic acid (11 mg, 0.08 mmol) was added and the mixture heated for a further hour.

After cooling to room temperature, the resulting mixture was partitioned between H2O (15 ml_) and EtOAc (20 mL), the organic portion was separated and the aqueous further extracted with EtOAc (2x25 mL). The combined organic extracts were dried over $Na_2SO_4$ and concentrated in vacuo. Purification by chromatography on silica eluting with 3% MeOH in DCM to afforded the title compound as a yellow solid.

LC-MS (Method 8B3): Rt 3.95 mins; MS m/z 430.3=[M+H]+

$^1$H NMR (500 MHz, DMSO-d$_6$) δ 9.44 (d, J=7.2 Hz, 1H), 8.21 (t, J=6.2 Hz, 1H), 7.94-7.90 (m, 2H), 7.84 (d, J=8.0 Hz, 1H), 7.73 (d, J=7.2 Hz, 1H), 7.67 (t, J=8.0 Hz, 1H), 7.63 (d, J=1.7 Hz, 1H), 6.33 (d, J=1.7 Hz, 1H), 4.69 (s, 1H), 3.94 (q, J=7.2 Hz, 2H), 3.29 (d, J=6.2 Hz, 2H), 1.20 (t, J=7.2 Hz, 3H), 1.09 (s, 6H).

The compounds of the following tabulated Examples (Table Ex12) were prepared analogously to Example 12 from 3-bromo-2-(3-cyanophenyl)-N-(2-hydroxy-2-methyl-propyl)pyrazolo[1,5-a]pyrimidine-5-carboxamide (Intermediate B) and the appropriate boronic acid or boronate ester.

TABLE EX12

| Ex. | Structure and Name | Retention Time, [M + H]+, 1H NMR |
|---|---|---|
| 12.1 | 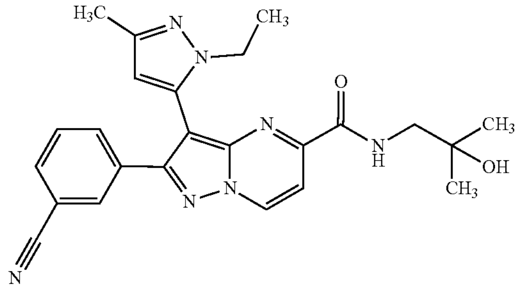 [SMILES: CCn1nc(C)cc1-c1c(-c2cccc(C#N)c2)nn2ccc(C(=O)NCC(C)(C)O)nc12] 2-(3-Cyanophenyl)-3-(2-ethyl-5-methyl-pyrazol-3-yl)-N-(2-hydroxy-2-methyl-propyl)pyrazolo[1,5-a]pyrimidine-5-carboxamide | LC-MS (Method 8B): Rt 4.06 mins; MS m/z 444.3 = [M + H]+ $^1$H NMR (500 MHz, DMSO-d6) δ 9.42 (d, J = 7.2 Hz, 1H), 8.22 (t, J = 6.2 Hz, 1H), 7.97 - 7.95 (m, 1H), 7.92 (d, J = 7.7 Hz, 1H), 7.84 (d, J = 7.9 Hz, 1H), 7.72 (d, J = 7.1 Hz, 1H), 7.67 (t, J = 7.8 Hz, 1H), 6.09 (s, 1H), 4.70 (s, 1H), 3.85 (q, J = 7.2 Hz, 2H), 3.30 (s, 2H), 2.22 (s, 3H), 1.17 (t, J = 7.2 Hz, 3H), 1.10 (s, 6H). |
| 12.2 | 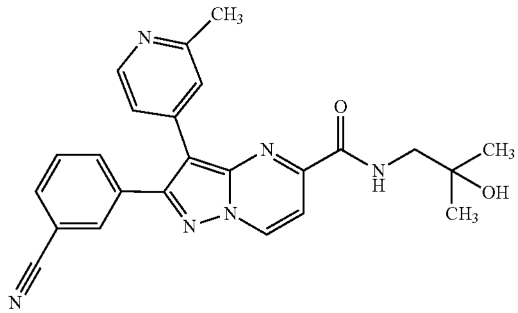 [SMILES: Cc1cc(-c2c(-c3cccc(C#N)c3)nn3ccc(C(=O)NCC(C)(C)O)nc23)ccn1] 2-(3-Cyanophenyl)-N-(2-hydroxy-2-methyl-propyl)-3-(2-methyl-4-pyridyl)pyrazolo[1,5-a]pyrimidine-5-carboxamide | LC-MS (Method 8B): Rt 3.90 mins; MS m/z 427.3 = [M + H]+ 1H NMR (500 MHz, Methanol-d4) δ 9.21 (d, J = 7.2 Hz, 1H), 8.39 (d, J = 5.3 Hz, 1H), 8.04 (s, 1H), 7.91 (d, J = 7.9 Hz, 1H), 7.85 (d, J = 7.7 Hz, 1H), 7.80 (d, J = 7.2 Hz, 1H), 7.66 - 7.58 (m, 2H), 7.36 (d, J = 5.4 Hz, 1H), 3.45 (s, 2H), 2.55 (s,3H), 1.27 (s, 6H). Exchangeable protons not observed. |

TABLE EX12-continued

| Ex. | Structure and Name | Retention Time, [M + H]+, 1H NMR |
|---|---|---|
| 12.3 | 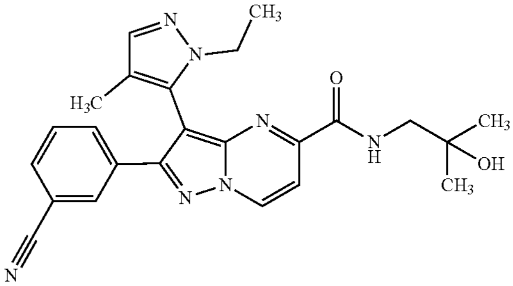 [SMILES: CCn1ncc(C)c1-c1c(-c2cccc(C#N)c2)nn2ccc(C(=O)NCC(C)(C)O)nc12] 2-(3-Cyanophenyl)-3-(2-ethyl-4-methyl-pyrazol-3-yl)-N-(2-hydroxy-2-methyl-propyl)pyrazolo[1,5-a]pyrimidine-5-carboxamide | LC-MS (Method 8B): Rt 3.48 mins; MS m/z 442.3 = [M − H]− $^{1}$H NMR (500 MHz, Methanol-d4) δ 9.24 (d, J = 7.2 Hz, 1H), 7.95 (d, J = 1.6 Hz, 1H), 7.84 − 7.79 (m, 2H), 7.77 (dt, J = 7.8, 1.3 Hz, 1H), 7.58 (t, J = 7.9 Hz, 1H), 7.52 (s, 1H), 3.92 (qd, J = 7.1,2.2 Hz, 2H), 3.40 (q, J = 13.5 Hz, 2H), 1.77 (s, 3H), 1.24 − 1.15 (m, 9H). Exchangeable protons not observed. |
| 12.4 | 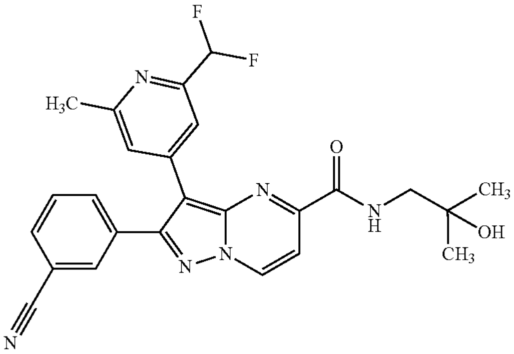 [SMILES: Cc1cc(-c2c(-c3cccc(C#N)c3)nn3ccc(C(=O)NCC(C)(C)O)nc23)cc(C(F)F)n1] 2-(3-Cyanophenyl)-3-[2-(difluoromethyl)-6-methyl-4-pyridyl]-N-(2-hydroxy-2-methyl-propyl)pyrazolo[1,5-a]pyrimidine-5-carboxamide | LC-MS (Method 8B): Rt 4.23 mins; MS m/z 477.2 = [M + H]+ $^{1}$H NMR (500 MHz, Methanol-d4) δ 9.23 (d, J = 7.2 Hz, 1H), 8.05 (s, 1H), 7.91 (d, J = 7.9 Hz, 1H), 7.87 (d, J = 8.0 Hz, 1H), 7.82 (d, J = 7.2 Hz, 1H), 7.76 (s, 1H), 7.66 (t, J = 7.9 Hz, 1H), 7.58 (s, 1H), 6.65 (t, J = 55.3 Hz, 1H), 3.45 (s, 2H), 2.60 (s, 3H), 1.28 (s, 6H). Exchangeable protons not observed. |
| 12.5 | 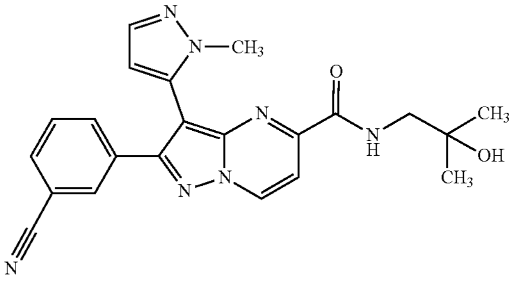 [SMILES: Cn1nccc1-c1c(-c2cccc(C#N)c2)nn2ccc(C(=O)NCC(C)(C)O)nc12] 2-(3-Cyanophenyl)-N-(2-hydroxy-2-methyl-propyl)-3-(2-methylpyrazol-3-yl)pyrazolo[1,5-a]pyrimidine-5-carboxamide | LC-MS (Method 8B): Rt 3.75 mins; MS m/z 416.3 = [M + H]+ 1H NMR (500 MHz, Methanol-d4) δ 9.22 (d, J = 7.2 Hz, 1H), 7.98 (d, J = 1.8 Hz, 1H), 7.89 − 7.85 (m, 1H), 7.81 (d, J = 7.2 Hz, 1H), 7.80 − 7.76 (m, 1H), 7.63 (d, J = 1.9 Hz, 1H), 7.58 (t, J = 7.8 Hz, 1H), 6.40 (d, J = 1.8 Hz, 1H), 3.67 (s, 3H), 3.41 (s, 2H), 1.21 (s, 6H). Exchangeable protons not observed. |

TABLE EX12-continued

| Ex. | Structure and Name | Retention Time, [M + H]+, 1H NMR |
|---|---|---|
| 12.6 | 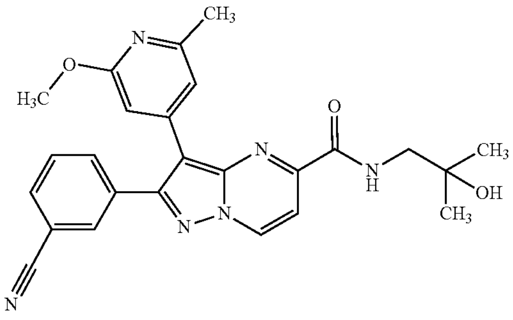 [SMILES: COc1cc(-c2c(-c3cccc(C#N)c3)nn3ccc(C(=O)NCC(C)(C)O)nc23)cc(C)n1] 2-(3-Cyanophenyl)-N-(2-hydroxy-2-methyl-propyl)-3-(2-methoxy-6-methyl-4-pyridyl)pyrazolo[1,5-a]pyrimidine-5-carboxamide | LC-MS (Method 8B): Rt 4.33 mins; MS m/z 457.2 = [M + H]+ 1H NMR (500 MHz, DMSO) δ 9.41 (d, J = 7.1 Hz, 1H), 8.35 (t, J = 6.0 Hz, 1H), 8.06 (s, 1H), 7.99 (d, J = 7.8 Hz, 1H), 7.89 (d, J = 7.8 Hz, 1H), 7.73 - 7.69 (m, 2H), 7.17 (s, 1H), 6.58 (s, 1H), 4.73 (s, 1H), 3.82 (s, 3H), 2.53 - 2.51 (m, 2H), 2.40 (s, 3H), 1.16 (s, 6H) |
| 12.7 | 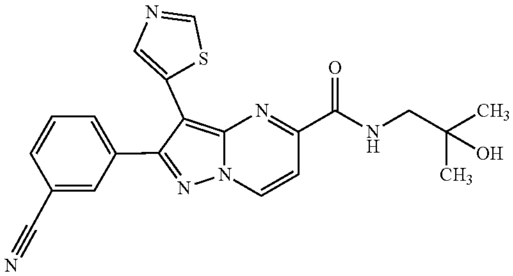 [SMILES: CC(C)(O)CNC(=O)c1ccn2nc(-c3cccc(C#N)c3)c(-c3cncs3)c2n1] 2-(3-Cyanophenyl)-N-(2-hydroxy-2-methyl-propyl)-3-thiazol-5-yl-pyrazolo[1,5-a]pyrimidine-5-carboxamide | LC-MS (Method 8B): Rt 3.79 mins; MS m/z 419.2 = [M + H]+ 1H NMR (500 MHz, DMSO-d6) δ 9.41 (d, J = 7.2 Hz, 1H), 9.13 (s, 1H), 8.46 (t, J = 5.8 Hz, 1H), 8.22 (s, 1H), 8.11 (s, 1H), 8.03 (d, J = 7.8 Hz, 1H), 7.99 (d, J = 7.8 Hz, 1H), 7.76 (t, J = 7.8 Hz, 1H), 7.72 (d, J = 7.2 Hz, 1H), 4.77 (s, 1H), 3.42-3.36 (m, 2H), 1.15 (s, 6H). |
| 12.8 | 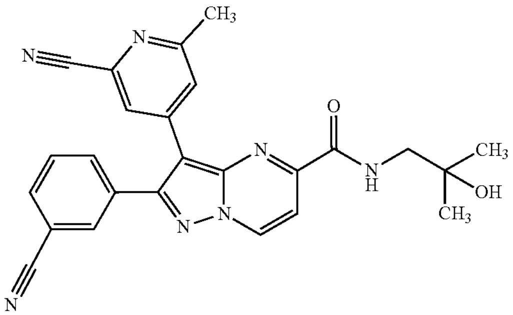 [SMILES: Cc1cc(-c2c(-c3cccc(C#N)c3)nn3ccc(C(=O)NCC(C)(C)O)nc23)cc(C#N)n1] 3-(2-Cyano-6-methyl-4-pyridyl)-2-(3-cyanophenyl)-N-(2-hydroxy-2-methyl-propyl)pyrazolo[1,5-a]pyrimidine-5-carboxamide | LC-MS (Method 8B): Rt 4.14 mins; MS m/z 452.2 = [M + H]+ 1H NMR (500 MHz, DMSO-d6) δ 9.48 (d, J = 7.2 Hz, 1H), 8.53 (t, J = 6.2 Hz, 1H), 8.12 (d, J = 1.8 Hz, 1H), 8.03 (d, J = 7.8 Hz, 1H), 7.93 (d, J = 7.9 Hz, 1H), 7.87 (d, J = 4.0 Hz, 2H), 7.79 - 7.70 (m, 2H), 4.72 (s, 1H), 3.35 - 3.31 (m, 2H), 2.54 (s, 3H), 1.17 (s, 6H). |

TABLE EX12-continued

| Ex. | Structure and Name | Retention Time, [M + H]+, 1H NMR |
|---|---|---|
| 12.9 | 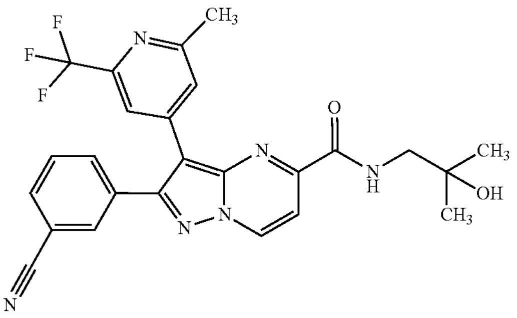 [SMILES: Cc1cc(-c2c(-c3cccc(C#N)c3)nn3ccc(C(=O)NCC(C)(C)O)nc23)cc(C(F)(F)F)n1] 2-(3-Cyanophenyl)-N-(2-hydroxy-2-methyl-propyl)-3-[2-methyl-6-(trifluoromethyl)-4-pyridyl]pyrazolo[1,5-a]pyrimidine-5-carboxamide | LC-MS (Method 8B): Rt 4.56 mins; MS m/z 495.2 = [M + H]+ 1H NMR (500 MHz, DMSO-d6) δ 9.48 (d, J = 7.2 Hz, 1H), 8.44 (t, J = 6.0 Hz, 1H), 8.11 (d, J = 1.8 Hz, 1H), 8.07-8.01 (m, 1H), 7.95 (d, J = 8.1 Hz, 1H), 7.92 (s, 1H), 7.79 - 7.71 (m, 2H), 7.60 (s, 1H), 4.72 (s, 1H), 3.37 - 3.28 (m, 2H), 2.58 (s, 3H), 1.17 (s, 6H). |

Example 13-2-(3-Cyanophenyl)-N-(2-hydroxy-2-methyl-propyl)-3-pyrimidin-4-yl-pyrazolo[1,5-a]pyrimidine-5-carboxamide

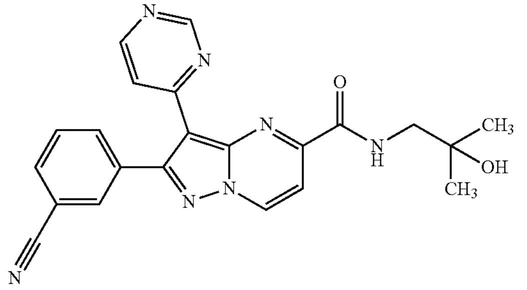 [SMILES: CC(C)(O)CNC(=O)c1ccn2nc(-c3cccc(C#N)c3)c(-c3ccncn3)c2n1]

To a degassed solution of 3-bromo-2-(3-cyanophenyl)-N-(2-hydroxy-2-methyl-propyl)pyrazolo[1,5-a]pyrimidine-5-carboxamide (Intermediate B) (50 mg, 0.12 mmol) in THF (2 mL) was added tributyl(pyrimidin-4-yl)stannane (0.04 mL, 0.13 mmol), copper(I) chloride (14 mg, 0.14 mmol), lithium chloride (6 mg, 0.14 mmol) and $Pd(PPh_3)_4$(14 mg, 0.01 mmol) and the mixture was heated to 90° C. for 3 h. The mixture was cooled to room temperature and after further degassing, additional tributyl(pyrimidin-4-yl)stannane (89 mg, 0.24 mmol) and $Pd(PPh_3)_4$(14 mg, 0.01 mmol) were added and the mixture heated for 1 h. The resulting mixture was cooled to room temperature and partitioned between EtOAc (15 mL) and $H_2O$ (15 mL). The organic portion was separated and the aqueous further extracted with EtOAc (2×20 mL). The combined organic extracts were washed with 5% aq. KF solution (2×20 mL), brine (2×20 mL), dried over $Na_2SO_4$ and the solvent removed in vacuo. Purification by chromatography on silica eluting with a gradient of 2 to 4% MeOH in DCM afforded a yellow solid. The solid was suspended in hexane, filtered, washed with $Et_2O$ and dried to afford the title compound as a yellow solid.

LC-MS (Method 8B): Rt 3.61 mins; MS m/z 414.2={M+H]+

$^1$H NMR (500 MHz, DMSO-$d_6$) δ 9.49 (d, J=7.1 Hz, 1H), 9.02 (s, 1H), 8.86 (d, J=5.3 Hz, 1H), 8.61 (t, J=6.2 Hz, 1H), 8.44 (d, J=5.3 Hz, 1H), 8.16 (s, 1H), 8.04 (d, J=7.8 Hz, 1H), 7.96 (d, J=7.8 Hz, 1H), 7.79 (d, J=7.1 Hz, 1H), 7.70 (t, J=7.8 Hz, 1H), 4.77 (s, 1H), 3.36 (d, J=6.2 Hz, 2H), 1.17 (s, 6H).

Example 14-3-Cyano-2-(3-cyanophenyl)-N-(2-hydroxy-2-methyl-propyl)pyrazolo[1,5-a]pyrimidine-5-carboxamide

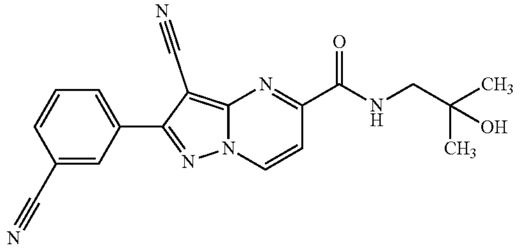 [SMILES: CC(C)(O)CNC(=O)c1ccn2nc(-c3cccc(C#N)c3)c(C#N)c2n1]

To a degassed solution of 3-bromo-2-(3-cyanophenyl)-N-(2-hydroxy-2-methyl-propyl)pyrazolo[1,5-a]pyrimidine-5-carboxamide (Intermediate B), (50 mg, 0.12 mmol) in DMA (2 mL) was added zinc dust (16 mg, 0.24 mmol), zinc cyanide (34 mg, 0.29 mmol) and $Pd(dpp)Cl_2.CH_2Cl_2$ (10 mg, 0.01 mmol) and the mixture was heated to 120° C. for 2 h.

The mixture was cooled to room temperature and $Pd(tBu_3P)_2$ (6 mg, 0.01 mmol) was added and stirring continued for 1.5 h. The resulting mixture was diluted with EtOAc (5 mL) and filtered through cotton wool. The mixture was further diluted with EtOAc (25 mL) and $H_2O$ (20 mL), the organic portion separated and the aqueous further extracted with EtOAc (2×15 mL).

The combined organic extracts were washed with brine (4×20 mL), dried over $Na_2SO_4$ and the solvent removed in vacuo. Purification by chromatography on silica eluting with 2% MeOH in DCM afforded a colourless solid. The solid was suspended in $Et_2O$, collected by filtration and dried to afford the title compound as a colourless solid.

LC-MS (Method 8B): Rt 3.84 mins; MS m/z 359.2=[M−H]−

$^1$H NMR (500 MHz, DMSO-$d_6$) δ 9.58 (d, J=7.1 Hz, 1H), 8.62 (t, J=6.2 Hz, 1H), 8.46 (s, 1H), 8.42 (d, J=7.9 Hz, 1H), 8.12 (d, J=7.9 Hz, 1H), 7.90 (t, J=7.9 Hz, with overlapping d, J=7.1 Hz, 2H), 4.79 (s, 1H), 3.36 (d, J=6.2 Hz, 2H), 1.16 (s, 6H).

Example 15-3-[3-(2-Chloro-6-methyl-4-pyridyl)-5-(2-hydroxy-2-methyl-propoxy) pyrazolo[1,5-a]pyrimidin-2-yl]benzonitrile

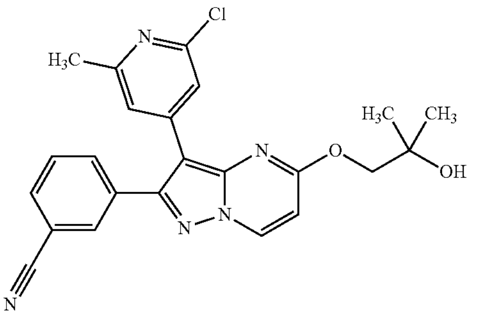 [SMILES: Cc1cc(-c2c(-c3cccc(C#N)c3)nn3ccc(OCC(C)(C)O)nc23)cc(Cl)n1]

A 1M solution of LiHMDS (0.24 mL, 0.24 mmol) in THF was added to a solution of 2-methylpropane-1,2-diol (0.02 mL, 0.24 mmol) in THF (1 mL) and the mixture was stirred at room temperature for 15 mins. 3-[5-Chloro-3-(2-chloro-6-methyl-4-pyridyl)pyrazolo[1,5-a]pyrimidin-2-yl]benzonitrile (Intermediate C), (70 mg, 0.18 mmol) was added and stirring continued at room temperature overnight. The resulting mixture was partitioned between EtOAc (5 mL) and water (3 mL) and the organic portion was separated. The aqueous layer was further extracted with EtOAc (2×5 mL) and the combined organic extracts were dried over $Na_2SO_4$ and concentrated in vacuo. Purification by chromatography on silica eluting with a gradient of 2 to 6% MeOH in DCM afforded the title compound as a colourless solid.

LC-MS (Method 8B): Rt 4.70 mins; MS m/z 434.2/436.2=[M+H]+

$^1$H NMR (500 MHz, DMSO-d6) δ 9.07 (d, J=7.5 Hz, 1H), 8.02 (s, 1H), 7.99 (d, J=7.8 Hz, 1H), 7.86 (d, J=7.8 Hz, 1H), 7.71 (t, J=7.8 Hz, 1H), 7.35 (s, 1H), 7.31 (s, 1H), 6.80 (d, J=7.5 Hz, 1H), 4.77 (s, 1H), 4.24 (s, 2H), 2.39 (s, 3H), 1.24 (s, 6H).

Example 16—N-[3-(2-Chloro-6-methyl-4-pyridyl)-2-(3-cyanophenyl)pyrazolo[1,5-a]pyrimidin-5-yl] methanesulfonamide

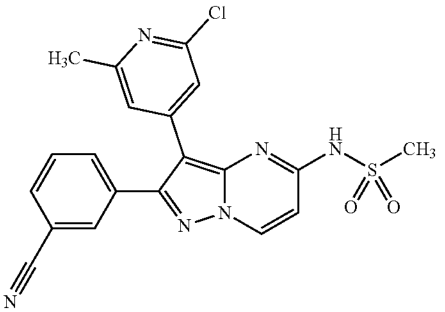

DBU (0.03 mL, 0.22 mmol) was added to a solution of 3-[5-chloro-3-(2-chloro-6-methyl-4-pyridyl)pyrazolo[1,5-a]pyrimidin-2-yl]benzonitrile (Intermediate C) (70 mg, 0.18 mmol) and methanesulfonamide (21 mg, 0.22 mmol) in NMP (1 mL) and the reaction mixture was stirred at 40° C. for 90 mins. Further methanesulfonamide (21 mg, 0.22 mmol) was added and stirring continued at 40° C. for 1 h. Additional methanesulfonamide (21 mg, 0.22 mmol) and DBU (0.03 mL, 0.22 mmol) were added and the reaction mixture was allowed to stir at 40° C. overnight. The resulting mixture was diluted with MeOH (2 mL) and water (0.5 mL) and the crude product purified sequentially under the following conditions: C18 reverse phase chromatography eluting with a gradient of 5 to 25% MeCN in water (+0.1 wt % $NH_4OH$) followed by chromatography on silica eluting with a gradient of 0-8% MeOH in DCM. The material was then further purified by C18 reverse phase chromatography with a gradient of 30 to 45% MeCN in water (+0.1 wt % formic acid), purification by reverse phase eluting with a gradient of 5 to 25% MeCN in water (+0.1 wt % $NH_4OH$) followed finally by chromatography on silica eluting with a gradient of 0-8% MeOH in DCM which afforded the title compound as an off-white solid.

LC-MS (Method 8B): Rt 3.08 mins; MS m/z 439.1/441.1=[M+H]+

$^1$H NMR (500 MHz, DMSO-d6) δ 11.64 (s, 1H), 9.05 (d, J=7.4 Hz, 1H), 8.04 (s, 1H), 8.00 (d, J=7.8 Hz, 1H), 7.88 (d, J=7.9 Hz, 1H), 7.72 (t, J=7.8 Hz, 1H), 7.42 (s, 1H), 7.34 (s, 1H), 6.69 (d, J=7.4 Hz, 1H), 3.46 (s, 3H), 2.38 (s, 3H).

Example 16.1-1-[3-(2-Chloro-6-methyl-4-pyridyl)-2-(3-cyanophenyl)pyrazolo[1,5-a]pyrimidin-5-yl] guanidine

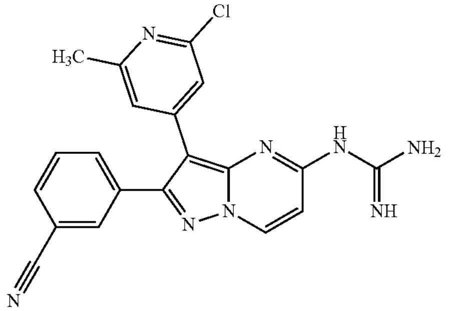

The title compound was prepared from 3-[5-chloro-3-(2-chloro-6-methyl-4-pyridyl)pyrazolo[1,5-a]pyrimidin-2-yl] benzonitrile (Intermediate C), guanidine hydrochloride and DBU (5 eq.) at 100° C. analogously to Example 16.

LC-MS (Method 8B): Rt 4.05 mins; MS m/z 403.2=[M+H]+

1H NMR (500 MHz, DMSO-d6) δ 8.63 (d, J=7.5 Hz, 1H), 7.98 (t, J=1.7 Hz, 1H), 7.94 (dt,J=7.7, 1.4 Hz, 1H), 7.83 (dt,J=8.0, 1.5 Hz, 1H), 7.68 (t, J=7.8 Hz, 1H), 7.54-7.27 (m, 4H), 7.24 (s, 1H), 7.15 (s, 1H), 6.36 (d, J=7.4 Hz, 1H), 2.39 (s, 3H).

Example 17-(2S)-2-[[3-(2-Chloro-6-methyl-4-pyridyl)-2-(3-cyanophenyl)pyrazolo[1,5-a]pyrimidin-5-yl]amino]propanoic acid

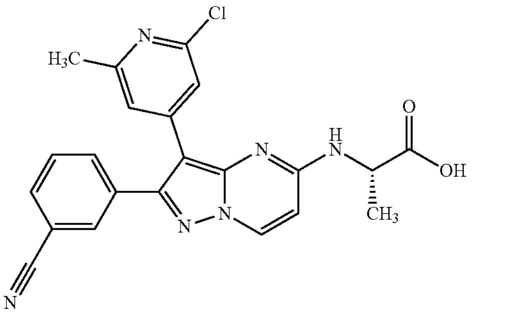 [SMILES: Cc1cc(-c2c(-c3cccc(C#N)c3)nn3ccc(N[C@@H](C)C(=O)O)nc23)cc(Cl)n1]

Step 1: Methyl(2S)-2-{[3-(2-chloro-6-methyl-4-pyridyl)-2-(3-cyanophenyl)pyrazolo[1,5-a]pyrimidin-5-yl]amino]propanoate

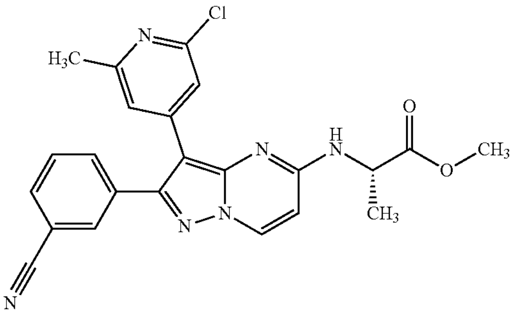 [SMILES: COC(=O)[C@H](C)Nc1ccn2nc(-c3cccc(C#N)c3)c(-c3cc(C)nc(Cl)c3)c2n1]

Methyl(2S)-2-aminopropanoate (25 mg, 0.24 mmol) was added to a suspension of DIPEA (0.1 mL, 0.55 mmol) and 3-[5-chloro-3-(2-chloro-6-methyl-4-pyridyl)pyrazolo[1,5-a]pyrimidin-2-yl]benzonitrile (Intermediate C)(70 mg, 0.18 mmol) in DMF (1 mL) and the mixture was stirred at 50° C. overnight and then at 70° C. for 1 h. Additional methyl(2S)-2-aminopropanoate (25 mg, 0.24 mmol) and DIPEA (0.1 mL, 0.55 mmol) were added and the mixture was stirred at 70° C. overnight. After cooling to room temperature, the resulting mixture was partitioned between EtOAc (20 mL) and water (20 mL). The aqueous layer was separated and the organic layer was washed with brine (20 mL), dried over $Na_2SO_4$, filtered and concentrated in vacuo. Purification by chromatography on silica eluting with a gradient of 2 to 10% MeOH in DCM afforded the title compound as an orange oil.

LC-MS (Method 5A): Rt 2.96 mins; MS m/z 447.2=[M+H]+

$^1$H NMR (500 MHz, DMSO-$d_6$) δ 8.68 (d, J=7.5 Hz, 1H), 8.40 (d, J=6.0 Hz, 1H), 7.99-7.95 (m, 2H), 7.83 (dt, J=7.9, 1.5 Hz, 1H), 7.70 (t, J=7.8 Hz, 1H), 7.30 (d, J=1.2 Hz, 1H), 7.18 (s, 1H), 6.55 (d, J=7.5 Hz, 1H), 4.53-4.44 (m, 1H), 3.63 (s, 3H), 2.37 (s, 3H), 1.48 (d, J=7.2 Hz, 3H).

Step 2: (2S)-2-[[3-(2-Chloro-6-methyl-4-pyridyl)-2-(3-cyanophenyl)pyrazolo[1,5-a]pyrimidin-5-yl]amino]propanoic acid A solution of LiOH (11 mg, 0.46 mmol) in water (1 mL) was added to a solution of methyl(2S)-2-[[3-(2-chloro-6-methyl-4-pyridyl)-2-(3-cyanophenyl)pyrazolo[1,5-a]pyrimidin-5-yl]amino]propanoate (step 1) (82 mg, 0.18 mmol) in THF (2 mL) and the mixture was stirred at room temperature for 30 mins. The resulting mixture was partitioned between EtOAc (20 mL) and water (20 mL). The organic layer was separated and the aqueous portion was acidified to -pH 1 with 2M HCl (aq). The mixture was extracted with EtOAc (20 mL) and the organic portion was dried over $Na_2SO_4$, filtered and concentrated in vacuo. Purification by C18 reverse phase chromatography eluting with a gradient of 20 to 45% MeCN in water (+0.1 wt % formic acid) afforded the title compound as an off-white solid.

LC-MS (Method 8A): Rt 4.29 mins; MS m/z 433.3/435.2=[M+H]+

$^1$H NMR (500 MHz, DMSO-$d_8$) δ 8.63 (d, J=7.6 Hz, 1H), 8.17 (s, 1H), 8.00-7.92 (m, 2H), 7.84 (d, J=7.8 Hz, 1H), 7.70 (t, J=7.7 Hz, 1H), 7.47 (s, 1H), 7.15 (s, 1H), 6.61 (d, J=7.6 Hz, 1H), 4.36-4.24 (m, 1H), 2.38 (s, 3H), 1.46 (d, J=7.1 Hz, 3H). OH proton not observed Example 18-3-[3-(2-Chloro-6-methyl-4-pyridyl)-5-[(3R)-pyrrolidin-3-yl]oxy-pyrazolo[1,5-a]pyrimidin-2-yl]benzonitrile formate

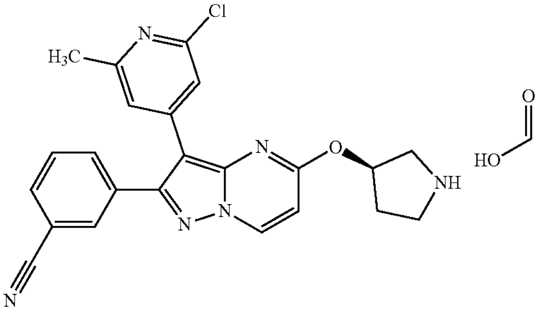

Step 1: tert-Butyl(3R)-3-[3-(2-chloro-6-methyl-4-pyridyl)-2-(3-cyanophenyl)pyrazolo[1,5-a]pyrimidin-5-yl]oxypyrrolidine-1-carboxylate

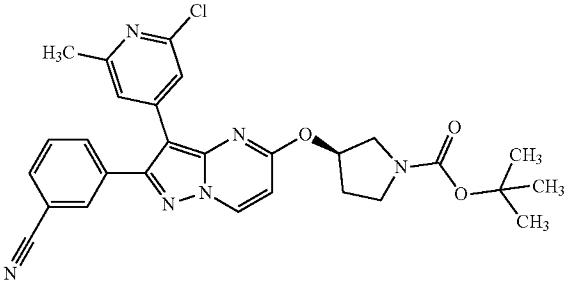 [SMILES: Cc1cc(-c2c(-c3cccc(C#N)c3)nn3ccc(O[C@@H]4CCN(C(=O)OC(C)(C)C)C4)nc23)cc(Cl)n1]

NaH (10 mg, 0.24 mmol) was added to a solution of tert-butyl(3R)-3-hydroxypyrrolidine-1-carboxylate (45 mg, 0.24 mmol) in THF (1 mL) and the mixture was stirred at room temperature for 45 mins. To this mixture was added 3-[5-chloro-3-(2-chloro-6-methyl-4-pyridyl)pyrazolo[1,5-a]pyrimidin-2-yl]benzonitrile (Intermediate C) (70 mg, 0.18 mmol) and stirring continued at room temperature overnight. The resulting mixture was partitioned between EtOAc (5 mL) and water (3 mL). The organic layer was separated and the aqueous layer was further extracted with EtOAc (2×5 mL). The organic layers were combined, dried over $Na_2SO_4$ and concentrated in vacuo to afford the title compound as an orange gum.

LC-MS (Method 3B): Rt 2.96 mins; MS m/z 531.2=[M+H]+

$^1$H NMR (400 MHz, DMSO-$d_6$) δ 9.15 (d, J=7.4 Hz, 1H), 8.10-8.07 (m, 1H), 8.05 (dt, J=7.7, 1.4 Hz, 1H), 7.92 (dt, J=7.9, 1.4 Hz, IH), 7.77 (t, J=7.8 Hz, IH), 7.42-7.33 (m, 2H), 6.87 (d, J=7.5 Hz, 1H), 5.61 (s, 1H), 3.88-3.71 (m, 1H), 3.59-3.51 (m, 1H), 3.20-3.10 (m, 1H), 2.46 (s, 3H), 2.37-2.26 (m, 2H), 1.84-1.72 (m, 1H), 1.45 (s, 9H).

Step 2: 3-[3-(2-Chloro-6-methyl-4-pyridyl)-5-[(3R)-pyrrolidin-3-yl]oxy-pyrazolo[1,5-a]pyrimidin-2-yl]benzonitrile formate 4M HCl in 1,4-dioxane (0.46 mL, 1.84 mmol) was added to a suspension of tert-butyl(3R)-3-[3-(2-chloro-6-.methyl-4-pyridyl)-2-(3-cyanophenyl)pyrazolo[1,5-a]pyrimidin-5-yl]oxy pyrrolidine-1-carboxylate (step 1) (98 mg, 0.18 mmol) in MeOH (0.50 mL) and the mixture was stirred at room temperature for 2 h. The resulting mixture was concentrated in vacuo and purification by C18 reverse phase eluting with a gradient of 5-90% MeCN in water (+0.1 wt % $NH_4OH$) followed by 5-60% MeCN in water (+0.1 wt % formic acid) afforded the title compound as a brown solid.

LC-MS (Method 15B): Rt 8.86 mins; MS m/z 431.1/433.0=[MH]+

$^1$H NMR (500 MHz, DMSO-$d_6$) δ 9.07 (d, J=7.5 Hz, 1H), 8.35 (s, 1H), 8.02 (d, J=1.9 Hz, 1H), 7.99 (d, J=7.8 Hz, 1H), 7.86 (d, J=7.9 Hz, 1H), 7.72 (t, J=7.8 Hz, 1H), 7.35 (s, 1H), 7.31 (s, 1H), 6.75 (d, J=7.4 Hz, 1H), 5.47 (t, J=6.0 Hz, 1H), 3.28 (dd, J=12.9, 5.5 Hz, 1H), 3.17-3.11 (m, 1H), 2.99 (dd, J=20.9, 12.9 Hz, 2H), 2.40 (s, 3H), 2.25-2.11 (m, 1H), 2.07-1.96 (m, 1H). NH proton not observed.

Example 19-3-[3-(2-Chloro-6-methyl-4-pyridyl)-5-(2-hydroxyethylamino)pyrazolo[1,5-a]pyrimidin-2-yl]benzonitrile

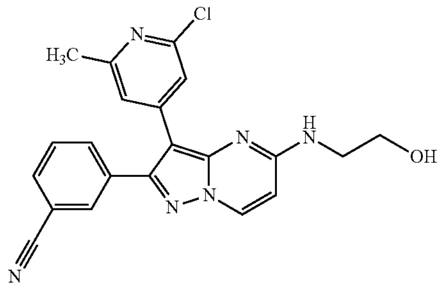 [SMILES: Cc1cc(-c2c(-c3cccc(C#N)c3)nn3ccc(NCCO)nc23)cc(Cl)n1]

Step 1: 3-[3-Bromo-5-(2-hydroxyethylamino)pyrazolo[1,5-a]pyrimidin-2-yl]benzonitrile

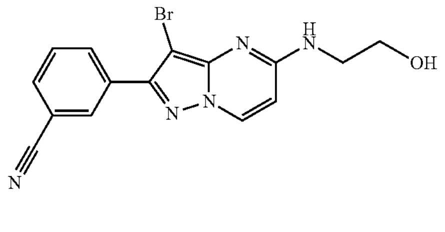 [SMILES: N#Cc1cccc(-c2nn3ccc(NCCO)nc3c2Br)c1]

2-Aminoethanol (0.09 mL, 1.5 mmol) was added to a suspension of 3-(3-bromo-5-chloro-pyrazolo[1,5-a]pyrimidin-2-yl)benzonitrile (Intermediate E1) (100 mg, 0.30 mmol) in DMF (1 mL) and stirred at 90° C. for 30 mins. The resulting mixture was allowed to cool to room temperature and added dropwise to stirring water (20 mL). The precipitate was collected by filtration, and washed with water (2×5 mL). The solid was azeotroped from acetone (30 ml) to afford the title compound as an off-white solid.

LC-MS (Method 5A): Rt 2.31 mins; MS m/z 358.0/360.1=[M+2+H]+

$^1$H NMR (500 MHz, DMSO-$d_6$) δ 8.53 (d, J=7.5 Hz, 1H), 8.31-8.29 (m, 1H), 8.26 (dt, J=7.9, 1.4 Hz, 1H), 7.93 (dt, J=7.7, 1.4 Hz, 1H), 7.86 (br s, 1H), 7.74 (t, J=7.8 Hz, 1H), 6.46 (d, J=7.6 Hz, 1H), 4.83 (t, J=5.1 Hz, 1H), 3.62 (q, J=5.7 Hz, 2H), 3.52-3.45 (m, 2H).

Step 2: 3-[3-(2-Chloro-6-methyl-4-pyridyl)-5-(2-hydroxyethylamino)pyrazolo[1,5-a]pyrimidin-2-yl]benzonitrile 3-[3-Bromo-5-(2-hydroxyethylamino)pyrazolo[1,5-a]pyrimidin-2-yl]benzonitrile (step 1) (107 mg, 0.30 mmol), (2-chloro-6-methyl-4-pyridyl)boronic acid (77 mg, 0.45 mmol) and $K_2CO_3$ (83 mg, 0.60 mmol) in water (1 mL) and 1,4-dioxane (4 mL) was degassed under a flow of $N_2$ and treated with $Pd(tBuaP)_2$ (23 mg, 0.04 mmol). The reaction mixture was stirred at 100° C. for 45 mins and then allowed to cool to room temperature. The reaction mixture was adsorbed onto silica before purification by chromatography on silica eluting with a gradient of 2 to 10% MeOH in DCM followed by a C18 reverse phase chromatography eluting with a gradient of 20-50% MeCN in water (+0.1 wt % $NH_4OH$) afforded the title compound as a colourless solid.

LC-MS (Method 8A): Rt 6.88 mins; MS m/z 405.1/407.0=[M+H]+

$^1$H NMR (500 MHz, DMSO-$d_6$) δ 8.58 (d, J=7.6 Hz, 1H), 8.05-7.99 (m, 1H), 8.00-7.95 (m, 2H), 7.82 (dt, J=7.9, 1.4 Hz, 1H), 7.69 (td, J=7.8, 0.8 Hz, 1H), 7.37-7.30 (m, 2H), 6.51 (d, J=7.6 Hz, 1H), 4.83 (t, J=5.2 Hz, 1H), 3.67 (q, J=5.6 Hz, 2H), 3.49 (q, J=5.6 Hz, 2H), 2.34 (s, 3H).

Example 20-3-[3-(2-Chloro-6-methyl-4-pyridyl)-5-(morpholinomethyl)pyrazolo[1,5-a]pyrimidin-2-yl]benzonitrile

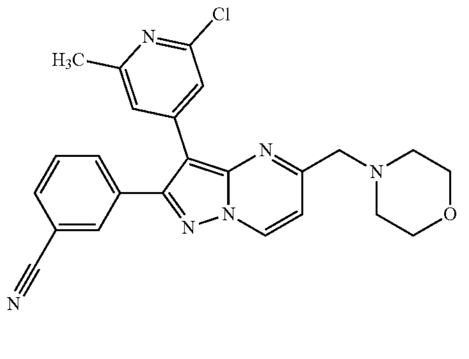 [SMILES: Cc1cc(-c2c(-c3cccc(C#N)c3)nn3ccc(CN4CCOCC4)nc23)cc(Cl)n1]

Step 1: 3-[5-(Morpholinomethyl)pyrazolo[1,5-a]pyrimidin-2-yl]benzonitrile

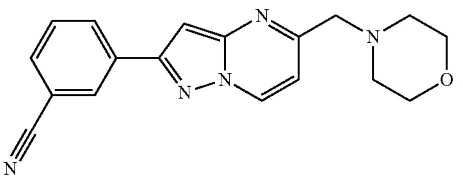 [SMILES: N#Cc1cccc(-c2cc3nc(CN4CCOCC4)ccn3n2)c1]

A suspension of 3-(5-chloropyrazolo[1,5-a]pyrimidin-2-yl)benzonitrile (Intermediate C2) (200 mg, 0.79 mmol), potassium (morpholin-4-yl)methyltrifluoroborate (195 mg, 0.94 mmol) and cesium carbonate (640 mg, 1.96 mmol) in a mixture of water (0.50 mL) and 1,4-dioxane (5 mL) under nitrogen was treated with $Pd(tBusP)_2$ (40 mg, 0.08 mmol) and stirred at 90° C. for 1 h. After cooling to room temperature, the resulting mixture was diluted with water (50 mL) and the precipitate was collected by filtration, washing with water (2×5 mL). The solid was suspended in acetone and filtered, washing with acetone (2×5 mL). The filtrate was concentrated in vacuo to afford the title compound as an off-white solid.

LC-MS (Method 3A): Rt 1.14 mins; MS m/z 320.2=[M+H]+

$^1$H NMR (500 MHz, DMSO-do) 5 9.08 (dd, J=7.2, 0.9 Hz, 1H), 8.47 (t, J=1.7 Hz, 1H), 8.37 (dt, J=8.0, 1.4 Hz, 1H), 7.90 (dt, J=7.6, 1.4 Hz, 1H), 7.72 (t, J=7.8 Hz, 1H), 7.32 (d, J=0.9 Hz, 1H), 7.16 (d, J=7.2 Hz, 1H), 3.65 (s, 2H), 3.64-3.61 (m, 4H), 2.49-2.45 (m, 4H).

Step 2: 3-[3-Iodo-5-(morpholinomethyl)pyrazolo[1,5-a]pyrimidin-2-yl]benzonitrile

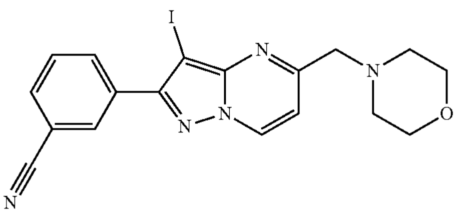 [SMILES: N#Cc1cccc(-c2nn3ccc(CN4CCOCC4)nc3c2I)c1]

A suspension of 3-[5-(morpholinomethyl)pyrazolo[1,5-a]pyrimidin-2-yl]benzonitrile (step 1) (203 mg, 0.64 mmol), N-iodosuccinimide (157 mg, 0.70 mmol) in MeCN (6 mL) and DMF (3 mL) was stirred at room temperature for 1.5 h. Additional N-iodosuccinimide (157 mg, 0.70 mmol) was added and the reaction mixture was stirred at room temperature for 45 mins. The resulting mixture was added dropwise to stirring water (50 mL) and the precipitate was collected by filtration, washing with water (2×5 mL). The solid was azeotroped from acetone (20 ml) to afford the title compound as a brown solid.

LC-MS (Method 5B): Rt 2.99 mins; MS m/z 446.0=[M+H]+

$^1$H NMR (500 MHz, DMSO-$d_6$) δ 9.40 (d, J=7.1 Hz, 1H), 8.46-8.27 (m, 2H), 8.07-7.98 (m, 1H), 7.88-7.75 (m, 1H), 7.29 (d, J=7.1 Hz, 1H), 4.77-4.60 (m, 2H), 4.14-3.96 (m, 2H), 3.89-3.67 (m, 4H), 3.70-3.52 (m, 2H).

Step 3: 3-[3-(2-Chloro-6-methyl-4-pyridyl)-5-(morpholinomethyl)pyrazolo[1,5-a]pyrimidin-2-yl]benzonitrile A mixture of 3-[3-iodo-5-(morpholinomethyl)pyrazolo[1,5-a]pyrimidin-2-yl]benzonitrile (step 2) (170 mg, 0.24 mmol), (2-chloro-6-methyl-4-pyridyl)boronic acid (61 mg, 0.36 mmol) and potassium carbonate (65 mg, 0.47 mmol) in water (1 mL) and 1,4-dioxane (4 mL) was degassed with $N_2$ and treated with $Pd(tBu_3P)_2$ (18 mg, 0.04 mmol). After stirring at 80° C. for 2 h 30 mins, additional (2-chloro-6-methyl-4-pyridyl)boronic acid (61 mg, 0.36 mmol) and $Pd(tBu_3P)_2$ (18 mg, 0.04 mmol) were added and stirring continued at 80° C. for 45 mins. The resulting mixture was allowed to cool to room temperature and the crude mixture was adsorbed onto silica. Purification by chromatography on silica eluting with a gradient of 2 to 10% MeOH in DCM followed by C18 reverse phase chromatography eluting with a gradient of 35 to 55% MeCN in water (+0.1 wt % $NH_4OH$) to afford the title compound as a yellow solid.

LC-MS (Method 15B): Rt 7.75 mins; MS m/z 445.1/447.0=[M+H]+

$^1$H NMR (500 MHz, DMSO-$d_6$) δ 9.21 (d, J=7.1 Hz, 1H), 8.05-8.03 (m, 1H), 7.99 (dt, J=7.8, 1.4 Hz, 1H), 7.86 (dt, J=8.0, 1.4 Hz, 1H), 7.71 (t, J=7.8 Hz, 1H), 7.39 (s, 1H), 7.34 (d, J=7.2 Hz, 1H), 7.33-7.31 (m, 1H), 3.74 (s, 2H), 3.67-3.60 (m, 4H), 2.54-2.49 (m, 4H), 2.41 (s, 3H).

Example 20.1-3-[3-(2,6-Dimethyl-4-pyridyl)-5-(piperazin-1-ylmethyl)pyrazolo[1,5-a]pyrimidin-2-yl]benzonitriletrifluoroacetate

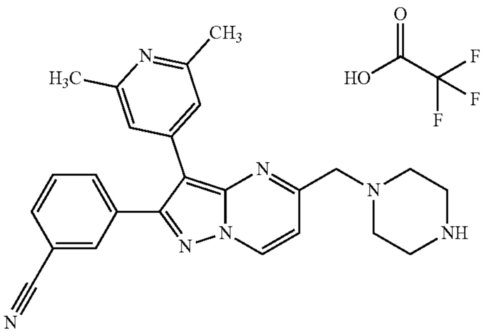

Step 1: tert-Butyl 4-[[2-(3-cyanophenyl)pyrazolo[1,5-a]pyrimidin-5-yl]methyl]piperazine-1-carboxylate

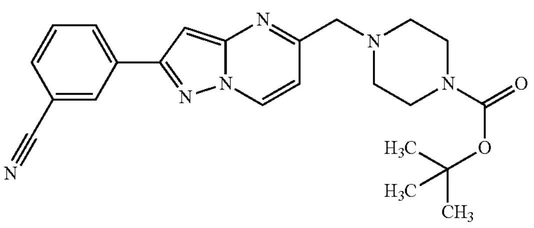 [SMILES: CC(C)(C)OC(=O)N1CCN(Cc2ccn3nc(-c4cccc(C#N)c4)cc3n2)CC1]

The title compound was prepared from 3-(5-chloropyrazolo[1,5-a]pyrimidin-2-yl)benzonitrile (Intermediate C2) and potassium (4-tert-butoxycarbonylpiperazin-1-yl)methyltrifluoroborate analogously to Example 20 step 1.

LC-MS (Method 5B): Rt 3.04 mins; MS m/z 419.6=[M+H]+

1H NMR (500 MHz, DMSO-d6) δ9.08 (d, J=7.2 Hz, 1H), 8.47 (t, J=1.7 Hz, 1H), 8.37 (dt,J=7.9, 1.5 Hz, 1H), 7.90 (dt,J=7.7, 1.4 Hz, 1H), 7.72 (t, J=7.8 Hz, 1H), 7.36-7.27 (m, 1H), 7.16 (d, J=7.2 Hz, 1H), 3.67 (s, 2H), 3.38-3.33 (m, 4H), 2.43 (t, J=5.1 Hz, 4H), 1.40 (s, 9H).

Step 2: tert-Butyl 4-[[2-(3-cyanophenyl)-3-iodo-pyrazolo[1,5-a]pyrimidin-5-yl]methyl]piperazine-1-carboxylate

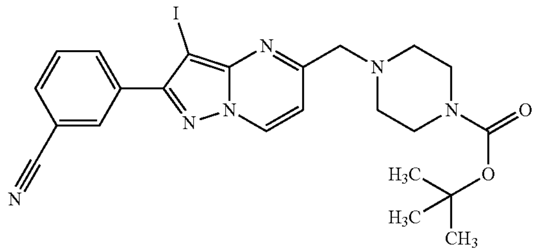 [SMILES: CC(C)(C)OC(=O)N1CCN(Cc2ccn3nc(-c4cccc(C#N)c4)c(I)c3n2)CC1]

The title compound was prepared from tert-butyl 4-[[2-(3-cyanophenyl)pyrazolo[1,5-a]pyrimidin-5-yl]methyl]piperazine-1-carboxylate (step 1) and N-iodosuccinimide analogously to Example 20 step 2.

LC-MS (Method 5B): Rt 3.42 mins; MS m/z 545.1=[M+H]+

1H NMR (500 MHz, DMSO-d6) δ 9.13 (d, J=7.2 Hz, 1H), 8.34 (d, J=1.7 Hz, 1H), 8.32-8.26 (m, 1H), 7.99 (dt,J=7.9, 1.5 Hz, 1H), 7.80 (t, J=7.8 Hz, 1H), 7.26 (d, J=7.1 Hz, 1H), 3.73 (s, 2H), 3.41-3.35 (m, 4H), 2.45 (t, J=5.1 Hz, 4H), 1.41 (s, 9H).

Step 3: tert-Butyl 4-[[2-(3-cyanophenyl)-3-(2,6-dimethyl-4-pyridyl)pyrazolo[1,5-a]pyrimidin-5-yl]methyl]piperazine-1-carboxylate

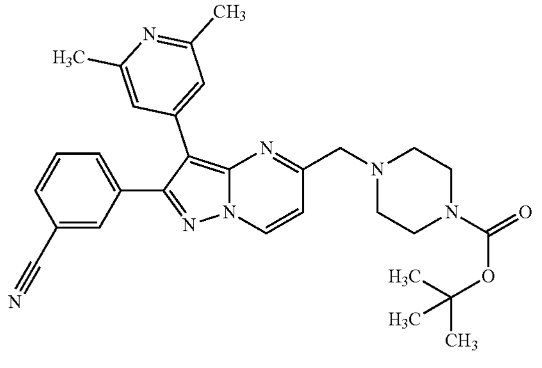 [SMILES: Cc1cc(-c2c(-c3cccc(C#N)c3)nn3ccc(CN4CCN(C(=O)OC(C)(C)C)CC4)nc23)cc(C)n1]

The title compound was prepared from tert-butyl 4-[[2-(3-cyanophenyl)-3-iodo-pyrazolo[1,5-a]pyrimidin-5-yl]methyl]piperazine-1-carboxylate (step 2) and bis(tri-tert-butylphosphine)palladium(0) analogously to Example 20 step 3.

LC-MS (Method 5B): Rt 3.09 mins; MS m/z 522.4=[M−H]−

1H NMR (500 MHz, DMSO-d6) δ 9.18 (d, J=7.3 Hz, 1H), 7.99 (t, J=1.7 Hz, 1H), 7.95 (d, J=7.7 Hz, 1H), 7.87.-7.80 (m, 1H), 7.68 (t, J=7.8 Hz, 1H), 7.28 (d, J=7.1 Hz, 1H), 7.12 (s, 2H), 3.74 (s, 2H), 3.39-3.35 (m, 4H), 2.47 (t, J=4.9 Hz, 4H), 2.39 (s, 6H), 1.40 (s, 9H).

Step 4: 3-[3-(2,6-Dimethyl-4-pyridyl)-5-(piperazin-1-ylmethyl)pyrazolo[1,5-a]pyrimidin-2-yl]benzonitrile trifluoroacetate Trifluoroacetic acid (0.15 mL, 1.91 mmol) was added to a suspension of tert-butyl 4-[[2-(3-cyanophenyl)-3-(2,6-dimethyl-4-pyridyl)pyrazolo[1,5-a]pyrimidin-5-yl]methyl]piperazine-1-carboxylate (step 3) (67 mg, 0.13 mmol) in DCM (1 mL) and stirred at room temperature overnight. The resulting mixture was concentrated in vacuo and the solid residue was triturated with diethyl ether (2 mL) and acetonitrile (2 mL) to afford the title compound as a yellow solid.

LC-MS (Method 8B): Rt 4.17 mins; MS m/z 424.3=[M #H]+

1H NMR (500 MHz, DMSO-d6) δ 9.35 (d, J=7.2 Hz, 1H), 8.59 (s, 2H), 8.09-8.02 (m, 2H), 7.90 (d, J=7.9 Hz, 1H), 7.78-7.64 (m, 3H), 7.44 (d, J=7.2 Hz, 1H), 3.89 (s, 2H), 3.18 (s, 4H), 2.75 (t, J=4.8 Hz, 4H), 2.60 (s, 6H)

Example 21-3-[5-(Aminomethyl)-3-(2-chloro-6-methyl-4-pyridyl)pyrazolo[1,5-a]pyrimidin-2-yl]benzonitrile

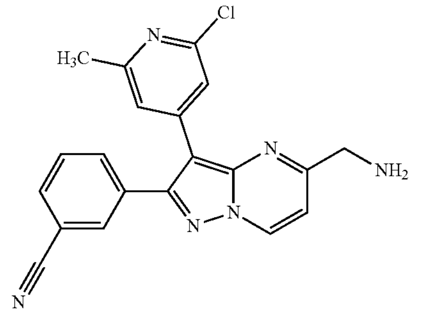 [SMILES: Cc1cc(-c2c(-c3cccc(C#N)c3)nn3ccc(CN)nc23)cc(Cl)n1]

Step 1: tert-Butyl N-[[2-(3-cyanophenyl)pyrazolo[1,5-a]pyrimidin-5-yl]methyl]carbamate

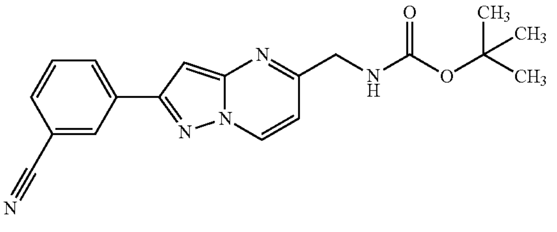 [SMILES: CC(C)(C)OC(=O)NCc1ccn2nc(-c3cccc(C#N)c3)cc2n1]

A mixture of 3-(5-chloropyrazolo[1,5-a]pyrimidin-2-yl)benzonitrile (Intermediate C2) (200 mg, 0.79 mmol), potassium (tert-butoxycarbonylamino)methyltrifluoroborate (223 mg, 0.94 mmol) and cesium carbonate (640 mg, 1.96 mmol) in water (0.50 mL) and 1,4-dioxane (5 mL) was degassed with $N_2$ and treated with $Pd(PPh_3)_2Cl_2$ (56 mg, 0.08 mmol). After stirring at 90° C. overnight, additional $Pd(PPh_3)_2Cl_2$ (56 mg, 0.08 mmol) was added and stirring continued at 100° C. for 3 h. Further potassium (tert-butoxycarbonylamino)methyltrifluoroborate (93 mg, 0.39 mmol) and $Pd(tBusP)_2$ (40 mg, 0.08 mmol) were added sequentially and the mixture was stirred at 100° C. for 3 h. The resulting mixture was partitioned between EtOAc (50 mL) and water (50 mL) and the mixture filtered, washing the collected material with EtOAc (10 mL).

The organic layer was separated, washed with brine (50 mL), dried over $Na_2SO_4$, filtered and concentrated in vacuo to afford the title compound as a black oil.

LC-MS (Method 5A): Rt 2.85 mins; MS m/z 250.1 [M-Boc+H]+

1H NMR (500 MHz, DMSO-d6) δ 9.09 (d, J=7.2 Hz, 1H), 8.48 (s, 1H), 8.42-8.33 (m, 1H), 7.90 (dt, J=7.6, 1.3 Hz, 1H), 7.72 (t, J=7.8 Hz, 1H), 7.67-7.60 (m, 1H), 7.31 (s, 1H), 7.05 (d, J=7.6 Hz, 1H), 4.28 (d, J=6.2 Hz, 2H), 1.37 (s, 9H).

Step 2: Tert-butyl N-[[2-(3-cyanophenyl)-3-iodo-pyrazolo[1,5-a]pyrimidin-5-yl]methyl]carbamate

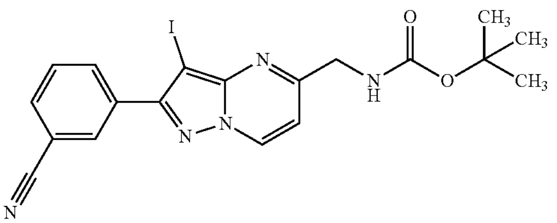 [SMILES: CC(C)(C)OC(=O)NCc1ccn2nc(-c3cccc(C#N)c3)c(I)c2n1]

A solution of tert-butyl N-[[2-(3-cyanophenyl)pyrazolo[1,5-a]pyrimidin-5-yl]methyl]carbamate (step 1)(274 mg, 0.79 mmol), N-iodosuccinimide (265 mg, 1.18 mmol) and MeCN (7 mL) was stirred at room temperature for 3 h. The resulting mixture was adsorbed onto silica and purification by chromatography eluting with a gradient of 1-3% MeOH in DCM afforded the title compound as a brown oil.

LC-MS (Method 5A): Rt 3.18 mins; MS m/z 376.0=[M-Boc+H]+

$^1$H NMR (500 MHz, DMSO-$d_6$) δ 9.13 (d, J=7.1 Hz, 1H), 8.35 (t, J=1.7 Hz, 1H), 8.33-8.27 (m, 1H), 8.03-7.97 (m, 1H), 7.80 (t, J=7.9 Hz, 1H), 7.61 (t, J=6.2 Hz, 1H), 7.05 (d, J=7.2 Hz, 1H), 4.33 (dd, J=6.4, 3.1 Hz, 2H), 1.37 (s, 9H).

Step 3: tert-Butyl N-[[3-(2-chloro-6-methyl-4-pyridyl)-2-(3-cyanophenyl)pyrazolo[1,5-a]pyrimidin-5-yl]methyl]carbamate

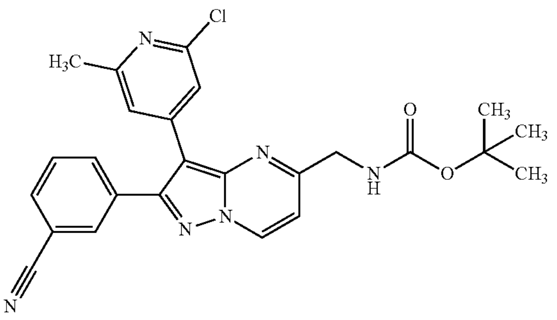 [SMILES: Cc1cc(-c2c(-c3cccc(C#N)c3)nn3ccc(CNC(=O)OC(C)(C)C)nc23)cc(Cl)n1]

A mixture of tert-butyl N-[[2-(3-cyanophenyl)-3-iodo-pyrazolo[1,5-a]pyrimidin-5-yl]methyl]carbamate (step 2) (65 mg, 0.14 mmol), (2-chloro-6-methyl-4-pyridyl)boronic acid (35 mg, 0.21 mmol) and potassium carbonate (38 mg, 0.27 mmol) in water (0.50 mL) and 1,4-dioxane (2 mL) was degassed with $N_2$ and treated with $Pd(tBu_3P)2$ (11 mg, 0.02 mmol). After stirring at 80° C. for 45 mins, the resulting mixture was cooled to room temperature and adsorbed onto silica. Purification by chromatography on silica eluting with a gradient of 1 to 8% MeOH in DCM afforded the title compound as a brown solid.

LC-MS (Method 5A): Rt 3.31 mins; MS m/z 475.0=[M+H]+

$^1$H NMR (500 MHz, DMSO-$d_6$) δ 9.22 (d, J=7.2 Hz, 1H), 8.05 (d, J=1.9 Hz, 1H), 7.99 (dt, J=7.8, 1.4 Hz, 1H), 7.87 (d, J=7.9 Hz, 1H), 7.71 (t, J=7.8 Hz, 1H), 7.60 (t, J=6.1 Hz, 1H), 7.39 (s, 1H), 7.34 (s, 1H), 7.15 (d, J=7.2 Hz, 1H), 4.35 (d, J=6.2 Hz, 2H), 2.41 (s, 3H), 1.41 (s, 9H).

Step 4: 3-[5-(Aminomethyl)-3-(2-chloro-6-methyl-4-pyridyl)pyrazolo[1,5-a]pyrimidin-2-yl]benzonitrile 4M HCl in 1,4-dioxane (0.34 mL, 1.37 mmol) was added to a suspension of tert-butyl N-[[3-(2-chloro-6-methyl-4-pyridyl)-2-(3-cyanophenyl)pyrazolo[1,5-a]pyrimidin-5-yl]methyl]carbamate (step 3)(65 mg, 0.14 mmol) in MeCOH (0.50 mL) and the mixture stirred at room temperature for 2 h. The crude reaction mixture was concentrated in vacuo and purification by C18 reverse phase chromatography eluting with a gradient of 5-45% MeCN in water (+0.1 wt % $NH_4OH$) afforded the title compound as an off-white solid.

LC-MS (Method 8B): Rt 4.01 mins; MS m/z 375.2/377.2=[M+H]+

$^1$H NMR (500 MHz, DMSO-$d_6$) δ 9.21 (d, J=7.2 Hz, 1H), 8.04 (t, J=1.7 Hz, 1H), 7.99 (dt, J=7.7, 1.4 Hz, 1H), 7.87 (dt, J=7.9, 1.4 Hz, 1H), 7.71 (t, J=7.8 Hz, 1H), 7.39-7.37 (m, 2H), 7.37-7.35 (m, 1H), 3.92 (s, 2H), 2.41 (s, 3H), 2.20 (br s, 2H).

Example 22-3-[3-(2-Chloro-6-methyl-4-pyridyl)-5-(3-hydroxy-3-methyl-butyl)pyrazolo [1,5-a]pyrimidin-2-yl]benzonitrile

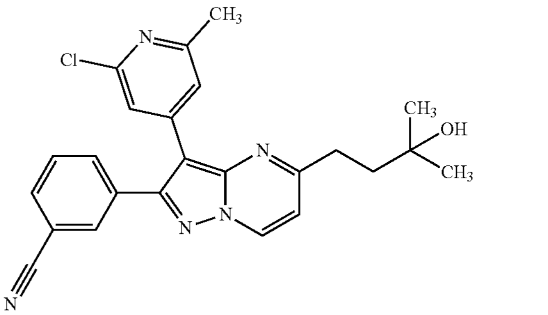 [SMILES: Cc1cc(-c2c(-c3cccc(C#N)c3)nn3ccc(CCC(C)(C)O)nc23)cc(Cl)n1]

Step 1: 3-[5-(3-Hydroxy-3-methyl-but-1-ynyl)pyrazolo[1.5-a]pyrimidin-2-yl]benzonitrile

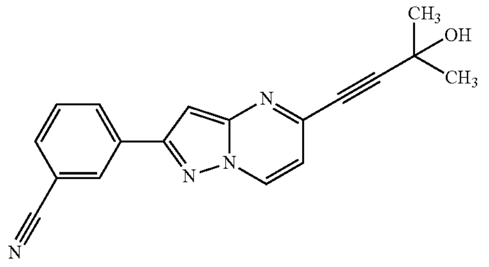 [SMILES: CC(C)(O)C#Cc1ccn2nc(-c3cccc(C#N)c3)cc2n1]

A mixture of 2-methylbut-3-yn-2-ol (0.23 mL, 2.36 mmol), 3-(5-chloropyrazolo[1,5-a]pyrimidin-2-yl)benzonitrile (Intermediate C2) (300 mg, 1.18 mmol) and DABCO (0.36 mL, 2.36 mmol) in DMF (12 mL) was degassed with $N_2$. CuI (45 mg, 0.24 mmol) and $PdCl_2(PPh_3)_2$(82.68 mg, 0.12 mmol) were added and the reaction mixture stirred at room temperature for 18 h. The resulting mixture was added dropwise to stirring water (100 mL) and after stirring for 5 mins the precipitate was collected by filtration. Purification by chromatography on silica eluting with a gradient of 0 to 5% MeOH in DCM afforded the title compound as an orange solid.

LC-MS (Method 5B): Rt 2.73 mins; MS m/z 303.1=[M+H]+

$^1$H NMR (500 MHz, DMSO-d6) δ 9.13 (d, J=7.1 Hz, 1H), 8.49 (s, 1H), 8.38 (d, J=7.9 Hz, 1H), 7.91 (d, J=7.7 Hz, 1H), 7.72 (t, J=7.8 Hz, 1H), 7.40 (s, 1H), 7.06 (d, J=7.2 Hz, 1H), 5.73 (s, 1H), 1.51 (s, 6H).

Step 2: 3-[5-(3-Hydroxy-3-methyl-butyl)pyrazolo[1,5-a]pyrimidin-2-yl]benzonitrile

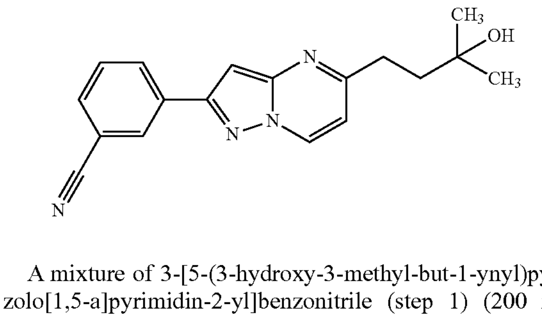

A mixture of 3-[5-(3-hydroxy-3-methyl-but-1-ynyl)pyrazolo[1,5-a]pyrimidin-2-yl]benzonitrile (step 1) (200 mg, 0.66 mmol) and 10% Pd on carbon (70 mg, 0.07 mmol) in MeOH (15 mL) was placed under a hydrogen atmosphere and stirred at room temperature for 1.5 h. Further portions of 10% Pd on carbon [2× (140 mg, 0.13 mmol)]were added and stirring continued for 4.5 h in total. The resulting mixture was placed under nitrogen and filtered through Celite® (filter material), washing with MeOH (3×20 mL). The filtrate was concentrated in vacuo and purification by chromatography on silica eluting with a gradient of 0 to 10% MeOH in DCM followed by chromatography on silica eluting with a gradient of 0 to 2% MeOH in DCM afforded the title compound as an orange solid.

LC-MS (Method 5B): Rt 2.57 mins; MS m/z 307=[M+H]+

$^1$H NMR (500 MHz, DMSO-d6) δ 8.99 (d, J=7.1 Hz, 1H), 8.44 (s, 1H), 8.35 (dd, J=7.9, 1.5 Hz, 1H), 7.88 (dd, J=7.8, 1.4 Hz, 1H), 7.71 (t, J=7.8 Hz, 1H), 7.23 (s, 1H), 6.99 (d, J=7.2 Hz, 1H), 4.32 (s, 1H), 2.94-2.73 (m, 2H), 1.87-1.74 (m, 2H), 1.16 (s, 6H).

Step 3: 3-[3-Bromo-5-(3-hydroxy-3-methyl-butyl)pyrazolo[1,5-a]pyrimidin-2-yl]benzonitrile

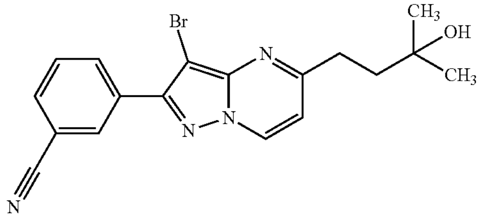 [SMILES: CC(C)(O)CCc1ccn2nc(-c3cccc(C#N)c3)c(Br)c2n1]

To a solution of 3-[5-(3-hydroxy-3-methyl-butyl)pyrazolo[1,5-a]pyrimidin-2-yl]benzonitrile (step 2)(130 mg, 0.42 mmol) in DMF (2 mL) was added NBS (76 mg, 0.42 mmol) and the reaction mixture stirred at room temperature for 1 h. The resulting mixture was added dropwise to stirring water (20 mL) and the precipitate was collected by filtration to afford the title compound as an orange solid.

LC-MS (Method 5B): Rt 3.01 mins; MS m/z 385.0/387.0=[M+H]+

$^1$H NMR (500 MHz, DMSO-d6) δ 9.08 (d, J=7.2 Hz, 1H), 8.36 (s, 1H), 8.32 (d, J=8.0 Hz, 1H), 7.99 (d, J=7.8 Hz, 1H), 7.79 (t, J=7.9 Hz, 1H), 7.13 (d, J=7.1 Hz, 1H), 4.36 (s, 1H), 2.96-2.88 (m, 2H), 1.87-1.79 (m, 2H), 1.17 (s, 6H).

Step 4: 3-[3-(2-Chloro-6-methyl-4-pyridyl)-5-(3-hydroxy-3-methyl-butyl)pyrazolo[1,5-a]pyrimidin-2-yl]benzonitrile A mixture of 3-[3-bromo-5-(3-hydroxy-3-methyl-butyl)pyrazolo[1,5-a]pyrimidin-2-yl]benzonitrile (step 3) (115 mg, 0.30 mmol), 2-chloro-6-methyl-4-(4,4,5,5-tetramethyl-1,3,2-dioxaborolan-2-yl)pyridine (79 mg, 0.31 mmol) and $K_2CO_3$ (124 mg, 0.90 mmol) in 1,4-dioxane (4 mL) and water (1 mL) was degassed under a flow of $N_2$. $Pd(tBu_3P)_2$ (15 mg, 0.03 mmol) was added and the reaction mixture heated to 80° C. for 30 mins. The reaction mixture cooled to room temperature and added dropwise to stirring water (40 mL). The precipitate was collected by filtration and purified by chromatography on silica eluting with a gradient of 0 to 5% MeOH in DCM. Further purification by C18 reverse phase chromatography eluting with a gradient of 40 to 80% MeCN in water (+0.1 wt % $NH_4OH$) afforded the title compound as a beige solid.

LC-MS (Method 8B): Rt 4.71 mins; MS m/z 432.3/434.2=[M+H]+

$^1$H NMR (500 MHz, DMSO-d6) δ 9.14 (d, J=7.1 Hz, 1H), 8.03 (s, 1H), 7.98 (d, J=7.7 Hz, 1H), 7.86 (d, J=7.8 Hz, 1H), 7.70 (t, J=7.8 Hz, 1H), 7.40 (s, 1H), 7.33 (s, 1H), 7.20 (d, J=7.2 Hz, 1H), 4.34 (s, 1H), 2.99-2.91 (m, 2H), 2.39 (s, 3H), 1.90-1.82 (m, 2H), 1.17 (s, 6H).

Example 23-3-[3-[2-(Difluoromethyl)-6-methyl-4-pyridyl]-5-[(2-hydroxy-2-methyl-propyl)amino]pyrazolo[1,5-a]pyrimidin-2-yl]benzonitrile

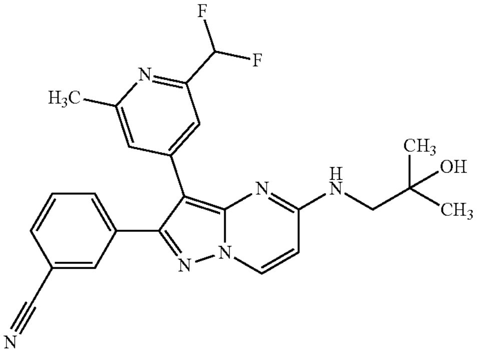 [SMILES: Cc1cc(-c2c(-c3cccc(C#N)c3)nn3ccc(NCC(C)(C)O)nc23)cc(C(F)F)n1]

Step 1: 3-[5-[(2-Hydroxy-2-methyl-propyl)amino]-3-iodo-pyrazolo[1,5-a]pyrimidin-2-yl]benzonitrile

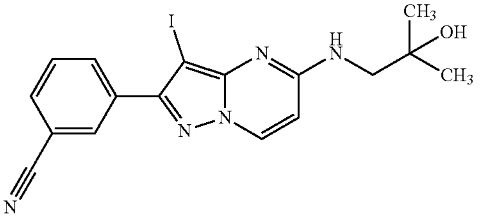 [SMILES: CC(C)(O)CNc1ccn2nc(-c3cccc(C#N)c3)c(I)c2n1]

1-Amino-2-methyl-propan-2-ol (0.08 mL, 0.85 mmol) was added to a suspension of DIPEA (0.15 mL, 0.85 mmol) and 3-(5-chloro-3-iodo-pyrazolo[1,5-a]pyrimidin-2-yl)benzonitrile (Intermediate C3) (250 mg, 0.66 mmol) in NMP (3 mL) and stirred at 60° C. overnight. The resulting mixture was allowed to cool to room temperature and added dropwise to stirring water (20 mL). EtOAc (50 mL) was added and the organic layer was separated. The aqueous portion was further extracted with EtOAc (20 mL) and the combined organic extracts were washed with a 1:1 mixture of brine and water (2×20 mL), brine (20 mL), dried over $Na_2SO_4$, filtered and concentrated in vacuo to afford the title compound as a brown oil.

LC-MS (Method SB): Rt 2.86 mins; MS m/z 434.1=[M+H]+

$^1$H NMR (500 MHz, DMSO-$d_6$) δ 8.50 (d, J=7.6 Hz, 1H), 8.27 (d, J=1.6 Hz, 1H), 8.23 (d, J=7.9 Hz, $^1$H), 7.92 (d, J=7.7 Hz, 1H), 7.73 (t, J=7.8 Hz, 1H), 7.70-7.63 (m, 1H), 6.55 (d, J=7.6 Hz, 1H), 4.70 (s, 1H), 3.41 (d, J=5.5 Hz, 2H), 1.18 (s, 6H).

Step 2: 3-[3-[2-Difluoromethyl)-6-methyl-4-pyridyl]-5-[(2-hydroxy-2-methyl-propyl)amino]pyrazolo[1,5-a]pyrimidin-2-yl]benzonitrile A mixture of 3-[5-[(2-hydroxy-2-methyl-propyl)amino]-3-iodo-pyrazolo[1,5-a]pyrimidin-2-yl]benzonitrile (step 1) (71 mg, 0.16 mmol) 2-(difluoromethyl)-6-methyl-4-(4,4,5,5-tetramethyl-1,3,2-dioxaborolan-2-yl)pyridine (66 mg, 0.25 mmol) and potassium carbonate (45 mg, 0.33 mmol) in water (0.50 mL) and 1,4-dioxane (2 mL) was degassed with N2 before $Pd(tBu_3P)_2$ (12.56 mg, 0.02 mmol) was added and the mixture stirred at 80° C. for 1 h. After cooling to room temperature, the mixture was adsorbed onto silica and purification by chromatography eluting with a gradient of 2 to 8% MeOH in DCM followed by trituration with diethyl ether (5 mL) afforded the title compound as a light brown solid.

LC-MS (Method 15B): Rt 7.48 mins; MS m/z 449.3=[M+H]+

$^1$H NMR (500 MHz, DMSO-$d_6$) δ 8.59 (d, J=7.6 Hz, 1H), 7.99-7.94 (m, 2H), 7.92 (t, J=6.1 Hz, 1H), 7.84 (d, J=7.8 Hz, 1H), 7.76 (s, 1H), 7.69 (t, J=7.7 Hz, 1H), 7.40 (s, 1H), 6.81 (t, J=55.3 Hz, 1H), 6.62 (d, J=7.6 Hz, 1H), 4.61 (s, 1H), 3.45 (d, J=5.9 Hz, 2H), 2.40 (s, 3H), 1.19 (s, 6H).

The compounds of the following tabulated Examples (Table Ex23) were prepared analogously to Example 23 from 3-(5-chloro-3-iodo-pyrazolo[1,5-a]pyrimidin-2-yl)benzonitrile (Intermediate C3) and the appropriate amine and boronic acid or boronate ester.

TABLE Ex23

| Ex. | Structure and Name | Retention Time, [M + H]+, 1H NMR |
|---|---|---|
| 23.1 | 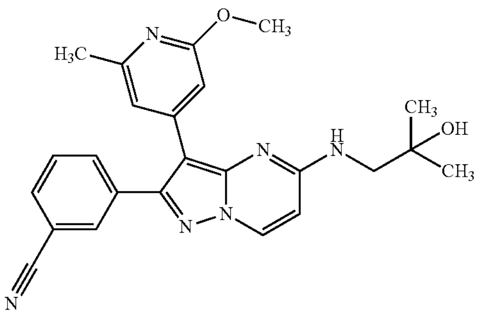 3-[5-[(2-Hydroxy-2-methyl-propyl)amino]-3-(2-methoxy-6-methyl-4-pyridyl)pyrazolo[1,5-a]pyrimidin-2-yl]benzonitrile | LC-MS (Method 15B): Rt 7.51 mins; MS m/z 429.3 = [M + H]+ $^1$H NMR (500 MHz, DMSO-$d_6$) δ 8.55 (d, J = 7.6 Hz, 1H), 7.95-7.90 (m, 2H), 7.82-7.75 (m, 2H), 7.66 (t, J = 7.8 Hz, 1H), 7.02 (s, 1H), 6.63-6.55 (m, 2H), 4.63 (s, 1H), 3.78 (s, 3H), 3.41 (d, J = 5.3 Hz, 2H), 2.30 (s, 3H), 1.19 (s, 6H). |

TABLE Ex23-continued

| Ex. | Structure and Name | Retention Time, [M + H]+, 1H NMR |
|---|---|---|
| 23.2 | 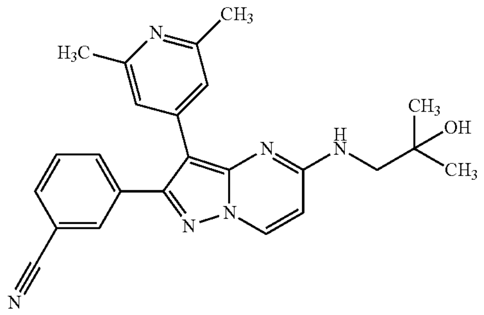 3-[3-(2,6-Dimethyl-4-pyridyl)-5-[(2-hydroxy-2-methyl-propyl)amino]pyrazolo[1,5-a]pyrimidin-2-yl]benzontrile | LC-MS (Method 15B): Rt 6.95 mins; MS m/z 413.3 = [M + H]+ $^1$H NMR (500 MHz, DMSO-d6) δ 8.56 (d, J = 7.5 Hz, 1H), 7.95-7.90 (m, 2H), 7.83-7.77 (m, 2H), 7.66 (t, J = 7.7 Hz, 1H), 7.13 (s, 2H), 6.58 (d, J = 7.6 Hz, 1H), 4.63 (s, 1H), 3.42 (d, J = 6.0 Hz, 2H), 2.33 (s, 6H), 1.19 (s, 6H). |
| 23.3 | 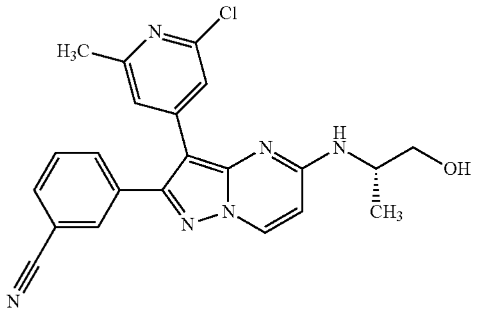 3-[3-(2-Chloro-6-methyl-4-pyridyl)-5-[[(1S)-2-hydroxy-1-methyl-ethyl]amino]pyrazolo[1,5-a]pyrimidin-2-yl]benzonitrile | LC-MS (Method 15B): Rt 7.30 mins; MS m/z 419.1 = [M + H]+ $^1$H NMR (500 MHz, DMSO-$d_6$) δ 8.58 (d, J = 7.5 Hz, 1H), 7.99-7.93 (m, 2H), 7.87-7.80 (m, 2H), 7.69 (t, J = 7.8 Hz, 1H), 7.34 (s, 2H), 6.50 (d, J = 7.6 Hz, 1H), 4.87 (s, 1H), 4.15-4.02 (m, 1H), 3.55 (d, J = 5.2 Hz, 2H), 2.34 (s, 3H), 1.24 (d, J = 6.6 Hz, 3H). |
| | Prepared via: 3-[3-iodo-5-[[(1S)-2-hydroxy-1-methyl-ethyl]amino]pyrazolo[1,5-a]pyrimidin-2-yl]benzonitrile 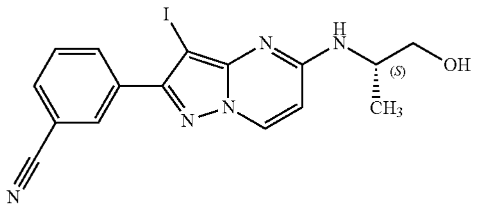 | Intermediate data: LC-MS (Method 5A): Rt 2.56 mins; MS m/z 420.0 = [M + H]+ $^1$H NMR (500 MHz, DMSO-$d_6$) δ 8.49 (d, J = 7.5 Hz, 1H), 8.29-8.26 (m, 1H), 8.23 (dt, J = 8.0, 1.4 Hz, 1H), 7.92 (dt, J = 7.8, 1.4 Hz, 1H), 7.73 (t, J = 7.8 Hz, 1H), 7.60 (d, J = 7.7 Hz, 1H), 6.39 (d, J = 7.5 Hz, 1H), 4.83 (t, J = 5.5 Hz, 1H), 4.19 (br s, 1H), 3.60-3.44 (m, 2H), 1.19 (d, J = 6.6 Hz, 3H). |

TABLE Ex23-continued

| Ex. | Structure and Name | Retention Time, [M + H]+, 1H NMR |
|---|---|---|
| 23.4 | 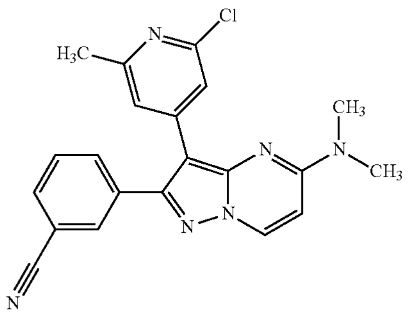<br>3-[3-(2-Chloro-6-methyl-4-pyridyl)-5-(dimethylamino)pyrazolo[1,5-a]pyrimidin-2-yl]benzonitrile | LC-MS (Method 15B): Rt 8.63 mins; MS m/z 389.1/391.0 = [M + H]+<br>$^{1}$H NMR (500 MHz, DMSO-$d_6$) δ 8.77 (d, J = 7.9 Hz, 1H), 8.01-7.94 (m, 2H), 7.85 (dt, J = 7.8, 1.5 Hz, 1H), 7.70 (t, J = 7.8 Hz, 1H), 7.39 (d, J = 1.3 Hz, 1H), 7.31 (d, J = 1.3 Hz, 1H), 6.80 (d, J = 7.9 Hz, 1H), 3.22 (s, 6H), 2.34 (s, 3H). |
| | Prepared via:<br>3-[5-(dimethylamino)-3-iodo-pyrazolo[1,5-a]pyrimidin-2-yl]benzonitrile<br>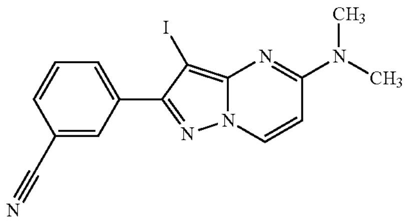<br>(Reaction by-product from Example 24 step 1) | Intermediate data:<br>LC-MS (Method 5A): Rt 3.24 mins; MS m/z 390.0 = [M + H]+<br>$^{1}$H NMR (500 MHz, DMSO-$d_6$) δ 8.69 (d, J = 7.8 Hz, 1H), 8.31-8.28 (m, 1H), 8.28-8.24 (m, 1H), 7.99-7.91 (m, 1H), 7.75 (t, J = 7.8 Hz, 1H), 6.71 (d, J = 7.8 Hz, 1H), 3.20 (s, 6H). |

Example 24-3-[3-(2-Chloro-6-methyl-4-pyridyl)-5-(4-piperldyloxy)pyrazolo[1,5-a]pyrimidin-2-yl]benzonitrile

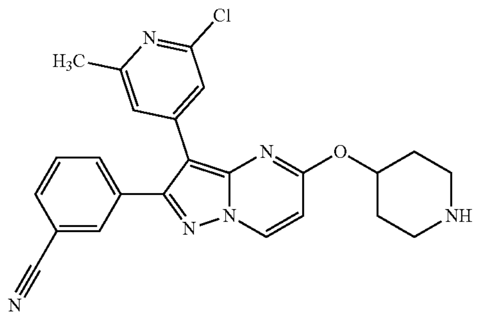 [SMILES: Cc1cc(-c2c(-c3cccc(C#N)c3)nn3ccc(OC4CCNCC4)nc23)cc(Cl)n1]

Step 1: tert-Butyl 4-[2-(3-cyanophenyl)-3-iodo-pyrazolo[1,5-a]pyrimidin-5-yl]oxypiperidine-1-carboxylate

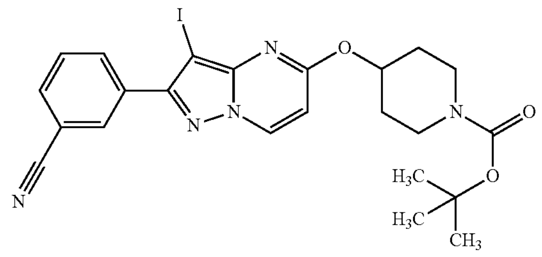 [SMILES: CC(C)(C)OC(=O)N1CCC(Oc2ccn3nc(-c4cccc(C#N)c4)c(I)c3n2)CC1]

Sodium hydride (14 mg, 0.34 mmol) was added to a solution of tert-butyl 4-hydroxypiperidine-1-carboxylate (69 mg, 0.34 mmol) in THF (1 mL) and the mixture was stirred at room temperature for 45 mins. 3-(5-Chloro-3-iodo-pyrazolo[1,5-a]pyrimidin-2-yl)benzonitrile (Intermediate C3) (100 mg, 0.26 mmol) was added and stirring continued at room temperature overnight. MeOH (5 mL) was added to quench the reaction and the resulting mixture was concentrated in vacuo. Purification by chromatography on silica eluting with a gradient of 0 to 100% EtOAc in petrol afforded the title compound as a yellow solid.

LC-MS (Method 5A): Rt 3.99 mins; MS m/z 546.1=[M+H]+

$^1$H NMR (500 MHz, DMSO-$d_6$) δ 8.99 (d, J=7.4 Hz, 1H), 8.32 (t, J=1.7 Hz, 1H), 8.28-8.22 (m, 1H), 7.98 (d, J=7.7 Hz, 1H), 7.78 (t, J=7.9 Hz, 1H), 6.67 (d, J=7.4 Hz, 1H), 5.43-5.29 (m, 1H), 3.73-3.62 (m, 2H), 3.45-3.32 (m, 2H), 2.13-2.02 (m, 2H), 1.78-1.62 (m, 2H), 1.46-1.33 (m, 9H).

Step 2: tert-Butyl 4-[3-(2-chloro-6-methyl-4-pyridyl)-2-(3-cyanophenyl)pyrazolo[1,5-a]pyriimidin-5-yl]oxypiperidine-1-carboxylate

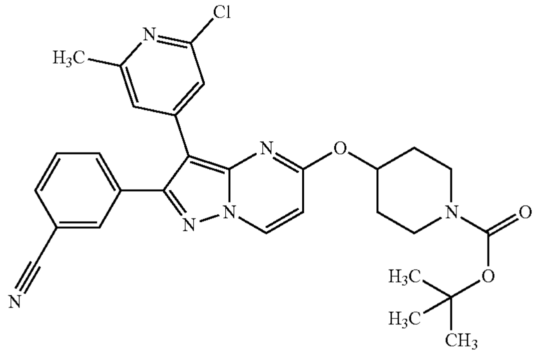 [SMILES: Cc1cc(-c2c(-c3cccc(C#N)c3)nn3ccc(OC4CCN(C(=O)OC(C)(C)C)CC4)nc23)cc(Cl)n1]

A mixture of tert-butyl 4-[2-(3-cyanophenyl)-3-iodo-pyrazolo[1,5-a]pyrimidin-5-yl]oxypiperidine-1-carboxylate (step 1) (95 mg, 0.17 mmol), (2-chloro-6-methyl-4-pyridyl) boronic acid (44.92 mg, 0.26 mmol) and $K_2CO_3$ (48 mg, 0.35 mmol)) in water (0.50 mL) and 1,4-dioxane (2 mL) was degassed with $N_2$ before $Pd(tBu_3P)_2$ (13.4 mg, 0.03 mmol) was added and the mixture stirred at 80° C. for 1 h. The resulting mixture was allowed to cool to room temperature and adsorbed onto silica. Purification by chromatography on silica eluting with a gradient of 0 to 10% MeOH in DCM afforded the title compound as a yellow solid.

LC-MS (Method 5A): Rt 3.99 mins; MS m/z 545.2=[M+H]+

$^1$H NMR (500 MHz, DMSO-$d_6$) δ 9.08 (d, J=7.5 Hz, 1H), 8.05-8.02 (m; 1H), 7.99 (d, J=7.8 Hz, 1H), 7.87 (dt, J=7.9, 1.5 Hz, 1H), 7.72 (t, J=7.8 Hz, 1H), 7.33 (s, 1H), 7.32-7.30 (m, 1H), 6.78 (d, J=7.5 Hz, 1H), 5.34-5.16 (m, 1H), 3.88-3.76 (m, 2H), 3.73-3.58 (m, 2H), 2.40 (s, 3H), 2.21-2.11 (m, 2H), 1.76-1.66 (m, 2H), 1.43 (s, 9H).

Step 3: 3-[3-(2-Chloro-6-methyl-4-pyridyl)-5-(4-piperidyloxy)pyrazolo{1,5-a]pyrimidin-2-yl]benzonitrile 4M HCl in 1,4-dioxane (0.44 mL, 1.75 mmol) was added to a suspension of tert-butyl 4-[3-(2-chloro-6-methyl-4-pyridyl)-2-(3-cyanophenyl)pyrazolo[1,5-a]pyrimidin-5-yl] oxypiperidine-1-carboxylate (step 2) (95 mg, 0.17 mmol) in MeOH (0.50 mL) and the mixture was stirred at room temperature for 1 h. The resulting mixture was concentrated in vacuo. Purification by C18 reverse phase chromatography eluting with a gradient of 10 to 45% MeCN in water (+0.1 wt % formic acid) followed by 10 to 70% MeCN in water (+0.1 wt % $NH_4OH$) afforded the title compound as a yellow solid.

LC-MS (Method 158): Rt 9.36 mins; MS m/z 445.2/447.0=[M+H]+

$^1$H NMR (500 MHz, DMSO-$d_6$) δ 9.06 (d, J=7.5 Hz, 1H), 8.06-8.02 (m, 1H), 8.00 (dt, J=7.7, 1.4 Hz, 1H), 7.88 (dt, J=7.9, 1.5 Hz, 1H), 7.72 (t, J=7.8 Hz, 1H), 7.38 (d, J=1.2 Hz, 1H), 7.28 (d, J=1.2 Hz, 1H), 6.76 (d, J=7.5 Hz, 1H), 5.19-5.06 (m, 1H), 3.03 (dt, J=12.8, 4.0 Hz, 2H), 2.70-2.59 (m, 2H), 2.38 (s, 3H), 2.17-2.07 (m, 2H), 1.65-1.51 (m, 2H). NH proton not observed.

The compounds of the following tabulated Examples (Table Ex24) were prepared analogously to Example 24 from 3-(5-chloro-3-iodo-pyrazolo[1,5-a]pyrimidin-2-yl) benzonitrile (Intermediate C3)(step 1) and the appropriate alcohol.

TABLE EX24

| Ex. | Structure and Name | Retention Time, [M + H]+, 1H NMR |
|---|---|---|
| 24.1 | 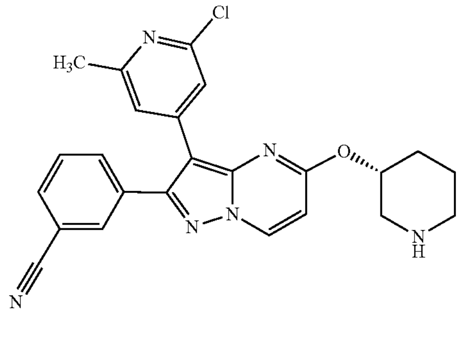 [SMILES: Cc1cc(-c2c(-c3cccc(C#N)c3)nn3ccc(O[C@@H]4CCCNC4)nc23)cc(Cl)n1] 3-[3-(2-Chloro-6-methyl-4-pyridyl)-5-[[(3R)-3-piperidyl]oxy]pyrazolo[1,5-a]pyrimidin-2-yl]benzonitrile | LC-MS (Method 8B): Rt 4.89 mins; MS m/z 445.2 / 447.2 = [M + H]+ $^1$H NMR (500 MHz, DMSO-d6) δ 9.05 (d, J = 7.4 Hz, 1H), 8.03 (t, J = 1.7 Hz, 1H), 7.99 (dt, J = 7.7, 1.4 Hz, 1H), 7.87 (dt, J = 7.9, 1.5 Hz, 1H), 7.72 (t, J = 7.8 Hz, 1H), 7.34 - 7.30 (m, 2H), 6.75 (d, J = 7.5 Hz, 1H), 5.06 - 4.95 (m, 1H), 3.24 - 3.17 (m, 1H), 2.81 (dt, J = 12.4, 4.2 Hz, 1H), 2.70 (dd, J = 11.9, 8.4 Hz, 1H), 2.57 - 2.46 (m, 1H), 2.40 (s, 3H), 2.32 - 2.22 (m, 1H), 1.83 - 1.69 (m, 1H), 1.66 - 1.57 (m, 1H), 1.57 - 1.47 (m, 1H). |
|  | Prepared via: | Intermediate Data: |

TABLE EX24-continued

| Ex. | Structure and Name | Retention Time, [M + H]+, 1H NMR |
|---|---|---|
| | 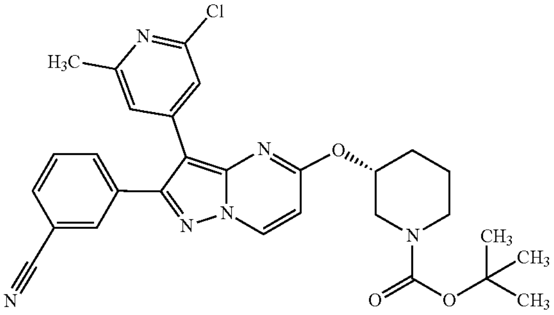 [SMILES: Cc1cc(-c2c(-c3cccc(C#N)c3)nn3ccc(O[C@@H]4CCCN(C(=O)OC(C)(C)C)C4)nc23)cc(Cl)n1]<br>tert-Butyl (3R)-3-[3-(2-chloro-6-methyl-4-pyridyl)-2-(3-cyanophenyl)pyrazolo[1,5-a]pyrimidin-5-yl]oxypiperidine-1-carboxylate | LC-MS (Method 5A): Rt 4.08 mins; MS m/z 545.3 = [M + H]+<br>$^{1}$H NMR (500 MHz, DMSO-d6) δ 9.09 (br s, 1H), 8.03 (s, 1H), 7.99 (dd, J = 7.7, 1.5 Hz, 1H), 7.86 (d, J = 7.9 Hz, 1H), 7.71 (t, J = 7.8 Hz, 1H), 7.33 - 7.27 (m, 2H), 6.76 (br s, 1H), 5.10 (s, 1H), 4.17 - 4.07 (m, 1H), 3.70 - 3.58 (m, 1H), 3.53 - 3.41 (m, 1H), 3.17 - 3.09 (m, 1H), 2.57 - 2.45 (m, 1H), 2.39 (s, 3H), 2.13 - 2.00 (m, 1H), 1.97 - 1.87 (m, 1H), 1.85 - 1.73 (m, 1H), 1.63 - 1.35 (m, 9H). |
| | Prepared via: | Intermediate data: |
| | 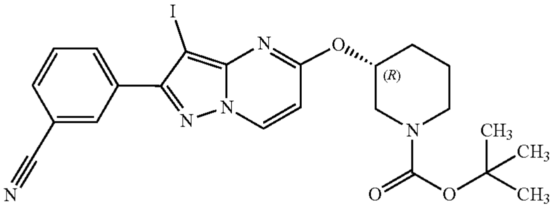<br>tert-butyl (3R)-3-[2-(3- cyanophenyl)-3-iodo-pyrazolo[1,5-a]pyrimidin-5-yl]oxypiperdine-1-carboxylate | LC-MS (Method 3B): Rt 3.10 mins; MS m/z 546.1 = [M + H]+<br>$^{1}$H NMR (500 MHz, DMSO-$d_6$) δ 9.09-9.01 (m, 1H), 8.38 (s, 1H), 8.33 (d, J = 7.9 Hz, 1H), 8.03 (dt, J = 7.7, 1.4 Hz, 1H), 7.83 (t, J = 7.8 Hz, 1H), 6.79 - 6.57 (m, 1H), 5.33 - 5.14 (m, 1H), 3.88 - 3.69 (m, 2H), 3.26-3.10 (m, 1H),2.84 (br s, 1H), 2.06 - 1.93 (m, 1H), 1.91 - 1.79 (m, 1H), 1.72 - 1.64 (m, 1H), 1.62 1.53 (m, 1H), 1.45 (s, 9H). |
| 24.2 | 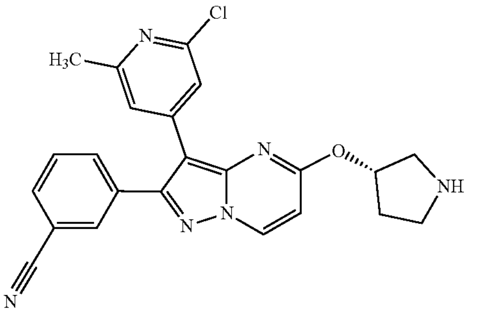 [SMILES: Cc1cc(-c2c(-c3cccc(C#N)c3)nn3ccc(O[C@H]4CCNC4)nc23)cc(Cl)n1]<br>3-[3-(2-Chloro-6-methyl-4-pyridyl)-5-[(3S)-pyrrolidin-3-yl]oxy-pyrazolo[1,5-a]pyrimidin-2-yl]benzonitrile | LC-MS (Method 8B): Rt 4.59 mins; MS m/z 431.2/433.2<br>(d, J = 7.5 Hz, 1H), 8.05 - 7.95 (m, 2H), 7.86 (dt, J = 8.0, 1.4 Hz, 1H), 7.72 (t, J = 7.8 Hz, 1H), 7.37 (s, 1H), 7.31 (s, 1H), 6.75 (d, J = 7.5 Hz, 1H), 5.46-5.35 (m, 1H), 3.20 (dd, J = 12.6, 5.7 Hz, 1H), 3.01 (dd, J = 12.5, 2.5 Hz, 1H), 2.98 - 2.88 (m, 1H), 2.83 (ddd, J = 10.7, 7.9, 5.0 Hz, 1H), 2.39 (s, 3H), 2.24 - 2.07 (m, 1H), 2.01 - 1.87 (m, 1H). NH proton not observed. |
| | Prepared via: | Intermediate Data: |
| | 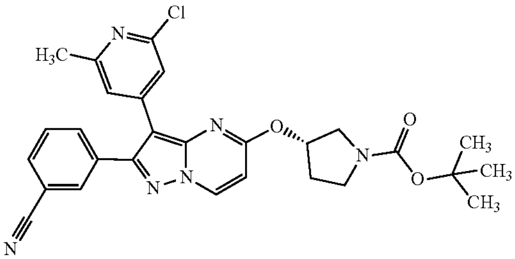 [SMILES: Cc1cc(-c2c(-c3cccc(C#N)c3)nn3ccc(O[C@H]4CCN(C(=O)OC(C)(C)C)C4)nc23)cc(Cl)n1]<br>tert-Butyl (3S)-3-[3-(2-chloro-6-methyl-4-pyridyl)-2-(3-cyanophenyl) pyrazolo[1,5-a]pyrimidin-5-yl]oxypyrrolidine-1-carboxylate | LC-MS (Method 3B): Rt 2.95 mins; MS m/z 531.3 = [M + H]+<br>$^{1}$H NMR (500 MHz, DMSO-d6) δ 9.09 (d, J = 7.4 Hz, 1H), 8.03 (d, J = 1.7 Hz, 1H), 7.99 (dt, J = 7.7, 1.4 Hz, 1H), 7.87 (dt, J = 8.0, 1.4 Hz, 1H), 7.72 (t, J = 7.8 Hz, 1H), 7.37 - 7.28 (m, 2H), 6.81 (d, J = 7.4 Hz, 1H), 5.56 (s, 1H), 3.83 - 3.65 (m, 1H), 3.54 - 3.45 (m, 1H), 3.14 - 3.04 (m, 1H), 2.41 (s, 3H), 2.30 - 2.22 (m, 2H), 1.76 - 1.66 (m, 1H), 1.40 (s, 9H). |

TABLE EX24-continued

| Ex. | Structure and Name | Retention Time, [M + H]+, 1H NMR |
| --- | --- | --- |
| 24.3 | 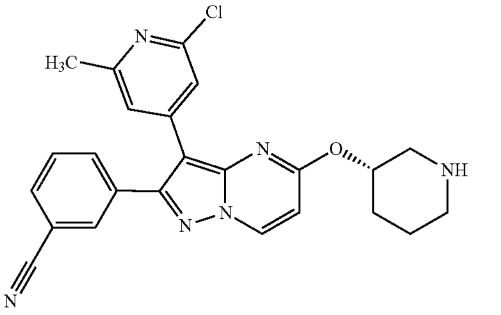 [SMILES: Cc1cc(-c2c(-c3cccc(C#N)c3)nn3ccc(O[C@H]4CCCNC4)nc23)cc(Cl)n1]<br>3-[3-(2-Chloro-6-methyl-4-pyridyl)-5-[[(3S)-3-piperidyl]oxy]pyrazolo[1,5-a]pyrimidin-2-yl]benzonitrile | LC-MS (Method 8B): Rt 4.80 mins; MS m/z 445.2 / 447.2 = [M + H]+<br>1H NMR (400 MHz, DMSO-d6) δ 9.05 (d, J = 7.5 Hz, 1H), 8.06-7.97 (m, 2H), 7.87 (dt, J = 7.9, 1.5 Hz, 1H), 7.72 (t, J = 7.8 Hz, 1H), 7.36 − 7.30 (m, 2H), 6.75 (d, J = 7.5 Hz, 1H), 5.05 − 4.95 (m, 1H), 3.25 − 3.17 (m, 1H), 2.89 − 2.78 (m, 1H), 2.70 (dd, J = 11.9, 8.4 Hz, 1H), 2.56 − 2.49 (m, 1H), 2.40 (s, 3H), 2.32 − 2.22 (m, 1H), 1.81 − 1.69 (m, 1H), 1.70 − 1.42 (m, 2H). NH proton not observed. |
| | Prepared via: | Intermediate Data: |
| | 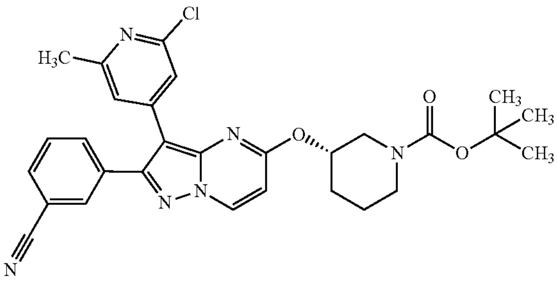 [SMILES: Cc1cc(-c2c(-c3cccc(C#N)c3)nn3ccc(O[C@H]4CCCN(C(=O)OC(C)(C)C)C4)nc23)cc(Cl)n1]<br>tert-Butyl (3S)-3-[3-(2-chloro-6-methyl-4-pyridyl)-2-(3-cyanophenyl)pyrazolo[1,5-a]pyrimidin-5-yl]oxypiperidine-1-carboxylate | LC-MS (Method 3B): Rt 3.06 mins; MS m/z 545.3 = [M + H]+<br>1H NMR (500 MHz, DMSO-d6) δ 9.09 (br s, 1H), 8.03 (s, 1H), 7.99 (dt, J = 7.8, 1.4 Hz, 1H), 7.86 (d, J = 7.9 Hz, 1H), 7.71 (t, J = 7.8 Hz, 1H), 7.30 (s, 2H), 6.75 (brs, 1H), 5.10 (brs, 1H), 4.11 (br s, 1H), 3.69 − 3.58 (m, 1H), 3.49 (br s, 1H), 3.15 (br s, 1H), 2.59 − 2.49 (m, 1H), 2.39 (s, 3H), 2.09 (br s, 1H), 1.91 (br s, 1H), 1.87 − 1.74 (m, 1H), 1.39 (s, 9H). |
| | Prepared via: | Intermediate data: |
| | 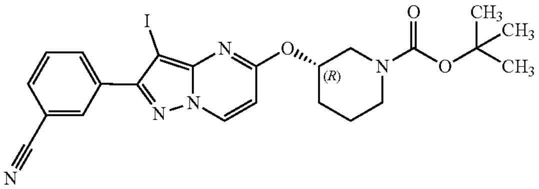<br>tert-butyl (3S)-3-(2-(3-cyanophenyl)-3-iodo-pyrazolo[1,5-a]pyrimidin-5-yl]oxypiperidine-1-carboxylate | LC-MS (Method 5A): Rt 3.92 mins; MS m/z 546.1 = [M + H]+<br>1H NMR (500 MHz, DMSO-d6) δ 9.06 (br s, 1H), 8.38 (s, 1H), 8.33 (d, J = 7.9 Hz, 1H), 8.03 (dt, J = 7.7, 1.4 Hz, 1H), 7.83 (t, J = 7.9 Hz, 1H), 6.80 − 6.58 (m, 1H), 5.21 (br s, 1H), 3.89 − 3.70 (m, 2H), 3.22 − 3.10 (m, 1H), 2.84 (br s, 1H), 2.09 − 1.97 (m, 1H), 1.92 − 1.79 (m, 1H), 1.74 − 1.65 (m, 1H), 1.63 − 1.53 (m, 1H), 1.45 (s, 9H) |

Example 26-3-[5-Amino-3-(6-amino-5-methyl-3-pyridyl)pyrazolo[1,5-a]pyrimidin-2-yl]benzonitrile

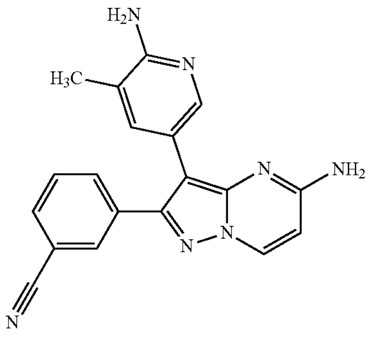 [SMILES: Cc1cc(-c2c(-c3cccc(C#N)c3)nn3ccc(N)nc23)cnc1N]

A mixture of 3-(5-amino-3-iodo-pyrazolo[1,5-a]pyrimidin-2-yl)benzonitrile (Intermediate D)(120 mg, 0.33 mmol), 3-methyl-5-(4,4,5,5-tetramethyl-1,3,2-dioxaborolan-2-yl) pyridin-2-amine (11 mg, 0.50 mmol) and $K_2CO_3$ (138 mg, 1.0 mmol) in 1,4-dioxane (4 mL) and water (1 mL) was degassed under a flow of $N_2$. $Pd(tBu_3P)_2$ (17 mg, 0.03 mmol) was added and the mixture was heated to 80° C. for 1 h 15 mins. Additional $Pd(tBu_3P)_2$ (17 mg, 0.03 mmol) and 3-methyl-5-(4,4,5,5-tetramethyl-1,3,2-dioxaborolan-2-yl) pyridin-2-amine (50 mg, 0.21 mmol) were added and the reaction was stirred at 80° C. for a further 1 h. The resulting mixture was cooled to room temperature and added dropwise to stirring water (40 mL). The precipitate was collected by filtration. Purification by chromatography on silica eluting with a gradient of 0 to 10% MeCOH in DCM afforded a yellow solid which was triturated with MeOH (2 mL), washed with MeOH (1 mL) and dried in vacuo to afford the title compound as a beige solid.

LC-MS (Method 8B): Rt 3.40 mins; MS m/z 342.0=[M+H]+

1H NMR (400 MHz, 1,4-Dioxane-d8) 5 8.55 (d, J=7.5 Hz, 1H), 7.92-7.88 (m, 1H), 7.83-7.76 (m, 2H), 7.68 (d, J=2.2 Hz, 1H), 7.57 (t, J=7.8 Hz, 1H), 7.25-7.20 (m, 1H), 6.96 (s, 2H), 6.30 (d, J=7.5 Hz, 1H), 5.66 (s, 2H), 2.03 (s, 3H).

The compounds of the following tabulated Examples (Table Ex26) were prepared analogously to Example 26 from 3-(5-amino-3-iodo-pyrazolo[1,5-a]pyrimidin-2-yl) benzonitrile (Intermediate D) and the appropriate boronic acid or borate ester.

TABLE EX26

| Ex. | Structure and Name | Retention Time, [M + H]+, 1H NMR |
|---|---|---|
| 26.1 | 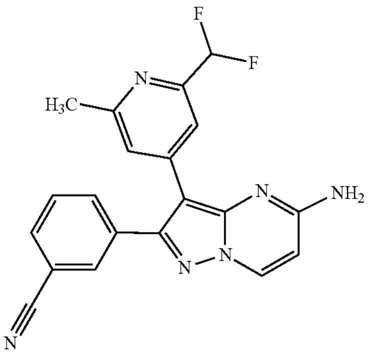 [SMILES: Cc1cc(-c2c(-c3cccc(C#N)c3)nn3ccc(N)nc23)cc(C(F)F)n1] 3-[5-Amino-3-[2-(difluoromethyl)-6-methyl-4-pyridyl]pyrazolo[1,5-a]pyrimidin-2-yl]benzonitrile | LC-MS (Method 8B): Rt 4.00 mins; MS m/z 377.2 = [M + H]+ $^1$H NMR (500 MHz, DMSO-d6) δ 8.63 (d, J = 7.5 Hz, 1H), 7.95 - 7.89 (m, 2H), 7.78 (dt, J = 7.9, 1.4 Hz, 1H), 7.65 (t, J = 7.7 Hz, 1H), 7.52 (s, 1H), 7.42 - 7.36 (m, 1H), 7.28 (s, 2H), 6.79 (t, J = 55.2 Hz, 1H), 6.41 (d, J = 7.5 Hz, 1H), 2.44 (s, 3H). |
| 26.2 | 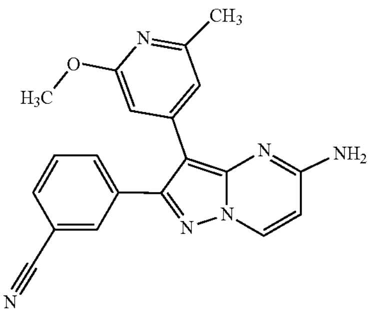 [SMILES: COc1cc(-c2c(-c3cccc(C#N)c3)nn3ccc(N)nc23)cc(C)n1] 3-[5-Amino-3-(2-methoxy-6-methyl-4-pyridyl)pyrazolo[1,5-a]pyrimidin-2-yl]benzonitrile | LC-MS (Method 8B): Rt 4.08 mins; MS m/z 357.2 = [M + H]+ $^1$H NMR (500 MHz, DMSO-d6) δ 8.60 (d, J = 7.5 Hz, 1H), 7.93 - 7.87 (m, 2H), 7.77 (dt, J = 7.9, 1.4 Hz, 1H), 7.63 (td, J = 7.8, 0.8 Hz, 1H), 7.21 (s, 2H), 6.80 - 6.78 (m, 1H), 6.67 - 6.65 (m, 1H), 6.37 (d, J = 7.5 Hz, 1H), 3.79 (s, 3H), 2.28 (s, 3H). |

TABLE EX26-continued

| Ex. | Structure and Name | Retention Time, [M + H]+, 1H NMR |
| --- | --- | --- |
| 26.3 | 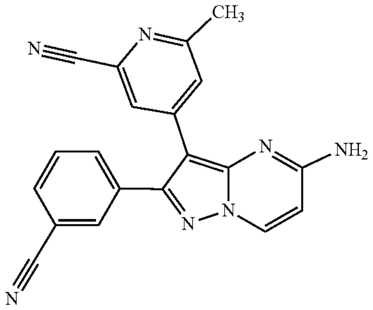 [SMILES: Cc1cc(-c2c(-c3cccc(C#N)c3)nn3ccc(N)nc23)cc(C#N)n1] 4-[5-Amino-2-(3-cyanophenyl)pyrazolo [1,5-a]pyrimidin-3-yl]-6-methyl-pyridine-2-carbonitrile | LC-MS (Method 8B): Rt 3.96 mins; MS m/z 352.2 = [M + H]+ $^1$H NMR (500 MHz, DMSO-d6) δ 8.64 (d, J = 7.5 Hz, 1H), 7.99 - 7.93 (m, 2H), 7.88 (d, J = 1.6 Hz, 1H), 7.79 (dt, J = 7.9, 1.5 Hz, 1H), 7.71 - 7.64 (m, 1H), 7.46 (d, J = 1.5 Hz, 1H), 7.40 (s, 2H), 6.43 (d, J = 7.5 Hz, 1H), 2.40 (s, 3H). |
| 26.4 | 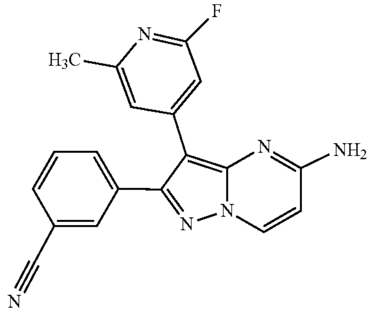 [SMILES: Cc1cc(-c2c(-c3cccc(C#N)c3)nn3ccc(N)nc23)cc(F)n1] 3-[5-Amino-3-(2-fluoro-6-methyl-4-pyridyl)pyrazolo[1,5-a]pyrimidin-2-yl]benzonitrile | LC-MS (Method 8B): Rt 3.96 mins; MS m/z 345.1 = [M + H]+ $^1$H NMR (500 MHz, DMSO-d6) δ 8.63 (d, J = 7.5 Hz, 1H), 7.99 - 7.91 (m, 2H), 7.80 (dt, J = 7.9, 1.5 Hz, 1H), 7.71 - 7.64 (m, 1H), 7.33 (s, 2H), 7.16 - 7.10 (m, 1H), 7.00 (s, 1H), 6.42 (d, J = 7.5 Hz, 1H), 2.31 (s, 3H). |
| 26.5 | 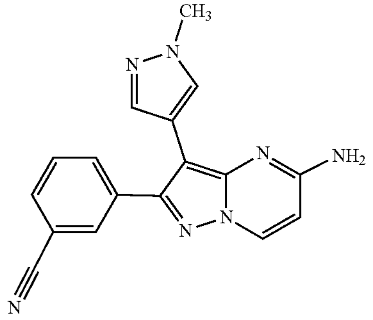 [SMILES: Cn1cc(-c2c(-c3cccc(C#N)c3)nn3ccc(N)nc23)cn1] 3-[5-Amino-3-(1-methylpyrazol-4-yl)pyrazolo[1,5-a]pyrimidin-2-yl]benzonitrile | LC-MS (Method 15B): Rt 5.76 mins; MS m/z 316.1 = [M + H]+ $^1$H NMR (500 MHz, DMSO-d6) δ 8.54 (d, J = 7.4 Hz, 1H), 7.98 (t, J = 1.7 Hz, 1H), 7.92 (dt, J = 7.9, 1.4 Hz, 1H), 7.85 (dt, J = 7.7, 1.4 Hz, 1H), 7.71 (s, 1H), 7.63 (t, J = 7.8 Hz, 1H), 7.38 (s, 1H), 6.98 (s, 2H), 6.30 (d, J = 7.5 Hz, 1H), 3.84 (s, 3H). |

Example 27-3-[5-Amino-3-(2,6-dimethyl-1-oxido-pyridin-1-ium-4-yl)pyrazolo[1,5-a]pyrimidin-2-yl]benzonitrile

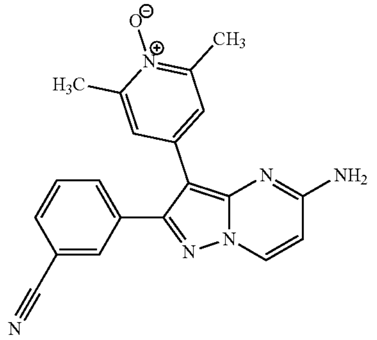 [SMILES: Cc1cc(-c2c(-c3cccc(C#N)c3)nn3ccc(N)nc23)cc(C)[n+]1[O-]]

A mixture of 4-bromo-2,6-dimethyl-1-oxido-pyridin-1-ium (Intermediate J) (201 mg, 1 mmol), bis(pinacolato) diboron (304 mg, 1.2 mmol) and potassium acetate (294 mg, 2.99 mmol) in 1,4-dioxane (10 mL) was degassed with $N_2$. Pd(dppf)$Cl_2$ (73 mg, 0.10 mmol) was added and the reaction mixture heated to 100° C. for 2 h and then at 50° C. for 6 h. The resulting mixture was filtered, washing with DCM (2×10 mL) and the filtrate was concentrated in vacuo. A mixture of the crude product, 3-(5-amino-3-iodo-pyrazolo[1,5-a]pyrimidin-2-yl)benzonitrile (Intermediate D) (120 mg, 0.33 mmol) and $K_2CO_3$ (137.77 mg, 1 mmol) in 1,4-dioxane (4 mL) and water (1 mL) was degassed with $N_2$ before Pd($tBu_3P)_2$ (17 mg, 0.03 mmol) was added and the reaction mixture stirred at 50° C. for 21.5 h. After cooling to room temperature, the resulting mixture was added dropwise to stirring water (60 mL) and the precipitate was collected by filtration and dried by azeotroping from MeOH (30 mL). The solid was purified by chromatography on silica eluting with a gradient of 0 to 10% MeOH in DCM followed by C18 reverse phase chromatography eluting with a gradient of 10 to 60% MeCN in water (+0.1 wt % $NH_4OH$) afforded the title compound as a light grey solid.

LC-MS (Method 8B): Rt 3.20 mins; MS m/z 357.3=[M+H]+

1H NMR (500 MHz, DMSO-d6) δ 8.60 (d, J=7.5 Hz, 1H), 7.95 (d, J=1.7 Hz, 1H), 7.89 (dt, J=7.7, 1.4 Hz, 1H), 7.79 (dt, J=8.0, 1.4 Hz, 1H), 7.63 (t, J=7.8 Hz, 1H), 7.32 (s, 2H), 7.20 (s, 2H), 6.37 (d, J=7.5 Hz, 1H), 2.30 (s, 6H).

Example 27.1-3-[5-Amino-3-(2-amino-6-methyl-4-pyridyl)pyrazolo[1,5-a]pyrimidin-2-yl]benzonitrile

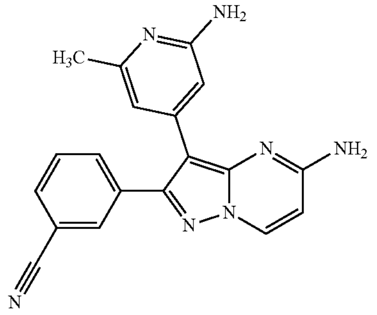 [SMILES: Cc1cc(-c2c(-c3cccc(C#N)c3)nn3ccc(N)nc23)cc(N)n1]

The title compound was prepared from 3-(5-amino-3-iodo-pyrazolo[1,5-a]pyrimidin-2-yl)benzonitrile (Intermediate D) and 4-bromo-6-methyl-pyridin-2-amine analogously to Example 27.

LC-MS (Method 8B): Rt 3.65 mins; MS m/z 342.2=[M+H]+

1H NMR (500 MHz, DMSO-d6) δ 8.59 (d, J=7.5 Hz, 1H), 7.91 (t, J=1.7 Hz, 1H), 7.86 (dt, J=7.7, 1.4 Hz, 1H), 7.79 (dt, J=8.0, 1.5 Hz, 1H), 7.62 (t, J=7.8 Hz, 1H), 7.11 (s, 2H), 6.42 (s, 1H), 6.36 (d, J=7.5 Hz, 1H), 6.26 (s, 1H), 5.84 (s, 2H), 2.19 (s, 3H).

Example 27.2-4-[5-Amino-2-(3-cyanophenyl)pyrazolo[1,5-a]pyrimidin-3-yl]-6-methyl-pyridine-2-carboxamide

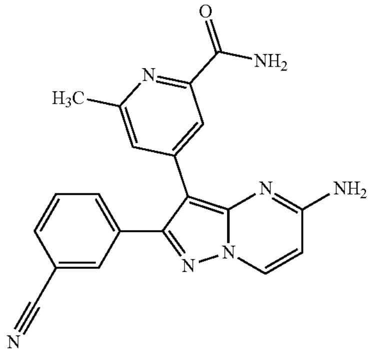 [SMILES: Cc1cc(-c2c(-c3cccc(C#N)c3)nn3ccc(N)nc23)cc(C(N)=O)n1]

The title compound was prepared from 3-(5-amino-3-iodo-pyrazolo[1,5-a]pyrimidin-2-yl)benzonitrile (Intermediate D) and 4-chloro-6-methyl-pyridine-2-carboxamide (Intermediate K) analogously to Example 27.

LC-MS (Method 8B): Rt 3.55 mins; MS m/z 370.2=[M+H]+

1H NMR (500 MHz, DMSO-d6) δ 8.63 (d, J=7.5 Hz, 1H), 7.96-7.88 (m, 3H), 7.81-7.79 (m, 1H), 7.75 (dt, J=7.9, 1.5 Hz, 1H), 7.63 (t, J=8.1 Hz, 1H), 7.56-7.46 (m, 2H), 7.25 (s, 2H), 6.40 (d, J=7.5 Hz, 1H), 2.46 (s, 3H).

Example 27.4-N-[4-[5-Amino-2-(3-cyanophenyl)pyrazolo[1,5-a]pyrimidin-3-yl]-6-methyl-2-pyridyl]acetamide

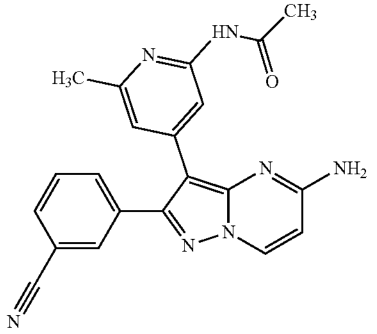 [SMILES: CC(=O)Nc1cc(-c2c(-c3cccc(C#N)c3)nn3ccc(N)nc23)cc(C)n1]

The title compound was prepared from 3-(5-amino-3-iodo-pyrazolo[1,5-a]pyrimidin-2-yl)benzonitrile (intermediate D) and N-(4-bromo-6-methyl-2-pyridyl)acetamide (Intermediate L) analogously to Example 27.

LC-MS (Method 88): Rt 6.05 mins; MS m/z 384.2=[M+H]+

$^1$H NMR (500 MHz, DMSO-d6) δ 10.26 (s, 1H), 8.60 (d, J=7.5 Hz, 1H), 7.88.-7.84 (m, 2H), 7.79 (s, 1H), 7.76 (dt, J=7.9, 1.4 Hz, 1H), 7.59 (t, J=7.8 Hz, 1H), 7.18-7.09 (m, 3H), 6.37 (d, J=7.5 Hz, 1H), 2.35 (s, 3H), 1.99 (s, 3H).

Example 27.5-3-[5-Amino-3-(5-methyl-[1,2,4]triazolo[1,5-a]pyridin-7-yl)pyrazolo[1,5-a]pyrimidin-2-yl]benzonitrile

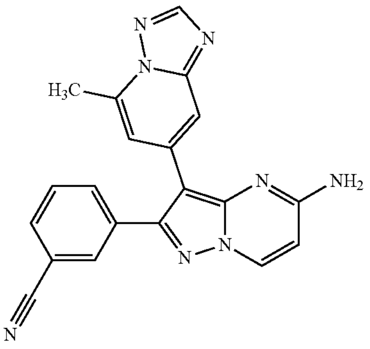 [SMILES: Cc1cc(-c2c(-c3cccc(C#N)c3)nn3ccc(N)nc23)cc2ncnn12]

The title compound was prepared from 3-(5-amino-3-iodo-pyrazolo[1,5-a]pyrimidin-2-yl)benzonitrile (Intermediate D) and 5-methyl-7-(4,4,5,5-tetramethyl-1,3,2-dioxaborolan-2-yl)-[1,2,4]triazolo[1,5-a]pyridine (Intermediate N) analogously to Example 27.

LC-MS (Method 156): Rt 6.14 mins; MS m/z 367.1=[M+H]+

$^1$H NMR (500 MHz, DMSO-d6) δ 8.64 (d, J=7.5 Hz, 1H), 8.43 (s, 1H), 7.99 (d, J=1.7 Hz, 1H), 7.91 (dt, J=7.7, 1.4 Hz, 1H), 7.80 (dt, J=7.9, 1.4 Hz, 1H), 7.69-7.59 (m, 2H), 7.27 (s, 2H), 7.07 (s, 1H), 6.41 (d, J=7.5 Hz, 1H), 2.65 (s, 3H).

Example 28-4-[5-Amino-2-(3-cyanophenyl)pyrazolo[1,5-a]pyrimidin-3-yl]-6-methyl-pyridine-2-carboxylic acid

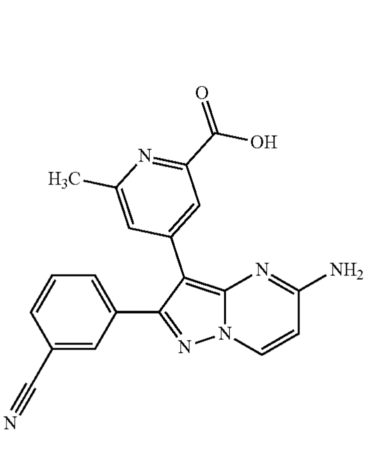 [SMILES: Cc1cc(-c2c(-c3cccc(C#N)c3)nn3ccc(N)nc23)cc(C(=O)O)n1]

Step 1: Isopropyl 4-[5-amino-2-(3-cyanophenyl)pyrazolo[1,5-a]pyrimidin-3-yl]-6-methyl-pyridine-2-carboxylate

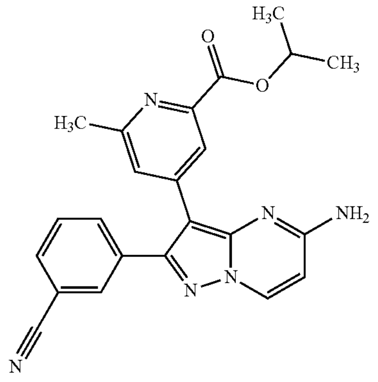 [SMILES: Cc1cc(-c2c(-c3cccc(C#N)c3)nn3ccc(N)nc23)cc(C(=O)OC(C)C)n1]

The title compound was prepared from 3-(5-amino-3-iodo-pyrazolo[1,5-a]pyrimidin-2-yl)benzonitrile (Intermediate D) and isopropyl 4-chloro-6-methyl-pyridine-2-carboxylate (Intermediate M) analogously to Example 27.

LC-MS (Method 5B): Rt 2.73 mins; MS m/z 413.3=[M+H]+

$^1$H NMR (400 MHz, DMSO-d6) δ 8.63 (d, J=7.5 Hz, 1H), 7.97-7.90 (m, 2H), 7.83-7.77 (m, 2H), 7.67 (t, J=7.8 Hz, 1H), 7.63 (d, J=1.6 Hz, 1H), 7.29 (s, 2H), 6.41 (d, J=7.6 Hz, 1H), 5.06 (p, J=6.3 Hz, 1H), 2.48 (s, 3H), 1.22 (d, J=6.3 Hz, 6H).

Step 2: 4-[5-Amino-2-(3-cyanophenyl)pyrazolo[1,5-a]pyrimidin-3-yl]-6-methyl-pyridine-2-carboxylic acid To a mixture of isopropyl 4-[5-amino-2-(3-cyanophenyl)pyrazolo[1,5-a]pyrimidin-3-yl]-6-methyl-pyridine-2-carboxylate (step 1)(24 mg, 0.06 mmol) in MeOH (1 mL) was added 2M NaOH (0.5 mL, 1 mmol) and the reaction mixture stirred at room temperature for 1 h. The resulting precipitate was collected by filtration and purified by C18 reverse phase chromatography eluting with a gradient of 5 to 40% MeCN in water (+0.1 wt % $NH_4OH$). The material was further purified by C18 reverse phase chromatography eluting with a gradient of 0 to 40% MeCN in water (+0.1 wt % formic acid) to afford the title compound as a beige solid.

LC-MS (Method 15B): Rt 2.16 mins; MS m/z 371.2=[M+H]+

$^1$H NMR (500 MHz, DMSO-d6) δ 8.56 (d, J=7.5 Hz, 1H), 8.29 (s, 1H), 7.85 (dd, J=17.4, 9.5 Hz, 3H), 7.77 (d, J=7.8 Hz, 1H), 7.62 (t, J=7.8 Hz, 1H), 7.43 (s, 1H), 7.21 (s, 1H), 6.41 (d, J=7.5 Hz, 1H), 2.37 (s, 4H).

Example 29-3-[5-Amino-3-[2-(dimethylamino)-6-methyl-4-pyridyl]pyrazolo[1,5-a]pyrimidin-2-yl]benzonitrile

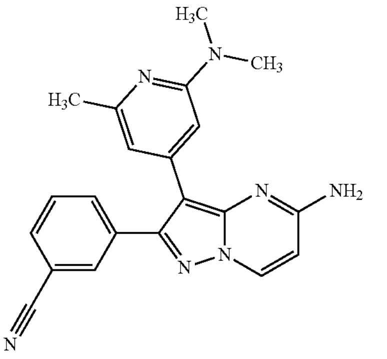 [SMILES: Cc1cc(-c2c(-c3cccc(C#N)c3)nn3ccc(N)nc23)cc(N(C)C)n1]

A mixture of 3-[5-amino-3-(2-chloro-6-methyl-4-pyridyl)pyrazolo[1,5-a]pyrimidin-2-yl]benzonitrile (Intermediate F) (100 mg, 0.28 mmol), dimethylamine hydrochloride (226 mg, 2.77 mmol) and DIPEA (0.48 mL, 2.77 mmol) in NMP (2 mL) was heated to 150° C. for 18 h. Additional dimethylamine hydrochloride (226 mg, 2.77 mmol) and DIPEA (0.48 mL, 2.77 mmol) was added and the reaction heated at 150° C. for 24 h. The resulting mixture was cooled to room temperature and added slowly to stirring water (40 mL). After stirring for 5 mins the precipitate was collected by filtration. The solid was purified by chromatography on silica eluting with a gradient of 0 to 10% MeOH in DCM followed by C18 reverse chromatography eluting with a gradient of 30 to 70% MeCN in water (+0.1% $NH_4OH$). The resulting material was loaded onto an Isolute® SCX-3 cartridge (1 g) that had been pre-wetted with MeOH. The cartridge was washed with MeOH (50 mL) and eluted with 3.5M ammonia in MeOH solution (20 mL). The product fractions were combined and concentrated in vacuo to afford the title compound as a beige solid.

LC-MS (Method 8B): Rt 4.26 mins; MS m/z 370.2=[M+H]+

$^1$H NMR (500 MHz, DMSO-d6) δ 8.59 (d, J=7.5 Hz, 1H), 7.93 (d, J=2.1 Hz, 1H), 7.87 (d, J=7.7 Hz, 1H), 7.81 (d, J=7.9 Hz, 1H), 7.63 (t, J=7.8 Hz, 1H), 7.12 (s, 2H), 6.57 (s, 1H), 6.39-6.33 (m, 2H), 2.89 (s, 6H), 2.25 (s, 3H).

Example 30-[3-(2-Chloro-6-methyl-4-pyridyl)-2-(3-cyanophenyl)pyrazolo[1,5-a]pyrimidin-5-yl]urea

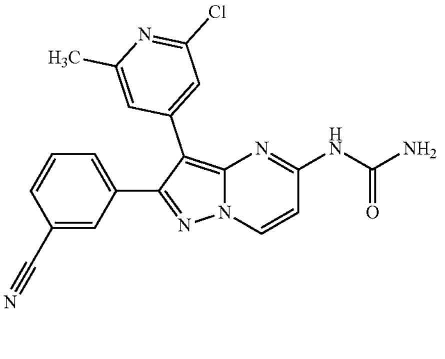 [SMILES: Cc1cc(-c2c(-c3cccc(C#N)c3)nn3ccc(NC(N)=O)nc23)cc(Cl)n1]

To a suspension of triphosgene (8 mg, 0.03 mmol) and 3-[5-amino-3-(2-chloro-6-methyl-4-pyridyl)pyrazolo[1,5-a]pyrimidin-2-yl]benzonitrile (Intermediate F) (20 mg, 0.06 mmol) in THE (1 mL) at 0° C. was added triethylamine (0.04 mL, 0.28 mmol) and the mixture was stirred at room temperature for 1 h. To this mixture was added a solution of 35% aqueous ammonia (0.08 mL, 2.77 mmol) in THF (0.50 mL) and stirring continued at room temperature for a further 20 min. The resulting mixture was partitioned between EtOAc (3 mL) and water (3 mL). The organic layer was separated and the aqueous layer was further extracted with EtOAc (2×3 mL). The combined organic extracts were dried over $Na_2SO_4$, concentrated in vacuo and the crude material was purified by chromatography on silica eluting with a gradient of 2 to 10% MecOH in DCM. Trituration of the solid with MeOH (2 mL) afforded the title compound as a brown solid.

LC-MS (Method 88): Rt 3.97 mins; MS m/z 404.2/406.2=[M+H]+

$^1$H NMR (500 MHz, DMSO-d6) δ 9.94 (s, 1H), 9.01 (d, J=7.6 Hz, 1H), 8.00 (s, 1H), 7.97 (d, J=7.8 Hz, 1H), 7.83 (d, J=7.8 Hz, 1H), 7.69 (t, J=7.8 Hz, 1H), 7.39-7.27 (m, 3H), 7.25 (s, 1H), 7.22 (s, 1H), 2.40 (s, 3H).

Example 30.1-1-[3-(2-Chloro-6-methyl-4-pyridyl)-2-(3-cyanophenyl)pyrazolo[1,5-a]pyrimidin-5-yl]-3-(2-hydroxy-2-methyl-propyl)urea

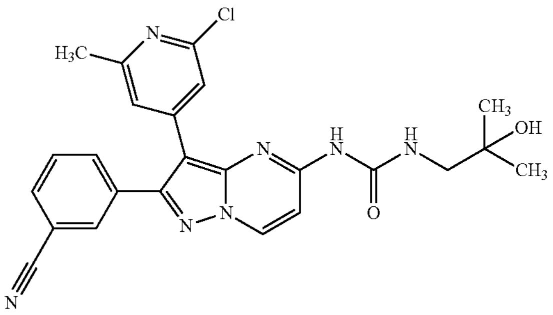 [SMILES: Cc1cc(-c2c(-c3cccc(C#N)c3)nn3ccc(NC(=O)NCC(C)(C)O)nc23)cc(Cl)n1]

The title compound was prepared from 3-[5-amino-3-(2-chloro-6-methyl-4-pyridyl)pyrazolo[1,5-a]pyrimidin-2-yl]benzonitrile (intermediate F) and 1-amino-2-methylpropan-2-ol analogously to Example 30.

LC-MS (Method 88): Rt 4.17 mins; MS m/z 476.2/478.2=[M+H]+

$^1$H NMR (500 MHz, DMSO-$d_6$) δ 10.02 (s, 1H), 9.02 (d, J=7.7 Hz, 1H), 8.00-7.98 (m, 1H), 7.96 (d, J=7.8 Hz, 1H), 7.93 (s, 1H), 7.81 (d, J=7.9 Hz, 1H), 7.69 (t, J=7.8 Hz, 1H), 7.47-7.40 (m, 1H), 7.25 (s, 2H), 4.50 (s, 1H), 3.15 (d, J=5.6 Hz, 2H), 2.41 (s, 3H), 1.03 (s, 6H).

Example 30.2-1-[3-(2-Chloro-6-methyl-4-pyridyl)-2-(3-cyanophenyl)pyrazolo[1,5-a]pyrimidin-5-yl]-3-(1-ethyl-4-piperidyl)urea

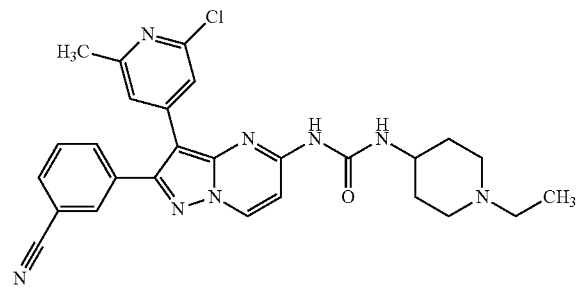 [SMILES: CCN1CCC(NC(=O)Nc2ccn3nc(-c4cccc(C#N)c4)c(-c4cc(C)nc(Cl)c4)c3n2)CC1]

The title compound was prepared from 3-[5-amino-3-(2-chloro-6-methyl-4-pyridyl)pyrazolo[1,5-a]pyrimidin-2-yl] benzonitrile (Intermediate F) and 4-amino-1-ethyl piperidine analogously to Example 30.

LC-MS (Method 8B): Rt 4.63 mins; MS m/z 515.2/517.2=[M+H]+

$^1$H NMR (500 MHz, DMSO-$d_6$) δ 10.03 (s, 1H), 9.03 (d, J=7.6 Hz, 1H), 8.20 (s, 1H), 7.99-7.92 (m, 2H), 7.78 (d, J=7.9 Hz, 1H), 7.68 (t, J=7.8 Hz, 1H), 7.24 (s, 2H), 7.21-7.12 (m, 1H), 3.62-3.52 (m, 1H), 2.65-2.56 (m, 2H), 2.45 (s, 3H), 2.27 (q, J=7.2 Hz, 2H), 2.00 (t, J=11.4 Hz, 2H), 1.89-1.81 (m, 2H), 1.44-1.32 (m, 2H), 0.99 (t, J=7.1 Hz, 3H).

Example 30.3-[2-(3-Cyanophenyl)-3-(2,6-dimethyl-4-pyridyl)pyrazolo[1,5-a]pyrimidin-5-yl]urea

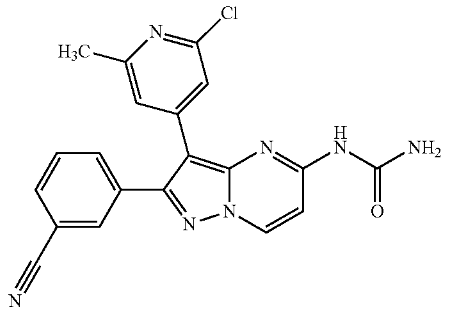 [SMILES: Cc1cc(-c2c(-c3cccc(C#N)c3)nn3ccc(NC(N)=O)nc23)cc(Cl)n1]

The title compound was prepared from 3-[5-amino-3-(2,6-dimethyl-4-pyridyl)pyrazolo[1,5-a]pyrimidin-2-yl]benzonitrile (Example 1.6) and 7M $NH_3$ in MeOH analogously to Example 30.

LC-MS (Method 8B): Rt 3.09 mins; MS m/z 384.2=[M+H]+

1H NMR (500 MHz, DMSO-d6) δ 9.93 (s, 1H), 8.97 (d, J=7.6 Hz, 1H), 7.95 (t, J=1.6 Hz, 1H), 7.92 (dd, J=7.8, 1.5 Hz, 1H), 7.81 (dd, J=8.0, 1.6 Hz, 1H), 7.72 (br s, 1H), 7.65 (t, J=7.8 Hz, 1H), 7.29 (br s, 1H), 7.13 (d, J=7.6 Hz, 1H), 7.01 (s, 2H), 2.37 (s, 6H).

Example 30.4-N-[2-(3-Cyanophenyl)-3-(2,6-dimethyl-4-pyridyl)pyrazolo[1,5-a]pyrimidin-5-yl]-2-oxa-6-azaspiro[3.3]heptane-6-carboxamide

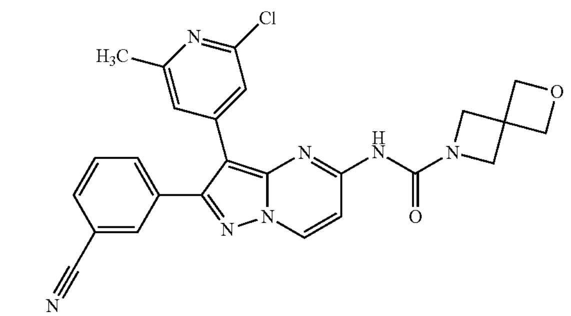 [SMILES: Cc1cc(-c2c(-c3cccc(C#N)c3)nn3ccc(NC(=O)N4CC5(COC5)C4)nc23)cc(Cl)n1]

The title compound was prepared from 3-[5-amino-3-(2,6-dimethyl-4-pyridyl)pyrazolo[1,5-a]pyrimidin-2-yl]benzonitrile (Example 1.6), 2-oxa-6-azaspiro[3.3]heptane and DMAP analogously to Example 30.

LC-MS (Method 88): Rt 3.90 mins; MS m/z 466.2=[M+H]+

1H NMR (500 MHz, DMSO-d6) δ 9.85 (s, 1H), 9.00 (d, J=7.7 Hz, 1H), 7.93 (s, 1H), 7.91 (d, J=7.8 Hz, 1H), 7.79 (t, J=7.0 Hz, 2H), 7.64 (t, J=7.8 Hz, 1H), 7.09 (s, 2H), 4.66 (s, 4H), 4.21 (s, 4H), 2.38 (s, 6H).

Example 30.5-4-Cyano-N-[2-(3-cyanophenyl)-3-(2,6-dimethyl-4-pyridyl)pyrazolo[1,5-a]pyrimidin-5-yl]-4-methyl-piperidine-1-carboxamide

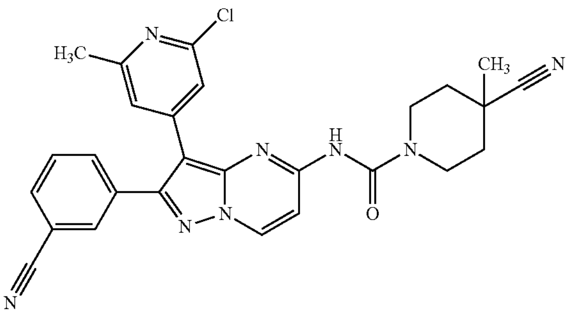 [SMILES: Cc1cc(-c2c(-c3cccc(C#N)c3)nn3ccc(NC(=O)N4CCC(C)(C#N)CC4)nc23)cc(Cl)n1]

The title compound was prepared from 3-[5-amino-3-(2,6-dimethyl-4-pyridyl)pyrazolo[1,5-a]pyrimidin-2-yl]benzonitrile (Example 1.6), 4-methylpiperidine-4-carbonitrile and DMAP analogously to Example 30.

LC-MS (Method 8B): Rt 4.40 mins; MS m/z 491.3=[M+H]+

1H NMR (500 MHz, DMSO-d6) δ 9.97 (s, 1H), 8.99 (d, J=7.7 Hz, 1H), 7.94 (d, J=1.6 Hz, 1H), 7.91 (dt, J=7.8, 1.6 Hz, 1H), 7.79 (dt, J=7.8, 1.6 Hz, 1H), 7.64 (t, J=7.8 Hz, 1H), 7.54-7.51 (m, 1H), 7.09 (s, 2H), 4.15 (d, J=14.0 Hz, 2H), 3.06-2.97 (m, 2H), 2.38 (s, 6H), 1.91 (d, J=13.5 Hz, 2H), 1.54 (td, J=13.1, 4.0 Hz, 2H), 1.37 (s, 3H).

Example 31—N-[3-(2-Chloro-6-methyl-4-pyridyl)-2-(3-cyanophenyl)pyrazolo[1,5-a]pyrimidin-5-yl] piperazine-1-carboxamide

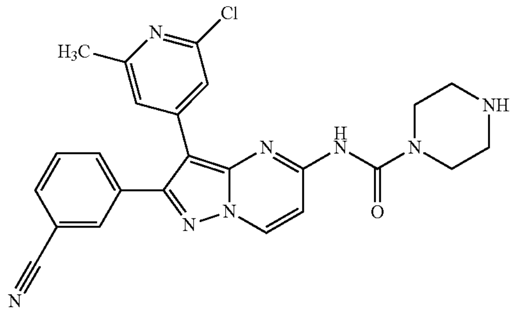 [SMILES: Cc1cc(-c2c(-c3cccc(C#N)c3)nn3ccc(NC(=O)N4CCNCC4)nc23)cc(Cl)n1]

Step 1: tert-Butyl 4-[[3-(2-chloro-6-methyl-4-pyridyl)-2-(3-cyanophenyl)pyrazolo[1,5-a]pyrimidin-5-yl]carbamoyl] piperazine-1-carboxylate

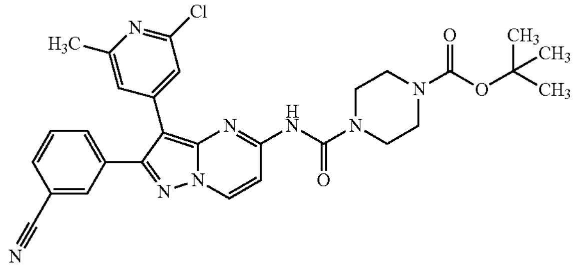 [SMILES: Cc1cc(-c2c(-c3cccc(C#N)c3)nn3ccc(NC(=O)N4CCN(C(=O)OC(C)(C)C)CC4)nc23)cc(Cl)n1]

To a suspension of triphosgene (41 mg, 0.14 mmol) and 3-[5-amino-3-(2-chloro-6-methyl-4-pyridyl)pyrazolo[1,5-a] pyrimidin-2-yl]benzonitrile (Intermediate F) (50 mg, 0.14 mmol) in DCM (1 mL) and THF (1 mL) at 0° C. was added triethylamine (0.1 mL, 0.69 mmol) and the mixture was stirred at room temperature for 1 h. 1-Boc-piperazine (26 mg, 0.14 mmol) was added and stirring continued for 2 h. The reaction was quenched with water (2 mL) and EtOAc (2 mL) was added. The organic layer was separated and the aqueous portion was further extracted with EtOAc (2×2 mL). The combined organic extracts were concentrated in vacuo and purification by chromatography on silica eluting with a gradient of 10 to 100% EtOAc in petrol afforded the title compound as a yellow solid.

LC-MS (Method 58): Rt 3.49 mins; MS m/z 573.2=[M+H]+

$^1$H NMR (500 MHz, DMSO-$d_6$) δ 10.06 (br s, 1H), 9.02 (d, J=8.0 Hz, 1H), 7.99 (s, 1H), 7.96 (d, J=8.7 Hz, 1H), 7.82 (d, J=8.0 Hz, 1H), 7.69 (t, J=7.9 Hz, 1H), 7.57 (d, J=7.7 Hz, 1H), 7.34 (s, 1H), 7.28 (s, 1H), 3.49 (t, J=5.1 Hz, 4H), 3.41-3.36 (m, 4H), 2.39 (s, 3H), 1.43 (s, 9H).

Step 2: N-[3-(2-Chloro-6-methyl-4-pyridyl)-2-(3-cyanophenyl)pyrazolo[1,5-a]pyrimidin-5-yl]piperazine-1-carboxamide Trifluoroacetic acid (0.08 mL, 0.99 mmol) was added to a suspension of tert-butyl 4-[[3-(2-chloro-6-methyl-4-pyridyl)-2-(3-cyanophenyl)pyrazolo[1,5-a]pyrimidin-5-yl] carbamoyl]piperazine-1-carboxylate (step 1) (28 mg, 0.05 mmol) in DCM (1 mL) and the mixture was stirred at room temperature overnight. The resulting mixture was concentrated in vacuo and purification by C18 reverse phase chromatography eluting with a gradient of 5 to 45% MeCN in water (+0.1 wt % $NH_4OH$) followed by purification by C18 reverse phase chromatography eluting with a gradient of 5 to 45% MeCN in water (+0.1 wt % formic acid) afforded the title compound as a colourless solid.

LC-MS (Method 15B): Rt 7.11 mins; MS m/z 473.1/475.1=[M+H]+

$^1$H NMR (500 MHz, DMSO-$d_6$) δ 9.93 (br s, 1H), 9.01 (d, J=7.7 Hz, 1H), 8.02-7.93 (m, 2H), 7.82 (d, J=7.9 Hz, 1H), 7.69 (t, J=7.8 Hz, 1H), 7.57 (d, J=7.7 Hz, 1H), 7.33 (s, 1H), 7.30 (s, 1H), 3.47-3.41 (m, 4H), 2.73 (t, J=4.9 Hz, 4H), 2.39 (s, 3H). NH proton not observed.

Example 31.1-1-[3-(2-Chloro-6-methyl-4-pyridyl)-2-(3-cyanophenyl)pyrazolo[1,5-a]pyrimidin-5-yl]-3-[(3S)-pyrrolidin-3-yl]urea trifluoroacetate

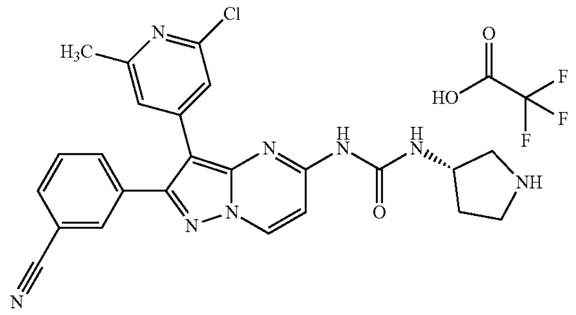

Step 1: tert-Butyl(3S)-3-{[3-(2-chloro-6-methyl-4-pyridyl)-2-(3-cyanophenyl)pyrazolo[1,5-a]pyrimidin-5-yl]carbamoylaminolpyrrolidine-1-carboxylate

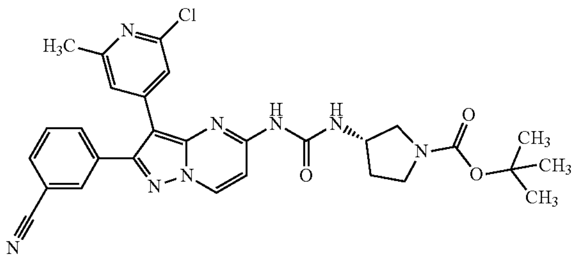 [SMILES: Cc1cc(-c2c(-c3cccc(C#N)c3)nn3ccc(NC(=O)N[C@H]4CCN(C(=O)OC(C)(C)C)C4)nc23)cc(Cl)n1]

The title compound was prepared from 3-[5-amino-3-(2-chloro-6-methyl-4-pyridyl)pyrazolo[1,5-a]pyrimidin-2-yl] benzonitrile (Intermediate F) and (S)-3-amino-1-N-Boc-pyrrolidine analogously to Example 31 (step 1).

LC-MS (Method 5B): Rt 3.24 mins; MS m/z 573.2=[M+H]+

$^1$H NMR (500 MHz, DMSO-$d_6$) δ 9.99 (d, J=12.6 Hz, IH), 9.03 (d, J=7.6 Hz, 1H), 8.21 (d, J=35.1 Hz, 1H), 8.01-7.91 (m, 2H), 7.79 (d, J=8.0 Hz, 1H), 7.68 (t, J=7.8 Hz, 1H), 7.37-7.24 (m, 2H), 7.21 (s, 1H), 4.32-4.17 (m, 1H), 3.63-3.44 (m, 1H), 3.28-3.22 (m, 1H), 3.20-3.15 (m, 1H), 3.12-2.95 (m, 1H), 2.39 (s, 3H), 2.20-2.05 (m, 1H), 1.78-1.62 (m, 1H), 1.40 (s, 9H).

Step 2: 1-{3-(2-Chloro-6-methyl-4-pyridyl)-2-(3-cyanophenyl)pyrazolo[1,5-a]pyrimidin-5-yl]-3-[(3S)-pyrrolidin-3-yl]urea trifluoroacetate The title compound was prepared from tert-butyl(3S)-3-[[3-(2-chloro-6-methyl-4-pyridyl)-2-(3-cyanophenyl)pyrazolo[1,5-a]pyrimidin-5-yl]carbamoylamino]pyrrolidine-1-carboxylate (step 1) and trifluoroacetic acid analogously to Example 31 step 2.

LC-MS (Method 15B): Rt 8.25 mins; MS m/z 473.1/475.0=[MH]+

$^1$H NMR (500 MHz, DMSO-d$_6$) δ 10.11 (s, 1H), 9.07 (d, J=7.6 Hz, 1H), 8.78 (br s, 2H), 8.13-8.05 (m, 1H), 8.00-7.92 (m, 2H), 7.79 (d, J=7.9 Hz, 1H), 7.68 (t, J=7.7 Hz, 1H), 7.38-7.31 (m, 2H), 7.21 (s, 1H), 4.37-4.25 (m, 1H), 3.42 (dd, J=11.9, 6.9 Hz, 1H), 3.25-3.18 (m, 2H), 3.09 (dd, J=12.0, 5.3 Hz, 1H), 2.40 (s, 3H), 2.35-2.20 (m, 1H), 1.85-1.73 (m, 1H).

Example 31.2-1-(2-Aminoethyl)-3-[3-(2-chloro-6-methyl-4-pyridyl)-2-(3-cyanophenyl) pyrazolo[1,5-a]pyrimidin-5-yl]urea trifluoroacetate

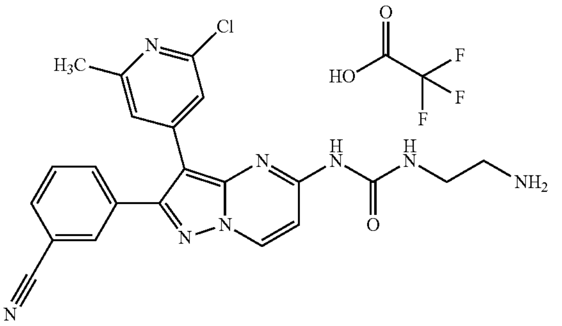

Step 1: tert-Butyl N-[2-[[3-(2-chloro-6-methyl-4-pyridyl)-2-(3-cyanophenyl)pyrazolo[1,5-a]pyrimidin-5-yl]carbamoylamino]ethyl]carbamate

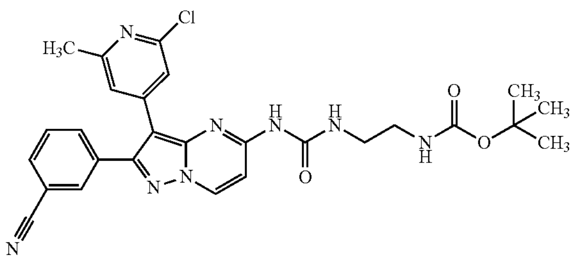 [SMILES: Cc1cc(-c2c(-c3cccc(C#N)c3)nn3ccc(NC(=O)NCCNC(=O)OC(C)(C)C)nc23)cc(Cl)n1]

The title compound was prepared from 3-[5-amino-3-(2-chloro-6-methyl-4-pyridyl)pyrazolo[1,5-a]pyrimidin-2-yl] benzonitrile (Intermediate F) and N-Boc-ethylenediamine analogously to Example 31 (step 1).

LC-MS (Method 5B): Rt 3.02 mins; MS m/z 547.2=[M+H]+

$^1$H NMR (500 MHz, DMSO-d$_6$) δ 10.09 (s, 1H), 9.02 (d, J=7.7 Hz, 1H), 8.09 (br s, 1H), 8.00 (s, 1H), 7.97 (d, J=7.8 Hz, 1H), 7.83 (d, J=7.9 Hz, 1H), 7.69 (t, J=7.9 Hz, 1H), 7.33-7.24 (m, 2H), 7.23 (s, 1H), 6.94-6.83 (m, 1H), 3.28-3.23 (m, 2H), 3.11-3.02 (m, 2H), 2.41 (s, 3H), 1.32 (s, 9H).

Step 2: 1-(2-Aminoethyl)-3-[3-(2-chloro-6-methyl-4-pyridyl)-2-(3-cyanophenyl)pyrazolo[1,5-a]pyrimidin-5-yl]urea trifluoroacetate The title compound was prepared from tert-butyl N-[2-[[3-(2-chloro-6-methyl-4-pyridyl)-2-(3-cyanophenyl)pyrazolo[1,5-a]pyrimidin-5-yl]carbamoylamino]ethyl]carbamate (step 1) and trifluoroacetic acid analogously to Example 31 step 2.

LC-MS (Method 8B): Rt 3.96 mins; MS m/z 447.2/449.2=[MH]+

$^1$H NMR (500 MHz, DMSO-d$_6$) δ 10.24 (s, 1H), 9.07 (d, J=7.7 Hz, 1H), 8.11 (br s, 1H), 8.00 (s, 1H), 7.98 (d, J=7.9 Hz, 1H), 7.84 (d, J=8.1 Hz, 1H), 7.77 (br s, 3H), 7.70 (t, J=7.8 Hz, 1H), 7.35 (s, 1H), 7.31 (d, J=7.6 Hz, 1H), 7.20 (s, 1H), 3.47 (q, J=6.2 Hz, 2H), 3.03-2.92 (m, 2H), 2.40 (s, 3H).

Example 31.3-1-[3-(2-Chloro-6-methyl-4-pyridyl)-2-(3-cyanophenyl)pyrazolo[1,5-a]pyrimidin-5-yl]-3-[(3R)-pyrrolidin-3-yl]urea trifluoroacetate

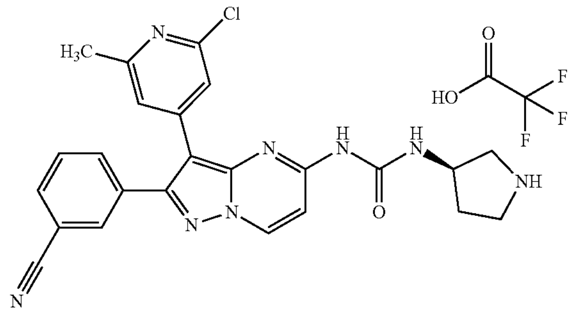

Step 1: tert-Butyl(3R)-3-[[3-(2-chloro-6-methyl-4-pyridyl)-2-(3-cyanophenyl)pyrazolo[1,5-a]pyrimidin-5-yl]carbamoylamino]pyrrolidine-1-carboxylate

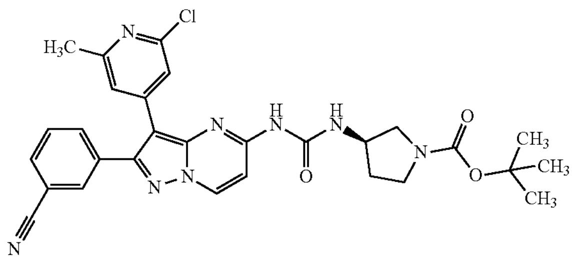 [SMILES: Cc1cc(-c2c(-c3cccc(C#N)c3)nn3ccc(NC(=O)N[C@@H]4CCN(C(=O)OC(C)(C)C)C4)nc23)cc(Cl)n1]

The title compound was prepared from 3-[5-amino-3-(2-chloro-6-methyl-4-pyridyl)pyrazolo[1,5-a]pyrimidin-2-yl] benzonitrile (Intermediate F) and (R)-3-amino-1-N-Boc-pyrrolidine analogously to Example 31 (step 1).

LC-MS (Method 5B): Rt 3.25 mins; MS m/z 573.2=[M+H]+

$^1$H NMR (500 MHz, DMSO-d$_6$) δ 10.06-9.94 (m, 1H), 9.03 (d, J=7.6 Hz, 1H), 8.33-8.12 (m, 1H), 8.01-7.90 (m, 2H), 7.79 (d, J=7.9 Hz, 1H), 7.67 (t, J=7.8 Hz, 1H), 7.36-7.24 (m, 2H), 7.21 (s, 1H), 4.30-4.18 (m, 1H), 3.61-3.45 (m, 1H), 3.30-3.22 (m, 1H), 3.23-3.11 (m, 1H), 3.12-2.94 (m, 1H), 2.39 (s, 3H), 2.18-2.06 (m, 1H), 1.77-1.63 (m, 1H), 1.40 (s, 9H).

Step 2: 1-[3-(2-Chloro-6-methyl-4-pyridyl)-2-(3-cyanophenyl)pyrazolo(1,5-a]pyrimidin-5-yl]-3-[(3R)-pyrrolidin-3-yl]urea trifluoroacetate The title compound was prepared from tert-butyl(3R)-3-[[3-(2-chloro-6-methyl-4-pyridyl)-2-(3-cyanophenyl)pyrazolo[1,5-a]pyrimidin-5-yl]carbamoylamino]pyrrolidine-1-carboxylate (step 1) and trifluoroacetic acid analogously to Example 31 step 2.

LC-MS (Method 15B): Rt 8.35 mins; MS m/z 473.0/475.0=[MH]+

$^1$H NMR (500 MHz, DMSO-$d_6$) δ 10.11 (s, 1H), 9.06 (d, J=7.6 Hz, 1H), 8.81 (br s, 2H), 8.17-8.03 (m, 1H), 8.00-7.93 (m, 2H), 7.79 (d, J=7.9 Hz, 1H), 7.68 (t, J=7.7 Hz, 1H), 7.40-7.30 (m, 2H), 7.21 (s, 1H), 4.36-4.28 (m, 1H), 3.43 (dd, J=11.9, 6.8 Hz, 1H), 3.21 (t, J=7.4 Hz, 2H), 3.10 (dd, J=11.9, 5.3 Hz, 1H), 2.40 (s, 3H), 2.33-2.23 (m, 1H), 1.87-1.72 (m, 1H).

Example 31.4-1-(2-Amino-2-methyl-propyl)-3-[3-(2-chloro-6-methyl-4-pyridyl)-2-(3-cyanophenyl)pyrazolo[1,5-a]pyrimidin-5-yl]urea trifluoroacetate

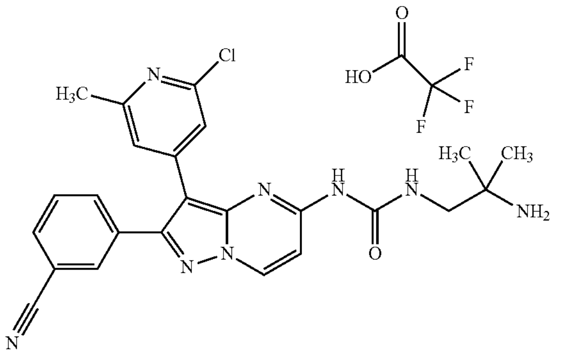

Step 1: tert-Butyl N-[2-{[3-(2-chloro-6-methyl-4-pyridyl)-2-(3-cyanophenyl)pyrazolo[1,5-a]pyrimidin-5-yl]carbamoylamino]-1,1-dimethyl-ethyl]carbamate

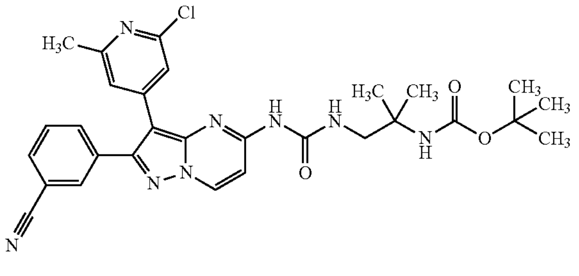 [SMILES: Cc1cc(-c2c(-c3cccc(C#N)c3)nn3ccc(NC(=O)NCC(C)(C)NC(=O)OC(C)(C)C)nc23)cc(Cl)n1]

The title compound was prepared from 3-[5-amino-3-(2-chloro-6-methyl-4-pyridyl)pyrazolo[1,5-a]pyrimidin-2-yl] benzonitrile (intermediate F) and tert-butyl N-(1-amino-2-methylpropan-2-yl)carbamate analogously to Example 31 (step 1).

LC-MS (Method 5B): Rt 3.08 mins; MS m/z 575.3/577.2=[M+H]+

1H NMR (500 MHz, DMSO-d6) δ 10.08 (s, 1H), 9.05 (d, J=7.6 Hz, 1H), 8.00 (s, 1H), 7.98 (dt,J=7.7, 1.4 Hz, 1H), 7.90-7.75 (m, 2H), 7.70 (t, J=7.8 Hz, 1H), 7.52-7.46 (m, 1H), 7.32 (s, 1H), 7.22 (s, 1H), 6.51 (s, 1H), 3.40 (d, J=6.5 Hz, 2H), 2.42 (s, 3H), 1.39 (s, 9H), 1.12 (s, 6H).

Step 2: 1-(2-amino-2-methyl-propyl)-3-[3-(2-chloro-6-methyl-4-pyridyl)-2-(3-cyanophenyl)pyrazolo[1,5-a]pyrimidin-5-yl]urea trifluoroacetate The title compound was prepared from tert-butyl N-[2-[[3-(2-chloro-6-methyl-4-pyridyl)-2-(3-cyanophenyl)pyrazolo[1,5-a]pyrimidin-5-yl]carbamoylamino]-1,1-dimethyl-ethyl]carbamate (step 1) and trifluoroacetic acid analogously to Example 31 step 2.

LC-MS (Method 88): Rt 4.22 mins; MS m/z 475.2/477.2=[MH]+

1H NMR (500 MHz, DMSO-d6) b 10.15 (s, 1H), 9.08 (d, J=7.6 Hz, 1H), 8.27 (br s, 1H), 8.05-7.92 (m, 2H), 7.86-7.74 (m, 4H), 7.69 (t, J=7.8 Hz, 1H), 7.40-7.29 (m, 2H), 7.19 (s, 1H), 3.38 (d, J=6.5 Hz, 2H), 2.40 (s, 3H), 1.13 (s, 6H).

Example 32-1-[3-(2-Chloro-6-methyl-4-pyridyl)-2-(3-cyanophenyl)pyrazolo[1,5-a]pyrimidin-5-yl]-2-cyano-guanidine

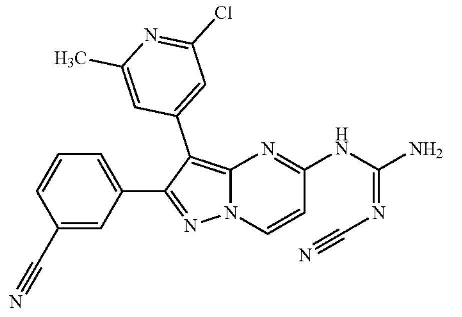 [SMILES: Cc1cc(-c2c(-c3cccc(C#N)c3)nn3ccc(N/C(N)=N\C#N)nc23)cc(Cl)n1]

Step 1: 1-[3-(2-Chloro-6-methyl-4-pyridyl)-2-(3-cyanophenyl)pyrazolo[1,5-a]pyrimidin-5-yl]-3-cyano-2-phenyl-isourea

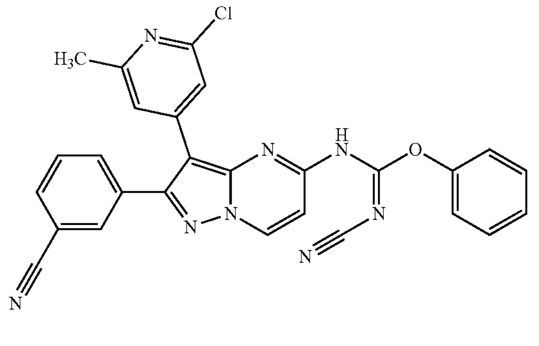 [SMILES: Cc1cc(-c2c(-c3cccc(C#N)c3)nn3ccc(N/C(=N\C#N)Oc4ccccc4)nc23)cc(Cl)n1]

DBU (0.06 mL, 0.42 mmol) was added to a solution of 3-[5-amino-3-(2-chloro-6-methyl-4-pyridyl)pyrazolo[1,5-a]pyrimidin-2-yl]benzonitrile (Intermediate F) (100 mg, 0.28 mmol) and diphenoxymethylenecyanamide (99 mg, 0.42 mmol) in NMP (1 mL) and the mixture was stirred at 120° C. overnight. Additional diphenoxymethylenecyanamide (99 mg, 0.42 mmol) and DBU (0.06 mL, 0.42 mmol) were added and stirring continued at 80° C. for 30 mins. The reaction mixture was allowed to cool to room temperature and MeOH (2 mL) and water (0.5 mL) were added. Purification of the resulting mixture by C18 reverse phase chromatography eluting with a gradient of 10 to 30% MeCN in water (+0.1 wt % $NH_4OH$) afforded the title compound as a brown solid.

LC-MS (Method 5B): Rt 1.98 mins; MS m/z 505.1/507.0=[M+H]+

$^1$H NMR (500 MHz, DMSO-$d_6$) δ 12.08 (br s, 1H), 8.96 (s, 1H), 8.01 (s, 1H), 7.96 (d, J=7.7 Hz, 1H), 7.84 (d, J=8.0 Hz, 1H), 7.69 (t, J=7.8 Hz, 1H), 7.42 (t, J=7.8 Hz, 2H), 7.33 (s, 1H), 7.31 (s, 1H), 7.29-7.21 (m, 3H), 7.11-7.05 (m, 1H), 2.31 (s, 3H).

Step 2: 1-[3-(2-Chloro-6-methyl-4-pyridyl)-2-(3-cyanophenyl)pyrazolo[1,5-a]pyrimidin-5-yl]-2-cyano-guanidine A solution of $NH_4OH$ (35 wt %, 0.38 mL, 3.4 mmol) was added to a solution of 1-[3-(2-chloro-6-methyl-4-pyridyl)-2-(3-cyanophenyl)pyrazolo[1,5-a]pyrimidin-5-yl]-3-cyano-2-phenyl-isourea (step 1)(86 mg, 0.17 mmol) in NMP (1 mL) and the reaction mixture was stirred at 100° C. for 1 h. The resulting mixture was allowed to cool to room temperature and diluted with water (1 mL). The mixture was purified by C18 reverse phase chromatography eluting with a gradient of 10 to 30% MeCN in water (+0.1 wt % $NH_4OH$) followed by trituration with MeOH (5 mL) to afford the title compound as a brown solid.

LC-MS (Method 8B): Rt 3.56 mins; MS m/z 428.2/430.1=[M+H]+

$^1$H NMR (500 MHz, DMSO-d6) δ 10.99 (s, 1H), 9.38 (br s, 1H), 9.10 (d, J=7.5 Hz, 1H), 8.99 (br s, 1H), 8.05-7.94 (m, 2H), 7.83 (d, J=8.0 Hz, 1H), 7.70 (t, J=7.8 Hz, 1H), 7.36 (s, 1H), 7.04 (s, 1H), 6.93 (d, J=7.5 Hz, 1H), 2.49 (s, 3H).

Example 32.1-1-[3-(2-Chloro-6-methyl-4-pyridyl)-2-(3-cyanophenyl)pyrazolo[1,5-a]pyrimidin-5-yl]-2-cyano-3-isopropyl-guanidine

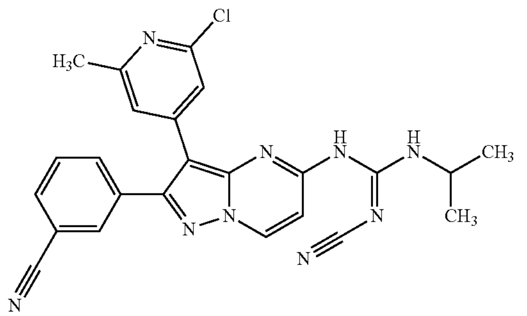 [SMILES: Cc1cc(-c2c(-c3cccc(C#N)c3)nn3ccc(N/C(=N\C#N)NC(C)C)nc23)cc(Cl)n1]

The title compound was prepared from 1-[3-(2-chloro-6-methyl-4-pyridyl)-2-(3-cyanophenyl)pyrazolo[1,5-a)pyrimidin-5-yl]-3-cyano-2-phenyl-isourea (Example 32 step 1) and isopropylamine analogously to Example 32 step 2.

LC-MS (Method 8B): Rt 4.47 mins; MS m/z 470.2/472.2=[M+H]+

1H NMR (500 MHz, DMSO-d6) δ 10.60 (s, 1H), 9.55 (d, J=7.4 Hz, 1H), 9.10 (d, J=7.5 Hz, 1H), 8.03-7.90 (m, 2H), 7.79-7.74 (m, 1H), 7.67 (t, J=7.8 Hz, 1H), 7.32 (s, 1H), 7.21 (s, 1H), 7.13 (d, J=7.6 Hz, 1H), 4.08-3.98 (m, 1H), 2.41 (s, 3H), 1.10 (d, J=6.5 Hz, 6H).

Example 32.2-1-[3-(2-Chloro-6-methyl-4-pyridyl)-2-(3-cyanophenyl)pyrazolo[1,5-a]pyrimidin-5-yl]-2-cyano-3-(2-hydroxy-2-methyl-propyl)guanidine

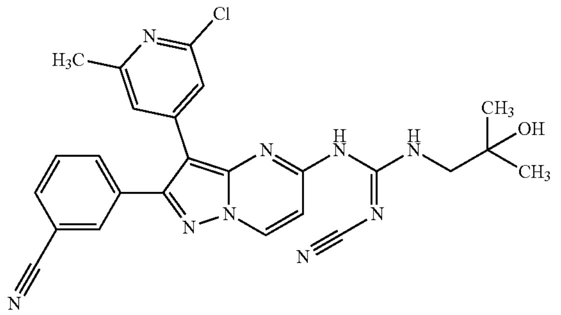 [SMILES: Cc1cc(-c2c(-c3cccc(C#N)c3)nn3ccc(N/C(=N\C#N)NCC(C)(C)O)nc23)cc(Cl)n1]

The title compound was prepared from 1-[3-(2-chloro-6-methyl-4-pyridyl)-2-(3-cyanophenyl)pyrazolo[1,5-a]pyrimidin-5-yl]-3-cyano-2-phenyl-isourea (Example 32 step 1) and 1-amino-2-methylpropan-2-ol analogously to Example 32 step 2.

LC-MS (Method 8B): Rt 3.70 mins; MS m/z 500.2/502.1=[M+H]+

1H NMR (500 MHz, DMSO-d6) δ 10.64 (s, 1H), 9.79-9.70 (m, 1H), 9.11 (d, J=7.4 Hz, 1H), 7.99-7.93 (m, 2H), 7.80 (d, J=7.9 Hz, 1H), 7.68 (t, J=7.9 Hz, 1H), 7.29 (s, 1H), 7.21-7.10 (m, 2H), 4.53 (s, 1H), 3.38 (d, J=5.9 Hz, 2H), 2.44 (s, 3H), 0.95 (s, 6H).

Example 33-3-[3-(2-Ethylpyrazol-3-yl)-5-[(2-hydroxy-2-methyl-propyl)amino]pyrazolo[1,5-a]pyrimidin-2-yl]benzonitrile

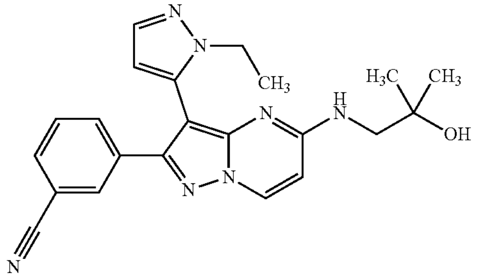 [SMILES: CCn1nccc1-c1c(-c2cccc(C#N)c2)nn2ccc(NCC(C)(C)O)nc12]

Amino-2-methyl-propan-2-ol (0.02 mL, 0.26 mmol) was added to a suspension of DIPEA (0.04 mL, 0.26 mmol) and 3-[5-chloro-3-(2-ethylpyrazol-3-yl)pyrazolo[1,5-a]pyrimidin-2-yl]benzonitrile (Intermediate G) (60 mg, 0.17 mmol) in DMF (1 mL) and stirred at 50° C. overnight. After cooling to room temperature, the resulting mixture was partitioned between EtOAc (20 mL) and water (20 mL). The organic layer was separated, washed with brine (20 mL), dried over $Na_2SO_4$, filtered and concentrated in vacuo. Purification by C18 reverse phase chromatography eluting with a gradient of 35-45% MeCN in water (+0.1 wt % $NH_4OH$) afforded the title compound as a colourless solid.

LC-MS (Method 8A): Rt 4.13 mins; MS m/z 402.3=[M+H]+

$^1$H NMR (500 MHz, DMSO-$d_6$) δ 8.57 (d, J=7.6 Hz, 1H), 7.81 (dt, J=7.6, 1.4 Hz, 1H), 7.79-7.76 (m, 1H), 7.72 (d, J=8.0 Hz, 1H), 7.64-7.54 (m, 2H), 7.53 (d, J=1.8 Hz, 1H), 6.62 (d, J=7.6 Hz, 1H), 6.10 (s, 1H), 4.63 (s, 1H), 3.95 (q, J=7.2 Hz, 2H), 3.26 (d, J=5.4 Hz, 2H), 1.20 (t, J=7.2 Hz, 3H), 1.12 (s, 6H).

The compounds of the following tabulated Examples (Table Ex33) were prepared analogously to Example 33 from 3-[5-chloro-3-(2-ethylpyrazol-3-yl)pyrazolo[1,5-a]pyrimidin-2-yl]benzonitrile (Intermediate G) and the appropriate amine.

TABLE Ex33

| Ex. | Structure and Name | Retention Time, [M + H]+, 1H NMR |
|---|---|---|
| 33.1 | 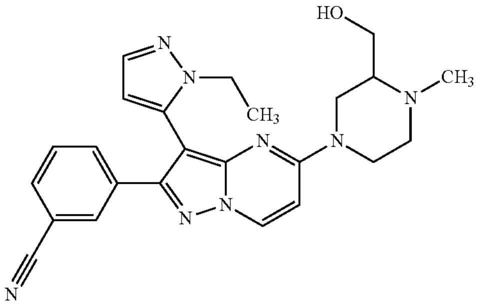 3-[3-(2-Ethylpyrazol-3-yl)-5-[3-(hydroxymethyl)-4-methyl-piperazin-1-yl]pyrazolo[1,5-a]pyrimidin-2-yl]benzonitrile | LC-MS (Method 15B): Rt 6.47 mins; MS M/z 443.3 = [M + H]+ $^1$H NMR (500 MHz, DMSO-$d_6$) δ 8.78 (d, J = 7.9 Hz, 1H), 7.83 (dt, J = 7.6, 1.4 Hz, 1H), 7.80 (d, J = 1.6 Hz, 1H), 7.74 (dt, J = 7.9, 1.4 Hz, 1H), 7.59 (t, J = 7.8 Hz, 1H), 7.53 (d, J = 1.8 Hz, 1H), 6.87 (d, J = 8.0 Hz, 1H), 6.11 (d, J = 1.8 Hz, 1H), 4.63 (t, J = 5.4 Hz, 1H), 4.39-4.24 (m, 1H), 4.18 (d, J = 12.9 Hz, 1H), 3.96 (q, J = 7.2 Hz, 2H), 3.71-3.53 (m, 1H), 3.40-3.36 (m, 1H), 3.16-3.04 (m, 1H), 2.97-2.86 (m, 1H), 2.81 (dd, J = 11.6, 3.3 Hz, 1H), 2.25 (s, 3H), 2.22-2.11 (m, 1H), 2.08-1.97 (m, 1H), 1.21 (t, J = 7.2 Hz, 3H). |
| 33.2 | 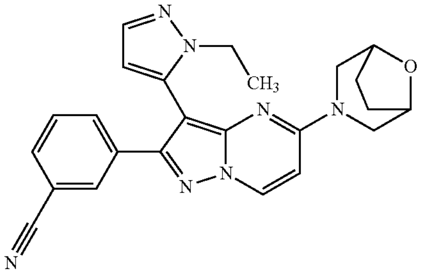 3-[3-(2-Ethylpyrazol-3-yl)-5-(8-oxa-3-azabicyclo[3.2.1]octan-3-yl)pyrazolo[1,5-a]pyrimidin-2-yl]benzonitrile | LC-MS (Method 8A): Rt 4.61 mins; MS m/z 426.3 = [M + H]+ $^1$H NMR (500 MHz, DMSO-d6) δ 8.81 (d, J = 7.9 Hz, 1H), 7.90-7.77 (m, 2H), 7.75 (d, J = 8.0 Hz, 1H), 7.59 (t, J = 7.8 Hz, 1H), 7.54 (d, J = 1.8 Hz, 1H), 6.82 (d, J = 7.9 Hz, 1H), 6.13 (d, J = 1.8 Hz, 1H), 4.56-4.28 (m, 2H), 4.14-3.75 (m, 4H), 3.19-3.00 (m, 2H), 1.93-1.79 (m, 2H), 1.73-1.56 (m, 2H), 1.20 (t, J = 7.2 Hz, 3H). |
| 33.3 | 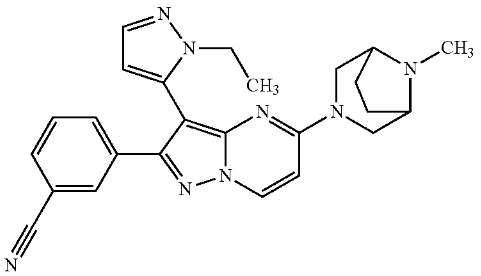 3-[3-(2-Ethylpyrazol-3-yl)-5-(8-methyl-3,8-diazabicyclo[3.2.1]octan-3-yl)pyrazolo[1,5-a]pyrimidin-2-yl]benzonitrile | LC-MS (Method 15B): Rt 7.61 mins; MS m/z 439.3 = [M + H]+ $^1$H NMR (500 MHz, DMSO-$d_6$) δ 8.77 (d, J = 7.9 Hz, 1H), 7.87-7.77 (m, 2H), 7.74 (d, J = 8.2 Hz, 1H), 7.59 (t, J = 7.9 Hz, 1H), 7.53 (d, J = 1.8 Hz, 1H), 6.79 (d, J = 7.9 Hz, 1H), 6.12 (d, J = 1.7 Hz, 1H), 4.03-3.85 (m, 4H), 3.25-3.18 (m, 2H), 3.13-3.00 (m, 2H), 2.22 (s, 3H), 1.99-1.87 (m, 2H), 1.53-1.41 (m, 2H), 1.20 (t, J = 7.2 Hz, 3H). |

TABLE Ex33-continued

| Ex. | Structure and Name | Retention Time, [M + H]+, 1H NMR |
| --- | --- | --- |
| 33.4 | 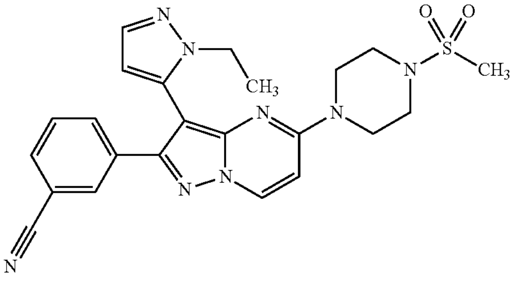 3-[3-(2-Ethylpyrazol-3-yl)-5-(4-methylsulfonylpiperazin-1-yl)pyrazolo[1,5-a]pyrimidin-2-yl]benzonitrile | LC-MS (Method 8A): Rt 4.29 mins; MS m/z 477.2 = [M + H]+ $^{1}$H NMR (500 MHz, DMSO-$d_6$) δ 8.86 (d, J = 7.9 Hz, 1H), 7.84 (dt, J = 7.7, 1.5 Hz, 1H), 7.83-7.79 (m, 1H), 7.74 (dt, J = 8.0, 1.5 Hz, 1H), 7.60 (t, J = 7.8 Hz, 1H), 7.55 (d, J = 1.8 Hz, 1H), 6.96 (d, J = 7.9 Hz, 1H), 6.15 (d, J = 1.8 Hz, 1H), 3.95 (q, J = 7.2 Hz, 2H), 3.85-3.74 (m, 4H), 3.27-3.18 (m, 4H), 2.90 (s, 3H), 1.19 (t, J = 7.2 Hz, 3H). |
| 33.5 | 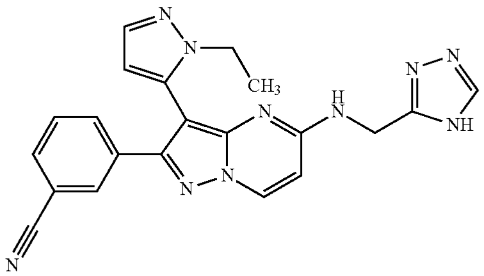 3-[3-(2-Ethylpyrazol-3-yl)-5-(4H-1,2,4-triazol-3-ylmethylamino)pyrazolo[1,5-a]pyrimidin-2-yl]benzonitrile | LC-MS (Method 15B): Rt 5.87 mins; MS m/z 411.2 = [M + H]+. $^{1}$H NMR (500 MHz, DMSO-$d_6$) δ 13.83 (br s, 1H), 8.65 (d, J = 7.6 Hz, 1H), 8.35-8.09 (m, 2H), 7.84-7.80 (m, 1H), 7.79 (d, J = 1.8 Hz, 1H), 7.72 (d, J = 8.0 Hz, 1H), 7.58 (t, J = 7.9 Hz, 1H), 7.49 (d, J = 1.8 Hz, 1H), 6.56 (d, J = 7.6 Hz, 1H), 6.06 (s, 1H), 4.57 (d, J = 4.9 Hz, 2H), 3.86 (q, J = 7.2 Hz, 2H), 1.12 (t, J = 7.2 Hz, 3H). |
| 33.6 | 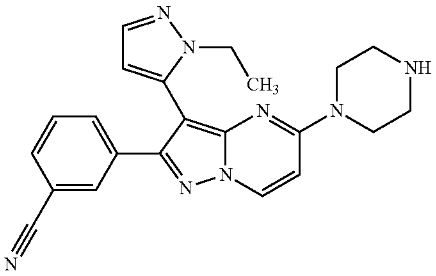 3-[3-(2-Ethylpyrazol-3-yl)-5-piperazin-1-yl-pyrazolo[1,5-a]pyrimidin-2-yl]benzonitrile | LC-MS (Method 8A): Rt 2.92 mins; MS m/z 399.3 = [M + H]+ $^{1}$H NMR (500 MHz, DMSO-$d_6$) δ 8.76 (d, J = 7.8 Hz, 1H), 7.94-7.78 (m, 2H), 7.75 (d, J = 8.0 Hz, 1H), 7.59 (t, J = 7.8 Hz, 1H), 7.54 (d, J = 1.8 Hz, 1H), 6.87 (d, J = 7.9 Hz, 1H), 6.13 (d, J = 1.7 Hz, 1H), 3.95 (q, J = 7.2 Hz, 2H), 3.58 (t, J = 5.0 Hz, 4H), 2.76 (t, J = 5.1 Hz, 4H). 1.20 (t, J = 7.2 Hz, 3H). NH proton not observed. |
| 33.7 | 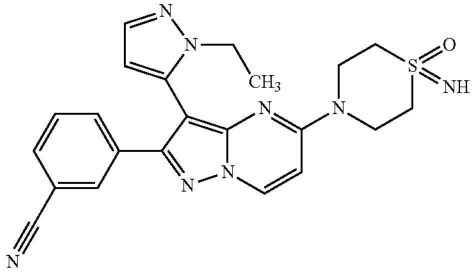 3-[3-(2-Ethylpyrazol-3-yl)-5-(1-imino-1-oxo-1,4-thiazinan-4-yl)pyrazolo[1,5-a]pyrimidin-2-yl]benzonitrile | LC-MS (Method 15B): Rt 6.18 mins; MS m/z 447.1 = [M + H]+ $^{1}$H NMR (500 MHz, DMSO-$d_6$) δ 8.90 (d, J = 7.9 Hz, 1H), 7.85 (dt, J = 7.7, 1.4 Hz, 1H), 7.81 (t, J = 1.7 Hz, 1H), 7.75 (dt, J = 8.0, 1.5 Hz, 1H), 7.60 (t, J = 7.9 Hz, 1H), 7.55 (d, J = 1.8 Hz, 1H), 7.03 (d, J = 7.9 Hz, 1H), 6.15 (d, J = 1.8 Hz, 1H), 4.35-4.21 (m, 2H), 3.96 (q, J = 7.2 Hz, 2H), 3.93-3.86 (m, 2H), 3.85 (s, 1H), 3.08 (t, J = 5.2 Hz, 4H), 1.19 (t, J = 7.2 Hz, 3H). |

Example 35-5-(Benzylamino)-2-(2-fluorophenyl) pyrazolo[1,5-a]pyrimidine-3-carbonitrile

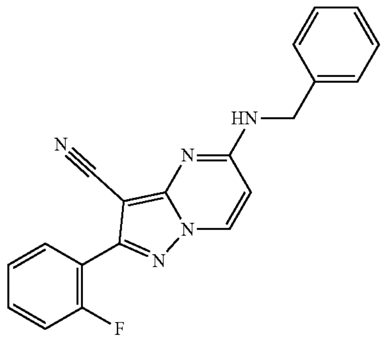 [SMILES: N#Cc1c(-c2ccccc2F)nn2ccc(NCc3ccccc3)nc12]

Step 1: 3-Bromo-5-chloro-2-(2-fluorophenyl)pyrazolo[1,5-a]pyrimidine

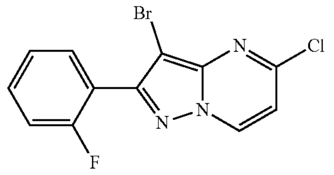 [SMILES: Fc1ccccc1-c1nn2ccc(Cl)nc2c1Br]

To a solution of 5-chloro-2-(2-fluorophenyl)pyrazolo[1,5-a]pyrimidine (Intermediate O) (150 mg, 0.61 mmol) in DMF (4 mL) was added NBS (113 mg, 0.64 mmol) in one portion. The reaction mixture was allowed to stir at room temperature under a nitrogen atmosphere for 90 mins. The resulting mixture was poured into water and the suspension was collected by filtration, washing with water to afford the title compound as a cream solid LC-MS (Method 3B): Rt 1.96 mins; MS m/z 328.0=[M+H]+

$^1$H NMR (500 MHz, Chloroform-d) δ 8.58 (d, J=7.2 Hz, 1H), 7.65 (td, J=7.4, 1.8 Hz, 1H), 7.50 (dddd, J=8.3, 7.1, 5.1, 1.8 Hz, 1H), 7.30 (td, J=7.6, 1.1 Hz, 1H), 7.27-7.22 (m, 1H), 6.89 (d, J=7.2 Hz, 1H)

Step 2: N-Benzyl-3-bromo-2-(2-fluorophenyl)pyrazolo[1,5-a]pyrimidin-5-amine

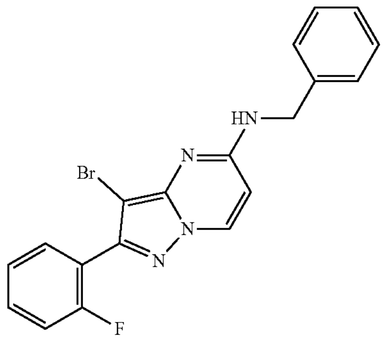 [SMILES: Fc1ccccc1-c1nn2ccc(NCc3ccccc3)nc2c1Br]

A mixture of 3-bromo-5-chloro-2-(2-fluorophenyl)pyrazolo[1,5-a]pyrimidine (step 1) (176 mg, 0.54 mmol), benzylamine (294 μL, 2.69 mmol) and DIPEA (188 μL, 1.08 mmol) in EtOH (3 mL) were heated using microwave irradiation to 120° C. for 90 mins. Additional benzylamine (59 μL, 0.54 mmol) was added and heating continued for a further 30 mins at 130° C. The resulting mixture was adsorbed onto silica and purified by chromatography eluting with 20% to 50% EtOAc in petroleum ether. The solid was recrystallised from diethyl ether to afford the title compound as a colourless solid.

LC-MS (Method 8B): Rt 5.30 mins; MS m/z 397.0/399.0=[M+H]+

$^1$H NMR (500 MHz, DMSO-d6) δ 8.55 (d, J=7.6 Hz, 1H), 8.24 (s, 1H), 7.59-7.50 (m, 2H), 7.42 (d, J=7.0 Hz, 2H), 7.39-7.30 (m, 4H), 7.30-7.24 (m, 1H), 6.42 (d, J=7.5 Hz, 1H), 4.60 (d, J=5.6 Hz, 2H).

Step 3: 5-(Benzylamino)-2-(2-fluorophenyl)pyrazolo[1,5-a]pyrimidine-3-carbonitrile To a degassed solution of N-benzyl-3-bromo-2-(2-fluorophenyl)pyrazolo[1,5-a]pyrimidin-5-amine (step 2) (100 mg, 0.25 mmol) in DMA (3 mL) was added zinc dust (16 mg, 0.25 mmol), $Pd_2$(dba)a (12 mg, 0.01 mmol), XPhos Pd (20 mg, 0.03 mmol) and zinc cyanide (71 mg, 0.60 mmol) and the mixture was heated at 130° C. for 18 h. Additional XPhos Pd (10 mg, 0.01 mmol), zinc cyanide (71 mg, 0.60 mmol) and zinc dust (16 mg, 0.25 mmol) were added and heating continued at 150° C. for a further 16 h. The resulting mixture was cooled to room temperature and EtOAc (10 mL) was added. The suspended solids were removed by filtration washing with EtOAc (10 mL). The filtrate was washed with water (2×10 mL), brine (10 mL), dried over $MgSO_4$ and concentrated in vacuo. Purification by chromatography on silica eluting with a gradient of 20 to 60% EtOAc in petroleum ether afforded the title compound as a pale yellow solid.

LC-MS (Method 8B): Rt 4.80 min; MS m/z 344.1=[M+H]+

$^1$H NMR (500 MHz, DMSO-d6) δ 8.69 (d, J=7.6 Hz, 1H), 8.65 (t, J=5.5 Hz, 1H), 7.72 (td, J=7.6, 1.8 Hz, 1H), 7.59 (dddd, J=8.5, 7.1, 5.2, 1.8 Hz, 1H), 7.46-7.34 (m, 6H), 7.32-7.27 (m, 1H), 6.57 (d, J=7.6 Hz, 1H), 4.64 (d, J=5.2 Hz, 2H).

Example 36—N-Benzyl-2-(2-fluorophenyl)pyrazolo[1,5-a]pyrimidin-5-amine

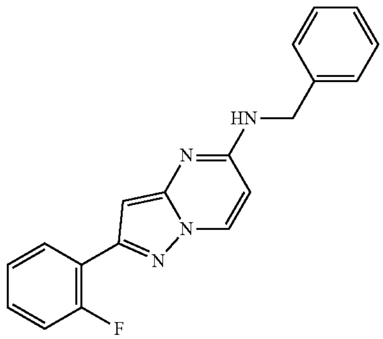 [SMILES: Fc1ccccc1-c1cc2nc(NCc3ccccc3)ccn2n1]

The title compound was prepared from 5-chloro-2-(2-fluorophenyl)pyrazolo[1,5-a]pyrimidine (Intermediate O) and benzylamine analogously to Example 35 step 2.

LC-MS (Method 8B): Rt 4.99 min; MS m/z 319.2=[M+H]+

$^1$H NMR (500 MHz, DMSO-d6) δ 8.55 (dd, J=7.6, 0.8 Hz, 1H), 8.04-7.96 (m, 2H), 7.46-7.39 (m, 1H), 7.39-7.32 (m, 4H), 7.32-7.24 (m, 3H), 6.41-6.35 (m, 2H), 4.57 (d, J=5.7 Hz, 2H).

Example 37-2-(2-Furyl)-5-[(3-methyl-2-pyridyl)methylamino]pyrazolo[1,5-a]pyrimidine-3-carbonitrile

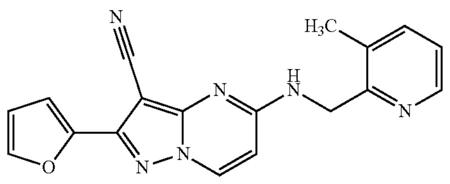 [SMILES: Cc1cccnc1CNc1ccn2nc(-c3ccco3)c(C#N)c2n1]

A solution of 5-chloro-2-(2-furyl)pyrazolo[1,5-a]pyrimidine-3-carbonitrile (Intermediate P) (100 mg, 0.41 mmol), (3-methyl-2-pyridyl)methanamine (100 mg, 0.82 mmol) and DIPEA (0.36 mL, 2.04 mmol) in NMP (2 mL) was stirred at 110° C. under nitrogen for 16 h. The reaction mixture was cooled to room temperature and diluted with EtOAc (20 mL). The organics were washed with brine (3×20 mL) and the resulting solid was collected by filtration. The solid was washed with diethyl ether and dried under high vacuum to afford the title compound as a colourless solid.

LC-MS (Method 8B): Rt 4.14 mins; MS m/z 331.0=[M+H]+(100% @254 nm)

$^1$H NMR (500 MHz, DMSO-d$_6$) δ 8.68 (t, J=5.0 Hz, 1H), 8.62 (d, J=7.6 Hz, 1H), 8.45-8.37 (br m, 1H), 7.92 (dd, J=1.9, 0.8 Hz, 1H), 7.64 (d, J=7.6 Hz, 1H), 7.26 (dd, J=7.6, 4.7 Hz, 1H), 7.11-7.02 (br m, 1H), 6.74 (d, J=7.7 Hz, 1H), 6.71 (dd, J=3.5, 1.8 Hz, 1H), 4.70 (d, J=5.0 Hz, 2H), 2.42 (s, 3H).

The compounds of the following tabulated Examples (Table Ex37) were prepared analogously to Example 37 from 5-chloro-2-(2-furyl)pyrazolo[1,5-a]pyrimidine-3-carbonitrile (Intermediate P) and the appropriate amine.

TABLE Ex37

| Ex. | Structure and Name | Retention Time, [M + H ]+, 1H NMR |
|---|---|---|
| 37.1 | 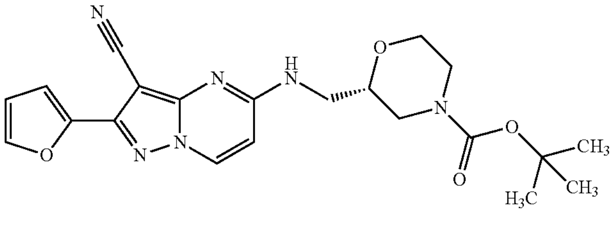 tert-Butyl (2S)-2-[[[3-cyano-2-(2-furyl)pyrazolo[1,5-a]pyrimidin-5-yl]amino]methyl]morpholine-4-carboxylate | LC-MS (Method 3B): Rt 1.86 mins; MS m/z 325 = [M − Boc + H]+ $^1$H NMR (500 MHz, DMSO-d$_6$) δ 8.60 (d, J = 7.6 Hz, 1H), 8.41-8.19 (m, 1H), 7.92 (dd, J = 1.8, 0.8 Hz, 1H), 7.06 (dd, J = 3.4, 0.8 Hz, 1H), 6.71 (dd, J = 3.4, 1.8 Hz, 1H), 6.55 (d, J = 7.6 Hz, 1H), 3.93-3.80 (m, 2H), 3.76-3.65 (m, 1H), 3.61-3.44 (m, 3H), 3.45-3.39 (m, 1H), 2.99-2.80 (m, 1H), 2.79-2.65 (m, 1H), 1.40 (s, 9H). |
| 37.2 | 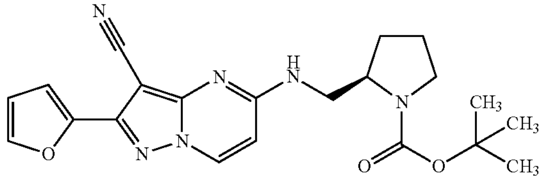 tert-Butyl (2R)-2-[[[3-cyano-2-(2-furyl)pyrazolo[1,5-a]pyrimidin-5-yl]amino]methyl]pyrrolidine-1-carboxylate | LC-MS (Method 8B): Rt 4.97 mins; MS m/z 309.1 = [M − Boc + H]+ $^1$H NMR (500 MHz, DMSO-d6) δ 8.62-8.54 (m, 1H), 8.25-8.14 (m, 1H), 7.96-7.87 (m, 1H), 7.12-7.01 (m, 1H), 6.71 (dd, J = 3.5, 1.8 Hz, 1H), 6.56-6.44 (m, 1H), 3.99-3.92 (m, 1H), 3.72-3.57 (m, 1H), 3.47-3.38 (m, 1H), 3.31-3.20 (m, 2H), 1.94-1.84 (m, 2H), 1.84-1.75 (m, 2H), 1.37 (s, 9H). |
| 37.3 | 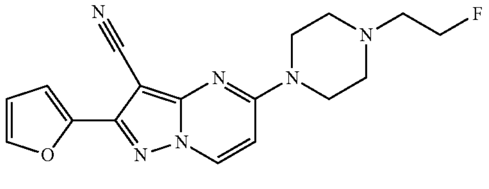 5-[4-(2-Fluoroethyl)piperazin-1-yl]-2-(2-furyl)pyrazolo[1,5-a]pyrimidine-3-carbonitrile | LC-MS (Method 8B): Rt 3.95 mins; MS m/z 341.2 = [M + H]+ $^1$H NMR (500 MHz, DMSO-d$_6$) δ 8.78 (d, J = 8.0 Hz, 1H), 7.94 (dd, J = 1.8, 0.8 Hz, 1H), 7.08 (dd, J = 3.5, 0.8 Hz, 1H), 6.97 (d, J = 8.0 Hz, 1H), 6.72 (dd, J = 3.5, 1.8 Hz, 1H), 4.58 (dt, J = 47.8, 4.9 Hz, 2H), 3.78 (s, 4H), 2.69 (dt, J = 28.9, 4.9 Hz, 2H), 2.59-2.55 (m, 4H). |

TABLE Ex37-continued

| Ex. | Structure and Name | Retention Time, [M + H ]+, 1H NMR |
|---|---|---|
| 37.4 | 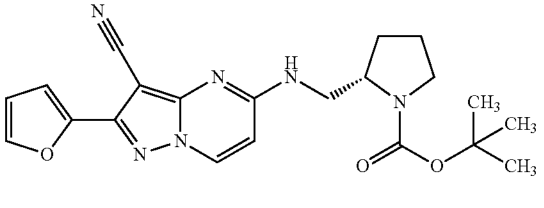 tert-Butyl (2S)-2-[[[3-cyano-2-(2-furyl)pyrazolo[1,5-a]pyrimidin-5-yl]amino]methyl]pyrrolidine-1-carboxylate | LC-MS (Method 3A): Rt 1.97 mins; MS m/z 309.1 = [M − Boc + H]+ $^1$H NMR (500 MHz, DMSO-d6) δ 8.62-8.53 (m, 1H), 8.24-8.17 (m, 1H), 7.92 (d, J = 1.7 Hz, 1H), 7.06 (d, J = 3.5 Hz, 1H), 6.71 (dd, J = 3.5, 1.8 Hz, 1H), 6.53-6.43 (m, 1H), 3.99-3.92 (m, 1H), 3.71-3.56 (m, 1H), 3.47-3.35 (m, 1H), 3.31-3.23 (m, 2H), 1.95-1.83 (m, 2H), 1.83-1.72 (m, 2H), 1.37 (s, 9H). |
| 37.5 | 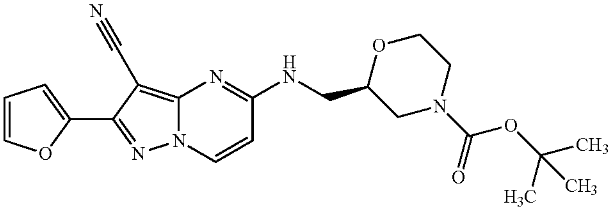 tert-Butyl (2R)-2-[[[3-cyano-2-(2-furyl)pyrazolo[1,5-a]pyrimidin-5-yl]amino]methyl]morpholine-4-carboxylate | LC-MS (Method 8B): Rt 4.77 mins; MS m/z 325.3 = [M − Boc + H]+ $^1$H NMR (500 MHz, DMSO-$d_6$) δ 8.60 (d, J = 7.6 Hz, 1H), 8.34-8.28 (m, 1H), 7.92 (dd, J = 1.9, 0.7 Hz, 1H), 7.06 (dd, J = 3.5, 0.8 Hz, 1H), 6.72 (dd, J = 3.5, 1.8 Hz, 1H), 6.55 (d, J = 7.6 Hz, 1H), 3.92-3.81 (m, 2H), 3.75-3.67 (m, 1H), 3.59-3.46 (m, 3H), 3.43 (td, J = 11.6, 2.8 Hz, 1H), 2.89 (s, 1H), 2.77-2.59 (m, 1H), 1.40 (s, 9H). |
| 37.6 | 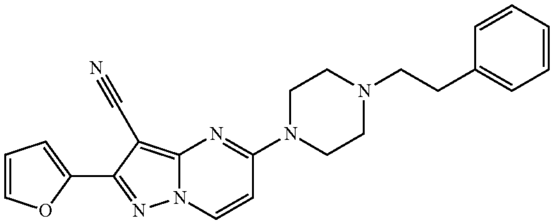 2-(2-Furyl-5-[4-(2-phenylethyl)piperazin-1-yl]pyrazolo[1,5-a]pyrimidine-3-carbonitrile | LC-MS (Method 8B): Rt 5.21 mins; MS m/z 399.5 = [M + H]+ $^1$H NMR (500 MHz, DMSO-$d_6$) δ 8.78 (d, J = 8.0 Hz, 1H), 7.94 (dd, J = 1.8, 0.8 Hz, 1H), 7.32-7.23 (m, 4H), 7.21-7.16 (m, 1H), 7.08 (dd, J = 3.5, 0.8 Hz, 1H), 6.98 (d, J = 8.0 Hz, 1H), 6.72 (dd, J = 3.5, 1.8 Hz, 1H), 3.78 (br s, 4H), 2.81-2.75 (m, 2H), 2.62-2.53 (m, 6H). |
| 37.7 | 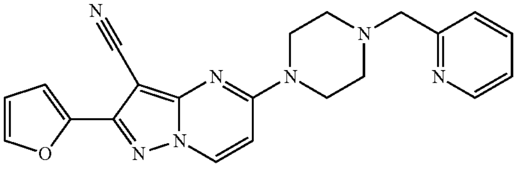 2-(2-Furyl)-5-[4-(2-pyridylmethyl) piperazin-1-yl]pyrazolo[1,5-a]pyrimidine-3-carbonitrile | LC-MS (Method 8B): Rt 4.08 mins; MS m/z 386.2 = [M + H]+ $^1$H NMR (500 MHz, DMSO-$d_6$) δ 8.77 (d, J = 7.9 Hz, 1H), 8.51 (ddd, J = 4.9, 1.9, 0.9 Hz, 1H), 7.93 (dd, J = 1.8, 0.8 Hz, 1H), 7.79 (td, J = 7.7, 1.9 Hz, 1H), 7.49 (dt, J = 7.7, 1.1 Hz, 1H), 7.28 (ddd, J = 7.5, 4.9, 1.1 Hz, 1H), 7.08 (dd, J = 3.5, 0.8 Hz, 1H), 6.95 (d, J = 7.9 Hz, 1H), 6.72 (dd, J = 3.5, 1.8 Hz, 1H), 3.79 (br s, 4H), 3.67 (s, 2H), 2.61-2.52 (m, 4H). |
| 37.8 | 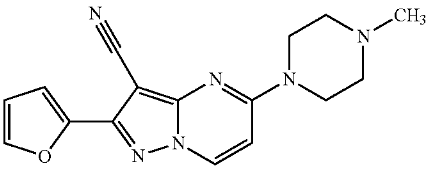 2-(2-Furyl)-5-(4-methylpiperazin-1-yl)pyrazolo[1,5-a]pyrimidine-3-carbonitrile | LC-MS (Method 8B): Rt 3.81 mins; MS m/z 309.2 = [M + H]+ $^1$H NMR (500 MHz, DMSO-$d_6$) δ 8.78 (d, J = 7.9 Hz, 1H), 7.94 (dd, J = 1.8, 0.8 Hz, 1H), 7.09 (dd, J = 3.5, 0.7 Hz, 1H), 6.98 (d, J = 7.9 Hz, 1H), 6.73 (dd, J = 3.5, 1.8 Hz, 1H), 3.77 (s, 4H), 2.42 (m, 4H), 2.24 (s, 3H). |

TABLE Ex37-continued

| Ex. | Structure and Name | Retention Time, [M + H ]+, 1H NMR |
|---|---|---|
| 37.9 | 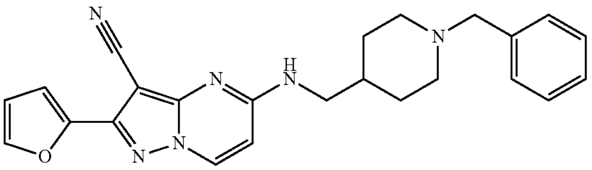 5-[(1-Benzyl-4-piperidyl)methylamino]-2-(2-furyl)pyrazolo[1,5-a]pyrimidine-3-carbonitrile | LC-MS (Method 8B): Rt 5.18 mins; MS m/z 413.3 = [M + H]+ $^1$H NMR (500 MHz, DMSO-$d_6$) δ 8.55 (d, J = 7.6 Hz, 1H), 8.15 (t, J = 5.5 Hz, 1H), 7.92 (dd, J = 1.9, 0.8 Hz, 1H), 7.34-7.21 (m, 5H), 7.05 (dd, J = 3.5, 0.8 Hz, 1H), 6.71 (dd, J = 3.5, 1.8 Hz, 1H), 6.48 (d, J = 7.6 Hz, 1H), 3.44 (s, 2H), 3.32-3.28 (m, 1H), 2.82 (d, J = 11.1 Hz, 2H), 1.98-1.85 (m, 2H), 1.75-1.66 (m, 2H), 1.65-1.53 (m, 1H), 1.32-1.18 (m, 3H). |
| 37.10 | 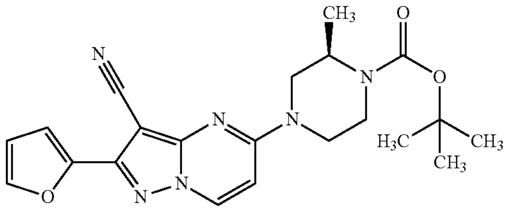 Tert-butyl (2R)-4-[3-cyano-2-(2-furyl)pyrazolo[1,5-a]pyrimidin-5-yl]-2-methyl-piperazine-1-carboxylate | LC-MS (Method 3B): Rt 1.98 mins; MS m/z 409.4 = [M + H]+ $^1$H NMR (500 MHz, DMSO-d6) δ 8.81 (d, J = 7.9 Hz, 1H), 7.94 (dd, J = 1.8, 0.8 Hz, 1H), 7.08 (dd, J = 3.5, 0.8 Hz, 1H), 6.95 (d, J = 8.0 Hz, 1H), 6.73 (dd, J = 3.5, 1.8 Hz, 1H), 4.70-4.07 (m, 3H), 3.88-3.78 (m, 1H), 3.47-3.37 (m, 1H), 3.26-3.05 (m, 2H), 1.43 (s, 9H), 1.10-1.06 (m, 3H). |
| 37.11 | 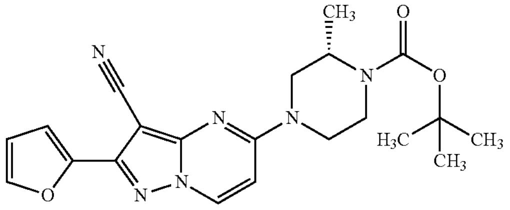 Tert-butyl (2S)-4-[3-cyano-2-(2-furyl)pyrazolo[1,5-a]pyrimidin-5-yl]-2-methyl-piperazine-1-carboxylate | LC-MS (Method 3B): Rt 1.97 mins; MS m/z 409.4 = [M + H]+ $^1$H NMR (500 MHz, Chloroform-d) δ 8.28 (d, 1H), 7.62-7.57 (m, 1H), 7.26-7.23 (m, 1H), 6.60-6.56 (m, 1H), 6.41 (d, J = 5.5 Hz, 1H), 4.72-3.73 (m, 4H), 3.57-3.45 (m, 1H), 3.31-3.15 (m, 2H), 1.49 (s, 9H), 1.21-1.14 (m, 3H). |
| 37.12 | 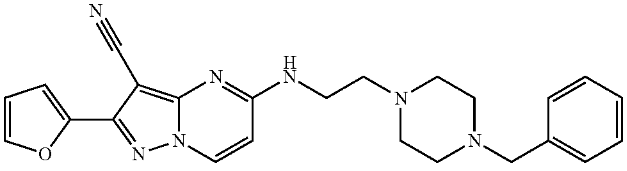 5-[2-(4-Benzylpiperazin-1-yl)ethylamino]-2-(2-furyl)pyrazolo[1,5-a]pyrimidine-3-carbonitrile | LC-MS (Method 8B): Rt 4.78 mins; MS m/z 428.2 = [M + H]+ $^1$H NMR (500 MHz, DMSO-d6) δ 8.56 (d, J = 7.6 Hz, 1H), 8.09 (s, 1H), 7.92 (s, 1H), 7.36-7.21 (m, 5H), 7.05 (d, J = 3.5 Hz, 1H), 6.74-6.67 (m, 1H), 6.52 (d, J = 7.6 Hz, 1H), 3.62-3.37 (m, 6H), 2.50-2.22 (m, 8H). |

Example 38-2-(2-Furyl)-5-[(3-methyl-2-pyridyl)methylamino]pyrazolo[1,5-a]pyrimidine-3-carboxamide

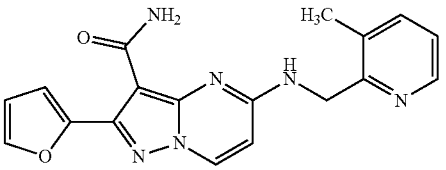 [SMILES: Cc1cccnc1CNc1ccn2nc(-c3ccco3)c(C(N)=O)c2n1]

A suspension of 2-(2-furyl)-5-[(3-methyl-2-pyridyl)methylamino]pyrazolo[1,5-a]pyrimidine-3-carbonitrile (Example 37) (40 mg, 0.12 mmol) and hydrido(dimethylphosphinous acid-kP)[hydrogen bis(dimethylphosphinito-kP)]platinum(II) (10 mg, 0.02 mmol) in EtOH (1 mL) and water (0.2 mL) was stirred and 80° C. for 16 h. Further hydrido(dimethylphosphinous acid-kP)[hydrogen bis(dimethylphosphinito-kP)]platinum(II) (5 mg, 0.01 mmol) and EtOH (1 mL) were added and the mixture was heated using microwave irradiation to 110° C. for 23 h. Additional hydrido(dimethylphosphinous acid-kP)[hydrogen bis(dimethylphosphinito-kP)]platinum(II) (3 mg, 0.01 mmol) was added and heating continued at 110° C. using microwave irradiation for a further6 h. The resulting solid was filtered, washed with MeOH, $Et_2O$, DCM and MeCN and dried to afford the title compound as a colourless solid.

LC-MS (Method 8B): Rt 3.30 mins; MS m/z 349.0=[M+H]+

$^1H$ NMR (500 MHz, DMSO-$d_6$) δ 8.66-8.54 (m, 2H), 8.39 (d, J=4.8 Hz, 1H), 8.10 (s, 1H), 7.86 (d, J=3.5 Hz, 1H), 7.74 (d, J=1.8 Hz, 1H), 7.60 (d, J=7.4 Hz, 1H), 7.24 (dd, J=7.6, 4.8 Hz, 1H), 7.19-7.10 (m, 1H), 6.63 (d, J=7.6 Hz, 1H), 6.58 (dd, J=3.5, 1.8 Hz, 1H), 4.69 (d, J=5.1 Hz, 2H), 2.36 (s, 3H).

Example 39-5-[4-(2-Fluoroethyl)piperazin-1-yl]-2-(2-furyl)pyrazolo[1,5-a]pyrimidine-3-carboxamide

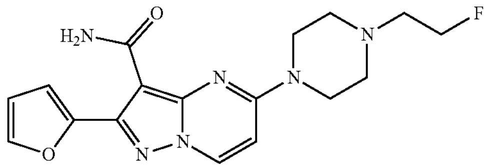 [SMILES: NC(=O)c1c(-c2ccco2)nn2ccc(N3CCN(CCF)CC3)nc12]

Step 1: 5-Chloro-2-(2-furyl)pyrazolo[1,5-a]pyrimidine-3-carboxamide

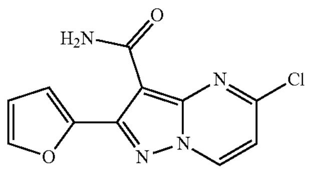 [SMILES: NC(=O)c1c(-c2ccco2)nn2ccc(Cl)nc12]

The title compound was prepared from 5-chloro-2-(2-furyl)pyrazolo[1,5-a]pyrimidine-3-carbonitrile (Intermediate P) and hydrido(dimethylphosphinous acid-kP)[hydrogen bis(dimethylphosphinito-kP)fplatinum(II) analogously to Example 38.

LC-MS (Method 3B): Rt 1.34 mins; MS m/z 263.0=[M+H]+

$^1H$ NMR (500 MHz, DMSO-$d_6$) δ 9.31 (d, J=7.2 Hz, 1H), 7.87 (s, 1H), 7.80 (d, J=3.5 Hz, 1H), 7.68-7.51 (br m, 2H), 7.37 (d, J=7.2 Hz, 1H), 6.72-6.66 (m, 1H).

Step 2: 5-[4-(2-Fluoroethyl)piperazin-1-yl]-2-(2-furyl)pyrazolo[1,5-a]pyrimidine-3-carboxamide The title compound was prepared from 5-chloro-2-(2-furyl)pyrazolo[1,5-a]pyrimidine-3-carboxamide (step 1) and 1-(2-fluoroethyl)piperazine dihydrochloride analogously to Example 2.

LC-MS (Method 8B): Rt 3.67 mins; MS m/z 359.3=[M+H]+

$^1H$ NMR (500 MHz, DMSO-$d_6$) δ 8.77 (br d, J=7.8 Hz, 1H), 7.88 (br dd, J=3.4, 0.9 Hz, 2H), 7.76 (dd, J=1.8, 0.9 Hz, 1H), 7.17 (br s, 1H), 6.93 (br d, J=7.8 Hz, 1H), 6.61 (dd, J=3.4, 1.8 Hz, 1H), 4.63 (br s, 1H), 4.54 (br s, 1H), 3.74 (br s, 4H), 2.72 (br s, 1H), 2.66 (br s, 1H), 2.59 (br s, 4H).

Example 39.1-5-[3-(Dimethylamino)azetidin-1-yl]-2-(2-furyl)pyrazolo[1,5-a]pyrimidine-3-carboxamide

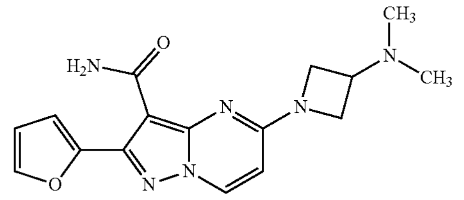 [SMILES: CN(C)C1CN(c2ccn3nc(-c4ccco4)c(C(N)=O)c3n2)C1]

The title compound was prepared from 5-chloro-2-(2-furyl)pyrazolo[1,5-a]pyrimidine-3-carboxamide (Example 39, step 1) and N,N-dimethylazetidin-3-amine dihydrochloride analogously to Example 39.

LC-MS (Method 8B): Rt 3.07 mins; MS m/z 327.0=[M+H]+

$^1H$ NMR (500 MHz, DMSO-d6) δ 8.74 (d, J=7.6 Hz, 1H), 8.00 (br s, 1H), 7.89 (d, J=3.5 Hz, 1H), 7.76 (d, J=1.8 Hz, 1H), 7.16 (br s, 1H), 6.60 (dd, J=3.5, 1.8 Hz, 1H), 6.39 (d, J=7.6 Hz, 1H), 4.20 (br s, 2H), 3.98 br (s, 2H), 3.26 (s, 1H), 2.15 (s, 6H).

Example 40—tert-Butyl 4-[3-cyano-2-(2-furyl)pyrazolo[1,5-a]pyrimidin-5-yl]-3,6-dihydro-2H-pyridine-1-carboxylate

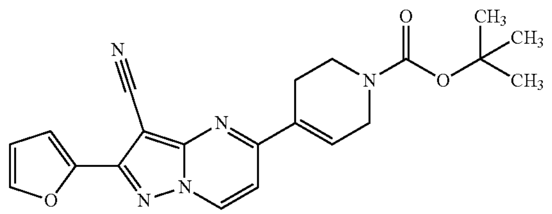 [SMILES: CC(C)(C)OC(=O)N1CC=C(c2ccn3nc(-c4ccco4)c(C#N)c3n2)CC1]

A suspension of 5-chloro-2-(2-furyl)pyrazolo[1,5-a]pyrimidine-3-carbonitrile (Intermediate P) (250 mg, 1.02 mmol), tert-butyl 4-(4,4,5,5-tetramethyl-1,3,2-dioxaborolan-2-yl)-3,6-dihydro-2H-pyridine-1-carboxylate (474 mg, 1.53 mmol) and potassium carbonate (282 mg, 2.04 mmol) in water (2.5 mL) and 1,4-dioxane (10 mL) was degassed with $N_2$ and Pd(amphos)$Cl_2$ (36 mg, 0.05 mmol) was added before the mixture was stirred at 100° C. for 1 h under nitrogen. The crude mixture was partitioned between EtOAc (30 mL) and $H_2O$ (30 mL), the organic portion was separated and the aqueous portion was further extracted with EtOAc (20 mL). The combined organic extracts were washed with water (20 mL), brine (20 mL), dried over $MgSO_4$ and the solvent removed in vacuo. Purification by chromatography on silica eluting with a gradient of 40 to 100% EtOAc in petroleum ether afforded the title compound as an off-white solid.

LC-MS (Method 8B): Rt 5.32 mins; MS m/z 392.5=[M+H]+

$^1H$ NMR (500 MHz, DMSO-d6) δ 9.24 (d, J=7.4 Hz, 1H), 8.02 (dd, J=1.8, 0.8 Hz, 1H), 7.66 (d, J=7.5 Hz, 1H), 7.22 (dd, J=3.5, 0.8 Hz, 1H), 7.13 (s, 1H), 6.78 (dd, J=3.5, 1.8 Hz, 1H), 4.16 (s, 2H), 3.57 (t, J=5.8 Hz, 2H), 2.66 (t, J=4.8 Hz, 2H), 1.44 (s, 9H).

Example 41 (=Intermediate R)-2-(2-Furyl)-5-piperazin-1-yl-pyrazolo[1,5-a]pyrimidine-3-carbonitrile

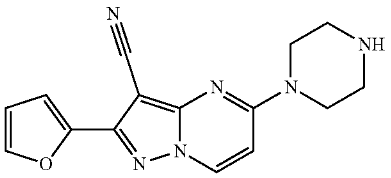 [SMILES: N#Cc1c(-c2ccco2)nn2ccc(N3CCNCC3)nc12]

To a solution of 5-chloro-2-(2-furyl)pyrazolo[1,5-a]pyrimidine-3-carbonitrile (Intermediate P) (80 mg, 0.33 mmol) in MeCN (4 mL) was added piperazine (141 mg, 1.64 mmol) and the mixture was heated at 80° C. for 1 h. The resulting mixture was cooled to room temperature and the solvent removed in vacuo. Purification by chromatography on silica eluting with 5% 7N $NH_3$ in MeOH in DCM afforded the title compound as a yellow solid.

LC-MS (Method 3B): Rt 1.35 mins; MS m/z 295.3=[M+H]+

$^1$H NMR (500 MHz, DMSO-$d_6$) δ 8.74 (d, J=8.0 Hz, 1H), 7.93 (dd, J=1.8, 0.8 Hz, 1H), 7.07 (dd, J=3.5, 0.8 Hz, 1H), 6.93 (d, J=8.0 Hz, 1H), 6.72 (dd, J=3.5, 1.8 Hz, 1H), 3.99 (s, 4H), 2.81-2.74 (m, 4H). NH proton not observed.

Example 42-2-(2-Furyl)-5-[[(2S)-morpholin-2-yl]methylamino]pyrazolo[1,5-a]pyrimidine-3-carbonitrile hydrochloride

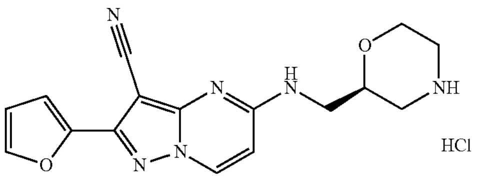 [SMILES: N#Cc1c(-c2ccco2)nn2ccc(NC[C@@H]3CNCCO3)nc12 ; Cl]

Step 1: tert-Butyl(2R)-2-[[[3-cyano-2-(2-furyl)pyrazolo[1,5-a]pyrimidin-5-yl]amino]methyl]morpholine-4-carboxylate

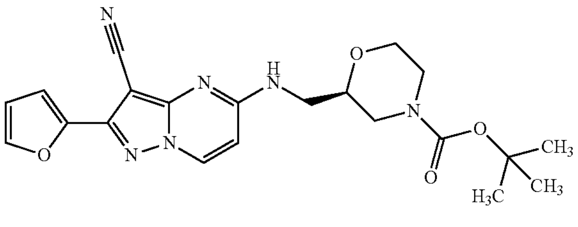 [SMILES: CC(C)(C)OC(=O)N1CCO[C@H](CNc2ccn3nc(-c4ccco4)c(C#N)c3n2)C1]

The title compound was prepared from 5-chloro-2-(2-furyl)pyrazolo[1,5-a]pyrimidine-3-carbonitrile (Intermediate P) and tert-butyl(2R)-2-(aminomethyl)morpholine-4-carboxylate analogously to Example 41.

LC-MS (Method 88): Rt 4.77 mins; MS m/z 325.3=[M-Boc+H]+

$^1$H NMR (500 MHz, DMSO-$d_6$) δ 8.60 (d, J=7.6 Hz, 1H), 8.34-8.28 (m, 1H), 7.92 (dd, J=1.9, 0.7 Hz, 1H), 7.06 (dd, J=3.5, 0.8 Hz, 1H), 6.72 (dd, J=3.5, 1.8 Hz, 1H), 6.55 (d, J=7.6 Hz, 1H), 3.92-3.81 (m, 2H), 3.75-3.67 (m, 1H), 3.59-3.46 (m, 3H), 3.43 (td, J=11.6, 2.8 Hz, 1H), 2.89 (s, 1H), 2.77-2.59 (m, 1H), 1.40 (s, 9H).

Step 2: 2-(2-Furyl)-5-[[(2S)-morpholin-2-yl]methylamino]pyrazolo[1,5-a]pyrimidine-3-carbonitrile hydrochloride 4 M HCl in 1,4-dioxane (0.74 mL, 2.94 mmol) was added to tert-butyl(2R)-2-[[[3-cyano-2-(2-furyl)pyrazolo[1,5-a]pyriimidin-5-yl]amino]methyl]morpholine-4-carboxylate (step 1) (50 mg, 0.12 mmol) and the reaction mixture was stirred at room temperature for 1 h.

The resulting mixture was concentrated in vacuo and the solid was washed with diethyl ether to afford the title compound as a yellow solid.

LC-MS (Method 8B): Rt 3.41 mins; MS m/z 325.1=[M+H]+

$^1$H NMR (500 MHz, Deuterium Oxide) 6 7.99 (d, J=7.6 Hz, 1H), 7.62 (d, J=1.8 Hz, 1H), 6.92 (d, J=3.5 Hz, 1H), 6.60 (dd, J=3.5, 1.8 Hz, 1H), 6.19 (d, J=7.7 Hz, 1H), 4.16 (dd, J=12.9, 3.7 Hz, 1H), 4.13-4.04 (m, 1H), 3.92-3.83 (m, 1H), 3.59-3.51 (m, 1H), 3.50-3.40 (m, 2H), 3.38-3.32 (m, 1H), 3.20 (td, J=12.6, 3.9 Hz, 1H), 3.07-2.99 (m, 1H). NH protons not observed.

Example 42.1-2-(2-Furyl)-5-[[(2R)-morpholin-2-yl]methylamino]pyrazolo[1,5-a]pyrimidine-3-carbonitrile hydrochloride

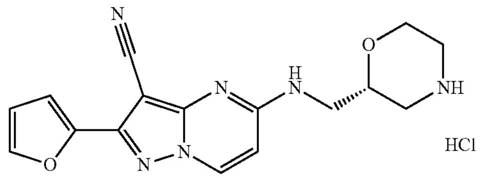 [SMILES: N#Cc1c(-c2ccco2)nn2ccc(NC[C@H]3CNCCO3)nc12 ; Cl]

Step 1: tert-Butyl(2S)-2-[[[3-cyano-2-(2-furyl)pyrazolo[1,5-a]pyrimidin-5-yl]amino]methyl]morpholine-4-carboxylate

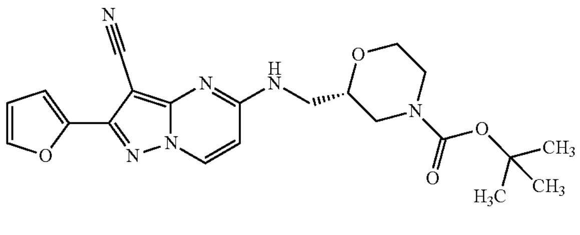 [SMILES: CC(C)(C)OC(=O)N1CCO[C@@H](CNc2ccn3nc(-c4ccco4)c(C#N)c3n2)C1]

The title compound was prepared from 5-chloro-2-(2-furyl)pyrazolo[1,5-a]pyrimidine-3-carbonitrile (Intermediate P) and tert-butyl(2S)-2-(aminomethyl)morpholine-4-carboxylate analogously to Example 41.

LC-MS (Method 3B): Rt 1.86 mins; MS m/z 325=[M-Boc+H]+

$^1$H NMR (500 MHz, DMSO-da) 6 8.60 (d, J=7.6 Hz, 1H), 8.41-8.19 (m, 1H), 7.92 (dd, J=1.8, 0.8 Hz, 1H), 7.06 (dd, J=3.4, 0.8 Hz, 1H), 6.71 (dd, J=3.4, 1.8 Hz, 1H), 6.55 (d, J=7.6 Hz, 1H), 3.93-3.80 (m, 2H), 3.76-3.65 (m, 1H), 3.61-3.44 (m, 3H), 3.45-3.39 (m, 1H), 2.99-2.80 (m, 1H), 2.79-2.65 (m, 1H), 1.40 (s, 9H).

Step 2: 2-(2-Furyl)-5-[[(2R)-morpholin-2-yl]methylamino]pyrazolo[1,5-a]pyrimidine-3-carbonitrile hydrochloride The title compound was prepared from tert-butyl(2S)-2-[[[3-cyano-2-(2-furyl)pyrazolo[1,5-a]pyrimidin-5-yl]amino]methyl]morpholine-4-carboxylate (step 1) and 4M HCl in 1,4-dioxane analogously to Example 42 step 2.

LC-MS (Method 8B): Rt 3.48 mins; MS m/z 325.3=[M+H]+

$^1$H NMR (500 MHz, DMSO-$d_6$) δ 9.25 (s, 2H), 8.62 (d, J=7.6 Hz, 1H), 8.43 (t, J=5.7 Hz, 1H), 7.93 (d, J=1.8 Hz, 1H), 7.07 (d, J=3.4 Hz, 1H), 6.72 (dd, J=3.5, 1.8 Hz, 1H), 6.57 (d, J=7.6 Hz, 1H), 4.03-3.92 (m, 2H), 3.81-3.73 (m, 1H), 3.68-3.44 (m, 2H), 3.36-3.27 (m, 1H), 3.22-3.14 (m, 1H), 3.06-2.94 (m, 1H), 2.93-2.81 (m, 1H).

Example 43-5-(4-Benzylpiperazin-1-yl)-2-(2-furyl)pyrazolo[1,5-a]pyrimidine-3-carbonitrile

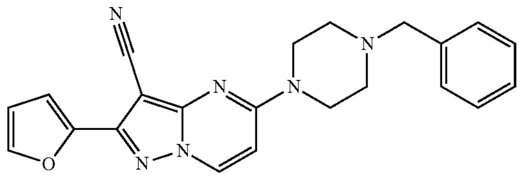 [SMILES: N#Cc1c(-c2ccco2)nn2ccc(N3CCN(Cc4ccccc4)CC3)nc12]

To a solution of 2-(2-furyl)-5-piperazin-1-yl-pyrazolo[1,5-a]pyrimidine-3-carbonitrile (Intermediate R)(20 mg, 0.07 mmol) in MeCN (1 mL) was added triethylamine (21 μL, 0.15 mmol) followed by bromomethylbenzene (10 μL, 0.08 mmol) and the mixture was stirred for 1 h. The resulting mixture was purified directly by mass directed LC-MS using MeCN/water/0.1% ammonia to afford the title compound as an off-white solid.

LC-MS (Method 8B): Rt 5.35 mins; MS m/z 385.2=[M+H]+

$^1$H NMR (500 MHz, DMSO-$d_6$) δ 8.77 (d, J=8.0 Hz, 1H), 7.94 (dd, J=1.8, 0.8 Hz, 1H), 7.37-7.32 (m, 4H), 7.30-7.25 (m, 1H), 7.08 (dd, J=3.4, 0.8 Hz, 1H), 6.94 (d, J=8.0 Hz, 1H), 6.72 (dd, J=3.4, 1.8 Hz, 1H), 3.78 (s, 4H), 3.54 (s, 2H), 2.49-2.46 (m, 4H).

Example 44—N-Benzyl-3-bromo-2-(2-furyl)pyrazolo[1,5-a]pyrimidin-5-amine

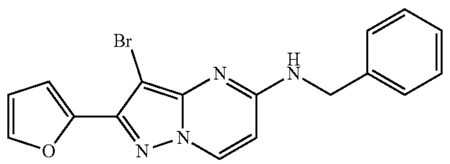 [SMILES: Brc1c(-c2ccco2)nn2ccc(NCc3ccccc3)nc12]

To a solution of N-benzyl-2-(2-furyl)pyrazolo[1,5-a]pyrimidin-5-amine (Intermediate S3) (83 mg, 0.29 mmol) in THF (5 mL) was added NBS (51 mg, 0.29 mmol) in one portion and the reaction mixture was stirred under a nitrogen atmosphere at room temperature for 30 mins. The resulting mixture was diluted with EtOAc (25 mL) and washed with saturated sodium thiosulphate solution (20 mL), water (20 mi) and saturated brine (10 mL). The organic layer was dried over $MgSO_4$, filtered and concentrated in vacuo. Purification by chromatography on silica eluting with 20% to 40% EtOAc in petroleum ether afforded the title compound as a colourless solid.

LC-MS (Method 8B): 4.72 mins; MS m/z 369.1/371.0=[M+H]+

$^1$H NMR (500 MHz, DMSO-d6) δ 8.51 (d, J=7.6 Hz, 1H), 8.22 (s, 1H), 7.84 (dd, J=1.8, 0.8 Hz, 1H), 7.45-7.39 (m, 2H), 7.39-7.32 (m, 2H), 7.31-7.24 (m, 1H), 7.10 (dd, J=3.5, 0.9 Hz, 1H), 6.67 (dd, J=3.4, 1.8 Hz, 1H), 6.40 (d, J=7.6 Hz, 1H), 4.59 (d, 2H).

Example 45-5-(Benzylamino)-2-(2-furyl)pyrazolo[1,5-a]pyrimidine-3-carbonitrile

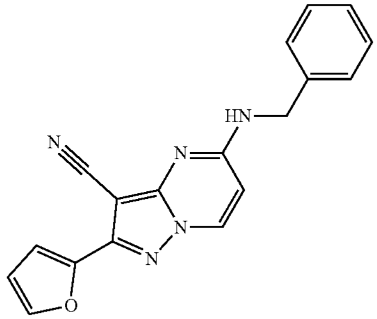 [SMILES: N#Cc1c(-c2ccco2)nn2ccc(NCc3ccccc3)nc12]

The title compound was prepared from N-benzyl-3-bromo-2-(2-furyl)pyrazolo[1,5-a]pyrimidin-5-amine (Example 44) analogously to Example 14.

LC-MS (Method 8B): 4.54 mins; MS m/z 316.1=[M+H]+

$^1$H NMR (500 MHz, DMSO-d6) δ 8.65-8.59 (m, 2H), 7.93 (dd, J=1.8, 0.8 Hz, 1H), 7.44-7.33 (m, 4H), 7.33-7.26 (m, 1H), 7.06 (dd, J=3.5, 0.8 Hz, 1H), 6.72 (dd, J=3.5, 1.8—Hz, 1H), 6.54 (d, J=7.7 Hz, 1H), 4.63 (s, 2H).

Example 46-5-(Benzylamino)-2-(2-furyl)pyrazolo[1,5-a]pyrimidine-3-carboxamide

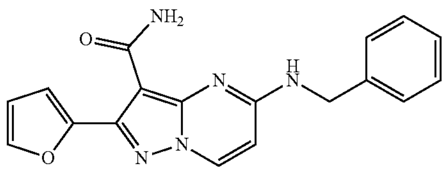 [SMILES: NC(=O)c1c(-c2ccco2)nn2ccc(NCc3ccccc3)nc12]

5-(Benzylamino)-2-(2-furyl)pyrazolo[1,5-a]pyrimidine-3-carbonitrile (Example 45) (50 mg, 0.16 mmol) was added to sulphuric acid (1 mL, 0.16 mmol) that had been cooled to 0° C. and the mixture was stirred at 0° C. for 30 mins. After warming to room temperature, the mixture was stirred for a further 2.5 h then added dropwise to a mixture of ice/water. The resulting colourless solid formed was collected by filtration and washed with water. The resulting material was loaded onto an Isolute® SCX cartridge that had been pre-wetted with MeOH. The cartridge was washed with MeOH (50 mL) and eluted with 3.5M ammonia in MeOH solution (20 mL). The product fractions were combined and concentrated in vacuo to afford a colourless oil which was further purified by chromatography on silica eluting with EtOAc. The resulting solid was triturated with diethyl ether to afford the title compound as a colourless solid.

LC-MS (Method 8B): Rt 3.65 mins; MS m/z 332.3=[M−H]−

$^1$H NMR (500 MHz, DMSO-d6) δ 8.64 (t, J=5.6 Hz, 1H), 8.61 (d, J=7.5 Hz, 1H), 8.00-7.94 (m, 1H), 7.86 (d, J=3.4 Hz, 1H), 7.77-7.72 (m, 1H), 7.41-7.33 (m, 4H), 7.31-7.25 (m, 1H), 7.10 (s, 1H), 6.61-6.57 (m, 1H), 6.50 (d, J=7.6 Hz, 1H), 4.58 (d, J=5.6 Hz, 2H).

Example 47-5-(Benzylamino)-2-(2-furyl)pyrazolo[1,5-a]pyrimidine-3-carbaldehyde

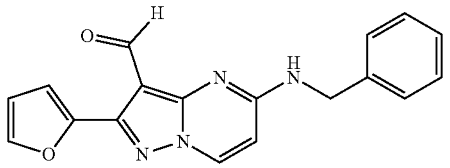 [SMILES: O=Cc1c(-c2ccco2)nn2ccc(NCc3ccccc3)nc12]

Step 1: 2-Bromo-5-chloro-pyrazolo[1,5-a]pyrimidine-3-carbaldehyde

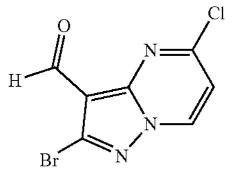 [SMILES: O=Cc1c(Br)nn2ccc(Cl)nc12]

To a solution of 2-bromo-5-chloro-pyrazolo[1,5-a]pyrimidine (Intermediate Q) (200 mg, 0.86 mmol) in DMF (3 mL) was added (chloromethylene)dimethylammonium chloride (220 mg, 1.72 mmol) followed by $POCl_3$ (0.4 mL, 4.3 mmol) and the reaction mixture was stirred at room temperature for 1 hour. Further portions of $POCl_3$[4× (1.2 mL, 12.9 mmol)]were added over a period of 6 days and stirring continued at room temperature. The reaction was quenched by adding to ice cold water (100 mL) and the resulting suspension was neutralised with 2M NaOH. The solid was collected by filtration, washed with water and dried under vacuum to afford the title compound as a colourless solid.

LC-MS (Method 3B): Rt 1.33 mins; MS m/z 260.0/262.0=[M+H]+

1H NMR (500 MHz, DMSO-d6) δ 10.03 (s, 1H), 9.36 (d, J=7.2 Hz, 1H), 7.56 (d, J=7.2 Hz, 1H).

Step 2: 5-(Benzylamino)-2-bromo-pyrazolo[1,5-a]pyrimidine-3-carbaldehyde

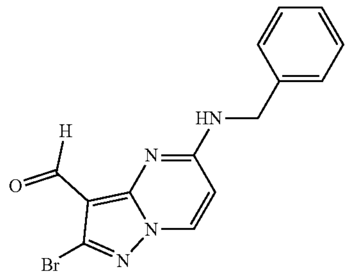 [SMILES: O=Cc1c(Br)nn2ccc(NCc3ccccc3)nc12]

A mixture of 2-bromo-5-chloro-pyrazolo[1,5-a]pyrimidine-3-carbaldehyde (step 1) (154 mg, 0.59 mmol), benzylamine (71 μL, 0.65 mmol) and DIPEA (206 μL, 1.18 mmol) in EtOH (10 mL) were heated to 85° C. for 2 h and allowed to stand at room temperature overnight. The resulting mixture was adsorbed onto silica and purification by chromatography on silica eluting with a gradient of 30 to 70% EtOAc in petroleum ether afforded the title compound as a cream solid.

LC-MS (Method 3B): Rt 1.55 mins; MS m/z 331.0/333.0=[M+H]+

1H NMR (500 MHz, DMSO-d6) δ 9.86 (s, 1H), 8.70 (t, J=5.7 Hz, 1H), 8.55 (d, J=7.6 Hz, 1H), 7.45-7.39 (m, 2H), 7.38-7.32 (m, 2H), 7.31-7.25 (m, 1H), 6.51 (d, J=7.6 Hz, 1H), 4.62 (d, J=5.7 Hz, 2H).

Step 3: 5-(Benzylamino)-2-(2-furyl)pyrazolo[1,5-a]pyrimidine-3-carbaldehyde

A mixture of 5-(benzylamino)-2-bromo-pyrazolo[1,5-a]pyrimidine-3-carbaldehyde (step 2) (64 mg, 0.19 mmol), 2-furylboronic acid (32 mg, 0.29 mmol) and potassium carbonate (53 mg, 0.39 mmol) in water (0.5 mL) and 1,4-dioxane (2 mL) was degassed with N2 and Pd(amphos)$Cl_2$ (7 mg, 0.01 mmol) was added before the mixture was stirred under nitrogen at 100° C. for 2 h. The resulting mixture was partitioned between EtOAc (15 mL) and $H_2O$ (15 mL), the organic portion was separated and the aqueous was further extracted with EtOAc (15 mL). The combined organic extracts were washed with water (15 mL), brine (15 mL), dried over $MgSO_4$ and the solvent removed in vacuo. Purification by chromatography on silica eluting with a gradient of 40 to 100% EtOAc in petroleum ether afforded the title compound as a cream solid.

LC-MS (Method 38): Rt 1.65 mins; MS m/z 319.1=[M+H]+

1H NMR (500 MHz, DMSO-d6) δ 10.09 (s, 1H), 8.67-8.59 (m, 2H), 7.84 (d, J=1.7 Hz, 1H), 7.79 (d, J=3.4 Hz, 1H), 7.46-7.40 (m, 2H), 7.39-7.33 (m, 2H), 7.28 (t, J=6.8 Hz, 1H), 6.70-6.64 (m, 1H), 6.55 (d, J=7.5 Hz, 1H), 4.65 (d, J=5.6 Hz, 2H).

Example 48—N-Benzyl-2-(2-furyl)pyrazolo[1,5-a]pyrimidin-5-amine

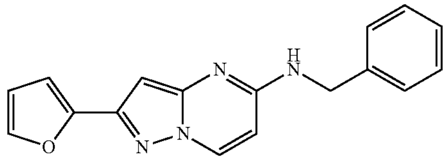 [SMILES: c1ccc(CNc2ccn3nc(-c4ccco4)cc3n2)cc1]

Step 1: N-Benzyl-2-bromo-pyrazolo[1,5-a]pyrimidin-5-amine

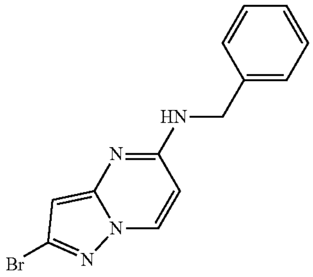 [SMILES: Brc1cc2nc(NCc3ccccc3)ccn2n1]

The title compound was prepared from 2-bromo-5-chloro-pyrazolo[1,5-a]pyrimidine (Intermediate Q) and benzylamine analogously to Example 35 step 2.

LC-MS (Method 3B): Rt 1.78 mins; MS m/z 304.0=[M+H]+

1H NMR (500 MHz, DMSO-d6) δ 8.44 (dd, J=7.6, 0.8 Hz, 1H), 8.07 (t, J=5.7 Hz, 1H), 7.36-7.31 (m, 4H), 7.26 (tdd, J=5.2, 3.9, 3.0 Hz, 1H), 6.34 (d, J=7.6 Hz, 1H), 6.11 (d, J=0.8 Hz, 1H), 4.53 (d, J=5.7 Hz, 2H).

Step 2: N-Benzyl-2-(2-furyl)pyrazolo[1,5-a]pyrimidin-5-amine

The title compound was prepared from N-benzyl-2-bromo-pyrazolo[1,5-a]pyrimidin-5-amine (step 1) and 2-furylboronic acid analogously to Example 47 step 3.

LC-MS (Method 8B): Rt 4.47 mins; MS m/z 291.0=[M+H]+

1H NMR (500 MHz, DMSO-d6) δ 8.47 (dd, J=7.6, 0.8 Hz, 1H), 7.95 (t, J=5.7 Hz, 1H), 7.75 (dd, J=1.8, 0.8 Hz, 1H), 7.39-7.30 (m, 4H), 7.25 (ddt, J=8.6, 5.9, 2.1 Hz, 1H), 6.83 (dd, J=3.3, 0.8 Hz, 1H), 6.59 (dd, J=3.4, 1.8 Hz, 1H), 6.34 (d, J=7.6 Hz, 1H), 6.23 (d, J=0.8 Hz, 1H), 4.55 (d, J=5.6 Hz, 2H).

This compound is also described as Intermediate S3. An alternative route to this compound is provided with Intermediate S3.

Example 49

5-Amino-2-(2-furyl)pyrazolo[1,5-a]pyrimidine-3-carbonitrile

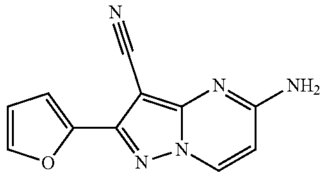 [SMILES: N#Cc1c(-c2ccco2)nn2ccc(N)nc12]

Step 1: 5-Amino-2-(2-furyl)pyrazolo[1 5-a]pyrimidine-3-carbonitrile

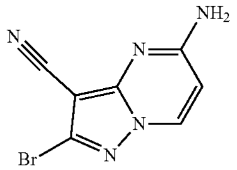 [SMILES: N#Cc1c(Br)nn2ccc(N)nc12]

A mixture of 2-bromo-5-chloro-pyrazolo[1,5-a]pyrimidine-3-carbonitrile (Intermediate U) (100 mg, 0.39 mmol), Ammonium hydroxide (1.5 mL of 28-30% aqueous solution) and EtOH (3 mL) were heated using microwave irradiation at 100° C. for 30 mins. The mixture was cooled to room temperature and the resulting colourless solid was collected by filtration and dried under vacuum to afford the title compound as a colourless solid.

LC-MS (Method 3B): Rt 1.22 mins; MS m/z 238.1/240.1=[M+H]+

1H NMR (500 MHz, DMSO-d6) δ 8.57 (d, J=7.6 Hz, 1H), 7.79 (d, J=48.2 Hz, 2H), 6.39 (d, J=7.7 Hz, 1H).

Step 2: 5-Amino-2-(2-furyl)pyrazolo[1,5-a]pyrimidine-3-carbonitrile

The title compound was prepared from 5-amino-2-(2-furyl)pyrazolo[1,5-a]pyrimidine-3-carbonitrile (step 1) and 2-furylboronic acid analogously to Example 47 step 3.

LC-MS (Method 8A): Rt 3.22 mins; MS m/z 226.2=[M+H]+

1H NMR (500 MHz, DMSO-d6) δ 8.62 (d, J=7.6 Hz, 1H), 7.93 (dd, J=1.8, 0.8 Hz, 1H), 7.68 (d, J=34.7 Hz, 2H), 7.05 (dd, J=3.5, 0.8 Hz, 1H), 6.71 (dd, J=3.5, 1.8 Hz, 1H), 6.42 (d, J=7.5 Hz, 1H).

Example 50-3-Bromo-2-(2-furyl)pyrazolo[1,5-a]pyrimidin-5-amine

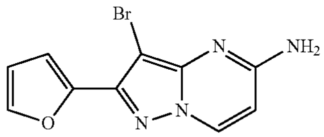 [SMILES: Nc1ccn2nc(-c3ccco3)c(Br)c2n1]

Step 1: 2-Brornopyrazolo[1,5-a]pyrimidin-5-amine

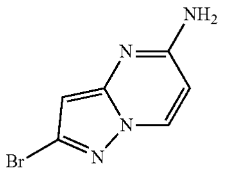 [SMILES: Nc1ccn2nc(Br)cc2n1]

A mixture of 2-bromo-5-chloro-pyrazolo[1,5-a]pyrimidine (Intermediate Q) (500 mg, 2.15 mmol) and $NH_4OH$ (30 wt %, 6 mL) in EtOH (6 mL) was heated using microwave irradiation to 110° C. for 1 h. The resulting mixture was concentrated in vacuo and the product was extracted into EtOAc (40 mL). The mixture was washed with water (40 mL), brine (20 mL), dried over $MgSO_4$, filtered and concentrated in vacuo to afford the title compound as a colourless solid.

LC-MS (Method 38): Rt 0.98 mins; MS m/z 215.0=[M+H]+

1H NMR (500 MHz, DMSO-d6) δ 8.43 (dd, J=7.5, 0.8 Hz, 1H), 7.00 (s, 2H), 6.22 (d, J=7.6 Hz, 1H), 6.02 (d, J=0.8 Hz, 1H).

Step 2: 2-(2-Furyl)pyrazolo[1,5-a]pyrimidin-5-amine

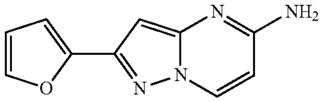 [SMILES: Nc1ccn2nc(-c3ccco3)cc2n1]

The title compound was prepared from 2-bromopyrazolo{1,5-a]pyrimidin-5-amine (step 1) and 2-furylboronic acid analogously to Example 47 step 3.

LC-MS (Method 3B): Rt 1.13 mins; MS m/z 201.1=[M+H]+

1H NMR (500 MHz, DMSO-d6) δ 8.48 (dd, J=7.4, 0.8 Hz, 1H), 7.75 (dd, J=1.8, 0.8 Hz, 1H), 6.89-6.82 (m, 3H), 6.60 (dd, J=3.3, 1.8 Hz, 1H), 6.22 (d, J=7.5 Hz, 1H), 6.15 (d, J=0.9 Hz, 1H).

Step 3: 3-Bromo-2-(2-furyl)pyrazolo[1,5-a]pyrimidin-5-amine

The title compound was prepared from 2-(2-furyl)pyrazolo[1,5-a]pyrimidin-5-amine (step 2) and NBS analogously to Example 44.

LC-MS (Method 8B): Rt 3.58 mins; MS m/z 278.9/280.9=[M+H]+

1H NMR (500 MHz, DMSO-d6) δ 8.52 (d, J=7.4 Hz, 1H), 7.84 (dd, J=1.8, 0.8 Hz, 1H), 7.26 (s, 2H), 7.09 (dd, J=3.5, 0.8 Hz, 1H), 6.66 (dd, J=3.4, 1.8 Hz, 1H), 6.30 (d, J=7.5 Hz, 1H).

Example 51-2-(2-Furyl)-5-[4-[(3-methyl-2-pyridyl)methyl]piperazin-1-yl]pyrazolo[1,5-a]pyrimidine-3-carbonitrile

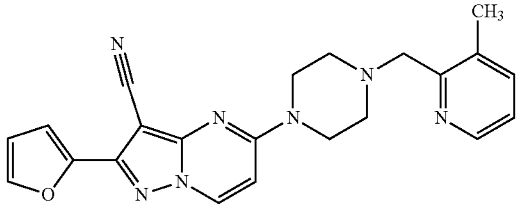 [SMILES: Cc1cccnc1CN1CCN(c2ccn3nc(-c4ccco4)c(C#N)c3n2)CC1]

To a solution of 2-(2-furyl)-5-piperazin-1-yl-pyrazolo[1,5-a]pyrimidine-3-carbonitrile (Intermediate R) (20 mg, 0.07 mmol) in MeCN (1 mL) was added 2-(bromomethyl)-3-methyl-pyridine hydrobromide (23 mg, 0.08 mmol) followed by triethylamine (38 μL, 0.27 mmol). The mixture was warmed to −50° C. to solubilise the reagents before being cooled and stirred at room temperature for 2 h. The resulting mixture was purified directly by mass directed LC-MS using MeCN/water/0.1% ammonia followed by chromatography on silica eluting with 5% MeOH/DCM to afford the title compound as a colourless solid.

LC-MS (Method 8B): Rt 4.77 mins; MS m/z 400.3=[M+H]+

$^1$H NMR (500 MHz, Chloroform-d) δ 8.42 (dd, J=4.8, 1.7 Hz, 1H), 8.23 (d, J=7.8 Hz, 1H), 7.58 (dd, J=1.8, 0.6 Hz, 1H), 7.49 (d, J=7.5 Hz, 1H), 7.23 (dd, J=3.5, 0.6 Hz, 1H), 7.15 (dd, J=7.5, 4.8 Hz, 1H), 6.56 (dd, J=3.5, 1.8 Hz, 1H), 6.42 (d, J=7.8 Hz, 1H), 3.80 (s, 4H), 3.72 (s, 2H), 2.69-2.59 (m, 4H), 2.43 (s, 3H).

Example 51.1-2-(2-Furyl)-5-[4-[(2,4,6-trifluorophenyl)methyl]piperazin-1-yl]pyrazolo [1,5-a]pyrimidine-3-carbonitrile

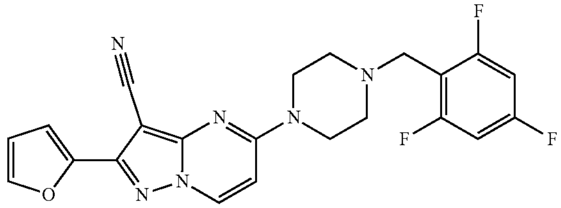 [SMILES: N#Cc1c(-c2ccco2)nn2ccc(N3CCN(Cc4c(F)cc(F)cc4F)CC3)nc12]

The title compound was prepared from 2-(2-furyl)-5-piperazin-1-yl-pyrazolo[1,5-a]pyrimidine-3-carbonitrile (Intermediate R) and 2-(bromomethyl)-1,3,5-trifluoro-benzene analogously to Example 51.

LC-MS (Method 88): Rt 5.36 mins; MS m/z 439.4=[M+H]+

$^1$H NMR (500 MHz, DMSO-$d_6$) δ 8.76 (d, J=7.9 Hz, 1H), 7.93 (dd, J=1.8, 0.8 Hz, 1H), 7.25-7.17 (m, 2H), 7.07 (dd, J=3.5, 0.8 Hz, 1H), 6.93 (d, J=7.9 Hz, 1H), 6.72 (dd, J=3.5, 1.8 Hz, 1H), 3.76 (s, 4H), 3.61 (s, 2H), 3.32 (s, 4H).

Example 51.2-2-(2-Furyl)-5-[4-[(1-methylimidazol-2-yl)methyl]piperazin-1-yl]pyrazolo [1,5-a]pyrimidine-3-carbonitrile

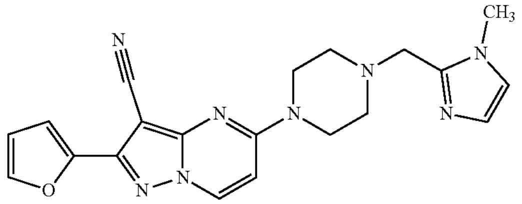 [SMILES: Cn1ccnc1CN1CCN(c2ccn3nc(-c4ccco4)c(C#N)c3n2)CC1]

To a solution of 2-(2-furyl)-5-piperazin-1-yl-pyrazolo[1,5-a]pyrimidine-3-carbonitrile (Intermediate R) (50 mg, 0.17 mmol) in DCM (4 mL) was added glacial acetic acid (24 μL, 0.42 mmol) followed by 1-methylimidazole-2-carbaldehyde (37 mg, 0.34 mmol) and the mixture was stirred for 30 mins. Sodium triacetoxyborohydride (36 mg, 0.17 mmol) was added and the mixture was stirred for 2.5 h. Additional 1-methylimidazole-2-carbaldehyde (37 mg, 0.34 mmol) was added and after stirring for 1 h, more sodium triacetoxyborohydride (36 mg, 0.17 mmol) was added. The mixture was stirred for a further hour. The resulting mixture was diluted with water and the organic portion was separated. The aqueous was further extracted with DCM and the combined organic extracts were concentrated in vacuo. The crude residue was purified directly by mass directed LC-MS using MeCN/water/0.1% ammonia to afford the title compound as a cream solid.

LC-MS (Method 88): Rt 3.99 mins; MS m/z 389.4=[M+H]+

$^1$H NMR (500 MHz, Chloroform-d) δ 8.25 (d, J=7.9 Hz, 1H), 7.58 (d, J=1.8 Hz, 1H), 7.23 (d, J=3.5 Hz, 1H), 6.98 (d, J=1.3 Hz, 1H), 6.90 (d, J=1.3 Hz, 1H), 6.57 (dd, J=3.5, 1.8 Hz, 1H), 6.42 (d, J=7.9 Hz, 1H), 3.78 (br s, 4H), 3.76 (s, 3H), 3.71 (s, 2H), 2.63-2.57 (m, 4H).

Example 52-2-(2-Furyl)-5-[4-(2-hydroxyethyl)piperazin-1-yl]pyrazolo[1,5-a]pyrimidine-3-carbonitrile

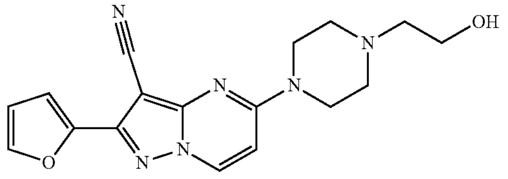 [SMILES: N#Cc1c(-c2ccco2)nn2ccc(N3CCN(CCO)CC3)nc12]

To a solution of 2-(2-furyl)-5-piperazin-1-yl-pyrazolo[1,5-a]pyrimidine-3-carbonitrile (Intermediate R) (20 mg, 0.07 mmol) in MeCN (1 mL) was added triethylamine (21 μL, 0.15 mmol) followed by 2-bromoethoxy-tert-butyl-dimethyl-silane (18 μL, 0.08 mmol) and the mixture was stirred at 60° C. for 18 h. Additional 2-bromoethoxy-tert-butyl-dimethyl-silane (18 μL, 0.08 mmol) and triethylamine (21 μL, 0.15 mmol) were added and the mixture heated for a further 8 h. The mixture was cooled, TBAF (1M in THF) (102 μL, 0.10 mmol) was added and the mixture stirred for 1 h at room temperature. Additional TBAF (1M in THF) (340 μL, 0.34 mmol) was added and the mixture warmed to 40° C. for 20 h. The solvent was removed in vacuo and the crude product was partitioned between DCM (10 mL) and $H_2O$ (10 mL). The aqueous portion was separated and further extracted with DCM (2×10 mL). The combined organic extracts were dried over $MgSO_4$ and the solvent removed in vacuo. Purification by chromatography on silica eluting with 5% MeOH/DCM afforded a yellow oil. The oil was loaded onto an Isolute® SCX column and was eluted with MeOH followed by -1M $NH_3$ in MeOH. The filtrate was concentrated in vacuo to afford the title compound as a yellow solid.

LC-MS (Method 8B): Rt 3.67 mins; MS m/z 339.2=[M+H]+

$^1$H NMR (500 MHz, Chloroform-d) δ 8.28 (d, J=7.9 Hz, 1H), 7.59 (dd, J=1.7, 0.8 Hz, 1H), 7.25 (dd, J=3.5, 0.8 Hz, 1H), 6.58 (dd, J=3.5, 1.8 Hz, 1H), 6.45 (d, J=7.9 Hz, 1H), 3.88 (s, 4H), 3.73 (s, 2H), 2.69 (s, 6H).

Example 53—N-benzyl-2-(2-furyl)-3-(1-methylpyrazol-4-yl)pyrazolo[1,5-a]pyrimidin-5-amine

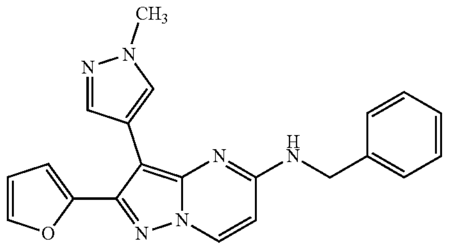 [SMILES: Cn1cc(-c2c(-c3ccco3)nn3ccc(NCc4ccccc4)nc23)cn1]

A mixture of (1-methylpyrazol-4-yl)boronic acid (36 mg, 0.29 mmol), N-benzyl-2-(2-furyl)-3-iodo-pyrazolo[1,5-a]pyrimidin-5-amine (Intermediate S) (80 mg, 0.19 mmol) and potassium carbonate (53 mg, 0.38 mmol) in 1,4-dioxane (5 mL) and water (1 mL) was degassed with N2 before Pd(amphos)$Cl_2$ (7 mg, 0.01 mmol) was added and the mixture heated at 100° C. for 3.5 h. The resulting mixture was cooled to room temperature and diluted with EtOAc (10 mL). The mixture was washed with water (2×10 mL), brine (5 mL), dried over $MgSO_4$, filtered and concentrated in vacuo. The crude product was adsorbed onto silica and purified by chromatography on silica eluting with 50-100% EtOAc in petroleum ether to afford the title compound as a pale yellow solid.

LC-MS (Method 8B): Rt 4.4 mins; MS m/z 371.4=[M+H]+

1H NMR (500 MHz, DMSO-d6) δ 8.49 (d, J=7.5 Hz, 1H), 8.12 (t, J=5.7 Hz, 1H), 7.83-7.80 (m, 2H), 7.66 (d, J=0.8 Hz, 1H), 7.43-7.39 (m, 2H), 7.38-7.33 (m, 2H), 7.29-7.24 (m, 1H), 6.75 (dd, J=3.4, 0.9 Hz, 1H), 6.62 (dd, J=3.3, 1.8 Hz, 1H), 6.39 (d, J=7.6 Hz, 1H), 4.59 (d, J=5.6 Hz, 2H), 3.84 (s, 3H).

Example 53.1-N-benzyl-2-(2-furyl)-3-(2-methylpyrazol-3-yl)pyrazolo[1,5-a]pyrimidin-5-amine

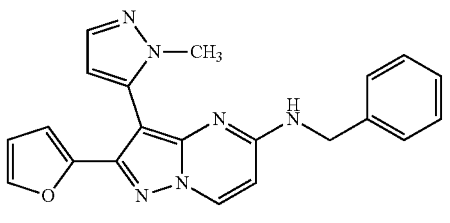 [SMILES: Cn1nccc1-c1c(-c2ccco2)nn2ccc(NCc3ccccc3)nc12]

The title compound was prepared from N-benzyl-2-(2-furyl)-3-iodo-pyrazolo[1,5-a]pyrimidin-5-amine (Intermediate S) and 1-methyl-5-(4,4,5,5-tetramethyl-1,3,2-dioxaborolan:2-yl)pyrazole analogously to Example 53.

LC-MS (Method 8B): Rt 4.49 mins; MS m/z 371.4=[M+H]+

1H NMR (500 MHz, DMSO-d6) δ 8.57 (d, J=7.6 Hz, 1H), 8.17 (t, J=5.6 Hz, 1H), 7.71 (dd, J=1.8, 0.8 Hz, 1H), 7.47 (d, J=1.8 Hz, 1H), 7.34-7.30 (m, 4H), 7.28-7.22 (m, 1H), 6.53 (dd, J=3.4, 1.8 Hz, 1H), 6.46-6.41 (m, 2H), 6.24 (d, J=1.9 Hz, 1H), 4.46 (d, J=5.7 Hz, 2H), 3.49 (s, 3H).

Example 54—Methyl(E)-3-[5-(benzylamino)-2-(2-furyl)pyrazolo[1,5-a]pyrimidin-3-yl]prop-2-enoate

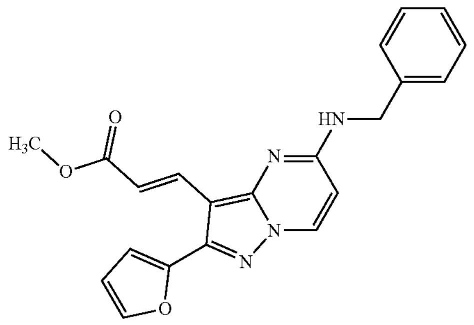 [SMILES: COC(=O)/C=C/c1c(-c2ccco2)nn2ccc(NCc3ccccc3)nc12]

A mixture of N-benzyl-2-(2-furyl)-3-iodo-pyrazolo[1,5-a]pyrimidin-5-amine (Intermediate S) (50 mg, 0.12 mmol), triethylamine (67 μL, 0.48 mmol) and methyl acrylate (33 μL, 0.36 mmol) in MeCN (3 mL) was degassed with N2 before $Pd(PPha)_2Cl_2$ (4.22 mg, 0.01 mmol) was added and the mixture heated at 85° C. under nitrogen for 16 h. The resulting mixture was partitioned between EtOAc (15 mL) and $H_2O$ (15 mL), the organic portion was separated and the aqueous further extracted with EtOAc (2×15 mL). The combined organic extracts were washed with water (15 mL), brine (15 mL), dried over $MgSO_4$ and the solvent removed in vacuo to afford crude product as a yellow oil. Purification by chromatography on silica eluting with a gradient of 50 to 70% EtOAc in petroleum ether afforded the title compound as a colourless solid.

LC-MS (Method 8B): Rt 4.91 mins; MS m/z 375.2=[M+H]+

1H NMR (500 MHz, DMSO-d6) δ 8.58 (t, J=6.7 Hz, 2H), 8.05 (d, J=15.6 Hz, 1H), 7.97-7.93 (m, 1H), 7.44 (d, J=7.5 Hz, 2H), 7.35 (t, J=7.6 Hz, 2H), 7.30-7.24 (m, 1H), 6.99 (d, J=15.6 Hz, 1H), 6.93-6.90 (m, 11H), 6.69 (dd, J=3.4, 1.8 Hz, 11H), 6.48 (d, J=7.6 Hz, 11H), 4.61 (d, J=5.6 Hz, 2H), 3.70 (s, 3H).

Example 54.1-(E)-3-[5-(Benzylamino)-2-(2-furyl)pyrazolo[1,5-a]pyrimidin-3-yl]prop-2-enoic acid

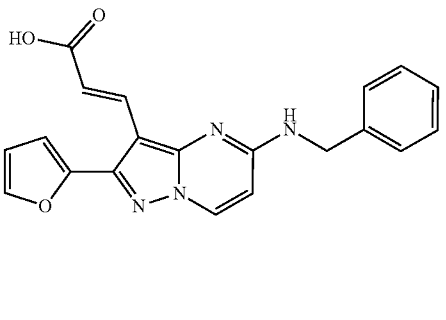 [SMILES: O=C(O)/C=C/c1c(-c2ccco2)nn2ccc(NCc3ccccc3)nc12]

LUOH (3 mg, 0.11 mmol) was added to a suspension of methyl(E)-3-[5-(benzylamino)-2-(2-furyl)pyrazolo[1,5-a]pyrimidin-3-yl]prop-2-enoate (Example 54) (14 mg, 0.04 mmol) in a mixture of EtOH (1 ml-) and water (0.25 mL) and the reaction mixture was stirred at 50° C. for 2 h. Additional LUOH (3 mg, 0.11 mmol) was added and the reaction heated at 50° C. for a further 16 h. More LUOH (3 mg, 0.11 mmol) was added and the reaction heated at 50° C. for a further 2 h. The resulting mixture was partitioned between EtOAc (10 ml-) and H2O (10 mL), the aqueous separated and the organic further extracted with $H_2O$ (10 mL). The pH of the combined aqueous extracts was adjusted to pH 5 by the dropwise addition of 2M aqueous HCl. The resulting mixture was extracted into EtOAc (2×10 ml-) and the combined organic extracts were dried over $MgSO_4$ and concentrated in vacuo to afford the title compound as a pale yellow solid.

LC-MS (Method 8A): Rt 4.09 mins; MS m/z 361.2=[M+H]+

1H NMR (500 MHz, DMSO-d6) δ 11.90 (s, 1H), 8.56 (d, J=7.6 Hz, 1H), 8.53 (t, J=5.7 Hz, 1H), 8.01 (d, J=15.6 Hz, 1H), 7.94 (d, J=1.6 Hz, 1H), 7.47-7.41 (m, 2H), 7.38-7.32 (m, 2H), 7.30-7.23 (m, 1H), 6.94 (d, J=15.6 Hz, 1H), 6.90 (d, J=3.3 Hz, 1H), 6.68 (dd, J=3.4, 1.8 Hz, 1H), 6.47 (d, J=7.6 Hz, 1H), 4.62 (d, J=5.6 Hz, 2H).

Example 55-2-(2-Furyl)-5-(4-phenylpiperazin-1-.yl)pyrazolo[1,5-a]pyrimidine-3-carbonitrile

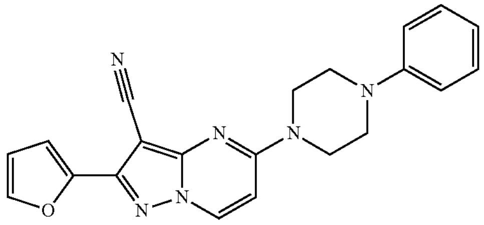 [SMILES: N#Cc1c(-c2ccco2)nn2ccc(N3CCN(c4ccccc4)CC3)nc12]

To a solution of 2-(2-furyl)-5-hydroxy-pyrazolo[1,5-a]pyrimidine-3-carbonitrile (Intermediate T) (20 mg, 0.09 mmol) in DMF (warming required to solubilise) was added HBTU (40 mg, 0.11 mmol) and the mixture was stirred for 2 mins before the addition of 1-phenylpiperazine (16 μL, 0.11 mmol) and DIPEA (62 μL, 0.35 mmol). After stirring for 2.5 h, additional HBTU (40 mg, 0.11 mmol), 1-phenylpiperazine (16 μL, 0.11 mmol) and DIPEA (62 μL, 0.35 mmol) were added and stirring was continued for 64 h. The resulting mixture was diluted with $H_2O$ (5 mL), extracted with EtOAc (3×10 mL) and the combined organic extracts were washed with $H_2O$ (2×15 mL), brine (15 mL), dried over $MgSO_4$ and the solvent removed in vacuo. Purification by chromatography on silica eluting with 1% MeOH in DCM afforded the title compound as an off-white solid.

LC-MS (Method 8B): Rt 4.84 mins; MS m/z 371.5=[M+H]+

$^1$H NMR (500 MHz, DMSO-d6) δ 8.82 (d, J=7.9 Hz, 1H), 7.94 (dd, J=1.8, 0.8 Hz, 1H), 7.28-7.22 (m, 2H), 7.09 (dd, J=3.5, 0.8 Hz, 1H), 7.04 (d, J=7.9 Hz, 1H), 7.02-6.98 (m, 2H), 6.82 (tt, J=7.2, 1.0 Hz, 1H), 6.73 (dd, J=3.5, 1.8 Hz, 1H), 4.00-3.86 (m, 4H), 3.30-3.27 (m, 4H).

Example 55.1-2-(2-Furyl)-5-(3-hydroxypropylamino)pyrazolo[1,5-a]pyrimidine-3-carbonitrile

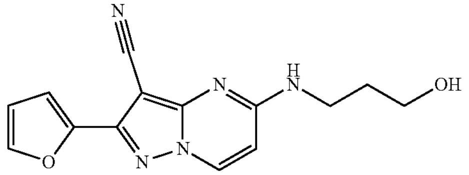 [SMILES: N#Cc1c(-c2ccco2)nn2ccc(NCCCO)nc12]

The title compound was prepared from 2-(2-furyl)-5-hydroxy-pyrazolo[1,5-a]pyrimidine-3-carbonitrile (Intermediate T) and 3-aminopropan-1-ol analogously to Example 55.

LC-MS (Method 8A): Rt 3.51 mins; MS m/z 284.1=[M+H]+

$^1$H NMR (500 MHz, DMSO-$d_6$) b 8.55 (d, J=7.6 Hz, 1H), 8.14 (t, J=5.3 Hz, 1H), 7.95-7.87 (m, 1H), 7.05 (d, J=3.5 Hz, 1H), 6.71 (dd, J=3.5, 1.7 Hz, 1H), 6.46 (d, J=7.6 Hz, 1H), 4.55 (t, J=5.1 Hz, 1H), 3.53-3.49 (m, 2H), 3.48-3.40 (m, 2H), 1.75 (p, J=6.6 Hz, 2H).

Example 55.2-2-(2-furyl)-5-(2-hydroxyethylamino)pyrazolo[1,5-a]pyrimidine-3-carbonitrile

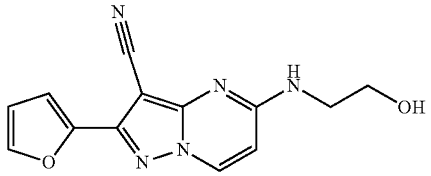 [SMILES: N#Cc1c(-c2ccco2)nn2ccc(NCCO)nc12]

The title compound was prepared from 2-(2-furyl)-5-hydroxy-pyrazolo[1,5-a]pyrimidine-3-carbonitrile (Intermediate T) and 2-aminoethanol analogously to Example 55.

LC-MS (Method 8B): Rt 3.40 mins; MS m/z 270.1=[M+H]+

1H NMR (500 MHz, DMSO-$d_6$) δ 8.56 (d, J=7.6 Hz, 1H), 8.24 (t, J=5.5 Hz, 1H), 7.92 (d, J=1.8 Hz, 1H), 7.05 (d, J=3.5 Hz, 1H), 6.71 (dd, J=3.5, 1.8 Hz, 1H), 6.53 (d, J=7.6 Hz, 1H), 4.86 (t, J=5.3 Hz, 1H), 3.60 (q, J=5.6 Hz, 2H), 3.51-3.46 (m, 2H).

Example 56-2-(2-Furyl)-5-(3-piperidylmethylamino)pyrazolo[1,5-a]pyrimidine-3-carbonitrile hydrochloride

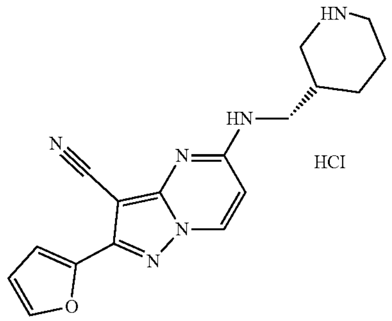

Step 1: 3(R)-[[[3-Cyano-2-(2-furyl)pyrazolo[1,5-a]pyrimidin-5-yl]amino]methyl]piperidine-1-carboxylate

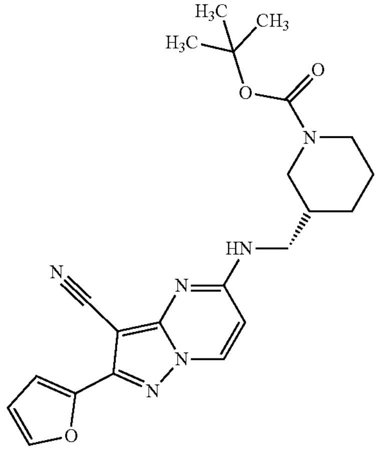

The title compound was prepared from 2-(2-furyl)-5-hydroxy-pyrazolo[1,5-a]pyrimidine-3-carbonitrile (Intermediate T) and tert-butyl(3R)-3-(aminomethyl)piperidine-1-carboxylate analogously to Example 55.

LC-MS (Method 3B): Rt 1.93 mins; MS m/z 421.4=[M−H]

$^1$H NMR (500 MHz, Chloroform-d) δ 8.15 (br s, 1H), 7.58 (dd, J=1.8, 0.8 Hz, 1H), 7.23 (dd, J=3.5, 0.8 Hz, 1H), 6.56 (dd, J=3.5, 1.8 Hz, 1H), 6.19 (d, J=7.5 Hz, 1H), 3.84-3.51 (m, 3H), 3.25 (m, 4H), 1.99-1.91 (m, 1H), 1.89-1.82 (m, 1H), 1.71-1.62 (m, 2H), 1.46 (s, 9H). NH proton not observed.

Step 2: 2-(2-Furyl)-5-(3-piperidylmethylamino)pyrazolo[1,5-a]pyrimidine-3-carbonitrile hydrochloride 4M HCl in 1,4-dioxane (1 mL, 0.13 mmol) was added to tert-butyl 3-[[[3-cyano-2-(2-furyl)pyrazolo[1,5-a]pyrimidin-5-yl]amino]methyl]piperidine-1-carboxylate (step 1)(54 mg, 0.13 mmol) and the mixture stirred for 30 mins. The solvent was removed in vacuo and the crude solid was suspended in $Et_2O$, filtered and dried to afford a cream solid. The solid was washed with MeCN and $Et_2O$ and dried to afford the title compound as a pale yellow solid.

LC-MS (Method 3B): Rt 1.48 mins; MS m/z 323.3=[M+H]+

$^1$H NMR (500 MHz, DMSO-$d_6$) δ 8.98 (apr br d, J=11.6 Hz, 1H), 8.82.-8.69 (m, 1H), 8.60 (d, J=7.6 Hz, 1H), 8.47 (t, J=5.7 Hz, 1H), 7.92 (d, J=1.8 Hz, 1H), 7.06 (d, J=3.5 Hz, 1H), 6.72 (dd, J=3.5, 1.8 Hz, 1H), 6.56 (d, J=7.6 Hz, 1H), 3.43-3.26 (m, 3H), 3.23-3.14 (m, 1H), 2.84-2.72 (m, 1H), 2.72-2.62 (m, 1H), 2.09 (s, 1H), 1.87-1.75 (m, 2H), 1.70-1.60 (m, 1H), 1.33-1.23 (m, 1H).

Example 57-5-(Benzylamino)-2-oxazol-2-yl-pyrazolo[1,5-a]pyrimidine-3-carbonitrile

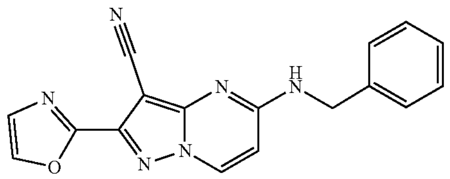 [SMILES: N#Cc1c(-c2ncco2)nn2ccc(NCc3ccccc3)nc12]

Step 2 1: 5-(Benzylamino)-2-bromo-pyrazolo[1,5-a]pyrimidine-3-carbonitrile

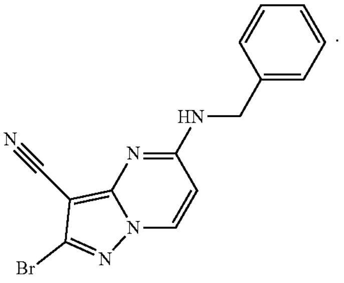 [SMILES: N#Cc1c(Br)nn2ccc(NCc3ccccc3)nc12]

The title compound was prepared from 2-bromo-5-chloro-pyrazolo[1,5-a]pyrimidine-3-carbonitrile (Intermediate U) and benzylamine analogously to Example 35 step 2.

LC-MS (Method 3B): Rt 1.78 mins; MS m/z 328.0/330.0=[M+H]+

1H NMR (500 MHz, DMSO-d6) δ 8.72 (s, 1H), 8.57 (d, J=7.6 Hz, 1H), 7.42-7.33 (m, 4H), 7.33-7.25 (m, 1H), 6.51 (d, J=7.6 Hz, 1H), 4.60 (s, 2H).

Step 2: 5-(Benzylamino)-2-oxazol-2-yl-pyrazolo[1,5-a]pyrimidine-3-carbonitrile

A mixture of 5-(benzylamino)-2-bromo-pyrazolo[1,5-a]pyrimidine-3-carbonitrile (step 1) (50 mg, 0.15 mmol), tributyl(oxazol-2-yl)stannane (48 μL, 0.23 mmol) and copper(l) iodide (7 mg, 0.04 mmol) suspended in 1,4-dioxane (2 mL) was degassed with N2 before $Pd(PPh_3)_4$(18 mg, 0.02 mmol) was added and the mixture stirred under nitrogen at 100° C. for 22 h. Additional $Pd(PPh_3)_4$(18 mg, 0.02 mmol) and tributyl(oxazol-2-yl)stannane (48 μL, 0.23 mmol) were added and the mixture was heated at 110° C. for a further 24 h. The resulting mixture was partitioned between EtOAc (15 mL) and $H_2O$ (15 mL), the organic portion was separated and the aqueous further extracted with EtOAc (10 mL). The combined organic extracts were washed with water (10 mL), brine (10 mL), dried over $MgSO_4$ and concentrated in vacuo. Purification by chromatography on silica eluting with a gradient of 50 to 70% EtOAc in petroleum ether followed by re-purification by chromatography on silica eluting with EtOAc afforded a colourless solid. The solid was recrystallised from MeOH to afford the title compound as a white solid.

LC-MS (Method 8B): Rt 4.23 mins; MS m/z 317.0=[M+H]+ d6) 6 8.76-8.71 (m, 1H), 8.70 (d, J=7.6 Hz, IH), 8.36 (d, J=0.8 Hz, 1H), 7.54 (d, J=0.8 Hz, 1H), 7.44-7.34 (m, 4H), 7.33-7.27 (m, 1H), 6.62 (d, J=7.7 Hz, 1H), 4.64 (d, J=5.3 Hz, 2H).

Example 58-5-(Benzylamino)-2-(3-cyanophenyl)pyrazolo[1,5-a]pyrimidine-3-carbonitrile

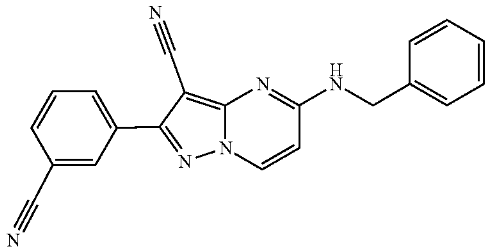 [SMILES: N#Cc1cccc(-c2nn3ccc(NCc4ccccc4)nc3c2C#N)c1]

The title compound was prepared from 5-(benzylamino)-2-bromo-pyrazolo[1,5-a]pyrimidine-3-carbonitrile (Example 57 step 1) and 3-(4,4,5,5-tetramethyl-1,3,2-dioxaborolan-2-yl)benzonitrile analogously to Example 47 step 3.

LC-MS (Method 8B): Rt 4.75 mins; MS m/z 351.2=[M+H]+

1H NMR (500 MHz, DMSO-d6) δ 8.69 (d, J=7.6 Hz, 2H), 8.31-8.23 (m, 2H), 8.00 (dt, J=7.8, 1.4 Hz, 1H), 7.80 (t, J=7.9 Hz, 1H), 7.44-7.34 (m, 4H), 7.34-7.26 (m, 1H), 6.58 (d, J=7.6 Hz, 1H), 4.64 (d, J=5.5 Hz, 2H).

Example 59-2-(3-Cyanophenyl)-5-[4-[(3-methyl-2-pyridyl)methyl]piperazin-1-yl]pyrazolo[1,5-a]pyrimidine-3-carbonitrile

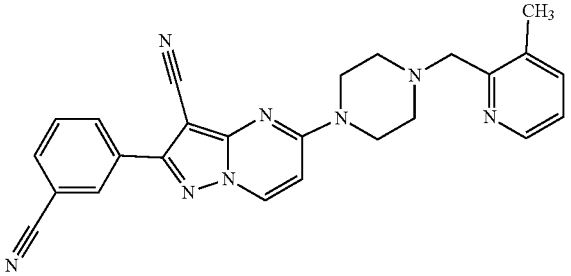 [SMILES: Cc1cccnc1CN1CCN(c2ccn3nc(-c4cccc(C#N)c4)c(C#N)c3n2)CC1]

Step 1: 2-Bromo-5-piperazin-1-yl-pyrazolo[1,5-a]pyrimidine-3-carbonitrile

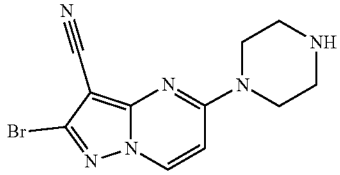 [SMILES: N#Cc1c(Br)nn2ccc(N3CCNCC3)nc12]

The title compound was prepared from 2-bromo-5-chloro-pyrazolo[1,5-a]pyrimidine-3-carbonitrile (Intermediate U) and piperazine analogously to Example 41.

LC-MS (Method 3B): Rt 1.30 mins; MS m/z 307.1/309.1=[M+H]+

$^1$H NMR (500 MHz, DMSO-$d_6$) δ 8.70 (d, J=8.0 Hz, 1H), 6.91 (d, J=8.0 Hz, 1H), 3.68 (br s, 4H), 2.80-2.74 (m, 4H). NH proton not observed.

Step 2: 2-Bromo-5-[4-[(3-methyl-2-pyridyl)methyl]piperazin-1-yl]pyrazolo[1,5-a]pyrimidine-3-carbonitrile

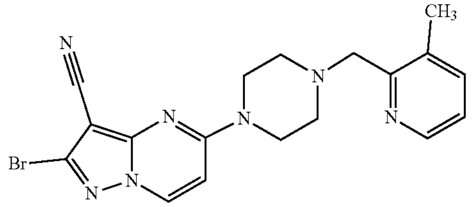 [SMILES: Cc1cccnc1CN1CCN(c2ccn3nc(Br)c(C#N)c3n2)CC1]

The title compound was prepared from 2-bromo-5-piperazin-1-yl-pyrazolo[1,5-a]pyrimidine-3-carbonitrile (step 1) and 2-(bromomethyl)-3-methyl-pyridine hydrobromide analogously to Example 51.

LC-MS (Method 8B): Rt 4.70 mins; MS m/z 412.0/414.3=[M+H]+

1H NMR (500 MHz, DMSO-d6) δ 8.74 (d, J=8.0 Hz, 1H), 8.31 (ddd, J=4.8, 1.7, 0.7 Hz, 1H), 7.58 (ddd, J=7.6, 1.7, 0.7 Hz, 1H), 7.22 (dd, J=7.6, 4.8 Hz, 1H), 6.92 (d, J=8.0 Hz, 1H), 3.72 (br s, 4H), 3.64 (s, 2H), 2.52-2.51 (m, 4H), 2.41 (s, 3H)

Step 3: 2-(3-Cyanophenyl)-5-[4-[(3-methyl-2-pyridyl)methyl]piperazin-1-yl]pyrazolo[1,5-a]pyrimidine-3-carbonitrile The title compound was prepared from 2-bromo-5-[4-[(3-methyl-2-pyridyl)methyl]piperazin-1-yl]pyrazolo[1,5-a]pyrimidine-3-carbonitrile (step 2) and (3-cyanophenyl)boronic acid analogously to Example 47 step 3.

LC-MS (Method 8B): Rt 4.99 mins; MS m/z 435.5=[M+H]+

1H NMR (500 MHz, DMSO-d6) δ 8.85 (d, J=8.0 Hz, 1H), 8.32 (dd, J=4.8, 1.0 Hz, 1H), 8.31-8.29 (m, 1H), 8.27 (apr dt, J=8.0, 1.3 Hz, 1H), 8.01 (apr dt, J=7.8, 1.3 Hz, 1H), 7.80 (t, J=7.8 Hz, 1H), 7.59 (d, J=7.5 Hz, 1H), 7.23 (dd, J=7.5, 4.8 Hz, 1H), 6.99 (d, J=8.0 Hz, 1H), 3.76 (br s, 4H), 3.65 (s, 2H), 2.56-2.51 (m, 4H), 2.42 (s, 3H)

Example 60-2-(3-Fluorophenyl)-5-[4-[(3-methyl-2-pyridyl)methyl]piperazin-1-yl]pyrazolo[1,5-a]pyrimidine-3-carbonitrile

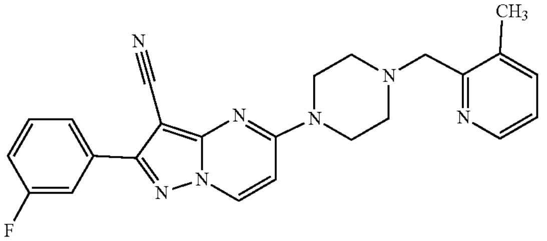 [SMILES: Cc1cccnc1CN1CCN(c2ccn3nc(-c4cccc(F)c4)c(C#N)c3n2)CC1]

The title compound was prepared from 2-bromo-5-[4-[(3-methyl-2-pyridyl)methyl]piperazin-1-yl]pyrazolo[1,5-a]pyrimidine-3-carbonitrile (Example 59 step 2) and (3-fluorophenyl)boronic acid analogously to Example 47 step 3.

LC-MS (Method 8B): Rt 5.01 mins; MS m/z 428.3=[M+H]+

$^1$H NMR (500 MHz, DMSO-$d_6$) δ 8.83 (d, J=8.0 Hz, 1H), 8.36-8.28 (m, 1H), 7.84 (d, J=7.9 Hz, 1H), 7.71 (br dt, J=10.1, 1.9 Hz, 1H), 7.67-7.58 (m, 1H), 7.59 (d, J=7.3 Hz, 1H), 7.38 (td, J=8.5, 2.3 Hz, 1H), 7.23 (dd, J=7.5, 4.8 Hz, 1H), 6.97 (d, J=8.0 Hz, 1H), 3.75 (br s, 4H), 3.65 (s, 2H), 2.55-2.51 (m, 4H), 2.42 (s, 3H).

Example 61-5-[4-(2-Fluoroethyl)piperazin-1-yl]-2-(3-fluorophenyl)pyrazolo[1,5-a]pyrimidine-3-carbonitrile

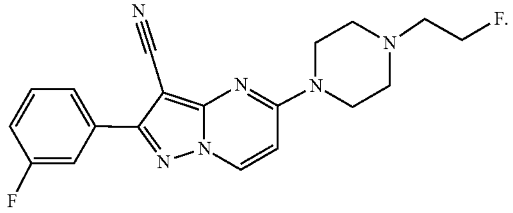 [SMILES: N#Cc1c(-c2cccc(F)c2)nn2ccc(N3CCN(CCF)CC3)nc12]

Step 1: 2-Bromo-5-[4-(2-fluoroethyl)piperazin-1-yl]pyrazolo[1,5-a]pyrimidine-3-carbonitrile

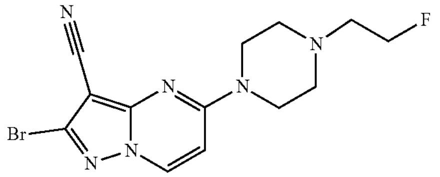 [SMILES: N#Cc1c(Br)nn2ccc(N3CCN(CCF)CC3)nc12]

A solution of 2-bromo-5-chloro-pyrazolo[1,5-a]pyrimidine-3-carbonitrile (Intermediate U)(521 mg, 2.02 mmol), 1-(2-fluoroethyl)piperazine dihydrochloride (457 mg, 2.23 mmol) and DIPEA (1.06 mL, 6.07 mmol) in MeCN (20 mL) was heated at reflux for 1 h. The resulting mixture was cooled to room temperature and concentrated in vacuo. The residue was partitioned between EtOAc (20 mL) and water (20 mL). The layers were separated and the aqueous layer was basified with sat, $NaHCO_3$ and extracted with 10% MeOH in EtOAc (5×20 mL). The organic portions were combined, dried over $MgSO_4$ and concentrated in vacuo. Purification by chromatography on silica eluting with a gradient of 0 to 4% MeOH in DCM afforded the title compound as a colourless solid.

LC-MS (Method 3B): Rt 1.62 mins; MS m/z 353.1/355.1=[M+H]+

$^1$H NMR (500 MHz, DMSO-$d_6$) δ 8.74 (d, J=8.0 Hz, 1H), 6.96 (d, J=8.0 Hz, 1H), 4.62 (apr t, J=4.8 Hz, 1H), 4.52 (apr t, J=5.0 Hz, 1H), 3.76 (s, 4H), 2.71 (apr t, J=4.8 Hz, 1H), 2.65 (apr t, J=4.8 Hz, 1H), 2.58-2.53 (m, 4H).

Step 2: 5-[4-(2-Fluoroethyl)piperazin-1-yl}-2-(3-fluorophenyl)pyrazolo[1,5-a]pyrimidine-3-carbonitrile The title compound was prepared from 2-bromo-5-[4-(2-fluoroethyl)piperazin-1-yl]pyrazolo[1,5-a]pyrimidine-3- carbonitrile (step 1) and (3-fluorophenyl)boronic acid analogously to Example 47 step 3, LC-MS (Method 8B): Rt 4.82 mins; MS m/z 369.2=[M+H]+

$^1$H NMR (500 MHz, DMSO-$d_6$) δ 8.83 (d, J=7.9 Hz, 1H), 7.88-7.81 (m, 1H), 7.71 (ddd, J=10.2, 2.6, 1.5 Hz, 1H), 7.67-7.58 (m, 1H), 7.42-7.34 (m, 1H), 7.01 (d, J=8.0 Hz, 1H), 4.63 (apr t, J=5.1 Hz, 1H), 4.54 (apr t, J=5.1 Hz,1H), 3.79 (s, 4H), 2.72 (apr t, J=4.8 Hz, 1H), 2.66 (apr t, J=4.8 Hz, 1H), 2.61-2.56 (m, 4H).

Example 62-5-[4-(2-Fluoroethyl)piperazin-1..yl]-2-oxazol-5-yl-pyrazolo[1,5-a]pyrimidine-3-carbonitrile

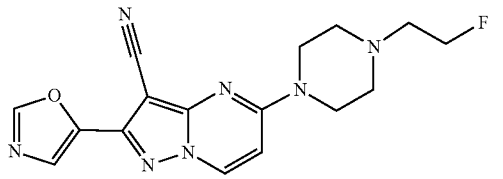 [SMILES: N#Cc1c(-c2cnco2)nn2ccc(N3CCN(CCF)CC3)nc12]

The title compound was prepared from 2-bromo-5-[4-(2-fluoroethyl)piperazin-1-yl]pyrazolo[1,5-a]pyrimidine-3-carbonitrile (Example 61 step 1) and 5-(4,4,5,5-tetramethyl-1,3,2-dioxaborolan-2-yl)oxazole analogously to Example 47 step 3.

LC-MS (Method 8B): Rt 3.56 mins; MS m/z 342.1=[M+H]+

$^1$H NMR (500 MHz, DMSO-da) 6 8.82 (d, J=7.9 Hz, 1H), 8.67 (s, 1H), 7.76 (s, 1H), 7.02 (d, J=8.0 Hz, 1H), 4.63 (apr t, J=4.8 Hz, 1H), 4.53 (apr t, J=4.8 Hz, 1H), 3.79 (s, 4H), 2.72 (apr t, J=4.6 Hz, 1H), 2.66 (apr t, J=4.7 Hz, 1H), 2.61-2.55 (m, 4H).

Example 63-5-(Benzylamino)-2-(4-fluorophenyl) pyrazolo[1,5-a]pyrimidine-3-carbonitrile

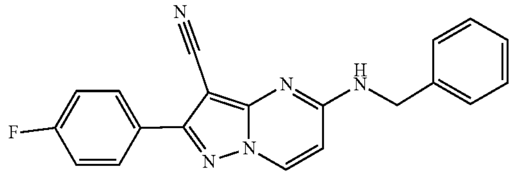 [SMILES: N#Cc1c(-c2ccc(F)cc2)nn2ccc(NCc3ccccc3)nc12]

Step 1: 5-(Benzylamino)-2-bromo-pyrazolo[1,5-a] pyrimidine-3-carbonitrile

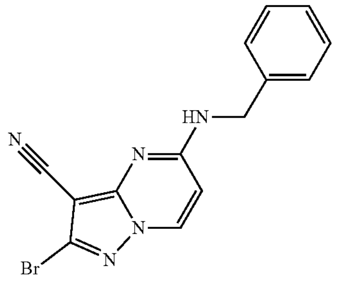 [SMILES: N#Cc1c(Br)nn2ccc(NCc3ccccc3)nc12]

A mixture of 2-bromo-5-chloro-pyrazolo[1,5-a]pyrimidine-3-carbonitrile (Intermediate U) (400 mg, 1.55 mmol), benzylamine (340 μL, 3.11 mmol) and DIPEA (541 μL, 3.11 mmol) in EtOH (18 mL) were heated to 85° C. for 1 h. The mixture was cooled to room temperature and the resulting suspension was collected by filtration, washed with EtOH and dried under vacuum to afford the title compound as a colourless solid.

LC-MS (Method 38): Rt 1.78 mins; MS m/z 328.0/330.0=[M+H]+

1H NMR (500 MHz, DMSO-d6) δ 8.72 (s, 1H), 8.57 (d, J=7.6 Hz, 1H), 7.42-7.33 (m, 4H), 7.33-7.25 (m, 1H), 6.51 (d, J=7.6 Hz, 1H), 4.60 (s, 2H).

Step 2: 5-(Benzylamino)-2-(4-fluorophenyl)pyrazolo[1,5-a]pyrimidine-3-carbonitrile The title compound was prepared from 5-(benzylamino)-2-bromo-pyrazolo[1,5-a]pyrimidine-3-carbonitrile (step 1) and (4-fluorophenyl)boronic acid analogously to Example 47 step 3.

LC-MS (Method 88): Rt 4.97 mins; MS m/z 344.2=[M+H]+

1H NMR (500 MHz, DMSO-d6) b 8.68-8.59 (m, 2H), 8.04-7.96 (m, 2H), 7.45-7.34 (m, 6H), 7.33-7.26 (m, 1H), 6.54 (d, J=7.6 Hz, 1H), 4.63 (d, J=5.6 Hz, 2H).

Example 64-5-(benzylamino)-2-(5-methyl-2-furyl) pyrazolo[1,5-a]pyrimidine-3-carbonitrile

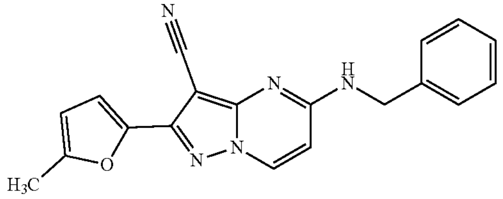 [SMILES: Cc1ccc(-c2nn3ccc(NCc4ccccc4)nc3c2C#N)o1]

The title compound was prepared from 5-(benzylamino)-2-bromo-pyrazolo[1,5-a]pyrimidine-3-carbonitrile (Example 63 step 1) and (5-methyl-2-furyl)boronic acid analogously to Example 47 step 3.

LC-MS (Method 8B): Rt 4.97 mins; MS m/z 330.1=[M+H]+

1H NMR (500 MHz, DMSO-d6) δ 8.63-8.55 (m, 2H), 7.43-7.34 (m, 4H), 7.33-7.26 (m, 1H), 6.95 (d, J=3.3 Hz, 1H), 6.52 (d, J=7.6 Hz, 1H), 6.35-6.30 (m, 1H), 4.62 (d, J=5.6 Hz, 2H), 2.37 (s, 3H).

Example 65-5-[4-[(3-Methyl-2-pyridyl)methyl]piperazin-1-y]-2-oxazol-5-yl-pyrazolo[1,5-a]pyrimidine-3-carbonitrile

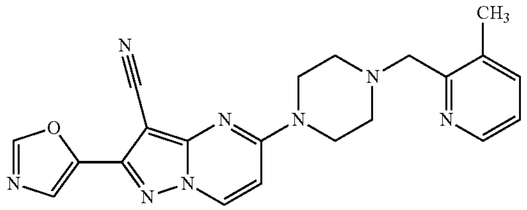 [SMILES: Cc1cccnc1CN1CCN(c2ccn3nc(-c4cnco4)c(C#N)c3n2)CC1]

A 5 mL microwave vial equipped with a stirrer bar was charged with 2-bromo-5-[4-[(3-methyl-2-pyridyl)methyl]piperazin-1-yl]pyrazolo[1,5-a]pyrimidine-3-carbonitrile (Example 59 step 2) and 5-(4,4,5,5-tetramethyl-1,3,2-dioxaborolan-2-yl)oxazole analogously to Example 47 step 3.

LC-MS (Method 8B): Rt 4.07 mins; MS m/z 401.3=[M+H]+

$^1$H NMR (500 MHz, DMSO-$d_6$) δ 8.82 (d, J=8.0 Hz, 1H), 8.67 (s, 1H), 8.35-8.30 (m, 1H), 7.76 (s, 1H), 7.62-7.56 (m, 1H), 7.23 (dd, J=7.6, 4.8 Hz, 1H), 6.99 (d, J=8.0 Hz, 1H), 3.75 (br s, 4H), 3.65 (s, 2H), 2.54-2.51 (m, 4H), 2.42 (s, 3H).

Example 66—N-benzyl-2-(3-fluorophenyl)pyrazolo[1,5-a]pyrimidin-5-amine

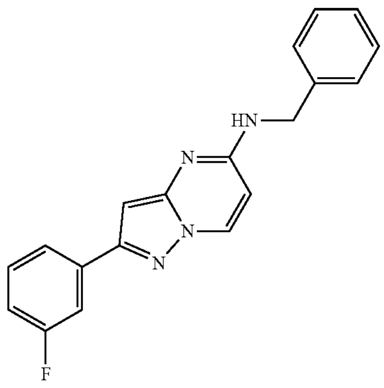 [SMILES: Fc1cccc(-c2cc3nc(NCc4ccccc4)ccn3n2)c1]

A mixture of 5-chloro-2-(3-fluorophenyl)pyrazolo[1,5-a]pyrimidine (Intermediate V) (18 mg, 0.07 mmol), benzylamine (16 μL, 0.15 mmol) and DIPEA (25 μL, 0.15 mmol) in EtOH (1 mL) were heated to 80° C. for 1 h. Additional benzylamine (30 μL, 0.14 mmol) was added and the mixture heated for a further 18 h. The mixture was allowed to cool to room temperature and the solvent was removed in vacuo. The crude residue was suspended in diethyl ether and the solid was removed by filtration. The filtrate was concentrated in vacuo and purification of the crude residue by chromatography on silica eluting with 30% EtOAc in hexane afforded the title compound as a cream solid.

LC-MS (Method 8B): Rt 5.05 mins; MS m/z 319.0=[M+H]+

$^1$H NMR (500 MHz, Chloroform-d) δ 8.23 (d, J=7.5 Hz, 1H), 7.70-7.65 (m, 1H), 7.64-7.59 (m, 1H), 7.43-7.34 (m, 5H), 7.34-7.29 (m, 1H), 7.05 (td, J=8.4, 2.7 Hz, 1H), 6.45 (s, 1H), 6.03 (d, J=7.5 Hz, 1H), 5.04 (s, 1H), 4.67 (d, J=5.4 Hz, 2H).

Example 66.1-2-(3-Fluorophenyl)-N-[(3-methyl-2-pyridyl)methyl]pyrazolo[1,5-a]pyrimidin-5-amine

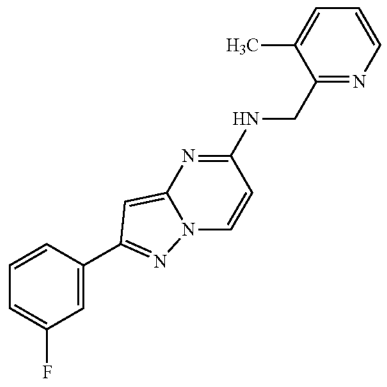 [SMILES: Cc1cccnc1CNc1ccn2nc(-c3cccc(F)c3)cc2n1]

The title compound was prepared from 5-chloro-2-(3-fluorophenyl)pyrazolo[1,5-a]pyrimidine (Intermediate V) and (3-methyl-2-pyridyl)methanamine analogously to Example 66.

LC-MS (Method 88): Rt 4.76 mins; MS m/z 334.1=[M+H]+

$^1$H NMR (500 MHz, Chloroform-d) δ 8.42 (dd, J=4.9, 1.5 Hz, 1H), 8.23 (d, J=7.5 Hz, 11H), 7.68 (dt, J=7.7, 1.2 Hz, 1H), 7.65-7.58 (m, 1H), 7.55-7.49 (m, 1H), 7.39 (td, J=8.0, 5.9 Hz, 1H), 7.18 (dd, J=7.6, 4.8 Hz, 1H), 7.05 (td, J=8.4, 2.6 Hz, 1H), 7.04-7.02 (m, 1H), 6.48 (s, 1H), 6.24 (d, J=7.5 Hz, 1H), 4.68 (d, J=3.9 Hz, 2H), 2.39 (s, 3H).

Example 66.2-2-(3-Fluorophenyl)-N-(2-phenylethyl)pyrazolo[1,5-a]pyrimidin-5-amine

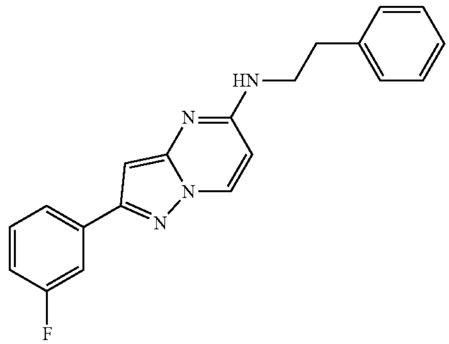 [SMILES: Fc1cccc(-c2cc3nc(NCCc4ccccc4)ccn3n2)c1]

The title compound was prepared from 5-chloro-2-(3-fluorophenyl)pyrazolo[1,5-a}pyrimidine (Intermediate V) and 2-phenylethanamine analogously to Example 66.

LC-MS (Method 8B): Rt 5.20 mins; MS m/z 333.1=[M+H]+

$^1$H NMR (500 MHz, DMSO-d6) δ 8.47 (d, J=7.6 Hz, 1H), 7.75 (dt, J=7.7, 1.2 Hz, 1H), 7.68 (ddd, J=10.4, 2.7, 1.4 Hz, 1H), 7.58 (t, J=5.5 Hz, 1H), 7.48 (td, J=8.1, 6.1 Hz, 1H), 7.34-7.25 (m, 4H), 7.24-7.15 (m, 2H), 6.58-6.54 (m, 1H), 6.27 (d, J=7.5 Hz, 1H), 3.56 (q, J=7.3, 5.6 Hz, 2H), 2.89 (t, J=7.3 Hz, 2H).

Example 66.3-N-(1H-Benzimidazol-2-ylmethyl)-2-(3-fluorophenyl)pyrazolo[1,5-a]pyrimidin-5-amine

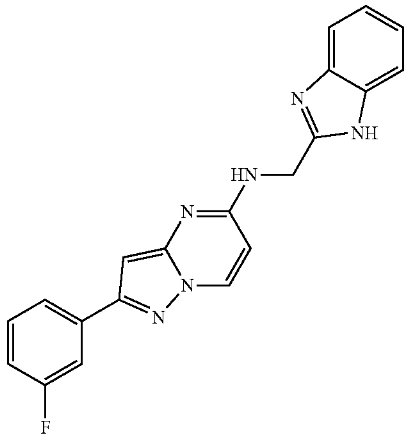 [SMILES: Fc1cccc(-c2cc3nc(NCc4nc5ccccc5[nH]4)ccn3n2)c1]

The title compound was prepared from 5-chloro-2-(3-fluorophenyl)pyrazolo[1,5-a]pyrimidine (Intermediate V) and 1H-benzimidazol-2-ylmethanamine analogously to Example 66.

LC-MS (Method 8B): Rt 4.18 mins; MS m/z 359.3=[M+H]+

1H NMR (500 MHz, DMSO-d6) δ 12.32 (s, 1H), 8.58 (d, J=7.5 Hz, 1H), 8.15 (t, J=5.7 Hz, 1H), 7.77-7.71 (m, 1H), 7.67 (dt, J=9.9, 2.1 Hz, 1H), 7.56 (d, J=7.4 Hz, 1H), 7.46 (ddd, J=17.0, 8.4, 6.3 Hz, 2H), 7.22-7.09 (m, 3H), 6.57 (s, 1H), 6.47 (d, J=7.6 Hz, 1H), 4.78 (d, J=5.4 Hz, 2H)

Example 66.4-2-(3-Fluorophenyl)-N-(2-isoindolin-2-ylethyl)pyrazolo[1,5-a]pyrimidin-5-amine

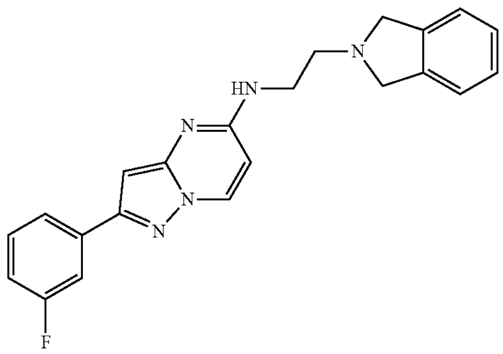 [SMILES: Fc1cccc(-c2cc3nc(NCCN4Cc5ccccc5C4)ccn3n2)c1]

The title compound was prepared from 5-chloro-2-(3-fluorophenyl)pyrazolo[1,5-a]pyrimidine (Intermediate V) and 2-isoindolin-2-ylethanamine analogously to Example 66.

LC-MS (Method 8B): Rt 4.98 mins; MS m/z 374.3=[M+H]+

1H NMR (500 MHz, DMSO-d6) δ 8.47 (d, J=7.5 Hz, 1H), 7.75 (d, J=7.8 Hz, 1H), 7.68 (dt, J=10.4, 2.1 Hz, 1H), 7.53 (s, 1H), 7.48 (td, J=8.0, 6.2 Hz, 1H), 7.24 (dd, J=5.4, 3.3 Hz, 2H), 7.19 (dq, J=6.7, 3.9 Hz, 3H), 6.56 (s, 1H), 6.35 (d, J=7.6 Hz, 1H), 3.93 (s, 4H), 3.53 (q, J=6.1 Hz, 2H), 2.91 (t, J=6.3 Hz, 2H).

Example 67—N-Benzyl-3-chloro-2-(3-fluorophenyl)pyrazolo[1,5-a]pyrimidin-5-amine

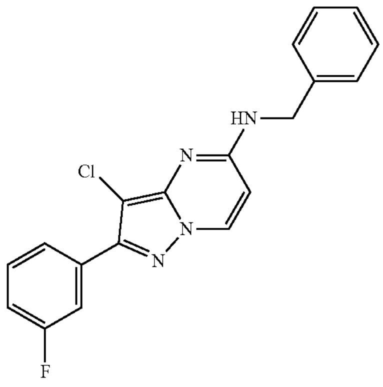 [SMILES: Fc1cccc(-c2nn3ccc(NCc4ccccc4)nc3c2Cl)c1]

Step 1: 3,5-Dichloro-2-(3-fluorophenyl)pyrazolo[1,5-a]pyrimidine

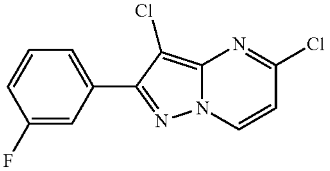 [SMILES: Fc1cccc(-c2nn3ccc(Cl)nc3c2Cl)c1]

To a solution of 5-chloro-2-(3-fluorophenyl)pyrazolo[1,5-a]pyrimidine (Intermediate V) (100 mg, 0.40 mmol) in DMF (4 mL) was added N-chlorosuccinimide (57 mg, 0.42 mmol) in one portion. The reaction was stirred under an atmosphere of nitrogen at room temperature for 24 h. Additional N-chlorosuccinimide (26.96 mg, 0.20 mmol) was added and the mixture was heated at 45° C. for 2 h. The mixture was allowed to cool to room temperature and added to water. The resulting suspension was collected by filtration and washed with water to afford the title compound as a pale yellow solid.

LC-MS (Method 8B): $R_t$: 2.09 mins; no ionisation observed

1H NMR (500 MHz, Chloroform-d) δ 8.52 (dd, J=7.2, 2.9 Hz, 1H), 7.94-7.85 (m, 1H), 7.85-7.76 (m, 1H), 7.53-7.39 (m, 1H), 7.17 (td, J=8.4, 4.6 Hz, 1H), 6.87 (dd, J=7.3, 2.9 Hz, 1H).

Step 2: N-Benzyl-3-chloro-2-(3-fluorophenyl)pyrazolo[1,5-a]pyrimidin-5-amine

The title compound was prepared from 3,5-dichloro-2-(3-fluorophenyl)pyrazolo[1,5-a]pyrimidine (step 1) and benzylamine analogously to Example 66.

LC-MS (Method 88): Rt 5.57 mins; MS m/z 353.1/355.1=[M+H]+

1H NMR (500 MHz, DMSO-d6) δ 8.55 (d, J=7.5 Hz, 1H), 8.25 (s, 1H), 7.82 (dt, J=7.8, 1.2 Hz, 1H), 7.70 (ddd, J=10.4, 2.7, 1.5 Hz, 1H), 7.56 (td, J=8.1, 6.2 Hz, 1H), 7.44-7.38 (m, 2H), 7.36 (dd, J=8.4, 6.8 Hz, 2H), 7.33-7.24 (m, 2H), 6.44 (d, J=7.6 Hz, 1H), 4.61 (d, J=5.6 Hz, 2H).

Example 68-3-Bromo-5-chloro-2-(3-fluorophenyl) pyrazolo[1,5-a]pyrimidine

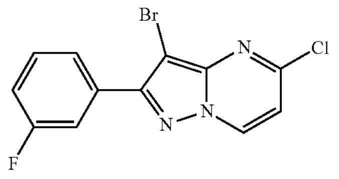 [SMILES: Fc1cccc(-c2nn3ccc(Cl)nc3c2Br)c1]

To a mixture of 5-chloro-2-(3-fluorophenyl)pyrazolo[1,5-a]pyrimidine (Intermediate V) (285 mg, 1.15 mmol) in DCM (5 mL) and DMF (4 mL) was added N-bromosuccinimide (215 mg, 1.21 mmol) and the mixture was stirred at room temperature for 10 mins. The DCM was removed in vacuo and water was added resulting in the formation of a precipitate. The solid was collected by filtration and dried to afford to afford the title compound as a cream solid.

LC-MS (Method 3B): Rt 2.04 mins; no ionisation observed

$^1$H NMR (500 MHz, Chloroform-d) δ 8.55 (d, J=7.1 Hz, 1H), 7.89 (ddd, J=7.9, 1.6, 1.0 Hz, 1H), 7.80 (ddd, J=10.0, 2.6, 1.6 Hz, 1H), 7.48 (dt, J=7.9, 5.9 Hz, 1H), 7.18 (tdd, J=8.4, 2.6, 1.0 Hz, 1H), 6.89 (d, J=7.1 Hz, 1H).

Example 69—N-Benzyl-3-bromo-2-(3-fluorophenyl)pyrazolo[1,5-a]pyrimidin-5-amine

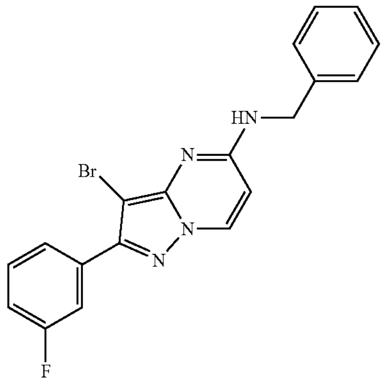 [SMILES: Fc1cccc(-c2nn3ccc(NCc4ccccc4)nc3c2Br)c1]

The title compound was prepared from 3-bromo-5-chloro-2-(3-fluorophenyl)pyrazolo[1,5-a]pyrimidine (Example 68=Intermediate W) and benzylamine analogously to Example 66, LC-MS (Method 8B): Rt 5.46 mins; MS m/z 397.1/399.0=[M+H]+

$^1$H NMR (500 MHz, Chloroform-d) δ 8.18 (d, J=7.5 Hz, 1H), 7.87-7.81 (m, 1H), 7.76 (ddd, J=10.2, 2.7, 1.6 Hz, 1H), 7.46-7.35 (m, 5H), 7.34-7.30 (m, 1H), 7.11 (tdd, J=8.5, 2.7, 1.0 Hz, 1H), 6.08 (d, J=7.5 Hz, 1H), 5.29 (s, 1H), 4.71 (d, J=5.6 Hz, 2H).

Example 70-5-(Benzylamino)-2-(3-fluorophenyl) pyrazolo[1,5-a]pyrimidine-3-carbonitrile

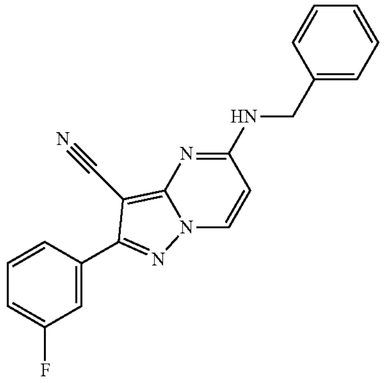 [SMILES: N#Cc1c(-c2cccc(F)c2)nn2ccc(NCc3ccccc3)nc12]

The title compound was prepared from N-benzyl-3-bromo-2-(3-fluorophenyl)pyrazolo[1,5-a]pyrimidin-5-amine (Example 69) and zinc cyanide analogously to Example 35 step 3.

LC-MS (Method 8B): Rt 5.12 mins; MS m/z 344.1=[M+H]+

$^1$H NMR (500 MHz, DMSO-do) b 8.67 (d, J=7.6 Hz, 1H), 8.65 (t, J=5.5 Hz, 1H), 7.82 (ddd, J=7.7, 1.6, 0.9 Hz, 1H), 7.70 (ddd, J=10.1, 2.7, 1.6 Hz, 1H), 7.62 (td, J=8.0, 6.0 Hz, 1H), 7.43-7.34 (m, 5H), 7.32-7.27 (m, 1H), 6.56 (d, J=7.6 Hz, 1H), 4.63 (d, J=5.5 Hz, 2H).

Example 71-3-Bromo-2-(3-fluorophenyl)pyrazolo[1,5-a]pyrimidin-5-amine

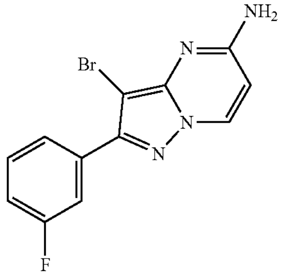 [SMILES: Nc1ccn2nc(-c3cccc(F)c3)c(Br)c2n1]

A mixture of 3-bromo-5-chloro-2-(3-fluorophenyl)pyrazolo[1,5-a]pyrimidine (Example 68=Intermediate W) (40 mg, 0.12 mmol) and $NH_4OH$ (35 wt %, 1.0 mL, 9.2 mmol) in EtOH (1 mL) were heated using microwave irradiation at 110° C. for 30 mins. After cooling to room temperature, the mixture was filtered, the solid washed with EtOH and dried to afford the title compound as an off-white solid, LC-MS (Method 8B): Rt 4.09 mins; MS m/z 306.9/308.9=[M+H]+

$^1$H NMR (500 MHz, DMSO-$d_6$) δ 8.56 (d, J=7.4 Hz, 1H), 7.82-7.77 (m, 1H), 7.69 (ddd, J=10.4, 2.7, 1.5 Hz, 1H), 7.55 (dt, J=8.1, 6.1 Hz, 1H), 7.34-7.23 (m, 3H), 6.33 (d, J=7.4 Hz, 1H).

Example 72-5-Amino-2-(3-fluorophenyl)pyrazolo[1,5-a]pyrimidine-3-carbonitrile

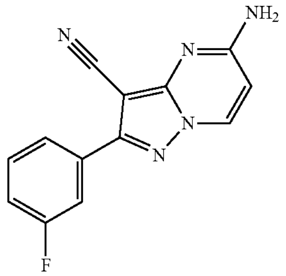 [SMILES: N#Cc1c(-c2cccc(F)c2)nn2ccc(N)nc12]

The title compound was prepared from 3-bromo-2-(3-fluorophenyl)pyrazolo[1,5-a]pyrimidin-5-amine (Example 71) and zinc cyanide analogously to Example 35 step 3.

LC-MS (Method 8B): Rt 3.90 mins; MS m/z 254.0=[M+H]+

1H NMR (500 MHz, DMSO-d6) δ 8.67 (d, J=7.5 Hz, 1H), 7.82 (dt, J=7.8, 1.1 Hz, 1H), 7.79-7.66 (m, 3H), 7.62 (td, J=8.1, 6.1 Hz, 1H), 7.40-7.34 (m, 1H), 6.45 (d, J=7.5 Hz, 1H).

Example 74-2-(2-Furyl)-N-(thiazol-2-ylmethyl)pyrazolo[1,5-a]pyrimidin-5-amine

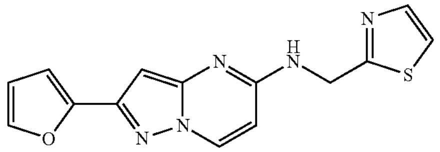 [SMILES: c1coc(-c2cc3nc(NCc4nccs4)ccn3n2)c1]

The title compound was prepared from 5-chloro-2-(2-furyl)pyrazolo[1,5-a]pyrimidine (Intermediate S2) and thiazol-2-ylmethanamine dihydrochloride analogously to Example 66.

LC-MS (Method 8B): Rt 3.82 mins; MS m/z 298.0=[M+H]+

$^1$H NMR (500 MHz, DMSO-$d_6$) δ 8.55 (d, J=7.6 Hz, 1H), 8.33 (t, J=6.0 Hz, 1H), 7.76 (d, J=1.8 Hz, 1H), 7.75 (d, J=3.3 Hz, 1H), 7.61 (d, J=3.3 Hz, 1H), 6.85 (d, J=3.4 Hz, 1H), 6.60 (dd, J=3.4, 1.8 Hz, 1H), 6.37 (d, J=7.6 Hz, 1H), 6.28 (s, 1H), 4.85 (d, J=6.0 Hz, 2H).

Example 75-[5-(Benzylamino)-2-(2-furyl)pyrazolo[1,5-a]pyrimidin-3-yl]methanol

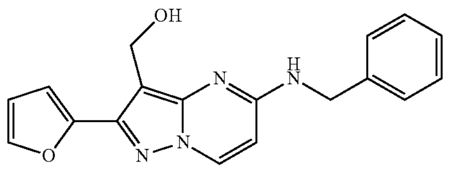 [SMILES: OCc1c(-c2ccco2)nn2ccc(NCc3ccccc3)nc12]

To a suspension of 5-(benzylamino)-2-(2-furyl)pyrazolo[1,5-a]pyrimidine-3-carbaldehyde (Example 47) (20 mg, 0.05 mmol) in MeOH (1 mL) at 0° C. was added $NaBH_4$ (1 mg, 0.03 mmol) and the mixture stirred for 30 mins. THF (1 mL) and DMF (1 mL) were added and the mixture was warmed to room temperature and stirred for 1 h. Additional $NaBH_4$ (1 mg, 0.03 mmol) was added and the mixture stirred for 16 h. A further portion of $NaBH_4$ was added (2 mg, 0.05 mmol) and stirring continued for 3 h. Additional $NaBH_4$ (4 mg, 0.1 mmol) was added and the mixture was stirred for 2 h before the volatile solvents were removed in vacuo. The crude mixture was partitioned between EtOAc (10 mL) and $H_2O$ (10 mL) and the organic portion was separated. The aqueous was further extracted with EtOAc (2×10 mL) and the combined organic extracts were washed with $H_2O$ (2×10 mL), brine, dried over $MgSO_4$ and the concentrated in vacuo. Purification by chromatography on silica eluting with 1% MeOH in DCM afforded the title compound as a white solid.

LC-MS (Method 8B): Rt 3.69 mins; MS m/z 321.3=[M+H]+

$^1$H NMR (500 MHz, DMSO-$d_6$) δ 8.46 (d, J=7.5 Hz, 1H), 7.95 (t, J=5.7 Hz, 1H), 7.78 (dd, J=1.8, 0.8 Hz, 1H), 7.44-7.38 (m, 2H), 7.38-7.32 (m, 2H), 7.30-7.23 (m, 1H), 6.97 (dd, J=3.4, 0.8 Hz, 1H), 6.62 (dd, J=3.4, 1.8 Hz, 1H), 6.32 (d, J=7.5 Hz, 1H), 4.66-4.57 (m, 5H).

Example 76-5-(Benzylamino)-2-(2-furyl)pyrazolo[1,5-a]pyrimidine-3-carboxylic acid

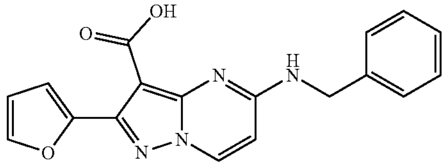

A solution of $NaClO_2$ (459 mg, 4.08 mmol) and $NaH_2PO_4$ (294 mg, 2.45 mmol) in water (0.5 mL) was added to a suspension of 5-(benzylamino)-2-(2-furyl)pyrazolo[1,5-a]pyrimidine-3-carbaldehyde (Example 47)(130 mg, 0.41 mmol) and 2-methy-2-butene (0.1 mL, 0.41 mmol) in 1,4-dioxane (10 mL) at 0° C. The mixture was stirred at room temperature for 18 h. Additional $NaClO_2$ (184 mg, 2.04 mmol) and $NaH_2PO_4$ (147 mg, 1.23 mmol) dissolved in water (0.5 mL) was added dropwise to the mixture at 0° C. and 1,4-dioxane (100 mL) was added to aid solubility. After stirring for a further 4.5 h, the resulting mixture was partitioned between EtOAc (100 mL) and $H_2O$ (50 mL). The organic portion was separated and the aqueous further extracted with EtOAc (50 mL). The combined organic extracts were washed with water (50 mL), brine (50 mL), dried over $MgSO_4$ and the solvent removed in vacuo. Purification by chromatography on silica eluting with a gradient of 40 to 90% EtOAc in petroleum ether afforded the title compound as a colourless solid.

LC-MS (Method 8A): Rt 4.25 mins; MS m/z 335.1=[M+H]+(100% @254 nm)

$^1$H NMR (500 MHz, DMSO-d6) δ 11.72 (s, 1H), 8.74 (t, J=5.7 Hz, 1H), 8.62 (d, J=7.5 Hz, 1H), 7.80 (dd, J=1.8, 0.9 Hz, 1H), 7.64 (dd, J=3.4, 0.9 Hz, 1H), 7.42 (d, J=7.2 Hz, 2H), 7.39-7.32 (m, 2H), 7.31-7.25 (m, 1H), 6.63 (dd, J=3.5, 1.8 Hz, 1H), 6.52 (d, J=7.6 Hz, 1H), 4.60 (d, J=5.6 Hz, 2H).

Example 77 (=Intermediate S)-N-Benzyl-2-(2-furyl)-3-iodo-pyrazolo[1,5-a]pyrimidin-5-amine

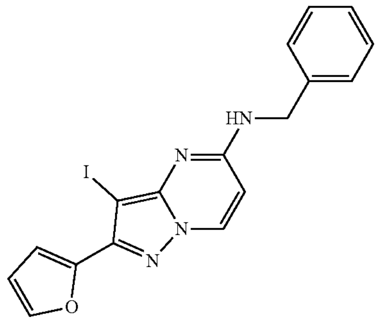 [SMILES: Ic1c(-c2ccco2)nn2ccc(NCc3ccccc3)nc12]

The title compound is prepared according to the procedure of Intermediate S.

LC-MS (Method 8B): Rt 4.96 mins; MS m/z 417.1=[M+H]+

$^1$H NMR (500 MHz, DMSO-d6) δ 8.50 (d, J=7.5 Hz, 1H), 8.20 (s, 1H), 7.84 (dd, J=1.8, 0.8 Hz, 1H), 7.46 (d, J=7.5 Hz, 2H), 7.39-7.32 (m, 2H), 7.31-7.24 (m, 1H), 7.17 (dd, J=3.4, 0.8 Hz, 1H), 6.66 (dd, J=3.4, 1.8 Hz, 1H), 6.37 (d, J=7.5 Hz, 1H), 4.60 (d, J=5.7 Hz, 2H).

Example 79-2-(2-Furyl)-3-(4-pyridyl)pyrazolo[1,5-a]pyrimidin-5-amine

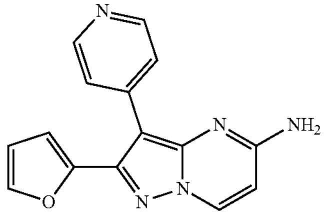 [SMILES: Nc1ccn2nc(-c3ccco3)c(-c3ccncc3)c2n1]

The title compound was prepared from 3-bromo-2-(2-furyl)pyrazolo[1,5-a]pyrimidin-5-amine (Example 50) and 4-pyridylboronic acid analogously to Example 53.

LC-MS (Method 8B): Rt 3.19 mins; MS m/z 278.0=[M+H]+

$^1$H NMR (500 MHz, DMSO-d6) δ 8.58 (d, J=7.5 Hz, 1H), 8.50-8.45 (m, 2H), 7.78 (dd, J=1.8, 0.8 Hz, 1H), 7.50-7.45 (m, 2H), 7.22 (s, 2H), 6.72 (dd, J=3.3, 0.8 Hz, 1H), 6.63 (dd, J=3.4, 1.8 Hz, 1H), 6.37 (d, J=7.4 Hz, 1H).

Example 80-2-(2-Furyl)-5-[[(2R)-pyrrolidin-2-yl]methylamino]pyrazolo[1,5-a]pyrimidine-3-carbonitrile hydrochloride

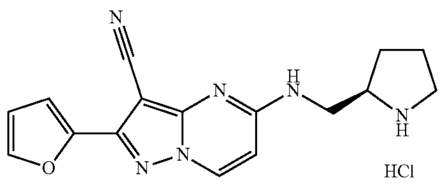 [SMILES: N#Cc1c(-c2ccco2)nn2ccc(NC[C@H]3CCCN3)nc12 ; Cl]

4M HCl in 1,4-dioxane (2.85 mL, 11.42 mmol) was added to tert-butyl(2R)-2-[[[3-cyano-2-(2-furyl)pyrazolo[1,5-a]pyrimidin-5-yl]amino]methyl]pyrrolidine-1-carboxylate (Example 37.2) (187 mg, 0.46 mmol) and the reaction mixture was stirred at room temperature for 1 h. The solvent was removed in vacuo to afford the title compound as a colourless solid.

LC-MS (Method 8B): Rt 4.00 mins; MS m/z 309=[M+H]+

$^1$H NMR (500 MHz, DMSO-da) 6 9.27 (s, 1H), 8.78 (s, 1H), 8.67 (d, J=7.6 Hz, 1H), 8.62-8.54 (m, 1H), 7.94 (dd, J=1.9, 0.7 Hz, 1H), 7.08 (dd, J=3.5, 0.7 Hz, 1H), 6.73 (dd, J=3.5, 1.8 Hz, 1H), 6.57 (d, J=7.6 Hz, 1H), 3.82-3.76 (m, 1H), 3.74-3.63 (m, 2H), 3.30-3.22 (m, 1H), 3.22-3.13 (m, 1H), 2.14-2.06 (m, 1H), 2.04-1.93 (m, 1H), 1.93-1.84 (m, 1H), 1.79-1.68 (m, 1H).

Example 81-2-(2-Furyl)-5-[[(2R)-1-methylpyrrolidin-2-yl]methylamino]pyrazolo[1,5-a]pyrimidine-3-carbonitrile

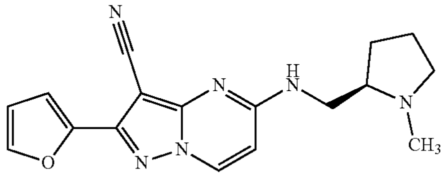 [SMILES: CN1CCC[C@@H]1CNc1ccn2nc(-c3ccco3)c(C#N)c2n1]

To 2-(2-furyl)-5-[[(2R)-pyrrolidin-2-yl]methylamino]pyrazolo[1,5-a]pyrimidine-3-carbonitrile hydrochloride (Example 80) (48 mg, 0.14 mmol) in DMF (3 mL) was added DIPEA (121 μL, 0.70 mmol) and methyl Iodide (10 μL, 0.17 mmol) and the reaction mixture was stirred at room temperature for 16 h followed by heating to 50° C. for 4 h. Additional DIPEA (24 μL, 0.14 mmol) and methyl Iodide (3 μL, 0.06 mmol) in DMF (1 mL) was added dropwise and the reaction mixture was stirred at 50° C. for 16 h. The resulting mixture was allowed to warm to room temperature and stirred overnight. The mixture was partitioned between EtOAc and sat.

$NaHCO_3$ solution and washed several times with sat. $NaHCO_3$ solution. The organic portion was dried over $MgSO_4$ and concentrated in vacuo. Purification by chromatography on silica eluting with 4% (7N $NH_3$ in MeOH) in DCM and subsequent trituration with diethyl ether afforded the title compound as a beige solid.

LC-MS (Method 8B): Rt 4.22 mins; MS m/z 323.3=[M+H)+

$^1$H NMR (500 MHz, DMSO-$d_6$) δ 8.56 (d, J=7.6 Hz, 1H), 8.12-8.02 (m, 1H), 7.92 (d, J=1.8 Hz, 1H), 7.05 (d, J=3.4 Hz, 1H), 6.71 (dd, J=3.5, 1.8 Hz, 1H), 6.59 (d, J=7.7 Hz, 1H), 3.67 (ddd, J=13.6, 6.4, 3.4 Hz, 1H), 3.30-3.25 (m, 1H), 3.04-2.93 (m, 1H), 2.47-2.40 (m, 1H), 2.35 (s, 3H), 2.23-2.11 (m, 1H), 1.94-1.84 (m, 1H), 1.71-1.61 (m, 2H), 1.61-1.51 (m, 1H).

Example 82-2-(2-Furyl)-5-[(3R)-3-methylpiperazin-1-yl]pyrazolo[1,5-a]pyrimidine-3-carbonitrile hydrochloride

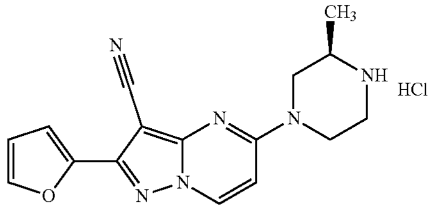 [SMILES: C[C@@H]1CN(c2ccn3nc(-c4ccco4)c(C#N)c3n2)CCN1 ; Cl]

The title compound was prepared from tert-butyl(2R)-4-[3-cyano-2-(2-furyl)pyrazolo[1,5-a]pyrimidin-5-yl}-2-methyl-piperazine-1-carboxylate (Example 37.10) and 4M HCl in 1,4-dioxane analogously to Example 80.

LC-MS (Method 8B): Rt 3.80 mins; MS m/z 309=[M+H]+

$^{1}H$ NMR (500 MHz, DMSO-$d_6$) δ 9.52-9.18 (m, 2H), 8.92 (d, J=7.9 Hz, 1H), 7.95 (d, J=1.8 Hz, 1H), 7.10 (d, J=3.5 Hz, 1H), 7.06 (d, J=8.0 Hz, 1H), 6.74 (dd, J=3.5, 1.8 Hz, 1H), 4.73-4.35 (m, 2H), 3.48-3.33 (m, 3H), 3.29-3.18 (m, 1H), 3.15-3.06 (m, 1H), 1.31 (d, J=6.4 Hz, 3H).

Example 83—Tert-butyl 4-[3-cyano-2-(2-furyl)pyrazolo[1,5-a]pyrimidin-5-yl]piperidine-1-carboxylate

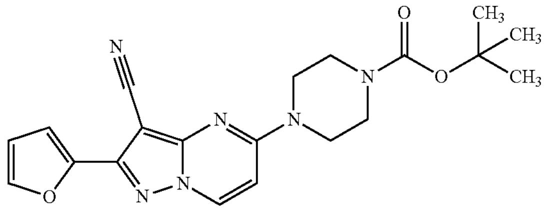 [SMILES: CC(C)(C)OC(=O)N1CCN(c2ccn3nc(-c4ccco4)c(C#N)c3n2)CC1]

To a solution of tert-butyl 4-[3-cyano-2-(2-furyl)pyrazolo[1,5-a]pyrimidin-5-yl]-3,6-dihydro-2H-pyridine-1-carboxylate (Example 40)(130 mg, 0.33 mmol) in EtOAc (5 mL) was added 10 wt % Pd on carbon (9 mg, 0.01 mmol) and the mixture was stirred under an atmosphere of hydrogen (1 bar, balloon pressure) for 1 h. Purification by chromatography on silica eluting with a gradient of 50 to 70% EtOAc in petroleum ether afforded the title compound as a colourless solid.

LC-MS (Method 8B): Rt 5.18 mins; MS m/z 392.2=[M−H]−

1H NMR (500 MHz, DMSO-d6) δ 9.25 (d, J=7.2 Hz, 1H), 8.02 (dd, J=1.8, 0.8 Hz, 1H), 7.39 (d, J=7.2 Hz, 1H), 7.22 (dd, J=3.5, 0.8 Hz, 1H), 6.78 (dd, J=3.5, 1.8 Hz, 1H), 4.14-4.05 (m, 2H), 3.08 (tt, J=11.7, 3.6 Hz, 1H), 2.87 (s, 2H), 1.93 (d, J=12.9 Hz, 2H), 1.64 (qd, J=12.5, 4.2 Hz, 2H), 1.42 (s, 9H).

Example 84—N-Benzyl-7-(2-furyl)pyrazolo[1,5-a][1,3,5]triazin-2-amine

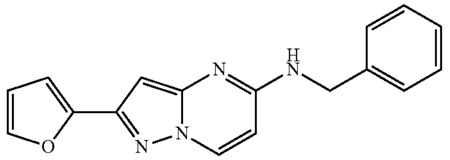 [SMILES: c1ccc(CNc2ccn3nc(-c4ccco4)cc3n2)cc1]

To a solution of 7-(2-furyl)-2-methylsulfonyl-pyrazolo[1,5-a][1,3,5]triazine (Intermediate X) (50 mg, 0.19 mmol) in NMP (1 mL) was added benzylamine (62 μL, 0.57 mmol) and the mixture was heated using microwave irradiation at 120° C. for 15 mins. After cooling to room temperature, MeOH (0.5 mL) was added followed by $H_2O$ (2 mL). The resulting solid was collected by filtration, dried and purified by chromatography on silica eluting with 1% MeCOH in DCM to afford the title compound as a colourless solid.

LC-MS (Method 8B): Rt 4.70 mins; MS m/z 292.1=[M+H]+

$^{1}H$ NMR (500 MHz, DMSO-$d_6$) δ 9.23 (s, 1H), 8.41 (t, J=6.3 Hz, 1H), 7.83 (d, J=1.7 Hz, 1H), 7.36-7.30 (m, 4H), 7.26-7.21 (m, 1H), 6.99 (d, J=3.4 Hz, 1H), 6.65 (dd, J=3.4, 1.7 Hz, 1H), 6.24 (s, 1H), 4.52 (d, J=6.3 Hz, 2H).

Example 85—N-Benzyl-2-(2-furyl)pyrazolo[1,5-a]pyrimidine-5-carboxamide

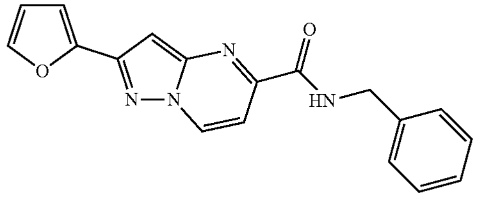 [SMILES: O=C(NCc1ccccc1)c1ccn2nc(-c3ccco3)cc2n1]

To a solution of 2-(2-furyl)pyrazolo[1,5-a]pyrimidine-5-carboxylic acid (Intermediate Y) (100 mg, 0.44 mmol) in DMF (5 mL) was added benzylamine (71 μL, 0.65 mmol), HATU (33 mg, 0.87 mmol) and DIPEA (380 μL, 2.18 mmol) and the mixture was stirred at room temperature overnight. The resulting mixture was partitioned between EtOAc (50 mL) and water (30 mL). The aqueous layer was extracted with EtOAc (2×20 mL) and the combined organic fractions were washed with water (3×10 mL), brine (10 mL), dried over $MgSO_4$ and concentrated in vacuo. The residue was triturated from EtOAc to afford the title compound as a yellow solid.

LC-MS (Method 8A): Rt 4.69 mins; MS m/z 319.1=[M+H]+

$^{1}H$ NMR (500 MHz, DMSO-da) 6 9.55 (t, J=6.3 Hz, 1H), 9.26 (dd, J=7.1, 1.0 Hz, 1H), 7.89 (dd, J=1.8, 0.8 Hz, 1H). 7.56 (d, J=7.1 Hz, 1H), 7.38-7.29 (m, 4H), 7.27-7.21 (m, 1H), 7.12 (dd, J=3.4, 0.8 Hz, 1H), 7.09 (d, J=1.0 Hz, 1H), 6.70 (dd, J=3.4, 1.8 Hz, 1H), 4.50 (d, J=6.3 Hz, 2H).

Example 87-2-(3-Cyanophenyl)-5-[4-(2-fluoroethyl)piperazin-1-yl]pyrazolo[1,5-a]pyrimidine-3-carbonitrile

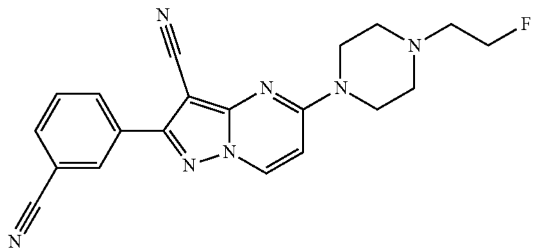 [SMILES: N#Cc1cccc(-c2nn3ccc(N4CCN(CCF)CC4)nc3c2C#N)c1]

Step 1: 2-(3-Cyanophenyl)-5-hydroxy-pyrazolo[1,5-a]pyrimidine-3-carbonitrile

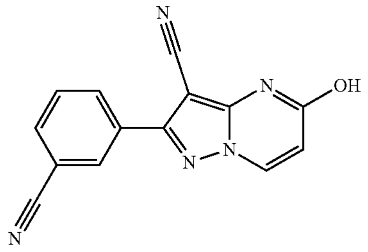 [SMILES: N#Cc1cccc(-c2nn3ccc(O)nc3c2C#N)c1]

The title compound was prepared from 5-amino-3-(3-cyanophenyl)-1H-pyrazole-4-carbonitrile (Intermediate Z) and ethyl(E)-3-ethoxyprop-2-enoate analogously to Intermediate T, step 3.

LC-MS (Method 3A): Rt 1.40 mins; MS m/z 260.1=[M−H]+

$^1$H NMR (500 MHz, DMSO-$d_6$) δ 13.46 (s, 1H), 8.78 (s, 1H), 8.27 (s, 1H), 8.23 (d, J=8.1 Hz, 1H), 8.05-8.00 (m, 1H), 7.81 (t, J=7.8 Hz, 1H), 6.41 (s, 1H).

Step 2: 5-Chloro-2-(3-cyanophenyl)pyrazolo[1,5-a]pyrimidine-3-carbonitrile

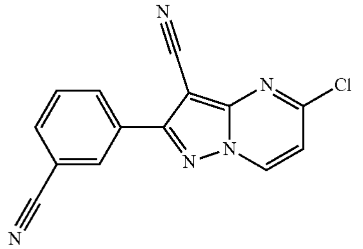 [SMILES: N#Cc1cccc(-c2nn3ccc(Cl)nc3c2C#N)c1]

The title compound was prepared from 2-(3-cyanophenyl)-5-hydroxy-pyrazolo[1,5-a]pyrimidine-3-carbonitrile (step 1) and $POCl_3$ analogously to Intermediate C2.

LC-MS (Method 3A): Rt 1.76 mins; MS m/z 260.1=[M−Cl+OH−H]−

$^1$H NMR (500 MHz, DMSO-$d_6$) δ 9.47 (d, J=7.1 Hz, 1H), 8.39 (s, 1H), 8.37-8.32 (m, 1H), 8.12-8.06 (m, 1H), 7.87 (t, J=7.9 Hz, 1H), 7.60 (d, J=7.1 Hz, 1H).

Step 3: 2-(3-Cyanophenyl)-5-[4-(2-fluoroethyl)piperazin-1-yl]pyrazolo[1,5-a]pyrimidine-3-carbonitrile A solution of 5-chloro-2-(3-cyanophenyl)pyrazolo[1,5-a]pyrimidine-3-carbonitrile (step 2) (75 mg, 0.27 mmol), 1-(2-fluoroethyl)piperazine dihydrochloride (66 mg, 0.32 mmol) and DIPEA (0.14 mL, 0.80 mmol) in MeCN (1 mL) was heated at reflux for 1 h. The resulting mixture was partitioned between EtOAc (10 mL) and brine (10 mL) and the organic portion was separated, dried over $MgSO_4$, filtered and concentrated in vacuo.

Purification by chromatography on silica eluting with 2.5% MeOH in DCM afforded a solid which was washed with diethyl ether and DCM to afford the title compound as a pale yellow solid.

LC-MS (Method 8A): Rt 3.01 mins; MS m/z 376.3=[M+H]+

$^1$H NMR (500 MHz, DMSO-$d_6$) δ 8.85 (d, J=7.9 Hz, 1H), 8.31-8.29 (m, 1H), 8.29-8.25 (m, 1H), 8.02-7.99 (m, 1H), 7.82-7.78 (m, 1H), 7.03 (d, J=8.0 Hz, 1H), 4.59 (dt, J=47.8, 4.8 Hz, 2H), 3.80 (s, 4H), 2.69 (dt, J=28.9, 4.9 Hz, 2H), 2.58 (t, J=5.1 Hz, 4H).

Example 87.1-2-(3-Cyanophenyl)-5-[2-(4-phenylpiperazin-1-yl)ethylamino]pyrazolo [1,5-a]pyrimidine-3-carbonitrile

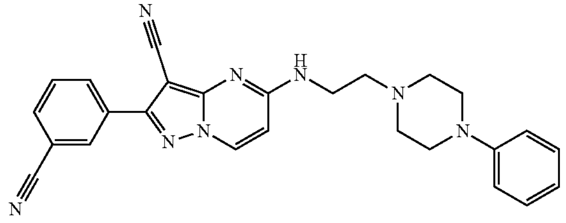 [SMILES: N#Cc1cccc(-c2nn3ccc(NCCN4CCN(c5ccccc5)CC4)nc3c2C#N)c1]

The title compound was prepared from 5-chloro-2-(3-cyanophenyl)pyrazolo[1,5-a]pyrimidine-3-carbonitrile (Example 87 step 2) and 2-(4-phenylpiperazin-1-yl)ethanamine analogously to Example 87 step 3.

LC-MS (Method 8B): Rt 5.14 mins; MS m/z 449.3=[M+H]+

1H NMR (500 MHz, DMSO-d6) δ 8.64 (d, J=7.6 Hz, 1H), 8.31-8.24 (m, 2H), 8.22 (s, 1H), 8.00 (dt, J=7.8, 1.4 Hz, 1H), 7.80 (t, J=7.9 Hz, 1H), 7.23-7.16 (m, 2H), 6.93 (d, J=8.1 Hz, 2H), 6.76 (t, J=7.2 Hz, 1H), 6.59 (d, J=7.6 Hz, 1H), 3.58 (d, J=7.4 Hz, 2H), 3.15 (t, J=5.0 Hz, 4H), 2.62 (dd, J=8.3, 3.7 Hz, 6H).

Example 88-3-(2-Chloro-6-methyl-4-pyridyl)-2-(4-fluorophenyl)pyrazolo[1,5-a]pyrimidin-5-amine

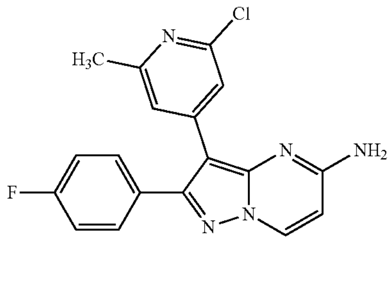 [SMILES: Cc1cc(-c2c(-c3ccc(F)cc3)nn3ccc(N)nc23)cc(Cl)n1]

Step 1: 2-(4-Fluorophenyl)pyrazolo[1,5-a]pyrimidin-5-ol

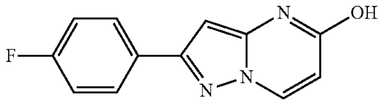 [SMILES: Oc1ccn2nc(-c3ccc(F)cc3)cc2n1]

The title compound was prepare from 3-4-fluorophenyl)-1H-pyrazol-5-amine and methyl prop-2-ynoate analogously to intermediate S1.

LC-MS (Method 3A): Rt 1.35 mins; MS m/z 228.1=[M]−

$^1$H NMR (500 MHz, DMSO-$d_6$) δ 12.23 (s, 1H), 8.51 (d, J=7.9 Hz, 1H), 7.98-7.90 (m, 2H), 7.30-7.24 (m, 2H), 6.30 (s, 1H), 5.96 (d, J=7.9 Hz, 1H).

Step 2: 5-Chloro-2-(4-fluorophenyl)pyrazolo[1,5-a]pyrimidine

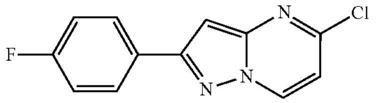

The title compound was prepared from 2-(4-fluorophenyl)-4H-pyrazolo[1,5-a]pyrimidin-7-one (step 1) and $POCl_3$ analogously to Intermediate C2.

LC-MS (Method 3A): Rt 1.86 mins; MS m/z 248.0=[M+H]+

1H NMR (500 MHz, DMSO-d6) δ 9.18 (dd, J=7.1, 0.8 Hz, 1H), 8.12-8.04 (m, 2H), 7.39-7.30 (m, 2H), 7.25 (d, J=0.8 Hz, 1H), 7.14 (d, J=7.1 Hz, 1H).

Step 3: 3-Bromo-5-chloro-2-(4-fluorophenyl)pyrazolo[1,5-a]pyrimidine

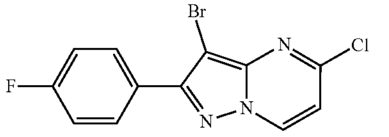 [SMILES: Fc1ccc(-c2nn3ccc(Cl)nc3c2Br)cc1]

The title compound was prepared from 5-chloro-2-(4-fluorophenyl)pyrazolo[1,5-a]pyrimidine (step 2) and NBS analogously to Intermediate El.

LC-MS (Method 3A): Rt 2.05 mins; MS m/z 325.9/327.9=[M+H]+

1H NMR (500 MHz, DMSO-d6) δ 9.25 (d, J=7.2 Hz, 1H), 8.08-8.01 (m, 2H), 7.46-7.38 (m, 2H), 7.28 (d, J=7.2 Hz, 1H).

Step 4: 3-Bromo-2-(4-fluorophenyl)pyrazolo[1,5-a]pyrimidin-5-amine

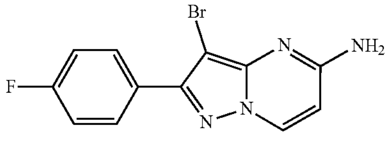 [SMILES: Nc1ccn2nc(-c3ccc(F)cc3)c(Br)c2n1]

The title compound was prepared from 3-bromo-5-chloro-2-(4-fluorophenyl)pyrazolo[1,5-a]pyrimidine (step 3) and $NH_4OH$ analogously to Intermediate E.

LC-MS (Method 3B): Rt 1.56 mins; MS m/z 306.9/308.9=[M+H]+

1H NMR (500 MHz, DMSO-d6) δ 8.54 (d, J=7.5 Hz, 1H), 7.99-7.91 (m, 2H), 7.38-7.31 (m, 2H), 7.25 (s, 2H), 6.31 (d, J=7.5 Hz, 1 H).

Step 0.5:.3-(2-Chloro-6-methyl-4-pyridyl)-2-(4-fluorophenyl)pyrazolo[1,5-a]pyrimidin-5-amine The title compound was prepared from 3-bromo-2-(4-fluorophenyl)pyrazolo[1,5-a]pyrimidin-5-amine (step 4) and (2-chloro-6-methyl-4-pyridyl)boronic acid analogously to Example 53.

LC-MS (Method 8B): Rt 4.67 mins; MS m/z 354.1=[M+H]+

$^1$H NMR (500 MHz, DMSO-$d_6$) δ 8.60 (d, J=7.5 Hz, 1H), 7.54-7.48 (m, 2H), 7.40-7.23 (m, 5H), 7.23-7.20 (m, 1H), 6.37 (d, J=7.5 Hz, 1H), 2.32 (s, 3H).

Example 90—N-tert-Butyl-3-(2-chloro-6-methyl-4-pyridyl)-2-(3-cyanophenyl)pyrazolo [1,5-a]pyrimidine-5-carboxamidine

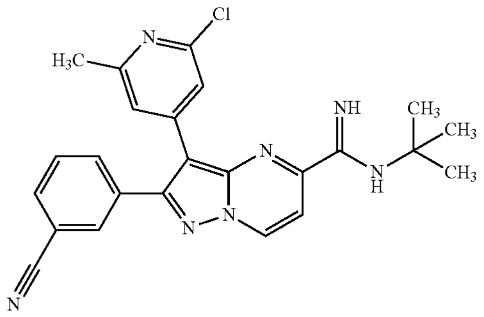 [SMILES: Cc1cc(-c2c(-c3cccc(C#N)c3)nn3ccc(C(=N)NC(C)(C)C)nc23)cc(Cl)n1]

Step 1: 3-Bromo-2-(3-cyanophenyl)pyrazolo[1,5-a]pyrimidine-5-carboxamide

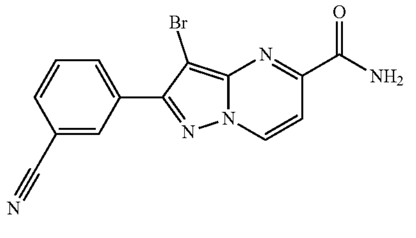 [SMILES: N#Cc1cccc(-c2nn3ccc(C(N)=O)nc3c2Br)c1]

To a mixture of 3-bromo-2-(3-cyanophenyl)pyrazolo[1,5-a]pyrimidine-5-carboxylic acid (Intermediate B1)(500 mg, 1.46 mmol) in DCM (15 mL) was added DMF (0.5 mL) followed by dropwise addition of oxalyl chloride (0.37 mL, 4.37 mmol) and the reaction mixture was stirred at room temperature for 5 h. The reaction was concentrated in vacuo. The residue was suspended in DCM (15 mL), cooled in an ice bath and ammonium hydroxide (0.62 mL, 36.43 mmol) was slowly added. The reaction was warmed to room temperature and stirred for 2 mins and the resulting mixture was concentrated in vacuo. The crude material was triturated with water (20 mL), the solid was collected by filtration and azeotroped from MeOH to afford the title compound as an orange solid.

LC-MS (Method 3B): Rt 1.56 mins; MS m/z 340.0/342.0={M–H]–

1H NMR (500 MHz, DMSO-d6) δ 9.36 (d, J=7.2 Hz, 1H), 8.42 (s, 1H), 8.37 (d, J=8.0 Hz, 1H), 8.17 (s, 1H), 8.06-7.97 (m, 2H), 7.82 (t, J=7.8 Hz, 1H), 7.67 (d, J=7.2 Hz, 1H).

Step 2: Ethyl 3-bromo-2-(3-cyanophenyl)pyrazolo[1,5-a]pyrimidine-5-carboximidate

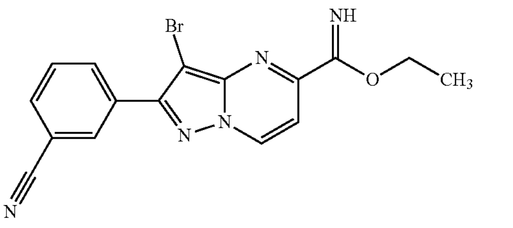 [SMILES: CCOC(=N)c1ccn2nc(-c3cccc(C#N)c3)c(Br)c2n1]

A mixture of 3-bromo-2-(3-cyanophenyl)pyrazolo[1,5-a]pyrimidine-5-carboxamide (step 1) (390 mg, 1.14 mmol) and triethyloxonium tetrafluoroborate (2166 mg, 11.4 mmol) in DCM (100 mL) was stirred at room temperature for 21 h. Additional triethyloxonium tetrafluoroborate 1083 mg, 5.7 mmol) was added and the mixture stirred for a further 16h before additional DCM (100 mL) was added and the mixture stirred for a further 24 h. A final addition of triethyloxonium tetrafluoroborate (2166 mg, 11.4 mmol) was made and the reaction was stirred at room temperature for a further 16 h. The reaction mixture was diluted with DCM (200 mL) and washed with $NaHCO_3$ (100 mL). The organic phase was dried over $MgSO_4$ and concentrated in vacuo to afford the title compound as a yellow solid which was used in the next step without further purification.

Step 3: 3-Bromo-N-tert-butyl-2-(3-cyanophenyl)pyrazolo[1,5-a]pyrimidine-5-carboxamidine

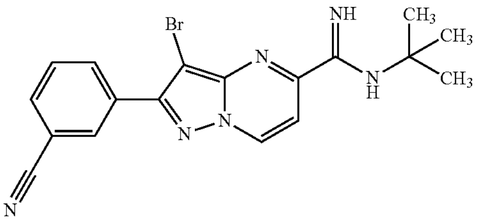 [SMILES: CC(C)(C)NC(=N)c1ccn2nc(-c3cccc(C#N)c3)c(Br)c2n1]

A mixture of ethyl 3-bromo-2-(3-cyanophenyl)pyrazolo[1,5-a]pyrimidine-5-carboximidate (step 2) (150 mg, 0.36 mmol), 2-methylpropan-2-amine (0.19 mL, 1.8 mmol) and DIPEA (0.31 mL, 1.8 mmol) in 1,4-dioxane (8 mL) was heated to 80° C. for 4 days, The resulting mixture was partitioned between EtOAc (20 mL) and $H_2O$ (20 mL), the organic portion was separated and the aqueous was further extracted with EtOAc (2×20 mL). The combined organic extracts were dried over $MgSO_4$ and the solvent removed in vacuo. Purification by chromatography on silica eluting with a gradient of 0 to 2% to 10% MeOH in DCM afforded the title compound as a brown solid.

LC-MS (Method 5B): Rt 3.72 mins; MS m/z 397.1/399.0=[M+H]+

$^1$H NMR (500 MHz, DMSO-$d_6$) b 9.31 (brs, 1H), 8.41 (d, J=1.6 Hz, 1H), 8.37 (dt, J=7.8, 1.6 Hz, 1H), 8.02 (dt, J=7.8,1.6 Hz, 1H), 7.85-7.79 (m, 2H), 1,43 (s, 9H). NH protons not observed.

Step 4: N-tert-butyl-3-(2-chloro-6-methyl-4-pyridyl)-2-(3-cyanophenyl)pyrazolo[1,5-a]pyrimidine-5-carboxamidine The title compound was prepared from 3-bromo-N-tert-butyl-2-(3-cyanophenyl)pyrazolo[1,5-a]pyrimidine-5-carboxamidine (step 3) and 2-chloro-6-methyl-4-(4,4,5,5-tetramethyl-1,3,2-dioxaborolan-2-yl)pyridine analogously to Intermediate A6.

LC-MS (Method 8B): Rt 5.17 mins; MS m/z 444.2/446.2=[M+H]+

NMR: $^1$H NMR (400 MHz, DMSO-$d_6$) δ 9.36 (s, 1H), 8.08 (s, 1H), 8.00 (dt, J=7.8, 1.5 Hz, 1H), 7.96-7.87 (m, 2H), 7.72 (t, J=7.8 Hz, 1H), 7.48-7.34 (m, 2H), 6.67 (s, 1H), 6.36 (s, 1H), 2.43 (s, 3H), 1.42 (s, 9H).

Example 91-3-(2-Amino-6-methyl-4-pyridyl)-N-tert-butyl-2-(3-cyanophenyl)pyrazolo [1,5-a]pyrimidine-5-carboxamide

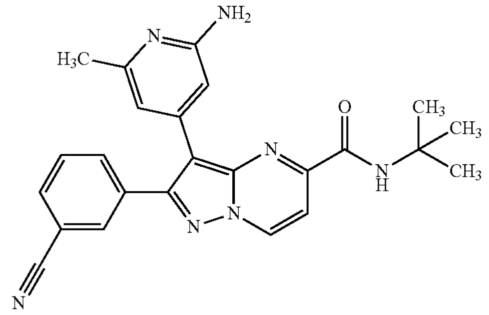 [SMILES: Cc1cc(-c2c(-c3cccc(C#N)c3)nn3ccc(C(=O)NC(C)(C)C)nc23)cc(N)n1]

Step 1: 3-Bromo-N-tert-butyl-2-(3-cyanophenyl)pyrazolo[1,5-a]pyrimidine-5-carboxamide

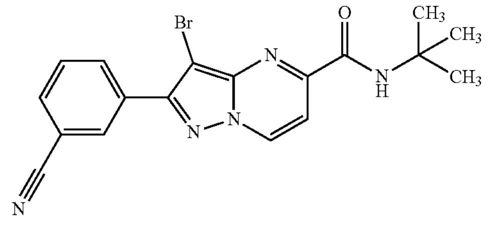 [SMILES: CC(C)(C)NC(=O)c1ccn2nc(-c3cccc(C#N)c3)c(Br)c2n1]

The title compound was prepared from 3-bromo-2-(3-cyanophenyl)pyrazolo[1,5-a]pyrimidine-5-carboxylic acid (Intermediate B1) and 2-methylpropan-2-amine analogously to Example 6.

LC-MS (Method 5B): Rt 3.67 mins; MS m/z 398.0/400.0=[M+H]+

$^1$H NMR (500 MHz, DMSO-$d_6$) δ 9.37 (d, J=7.1 Hz, 1H), 8.42 (s, 1H), 8.37 (d, J=7.9 Hz, 1H), 8.03 (d, J=7.9 Hz, 1H), 7.98 (s, 1H), 7.82 (t, J=7.9 Hz, 1H), 7.66 (d, J=7.1 Hz, 1H), 1.46 (s, 9H).

Step 2: 3-(2-Amino-6-methyl-4-pyridyl)-N-tert-butyl-2-(3-cyanophenyl)pyrazolo[1,5-a]pyrimidine-5-carboxamide The title compound was prepared from 3-[3-bromo-5-[(tert-butylamino)methyl]pyrazolo[1,5-a]pyrimidin-2-yl]benzonitrile (step 1) and 4-bromo-6-methyl-pyridin-2-amine analogously to Example 27.

LC-MS (Method 8B): Rt 4.48 mins; MS m/z 426.3=[M+H]+

1H NMR (500 MHz, DMSO-d6) δ 9.37 (d, J=7.2 Hz, 1H), 8.06 (s, 1H), 7.95 (t, J=7.9 Hz, 2H), 7.90 (s, 1H), 7.70 (t, J=7.8 Hz, 1H), 7.64 (d, J=7.2 Hz, 1H), 6.57 (s, 1H), 6.42-(s, 1H), 5.88 (s, 2H), 2.23 (s, 3H), 1.44 (s, 9H).

Example 92-2-(3-Cyanophenyl)-3-(2,6-dimethyl-4-pyridyl)-N-[(1S)-2-hydroxy-1,2-dimethyl-propyl]pyrazolo[1,5-a]pyrimidine-5-carboxamide

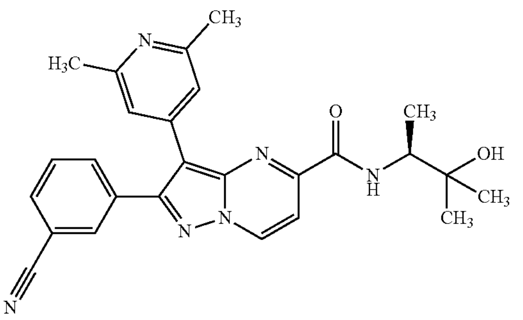 [SMILES: Cc1cc(-c2c(-c3cccc(C#N)c3)nn3ccc(C(=O)N[C@@H](C)C(C)(C)O)nc23)cc(C)n1]

Step 1a: Ethyl 2-(3-cyanophenyl)-3-(2,6-dimethyl-4-pyridyl)pyrazolo[1,5-a]pyrimidine-5-carboxylate

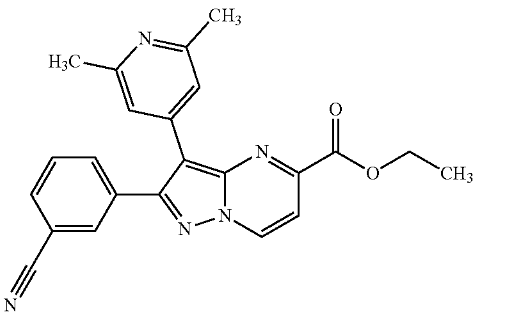 [SMILES: CCOC(=O)c1ccn2nc(-c3cccc(C#N)c3)c(-c3cc(C)nc(C)c3)c2n1]

To a degassed solution of 1,4-dioxane (10 mL) and water (2 mL) was added ethyl 3-bromo-2-(3-cyanophenyl)pyrazolo[1,5-a]pyrimidine-5-carboxylate (Intermediate A5) (700 mg, 1.89 mmol), 2,6-dimethyl-4-(4,4,5,5-tetramethyl-1,3,2-dioxaborolan-2-yl)pyridine (484 mg, 2.07 mmol), $K_2CO_3$ (521 mg, 3.77 mmol) and $Pd(tBu_3P)_2$ (72 mg, 0.14 mmol) and the mixture heated to 50° C. for 2 h. The resulting mixture was partitioned between DCM (50 mL) and $H_2O$ (30 mL) and the layers were separated. The aqueous was further extracted with DCM (2×30 mL) and the combined organic extracts were dried over $MgSO_4$. Purification by chromatography on silica eluting with a gradient of 2 to 3% MeOH in DCM afforded the title compound as a yellow solid.

LC-MS (Method 5B): Rt 3.10 mins; MS m/z 398.3=[M+H)+

$^1$H NMR (500 MHz, DMSO-$d_6$) δ 9.41 (d, J=7.2 Hz, 1H), 8.02 (s, 1H), 7.96 (d, J=7.8 Hz, 1H), 7.85 (d, J=7.8 Hz, 1H), 7.71-7.64 (m, 2H), 7.16 (s, 2H), 4.40 (q, J=7.1 Hz, 2H), 2.41 (s, 6H), 1.37 (t, J=7.1 Hz, 3H).

Step 2a: 2-(3-Cyanophenyl)-3-(2,6-dimethyl-4-pyridyl)pyrazolo[1,5-a]pyrimidine-5-carboxylic acid hydrochloride

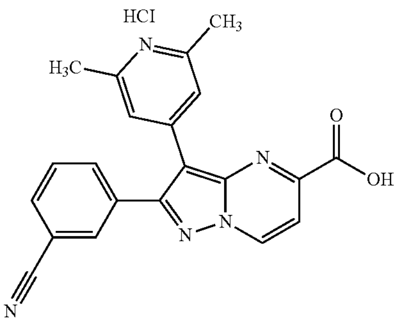

A solution of lithium hydroxide (119 mg, 4.95 mmol) in water (8 ml-) was added to a stirred mixture of ethyl 2-(3-cyanophenyl)-3-(2,6-dimethyl-4-pyridyl)pyrazolo[1,5-a]pyrimidine-5-carboxylate (step 1a) (656 mg, 1.65 mmol) in 1,4-dioxane (20 ml-) and stirred at room temperature for 1 h. The resulting mixture was partitioned between water (50 ml-) and $Et_2O$ (50 mL) and the layers were separated. The aqueous portion was acidified with 2M HCl and concentrated in vacuo. The solid residue was suspended in water (5 mL), collected by filtration and washed with water (2×5 mL). The resulting material was azeotroped with MecOH to afford the title compound as a yellow solid.

LC-MS (Method 5B3): Rt 1.37 mins; MS m/z 370.1=[M+H]+

$^1$H NMR (500 MHz, DMSO-$d_6$) δ 9.51 (d, J=7.1 Hz, IH), 8.11 (s, 1H), 8.04 (d, J=7.8 Hz, 1IH), 7.92 (d, J=7.8 Hz, I H), 7.79 (d, J=7.1 Hz, 1IH), 7.77-7.65 (m, 3H), 2.62 (s, 6H). Carboxylic acid proton not observed.

Step 3a: 2-(3-Cyanophenyl)-3-(2,6-dimethyl-4-pyridyl)-N-[(1S)-2-hydroxy-1,2-dimethyl-propyl]pyrazolol1,5-a]pyrimidine-5-carboxamide To a mixture of-2-(3-cyanophenyl)-3-(2,6-dimethyl-4-pyridyl)pyrazolo[1,5-a]pyrimidine-5-carboxylic acid hydrochloride (step 2a) (50 mg, 0.13 mmol) and (3S)-3-amino-2-methyl-butan-2-ol hydrochloride (27 mg, 0.19 mmol) in DMF (2 mL) was added DIPEA (153 μL, 0.88 mmol) followed by dropwise addition of T3P® (50% in DMF) (0.18 mL, 0.25 mmol) and the reaction mixture was stirred at room temperature for 1 h. The resulting mixture was partitioned between ethyl acetate (10 mL) and water (10 mL) and the layers were separated. The aqueous layer was further extracted with ethyl acetate (3×10 mL) and the combined organic extracts were washed with 50% brine (3×10 mL), dried over $MgSO_4$, filtered and concentrated in vacuo. Purification by chromatography on silica eluting with a gradient of 1 to 3% MeOH in DCM afforded the title compound as a yellow solid.

LC-MS (Method 8B): Rt 4.23 mins; MS m/z 455.3=[M+H]+

$^1$H NMR (500 MHz, DMSO-$d_6$) b 9.41 (d, J=7.2 Hz, 1H), 8.27 (d, J=8.9 Hz, 1H), 8.06 (s, 1H), 7.99 (d, J=7.8 Hz, 1H), 7.92 (d, J=7.9 Hz, 1H), 7.75-7.67 (m, 2H), 7.21 (s, 2H), 4.76 (s, 1H), 3.91-3.83 (m, 1H), 2.40 (s, 6H), 1.22-1.13 (m, 9H).

Alternatively, 2-(3-cyanophenyl)-3-(2,6-dimethyl-4-pyridyl)-N-[(1S)-2-hydroxy-1,2-dimethyl-propyl]pyrazolo[1,5-a]pyrimidine-5-carboxamide (Example 92) may be prepared as follows:

Step 1b: Ethyl 2-(3-cyanophenyl)-3-(2,6-dimethyl-4-pyridyl)pyrazolo[1,5-a]pyrimidine-5-carboxylate

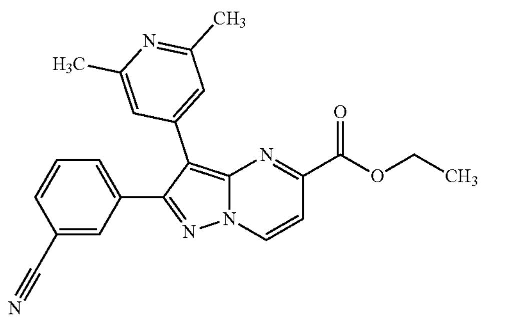 [SMILES: CCOC(=O)c1ccn2nc(-c3cccc(C#N)c3)c(-c3cc(C)nc(C)c3)c2n1]

A partial suspension of sodium bicarbonate (33.38 g, 397.37 mmol) in water (295 mL) was added to a solution of ethyl 3-bromo-2-(3-cyanophenyl)pyrazolo[1,5-a]pyrimidine-5-carboxylate (Intermediate A5) (59 g, 158.95 mmol) in 1,4-dioxane (1180 mL) and the reaction mixture deoxygenated via nitrogen sparging for 15 mins. $Pd(tBu_3P)_2$ (4.06 g, 7.95 mmol) and 2,6-dimethyl-4-(4,4,5,5-tetramethyl-1,3,2-dioxaborolan-2-yl)pyridine (44.46 g, 190.74 mmol) were added and the mixture was stirred under nitrogen at 50° C. for 3.5 h. The resulting mixture was cooled to room temperature and poured into water (3000 mL) to form a suspension. The suspension was stirred vigorously for 10 mins and then filtered. The solids were washed with water (2×1500 mL) and vacuum dried overnight to afford a pale yellow solid. This material was azeotroped with MaCN (600 mL) and concentrated in vacuo to afford a yellow-brown solid. This solid was re-dissolved in chloroform (300 mL), activated decolourising charcoal (3 g) added, and the mixture was stirred at reflux for 10 mins. After cooling to room temperature, the mixture was filtered through a plug of Celite® (filter material), eluting with chloroform (3×200 mL). The combined filtrates were concentrated in vacuo and the crude product triturated with MeCN (200 mL). The resulting suspension was filtered and the collected solids washed with MeCN (2×100 mL) then vacuum dried to afford the title compound as a pale yellow solid.

LC-MS (Method 3B): Rt 1.80 mins; MS m/z 398.2=[M+H]+

$^1$H NMR (500 MHz, DMSO) b 9.41 (d, J=7.2 Hz, 1H), 8.02 (s, 1H), 7.96 (d, J=7.8 Hz, 1H), 7.85 (d, J=8.1 Hz, 1H), 7.71-7.65 (m, 2H), 7.15 (s, 2H), 4.40 (q,J=7.1 Hz, 2H), 2.41 (s, 6H), 1.36 (t, J=7.1 Hz, 3H).

Step 2b: 2-(3-Cyanophenyl)-3-(2,6-dimethyl-4-pyridyl)pyrazolo[1,5-a]pyrimidine-5-carboxylic acid

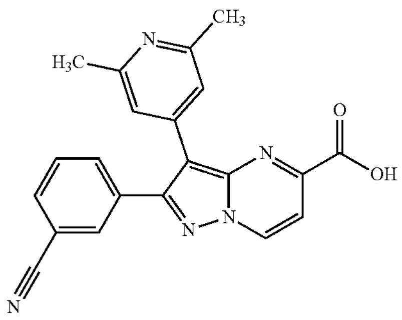 [SMILES: Cc1cc(-c2c(-c3cccc(C#N)c3)nn3ccc(C(=O)O)nc23)cc(C)n1]

A solution of LiOH (3.56 g, 148.44 mmol) in water (300 mL) was added to a stirred partial suspension of ethyl 2-(3-cyanophenyl)-3-(2,6-dimethyl-4-pyridyl)pyrazolo[1,5-a]pyrimidine-5-carboxylate (step 1b) (53.63 g, 134.94 mmol) in THF (900 mL) and the solution was stirred at room temperature for 45 mins. The mixture was diluted with water (1200 mL) and extracted with $Et_2O$ (3×1500 mL). To the resulting aqueous solution was added 1M HCl solution (147 mL) [resulting in a pH of ~5], followed by re-adjustment to pH 6 via addition of 10% aqueous NaOH (30 drops) causing a thick yellow precipitate to form. The suspension was stirred at room temperature for 15 mins and filtered. The solids were washed with water (2×500 mL) and vacuum dried overnight. The resulting material was mechanically broken up, placed in a wide dish and dried to constant weight in a vacuum oven at 40° C. (alongside a tray of KOH flakes as desiccant) to afford the title compound as a pale yellow solid.

LC-MS (Method 3B): Rt 1.06 mins; MS m/z 370.2=[M+H]+

$^1$H NMR (500 MHz, DMSO) δ 13.68 (br s, 1H), 9.37 (d, J=7.2 Hz, 1H), 8.01 (s, 1H), 7.96 (d, J=7.7 Hz, 1H), 7.84 (d, J=7.9 Hz, 1H), 7.67 (apr t,J=7.8 Hz, 1H), 7.65 (d, J=7.2 Hz, 1H), 7.16 (s, 2H), 2.41 (s, 6H).

Step 3b: 2-(3-Cyanophenyl)-3-(2,6-dimethyl-4-pyridyl)-N-[(1S)-2-hydroxy-1,2-dimethyl-propyl]pyrazolo[1,5-a]pyrimidine-5-carboxamide A solution of DIPEA (187.75 mL, 1077.9 mmol) in anhydrous THF (1000 mL) was added to 2-(3-cyanophenyl)-3-(2,6-dimethyl-4-pyridyl)pyrazolo[1,5-a]pyrimidine-5-carboxylic acid (step 2b) (49.77 g, 134.74 mmol) under nitrogen and the mixture was stirred until a solution formed. (3S)-3-Amino-2-methyl-butan-2-ol hydrochloride (28.22 g, 202.11 mmol) was added and stirring continued for 5 mins to homogenise the suspended solids. To this mixture was added dropwise a solution of T3P® (50% in THF) (198.44 mL, 269.48 mmol) over 20 mins and the mixture was stirred at room temperature for 45 mins. The resulting mixture was diluted with EtOAc (500 mL) and water (500 mL) and the layers were separated. The aqueous portion was extracted with EtOAc (500 mL) and the combined organic extracts were washed with water (2×500 mL), brine (250 mL), dried over $Na_2SO_4$ and concentrated in vacuo to afford a yellow foam. The foam was azeotroped with EtOAc and vacuum dried to afford a yellow solid. The solid was dissolved in a minimum volume of refluxing MeCN (3150 mL for 116g of crude material) and then allowed to cool to room temperature overnight. [NB when the mixture had reached a temperature of ~60° C., it was seeded with approx. 2 mg of ground crystals from a small scale MeCN recrystallised batch]. The resulting suspension was filtered and the solids washed with chilled (5° C.) MeCN (2×200 mL) and vacuum dried for 1 h to afford large yellow crystals. The crystallised solids were ground into a fine pale yellow powder and dried in a vacuum oven at 55° C. to afford the title compound as a pale yellow powder.

LC-MS (Method 8B): Rt 4.22 mins; MS m/z 455.3=[M+H]+

1H NMR (500 MHz, DMSO) δ 9.39 (d, J=7.1 Hz, 1H), 8.25 (d, J=8.9 Hz, 1H), 8.04 (s, 1H), 7.98 (d, J=7.7 Hz, 1H), 7.89 (d, J=8.0 Hz, 1H), 7.70 (apr t, J=7.8 Hz, 1H), 7.68 (d, J=7.1 Hz, 1H), 7.19 (s, 2H), 4.77 (s, 1H), 3.89-3.82 (m, 1H), 2.39 (s, 6H), 1.19 (s, 3H), 1.18-1.13 (m, 6H).

The compounds of the following tabulated Examples (Table Ex92) were prepared analogously to Example 92 from 2-(3-cyanophenyl)-3-(2,6-dimethyl-4-pyridyl)pyrazolo[1,5-a]pyrimidine-5-carboxylic acid hydrochloride (Example 92 step 2a) or 2-(3-cyanophenyl)-3-(2,6-dimethyl-4-pyridyl)pyrazolo[1,5-a]pyrimidine-5-carboxylic acid (Example 92 step 2b) and the appropriate amine.

TABLE Ex92

| Ex. | Structure and Name | Retention Time, [M + H]+, 1H NMR |
|---|---|---|
| 92.1 | 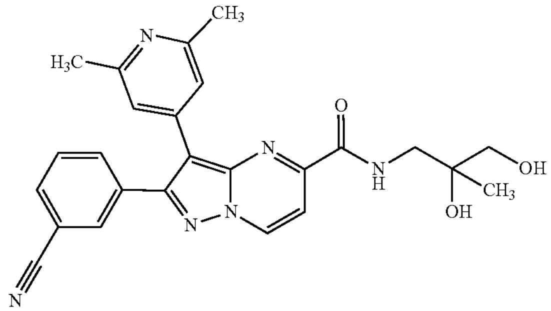 2-(3-Cyanophenyl)-N-(2,3-dihydroxy-2-methyl-propyl)-3-(2,6-dimethyl-4-pyridyl)pyrazolo[1,5-a]pyrimidine-5-carboxamide | LC-MS (Method 7A): Rt 1.41 mins; MS m/z 457.3 = [M + H]+ 1H NMR (500 MHz, DMSO-d6) δ 9.42 (d, J = 7.2 Hz, 1H), 8.43 (t, J = 5.7 Hz, 1H), 8.06 (t, J = 1.4 Hz, 1H), 7.99 (dt, J = 7.7, 1.3 Hz, 1H), 7.90 (dt, J = 7.9, 1.3 Hz, 1H), 7.71 (dt, J = 7.9, 4.3 Hz, 2H), 7.22 (s, 2H), 3.39-3.36 (m, 2H), 3.34 (d, J = 10.8 Hz, 1H), 3.28 (d, J = 10.8 Hz, 1H), 2.41 (s, 6H), 1.10 (s, 3H). OH protons not observed |
| 92.2 | 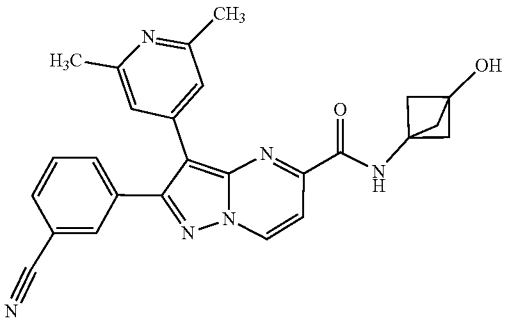 2-(3-Cyanophenyl)-3-(2,6-dimethyl-4-pyridyl)-N-(3-hydroxy-1-bicyclo[1.1.1]pentanyl)pyrazolo[1,5-a]pyrimidine-5-carboxamide | LC-MS (Method 8B): Rt 3.97 min; MS m/z 451.3 = [M + H]+ $^1$H NMR (500 MHz, DMSO-$d_6$) δ 9.38 (d, J = 7.2 Hz, 1H), 9.13 (s, 1H), 8.01 (s, 1H), 7.96 (d, J = 7.7 Hz, 1H), 7.85 (d, J = 7.7 Hz, 1H), 7.68 (t, J = 7.7 Hz, 1H), 7.62 (d, J = 7.2 Hz, 1H), 7.20 (s, 2H), 6.28 (s, 1H), 2.41 (s, 6H), 2.17 (s, 6H). |
| 92.3 | 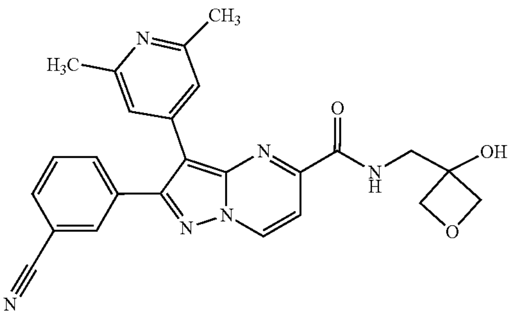 2-(3-Cyanophenyl)-3-(2,6-dimethyl-4-pyridyl)-N-[(3-hydroxyoxetan-3-yl)methyl]pyrazolo[1,5-a]pyrimidine-5-carboxamide | LC-MS (Method 8B): Rt 3.77 mins; MS m/z 455.3 = [M + H]+ 1H NMR (500 MHz, DMSO-d6) δ 9.43 (d, J = 7.2 Hz, 1H), 8.61 (t, J = 6.2 Hz, 1H), 8.06 (s, 1H), 7.99 (d, J = 7.8 Hz, 1H), 7.90 (d, J = 7.8 Hz, 1H), 7.75-7.68 (m, 2H), 7.21 (s, 2H), 6.10 (s, 1H), 4.47 (apr q, J = 6.5 Hz, 4H), 3.68 (d, J = 6.2 Hz, 2H), 2.41 (s, 6H). |

TABLE Ex92-continued

| Ex. | Structure and Name | Retention Time, [M + H]+, 1H NMR |
|---|---|---|
| 92.4 | 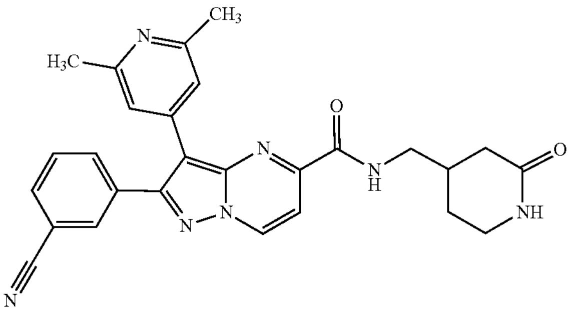 2-(3-Cyanophenyl)-3-(2,6-dimethyl-4-pyridyl)-N-[(2-oxo-4-piperidyl)methyl]pyrazolo[1,5-a]pyrimidine-5-carboxamide | LC-MS (Method 8B): Rt 3.77 mins; MS m/z 480.3 = [M + H]+ 1H NMR (500 MHz, Methanol-d4) δ 9.18 (d, J = 7.2 Hz, 1H), 8.02 (s, 1H), 7.88 (d, J = 8.0 Hz, 1H), 7.83 (d, J = 7.8 Hz, 1H), 7.76 (d, J = 7.2 Hz, 1H), 7.62 (t, J = 7.8 Hz, 1H), 7.28 (s, 2H), 3.44 (d, J = 6.8 Hz, 2H), 3.42-3.35 (m, 1H), 3.29-3.24 (m, 1H), 2.50 (s, 6H), 2.49-2.42 (m, 1H), 2.27-2.18 (m, 1H), 2.10 (dd, J = 17.4, 10.9 Hz, 1H), 2.01-1.94 (m, 1H), 1.58-1.49 (m, 1H). NH protons not observed |
| 92.5 | 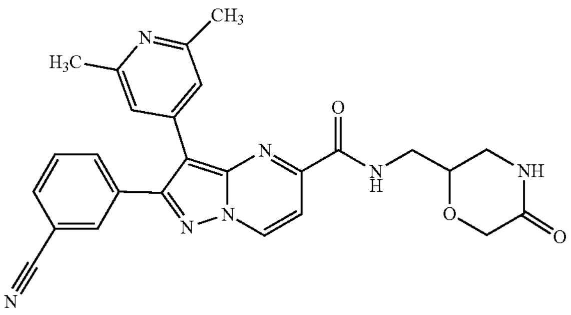 2-(3-Cyanophenyl)-3-(2,6-dimethyl-4-pyridyl)-N-[(5-oxomorpholin-2-yl)methyl]pyrazolo[1,5-a]pyrimidine-5-carboxamide | LC-MS (Method 8B): Rt 3.72 mins; MS m/z 482.3 = [M + H]+ 1H NMR (500 MHz, DMSO-d6) δ 9.40 (d, J = 7.2 Hz, 1H), 8.70 (t, J = 6.0 Hz, 1H), 8.07-8.01 (m, 2H), 7.98 (d, J = 7.9 Hz, 1H), 7.87 (d, J = 7.9 Hz, 1H), 7.73-7.65 (m, 2H), 7.20 (s, 2H), 4.11-4.00 (m, 2H), 3.96-3.89 (m, 1H), 3.59-3.46 (m, 2H), 3.26 (dt, J = 12.4, 3.5 Hz, 1H), 3.16 (t, J = 11.2 Hz, 1H), 2.42 (s, 6H). |
| 92.6 | 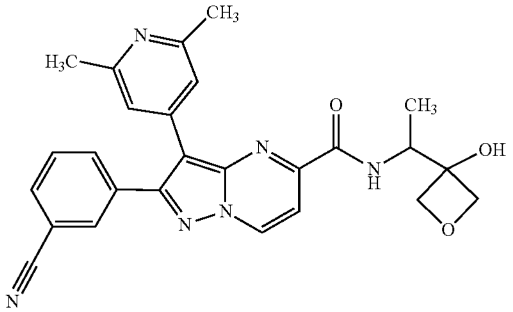 2-(3-Cyanophenyl)-3-(2,6-dimethyl-4-pyridyl)-N-[1-(3-hydroxyoxetan-3-yl)ethyl]pyrazolo[1,5-a]pyrimidine-5-carboxamide | LC-MS (Method 8B): Rt 3.97 mins; MS m/z 469.3 = [M + H]+ 1H NMR (500 MHz, DMSO-d6) δ 9.42 (d, J = 7.2 Hz, 1H), 8.26 (d, J = 9.3 Hz, 1H), 8.06 (t, J = 1.5 Hz, 1H), 7.99 (dt, J = 7.9, 1.5 Hz, 1H), 7.91 (dt, J = 7.9, 1.5 Hz, 1H), 7.74-7.67 (m, 2H), 7.20 (s, 2H), 6.27 (s, 1H), 4.51-4.39 (m, 5H), 2.40 (s, 6H), 1.16 (d, J = 6.6 Hz, 3H). |

TABLE Ex92-continued

| Ex. | Structure and Name | Retention Time, [M + H]+, 1H NMR |
|---|---|---|
| 92.7 | 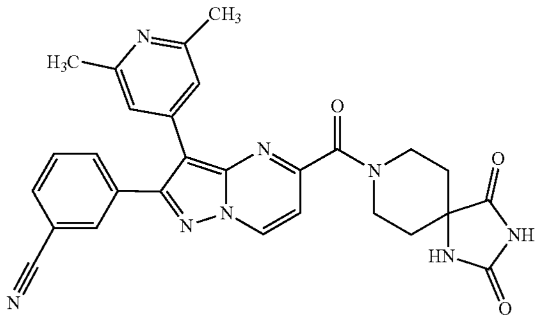 3-[3-(2,6-Dimethyl-4-pyridyl)-5-(2,4-dioxo-1,3,8-triazaspiro[4.5]decane-8-carbonyl)pyrazolo[1,5-a]pyrimidin-2-yl]benzonitrile | LC-MS (Method 8B): Rt 3.35 mins; MS m/z 521.3 = [M + H]+ 1H NMR (500 MHz, DMSO-d6) δ 10.85 (s, 1H), 9.42 (d, J = 7.2 Hz, 1H), 8.74 (s, 1H), 8.07 (t, J = 1.7 Hz, 1H), 8.02 (dt, J = 7.8, 1.4 Hz, 1H), 7.91 (dt, J = 8.0, 1.4 Hz, 1H), 7.74 (t, J = 7.8 Hz, 1H), 7.44 (d, J = 7.1 Hz, 1H), 7.14 (s, 2H), 4.43-4.34 (m, 1H), 4.13-4.07 (m, 1H), 3.55-3.47 (m, 1H), 2.43 (s, 6H), 2.10 (td, J = 12.9, 3.9 Hz, 2H), 1.92 (td, J = 12.6, 4.5 Hz, 1H), 1.81-1.71 (m, 2H). |
| 92.8 | 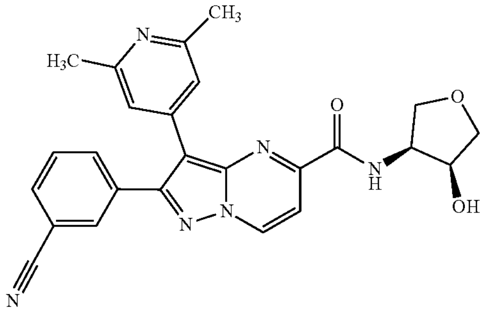 2-(3-Cyanophenyl)-3-(2,6-dimethyl-4-pyridyl)-N-[(3S,4S)-4-hydroxytetrahydrofuran-3-yl]pyrazolo[1,5-a]pyrimidine-5-carboxamide | LC-MS (Method 8B): Rt 3.81 mins; MS m/z 455.3 = [M + H]+ 1H NMR (500 MHz, DMSO-d6) δ 9.44 (d, J = 7.2 Hz, 1H), 8.60 (d, J = 7.0 Hz, 1H), 8.07 (t, J = 1.6 Hz, 1H), 8.00 (dt, J = 7.8, 1.6 Hz, 1H), 7.92 (dt, J = 7.8, 1.6 Hz, 1H), 7.74-7.69 (m, 2H), 7.20 (s, 2H), 5.86 (d, J = 4.6 Hz, 1H), 4.39-4.35 (m, 1H), 4.31 (apr p, J = 7.0 Hz, 1H), 4.01 (dd, J = 8.5, 7.0 Hz, 1H), 3.96 (dd, J = 9.7, 4.6 Hz, 1H), 3.66 (dd, J = 9.7, 2.6 Hz, 1H), 3.54 (dd, J = 8.5, 7.0 Hz, 1H), 2.41 (s, 6H). |
| 92.9 | 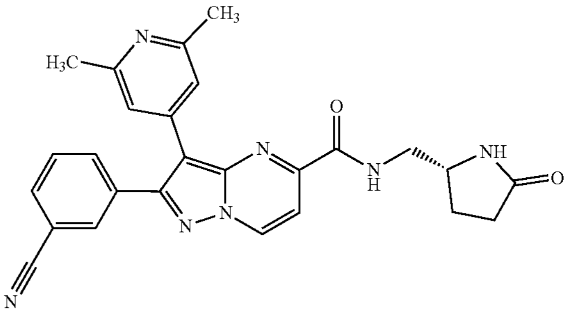 2-(3-Cyanophenyl)-3-(2,6-dimethyl-4-pyridyl)-N-[[(2R)-5-oxopyrrolidin-2-yl]methyl]pyrazolo[1,5-a]pyrimidine-5-carboxamide | LC-MS (Method 8B): Rt 3.69 mins; MS m/z 466.3 = [M + H]+ 1H NMR (500 MHz, DMSO-d6) δ 9.40 (d, J = 7.2 Hz, 1H), 8.75 (t, J = 6.3 Hz, 1H), 8.04 (t, J = 1.6 Hz, 1H), 7.98 (dt, J = 7.9, 1.6 Hz, 1H), 7.87 (dt, J = 7.9, 1.6 Hz, 1H), 7.75 (s, 1H), 7.70 (t, J = 7.8 Hz, 1H), 7.68 (d, J = 7.2 Hz, 1H), 7.21 (s, 2H), 3.77 (apr p, J = 5.5 Hz, 1H), 3.47-3.36 (m, 2H), 2.43 (s, 6H), 2.23-2.06 (m, 3H), 1.90-1.83 (m, 1H). |

TABLE Ex92-continued

| Ex. | Structure and Name | Retention Time, [M + H]+, 1H NMR |
|---|---|---|
| 92.10 | 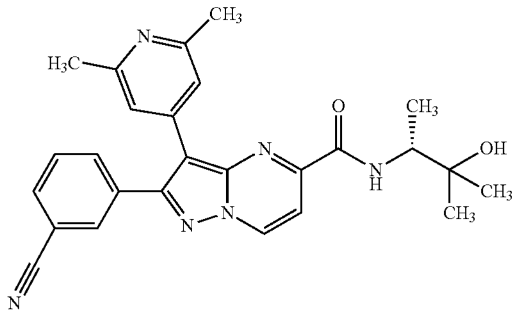 2-(3-Cyanophenyl)-3-(2,6-dimethyl-4-pyridyl)-N-[(1R)-2-hydroxy-1,2-dimethyl-propyl]pyrazolo[1,5-a]pyrimidine-5-carboxamide | LC-MS (Method 8B): Rt 4.20 mins; MS m/z 455.3 = [M + H]+ 1H NMR (500 MHz, DMSO-d6) δ 9.42 (d, J = 7.1 Hz, 1H), 8.27 (d, J = 8.9 Hz, 1H), 8.07 (s, 1H), 8.00 (d, J = 7.8 Hz, 1H), 7.92 (d, J = 7.9 Hz, 1H), 7.75-7.68 (m, 2H), 7.22 (s, 2H), 4.77 (s, 1H), 3.91-3.83 (m, 1H), 2.41 (s, 6H), 1.20 (s, 3H), 1.17 (d, J = 7.3 Hz, 3H), 1.16 (s, 3H) |
| 92.11 | 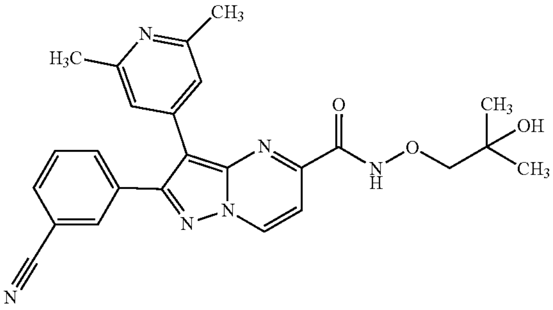 2-(3-Cyanophenyl)-3-(2,6-dimethyl-4-pyridyl)-N-(2-hydroxy-2-methyl-propoxy)pyrazolo[1,5-a]pyrimidine-5-carboxamide (Prepared using Intermediate ZA) | LC-MS (Method 15B): Rt 4.83 mins; MS m/z 457.1 = [M + H]+ 1H NMR (500 MHz, DMSO-d6) δ 12.10 (br. s, 1H), 9.38 (d, J = 7.1 Hz, 1H), 8.02 (s, 1H), 7.98 (d, J = 7.8 Hz, 1H), 7.86 (d, J = 7.8 Hz, 1H), 7.70 (t, J = 7.8 Hz, 1H), 7.62 (d, J = 7.1 Hz, 1H), 7.19 (s, 2H), 4.79 (br. s, 1H), 3.76 (s, 2H), 2.42 (s, 6H), 1.20 (s, 6H). |
| 92.12 | 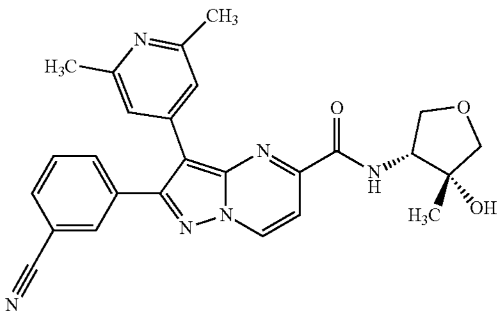 2-(3-Cyanophenyl)-3-(2,6-dimethyl-4-pyridyl)-N-[cis-4-hydroxy-4-methyl-tetrahydrofuran-3-yl]pyrazolo[1,5-a]pyrimidine-5-carboxamide (Prepared using Intermediate ZB) | LC-MS (Method 8B): Rt 4.08 mins; MS m/z 469.3 = [M + H]+ 1H NMR (500 MHz, DMSO-d6) δ 9.43 (d, J = 7.1 Hz, 1H), 8.47 (d, J = 7.0 Hz, 1H), 8.07 (t, J = 1.8 Hz, 1H), 7.99 (dt, J = 7.7, 1.4 Hz, 1H), 7.92 (dt, J = 7.9, 1.4 Hz, 1H), 7.76-7.69 (m, 2H), 7.21 (s, 2H), 5.59 (s, 1H), 4.15-4.06 (m, 2H), 3.74 (d, J = 9.2 Hz, 1H), 3.71 (d, J = 9.2 Hz, 1H), 3.58 (t, J = 7.1 Hz, 1H), 2.41 (s, 6H), 1.30 (s, 3H). |

TABLE Ex92-continued

| Ex. | Structure and Name | Retention Time, [M + H]+, 1H NMR |
|---|---|---|
| 92.13 | 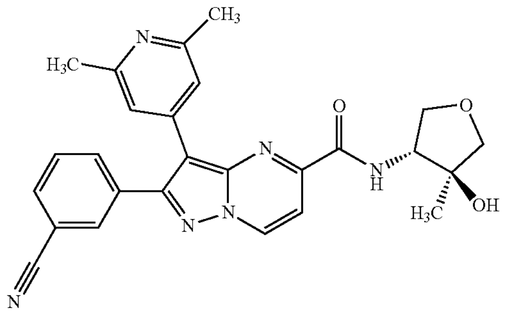 2-(3-Cyanophenyl)-3-(2,6-dimethyl-4-pyridyl)-N-[trans-4-hydroxy-4-methyl-tetrahydrofuran-3-yl]pyrazolo[1,5-a]pyrimidine-5-carboxamide (Prepared using Intermediate ZC) | LC-MS (Method 8B): Rt 3.91 mins; MS m/z 469.3 = [M + H]+ 1H NMR (500 MHz, DMSO-d6) δ 9.41 (d, J = 7.2 Hz, 1H), 8.47 (d, J = 9.2 Hz, 1H), 8.07 (t, J = 1.5 Hz, 1H), 7.99 (dt, J = 7.8, 1.5 Hz, 1H), 7.91 (dt, J = 7.8, 1.5 Hz, 1H), 7.71 (t, J = 7.8 Hz, 1H), 7.64 (d, J = 7.2 Hz, 1H), 7.26 (s, 2H), 5.22 (s, 1H), 4.40-4.34 (m, 1H), 4.18 (dd, J = 9.0, 6.2 Hz, 1H), 3.70-3.61 (m, 3H), 2.39 (s, 6H), 1.29 (s, 3H). |
| 92.14 | 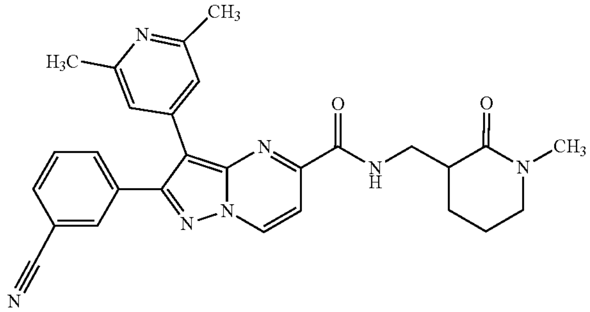 2-(3-Cyanophenyl)-3-(2,6-dimethyl-4-pyridyl)-N-[(1-methyl-2-oxo-3-piperidyl)methyl]pyrazolo[1,5-a]pyrimidine-5-carboxamide | LC-MS (Method 8B): Rt 4.23 mins; MS m/z 494.3 = [M + H]+ 1H NMR (500 MHz, DMSO-d6) δ 9.40 (d, J = 7.1 Hz, 1H), 9.18 (dd, J = 7.9, 3.8 Hz, 1H), 8.05 (s, 1H), 7.99 (d, J = 7.4 Hz, 1H), 7.89 (d, J = 8.1 Hz, 1H), 7.71 (t, J = 6.7 Hz, 2H), 7.21 (s, 2H), 3.69-3.57 (m, 1H), 3.45-3.37 (m, 2H), 3.30-3.24 (m, 2H), 2.86 (s, 3H), 2.44 (s, 6H), 1.94-1.83 (m, 2H), 1.81-1.69 (m, 1H), 1.61-1.49 (m, 1H). |
| 92.15 | 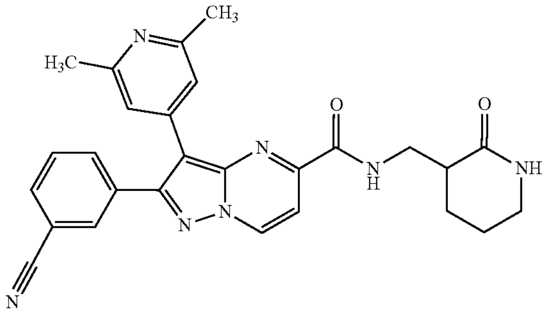 2-(3-Cyanophenyl)-3-(2,6-dimethyl-4-pyridyl)-N-[(2-oxo-3-piperidyl)methyl]pyrazolo[1,5-a]pyrimidine-5-carboxamide | LC-MS (Method 8B): Rt 3.99 mins; MS m/z 480.3 = [M + H]+ 1H NMR (500 MHz, DMSO-d6) δ 9.40 (d, J = 7.1 Hz, 1H), 9.13 (dd, J = 7.8, 4.0 Hz, 1H), 8.04 (s, 1H), 7.98 (d, J = 7.8, 1.4 Hz, 1H), 7.89 (d, J = 8.0, 1.4 Hz, 1H), 7.70 (t, J = 8.9, 7.4 Hz, 2H), 7.58 (s, 1H), 7.20 (s, 2H), 3.61 (dt, J = 13.6, 7.0 Hz, 1H), 3.48-3.41 (m, 1H), 3.19-3.08 (m, 3H), 2.43 (s, 6H), 1.96-1.87 (m, 1H), 1.85-1.75 (m, 1H), 1.71-1.60 (m, 1H), 1.58-1.46 (m, 1H). |

TABLE Ex92-continued

| Ex. | Structure and Name | Retention Time, [M + H]+, 1H NMR |
|---|---|---|
| 92.16 | 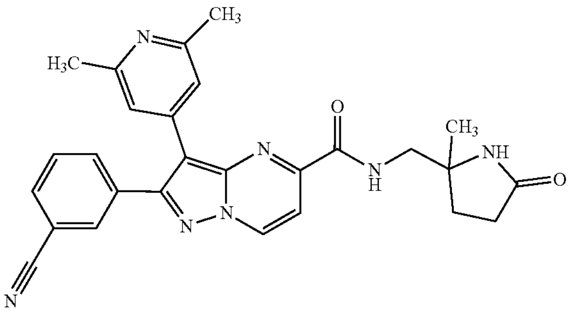 2-(3-Cyanophenyl)-3-(2,6-dimethyl-4-pyridyl)-N-[(2-methyl-5-oxo-pyrrolidin-2-yl)methyl]pyrazolo[1,5-a]pyrimidine-5-carboxamide | LC-MS (Method 8B): Rt 3.85 mins; MS m/z 480.3 = [M + H]+ 1H NMR (500 MHz, DMSO-d6) δ 9.41 (d, J = 7.2 Hz, 1H), 8.67 (t, J = 6.6 Hz, 1H), 8.06 (t, J = 1.7 Hz, 1H), 7.99 (dt, J = 7.8, 1.4 Hz, 1H), 7.90 (dt, J = 8.0, 1.4 Hz, 1H), 7.71 (t, J = 7.9 Hz, 1H), 7.68 (d, J = 7.6 Hz, 2H), 7.23 (s, 2H), 3.46-3.39 (m, 2H), 2.42 (s, 6H), 2.32-2.23 (m, 1H), 2.22-2.09 (m, 2H), 1.79-1.70 (m, 1H), 1.24 (s, 3H). |
| 92.17 | 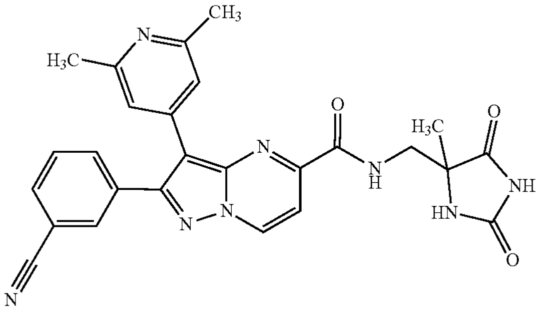 2-(3-Cyanophenyl)-3-(2,6-dimethyl-4-pyridyl)-N-[(4-methyl-2,5-dioxo-imidazolidin-4-yl)methyl]pyrazolo[1,5-a]pyrimidine-5-carboxamide | LC-MS (Method 8B): 3.44 mins; MS m/z 495.3 = [M + H]+ 1H NMR (500 MHz, DMSO-d6) δ 10.72 (s, 1H), 9.42 (d, J = 7.2 Hz, 1H), 8.53-8.49 (m, 1H), 8.04 (d, J = 1.7 Hz, 1H), 7.98 (dt, J = 7.7, 1.4 Hz, 1H), 7.96 (s, 1H), 7.88 (dt, J = 8.0, 1.5 Hz, 1H), 7.70 (dd, J = 8.7, 7.4 Hz, 2H), 7.18 (s, 2H), 3.78 (dd, J = 13.5, 7.7 Hz, 1H), 3.46-3.41 (m, 1H), 2.43 (s, 6H), 1.33 (s, 3H). |
| 92.18 | 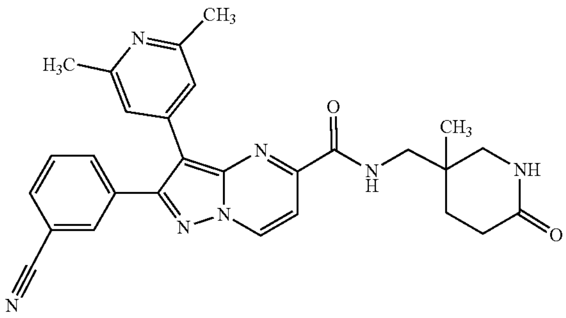 2-(3-Cyanophenyl)-3-(2,6-dimethyl-4-pyridyl)-N-[(3-methyl-6-oxo-3-piperidyl)methyl]pyrazolo[1,5-a]pyrimidine-5-carboxamide | LC-MS (Method 8B): Rt 3.90 mins; MS m/z 494.3 = [M + H]+ 1H NMR (500 MHz, DMSO-d6) δ 9.41 (d, J = 7.1 Hz, 1H), 8.69 (t, J = 6.7 Hz, 1H), 8.06 (s, 1H), 7.99 (d, J = 7.8 Hz, 1H), 7.91 (d, J = 7.9 Hz, 1H), 7.71 (t, J = 7.8 Hz, 1H), 7.65 (d, J = 7.0 Hz, 1H), 7.40 (s, 1H), 7.26 (s, 2H), 3.05 (d, J = 12.4 Hz, 1H), 2.89 (d, J = 12.4 Hz, 1H), 2.40 (s, 6H), 2.32-2.26 (m, 1H), 2.17-2.12 (m, 1H), 1.68 (dt, J = 14.0, 7.3 Hz, 2H), 1.58-1.51 (m, 2H), 1.02 (s, 3H). |

TABLE Ex92-continued

| Ex. | Structure and Name | Retention Time, [M + H]+, 1H NMR |
|---|---|---|
| 92.19 | 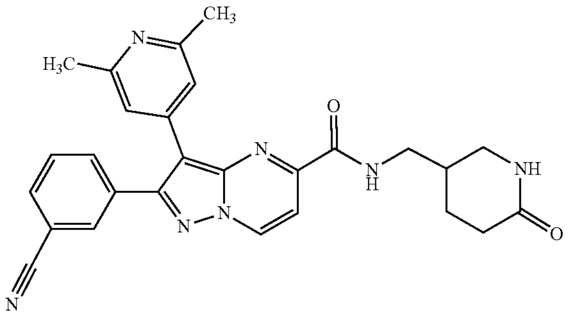 2-(3-Cyanophenyl)-3-(2,6-dimethyl-4-pyridyl)-N-[(6-oxo-3-piperidyl)methyl]pyrazolo[1,5-a]pyrimidine-5-carboxamide | LC-MS (Method 8B): Rt 3.78 mins; MS m/z 480.3 = [M + H]+ 1H NMR (500 MHz, DMSO-d6) δ 9.39 (d, J = 7.2 Hz, 1H), 8.82 (t, J = 6.3 Hz, 1H), 8.03 (s, 1H), 7.98 (d, J = 7.8 Hz, 1H), 7.90-7.84 (m, 1H), 7.70 (t, J = 7.8 Hz, 1H), 7.65 (d, J = 7.2 Hz, 1H), 7.44 (s, 1H), 7.22 (s, 2H), 3.24-3.15 (m, 1H), 2.92 (t, J = 10.9 Hz, 1H), 2.41 (s, 6H), 2.27-2.10 (m, 3H), 2.10-2.01 (m, 1H), 1.83 (s, 1H), 1.50 (tt, J = 17.0, 8.6 Hz, 2H). |
| 92.20 | 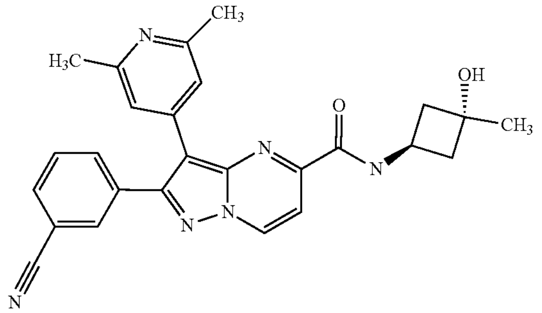 2-(3-Cyanophenyl)-3-(2,6-dimethyl-4-pyridyl)-N-(trans-3-hydroxy-3-methyl-cyclobutyl)pyrazolo[1,5-a]pyrimidine-5-carboxamide | LC-MS (Method 8B): Rt 3.93 mins; MS m/z 453.2 = [M + H]+ 1H NMR (500 MHz, DMSO-d6) δ 9.38 (d, J = 7.2 Hz, 1H), 8.78 (d, J = 7.6 Hz, 1H), 8.04 (d, J = 1.8 Hz, 1H), 7.98 (dt, J = 7.7, 1.5 Hz, 1H), 7.88 (dt, J = 7.8, 1.5 Hz, 1H), 7.70 (t, J = 7.8 Hz, 1H), 7.62 (d, J = 7.2 Hz, 1H), 7.25 (s, 2H), 4.92 (s, 1H), 4.49 (q, J = 7.7 Hz, 1H), 2.41 (s, 6H), 2.34-2.29 (m, 2H), 2.19-2.13 (m, 2H), 1.31 (s, 3H). |
| 92.21 | 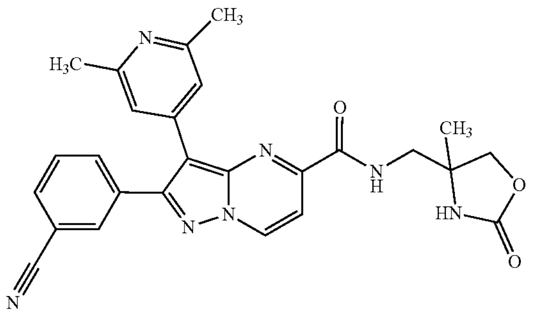 2-(3-Cyanophenyl)-3-(2,6-dimethyl-4-pyridyl)-N-[(4-methyl-2-oxo-oxazolidin-4-yl)methyl]pyrazolo[1,5-a]pyrimidine-5-carboxamide | LC-MS (Method 8B): Rt 3.74 mins; MS m/z 482.2 = [M + H]+ 1H NMR (500 MHz, DMSO-d6) δ 9.41 (d, J = 7.2 Hz, 1H), 8.76 (t, J = 6.6 Hz, 1H), 8.05 (d, J = 1.8 Hz, 1H), 7.98 (dt, J = 7.8, 1.4 Hz, 1H), 7.90-7.87 (m, 1H), 7.74 (s, 1H), 7.73-7.67 (m, 2H), 7.22 (s, 2H), 4.37 (d, J = 8.7 Hz, 1H), 3.97 (d, J = 8.6 Hz, 1H), 3.47 (d, J = 6.5 Hz, 2H), 2.42 (s, 6H), 1.29 (s, 3H). |

TABLE Ex92-continued

| Ex. | Structure and Name | Retention Time, [M + H]+, 1H NMR |
| --- | --- | --- |
| 92.22 | 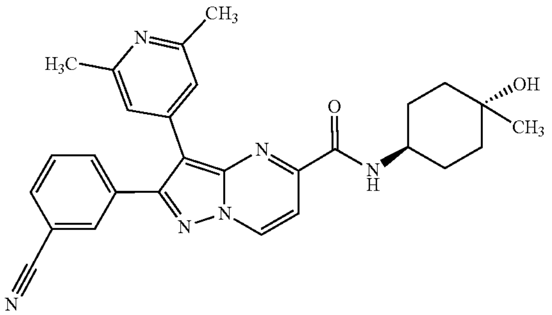 2-(3-Cyanophenyl)-3-(2,6-dimethyl-4-pyridyl)-N-(trans-4-hydroxy-4-methyl-cyclohexyl)pyrazolo[1,5-a]pyrimidine-5-carboxamide | LC-MS (Method 8B): Rt 4.10 mins; MS m/z 481.2 = [M + H]+ 1H NMR (500 MHz, DMSO-d6) δ 9.39 (d, J = 7.1 Hz, 1H), 8.34 (d, J = 8.0 Hz, 1H), 8.04 (d, J = 1.8 Hz, 1H), 7.98 (d, J = 7.7 Hz, 1H), 7.88 (d, J = 7.9 Hz, 1H), 7.70 (t, J = 7.8 Hz, 1H), 7.65 (d, J = 7.2 Hz, 1H), 7.24 (s, 2H), 4.29 (s, 1H), 3.87 (dt, J = 8.6, 4.4 Hz, 1H), 2.40 (s, 6H), 1.88-1.81 (m, 2H), 1.63-1.52 (m, 4H), 1.51-1.43 (m, 2H), 1.15 (s, 3H). |
| 92.23 | 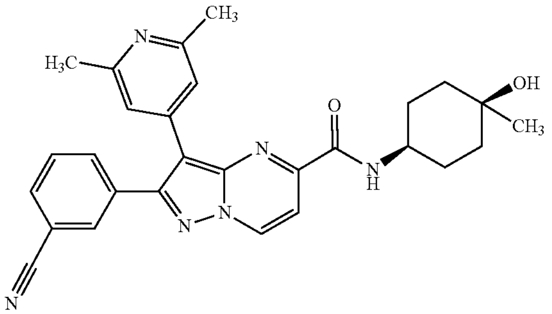 2-(3-Cyanophenyl)-3-(2,6-dimethyl-4-pyridyl)-N-(cis-4-hydroxy-4-methyl-cyclohexyl)pyrazolo[1,5-a]pyrimidine-5-carboxamide | LC-MS (Methood 8B): Rt 4.25 mins; MS m/z 481.4 = [M + H]+ 1H NMR (500 MHz, DMSO-d6) δ 9.38 (d, J = 7.2 Hz, 1H), 8.33 (d, J = 8.1 Hz, 1H), 8.04 (d, J = 1.8 Hz, 1H), 7.98 (d, J = 7.7 Hz, 1H), 7.89 (d, J = 7.9 Hz, 1H), 7.70 (t, J = 7.8 Hz, 1H), 7.64 (d, J = 7.2 Hz, 1H), 7.24 (s, 2H), 4.12 (s, 1H), 3.73 (s, 1H), 2.41 (s, 6H), 1.78 (dt, J = 12.6, 9.9 Hz, 2H), 1.68-1.55 (m, 4H), 1.40 (td, J = 13.2, 3.9 Hz, 2H), 1.12 (s, 3H). |
| 92.24 | 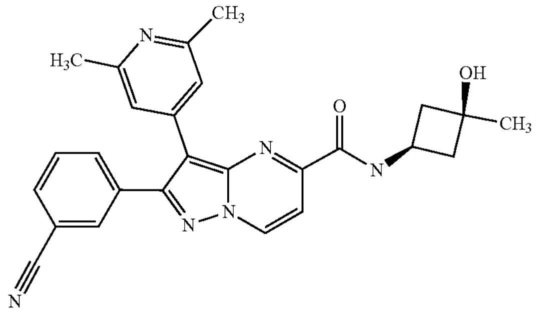 2-(3-Cyanophenyl)-3-(2,6-dimethyl-4-pyridyl)-N-(cis-3-hydroxy-3-methyl-cyclobutyl)pyrazolo[1,5-a]pyrimidine-5-carboxamide | LC-MS (Method 8B): Rt 4.00 mins; MS m/z 453.3 = [M + H]+ 1H NMR (500 MHz, DMSO-d6) δ 9.38 (d, J = 7.2 Hz, 1H), 8.70 (d, J = 7.5 Hz, 1H), 8.04 (d, J = 1.8 Hz, 1H), 7.98 (d, J = 7.8 Hz, 1H), 7.89-7.85 (m, 1H), 7.70 (t, J = 7.8 Hz, 1H), 7.63 (d, J = 7.2 Hz, 1H), 7.24 (s, 2H), 5.02 (s, 1H), 4.05-3.99 (m, 1H), 2.43 (s, 6H), 2.39-2.33 (m, 2H), 2.16 (dd, J = 11.1, 8.2 Hz, 2H), 1.27 (s, 3H). |

TABLE Ex92-continued

| Ex. | Structure and Name | Retention Time, [M + H]+, 1H NMR |
|---|---|---|
| 92.25 | 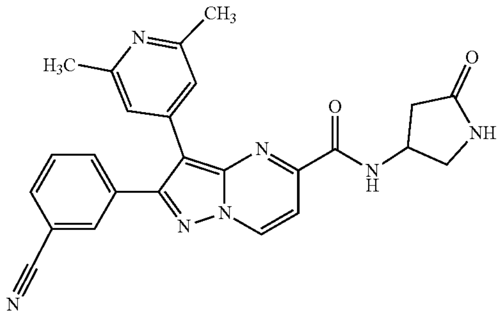 2-(3-Cyanophenyl)-3-(2,6-dimethyl-4-pyridyl)-N-(5-oxopyrrolidin-3-yl)pyrazolo[1,5-a]pyrimidine-5-carboxamide | LC-MS (Method 8B): Rt 3.68 mins; MS m/z 452.3 = [M + H]+ 1H NMR (500 MHz, DMSO-d6) δ 9.40 (d, J = 7.2 Hz, 1H), 9.00 (d, J = 7.4 Hz, 1H), 8.04 (d, J = 1.8 Hz, 1H), 7.98 (d, J = 7.7 Hz, 1H), 7.88 (d, J = 7.9 Hz, 1H), 7.73-7.67 (m, 2H), 7.65 (d, J = 7.2 Hz, 1H), 7.23 (s, 2H), 4.66 (h, J = 7.0 Hz, 1H), 3.61 (br d, J = 9.8 Hz, 1H), 3.25 (dd, J = 9.9, 5.3 Hz, 1H), 2.41 (s, 6H), 2.40-2.35 (m, 2H). |
| 92.26 | 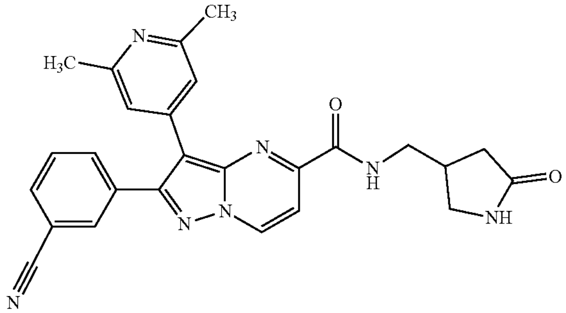 N-[2-(3-cyanophenyl)-3-(2,6-dimethylpyridin-4-yl)pyrazolo[1,5-a]pyrimidin-5-yl]-2-(5-oxopyrrolidin-3-yl)acetamide | LC-MS (Method 8B): Rt 3.72 mins; MS m/z 466.3 = [M + H]+ 1H NMR (500 MHz, Methanol-d4) δ 9.17 (d, J = 7.2 Hz, 1H), 8.00 (s, 1H), 7.87 (d, J = 7.8 Hz, 1H), 7.83 (d, J = 7.8 Hz, 1H), 7.75 (d, J = 7.2 Hz, 1H), 7.62 (t, J = 7.8 Hz, 1H), 7.26 (s, 2H), 3.53 (q, J = 5.7, 3.3 Hz, 3H), 3.24 (dd, J = 10.2, 5.4 Hz, 1H), 2.86 (p, J = 7.2 Hz, 1H), 2.50 (s, 6H), 2.47 (d, J = 9.0 Hz, 1H), 2.21 (dd, J = 17.0, 6.3 Hz, 1H). 2 NH protons not observed |
| 92.27 | 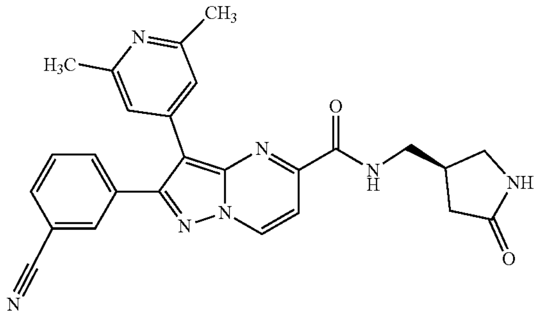 N-[2-(3-cyanophenyl)-3-(2,6-dimethylpyridin-4-yl)pyrazolo[1,5-a]pyrimidin-5-yl]-2-[(3R)-5-oxopyrrolidin-3-yl]acetamide | LC-MS (Method 8B): Rt 3.70 mins; MS m/z 466.3 = [M + H]+ 1H NMR (500 MHz, Methanol-d4) δ 9.18 (d, J = 7.3 Hz, 1H), 8.01 (s, 1H), 7.87 (d, J = 7.9 Hz, 1H), 7.83 (d, J = 7.8 Hz, 1H), 7.76 (d, J = 7.2 Hz, 1H), 7.63 (t, J = 7.9 Hz, 1H), 7.27 (s, 2H), 3.57-3.50 (m, 3H), 3.24 (dd, J = 10.1, 5.4 Hz, 1H), 2.86 (p, J = 7.1 Hz, 1H), 2.51 (s, 6H), 2.50-2.45 (m, 1H), 2.21 (dd, J = 17.0, 6.5 Hz, 1H). 2 NH protons not observed |

TABLE Ex92-continued

| Ex. | Structure and Name | Retention Time, [M + H]+, 1H NMR |
|---|---|---|
| 92.28 | 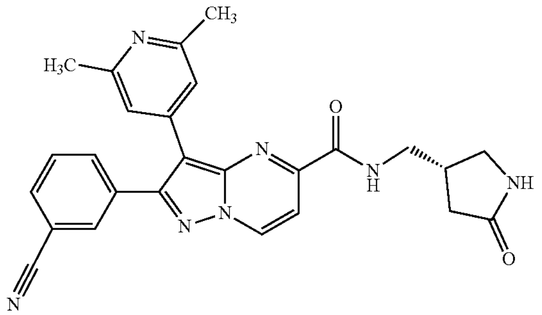 N-[2-(3-cyanophenyl)-3-(2,6-dimethylpyridin-4-yl)pyrazolo[1,5-a]pyrimidin-5-yl]-[(3S)-5-oxopyrrolidin-3-yl]acetamide | LC-MS (Method 8B): Rt 3.71 mins; MS m/z 466.3 = [M + H]+ 1H NMR (500 MHz, Methanol-d4) δ 9.16 (d, J = 7.2 Hz, 1H), 7.99 (s, 1H), 7.86 (d, J = 7.9 Hz, 1H), 7.82 (d, J = 7.7 Hz, 1H), 7.75 (d, J = 7.2 Hz, 1H), 7.62 (t, J = 7.8 Hz, 1H), 7.25 (s, 2H), 3.56-3.50 (m, 3H), 3.24 (dd, J = 10.1, 5.4 Hz, 1H), 2.85 (dq, J = 14.3, 7.2 Hz, 1H), 2.50 (s, 6H), 2.47 (d, J = 8.8 Hz, 1H), 2.21 (dd, J = 17.1, 6.5 Hz, 1H). 2 NH protons not observed |
| 92.29 | 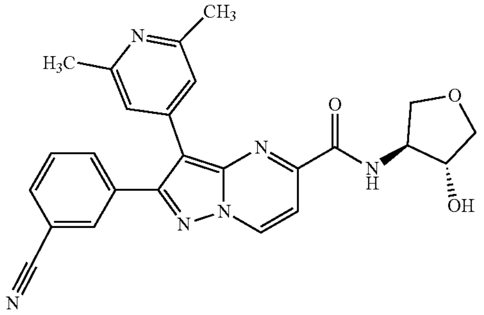 2-(3-Cyanophenyl)-3-(2,6-dimethyl-4-pyridyl)-N-[(3S,4R)-4-hydroxytetrahydrofuran-3-yl]pyrazolo[1,5-a]pyrimidine-5-carboxamide | LC-MS (Method 8B): Rt 3.88 mins; MS m/z 455.3 = [M + H]+ 1H NMR (500 MHz, DMSO-d6) δ 9.41 (d, J = 7.2 Hz, 1H), 8.59 (d, J = 7.5 Hz, 1H), 8.06 (d, J = 1.9 Hz, 1H), 7.99 (d, J = 7.8 Hz, 1H), 7.90 (d, J = 7.9 Hz, 1H), 7.71 (t, J = 7.8 Hz, 1H), 7.66 (d, J = 7.1 Hz, 1H), 7.25 (s, 2H), 5.41 (d, J = 4.1 Hz, 1H), 4.31 (d, J = 5.1 Hz, 1H), 4.24 (t, J = 5.4 Hz, 1H), 4.02 (dd, J = 9.1, 5.6 Hz, 1H), 3.98 (dd, J = 9.5, 4.8 Hz, 1H), 3.71 (dd, J = 9.1, 3.4 Hz, 1H), 3.58 (dd, J = 9.4, 2.5 Hz, 1H), 2.41 (s, 6H). |
| 92.30 | 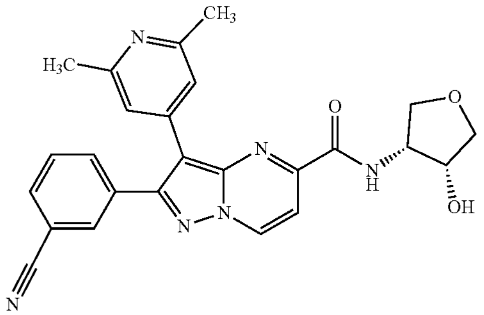 2-(3-Cyanophenyl)-3-(2,6-dimethyl-4-pyridyl)-N-[(3R,4R)-4-hydroxytetrahydrofuran-3-yl]pyrazolo[1,5-a]pyrimidine-5-carboxamide | LC-MS (Method 8B): Rt 3.80 mins; MS m/z 455.3 = [M + H]+ 1H NMR (500 MHz, DMSO-d6) δ 9.43 (d, J = 7.2 Hz, 1H), 8.60 (d, J = 7.0 Hz, 1H), 8.06 (d, J = 1.8 Hz, 1H), 8.01-7.97 (m, 1H), 7.91 (d, J = 7.9 Hz, 1H), 7.71 (t, J = 7.2 Hz, 2H), 7.19 (s, 2H), 5.85 (d, J = 4.2 Hz, 1H), 4.36 (s, 1H), 4.31 (p, J = 7.0 Hz, 1H), 4.00 (dd, J = 8.6, 7.0 Hz, 1H), 3.95 (dd, J = 9.6, 4.8 Hz, 1H), 3.66 (s, 1H), 3.55-3.51 (m, 1H), 2.40 (s, 6H). |

TABLE Ex92-continued

| Ex. | Structure and Name | Retention Time, [M + H]+, 1H NMR |
|---|---|---|
| 92.31 | 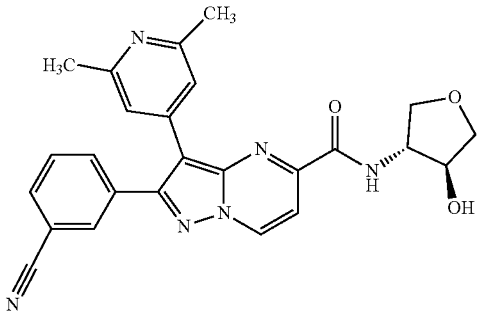 2-(3-Cyanophenyl)-3-(2,6-dimethyl-4-pyridyl)-N-[(3R,4S)-4-hydroxytetrahydrofuran-3-yl]pyrazolo[1,5-a]pyrimidine-5-carboxamide | LC-MS (Method 8B): Rt 3.81 mins; MS m/z 455.3 = [M + H]+ 1H NMR (500 MHz, DMSO-d6) δ 9.40 (d, J = 7.1 Hz, 1H), 8.58 (d, J = 7.5 Hz, 1H), 8.05 (d, J = 1.8 Hz, 1H), 7.98 (dt, J = 7.7, 1.4 Hz, 1H), 7.89 (dt, J = 7.8, 1.5 Hz, 1H), 7.70 (t, J = 7.8 Hz, 1H), 7.65 (d, J = 7.2 Hz, 1H), 7.24 (s, 2H), 5.41 (d, J = 4.1 Hz, 1H), 4.31 (s, 1H), 4.24 (q, J = 5.2 Hz, 1H), 4.02 (dd, J = 9.1, 5.5 Hz, 1H), 3.95 (dd, J = 9.5, 4.8 Hz, 1H), 3.70 (dd, J = 9.1, 3.3 Hz, 1H), 3.57 (dd, J = 9.4, 2.4 Hz, 1H), 2.41 (s, 6H). |
| 92.32 | 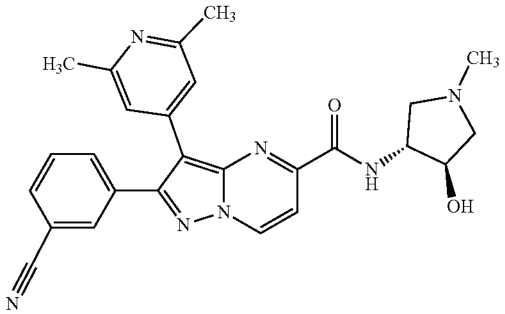 2-(3-Cyanophenyl)-3-(2,6-dimethyl-4-pyridyl)-N-[(3R,4R)-4-hydroxy-1-methyl-pyrrolidin-3-yl]pyrazolo[1,5-a]pyrimidine-5-carboxamide | LC-MS (Method 8B): Rt 3.99 mins; MS m/z 468.3 = [M + H]+ 1H NMR (500 MHz, MeOD-d4) δ 9.19 (dd, J = 7.4, 2.9 Hz, 1H), 8.04 (s, 1H), 7.87 (dd, J = 22.9, 7.9 Hz, 2H), 7.77 (d, J = 7.2 Hz, 1H), 7.63 (t, J = 7.9 Hz, 1H), 7.30 (s, 2H), 4.35-4.25 (m, 2H), 3.14 (dd, J = 10.3, 6.5 Hz, 1H), 2.98 (dd, J = 10.2, 6.8 Hz, 1H), 2.68 (dd, J = 10.2, 4.5 Hz, 1H), 2.51 (s, 6H), 2.43 (dd, J = 10.3, 4.8 Hz, 1H), 2.40 (s, 3H). Exchangeable protons not observed |
| 92.33 | 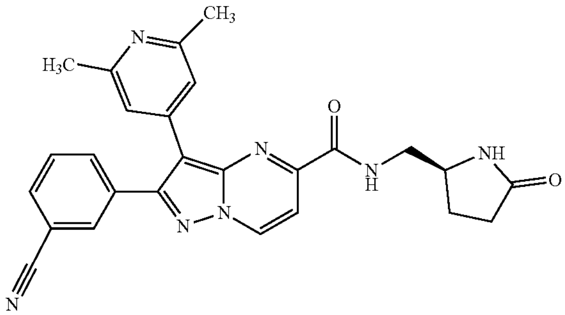 2-(3-Cyanophenyl)-3-(2,6-dimethyl-4-pyridyl)-N-[[(2S)-5-oxopyrrolidin-2-yl]methyl]pyrazolo[1,5-a]pyrimidine-5-carboxamide | LC-MS (Method 8B): Rt 3.89 mins; MS m/z 466.3 = [M + H]+ 1H NMR (500 MHz, DMSO-d6) δ 9.39 (d, J = 7.2 Hz, 1H), 8.74 (t, J = 6.2 Hz, 1H), 8.03 (s, 1H), 7.97 (d, J = 7.8 Hz, 1H), 7.87 (d, J = 7.9 Hz, 1H), 7.73 (d, J = 16.4 Hz, 1H), 7.70-7.65 (m, 1H), 7.20 (s, 2H), 3.76 (s, 1H), 3.45-3.35 (m, 3H), 2.42 (s, 6H), 2.22-2.15 (m, 1H), 2.14-2.05 (m, 2H), 1.84 (s, 1H). |

TABLE Ex92-continued

| Ex. | Structure and Name | Retention Time, [M + H]+, 1H NMR |
| --- | --- | --- |
| 92.34 | 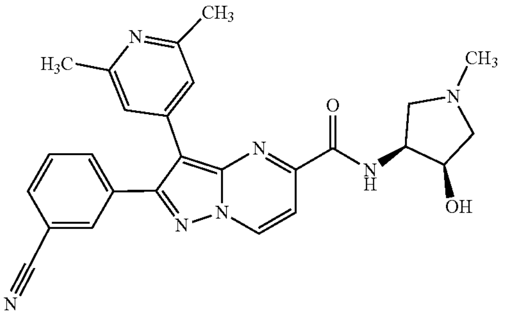 rac-2-(3-Cyanophenyl)-3-(2,6-dimethyl-4-pyridyl)-N-[(3S,4R)-4-hydroxy-1-methyl-pyrrolidin-3-yl]pyrazolo[1,5-a]pyrimidine-5-carboxamide | LC-MS (Method 8B): Rt 3.97 mins; MS m/z 468.3 = [M + H]+ 1H NMR (500 MHz, DMSO-d6) δ 9.42 (d, J = 7.2 Hz, 1H), 8.72 (d, J = 6.8 Hz, 1H), 8.06 (s, 1H), 7.99 (d, J = 7.8 Hz, 1H), 7.91 (d, J = 7.9 Hz, 1H), 7.71 (t, J = 7.3 Hz, 2H), 7.19 (s, 2H), 5.66 (d, J = 5.2 Hz, 1H), 4.32 (q, J = 5.8, 5.3 Hz, 1H), 4.19 (q, J = 6.8 Hz, 1H), 2.92-2.84 (m, 2H), 2.40 (s, 6H), 2.38-2.34 (m, 2H), 2.23 (s, 3H). |

Example 93-3-(2-chloro-6-methyl-4-pyridyl)-2-(3-cyanophenyl)-5-(sulfamoylamino)pyrazolo[1,5-a]pyrimidine

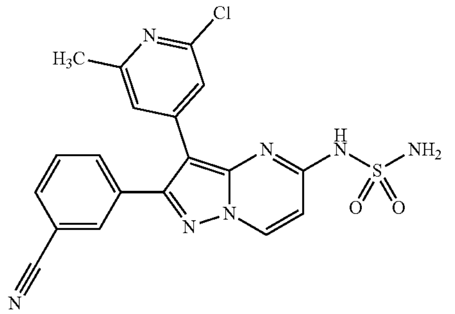 [SMILES: Cc1cc(-c2c(-c3cccc(C#N)c3)nn3ccc(NS(N)(=O)=O)nc23)cc(Cl)n1]

A suspension of NaH (60 wt %, 10 mg, 0.24 mmol) was added to a solution of sulfamide (23 mg, 0.24 mmol) in THF (2 mL). After stirring at room temperature for 30 mins, a solution of 3-[5-chloro-3-(2-chloro-6-methyl-4-pyridyl)pyrazolo[1,5-a]pyrimidin-2-yl]benzonitrile (Intermediate C) (70 mg, 0.18 mmol) in NMP (1 mL) was added and the suspension was heated at 80° C. for 3 days. The resulting mixture was partitioned between a layer of 3:1 mixture of chloroform and MeOH (40 mL) and water (40 mL). The organic layer was separated and the aqueous layer was extracted with a 3:1 mixture of chloroform and MeOH (2×40 mL). The combined organic extracts were concentrated in vacuo and purification by C18 reverse phase chromatography eluting with a gradient of 5 to 20% MeCN in water (+0.1 wt % $NH_4OH$) followed by preparative HPLC eluting with a gradient of 40-45% MeCN in water (+0.1 wt % formic acid) afforded the title compound as a colourless solid.

LC-MS (Method 8A): Rt 4.22 mins; MS m/z 440.1/442.1=[M+H]+

$^1$H NMR (500 MHz, DMSO-$d_6$) b 11.40 (br s, 1H), 9.00 (br s, 1H), 8.02 (s, 1H), 7.99 (d, J=7.8 Hz, 1H), 7.86 (d, J=7.9 Hz, 1H), 7.71 (t, J=7.8 Hz, 1H), 7.49 (s, 1H), 7.27 (s, 1H), 7.20 (br s, 2H), 6.77 (s, 1H), 2.38 (s, 3H).

Example 94—N-[3-(2-Chloro-6-methyl-4-pyridyl)-2-(3-cyanophenyl)pyrazolo[1,5-a]pyrimidin-5-yl]-2-hydroxy-2-methyl-propanamide

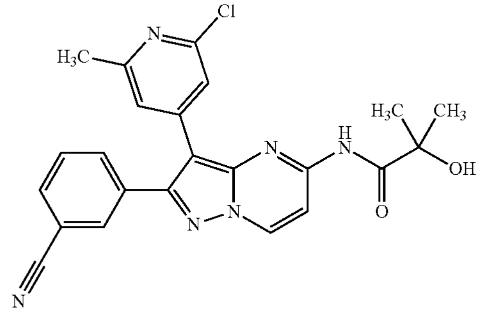 [SMILES: Cc1cc(-c2c(-c3cccc(C#N)c3)nn3ccc(NC(=O)C(C)(C)O)nc23)cc(Cl)n1]

A suspension of 3-[5-chloro-3-(2-chloro-6-methyl-4-pyridyl)pyrazolo[1,5-a]pyrimidin-2-yl]benzonitrile (Intermediate C) (60 mg, 0.16 mmol), 2-hydroxy-2-methyl-propanamide (18 mg, 0.17 mmol), Xantphos (9 mg, 0.02 mmol) and cesium carbonate (57 mg, 0.17 mmol) in 1,4-dioxane (1 mL) was degassed with N2 before palladium acetate (2 mg, 0.01 mmol) was added and the mixture stirred at 110° C. overnight. After cooling to room temperature, the mixture was partitioned between EtOAc (3 mL) and water (3 mL). The organic layer was separated and the aqueous layer was further extracted with EtOAc (2×3 mL). The combined organic extracts were concentrated in vacuo and purification by chromatography on silica eluting with a gradient of 0-3% MeOH in DCM (carried out twice) afforded the title compound as an off-white solid LC-MS (Method 8B): Rt 4.53 mins; MS m/z 447.2/449.2=[M+H]+

1H NMR (500 MHz, DMSO-d6) δ 9.99 (s, 1H), 9.23 (d, J=7.6 Hz, 1H), 8.03 (d, J=1.7 Hz, 1H), 8.00-7.97 (m, 2H), 7.85 (dt, J=7.9, 1.4 Hz, 1H), 7.71 (t, J=7.8 Hz, 1H), 7.34 (s, 1H), 7.32 (s, 1H), 6.16 (s, 1H), 2.41 (s, 3H), 1.42 (s, 6H).

Example 94.1-N-[3-(2-Chloro-6-methyl-4-pyridyl)-2-(3-cyanophenyl)pyrazolo[1,5-a]pyrimidin-5-yl]acetamide

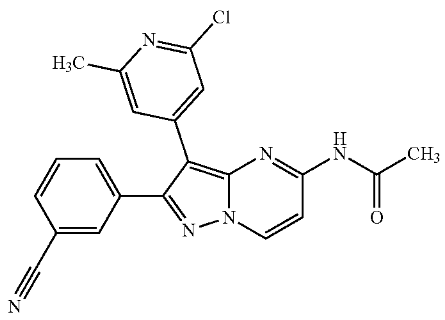 [SMILES: CC(=O)Nc1ccn2nc(-c3cccc(C#N)c3)c(-c3cc(C)nc(Cl)c3)c2n1]

The title compound was prepared from 3-[5-chloro-3-(2-chloro-6-methyl-4-pyridyl)pyrazolo[1,5-a]pyrimidin-2-yl]benzonitrile (Intermediate C) and 3-hydroxy-3-methyl-butanamide analogously to Example 94. (The reaction was carried out at 110° C. overnight.)

LC-MS (Method 8B): Rt 4.36 mins; MS m/z 403.2=[M+H]+

1H NMR (500 MHz, DMSO-d6) δ 11.08 (s, 1H), 9.15 (d, J=7.6 Hz, 1H), 8.01 (t, J=1.6 Hz, 1H), 7.99-7.92 (m, 2H), 7.83 (dt,J=7.9, 1.4 Hz, 11H), 7.70 (t, J=7.8 Hz, 1H), 7.35 (s, 1H), 7.28 (s, 1H), 2.40 (s, 3H), 2.21 (s, 3H).

Example 94.2-N-[3-(2-chloro-6-methyl-4-pyridyl)-2-(3-cyanophenyl)pyrazolo[1,5-a]pyrimidin-5-yl]-3-hydroxy-3-methyl-butanamide

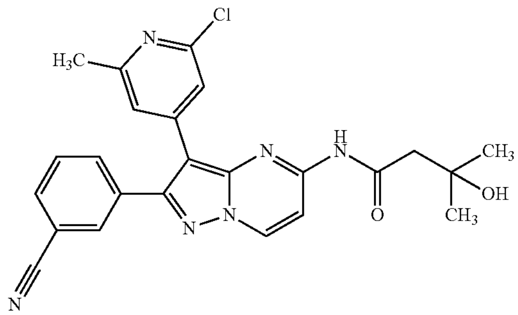 [SMILES: Cc1cc(-c2c(-c3cccc(C#N)c3)nn3ccc(NC(=O)CC(C)(C)O)nc23)cc(Cl)n1]

The title compound was prepared from 3-[5-chloro-3-(2-chloro-6-methyl-4-pyridyl)pyrazolo[1,5-a]pyrimidin-2-yl]benzonitrile (Intermediate C) and 3-hydroxy-3-methyl-butanamide analogously to Example 94. (The reaction was carried out at 80° C. for 1 h.)

LC-MS (Method 8B): Rt 4.45 mins; MS m/z 461.2=[M+H]+

1H NMR (500 MHz, DMSO-d6) δ 10.83 (s, 1H), 9.16 (d, J=7.7 Hz, 1H), 8.03-8.00 (m, 2H), 7.97 (dt,J=7.8, 1.4 Hz, 1H), 7.83 (dt,J=8.0, 1.4 Hz, 1H), 7.70 (t, J=7.8 Hz, 1H), 7.34 (s, 1H), 7.28 (s, 1H), 4.82 (s, 1H), 2.61 (s, 2H), 2.40 (s, 3H), 1.26 (s, 6H).

Example 94.3-(2S)-N-[2-(3-Cyanophenyl)-3-(2,6-dimethyl-4-pyridyl)pyrazolo[1,5-a]pyrimidin-5-yl]-3,3,3-trifluoro-2-hydroxy-2-methyl-propanamide

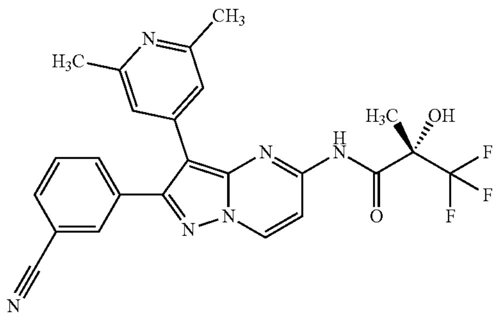 [SMILES: Cc1cc(-c2c(-c3cccc(C#N)c3)nn3ccc(NC(=O)[C@](C)(O)C(F)(F)F)nc23)cc(C)n1]

The title compound was prepared from 3-[5-chloro-3-(2,6-dimethyl-4-pyridyl)pyrazolo[1,5-a]pyrimidin-2-yl]benzonitrile (Intermediate CA) and (2S)-3,3,3-trifluoro-2-hydroxy-2-methyl-propanamide (Intermediate ZF) analogously to Example 94.

LC-MS-2 (Method 8B): Rt 3.59 mins; MS m/z 481.1=[M+H]+

1H NMR (500 MHz, DMSO) b 10.16 (br s, 1H), 9.23 (d, J=7.6 Hz, 1H), 7.98 (br t,J=1.6 Hz, 1H), 7.94 (brdt,J=7.7, 1.6 Hz, 1H), 7.91 (br s, 1H), 7.86-7.81 (m, 2H), 7.67 (apr t,J=7.8 Hz, 1H), 7.12 (s, 2H), 2.39 (s, 6H), 1.64 (s, 3H).

Example 94.4-N-[2-(3-Cyanophenyl)-3-(2,6-dimethyl-4-pyridyl)pyrazolo[1,5-a]pyrimidin-5-yl]-3-hydroxy-3-methyl-butanamide

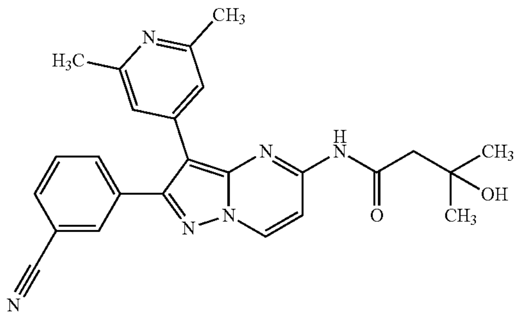 [SMILES: Cc1cc(-c2c(-c3cccc(C#N)c3)nn3ccc(NC(=O)CC(C)(C)O)nc23)cc(C)n1]

The title compound was prepared from 3-[5-chloro-3-(2,6-dimethyl-4-pyridyl)pyrazolo[1,5-a]pyrimidin-2-yl]benzonitrile (Intermediate CA) and 3-hydroxy-3-methyl-butanamide analogously to Example 94.

LC-MS (Method 8B): Rt 4.15 mins; MS m/z 441.3=[M+H]+

1H NMR (500 MHz, DMSO) δ 10.82 (s, 1H), 9.20 (d, J=7.7 Hz, 1H), 8.06-8.01 (m, 2H), 7.99 (d, J=7.7 Hz, 1H), 7.87 (d, J=8.0 Hz, 1H), 7.72 (t, J=7.8 Hz, 1H), 7.15 (s, 2H), 4.86 (s, 1H), 2.65 (s, 2H), 2.45 (s, 6H), 1.31 (s, 6H).

Example 94.5-N-[2-(3-cyanophenyl)-3-(2,6-dimethyl-4-pyridyl)pyrazolo[1,5-a]pyrimidin-5-yl]-2-hydroxy-2-methyl-propanamide

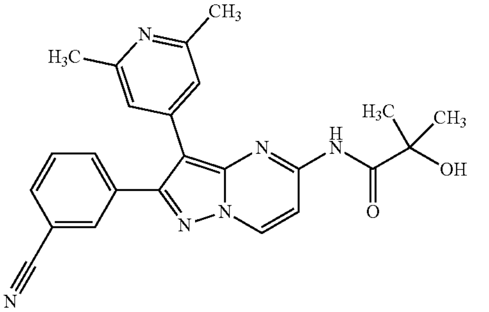 [SMILES: Cc1cc(-c2c(-c3cccc(C#N)c3)nn3ccc(NC(=O)C(C)(C)O)nc23)cc(C)n1]

The title compound was prepared from 3-[5-chloro-3-(2,6-dimethyl-4-pyridyl)pyrazolo[1,5-a]pyrimidin-2-yl]benzonitrile (Intermediate CA) and 2-hydroxy-2-methyl-propanamide analogously to Example 94.

LC-MS (Method 8B): Rt 4.18 mins; MS m/z 427.3=[M+H]+

1H NMR (500 MHz, DMSO) δ 9.87 (s, 1H), 9.21 (d, J=7.6 Hz, 1H), 7.99-7.92 (m, 3H), 7.82 (d, J=7.9 Hz, 1H), 7.67 (t, J=7.8 Hz, 1H), 7.10 (s, 2H), 6.15 (s, 1H), 2.39 (s, 6H), 1.41 (s, 6H).

Example 95—N-[3-(2-Chloro-6-methyl-4-pyridyl)-2-(3-cyanophenyl)pyrazolo[1,5-a]pyrimidin-5-yl]-2,2-dimethyl-propanamide

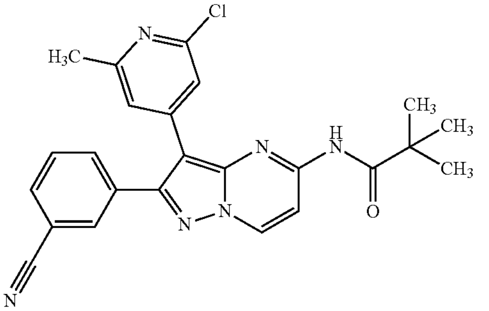 [SMILES: Cc1cc(-c2c(-c3cccc(C#N)c3)nn3ccc(NC(=O)C(C)(C)C)nc23)cc(Cl)n1]

Pivaloyl chloride (0.03 mL, 0.21 mmol) was added to a suspension of triethylamine (0.03 mL, 0.21 mmol) and 3-[5-amino-3-(2-chloro-6-methyl-4-pyridyl)pyrazolo[1,5-a]pyrimidin-2-yl]benzonitrile (Intermediate F) (50 mg, 0.14 mmol) in THF (2 mL) at 0° C. The resulting mixture was heated at 90° C. for 3 days. Additional triethylamine (0.03 mL, 0.21 mmol) and pivaloyl chloride (0.03 mL, 0.21 mmol) were added and the mixture was heated at 110° C. overnight. After cooling to room temperature, the reaction mixture was partitioned between EtOAc (3 mL) and water (3 mL). The organic layer was separated and the aqueous layer was further extracted with EtOAc (2×3 mL). The combined organic extracts were concentrated in vacuo. The resulting mixture was added dropwise to stirring water (20 mL) and the precipitate was collected by filtration, washing with water (2×5 mL). The solid was dissolved in acetone (20 ml) and concentrated in vacuo. Purification by chromatography on silica eluting with a gradient of 0 to 3% MeOH in DCM followed by trituration with MeOH (2 mL) afforded the title compound as a light brown solid.

LC-MS (Method 88): Rt 5.15 mins; MS m/z 445.2/447.2=[M+H]+

$^1$H NMR (500 MHz, DMSO-$d_6$) b 10.39 (s, 1H), 9.15 (d, J=7.7 Hz, 1H), 8.01-7.99 (m, 1H), 7.96 (dt, J=7.7, 1.4 Hz, 1H), 7.91 (d, J=7.7 Hz, 1H), 7.82 (dt, J=8.0, 1.4 Hz, 1H), 7.69 (t, J=7.8 Hz, 1H), 7.36 (s, 1H), 7.32 (s, 1H), 2.41 (s, 3H), 1.29 (s, 9H).

Example 96—N-(3-Amino-3-methyl-butyl)-2-(3-cyanophenyl)-3-(2,6-dimethyl-4-pyridyl)pyrazolo[1,5-a]pyrimidine-5-carboxamide

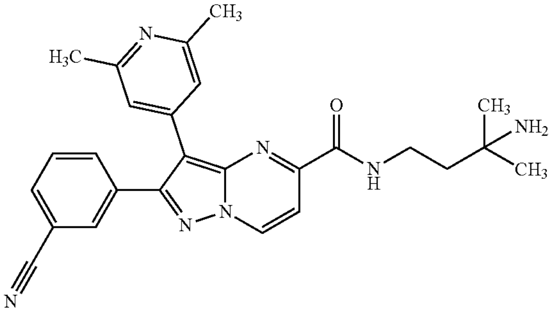 [SMILES: Cc1cc(-c2c(-c3cccc(C#N)c3)nn3ccc(C(=O)NCCC(C)(C)N)nc23)cc(C)n1]

Step 1: tert-Butyl N-[3-[[2-(3-cyanophenyl)-3-(2,6-dimethyl-4-pyridyl)pyrazolo[1,5-a]pyrimidine-5-carbonyl]amino]-1,1-dimethyl-propyl]carbamate

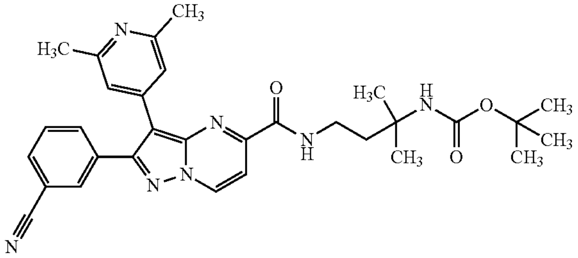 [SMILES: Cc1cc(-c2c(-c3cccc(C#N)c3)nn3ccc(C(=O)NCCC(C)(C)NC(=O)OC(C)(C)C)nc23)cc(C)n1]

The title compound was prepared from 2-(3-cyanophenyl)-3-(2,6-dimethyl-4-pyridyl)pyrazolo[1,5-a]pyrimidine-5-carboxylic acid (Example 92 step 2b) and tert-butyl N-(3-amino-1,1-dimethyl-propyl)carbamate analogously to Example 6.

LC-MS (Method 2A): Rt 1.06 mins: MS m/z 554.3=[M+H]+

$^1$H NMR (500 MHz, DMSO-$d_8$) δ 9.38 (d, J=7.2 Hz, 1H), 8.60 (t, J=5.7 Hz, 1H), 8.02 (t, J=1.5 Hz, 1H), 7.97 (dt, J=7.7, 1.4 Hz, 1H), 7.86 (dt, J=7.9, 1.3 Hz, 1H), 7.69 (t, J=7.8 Hz, 1H), 7.66 (d, J=7.2 Hz, 1H), 7.19 (s, 2H), 6.45 (s, 1H), 3.38-3.32 (m, 2H), 2.42 (s, 6H), 1.89 (t, J=7.4 Hz, 2H), 1.35 (s, 9H), 1.23 (s, 6H).

Step 2: N-(3-Amino-3-methyl-butyl)-2-(3-cyanophenyl)-3-(2,6-dimethyl-4-pyridyl)pyrazolo[1,5-a]pyrimidine-5-carboxamide The title compound was prepared from tert-butyl N-[3-[[2-(3-cyanophenyl)-3-(2,6-dimethyl-4-pyridyl)pyrazolo[1, 5-a]pyrimidine-5-carbonyl]amino]-1,1-dimethyl-propyl] carbamate (step 1) and 4M HCl in 1,4-dioxane analogously to Example 4 step 2.

LC-MS (Method 7B): Rt 2.90 mins; MS m/z 454.4=[M+H]+

1H NMR (500 MHz, DMSO-d6) δ 9.37 (d, J=7.2 Hz, 1H), 9.28 (t, J=5.0 Hz, 1H), 8.01 (t, J=1.5 Hz, 1H), 7.97 (dt, J=7.7, 1.3 Hz, 1H), 7.85 (dt, J=7.9, 1.3 Hz, 1H), 7.69 (t, J=7.8 Hz, 1H), 7.67 (d, J=7.2 Hz, 1H), 7.16 (s, 2H), 3.44 (q, J=6.7 Hz, 2H), 2.41 (s, 6H), 1.61 (t, J=7.0 Hz, 2H), 1.12 (s, 6H). NH2 protons not observed Example 97-2-(3-Cyanophenyl)-3-(2,6-dimethyl-4-pyridyl)pyrazolo[1,5-a]pyrimidine-5-carboxamidine

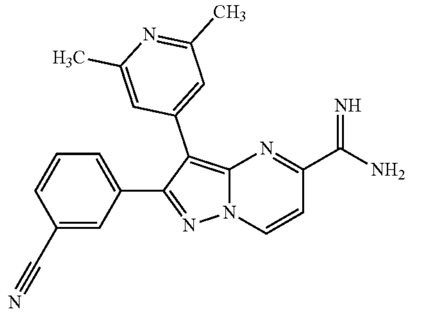 [SMILES: Cc1cc(-c2c(-c3cccc(C#N)c3)nn3ccc(C(=N)N)nc23)cc(C)n1]

Step 1: Ethyl 2-(3-cyanophenyl)-3-(2,6-dimethyl-4-pyridyl)pyrazolo[1,5-a]pyrimidine-5-carboximidate

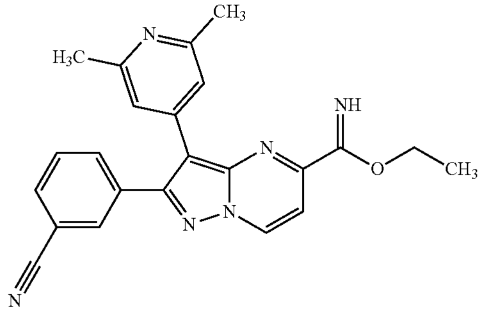 [SMILES: CCOC(=N)c1ccn2nc(-c3cccc(C#N)c3)c(-c3cc(C)nc(C)c3)c2n1]

Triethyloxonium tetrafluoroborate (1031.46 mg, 5.43 mmol) was added to a mixture of 2-(3-cyanophenyl)-3-(2,6-dimethyl-4-pyridyl)pyrazolo[1,5-a]pyrimidine-5-carboxamide (Example 5.8) (100 mg, 0.27 mmol) in DCM (10 mL) and stirred at room temperature for 96 h. Additional triethyloxonium tetrafluoroborate (256 mg, 1.36 mmol) was added and stirring continued for 24 h. The resulting mixture was diluted with DCM (20 mL) and washed with sat, aq. $NaHCO_3$ (50 mL). The layers were separated and the aqueous further extracted with DCM (2×20 mL). The combined organic extracts were dried over $Na_2SO_4$, filtered and concentrated in vacuo to afford the title compound as a yellow solid.

LC-MS (Method 3.5 B): Rt 2.02 mins; MS m/z 397.5=[M+H]+

Step 2: 2-(3-Cyanophenyl)-3-(2,6-dimethyl-4-pyridyl)pyrazolo[1,5-a]pyrimidine-5-carboxamidine A mixture of ethyl 2-(3-cyanophenyl)-3-(2,6-dimethyl-4-pyridyl)pyrazolo[1,5-a]pyrimidine-5-carboximidate (step 1)(85 mg, 0.21 mmol) and 7M NH3 in MeOH (0.61 mL, 4.29 mmol) in MeOH (0.5 mL) was heated in a sealed vessel to 45° C. overnight. The resulting mixture was purified by C18 reverse phase chromatography eluting with a gradient of 20 to 40% MeCN in water with 0.1% ammonium hydroxide modifier to afford the title compound as a yellow solid.

LC-MS (Method 8B): Rt 3.77/3.85 mins; MS m/z 368.2/369.2=[M+H]+

1H NMR (500 MHz, Methanol-d4) δ 9.17 (d,J=7.2 Hz, 0.3H), 9.13 (d,J=7.3 Hz, 0.7H), 8.02 (s, 1H), 7.88 (d, J=7.9 Hz, 1H), 7.85-7.76 (m, 2H), 7.63 (t, J=7.9 Hz, 1H), 7.26 (s, 2H), 2.50 (s, 1.8 H), 2.49 (s, 4.2 H). NH and NH2 protons not observed Example 98—N-(2-Acetamido-2-methyl-propyl)-3-(2-chloro-6-methyl-4-pyridyl)-2-(3-cyanophenyl)pyrazolo[1,5-a]pyrimidine-5-carboxamide

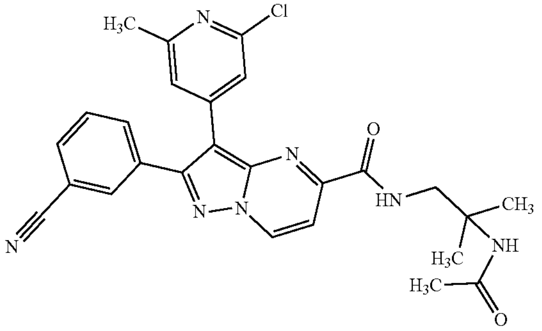 [SMILES: CC(=O)NC(C)(C)CNC(=O)c1ccn2nc(-c3cccc(C#N)c3)c(-c3cc(C)nc(Cl)c3)c2n1]

A mixture of N-(2-amino-2-methyl-propyl)-3-(2-chloro-6-methyl-4-pyridyl)-2-(3-cyanophenyl)pyrazolo[1,5-a]pyrimidine-5-carboxamide (Example 6.1)(25 mg, 0.05 mmol), acetic anhydride (26 μL, 0.27 mmol) and pyridine (1.5 mL) was stirred at room temperature overnight. The resulting mixture was diluted with ethyl acetate (30 mL) and washed with 10% copper sulfate aqueous solution (3×15 mL). The organic phase was dried over $MgSO_4$, filtered and concentrated in vacuo. Purification by chromatography on silica eluting with a gradient of 0 to 2.5% MeOH in DCM afforded the title compound as a yellow solid.

LC-MS (Method 8B): Rt 4.40 mins; MS m/z 502.2/504.2=[M+H]+

1H NMR (500 MHz, DMSO-d6) δ 9.43 (d, J=7.2 Hz, 1H), 9.17 (t, J=6.1 Hz, 1H), 8.08 (s, 1H), 8.01 (dt,J=7.8, 1.5 Hz, 1H), 7.90 (dt,J=8.0, 1.5 Hz, 1H), 7.76-7.70 (m, 2H), 7.69 (s, 1H), 7.60 (s, 1H), 7.29 (s, 1H), 3.57 (d, J=6.1 Hz, 2H), 2.47 (s, 3H), 1.80 (s, 3H), 1.27.(s, 6H).

Example 99-2-(3-Cyanophenyl)-N-[(1S)-1,2-dimethylallyl]-3-(2,6-dimethyl-4-pyridyl)pyrazolo[1,5-a]pyrimidine-5-carboxamide

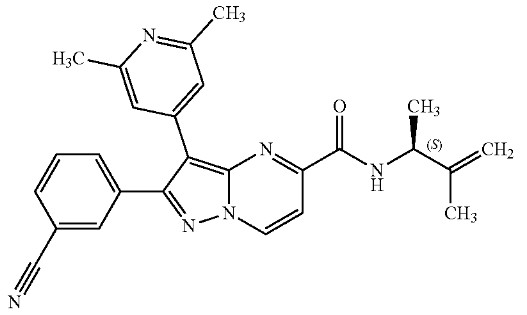

To a cooled (−10° C.) solution of 2-(3-cyanophenyl)-3-(2,6-dimethyl-4-pyridyl)-N-[(1S)-2-hydroxy-1,2-dimethyl-propyl]pyrazolo[1,5-a]pyrimidine-5-carboxamide (Example 92) (50 mg, 0.11 mmol) in DCM (0.5 mL) was added methanesulfonyl chloride (0.09 mL, 1.1 mmol) and triethylamine (0.23 mL, 1.65 mmol)and the mixture was allowed to warm to room temperature, stirring for 2 h. The resulting mixture was concentrated in vacuo and the crude material was purified by chromatography on silica eluting with a gradient of 0 to 10% MeOH in DCM. Further purification by C18 reverse phase chromatography eluting with a gradient of 10 to 60% MeCN in water, 0.1% $NH_4OH$ afforded the title compound as a yellow solid.

LC-MS (Method 8B): Rt 4.78 mins; MS m/z 437.3=[M+H]+

1H NMR (500 MHz, DMSO-d6) δ 9.40 (d, J=7.2 Hz, 1H), 8.56 (d, J=8.7 Hz, 1H), 8.06 (s, 1H), 7.99 (d, J=7.8 Hz, 1H), 7.90 (d, J=7.9 Hz, 1H), 7.71 (t, J=7.9 Hz, 1H), 7.63 (d, J=7.2 Hz, 1H), 7.26 (s, 2H), 4.98 (s, 1H), 4.85 (s, 1H), 4.53 (t, J=7.7 Hz, 1H), 2.39 (s, 6H), 1.80 (s, 3H), 1.32 (d, J=6.9 Hz, 3H).

Example 100-2-(3-Cyanophenyl)-N-[(1S)-2-hydroxy-1,2-dimethyl-propyl]-3-[2-(hydroxymethyl)-6-methyl-4-pyridyl]pyrazolo[1,5-a]pyrimidine-5-carboxamide

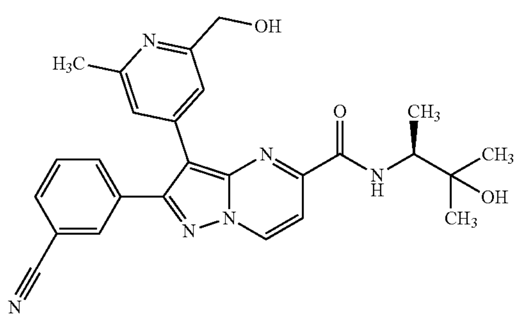 [SMILES: Cc1cc(-c2c(-c3cccc(C#N)c3)nn3ccc(C(=O)N[C@@H](C)C(C)(C)O)nc23)cc(CO)n1]

Step 1: Ethyl 3-[2-[[tert-butyl(dimethyl)silyl]oxymethyl]-6-methyl-4-pyridyl]-2-(3-cyanophenyl)pyrazolo[1,5-a]pyrimidine-5-carboxylate

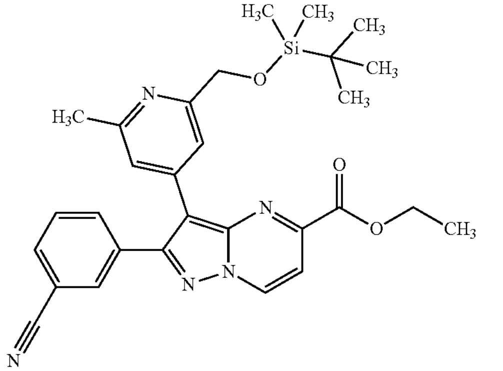 [SMILES: CCOC(=O)c1ccn2nc(-c3cccc(C#N)c3)c(-c3cc(C)nc(CO[Si](C)(C)C(C)(C)C)c3)c2n1]

Bis(tri-tert-butylphosphine)palladium(0) (25 mg, 0.05 mmol) was added to a degassed mixture of ethyl 3-bromo-2-(3-cyanophenyl)pyrazolo[1,5-a]pyrimidine-5-carboxylate (Intermediate A5)(180 mg, 0.48 mmol), 2-([[(1,1-Dimethylethyl)dimethylsilyl]oxy]methyl]-6-methyl-4-(4,4,5,5-tetramethyl-1,3,2-dioxaborolan-2-yl)pyridine (Intermediate ZD) (407 mg, 0.73 mmol) and $NaHCO_3$ (122 mg, 1.45 mmol) in water (0.8 mL) and 1,4-dioxane (4 mL). The flask was evacuated and filled with $N_2$ (three cycles) and then stirred at 50 0C for 1 h. The resulting mixture was allowed to cool to room temperature and diluted with EtOAc (10 mL) and water (10 mL). The layers were separated and the aqueous layer was further extracted with EtOAc (2×10 mL). The combined organic layers were dried over $Na_2SO_4$ and concentrated in vacuo to give a brown oil. Purification by chromatography on silica eluting with a gradient of 0 to 3% MeOH in DCM afforded the title compound as a yellow solid.

LC-MS (Method 3B): Rt 2.39 mins; MS m/z 528.3=[M+H]+(92% @254 nm)

1H NMR (500 MHz, DMSO) b 9.43 (d, J=7.2 Hz, 1H), 8.01 (t, J=1.7 Hz, 1H), 7.97 (dt,J=7.7, 1.4 Hz, 1H), 7.87 (dt,J=7.9, 1.4 Hz, 1H), 7.69 (dd, J=7.5, 5.2 Hz, 2H), 7.47 (d, J=1.6 Hz, 1H), 7.21 (d, J=1.4 Hz, 1H), 4.69 (s, 2H), 4.42 (q,J=7.1 Hz, 2H), 2.48 (s, 3H), 1.38 (t, J=7.1 Hz, 3H), 0.77 (s, 9H), 0.00 (s, 6H1).

Step 2: 3-[2-[[tert-Butyl(dimethyl)silyl]oxymethyl]-6-methyl-4-pyridyl]-2-(3-cyanophenyl)pyrazolo[1,5-a]pyrimidine-5-carboxylic acid

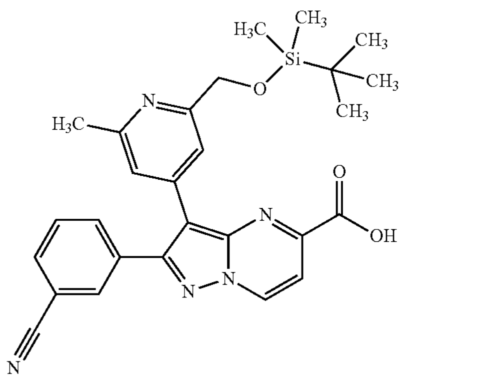 [SMILES: Cc1cc(-c2c(-c3cccc(C#N)c3)nn3ccc(C(=O)O)nc23)cc(CO[Si](C)(C)C(C)(C)C)n1]

The title compound was prepared from ethyl 3-[2-[[tert-butyl(dimethyl)silyl]oxymethyl)-6-methyl-4-pyridyl]-2-(3-cyanophenyl)pyrazolo[1,5-a]pyrimidine-5-carboxylate (step 1) and an aqueous solution of LiOH analogously to Example 17 step 2.

LC-MS (Method 3A): Rt 1.89 mins; MS m/z 500.3=[M+H]+

1H NMR (500 MHz, DMSO) δ 9.37 (d, J=7.2 Hz, 1H), 7.99 (d, J=1.8 Hz, 1H), 7.95 (dt,J=7.7, 1.5 Hz, 1H), 7.85 (dt,J=7.9, 1.5 Hz, 1H), 7.73-7.61 (m, 2H), 7.44 (d, J=1.5 Hz, 1H), 7.20 (s, 1H), 4.67 (s, 2H), 2.47 (s, 3H), 0.76 (s, 9H), −0.01 (s, 6H). Carboxylic acid proton not observed.

Step 3: 3-[2-[[tert-Butyl(dimethyl)silyl]oxymethyl]-6-methyl-4-pyridyl]-2-(3-cyanophenyl)-N-[(1S)-2-hydroxy-1,2-dimethyl-propyl]pyrazolo[1,5-a]pyrimidine-5-carboxamide

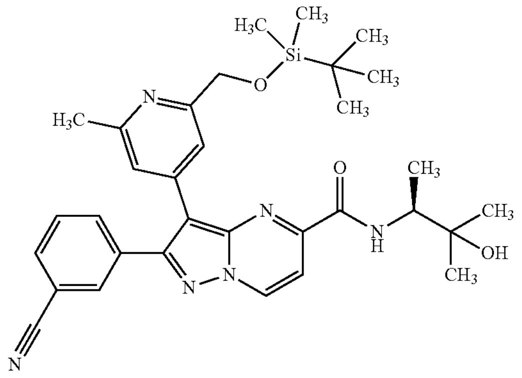 [SMILES: Cc1cc(-c2c(-c3cccc(C#N)c3)nn3ccc(C(=O)N[C@@H](C)C(C)(C)O)nc23)cc(CO[Si](C)(C)C(C)(C)C)n1]

The title compound was prepared from 3-[2-[[tert-butyl(dimethyl)silyl]oxymethyl]-6-methyl-4-pyridyl]-2-(3-cyanophenyl)pyrazolo[1,5-a]pyrimidine-5-carboxylic acid (step 2) and (3S)-3-amino-2-methyl-butan-2-ol hydrochloride analogously to Example 6.

LC-MS (Method 3B): Rt 2.26 mins; MS m/z 585.3=[M+H]+

1H NMR (500 MHz, DMSO) δ 9.47 (d, J=7.2 Hz, 1H), 8.32 (d, J=9.0 Hz, 1H), 8.08 (t, J=1.8 Hz, 1H), 8.03 (dt,J=7.8, 1.4 Hz, 1H), 7.96 (dt,J=7.9, 1.5 Hz, 1H), 7.82 (d, J=1.5 Hz, 1H), 7.78-7.72 (m, 2H), 7.07 (s, 1H), 4.81 (s, 1H), 4.68 (s, 2H), 3.92 (dq,J=8.9, 6.6 Hz, 1H), 2.59 (s, 3H), 1.26-1.19 (m, 9H), 0.77 (s, 9H), 0.00 (s, 6H).

Step 4: 2-(3-Cyanophenyl)-N-[(1S)-2-hydroxy-1,2-dimethyl-propyl]-3-[2-(hydroxymethyl)-6-methyl-4-pyridyl]pyrazolo[1,5-a]pyrimidine-5-carboxamide 1M TBAF in THF (0.34 mL, 0.34 mmol) was added to a stirred solution of 3-[2-[[tert-butyl(dimethyl)silyl]oxymethyl]-6-methyl-4-pyridyl]-2-(3-cyanophenyl)-N-[(1S)-2-hydroxy-1,2-dimethyl-propyl]pyrazolo[1,5-a]pyrimidine-5-carboxamide (step 3) (105 mg, 0.17 mmol) in THF (2 mL) and stirred at room temperature for 20 mins. The resulting mixture was diluted with EtOAc (10 mL) and water (10 mL). The layers were separated and the aqueous layer was extracted with EtOAc (2×10 mL). The combined organic layers were dried over $Na_2SO_4$ and concentrated in vacuo to give a yellow oil. Purification by chromatography on silica eluting with a gradient of 0 to 4% MeOH in DCM afforded the title compound as a yellow solid.

LC-MS (Method 8B): Rt 3.87 mins; MS m/z 471.3=[M+H]+

1H NMR (500 MHz, DMSO) δ 9.43 (d, J=7.1 Hz, 1H), 8.25 (d, J=9.1 Hz, 1H), 8.07 (t, J=1.7 Hz, 1H), 7.99 (dt,J=7.7, 1.4 Hz, 1H), 7.93 (dt,J=8.0, 1.4 Hz, 1H), 7.72 (t, J=7.2 Hz, 2H), 7.45 (d, J=1.6 Hz, 1H), 7.35 (d, J=1.5 Hz, 1H), 5.20 (t, J=5.7 Hz, 1H), 4.78 (s, 1H), 4.49 (d, J=5.7 Hz, 2H), 3.88 (dq,J=9.1, 6.7 Hz, 1H), 2.47 (s, 3H), 1.21-1.14 (m, 9H).

Example 101-2-(3-Cyanophenyl)-3-(3-fluoro-2,6-dimethyl-4-pyridyl)-N-[(4-methyl-2,5-dioxo-imidazolidin-4-yl)methyl]pyrazolo[1,5-a]pyrimidine-5-carboxamide

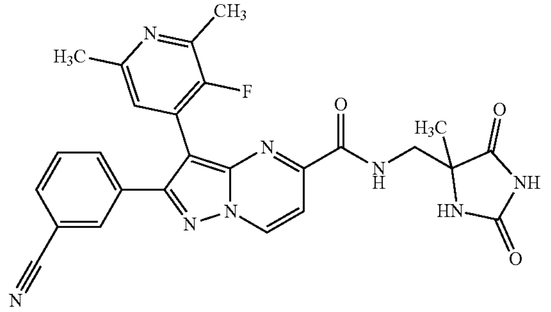 [SMILES: Cc1cc(-c2c(-c3cccc(C#N)c3)nn3ccc(C(=O)NCC4(C)NC(=O)NC4=O)nc23)c(F)c(C)n1]

Step 1: Ethyl 2-(3-cyanophenyl)-3-(3-fluoro-2,6-dimethyl-4-pyridyl)pyrazolo[1,5-a]pyrimidine-5-carboxylate

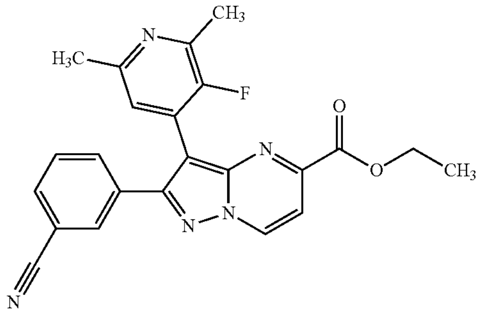 [SMILES: CCOC(=O)c1ccn2nc(-c3cccc(C#N)c3)c(-c3cc(C)nc(C)c3F)c2n1]

The title compound was prepared from ethyl 3-bromo-2-(3-cyanophenyl)pyrazolo[1,5-a]pyrimidine-5-carboxylate (Intermediate A5) and 3-fluoro-2,6-dimethyl-4-(4,4,5,5-tetramethyl-1,3,2-dioxaborolan-2-yl)pyridine (Intermediate ZE) analogously to Example 100 step 1.

LC-MS (Method 5B): Rt 3.24 mins; MS m/z 416.3=[M+H]+

1H NMR (500 MHz, DMSO-d6) δ 9.46 (d, J=7.2 Hz, 1H), 8.03 (s, 1H), 7.94 (d, J=7.8 Hz, 1H), 7.83 (d, J=7.8 Hz, 1H), 7.70 (d, J=7.2 Hz, 1H), 7.67 (t, J=7.8 Hz, 1H), 7.33 (d, J=4.8 Hz, 1H), 4.40 (q,J=7.1 Hz, 2H), 2.45-2.32 (m, 6H), 1.35 (t, J=7.1 Hz, 3H).

Step 2: 2-(3-Cyanophenyl)-3-(3-fluoro-2,6-dimethyl-4-pyridyl)pyrazolo[1,5-a]pyrimidine-5-carboxylic acid

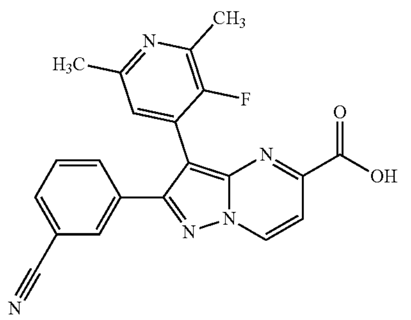 [SMILES: Cc1cc(-c2c(-c3cccc(C#N)c3)nn3ccc(C(=O)O)nc23)c(F)c(C)n1]

The title compound was prepared from ethyl 2-(3-cyanophenyl)-3-(3-fluoro-2,6-dimethyl-4-pyridyl)pyrazolo[1,5-a]pyrimidine-5-carboxylate (step 1) and an aqueous solution of LiOH analogously to Example 17 step 2.

LC-MS (Method 5B): Rt 1.60 mins; MS m/z 388.3=[M+H]+

1H NMR (500 MHz, DMSO-d6) δ 9.42 (d, J=7.2 Hz, 1H), 8.03 (s, 1H), 7.94 (d, J=7.7 Hz, 1H), 7.82 (d, J=8.0 Hz, 1H), 7.67 (t, J=8.1 Hz, 2H), 7.32 (d, J=4.8 Hz, 1H), 2.44-2.31 (m, 6H). Carboxylic acid proton not observed.

Step 3: 2-(3-Cyanophenyl)-3-(3-fluoro-2,6-dimethyl-4-pyridyl)-N-[(4-methyl-2,5-dioxo-imidazolidin-4-yl)methyl]pyrazolo[1,5-a]pyrimidine-5-carboxamide The title compound was prepared from 2-(3-cyanophenyl)-3-(3-fluoro-2,6-dimethyl-4-pyridyl)pyrazolo[1,5-a]pyrimidine-5-carboxylic acid (step 2) and 5-(aminomethyl)-5-methyl-imidazolidine-2,4-dione hydrochloride analogously to Example 6.

LC-MS (Method 8B): Rt 2.64 mins; MS m/z 513.3=[M+H]+

1H NMR (500 MHz, DMSO-d6) δ 10.71 (s, 1H), 9.45 (d, J=7.1 Hz, 1H), 8.45 (dd, J=7.7, 5.2 Hz, 1H), 8.02 (d, J=1.8 Hz, 1H), 7.98-7.90 (m, 2H), 7.85 (dt, J=8.0, 1.5 Hz, 1H), 7.71 (d, J=7.1 Hz, 1H), 7.67 (t, J=7.8 Hz, 1H), 7.38 (d, J=4.9 Hz, 1H), 3.75 (dd, J=13.5, 7.7 Hz, 1H), 3.41 (dd, J=13.5, 5.2 Hz, 1H), 2.42-2.33 (m, 3H), 1.30 (s, 3H). 1× CH3 under solvent peak Example 101.1-2-(3-Cyanophenyl)-3-(3-fluoro-2,6-dimethyl-4-pyridyl)-N-(2-hydroxy-2-methyl-propyl)pyrazolo[1,5-a]pyrimidine-5-carboxamide

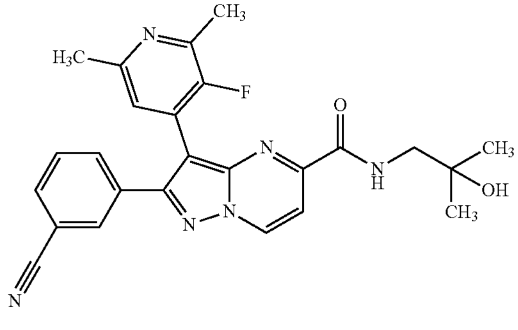 [SMILES: Cc1cc(-c2c(-c3cccc(C#N)c3)nn3ccc(C(=O)NCC(C)(C)O)nc23)c(F)c(C)n1]

The title compound was prepared from 2-(3-cyanophenyl)-3-(3-fluoro-2,6-dimethyl-4-pyridyl)pyrazolo[1,5-a]pyrimidine-5-carboxylic acid (Example 101 step 2) and 1-amino-2-methyl-propan-2-ol analogously to Example 6.

LC-MS (Method 88): Rt 3.54 mins; MS m/z 457.4=[M−H]−

1H NMR (500 MHz, DMSO-d6) δ9.46 (d, J=7.2 Hz, 1H), 8.31 (t, J=6.0 Hz, 1H), 8.05 (s, 1H), 7.96 (d, J=7.8 Hz, 1H), 7.88 (d, J=7.8 Hz, 1H), 7.73 (d, J=7.2 Hz, 1H), 7.69 (t, J=7.8 Hz, 1H), 7.43 (d, J=4.8 Hz, 1H), 4.72 (s, 1H), 3.29 (d, J=6.0 Hz, 2H), 2.47 (s, 3H), 2.40-2.35 (m, 3H), 1.14 (s, 6H).

Example 102-3-(2-Chloro-6-methyl-4-pyridyl)-2-(3-cyano-2-methyl-phenyl)-N-(2-hydroxy-2-methyl-propyl)pyrazolo[1,5-a]pyrimidine-5-carboxamide

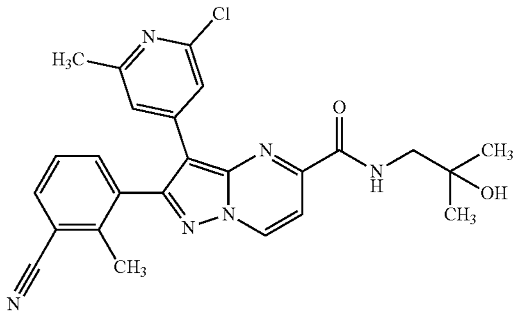 [SMILES: Cc1cc(-c2c(-c3cccc(C#N)c3C)nn3ccc(C(=O)NCC(C)(C)O)nc23)cc(Cl)n1]

Step 1: 3-Bromo-2-(3-cyano-2-methyl-phenyl)pyrazolo[1,5-a]pyrimidine-5-carboxylic acid

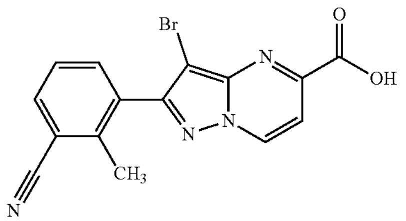 [SMILES: Cc1c(C#N)cccc1-c1nn2ccc(C(=O)O)nc2c1Br]

The title compound was prepared from ethyl 3-bromo-2-(3-cyano-2-methyl-phenyl)pyrazolo[1,5-a]pyrimidine-5-carboxylate (Intermediate AB) and lithium hydroxide analogously to Intermediate B1.

LC-MS (Method 58): Rt 1.46 mins; MS m/z 357.1/359.1=[M+H]+(100% @254 nm)

1H NMR (500 MHz, DMSO-d6) δ 14.02 (s, 1H), 9.36 (d, J=7.2 Hz, 1H), 7.99 (d, J=7.7 Hz, 1H), 7.77 (d, J=7.7 Hz, 1H), 7.64 (d, J=7.2 Hz, 1H), 7.58 (t, J=7.7 Hz, 1H), 2.45 (s, 3H).

Step 2: 3-Bromo-2-(3-cyano-2-methyl-phenyl)-N-(2-hydroxy-2-methyl-propyl)pyrazolo[1,5-a]pyrimidine-5-carboxamide

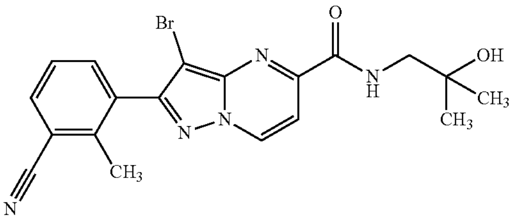 [SMILES: Cc1c(C#N)cccc1-c1nn2ccc(C(=O)NCC(C)(C)O)nc2c1Br]

To a mixture of 3-bromo-2-(3-cyano-2-methyl-phenyl)pyrazolo[1,5-a]pyrimidine-5-carboxylic acid (step 1) (335 mg, 0.94 mmol) and 1-amino-2-methyl-propan-2-ol (125 mg, 1.41 mmol) in DMF (12 mL) was added DIPEA (1.14 mL, 6.57 mmol) followed by dropwise addition of T3P® (50% in DMF) (1.32 mL, 1.88 mmol) and the reaction mixture was stirred at room temperature for 1 h. The resulting mixture was diluted in ethyl acetate (60 mL) and water (60 mL). The layers were separated and the aqueous layer was extracted with ethyl acetate (2×60 mL). The combined organic layers were washed with 50% brine (3×60 mL), dried over $MgSO_4$, filtered and concentrated in vacuo. Purification by chromatography on silica eluting with a gradient of 0.0 to 2% MeOH in DCM afforded a sticky oil. The oil was dissolved in ethyl acetate (60 mL) and washed with 50% brine (3×60 mL), dried over $MgSO_4$, filtered and concentrated in vacuo to afford the title compound as a yellow foam.

LC-MS (Method 5B): Rt 2.42 mins; MS m/z 428.0/430.0=[M+H]+(99% @254 nm)

1H NMR (500 MHz, DMSO-d6) δ 9.38 (d, J=7.2 Hz, 1H), 8.43 (t, J=6.2 Hz, 1H), 7.99 (d, J=7.7 Hz, 1H), 7.76 (d, J=7.7 Hz, 1H), 7.70 (d, J=7.2 Hz, 1H), 7.59 (t, J=7.7 Hz, 1H), 4.78 (s, 1H), 3.35 (d, J=6.2 Hz, 2H), 2.45 (s, 3H), 1.15 (s, 6H).

Step 3: 3-(2-Chloro-6-methyl-4-pyridyl)-2-(3-cyano-2-methyl-phenyl)-N-(2-hydroxy-2-methyl-propyl)pyrazolo[1,5-a]pyrimidine-5-carboxamide The title compound was prepared from 3-bromo-2-(3-cyano-2-methyl-phenyl)-N-(2-hydroxy-2-methyl-propyl)pyrazolo[1,5-a]pyrimidine-5-carboxamide (step 2) and 2-chloro-6-methyl-4-(4,4,5,5-tetramethyl-1,3,2-dioxaborolan-2-yl)pyridine analogously to Example 12.

LC-MS (Method 8B): Rt 4.37 mins; MS m/z 475.2=[M+H]+

1H NMR (500 MHz, DMSO-d6) δ 9,46 (d, J=7.1 Hz, 1H), 8.50 (t, J=6.0 Hz, 1H), 8.03 (d, J=7.8 Hz, 1H), 7.75 (d, J=7.2 Hz, 1H), 7.72 (d, J=7.8 Hz, 1H), 7.62-7.54 (m, 2H), 7.10 (s, 1H), 4.76 (s, 1H), 3.34 (d, J=6.0 Hz, 2H), 2.40 (s, 3H), 2.29 (s, 3H), 1.19 (s, 6H).

Example 103-2-(3-Cyano-2-methyl-phenyl)-3-(2,6-dimethyl-4-pyridyl)-N-(2-hydroxy-2-methyl-propyl)pyrazolo[1,5-a]pyrimidine-5-carboxamide

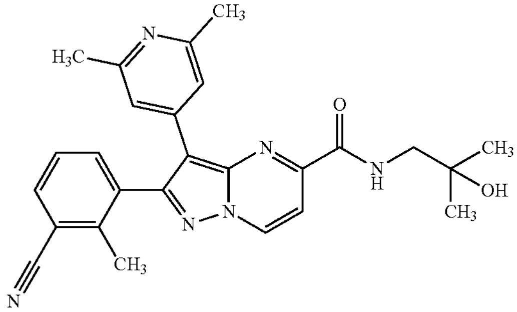 [SMILES: Cc1cc(-c2c(-c3cccc(C#N)c3C)nn3ccc(C(=O)NCC(C)(C)O)nc23)cc(C)n1]

The title compound was prepared from 3-bromo-2-(3-cyano-2-methyl-phenyl)-N-(2-hydroxy-2-methyl-propyl)pyrazolo[1,5-a]pyrimidine-5-carboxamide (Example 102 step 2) and 2,6-dimethyl-4-(4,4,5,5-tetramethyl-1,3,2-dioxaborolan-2-yl)pyridine analogously to Example 102 step 3.

LC-MS (Method 8B): Rt 4.06 mins; MS m/z 455.3=[M+H]+

1H NMR (500 MHz, DMSO-d6) δ 9.42 (d, J=7.1 Hz, 1H), 8.46 (t, J=6.0 Hz, 1H), 8,00 (d, J=7.7 Hz, 1H), 7.74-7.67 (m, 2H), 7.56 (t, J=7.7 Hz, 1H), 7.13 (s, 2H), 4.78 (s, 1H), 3.34 (d, J=6.0 Hz, 2H), 2.32 (s, 6H), 2.26 (s, 3H), 1.18 (s, 6H).

Example 104-2-(3-Cyano-2-methyl-phenyl)-3-(2,6-dimethyl-4-pyridyl)-N-[(1R)-2-hydroxy-1,2-dimethyl-propyl]pyrazolo[1,5-a]pyrimidine-5-carboxamide

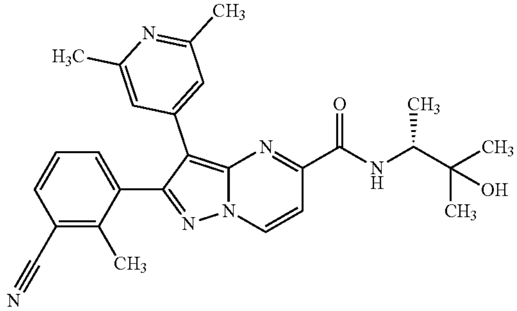 [SMILES: Cc1cc(-c2c(-c3cccc(C#N)c3C)nn3ccc(C(=O)N[C@H](C)C(C)(C)O)nc23)cc(C)n1]

Step 1: Ethyl 2-(3-cyano-2-methyl-phenyl)-3-(2,6-dimethyl-4-pyridyl)pyrazolo[1,5-a]pyrimidine-5-carboxylate

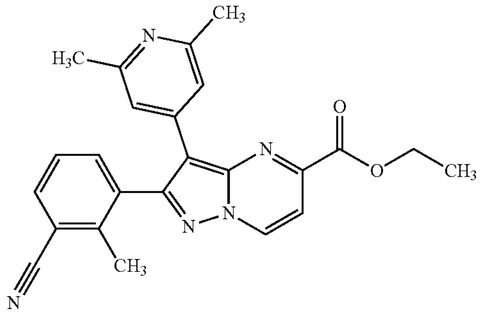 [SMILES: CCOC(=O)c1ccn2nc(-c3cccc(C#N)c3C)c(-c3cc(C)nc(C)c3)c2n1]

The title compound was prepared from ethyl 3-bromo-2-(3-cyano-2-methyl-phenyl)pyrazolo[1,5-a]pyrimidine-5-carboxylate (Intermediate AB) and 2,6-dimethyl-4-(4,4,5,5-tetramethyl-1,3,2-dioxaborolan-2-yl)pyridine analogously to Example 92 step 1.

LC-MS (Method 5B): Rt 3.12 mins; MS m/z 412.2=[M+H]+

1H NMR (500 MHz, DMSO-d6) δ 9.43 (d, J=7.3 Hz, 1H), 8.00 (d, J=7.7 Hz, 1H), 7.73-7.65 (m, 2H), 7.55 (t, J=7.7 Hz, 1H), 7.12 (s, 2H), 4.44 (q,J=7.1 Hz, 2H), 2.33 (s, 6H), 2.26 (s, 3H), 1.40 (t, J=7.1 Hz, 3H).

Step 2: 2-(3-Cyano-2-methyl-phenyl)-3-(2,6-dimethyl-4-pyridyl)pyrazolo[1,5-a]pyrimidine-5-carboxylic acid

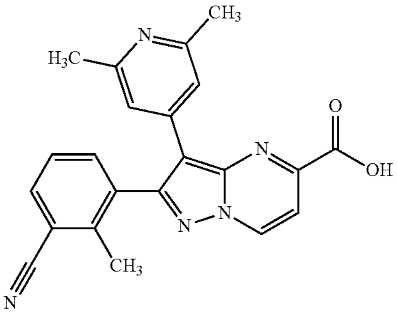 [SMILES: Cc1cc(-c2c(-c3cccc(C#N)c3C)nn3ccc(C(=O)O)nc23)cc(C)n1]

The title compound was prepared from ethyl 2-(3-cyano-2-methyl-phenyl)-3-(2,6-dimethyl-4-pyridyl)pyrazolo[1,5-a]pyrimidine-5-carboxylate (step 1) and lithium hydroxide analogously to Intermediate B1.

LC-MS (Method 5B): Rt 1.20 mins; MS m/z 384.0=[M+H]+

1H NMR (500 MHz, DMSO-d6) δ 9.54 (d, J=7.1 Hz, 1H), 8.06 (d, J=7.7 Hz, 1H), 7.84 (d, J=7.1 Hz, 1H), 7.71 (d, J=7.7 Hz, 1H), 7.68-7.54 (m, 3H), 2.56 (s, 6H), 2.32 (s, 3H). carboxylic acid proton not observed.

Step 3: 2-(3-Cyano-2-methyl-phenyl)-3-(2,6-dimethyl-4-pyridyl)-N-[(1R)-2-hydroxy-1,2-dimethyl-propyl]pyrazolo[1,5-a]pyrimidine-5-carboxamide The title compound was prepared from 2-(3-cyano-2-methyl-phenyl)-3-(2,6-dimethyl-4-pyridyl)pyrazolo[1,5-a]pyrimidine-5-carboxylic acid (step 2) and (3R)-3-amino-2-methyl-butan-2-ol analogously to Example 102 step 2.

LC-MS (Method 8B): Rt 4.25 mins; MS m/z 469.3=[M+H]+

1H NMR (500 MHz, DMSO-d6) b 9.43 (d, J=7.2 Hz, 1H), 8.36 (d, J=9.0 Hz, 1H), 8.01 (d, J=7.8 Hz, 1H), 7.76-7.67 (m, 2H), 7.58 (t, J=7.8 Hz, 1H), 7.13 (s, 2H), 4.80 (s, 1H), 3.93-3.86 (m, 1H), 2.33 (s, 6H), 2.26 (s, 3H), 1.25-1.15 (m, 9H).

Example 104.1-2-(3-Cyano-2-methyl-phenyl)-3-(2,6-dimethyl-4-pyridyl)-N-[(1S)-2-hydroxy-1,2-dimethyl-propyl]pyrazolo[1,5-a]pyrimidine-5-carboxamide

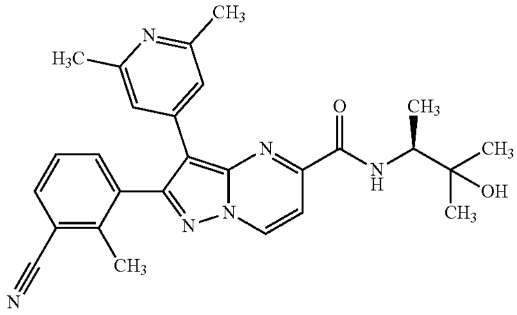 [SMILES: Cc1cc(-c2c(-c3cccc(C#N)c3C)nn3ccc(C(=O)N[C@@H](C)C(C)(C)O)nc23)cc(C)n1]

The title compound was prepared from 2-(3-cyano-2-methyl-phenyl)-3-(2,6-dimethyl-4-pyridyl)pyrazolo[1,5-a]pyrimidine-5-carboxylic acid (Example 104 step 2) and (3S)-3-amino-2-methyl-butan-2-ol hydrochloride analogously to Example 102 step 2.

LC-MS (Method 8B): Rt 4.30 mins; MS m/z 469.3=[M+H]+

1H NMR (500 MHz, DMSO-d6) δ 9.42 (d, J=7.2 Hz, 1H), 8.35 (d, J=9.0 Hz, 1H), 8.01 (d, J=7.7 Hz, 1H), 7.77-7.66 (m, 2H), 7.57 (t, J=7.7 Hz, 1H), 7.13 (s, 2H), 4.79 (s, 1H), 3.93-3.85 (m, 1H), 2.33 (s, 6H), 2.25 (s, 3H), 1.34-1.08 (m, 9H).

Example 106-3-[3-(2,6-Dimethyl-4-pyridyl)-5-(3-oxo-2,8-diazaspiro[4.5]decan-8-yl)pyrazolo[1,5-a]pyrimidin-2-yl]benzonitrile

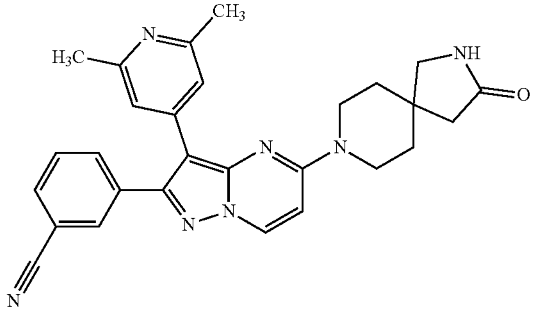 [SMILES: Cc1cc(-c2c(-c3cccc(C#N)c3)nn3ccc(N4CCC5(CC4)CNC(=O)C5)nc23)cc(C)n1]

The title compound was prepared from 3-[5-chloro-3-(2,6-dimethyl-4-pyridyl)pyrazolo[1,5-a]pyrimidin-2-yl]benzonitrile (Intermediate CA) and 2,8-diazaspiro[4.5]decan-3-one hydrochloride analogously to Example 2.

LC-MS (Method 8B): Rt 4.02 mins; MS m/z 478.4=[M+H]+

1H NMR (500 MHz, DMSO) b 8.74 (d, J=7.9 Hz, 1H), 7.95-7.90 (m, 2H), 7.81 (dt,J=7.9, 1.5 Hz, 1H), 7.69-7.62 (m, 1H), 7.57 (s, 1H), 7.11 (s, 2H), 6.94 (d, J=7.9 Hz, 1H), 3.92-3.82 (m, 2H), 3.70-3.61 (m, 2H), 3.12 (s, 2H), 2.33 (s, 6H), 2.16 (s, 2H), 1.68-1.59 (m, 4H).

Example 105.1-3-[5-[(1-Acetyl-4-piperidyl)amino]-3-(2,6-dimethyl-4-pyridyl)pyrazolo[1,5-a]pyrimidin-2-yl]benzonitrile

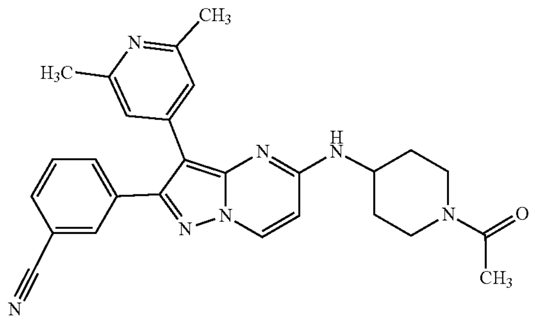 [SMILES: CC(=O)N1CCC(Nc2ccn3nc(-c4cccc(C#N)c4)c(-c4cc(C)nc(C)c4)c3n2)CC1]

The title compound was prepared from 3-[5-chloro-3-(2,6-dimethyl-4-pyridyl)pyrazolo[1,5-a]pyrimidin-2-yl]benzonitrile (Intermediate CA) and 1-(4-amino-I-piperidyl)ethanone analogously Example 2.

LC-MS (Method 8B): Rt 4.08 mins; MS m/z 466.4=[M+H]+

1H NMR (500 MHz, DMSO) δ 8.60 (d, J=7.5 Hz, 1H), 7.97-7.91 (m, 2H), 7.88-7.80 (m, 2H), 7.67 (t, J=7.8 Hz, 1H), 7.14 (s, 2H), 6.41 (d, J=7.6 Hz, 1H), 4.34 (d, J=13.4 Hz, 1H), 4.02 (s, 1H), 3.87 (d, J=13.7 Hz, 1H), 3.25-3.16 (m, 1H), 2.80 (t, J=12.2 Hz, 1H), 2.33 (s, 6H), 2.11 (t, J=15.1 Hz, 2H), 2.04 (s, 3H), 1.51-1.43 (m, 1H), 1.39-1.28 (m, 1H).

Example 105.2-3-[3-(2,6-Dimethyl-4-pyridyl)-5-[(1-methyl-2-oxo-4-piperidyl)amino]pyrazolo[1,5-a]pyrimidin-2-yl]benzonitrile

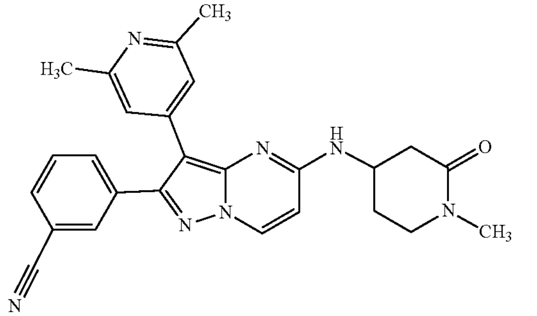 [SMILES: Cc1cc(-c2c(-c3cccc(C#N)c3)nn3ccc(NC4CCN(C)C(=O)C4)nc23)cc(C)n1]

The title compound was prepared from 3-[5-chloro-3-(2,6-dimethyl-4-pyridyl)pyrazolo[1,5-a]pyrimidin-2-yl]benzonitrile (Intermediate CA) and 4-amino-1-methyl-piperidin-2-one analogously to Example 2.

LC-MS (Method 8b): Rt 3.93 mins; MS m/z 452.3=[M+H]+

1H NMR (500 MHz, MeOD) δ 8.36 (d, J=7.5 Hz, 1H), 7.88 (s, 1H), 7.79 (t, J=8.0 Hz, 2H), 7.60 (t, J=7.8 Hz, 1H), 7.19 (s, 2H), 6.40 (d, J=7.5 Hz, 1H), 4.40-4.31 (m, 1H), 3.56-3.43 (m, 2H), 3.01 (s, 3H), 2.94 (dd, J=17.3, 5.4 Hz, 1H), 2.47 (dd, J=17.3, 8.4 Hz, 1H), 2.40 (s, 6H), 2.37-2.31 (m, 1H), 2.10-1.99 (m, 1H). NH proton not observed.

Example 105.3-3-[3-(2,6-Dimethyl-4-pyridyl)-5-[[1-(2-hydroxy-2-methyl-propyl)-4-piperidyl]amino]pyrazolo[1,5-a]pyrimidin-2-yl]benzonitrile

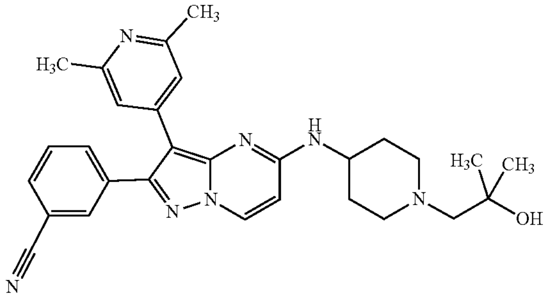 [SMILES: Cc1cc(-c2c(-c3cccc(C#N)c3)nn3ccc(NC4CCN(CC(C)(C)O)CC4)nc23)cc(C)n1]

The title compound was prepared from 3-[5-chloro-3-(2,6-dimethyl-4-pyridyl)pyrazolo[1,5-a]pyrimidin-2-yl]benzonitrile (Intermediate CA) and 1-(4-amino-1-piperidyl)-2-methyl-propan-2-ol dihydrochloride analogously to Example 2.

LC-MS-1 (Method 8B): Rt 4.58 mins; MS m/z 496.3=[M+H]+

1H NMR (500 MHz, DMSO-d6) δ 8.55 (d, J=7.6 Hz, 1H), 7.96-7.90 (m, 2H), 7.82 (d, J=7.8 Hz, 1H), 7.75 (d, J=6.8 Hz, 1H), 7.66 (t, J=7.8 Hz, 1H), 7.14 (s, 2H), 6.39 (d, J=7.6 Hz, 1H), 4.05 (s, 1H), 3.81-3.72 (m, 1H), 2.99 (apr d, J=11.4 Hz, 2H), 2.32 (s, 6H), 2.28-2.18 (m, 4H), 2.05-1.97 (m, 2H), 1.58-1.47 (m, 2H), 1.09 (s, 6H).

Preparation of Intermediate Compounds

Intermediate A -3-(2-Chloro-6-methyl-4-pyridyl)-2-(3-cyanophenyl)pyrazolo[1,5-a]pyrimidine-5-carboxylic acid

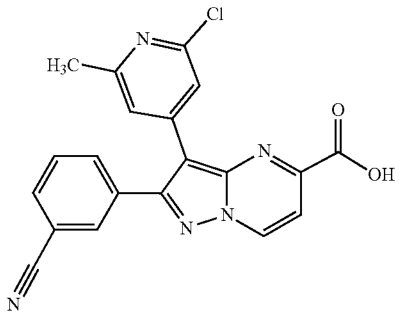 [SMILES: Cc1cc(-c2c(-c3cccc(C#N)c3)nn3ccc(C(=O)O)nc23)cc(Cl)n1]

Intermediate A1: 3-(5-Amino-1H-pyrazol-3-vl)benzonitrile

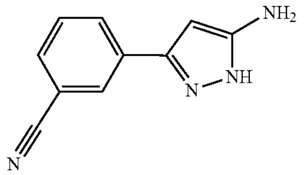 [SMILES: N#Cc1cccc(-c2cc(N)[nH]n2)c1]

A mixture of 3-(2-cyanoacetyl)benzonitrile (20 g, 118 mmol) and hydrazine hydrate (28.59 mL, 588 mmol) in EtOH (400 mL) was heated to 80° C. for 6 h. The resulting mixture was allowed to cool to room temperature and left to stand overnight. The EtOH was removed under vacuum and the remaining mixture was added to water (250 mL) and agitated for 20 mins. The resulting suspension was filtered and the solid was washed with water (2×50 mL) and dried by azeotroping from MeOH to afford the title compound as a beige solid.

LC-MS (Method 5B): Rt 1.83 mins; MS m/z 185.2=[M+H]+

$^1$H NMR (500 MHz, DMSO-$d_6$) δ 11.90 (s, 1H), 8.08 (td,J=1.7, 0.5 Hz, 1H), 7.99 (ddd, J=7.8, 1.7, 1.2 Hz, 1H), 7.70 (apr dt,J=7.8, 1.7 Hz, 1H), 7.57 (t, J=7.8 Hz, 1H), 5.85 (s, 1H).

Intermediate A2: Ethyl 2-(3-cyanophenyl)-7-hydroxy-pyrazolo[1,5-a]pyrimidine-5-carboxylate

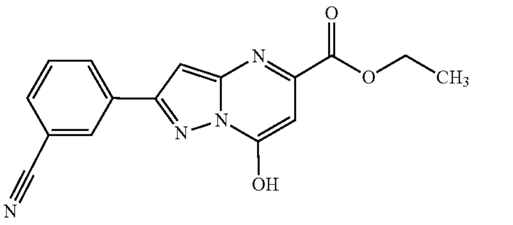 [SMILES: CCOC(=O)c1cc(O)n2nc(-c3cccc(C#N)c3)cc2n1]

A solution of diethyl acetylenedicarboxylate (119.66 mL, 747.5 mmol) in IMS (50 mL) was added dropwise over 20 mins to a stirred solution of 3-(5-amino-1H-pyrazol-3-yl) benzonitrile (Intermediate A1)(98.35 g, 533.93 mmol) and acetic acid (152.82 mL, 2669.7 mmol) in IMS (1475 mL) and the reaction mixture was stirred at room temperature for 69 h. The resulting suspension was cooled in an ice bath, filtered and the collected solids washed with IMS (2×500 mL), $Et_2O$ (3×500 mL) and vacuum dried to afford the title compound as a cream solid.

LC-MS (Method 3A): Rt 1.52 mins; MS m/z 309.1=[M+H]+

$^1$H NMR (500 MHz, DMSO) δ 13.11 (br s, 1H), 8.44 (br t,J=1.5 Hz, 1H), 8.35 (br dt,J=8.0, 1.5 Hz, 1H), 7.90 (br dt,J=7.6, 1.5 Hz, 1H), 7.70 (apr t,J=7.8 Hz, 1H), 6.85 (s, 1H), 6.33 (s, 1H), 4.42 (q,J=7.1 Hz, 2H), 1.37 (t, J=7.1 Hz, 3H).

Intermediate A3: Ethyl 7-chloro-2-(3-cyanophenyl) pyrazolo[1,5-a]pyrimidine-5-carboxylate

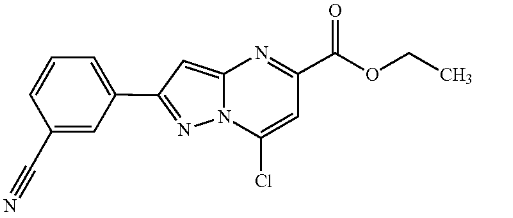 [SMILES: CCOC(=O)c1cc(Cl)n2nc(-c3cccc(C#N)c3)cc2n1]

Ethyl 2-(3-cyanophenyl)-7-hydroxy-pyrazolo[1,5-a]pyrimidine-5-carboxylate (Intermediate A2) (131.0 g, 424.92 mmol) was suspended in $POCl_3$ (619.91 mL, 8498.5 mmol) and stirred at 110° C. for 5 h. The mixture was allowed to cool before being concentrated in vacuo at 45° C. The resulting residue was azeotroped with toluene (3×600 mL) to afford an orange residue. The flask was placed in an ice bath and chilled MeOH (600 mL) was added cautiously. After addition of the solvent, the mixture was stirred for 20 mins at room temperature before the solid was collected by filtration. The solid was thoroughly washed with MeOH (4×400 mL) and dried to afford the title compound as a yellow solid.

LC-MS (Method 3A): Rt 2.08 mins; MS m/z 327.0/329.0=[M+H]+

$^1$H NMR (500 MHz, DMSO-$d_6$) δ 8.55 (t, J=1.8 Hz, 1H), 8.45 (td,J=7.8, 1.8 Hz, 1H), 7.96 (td,J=7.8, 1.8 Hz, 1H), 7.87 (s, 1H), 7.84 (s, 1H), 7.77 (t, J=7.8 Hz, 1H), 4.42 (q,J=7.1 Hz, 2H), 1.38 (t, J=7.1 Hz, 3H).

Intermediate A4a: Ethyl 2-(3-cyanophenyl)pyrazolo[1,5-a]pyrimidine-5-carboxylate and ethyl 2-(3-cyanophenyl)-4,7-dihydropyrazolo[1,5-a]pyrimidine-5-carboxylate

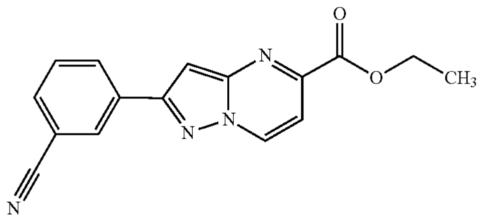 [SMILES: CCOC(=O)c1ccn2nc(-c3cccc(C#N)c3)cc2n1]

and

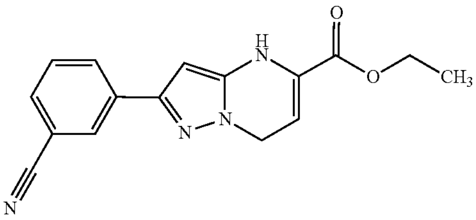

Ethyl 7-chloro-2-(3-cyanophenyl)pyrazolo[1,5-a]pyrimidine-5-carboxylate (Intermediate A3) (53.43 g, 163.52 mmol) and palladium on carbon (10%) (4.35 g, 4.09 mmol) in ethyl acetate (3200 mL) was treated with triethylamine (113.96 mL, 817.62 mmol). The flask was sealed, and whilst stirring vigorously the flask contents were evacuated, back-filled with nitrogen (3× cycles), then evacuated and back-filled with hydrogen (5× cycles). After stirring vigorously at room temperature for 75 mins, the resulting suspension was diluted portion-wise with chloroform (6 litres) to solubilise the mixture. The resulting mixture was filtered through a plug of Celite®, eluting with chloroform (4×500 mL). The combined filtrates were concentrated in vacuo to afford the title compounds as a 5: 1 mixture of ethyl 2-(3-cyanophenyl) pyrazolo[1,5-a]pyrimidine-5-carboxylate and ethyl 2-(3-cyanophenyl)-4,7-dihydropyrazolo[1,5-a]pyrimidine-5-carboxylate.

LC-MS (Method 3A): Rt 1.76 mins; MS m/z 293.1/295.1=[M+H]+

Intermediate A4: Ethyl 2-(3-cyanophenyl)pyrazolo [1,5-a]pyrimidine-5-carboxylate

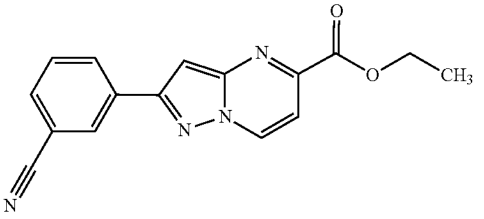

Activated manganese dioxide (142.18 g, 1635.4 mmol) was added to a solution of a crude mixture of ethyl 2-(3-cyanophenyl)pyrazolo[1,5-a]pyrimidine-5-carboxylate and ethyl 2-(3-cyanophenyl)-4,7-dihydropyrazolo[1,5-a]pyrimidine-5-carboxylate (Intermediate A4a)(95.71 g, 327.08 mmol) in chloroform (3200 mL) and stirred vigorously at room temperature for 3 h. The resulting mixture was filtered through a plug of Celite® (filter material), eluting with chloroform (4×1000 mL). The combined filtrates were concentrated in vacuo to approximately 2000 mL and washed with water (2×1000 mL). The combined aqueous portions were extracted with chloroform (500 mL) and the combined organic portions were dried over $Na_2SO_4$, filtered and concentrated in vacuo to afford the title compound as a yellow solid.

LC-MS (Method 3A): Rt 1.78 mins; MS m/z 293.1=[M+H]+

$^1$H NMR (500 MHz, DMSO-$d_6$) δ 9.31 (d, J=7.2 Hz, 1H), 8.51 (br t,J=1.5 Hz, 1H), 8.40 (br dt,J=8.0, 1.5 Hz, 1H), 7.92 (br dt,J=7.7, 1.5 Hz, 1H), 7.74 (apr t,J=7.8 Hz, 1H), 7.65 (s, 1H), 7.55 (d, J=7.2 Hz, 1H), 4.40 (q,J=7.1 Hz, 2H), 1.37 (t, J=7.1 Hz, 3H).

Intermediate A5: Ethyl 3-bromo-2-(3-cyanophenyl) pyrazolo[1,5-a]pyrimidine-5-carboxylate

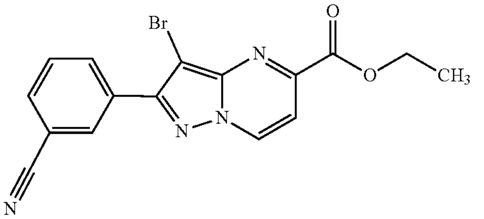 [SMILES: CCOC(=O)c1ccn2nc(-c3cccc(C#N)c3)c(Br)c2n1]

NBS (67.88 g, 381.4 mmol) was added in one- portion to a stirred partial suspension of ethyl 2-(3-cyanophenyl)pyrazolo[1,5-a]pyrimidine-5-carboxylate (Intermediate A4) (92.9 g, 317.84 mmol) in DMF (1590 mL) and the mixture was stirred at room temperature for 1 h.

The resulting mixture was cooled in an ice bath and water (3200 mL) was added slowly causing a suspension to form. The suspension was stirred in the ice bath for 5 mins, then at room temperature for 30 mins. The solids were collected by filtration, washed with water (4×800 mL) and vacuum dried to afford the title compound as a yellow solid.

LC-MS (Method 3A): Rt 1.94 mins; MS m/z 371.0/373.1=[M+H]+

$^1$H NMR (500 MHz, DMSO) δ 9.40 (d, J=7.2 Hz, 1H), 8.41 (brt,J=1.5 Hz, 1H), 8.37 (br dt,J=8.0, 1.5 Hz, 1H), 8.03 (br dt,J=7.8, 1.5 Hz, 1H), 7.82 (apr t,J=7.9 Hz, 1H), 7.67 (d, J=7.2 Hz, 1H), 4.44 (q,J=7.1 Hz, 2H), 1.39 (t, J=7.1 Hz, 3H).

Intermediate A6: Ethyl 3-(2-chloro-6-methyl-4-pyridyl)-2-(3-cyanophenyl)pyrazolo[1,5-a]pyrimidine-5-carboxylate

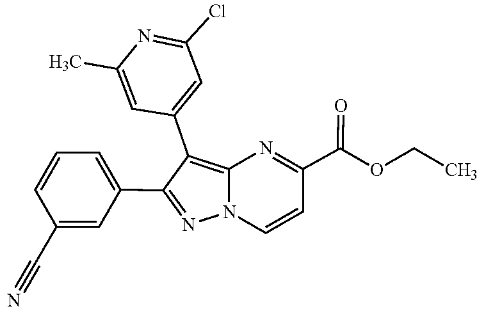 [SMILES: CCOC(=O)c1ccn2nc(-c3cccc(C#N)c3)c(-c3cc(C)nc(Cl)c3)c2n1]

A mixture of ethyl 3-bromo-2-(3-cyanophenyl)pyrazolo [1,5-a]pyrimidine-5-carboxylate (Intermediate A5) (1.5 g, 4.04 mmol), 2-chloro-6-methyl-4-(4,4,5,5-tetramethyl-1,3,2-dioxaborolan-2-yl)pyridine (1.08 g, 4.24 mmol) and $K_2C0s$ (1.12 g, 8.08 mmol) in 1,4-dioxane (4 mL) and water (0.5 mL) was degassed with $N_2$ before Pd(tBu$_3$P)2 (155 mg, 0.30 mmol) was added and the reaction mixture heated to 50° C. for 1 h. The resulting mixture was poured into water (100 mL) and the precipitate was collected by filtration. Purification by chromatography on silica eluting with a gradient of 25 to 100% EtOAc in petroleum ether afforded the title compound as an orange solid.

LC-MS (Method 5B): Rt 3.40 mins; MS m/z 418.2/420.0=[M+H]+

$^1$H NMR (500 MHz, DMSO-$d_6$) δ 9.46 (d, J=7.2 Hz, 1H), 8.08 (s, 1H), 8.01 (dd, J=7.8, 1.6 Hz, 1H), 7.89 (d, J=8.0 Hz, 1H), 7.76-7.69 (m, 2H), 7.46 (s, 1H), 7.36 (s, 1H), 4.42 (q, J=7.0 Hz, 2H), 2.43 (s, 3H), 1.38 (d, J=7.0 Hz, 3H).

Intermediate A: 3-(2-Chloro-6-methyl-4-pyridyl)-2-(3-cyanophenyl)pyrazolo[1,5-a]pyrimidine-5-carboxylic acid The preparation of the title compound is described in Example 9

Intermediate AB—Ethyl 3-bromo-2-(3-cyano-2-methyl-phenyl)pyrazolo[1,5-a]pyrimidine-5-carboxylate

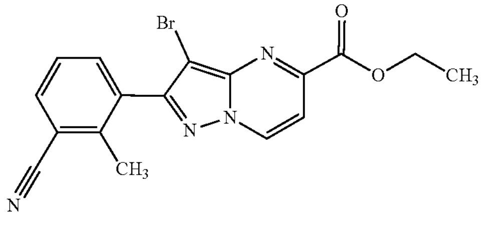 [SMILES: CCOC(=O)c1ccn2nc(-c3cccc(C#N)c3C)c(Br)c2n1]

Intermediate AB1: 3-(5-Amino-1H-pyrazol-3-yl)-2-methyl-benzonitrile

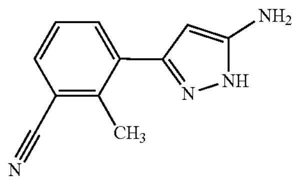

The title compound was prepared from 3-(2-cyanoacetyl)-2-methyl-benzonitrile (Intermediate ZG) and hydrazine hydrate analogously to Intermediate A1.

LC-MS (Method 3A): Rt 1.13 mins; MS m/z 199.2=[M+H]+

1H NMR (500 MHz, DMSO-d6) b 11.74 (s, 1H), 7.93-7.60 (m, 2H), 7.52-7.32 (m, 1H), 5.59 (s, 1H), 5.19-4.54 (m, 2H), 2.60 (s, 3H).

Intermediate AB2: Ethyl 2-(3-cyano-2-methyl-phenyl)-7-hydroxy-pyrazolo[1,5-a]pyrimidine-5-carboxylate

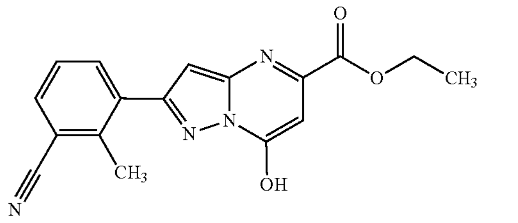

The title compound was prepared from 3-(5-amino-1H-pyrazol-3-yl)-2-methyl-benzonitrile (Intermediate AB1) and diethyl acetylenedicarboxylate analogously to Intermediate A2.

LC-MS (Method 5B): Rt 1.22 mins; MS m/z 323.1=[M+H]+

1H NMR (500 MHz, DMSO-d6) δ 13.00 (s, 1H), 7.93 (d, J=7.8 Hz, 1H), 7.88 (d, J=7.8 Hz, 1H), 7.52 (t, J=7.8 Hz, 1H), 6.55 (s, 1H), 6.34 (s, 1H), 4.42 (q,J=7.1 Hz, 2H), 2.67 (s, 3H), 1.37 (t, J=7.1 Hz, 3H).

Intermediate AB3: Ethyl 7-chloro-2-(3-cyano-2-methyl-phenyl)pyrazolo[1,5-a]pyrimidine-5-carboxylate

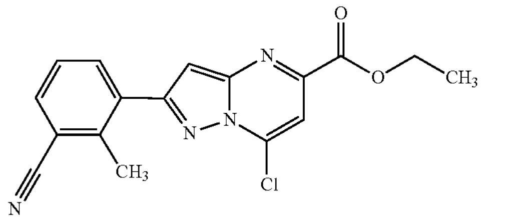 [SMILES: CCOC(=O)c1cc(O)n2nc(-c3cccc(C#N)c3C)cc2n1]

The title compound was prepared from ethyl 2-(3-cyano-2-methyl-phenyl)-7-hydroxy-pyrazolo[1,5-a]pyrimidine-5-carboxylate (Intermediate AB2) and $POCl_3$ analogously to Intermediate A3.

LC-MS (Method 58): Rt 3.05 mins; MS m/z 341.1/343.1=[M+H]+

1H NMR (500 MHz, DMSO-d6) δ 8.04 (d, J=7.7 Hz, 1H), 7.94 (d, J=7.7 Hz, 1H), 7.90 (s, 1H), 7.61-7.54 (m, 2H), 4.42 (q, J=7.1 Hz, 2H), 2.73 (s, 3H), 1.38 (t, J=7.1 Hz, 3H).

Intermediate AB4: Ethyl 2-(3-cyano-2-methyl-phenyl)pyrazolo[1,5-a]pyrimidine-5-carboxylate

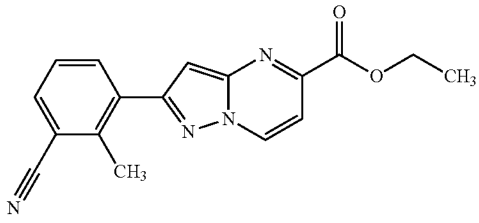 [SMILES: CCOC(=O)c1ccn2nc(-c3cccc(C#N)c3C)cc2n1]

The title compound was prepared from ethyl 7-chloro-2-(3-cyano-2-methyl-phenyl)pyrazolo[1,5-a]pyrimidine-5-carboxylate (Intermediate AB3) and 10 wt % Pd on carbon followed by oxidation with manganese dioxide analogously to Intermediate A4.

LC-MS (Method 5B): Rt 2.66 mins; MS m/z 307.1=[M+H]+

1H NMR (500 MHz, DMSO-d6) δ 9.36 (d, J=5.9 Hz, 1H), 8.02 (d, J=7.5 Hz, 1H), 7.92 (d, J=7.5 Hz, 1H), 7.66-7.50 (m, 2H), 7.39 (s, 1H), 4.41 (q,J=7.0 Hz, 2H), 2.72 (s, 3H), 1.38 (t, J=7.0 Hz, 3H). NMR showed to contain 1eq of $Et_3N.HCl$.

Intermediate AB: Ethyl 3-bromo-2-(3-cyano-2-methyl-phenyl)pyrazolo[1,5-a]pyrimidine-5-carboxylate The title compound was prepared from ethyl 2-(3-cyano-2-methyl-phenyl)pyrazolo[1,5-a]pyrimidine-5-carboxylate (Intermediate AB4) and NBS analogously to Intermediate A5.

LC-MS (Method 5B): Rt 2.90 mins; MS m/z 385.0/387.0=[M+H]+

1H NMR (500 MHz, DMSO-d6) δ 9.39 (d, J=7.2 Hz, 1H), 8.00 (d, J=7.7 Hz, 1H), 7.77 (d, J=7.7 Hz, 1H), 7.67 (d, J=7.2 Hz, 1H), 7.59 (t, J=7.7 Hz, 1H), 4.45 (q,J=7.1 Hz, 2H), 2.44 (s, 3H), 1.39 (t, J=7.1 Hz, 3H).

Intermediate B -3-Bromo-2-(3-cyanophenyl)-N-(2-hydroxy-2-methyl-propyl)pyrazolo[1,5-a]pyrimidine-5-carboxamide

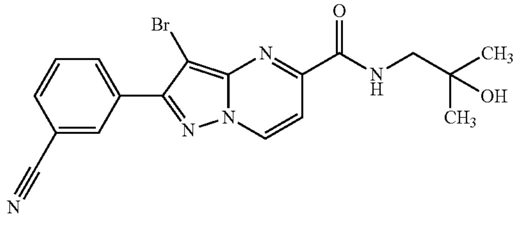 [SMILES: CC(C)(O)CNC(=O)c1ccn2nc(-c3cccc(C#N)c3)c(Br)c2n1]

Intermediate B1: 3-Bromo-2-(3-cyanophenyl)pyrazolo[1,5-a]pyrimidine-5-carboxylic acid

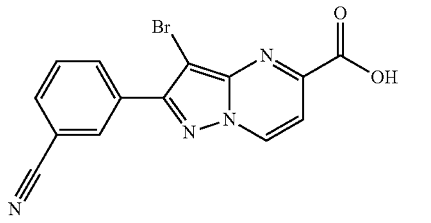 [SMILES: N#Cc1cccc(-c2nn3ccc(C(=O)O)nc3c2Br)c1]

To a suspension of ethyl 3-bromo-2-(3-cyanophenyl)pyrazolo[1,5-a]pyrimidine-5-carboxylate (Intermediate A5) (404 mg, 1.09 mmol) in THF (5 mL) was added a solution of lithium hydroxide (52 mg, 2.18 mmol) in water (1 mL) and the mixture stirred for 2 h. Water (20 mL) was added and the mixture was washed with $Et_2O$ (25 mL). The organic portion was discarded and the aqueous acidified with 2M HCl until acidic at which point a thick yellow precipitate formed. The solid was collected by filtration, washed with water (2×15 mL) and dried under vacuum. The remaining water was removed by azeotroping from MeOH (2×10 mL) and further drying under vacuum afforded the title compound as a yellow solid.

LC-MS (Method 5A): Rt 2.28 mins; MS m/z 343.0/345.0=[M+H]+

$^1$H NMR (500 MHz, DMSO-$d_6$) δ 14.03 (br s, 1H), 9.37 (d, J=7.2 Hz, 1H), 8.41 (apr s, 1H), 8.37 (apr d, J=7.8 Hz, 1H), 8.03 (apr d, J=7.8 Hz, 1H), 7.82 (t, J=7.8 Hz, 1H), 7.65 (d, J=7.2 Hz, 1H).

Intermediate B: 3-Bromo-2-(3-cyanophenyl)-N-(2-hydroxy-2-methyl-propyl)pyrazolo[1,5-a]pyrimidine-5-carboxamide To a suspension of 3-bromo-2-(3-cyanophenyl)pyrazolo[1,5-a]pyrimidine-5-carboxylic acid (Intermediate B1)(326 mg, 0.95 mmol) in DCM (10 mL) was added DMF (2 drops) followed by oxalyl chloride (241 μL, 2.85 mmol) dropwise and the mixture stirred for 30 mins. The solvent was removed in vacuo. A suspension of the formed acid chloride in DCM (10 mL) was added dropwise to a solution of 1-amino-2-methyl-propan-2-ol (0.13 mL, 1.43 mmol) and DIPEA (0.5 mL, 2.85 mmol) in DCM (10 mL) and the mixture stirred for 10 mins.

The resulting mixture was partitioned between water (10 mL) and DCM (10 mL), the organic portion separated and the aqueous further extracted with DCM (2×10 mL). The combined organic extracts were washed with brine (10 mL), dried over $MgSO_4$ and the solvent removed in vacuo. Purification by chromatography on silica eluting with 2% MeCOH in DCM afforded the title compound as a yellow solid.

LC-MS (Method 5A): Rt 2.51 mins; MS m/z 414.0/416.0=[M+H]+

$^1$H NMR (500 MHz, DMSO-$d_6$) δ 9.39 (d, J=7.1 Hz, 1H), 8.43-8.41 (m, 2H), 8.37 (d, J=7.9 Hz, 1H), 8.03 (d, J=7.9 Hz, 1H), 7.82 (t, J=7.9 Hz, 1H), 7.70 (d, J=7.1 Hz, 1H), 4.78 (s, 1H), 3.35 (d, J=6.2 Hz, 2H), 1.15 (s, 6H).

Intermediate C -3-[5-Chloro-3-(2-chloro-6-methyl-4-pyridyl)pyrazolo[1,5-a]pyrimidin-2-yl]benzonitrile

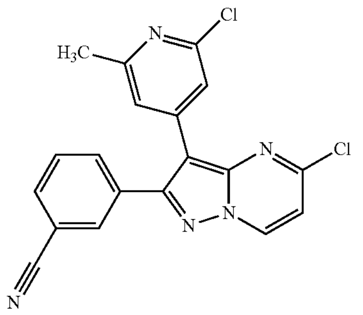 [SMILES: Cc1cc(-c2c(-c3cccc(C#N)c3)nn3ccc(Cl)nc23)cc(Cl)n1]

Intermediate C1: 3-(5-Hydroxypyrazolo[1,5-a]pyrimidin-2-yl)benzonitrile

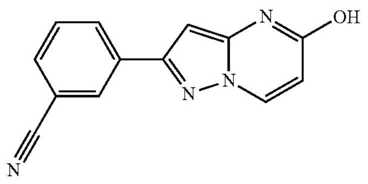 [SMILES: N#Cc1cccc(-c2cc3nc(O)ccn3n2)c1]

A mixture of 3-(5-amino-1H-pyrazol-3-yl)benzonitrile (Intermediate A1) (5 g, 27.1 mmol), ethyl(E)-3-ethoxyprop-2-enoate (4.9 mL, 33.9 mmol) and $Cs_2CO_3$ (17.69 g, 54.3 mmol) in DMF (100 mL) was heated to 110° C. for 2 h. The resulting mixture was allowed to cool to room temperature before 2M HCl (80 mL) was added slowly and the mixture stirred at room temperature for 2 h. The resulting precipitate was collected by filtration, washed with water (2×300 mL) and azeotroped from MeOH (100 mL) to afford the title compound as a brown solid.

LC-MS (Method 5A): Rt 1.85 mins; MS m/z 237.1=[M+H]+

$^1$H NMR (500 MHz, DMSO-$d_6$) δ 12.31 (s, 1H), 8.54 (d, J=7.9 Hz, 1H), 8.36 (d, J=1.7 Hz, 1H), 8.25 (dd, J=7.9, 1.6 Hz, 1H), 7.91.-7.81 (m, 1H), 7.67 (t, J=7.8 Hz, 1H), 6.49 (s, 1H), 6.02 (d, J=7.9 Hz, 1H).

Intermediate C2: 3-(5-Chloropyrazolo[1,5-a]pyrimidin-2-yl)benzonitrile

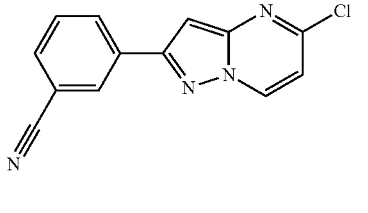 [SMILES: N#Cc1cccc(-c2cc3nc(Cl)ccn3n2)c1]

A mixture of 3-(5-hydroxypyrazolo[1,5-a]pyrimidin-2-yl)benzonitrile (Intermediate C1) (5.74 g, 24.3 mmol) and $POCl_3$ (35.46 mL, 486 mmol) was heated to 110° C. for 1 h. Additional $POCl_3$ (17.73 mL, 243 mmol) was added and stirring continued at 110° C. for a further 45 mins. The resulting mixture was cooled to room temperature and added slowly to stirring water (500 mL). The precipitate was collected by filtration washing with water (2×50 mL). The solid was azeotroped from MeOH (50 mL) to afford the title compound as a brown solid.

LC-MS (Method 5A): Rt 2.94 mins; MS m/z 255.0=[M+H]+

$^1$H NMR (500 MHz, DMSO-d6) δ 9.22 (d, J=7.2 Hz, 1H), 8.49 (s, 1H), 8.39 (d, J=8.1 Hz, 1H), 7.93 (d, J=7.8 Hz, 1H), 7.74 (t, J=7.8 Hz, 1H), 7.42 (s, 1H), 7.20 (d, J=7.2 Hz, 1H).

Intermediate C3: 3-(5-Chloro-3-iodo-pyrazolo[1,5-a]pyrimidin-2-yl)benzonitrile

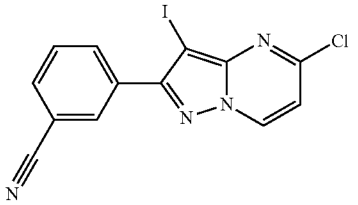 [SMILES: N#Cc1cccc(-c2nn3ccc(Cl)nc3c2I)c1]

A suspension of 3-(5-chloropyrazolo[1,5-a]pyrimidin-2-yl)benzonitrile (Intermediate C2)(6.19 g, 24.3 mmol), N-iodosuccinimide (6.02 g, 26.7 mmol) and MeCN (160 mL) was stirred at room temperature for 1 h. The resulting mixture was added to water (500 mL) and the precipitate was collected by filtration, washing with water (2×50 mL). The resultant solid was azeotroped from MeOH (100 mL) to afford the title compound as a light brown solid.

LC-MS (Method 5B): Rt 3.23 mins; MS m/z 380.9/382.9=[M+H]+

$^1$H NMR (500 MHz, DMSO-do) 6 9.27 (d, J=7.2 Hz, 1H), 8.34 (d, J=1.7 Hz, 1H), 8.29 (d, J=7.9 Hz, 1H), 8.02 (d, J=7.7 Hz, 1H), 7.81 (t, J=7.8 Hz, 1H), 7.30 (d, J=7.2 Hz, 1H).

Intermediate C: 3-[5-Chloro-3-(2-chloro-6-methyl-4-pyridyl)pyrazolo[1,5-a]pyrimidin-2-yl]benzonitrile A mixture of $Pd(tBu_3P)_2$ (269 mg, 0.53 mmol), $K_2CO_3$ (1.45 g, 10.5 mmol) and 2-chloro-6-methyl-4-(4,4,5,5-tetramethyl-1,3,2-dioxaborolan-2-yl)pyridine (1.60 g, 6.31 mmol) in 1,4-dioxane (30 mL) and water (6 mL) was degassed with $N_2$ before 3-(5-chloro-3-iodo-pyrazolo[1,5-a]pyrimidin-2-yl)benzonitrile (Intermediate C3)(2 g, 5.26 mmol) was added and the reaction mixture heated to 60° C. for 1 h. After cooling to room temperature, the resulting mixture was partitioned between a 3:1 mixture of chloroform and MeOH (100 mL) and water (100 mL). The organic layer was separated and the aqueous layer was further extracted with a 3:1 mixture of chloroform and MeOH (3×100 mL) before the organic fractions were combined and concentrated in vacuo. Purification by chromatography on silica eluting with a gradient of 0-100% EtOAc in DCM followed by a second purification by chromatography on silica eluting with a gradient of 0-20% EtOAc in DCM afforded the title compound as a pale yellow solid.

LC-MS (Method 5B): Rt 3.29 mins; MS m/z 380.1=[M+H]+

$^1$H NMR (500 MHz, DMSO-$d_6$) δ 9.35 (d, J=7.2 Hz, 1H), 8.03 (s, 1H), 7.99 (d, J=7.8 Hz, 1H), 7.84 (d, J=7.8 Hz, 1H), 7.71 (t, J=7.8 Hz, 1H), 7.39 (d, J=7.2 Hz, 1H), 7.31 (s, 1H), 7.27 (s, 1H), 2.42 (s, 3H).

Intermediate CA -3-[5-Chloro-3-(2,6-dimethyl-4-pyridyl)pyrazolo[1,5-a]pyrimidin-2-yl]benzonitrile

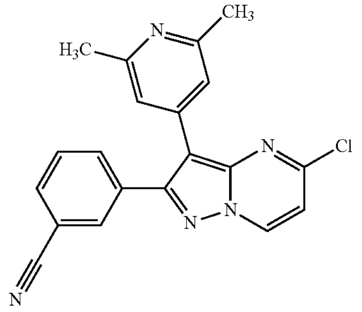 [SMILES: Cc1cc(-c2c(-c3cccc(C#N)c3)nn3ccc(Cl)nc23)cc(C)n1]

The title compound was prepared from 3-(5-chloro-3-iodo-pyrazolo[1,5-a]pyrimidin-2-yl)benzonitrile (Intermediate C3) and 2,6-dimethyl-4-(4,4,5,5-tetramethyl-1,3,2-dioxaborolan-2-yl)pyridine analogously to Intermediate C.

LC-MS (Method 5A): Rt 2.09 mins; MS m/z 360.1=[M+H]+

1H NMR (500 MHz, DMSO-d6) δ 9.32 (d, J=7.2 Hz, 1H), 7.99 (s, 1H), 7.96 (d, J=7.8 Hz, 1H), 7.82 (d, J=7.9 Hz, 1H), 7.68 (t, J=7.8 Hz, 1H), 7.34 (d, J=7.2 Hz, 1H), 7.07 (s, 2H), 2.41 (s, 6H).

Intermediate D -3-(5-Amino-3-iodo-pyrazolo[1,5-a]pyrimidin-2-yl)benzonitrile

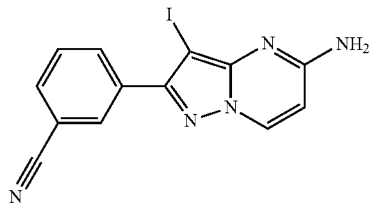 [SMILES: N#Cc1cccc(-c2nn3ccc(N)nc3c2I)c1]

A mixture of 3-(5-chloro-3-iodo-pyrazolo[1,5-a]pyrimidin-2-yl)benzonitrile (Intermediate C3) (2 g, 5.26 mmol) and $NH_4OH$ (35 wt %, 6 mL, 53.9 mmol) in NMP (60 mL) in a sealed vial was heated to 50° C. for 18 h. After cooling to room temperature, the mixture was added slowly to stirring water (500 mL) and the resulting precipitate was collected by filtration. The solid was azeotroped from MeOH (100 mL) to afford the title compound as a beige solid.

LC-MS (Method 5B): Rt 2.56 mins; MS m/z 362.0=[M+H]+

1H NMR (500 MHz, DMSO-d6) δ 8.55 (d, J=7.4 Hz, 1H), 8.29-8.17 (m, 2H), 7.92 (d, J=7.7 Hz, 1H), 7.73 (t, J=7.8 Hz, 1H), 7.24 (s, 2H), 6.33 (d, J=7.5 Hz, 1H).

Intermediate E -3-(5-Amino-3-bromo-pyrazolo[1,5-a]pyrimidin-2-yl)benzonitrile

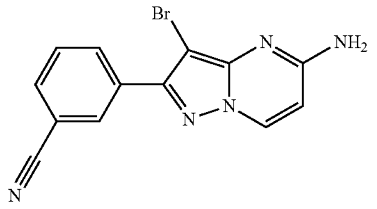 [SMILES: N#Cc1cccc(-c2nn3ccc(N)nc3c2Br)c1]

Intermediate E1: 3-(3-Bromo-5-chloro-pyrazolo[1,5-a]pyrimidin-2-yl)benzonitrile

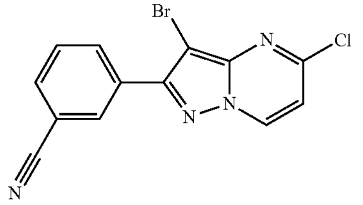 [SMILES: N#Cc1cccc(-c2nn3ccc(Cl)nc3c2Br)c1]

To a suspension of 3-(5-chloropyrazolo[1,5-a]pyrimidin-2-yl)benzonitrile (Intermediate C2) (100 mg, 0.39 mmol) in DMF (2 mL) was added NBS (74 mg, 0.41 mmol) and the mixture was stirred at room temperature for 1 h. The resulting mixture was added dropwise to stirring water (20 mL) and the precipitate was collected by filtration, washing with water (2×2 mL). The solid was azeotroped from MeOH (4 ml) to afford the title compound as a beige solid.

LC-MS (Method 5B): Rt 3.36 mins. No ionisation observed.

1H NMR (500 MHz, DMSO-d6) b 9.29 (d, J=7.2 Hz, 1H), 8.36 (t, J=1.7 Hz, 1H), 8.32 (dt, J=7.9, 1.4 Hz, 1H), 8.02 (dt, J=7.8, 1.4 Hz, 1H), 7.81 (t, J=7.8 Hz, 1H), 7.33 (d, J=7.2 Hz, 1H).

Intermediate E: 3-(5-Amino-3-bromo-pyrazolo[1,5-a]pyrimidin-2-yl)benzonitrile

A mixture. of 3-(3-bromo-5-chloro-pyrazolo[1,5-a]pyrimidin-2-yl)benzonitrile (Intermediate E1)(116 mg, 0.35 mmol) and $NH_4OH$ (35 wt %, 0.39 mL, 3.48 mmol) in NMP (2 mL) was heated to 110° C. for 45 mins. After cooling to room temperature, the resulting mixture was added dropwise to stirring water (15 mL). The precipitate was collected by filtration, washing with water (2×2 mL). The solid was azeotroped from MeOH to afford the title compound as a beige solid.

LC-MS (Method 5B): Rt 2.53 mins; MS m/z 314.1/316.1=[M+H]+

1H NMR (500 MHz, DMSO-d6) δ 8.57 (d, J=7.5 Hz, 1H), 8.30-8.21 (m, 2H), 7.92 (d, J=7.7 Hz, 1H), 7.73 (t, J=7.8 Hz, 1H), 7.30 (s, 2H), 6.35 (d, J=7.5 Hz, 1H).

Intermediate F (Same as Example 1.4)-3-[5-Amino-3-(2-chloro-6-methyl-4-pyridyl)pyrazolo[1,5-a]pyrimidin-2-yl]benzonitrile

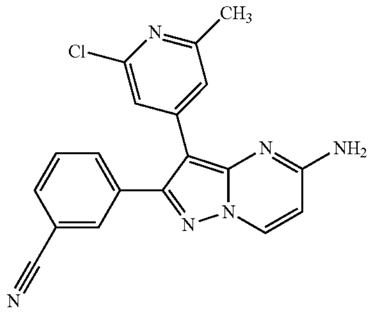 [SMILES: Cc1cc(-c2c(-c3cccc(C#N)c3)nn3ccc(N)nc23)cc(Cl)n1]

A mixture of 3-(5-amino-3-iodo-pyrazolo[1,5-a]pyrimidin-2-yl)benzonitrile (Intermediate D) (1.83 g, 5.07 mmol), 2-chloro-6-methyl-4-(4,4,5,5-tetramethyl-1,3,2-dioxaborolan-2-yl)pyridine (1.35 g, 5.32 mmol) and $K_2CO_3$ (2.10 g, 15.2 mmol) in 1,4-dioxane (70 mL) and water (17.5 mL) was degassed under a flow of $N_2$ before $Pd(tBu_3P)2$ (259 mg, 0.51 mmol) was added and the mixture heated to 80° C. for 50 mins. After cooling to room temperature, the resulting mixture was added dropwise to stirring water (500 mL) and the solid was collected by filtration. Purification by chromatography on silica eluting with a gradient of 0 to 10% MeOH in DCM afforded the title compound as a brown solid.

LC-MS (Method 5B): Rt 2.75 mins; MS m/z 361.1/363.1=[M+H]+

1H NMR (500 MHz, DMSO-d6) b 8.62 (d, J=7.5 Hz, 1H), 7.97-7.88 (m, 2H), 7.81-7.74 (m, 1H), 7.70-7.63 (m, 1H), 7.35-7.29 (m, 3H), 7.19 (s, 1H), 6.41 (d, J=7.5 Hz, 1H), 2.33 (s, 3H).

Intermediate G -3-[5-Chloro-3-(2-ethylpyrazol-3-yl)pyrazolo[1,5-a]pyrimidin-2-yl]benzonitrile

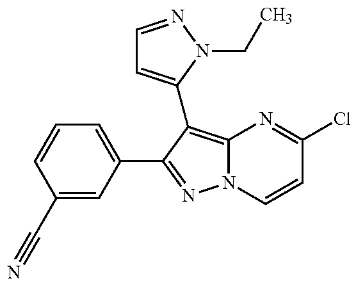 [SMILES: CCn1nccc1-c1c(-c2cccc(C#N)c2)nn2ccc(Cl)nc12]

The title compound was prepared from 3-(5-chloro-3-iodo-pyrazolo[1,5-a]pyrimidin-2-yl)benzonitrile (Intermediate C3) (600 mg, 1.58 mmol) and (2-ethylpyrazol-3-yl) boronic acid analogously to Intermediate F.

LC-MS (Method 5A): Rt 2.84 mins; MS m/z 349.1=[M+H]+

$^1H$ NMR (500 MHz, DMSO-$d_6$) δ 9.35 (d, J=7.2 Hz, 1H), 7.94.-7.89 (m, 2H), 7.83 (dt, J=8.0, 1.4 Hz, 1H), 7.72-7.49 (m, 2H), 7.35 (d, J=7.2 Hz, 1H), 6.36 (d, J=1.8 Hz, 1H), 3.86 (q, J=7.2 Hz, 2H), 1.15-1.12 (m, 3H).

Intermediate I-3-Aminobicyclo[1.1.1]pentane-1-carboxylic acid hydrochloride

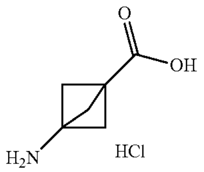

The title compound was prepared according to the procedure detailed in WO 2018/211275 page 302.

A solution of 3-(tert-butoxycarbonylamino)bicyclo[1.1.1]pentane-1-carboxylic acid (200 mg, 0.88 mmol) in 4M HCl in 1,4-dioxane (5.0 mL, 20 mmol) was stirred at room temperature for 1 h. The resulting mixture was concentrated in vacuo to afford the title compound as a colourless powder.

LC-MS (Method 2.5B): Rt 0.28 mins; MS m/z 128.1=[M+H]+

$^1$H NMR (500 MHz, MeOH-$d_4$) b 2.34 (s, 6H).

Intermediate J

-4-Bromo-2,6-dimethyl-1-oxido-pyridin-1-ium

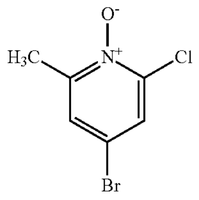

To a solution of 4-bromo-2,6-dimethyl-pyridine (500 mg, 2.69 mmol) in DCM (15 mL) at 0° C. was added mCPBA (695 mg, 4.03 mmol). The reaction mixture was warmed to room temperature and stirred for 1 h. The resulting mixture was diluted in DCM (10 mL) and washed with $NaHCO_3$ (2×20 mL) before the organic phase was dried over $MgSO_4$ and concentrated in vacuo. Purification by chromatography on silica eluting with a 0-5% MeCOH in DCM afforded the title compound.

LC-MS (Method 58): Rt 1.59 mins; MS m/z 202.0/204.0=[M+H]+

$^1$H NMR (500 MHz, DMSO-d6) δ 7.66 (s, 2H), 2.34 (s, 6H).

Intermediate K

-4-Chloro-6-methyl-pyridine-2-carboxamide

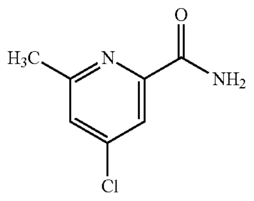

A mixture of 4-chloro-6-methyl-pyridine-2-carboxylic acid (400 mg, 2.33 mmol) and $SOCl_2$ (7 mL, 96 mmol) was heated to 75° C. for 2 h. The cooled mixture was concentrated in vacuo and residual $SOCl_2$ removed by co-evaporation with toluene (3×5 mL). The residue was dissolved in 1,4-dioxane (4 mL) and slowly added to a mixture of $NH_4OH$ (35 wt %, 3.02 mL, 77.6 mmol) in 1,4-dioxane (3 mL) at room temperature and the reaction mixture stirred at room temperature for 30 mins. The mixture was concentrated in vacuo and purification by chromatography on silica eluting with a gradient of 0-9% MeOH in DCM afforded the title compound as a colourless solid.

LC-MS (Method 5B): Rt 2.03 mins; MS m/z 171.1=[M+H]+

1H NMR (500 MHz, DMSO-d6) δ 8.06 (s, 1H), 7.82 (d, J=1.9 Hz, 1H), 7.76 (s, 1H), 7.64 (d, J=1.9 Hz, 1H), 2.55 (s, 3H).

Intermediate L

-N-(4-Bromo-6-methyl-2-pyridyl)acetamide

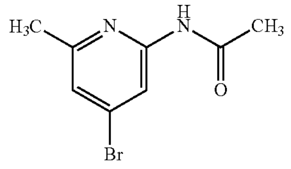

A mixture of 4-bromo-6-methyl-pyridin-2-amine (250 mg, 1.34 mmol) and acetic anhydride (0.19 mL, 2 mmol) in $CHCl_3$ (2 mL) was heated to 60° C. for 2.5 h. After cooling to room temperature, the mixture was diluted with DCM (20 mL) and washed with $NaHCO_3$ (2×30 mL). The organic phase was dried over $MgSO_4$ and concentrated in vacuo to afford the title compound as a colourless solid.

LC-MS (Method 5B): Rt 2.37 mins; MS m/z 229.0/231.9=[M+H]+

1H NMR (500 MHz, DMSO-d6) δ 10.66 (s, 1H), 8.13 (d, J=1.6 Hz, 1H), 7.25 (d, J=1.6 Hz, 1H), 2.39 (s, 3H), 2.07 (s, 3H).

Intermediate M—Isopropyl 4-chloro-6-methyl-pyridine-2-carboxylate

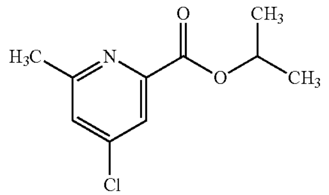

A mixture of 4-chloro-6-methyl-pyridine-2-carboxylic acid (485 mg, 2.83 mmol) and $SOCl_2$ (8.5 mL, 116.53 mmol) was heated to 75° C. for 1 h. The cooled mixture was concentrated in vacuo and residual $SOCl_2$ removed by co-evaporation from toluene (3×8 mL).

The residue was dissolved in DCM (4 mL) and added dropwise to a mixture of 2-propanol (6 mL, 78.37 mmol) and DIPEA (4.5 mL, 25.84 mmol) in DCM (6 mL). The mixture was stirred at room temperature for 18 h before being diluted with DCM (50 mL), washed with water (50 mL), brine (30 mL), dried over $MgSO_4$ and concentrated in vacuo. Purification by chromatography on silica eluting with a gradient of 0-6% MeOH in DCM followed by a second purification by chromatography on silica eluting with a gradient of 0-5% MeOH in DCM afforded the title compound as a brown oil.

LC-MS (Method 5B): Rt 2.87 mins; MS m/z 214.1=[M+H]+

$^1$H NMR (500 MHz, DMSO-d6) δ 7.86 (d, J=1.9 Hz, 1H), 7.70 (d, J=1.9 Hz, 1H), 5.16 (hept, J=6.2 Hz, 1H), 2.54 (s, 3H), 1.33 (d, J=6.3 Hz, 6H).

Intermediate N -5-Methyl-7-(4,4,5,5-tetramethyl-1,3,2-dioxaborolan-2-yl)-[1,2,4]triazolo [1,5-a]pyridine

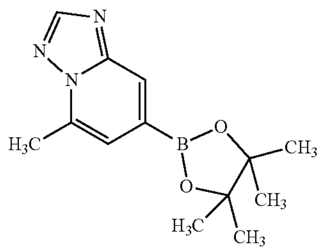

Intermediate N1: N-(4-Bromo-6-methyl-2-pyridyl)-N'-hydroxy-formamidine

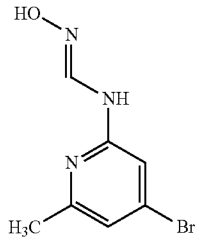

A mixture of 4-bromo-6-methyl-pyridin-2-amine (886 mg, 4.74 mmol) and dimethyl formamide-dimethylacetal (1.64 mL, 12.32 mmol) in IPA (9 mL) was heated to 80° C. for 1 h. Hydroxylamine hydrochloride (494 mg, 7.11 mmol) was added and the mixture was stirred at 50° C. for 18 h. After cooling to room temperature, the mixture was poured into $NaHCO_3$ (10 mL) and extracted with EtOAc (2×20 mL) and EtOAc/THF (10:1, 50 mL). The combined organic extracts were dried over $MgSO_4$ and concentrated in vacuo to afford the title compound as a grey solid.

LC-MS (Method 5B): Rt 2.32 mins; MS m/z 229.9/331.9=[M+H]+

$^1$H NMR (500 MHz, DMSO-d6) δ 10.17 (s, 1H), 9.44 (d, J=9.9 Hz, 1H), 7.81 (d, J=9.9 Hz, 1H), 7.11 (d, J=1.5 Hz, 1H), 6.95 (d, J=1.5 Hz, 1H), 2.33 (s, 3H).

Intermediate N2: 7-Bromo-5-methyl-[1,2,4]triazolo [1,5-a]pyridine

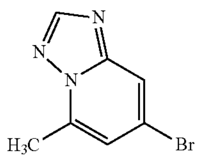

A mixture of N-(4-bromo-6-methyl-2-pyridyl)-N'-hydroxy-formamidine (Intermediate N1) (1.1 g, 4.78 mmol) in THF (22 mL) was warmed to 60° C. to aid dissolution and cooled to room temperature before T3P® (50% in EtOAc) (4.27 mL, 7.17 mmol) was added slowly. The reaction was re-heated to 60° C. for 1 h and allowed to cool to room temperature. The resulting mixture was poured into $NaHCO_3$ (30 mL) and extracted with EtOAc (2×40 mL). The organic extracts were dried over $MgSO_4$ and concentrated in vacuo. The crude material was purified by chromatography on silica eluting with 2% MeOH in DCM to afford the title compound as a pale yellow solid.

LC-MS (Method 5B): Rt 2.09 mins; MS m/z 212.0/214.0=[M+H]+

$^1$H NMR (500 MHz, DMSO-d6) δ 8.53 (s, 1H), 8.08 (dd, J=2.0, 0.8 Hz, 1H), 7.36 (dd, J=2.1, 1.1 Hz, 1H), 2.74-2.69 (m, 3H).

Intermediate N: 5-Methyl-7-(4,4,5,5-tetramethyl-1,3,2-dioxaborolan-2-yl)-[1,2,4]triazolo[1,5-a]pyridine A mixture of 7-bromo-5-methyl-[1,2,4]triazolo[1,5-a]pyridine (Intermediate N2)(75 mg, 0.3500 mmol), bis(pinacolato)diboron (179.63 mg, 0.7100 mmol) and potassium acetate (104.13 mg, 1.06 mmol) in dioxane (3 mL) was degassed under a flow of N2. Pd(dppf)C12 (25.88 mg, 0.0400 mmol) was added and the reaction was stirred at 120° C. for 20 min. The reaction mixture was cooled to room temperature and filtered trough Celite @(filter material), eluting with DCM before being concentrated in vacuo. Purification by chromatography on silica eluting with a gradient of 0 to 10% MeOH in DCM afforded the title compound as a brown oil.

LC-MS (Method 5B): Rt 0.99 mins; MS m/z 260.1=[M+H]+

$^1$H NMR (500 MHz, DMSO-d6) b 8.56 (s, 1H), 7.92-7.88 (m, 1H), 7.25-7.22 (m, 1H), 2.76-2.74 (m, 3H), 1.34 (s, 12H).

Intermediate 0-5-Chloro-2-(2-fluorophenyl)pyrazolo [1,5-a]pyrimidine

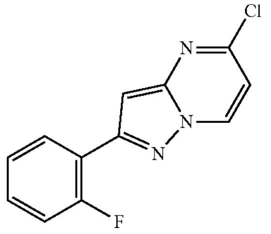 [SMILES: Fc1ccccc1-c1cc2nc(Cl)ccn2n1]

Intermediate 01: 3-(2-Fluorophenyl)-1H-pyrazol-5-amine

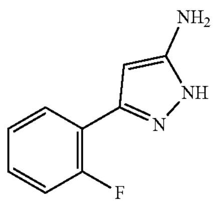 [SMILES: Nc1cc(-c2ccccc2F)n[nH]1]

To a solution of 3-(2-fluorophenyl)-3-oxo-propanenitrile (1 g, 6.13 mmol) in EtOH (7 mL) was added hydrazine monohydrate (1.49 mL, 30.65 mmol) and the mixture was heated in a sealed tube at 80° C. for 18 h. The solvent was removed in vacuo and the crude product purified by chromatography on silica eluting with 5% MeOH in DCM to afford the title compound.

LC-MS (Method 3B): Rt 1.17 mins; MS m/z 178.2=[M+H]+

$^1$H NMR (500 MHz, Chloroform-d) 67.60 (td, J=7.7, 1.8 Hz, 1H), 7.30 (m, 1H), 7.20 (td, J=7.7, 1.2 Hz, 1H), 7.15 (ddd, J=11.8, 8.3, 1.2 Hz, 1H), 6.05 (d, J=0.9 Hz, 1H), 5.08 (s, 3H).

Intermediate 02: 2-(2-Fluorophenyl)pyrazolo[1,5-a]pyrimidin-5-ol

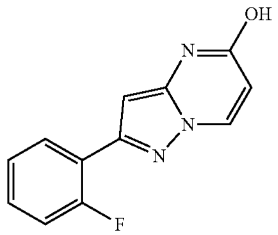 [SMILES: Oc1ccn2nc(-c3ccccc3F)cc2n1]

A mixture of 3-(2-fluorophenyl)-1H-pyrazol-5-amine (Intermediate 01) (840 mg, 4.74 mmol) and 1,3-dimethylpyrimidine-2,4-dione (664 mg, 4.74 mmol) in 21% sodium ethoxide in EtOH (42.14 mL, 23.7 mmol) was heated at 80° C. for 2.5 h. Additional 1,3-dimethylpyrimidine-2,4-dione (332 mg, 2.37 mmol) was added and the mixture stirred at 80° C. for a further 5 h. After cooling to room temperature, the solvent was removed in vacuo and the crude material was partitioned between $H_2O$ (25 mL) and EtOAc (25 mL). The organic fraction was discarded and the aqueous was acidified with acetic acid. The resulting solid was collected by filtration, washed with water, MeCN (2×20 mL) and dried- to afford the title compound as a cream solid.

LC-MS (Method 3A): Rt 1.38 mins; MS m/z 230.2=[M+H)+

$^1$H NMR (500 MHz, DMSO-$d_6$) δ 12.20 (s, 1H), 8.55 (d, J=8.0 Hz, 1H), 7.99 (td, J=7.8, 1.9 Hz, 1H), 7.49-7.43 (m, 1H), 7.37-7.27 (m, 2H), 6.19 (d, J=3.7 Hz, 1H), 6.01 (d, J=8.0 Hz, 1H).

Intermediate O: 5-Chloro-2-(2-fluorophenyl)pyrazolo[1,5-a]pyrimidine

A mixture of 2-(2-fluorophenyl)pyrazolo[1,5-a]pyrimidin-5-ol (Intermediate 02) (0.66 g, 2.86 mmol) and $POCl_3$ (14.38 mL, 154.26 mmol) was heated to 100° C. for 1 h. The resulting mixture was concentrated in vacuo and the residue was dissolved in EtOAc (50 mL).

The mixture was washed with water (40 mL), sat. aq. $NaHCO_3$ (30 mL), water (20 mL), brine (20 mL), dried over $MgSO_4$, filtered and concentrated in vacuo to afford the title compound as a beige solid.

LC-MS (Method 3B): Rt 1.91 mins; MS m/z 248.0=[M+H]+

NMR (500 MHz, Chloroform-d) b 8.59 (dd, J=7.3, 0.9 Hz, 1H), 8.11 (td, J=7.7, 1.8 Hz, 1H), 7.40 (dddd, J=8.3, 7.1, 5.1, 1.8 Hz, 1H), 7.29-7.23 (m, 1H), 7.20 (ddd, J=11.3, 8.3, 1.2 Hz, 1H), 7.08 (dd, J=3.6, 0.9 Hz, 1H), 6.81 (d, J=7.2 Hz, 1H).

Intermediate P -5-Chloro-2-(2-furyl)pyrazolo[1,5-a]pyrimidine-3-carbonitrile

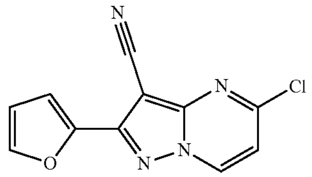 [SMILES: N#Cc1c(-c2ccco2)nn2ccc(Cl)nc12]

The title compound was prepared from 2-(2-furyl)-5-hydroxy-pyrazolo[1,5-a]pyrimidine-3-carbonitrile (Intermediate T) and $POCl_3$ analogously to Intermediate C2.

LC-MS (Method 3A): Rt 1.76 mins; MS m/z 225.1=[M−Cl+OH−H]−

$^1$H NMR (500 MHz, DMSO-$d_6$) δ 9.39 (d, J=7.2 Hz, 1H), 8.06 (d, J=1.8 Hz, 1H), 7.54 (d, J=7.2 Hz, 1H), 7.26 (d, J=3.6 Hz, 1H), 6.80 (dd, J=3.6, 1.8 Hz, 1H).

Intermediate Q -2-Bromo-5-chloro-pyrazolo[1,5-a]pyrimidine

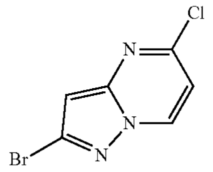 [SMILES: Clc1ccn2nc(Br)cc2n1]

Intermediate Q1: 2-Bromopyrazolo[1,5-a]pyrimidin-5-ol

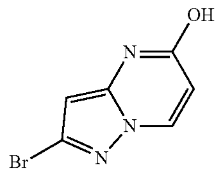 [SMILES: Oc1ccn2nc(Br)cc2n1]

The title compound was prepared from 3-bromo-1H-pyrazol-5-amine and 1,3-dimethylpyrimidine-2,4-dione analogously to Intermediate 02.

LC-MS (Method 3A): Rt 1.00 mins; MS m/z 214.1/216.1=[M+H]+

1H NMR (500 MHz, DMSO-d6) δ 12.26 (s, 1H), 8.43 (d, J=7.9 Hz, 1H), 5.98 (d, J=7.6 Hz, 2H).

Intermediate Q: 2-Bromo-5-chloro-pyrazolo[1,5-a]pyrimidine

The title compound was prepared from 2-bromopyrazolo[1,5-a]pyrimidin-5-ol (Intermediate Q1) and $POCl_3$ analogously to Intermediate 03.

LC MS (acidic method): 1.57 mins -232.0/234.0=[M+H]+

$^1$H NMR (500 MHz, Chloroform-d) δ 8.49 (dd, J=7.2, 0.8 Hz, 1H), 6.82 (d, J=7.2 Hz, 1H), 6.66 (d, J=0.8 Hz, 1H).

Intermediate R -2-(2-Furyl)-5-piperazin-1-yl-pyrazolo[1,5-a]pyrimidine-3-carbonitrile

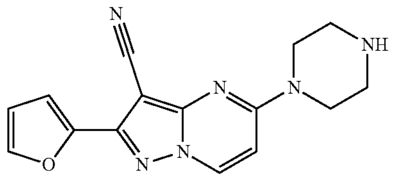 [SMILES: N#Cc1c(-c2ccco2)nn2ccc(N3CCNCC3)nc12]

Preparation described in Example 41

Intermediate S -N-Benzyl-2-(2-furyl)-3-iodo-pyrazolo[1,5-a]pyrimidin-5-amine

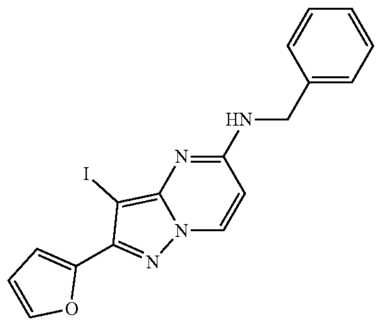 [SMILES: Ic1c(-c2ccco2)nn2ccc(NCc3ccccc3)nc12]

Intermediate S1: 2-(2-Furyl)pyrazolo[1,5-a]pyrimidin-5-ol

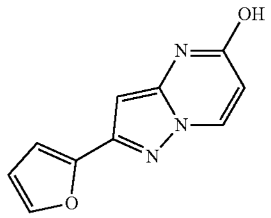 [SMILES: Oc1ccn2nc(-c3ccco3)cc2n1]

To a solution of 3-(2-furyl)-1H-pyrazol-5-amine (430 mg, 2.88 mmol) and ethyl(E)-3-ethoxyprop-2-enoate (520.59 uL, 3.6 mmol) in DMF (15 mL) was added Cs2CO3 (1.88 g, 5.77 mmol) and the mixture was heated to 110° C. for 4 hours. The reaction mixture was cooled to room temperature and poured into $H_2O$ (20 mL) before being cooled to 0° C. and the solution acidified with conc HCl. The formed precipitate was collected by filtration, washed with water and dried to afford the title compound as a cream solid.

LC-MS (Method 3A): Rt 1.11 mins; MS m/z 202.2=[M+H]+

1H NMR (500 MHz, DMSO-d6) δ 12.19 (s, 1H), 8.48 (dd, J=7.9, 0.8 Hz, 1H), 7.78 (dd, J=1.8, 0.8 Hz, 1H), 6.95 (dd, J=3.4, 0.8 Hz, 1H), 6.62 (dd, J=3.4, 1.8 Hz, 1Hf), 6.10-6.07 (m, 1FH), 5.97 (d, J=7.9 Hz, 1H).

Intermediate S2: 5-Chloro-2-(2-furyl)pyrazolo[1,5-a]pyrimidine

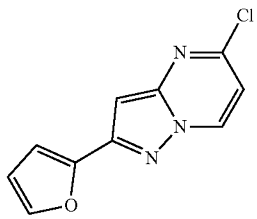 [SMILES: Clc1ccn2nc(-c3ccco3)cc2n1]

A solution of 2-(2-furyl)pyrazolo[1,5-a]pyrimidin-5-ol (intermediate S1) (630 mg, 3.13 mmol) in Phosphorus(V) oxychloride (7.3 mL, 78.29 mmol) was stirred at 80° C. under nitrogen for 90 minutes. The reaction mixture was cooled to room temperature and concentrated in vacuo. The obtained residue was carefully quenched into water (50 mL) and the mixture neutralised with saturated sodium bicarbonate (50 mL). The solution was extracted with EtOAc (2×100 mL) and the combined organic fractions were washed with water (100 mL), brine (50 mL), dried over $MgSO_4$, filtered and concentrated in vacuo to afford the title compound as a yellow solid.

LC-MS (Method 3A): Rt 1.68 mins; MS m/z 220.1/222.1=[M+H]+

1H NMR (500 MHz, DMSO-d6) δ 9.16 (dd, J=7.2, 0.8 Hz, 1H), 7.87 (dd, J=1.8, 0.8 Hz, 1H), 7.15 (d, J=7.2 Hz, 1H), 7.08 (dd, J=3.4, 0.8 Hz, 1H), 6.98 (d, J=0.8 Hz, 1H), 6.68 (dd, J=3.4, 1.8 Hz, 1H).

Intermediate S3: N-Benzyl-2-(2-furyl)pyrazolo[1,5-a]pyrimidin-5-amine

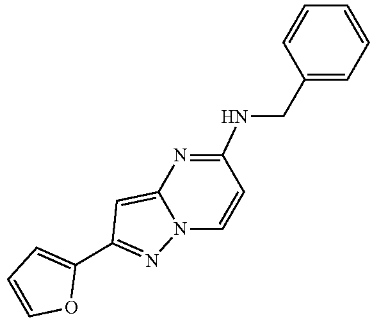 [SMILES: c1ccc(CNc2ccn3nc(-c4ccco4)cc3n2)cc1]

A suspension of 5-chloro-2-(2-furyl)pyrazolo[1,5-a]pyrimidine (Intermediate S2) (640 mg, 2.91 mmol), benzylamine (1.59 mL, 14.57 mmol) and DIPEA (1.02 mL, 5.83 mmol) in EtOH (12 mL) was heated in a sealed tube using microwave irradiation at 120° C. for 1 hour. The mixture was concentrated in vacuo and the residue was purified by chromatography on silica, eluting with 2% MeOH in DCM to yield a solid which was triturated from diethyl ether (10 mL) and dried under vacuum to afford the title compound as a colourless solid.

LC-MS (Method 3B): Rt 1.78 mins; MS m/z 291.1=[M+H]+

$^1$H NMR (500 MHz, DMSO-$d_6$) δ 8.48 (d, J=7.6 Hz, 1H), 7.95 (t, J=5.7 Hz, 1H), 7.75 (dd, J=1.8, 0.6 Hz, 1H), 7.42-7.31 (m, 4H), 7.30-7.21 (m, 1H), 6.83 (dd, J=3.4, 0.6 Hz, 1H), 6.60 (dd, J=3.4, 1.8 Hz, 1H), 6.34 (d, J=7.6 Hz, 1H), 6.23 (d, J=0.8 Hz, 1H), 4.55 (d, J=5.7 Hz, 2H).

Intermediate S: N-Benzyl-2-(2-furyl)-3-iodo-pyrazolo[1,5-a]pyrimidin-5-amine

To a solution of N-benzyl-2-(2-furyl)pyrazolo[1,5-a]pyrimidin-5-amine (Intermediate S3) (200 mg, 0.69 mmol) in DMF (5 mL) was added N-iodosuccinimide (155 mg, 0.69 mmol) in 1 portion and the mixture was stirred at room temperature for 1 h. Additional N-iodosuccinimide (5 mg, 0.02 mmol) was added and stirring continued for a further 30 mins. The resulting mixture was poured into $H_2O$ (20 mL) and extracted with EtOAc (3x25 mL). The combined organic extracts were washed with $H_2O$ (25 mL), brine (25 mL) and dried over $MgSO_4$. Purification by chromatography on silica eluting with 1% to 5% MeOH in DCM afforded the title compound as a yellow solid.

LC-MS (Method 8B): Rt 4.96 mins; MS m/z 417.1=[M+H]+

$^1$H NMR (500 MHz, DMSO-d6) δ 8.50 (d, J=7.5 Hz, 1H), 8.20 (s, 1H), 7.84 (dd, J=1.8, 0.8 Hz, 1H), 7.46 (d, J=7.5 Hz, 2H), 7.39-7.32 (m, 2H), 7.31-7.24 (m, 1H), 7.17 (dd, J=3.4, 0.8 Hz, 1H), 6.66 (dd, J=3.4, 1.8 Hz, 1H), 6.37 (d, J=7.5 Hz, 1H), 4.60 (d, J=5.7 Hz, 2H).

Intermediate T -2-(2-Furyl)-5-hydroxy-pyrazolo[1,5-a]pyrimidine-3-carbonitrile

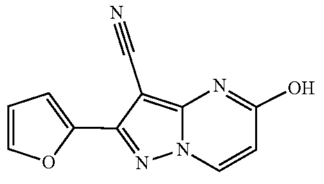 [SMILES: N#Cc1c(-c2ccco2)nn2ccc(O)nc12]

Intermediate T1: 2-[2-Furyl(methoxy)methylene]propanedinitrile

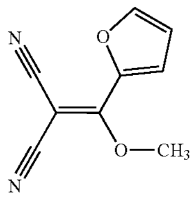

To a solution of furan-2-carbonyl chloride (3.78 mL, 38.31 mmol) in DCM (50 mL) at 0° C. was added triethylamine (10.68 mL, 76.61 mmol) followed by propanedinitrile (2.89 mL, 45.97 mmol) dropwise over 15 mins after which time the ice bath was removed and the solution allowed to stir at room temperature for 2 h. The mixture was washed with ice cold 2M HCl (150 mL) and $H_2O$ (150 mL), dried and the solvent removed in vacuo. The resulting oil was dissolved in 1,4-dioxane (50 mL) and water (5 mL) and treated with sodium bicarbonate (16.09 g, 191.53 mmol) and dimethyl sulfate (18.12 mL, 191.53 mmol). The mixture was heated to 80° C. for 90 mins and then allowed to cool to room temperature. The mixture was diluted with $H_2O$ (100 mL), extracted with EtOAc (3x75 mL) and the combined organic extracts were washed with 5% $NaHCO_3$ (100 mL), $H_2O$ (100 mL), brine (100 mL) and dried over $Na_2SO_4$. The solvent was removed in vacuo and purification of the crude product by chromatography on silica eluting with a gradient of 30 to 40% EtOAc in petrol afforded the title compound as a yellow oil which solidified in vacuo.

LC-MS (Method 3B): Rt 1.33 mins; MS m/z 158.2=[M−CH3]+

1H NMR (500 MHz, Chloroform-d) δ 7.75 (dd, J=1.8, 0.8 Hz, 1H), 7.41 (dd, J=3.8, 0.8 Hz, 1H), 6.67 (dd, J=3.8, 1.8 Hz, 1H), 4.25 (s, 3H).

Intermediate T2: 5-Amino-3-(2-furyl)-1H-pyrazole-4-carbonitrile

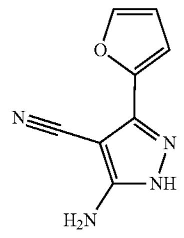 [SMILES: N#Cc1c(-c2ccco2)n[nH]c1N]

To a solution of 2-[2-furyl(methoxy)methylene]propanedinitrile (Intermediate T1)(1.5 g, 8.61 mmol) in methanol (80 mL) at 0° C. was added hydrazine hydrate (2.09 mL, 43.06 mmol) dropwise and the mixture was stirred for 10 mins. The resulting mixture was concentrated in vacuo to afford a yellow gum which was partitioned between EtOAc (50 mL) and $H_2O$ (50 mL). The organic portion was separated and the aqueous further extracted with EtOAc (50 mL) before the combined organic extracts were washed with water (40 mL), brine (40 mL), dried over $MgSO_4$ and the solvent removed in vacuo to afford the title compound as a pale yellow solid.

LC-MS (Method 3B): Rt 1.02 mins; MS m/z 175.1={M+H]+

1H NMR (500 MHz, DMSO-d6) δ 12.23 (s, 1H), 7.78 (s, 1H), 6.78 (s, 1H), 6.61 (dd, J=3.5, 1.8 Hz, 1H), 6.44 (s, 2H).

Intermediate T: 2-(2-Furyl)-5-hydroxy-pyrazolo[1,5-a]pyrimidine-3-carbonitrile

The title compound was prepared according to the procedure detailed in

To a solution of 5-amino-3-(2-furyl)-1H-pyrazole-4-carbonitrile (Intermediate T2) (150 mg, 0.86 mmol) in DMF (5 mL) was added $Cs_2CO_3$ (561 mg, 1.72 mmol) followed by ethyl(E)-3-ethoxyprop-2-enoate (187 μL, 1.29 mmol) and the mixture was heated to 110° C. for 4 h. The resulting mixture was cooled to room temperature and poured into $H_2O$ (20 mL). The mixture was cooled to O ° C. and acidified with concentrated HCl yielding a precipitate that was collected by filtration, washed with water and dried to afford the title compound as a cream solid.

LC-MS (Method 3A): Rt 1.26 mins; MS m/z 227.1=[M+H]+

1H NMR (500 MHz, DMSO-$d_6$) δ 13.37 (s, 1H), 8.71 (s, 1H), 7.95 (d, J=1.8 Hz, 1H), 7.10 (d, J=3.5 Hz, 1H), 6.73 (dd, J=3.5, 1.8 Hz, 1H), 6.35 (s, 1H).

Intermediate U -2-Bromo-5-chloro-pyrazolo[1,5-a]pyrimidine-3-carbonitrile

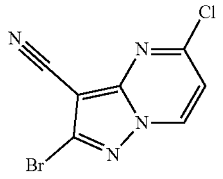 [SMILES: N#Cc1c(Br)nn2ccc(Cl)nc12]

Intermediate U1: (3E)-2-Bromo-5-chloro-pyrazolo[1,5-a]pyrimidine-3-carbaldehyde oxime

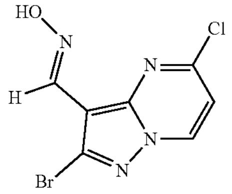 [SMILES: O/N=C/c1c(Br)nn2ccc(Cl)nc12]

To a suspension of 2-bromo-5-chloro-pyrazolo[1,5-a]pyrimidine-3-carbaldehyde (Example 47 step 1) (1.8 g, 6.91 mmol) in EtOH (50 mL) was added hydroxylamine hydrochloride (0.72 g, 10.37 mmol) and the suspension was heated to 85° C. for 1 h. The mixture was cooled to room temperature and the solvent removed in vacuo.

The pH of the crude material was adjusted to pH 7 by the addition of saturated sodium bicarbonate solution and the resulting solid was collected by filtration, washed with water and dried under vacuum to afford the title compound as a yellow solid.

LC-MS (Method 3B): Rt 1.27 mins; MS m/z 275.0/277.0=[M+H]+

$^1$H NMR (500 MHz, DMSO-$d_6$) δ 11.47 (s, 1H), 9.19 (d, J=7.2 Hz, 1H), 8.09 (s, 1H), 7.31 (d, J=7.3 Hz, 1H).

Intermediate U 2-Bromo-5-chloro-pyrazolo[1.5-a]pyrimidine-3-carbonitrile

To (3E)-2-bromo-5-chloro-pyrazolo[1,5-a]pyrimidine-3-carbaldehyde oxime (Intermediate U1) (1.88 g, 6.81 mmol) was added acetic anhydride (130 mL) and the mixture was heated at 140° C. for 3 h. The resulting mixture was adsorbed onto silica and purified by chromatography on silica eluting with 20% EtOAc in petroleum ether to afford the title compound as colourless solid.

LC-MS (Method 38): Rt 1.51 mins; MS m/z 257.01259.0=[M+H]+

$^1$H NMR (500 MHz, DMSO-d6) δ 9.40 (d, J=7.2 Hz, 1H), 7.57 (d, J=7.3 Hz, 1H),

Intermediate V -5-Chloro-2-(3-fluorophenyl)pyrazolo[1,5-a]pyrimidine

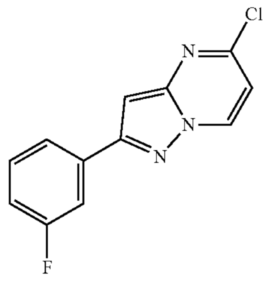 [SMILES: Fc1cccc(-c2cc3nc(Cl)ccn3n2)c1]

Intermediate V1: 3-(3-Fluorophenyl)-1H-pyrazo)-5-amine

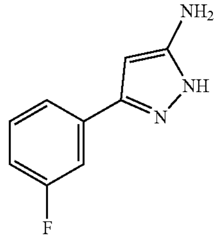 [SMILES: Nc1cc(-c2cccc(F)c2)n[nH]1]

The title compound was prepared from 3-(3-fluorophenyl)-3-oxo-propanenitrile and hydrazine monohydrate analogously to Intermediate 01.

LC-MS (Method 3B): Rt 1.44 mins; MS m/z 178.1=[M+H]+

$^1$H NMR (500 MHz, Chloroform-d) δ 10.29 (v br s, 1H), 7.36-7.30 (m, 2H), 7.26-7.21 (m, 1H), 7.04-6.97 (m, 1H), 5.91 (s, 1H), 3.79 (br s, 1H). NH not observed.

Intermediate V2: Sodium 2-(3-fluorophenyl)pyrazolo[1,5-a]pyrimidin-5-olate

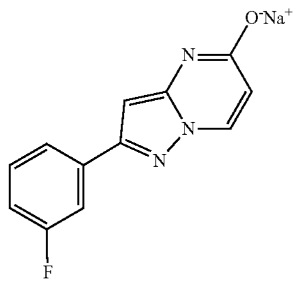

The title compound was prepared from 3-(3-fluorophenyl)-1H-pyrazol-5-amine (Intermediate V1) and 1,3-dimethylpyrimidine-2,4-dione analogously to Intermediate 02.

LC-MS (Method 3B): Rt 0.91 mins; MS m/z 230.1=[M+H]+

$^1H$ NMR (500 MHz, DMSO-$d_6$) δ 8.02 (d, J=7.5 Hz, 1H), 7.64 (d, J=7.9 Hz, 1H), 7.59-7.53 (m, 1H), 7.41 (dt, J=7.9, 6.1 Hz, 1H), 7.09 (td, J=8.6, 2.7 Hz, 1H), 5.88 (s, 1H), 5.67 (d, J=7.5 Hz, 1H).

Intermediate V: 5-Chloro-2-(3-fluorophenyl)pyrazolo[1,5-a]pyrimidine

The title compound was prepared from sodium 2-(3-fluorophenyl)pyrazolo[1,5-a]pyrimidin-5-olate (Intermediate V2) and $POCl_3$ analogously to Intermediate 03.

LC-MS (Method 3B): Rt 1.89 mins. No ionisation observed.

$^1H$ NMR (500 MHz, Chloroform-d) δ 8.57 (dd, J=7.2, 0.8 Hz, 1H), 7.73 (dt, J=7.7, 1.2 Hz, 1H), 7.67 (ddd, J=9.9, 2.6, 1.6 Hz, 1H), 7.44 (dt, J=8.0, 5.8 Hz, 1H), 7.12 (tdd, J=8.5, 2.6, 0.9 Hz, 1H), 6.89 (d, J=0.8 Hz, 1H), 6.81 (d, J=7.2 Hz, 1H).

Intermediate W -3-Bromo-5-chloro-2-(3-fluorophenyl)pyrazolo[1,5-a]pyrimidine

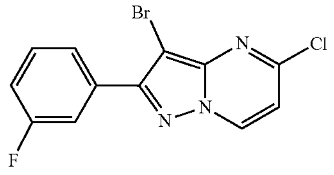 [SMILES: Fc1cccc(-c2nn3ccc(Cl)nc3c2Br)c1]

The preparation of the title compound is described in Example 68.

Intermediate X -7-(2-Furyl)-2-methylsulfonyl-pyrazolo[1,5-a][1,3,5]triazine

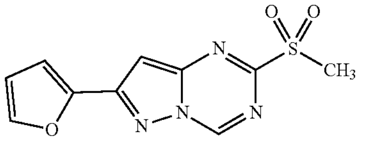 [SMILES: CS(=O)(=O)c1ncn2nc(-c3ccco3)cc2n1]

Intermediate X1: Ethyl N-[[3-(2-furyl)-1H-pyrazol-5-yl]carbamothioyl]carbamate

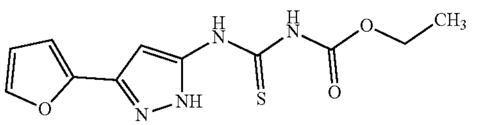 [SMILES: CCOC(=O)NC(=S)Nc1cc(-c2ccco2)n[nH]1]

The title compound was prepared from 3-(2-furyl)-1H-pyrazol-5-amine and ethyl N-(thioxomethylene)carbamate according to the procedure detailed in WO2016160617 A2, pages 178 and 179.

To a mixture of ethyl N-(thioxomethylene)carbamate (1.57 mL, 13.41 mmol) in EtOH (25 mL) was added 3-(2-furyl)-1H-pyrazol-5-amine (2.0 g, 13.41 mmol) and the mixture was heated to 80° C. for 5 h. Additional ethyl N-(thioxomethylene)carbamate (0.16 mL, 1.34 mmol) was added and the mixture heated for 16 h. The solvent was removed in vacuo and the resulting brown solid suspended in $CHCl_3$ (50 mL), filtered and dried to afford the title compound as a pale brown solid.

LC-MS (Method 3A): Rt 1.54 mins; MS m/z 281.0=[M+H]+

$^1H$ NMR (500 MHz, DMSO-$d_6$) δ 13.28 (s, 1H), 12.07 (s, 1H), 11.40 (s, 1H), 7.79 (s, 1H), 7.29 (d, J=1.9 Hz, 1H), 6.87 (d, J=3.4 Hz, 1H), 6.63 (dd, J=3.4, 1.9 Hz, 1H), 4.23 (q, J=7.1 Hz, 2H), 1.27 (t, J=7.1 Hz, 3H).

Intermediate X2: 7-(2-Furyl)-2-thioxo-1H-pyrazolo[1,5-a][1,3,5]triazin-4-one

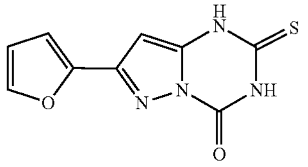 [SMILES: O=c1[nH]c(=S)[nH]c2cc(-c3ccco3)nn12]

To a solution of ethyl N-[[3-(2-furyl)-1H-pyrazol-5-yl]carbamothioyl]carbamate (Intermediate X1) (3 g, 10.17 mmol) in MeCN (30 mL) was added potassium carbonate (4.22 g, 30.5 mmol) and the mixture was heated to 80° C. for 3.5 h. The resulting mixture was cooled to room temperature and concentrated in vacuo. The crude solid was suspended in $H_2O$ (50 mL) and AcOH was added dropwise until the mixture became acidic resulting in a precipitate.

The solid was collected by filtration and dried to afford the title compound as a brown solid.

LC-MS (Method 3A): Rt 1.07/1.10 mins; MS m/z 235.1=[M+H]+

$^1H$ NMR (500 MHz, DMSO-$d_6$) δ 12.31 (vbrs, 1H), 7.80 (m, 1H), 7.00 (d, J=3.4 Hz, 1H), 6.63 (dd, J=3.4, 1.8 Hz, 1H), 6.06 (s, 1H). 1 proton not observed.

Intermediate X3: 7-(2-Furyl)-2-methylsulfanyl-3H-pyrazolo[1,5-a][1,3,5]triazin-4-one

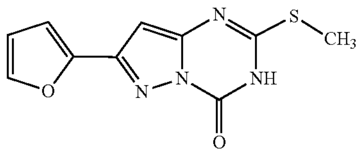 [SMILES: CSc1nc2cc(-c3ccco3)nn2c(=O)[nH]1]

To a suspension of 7-(2-furyl)-2-thioxo-1H-pyrazolo[1,5-a][1,3,5]triazin-4-one (Intermediate X2)(1 g, 4.27 mmol) in EtOH (20 mL) was added a solution of NaOH (341 mg, 8.54 mmol) in water (5 mL). To this solution was added iodomethane (266 μL, 4.27 mmol) dropwise and the mixture was stirred at room temperature for 1.5 h Additional iodomethane (27 μL, 0.43 mmol) was added and stirring continued for 30 mins. The resulting mixture was cooled to 0° C. and 2M HCl was added. The resulting precipitate was collected by filtration, washed with $H_2O$ and dried to afford the title compound as a pale brown solid.

LC-MS (Method 3A): Rt 1.41 mins; MS m/z 249.2=[M+H]+

$^1$H NMR (500 MHz, DMSO-$d_6$) δ 12.94 (br s, 1H), 7.84 (dd, J=1.8, 0.8 Hz, 1H), 7.03 (dd, J=3.4, 0.8 Hz, 1H), 6.65 (dd, J=3.4, 1.8 Hz, 1H), 6.62 (s, 1H), 2.55 (s, 3H).

Intermediate X4: 4-Chloro-7-(2-furyl)-2-methylsulfanyl-pyrazolo[1,5-a][1,3,5]triazine

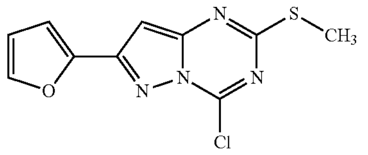 [SMILES: CSc1nc(Cl)n2nc(-c3ccco3)cc2n1]

A mixture of 7-(2-furyl)-2-methylsulfanyl-3H-pyrazolo[1,5-a][1,3,5]triazin-4-one (Intermediate X3)(840 mg, 3.38 mmol), N,N-diethylaniline (2.16 mL, 13.54 mmol) and $POCl_3$ (12.62 mL, 135.34 mmol) was heated to 80° C. for 2.5 h. The solvent was removed in vacuo and the crude mixture was poured slowly onto ice water and stirred for 5 mins. The resulting mixture was diluted with EtOAc (25 mL) and the organic portion was separated. The aqueous layer was further extracted with EtOAc (2×25 mL) and the combined organic extracts were washed with sat. $NaHCO_3$, dried over $MgSO_4$ and the solvent removed in vacuo. Purification by chromatography on silica eluting with DCM afforded a yellow solid which was suspended in hexane, filtered and dried to afford the title compound as a yellow solid.

LC-MS (Method 3B): Rt 1.88 mins; MS m/z 249.0=[M−Cl+OH]+

$^1$H NMR (500 MHz, Chloroform-d) δ 7.60 (dd, J=1.8, 0.8 Hz, 1H), 7.05 (dd, J=3.5, 0.8 Hz, 1H), 6.69 (s, 1H), 6.57 (dd, J=3.5, 1.8 Hz, 1H), 2,61 (s, 3H).

Intermediate X5: 7-(2-Furyl)-2-methylsulfanyl-pyrazolo[1,5-a][1,3,5]triazine

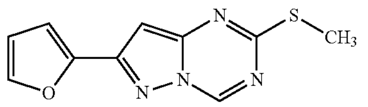 [SMILES: CSc1ncn2nc(-c3ccco3)cc2n1]

To a solution of 4-chloro-7-(2-furyl)-2-methylsulfanyl-pyrazolo[1,5-a][1,3,5]triazine (Intermediate X4) (500 mg, 1.87 mmol) in IPA (20 mL) at 0° C. was added $NaBH_4$ (106 mg, 2.81 mmol) followed by THF (10 mL) and the mixture was warmed to room temperature and stirred for 1 h. The solvent was removed in vacuo and the material was re-dissolved in DCM (100 mL) before manganese (IV) dioxide (1.63 g, 18.75 mmol) was added and the mixture stirred at room temperature for 1.5 h. The resulting mixture was filtered through a plug of Celite® (filter material), eluting with DCM and concentrated in vacuo to afford the title compound as a colourless solid.

LC-MS (Method 3B): Rt 1.69 mins; MS m/z 233.1=[M+H]+

$^1$H NMR (500 MHz, Chloroform-d) δ 8.99 (d, J=0.9 Hz, 1H), 7.59 (dd, J=1.8, 0.8 Hz, 1H), 6.98 (dd, J=3.4, 0.8 Hz, 1H), 6.60 (d, J=0.9 Hz, 1H), 6.56 (dd, J=3.4, 1.8 Hz, 1H), 2.61 (s, 3H).

Intermediate X: 7-(2-Furyl)-2-methylsulfonyl-pyrazolo[1,5-a][1,3,5]triazine

To a solution of 7-(2-furyl)-2-methylsulfanyl-pyrazolo[1,5-a][1,3,5]triazine (Intermediate X5)(361 mg, 1.55 mmol) in DCM (50 mL) was added mCPBA (1.15 g, 4.66 mmol) and the mixture was stirred for 16 h. The resulting mixture was washed with sat. $NaHCO_3$ and the aqueous washings re-extracted with DCM (2×10 mL). The combined organic extracts were dried over $MgSO_4$ and the solvent removed in vacuo. The resulting solid was suspended in $CHCl_3$, filtered and dried to afford the title compound as a colourless solid.

LC-MS (Method 3A): Rt 1.30 mins; MS m/z 265.0=[M+H)+

$^1$H NMR (500 MHz, Chloroform-d) δ 9.44 (d, J=0.9 Hz, 1H), 7.65 (dd, J=1.8, 0.8 Hz, 1H), 7.13 (dd, J=3.5, 0.8 Hz, 1H), 7.10 (d, J=0.9 Hz, 1H), 6.62 (dd, J=3.5, 1.8 Hz, 1H), 3.41 (s, 3H).

Intermediate Y -2-(2-furyl)pyrazolo[1,5-a]pyrimidine-5-carboxylic acid

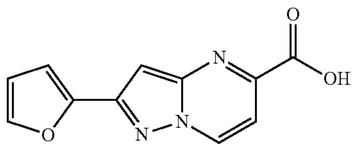 [SMILES: O=C(O)c1ccn2nc(-c3ccco3)cc2n1]

Intermediate Y1: 3-(2-Furyl)-1H-pyrazol-5-amine

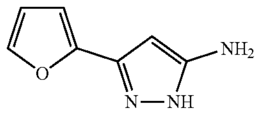 [SMILES: Nc1cc(-c2ccco2)n[nH]1]

The title compound was prepared according to the procedure detailed in N. Suryakiran, T. Srikanth Reddy, K. Asha Latha, P. Prabhakar, K. Yadagiri, Y. Venkateswarlu, Journal of Molecular Catalysis A: Chemical 258 (2006) 371-375.

To a solution of 3-(2-furyl)-3-oxo-propanenitrile (5.0 g, 37 mmol) and hydrazine hydrate (2.15 mL, 44.4 mmol) in EtOH (150 mL) was added methanesulfonic acid (240 μL, 3.7 mmol) and the mixture was heated to 80° C. for 2 h. After cooling to room temperature, the mixture was concentrated in vacuo. The residue was triturated with DCM to afford the title compound as a pale brown solid.

LC-MS (Method 3B): Rt 0.91 mins; MS m/z 150.1=[M+H]+

$^1$H NMR (500 MHz, Chloroform-d) δ 7.43 (dd, J=1.8, 0.8 Hz, 1H), 6.57 (dd, J=3.4, 0.8 Hz, 1H), 6.46 (dd, J=3.4, 1.8 Hz, 1H), 5.85 (s, 1H), 4.86 (br s)

Intermediate Y2: Ethyl 2-(2-furyl)-7-hydroxy-pyrazolo[1,5-a]pyrimidine-5-carboxylate

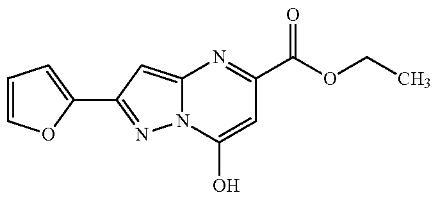

The title compound was prepared from 3-(2-furyl)-1H-pyrazol-5-amine (Intermediate Y1) and diethyl acetylenedicarboxylate analogously to Intermediate A2.

LC-MS (Method 3A): Rt 1.31 mins; MS m/z 274.0=[M+H]+

$^1$H NMR (500 MHz, DMSO-$d_6$) δ 12.94 (s, 1H), 7.85 (dd, J=1.9, 0.8 Hz, 1H), 7.06 (dd, J=3.4, 0.8 Hz, 1H), 6.66 (dd, J=3.4, 1.9 Hz, 1H), 6.48 (s, 1H), 6.31 (s, 1H), 4.41 (q, J=7.1 Hz, 2H), 1.36 (t, J=7.1 Hz, 3H).

Intermediate Y3: Ethyl 7-chloro-2-(2-furyl)pyrazolo[1,5-a]pyrimidine-5-carboxylate

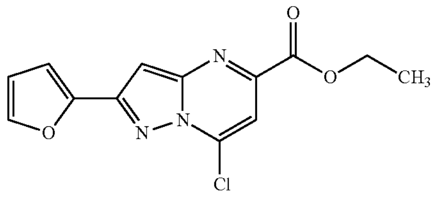 [SMILES: CCOC(=O)c1cc(Cl)n2nc(-c3ccco3)cc2n1]

The title compound was prepared from ethyl 2-(2-furyl)-7-hydroxy-pyrazolo[1,5-a]pyrimidine-5-carboxylate (Intermediate Y2) and $POCl_3$ analogously to Intermediate A3.

$^1$H NMR (500 MHz, Chloroform-d) 6 7.72 (s, 1H), 7.61 (dd, J=1.8, 0.8 Hz, 1H), 7.23 (s, 1H), 7.08 (dd, J=3.4, 0.8 Hz, 1H), 6.58 (dd, J=3.4, 1.8 Hz, 1H), 4.55 (q, J=7.1 Hz, 2H), 1.49 (t, J=7.1 Hz, 3H).

Intermediate Y4: Ethyl 2-(2-furyl)pyrazolo[1,5-a]pyrimidine-5-carboxylate

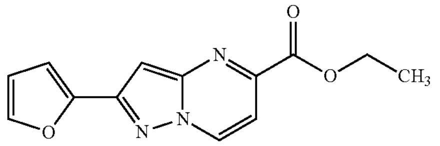 [SMILES: CCOC(=O)c1ccn2nc(-c3ccco3)cc2n1]

The title compound was prepared from ethyl 7-chloro-2-(2-furyl)pyrazolo[1,5-a]pyrimidine-5-carboxylate (Intermediate Y3) (615 mg, 2.11 mmol) and 10 wt % Pd on carbon analogously to Intermediate A4.

LC-MS (Method 8A): Rt 4.07 mins; MS m/z 258.0=[M+H]+

$^1$H NMR (500 MHz, DMSO-$d_6$) δ 9.27 (dd, J=7.2, 1.0 Hz, 1H), 7.90 (dd, J=1.8, 0.8 Hz, 1H), 7.53 (d, J=7.2 Hz, 1H), 7.24 (d, J=1.0 Hz, 1H), 7.11 (dd, J=3.3, 0.8 Hz, 1H), 6.70 (dd, J=3.3, 1.8 Hz, 1H), 4.40 (q, J=7.1 Hz, 2H), 1.37 (t, J=7.1 Hz, 3H).

Intermediate Y: 2-(2-Furyl)pyrazolo[1,5-a]pyrimidine-5-carboxylic acid

To a solution of ethyl 2-(2-furyl)pyrazolo[1,5-a]pyrimidine-5-carboxylate (Intermediate Y4) (405 mg, 1.56 mmol) in THF (10 mL) was added LiGH (74 mg, 3.12 mmol) in water (10 mL) and the mixture was stirred at room temperature for 2 h. The resulting mixture was acidified with 2M HCl before the THF was removed in vacuo. The resulting yellow precipitate was collected by filtration, azeotroped with MeOH and dried to afford the title compound as a yellow solid.

LC-MS (Method 8A): Rt 3.25 mins; MS m/z 230.1=[M+H]+

$^1$H NMR (500 MHz, DMSO-$d_6$) b 13.82 (s, 1H), 9.24 (dd, J=7.2, 1.0 Hz, 1H), 7.89 (dd, J=1.8, 0.8 Hz, 1H), 7.52 (d, J=7.2 Hz, 1H), 7.20 (d, J=1.0 Hz, 1H), 7.11 (dd, J=3.4, 0.8 Hz, 1H), 6.70 (dd, J=3.4, 1.8 Hz, 1H).

Intermediate Z -5-Amino-3-(3-cyanophenyl)-1H-pyrazole-4-carbonitrile

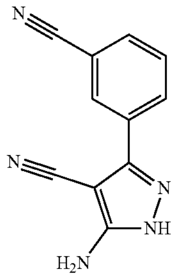 [SMILES: N#Cc1cccc(-c2n[nH]c(N)c2C#N)c1]

Intermediate Z1: 2-[(3-Cyanophenyl)-hydroxy-methylene]propanedinitrile

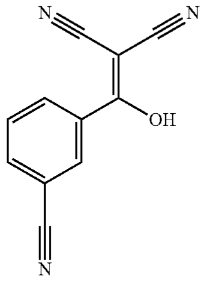 [SMILES: N#CC(C#N)=C(O)c1cccc(C#N)c1]

A solution of propanedinitrile (761 μL, 12.08 mmol) and DIPEA (4.21 mL, 24.16 mmol) in THE (50 mL) at 0° C. was stirred for 30 mins and then treated portonwise with 3-cyanobenzoyl chloride (2 g, 12.08 mmol) over 30 mins. After stirring at room temperature for 90 mins, the mixture was partitioned between EtOAc (50 mL) and 2M HCl (25 mL). The organic phase was separated and washed with brine (25 mL), dried over $MgSO_4$ and concentrated in vacuo to afford the title compound as a yellow solid.

LC-MS (Method 3A): Rt 1.55 mins; MS m/z 194.0=[M−H]−

1H NMR (500 MHz, DMSO-d6) b 7.92-7.90 (m, 1H), 7.88-7.86 (m, 1H), 7.86-7.85 (m, 1H), 7.59 (td, 1H). OH proton not observed.

Intermediate Z2: 2-[Chloro-(3-cyanophenyl)methylene]propanedinitrile

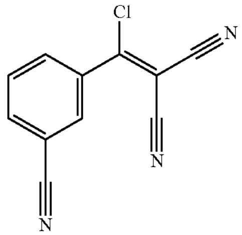 [SMILES: N#CC(C#N)=C(Cl)c1cccc(C#N)c1]

A solution of 2-[(3-cyanophenyl)-hydroxy-methylene] propanedinitrile (Intermediate Z1) (2.5 g, 12.81 mmol) in $POCl_3$ (11.94 mL, 128.09 mmol) was heated to 110° C. for 16 h. After cooling to room temperature, the solvent was removed in vacuo. The resulting crude mixture was dissolved in EtOAc (100 mL) and washed with sat. $NaHCO_3$ solution. The organic portion was separated, dried and concentrated in vacuo to afford the title compound as a brown solid.

LC-MS (Method 3A): Rt 1.60 mins; MS m/z 194=[M−Cl+OH−H]−

1H NMR (500 MHz, Chloroform-d) δ 8.07-8.03 (m, 2H), 7.93 (dt, J=7.8, 1.3 Hz, 1H), 7.75-7.70 (m, 1H).

Intermediate Z: 5-Amino-3-(3-cyanophenyl)-1 H-pyrazole-4-carbonitrile

To a solution of 2-[chloro-(3-cyanophenyl)methylene] propanedinitrile (Intermediate Z2) (2.63 g, 12.31 mmol) in methanol (60 mL) at 0° C. was added hydrazine hydrate (2.99 mL, 61.56 mmol) dropwise and the mixture was stirred at ambient temperature for 16 h. The solvent was removed in vacuo and purification of the crude product by chromatography on silica eluting with 80% to 100% EtOAc in petrol afforded the title compound as a pale yellow solid.

LC-MS (Method 3A): Rt 1.23 mins; MS m/z 210=[M+H]+

1H NMR (500 MHz, DMSO-d6) δ 12.37 (s, 1H), 8.14-8.12 (m, 1H), 8.10 (d, J=7.9 Hz, 1H), 7.87 (d, J=7.7 Hz, 1H), 7.69 (t, J=7.7 Hz, 1H), 6.61 (s, 2H).

Intermediate ZA -1-Aminooxy-2-methyl-propan-2-ol

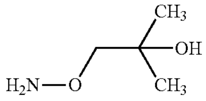

Intermediate ZA1: 2-(2-Hydroxy-2-methyl-propoxy) isoindoline-1,3-dione

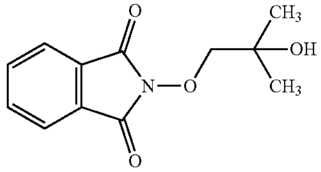 [SMILES: CC(C)(O)CON1C(=O)c2ccccc2C1=O]

To 2-hydroxyisoindoline-1,3-dione (4.98 g, 30.51 mmol) and triethylamine (4.64 mL, 33.28 mmol) in MeCN (10 mL) was added 2,2-dimethyloxirane (2.5 mL, 27.74 mmol) and the reaction mixture was stirred at 85° C. After 18 h, the resulting mixture was diluted with water (100 mL) and extracted with ethyl acetate (3×70 mL). The combined organic extracts were dried over $MgSO_4$, filtered and concentrated in vacuo. The crude product was treated with DCM (100 mL) forming of a white precipitate. The white precipitate was removed by filtration and the filtrate concentrated to dryness. The crude product was dry loaded onto Celite® and purified by chromatography on silica eluting with a gradient of 0 to 10% MeOH in DCM to afford the title compound.

MS18 LC-MS (Method 2A): Rt 0.97 mins; MS m/z 257.95=[M+Na]+

1H NMR (500 MHz, DMSO-d6) δ 7.85 (s, 4H), 4.66 (s, 1H), 3.94 (s, 2H), 1.23 (s, 6H).

Intermediate ZA: 1-aminooxy-2-methyl-propan-2-ol

To a solution of 2-(2-hydroxy-2-methyl-propoxy)isoindoline-1,3-dione (Intermediate ZA1)(22.69 g, 90.68 mmol) in DCM (200 mL) at 0° C. was added hydrazine hydrate (6 mL, 123.33 mmol) and the mixture was stirred at 0° C. for 2 h. The resulting mixture was filtered and the filtrate was concentrated in vacuo. The crude product was loaded onto an Isolute SCX cartridge, pre-wetted with MeOH and eluted with 7M $NH_3$ in MeOH to afford the title compound as a yellow oil.

1H NMR (400 MHz, Chloroform-d) δ 3.55 (s, 2H), 1.20 (s, 6H). Exchangeable protons not observed.

Intermediate ZB—cis-4-Amino-3-methyl-tetrahydrofuran-3-ol hydrochloride

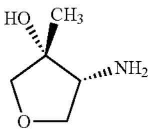

HCl

Intermediate ZB1: cis-tert-Butyl N-[4-hydroxy-4-methyl-tetrahydrofuran-3-yl]carbamate and

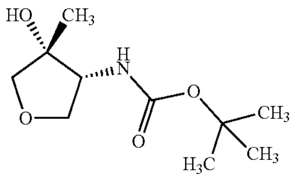

Intermediate ZB2: trans-tert-butyl N-[-4-hydroxy-4-methyl-tetrahydrofuran-3-yl]carbamate

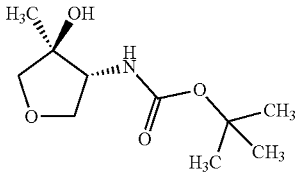

[001211]The title compound (Intermediate ZB) was prepared according to the procedure detailed by P. K. Jadhav, A. Saeed, J. E. Green, V. Krishnan, D. P. Matthews, and G. A. Stephenson in WO2013055577.

A solution of methylmagnesium bromide (3.4M in 2-Me-THF, 2.19 mL, 7.45 mmol) was added dropwise via syringe over 5 mins to a stirred solution of tert-butyl N-(4-oxotetrahydrofuran-3-yl)carbamate (500 mg, 2.48 mmol) in anhydrous THF (10 mL) under nitrogen at 0° C. Once the addition was complete, the resulting solution was stirred at 0° C. for a further 5 mins before the ice bath was removed and the mixture stirred at room temperature for 2 days. Additional methylmagnesium bromide (3.4M in 2-Me-THF, 1.46 mL, 4.97 mmol) was added and stirring continued for 5 h. The reaction was quenched by addition of saturated aqueous $NH_4Cl$ (2.5 mL) and water 50 mL). The aqueous layer was extracted with EtOAc (3×50 mL) and the combined organic portions were dried over $MgSO_4$, filtered and concentrated in vacuo. Purification by chromatography on silica eluting with a gradient of 10 to 50% EtOAc in 1:1 DCM/hexane afforded:

Intermediate ZB1: cis-tert-Butyl N-[4-hydroxy-4-methyl-tetrahydrofuran-3-yl]carbamate as a yellow solid 1H NMR (500 MHz, Chloroform-d) 64.99 (s, 1H), 4.14 (t,J=0.8.3 Hz, 1H), 4.00 (d, J=8.2 Hz, 1H), 3.79 (d, J=9.8 Hz, 1H), 3.72 (d, J=9.8 Hz, 1H), 3.57 (t, J=8.4 Hz, 1H), 1.45 (s, 9H), 1.36 (s, 3H). 1 proton not observed.

The column was then flushed with 100% EtOAc to afford: Intermediate ZB2: trans-tert-Butyl N-[-4-hydroxy-4-methyl-tetrahydrofuran-3-yl]carbamate as a yellow oil.

1H NMR (500 MHz, Chloroform-d) δ 4.64 (s, 1H), 4.26 (dd, J=9.2, 6.9 Hz, 1H), 4.07 (q,J=6.5 Hz, 1H), 3.80 (d, J=9.3 Hz, 1H), 3.65 (d, J=9.3 Hz, 1H), 3.51 (dd, J=9.2, 5.5 Hz, 1H), 1.45 (s, 9H), 1.32 (s, 3H). 1 proton not observed.

Intermediate ZB: (3R,4R)-4-Amino-3-methyl-tetrahydrofuran-3-ol hydrochloride

To a solution of tert-butyl N-[(3R,4R)-4-hydroxy-4-methyl-tetrahydrofuran-3-yl]carbamate (96 mg, 0.4400 mmol) (Intermediate ZB1) in 1,4-dioxane (1 mL) and MeOH (0.2 mL) was slowly added 4N HCl in 1,4-dioxane (1.1 mL, 4.42 mmol) and the reaction mixture was stirred at room temperature for 4 h. The resulting mixture was concentrated in vacuo to afford the title compound as a brown oil.

1H NMR (500 MHz, DMSO-d6) δ 8.12-7.96 (m, 2H), 5.73 (s, 1H), 3.98 (dd, J=9.5, 7.2 Hz, 1H), 3.69 (d, J=9.2 Hz, 1H), 3.68-3.64 (m, 1H), 3.56-3.55 (m, 1H), 1.32 (s, 3H). 2× protons not observed Intermediate ZC—trans-4-Amino-3-methyl-tetrahydrofuran-3-ol hydrochloride

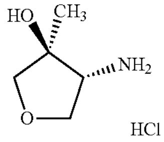

The title compound (Intermediate Z C) was prepared according to the procedure detailed by P. K. Jadhav, A. Saeed, J. E. Green, V. Krishnan, D. P. Matthews, and G. A. Stephenson in WO2013055577.

The title compound was prepared from tert-butyl N-[(3R, 4S)-4-hydroxy-4-methyl-tetrahydrofuran-3-yl]carbamate (Intermediate ZB2) and 4N HCl in 1,4-dioxane analogously to Intermediate ZB.

1H NMR (500 MHz, Methanol-d4) δ 4.27 (dd, J=10.4, 5.2 Hz, 1H), 3.85-3.75 (m, 3H), 3.52 (dd, J=5.3, 2.3 Hz, 1H), 1.43 (s, 3H). Exchangeable protons not observed.

Intermediate ZD -6-Methyl-2-pyridyl)methoxy-tert-butyl-dimethyl-silane boronic ester

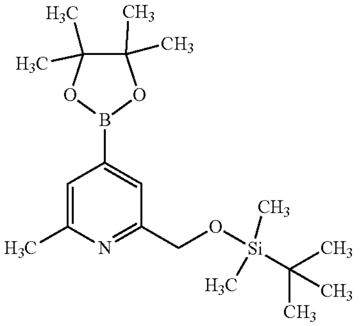 [SMILES: Cc1cc(B2OC(C)(C)C(C)(C)O2)cc(CO[Si](C)(C)C(C)(C)C)n1]

Intermediate ZD1: 4-Bromo-2-({[(1,1-dimethylethyl)dimethylsilyl]oxy]methyl]-6methylpyridine

B

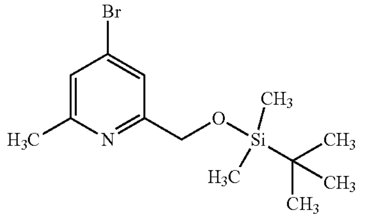

To a solution of (4-bromo-6-methyl-2-pyridyl)methanol (2 g, 9.9 mmol) in DMF (15 mL) at 0° C. was added imidazole (0.03 mL, 12.87 mmol) followed by tert-butyldimethylsilyl chloride (1.11 mL, 10.89 mmol) and the reaction mixture was stirred at room temperature for 1 h. The resulting mixture was partitioned between EtOAc (150 mL) and $H_2O$ (150 mL) and the layers were separated. The aqueous was further extracted with EtOAc (100 mL) and the combined organic extracts were washed with sat. $NaHCO_3$ (150 mL), brine (150 mL), dried over $MgSO_4$, filtered and concentrated in vacuo to afford the title compound as a yellow semi-solid.

1H NMR (500 MHz, DMSO-d6) δ 7.45 (d, J=0.8 Hz, 1H), 7.38 (s, 1H), 4.70 (s, 2H), 2.43 (s, 3H), 0.91 (s, 9H), 0.10 (s, 6H).

Intermediate ZD: 2-[[[(1,1-Dimethylethyl)dimethylsilyl]oxy]methyl]-6-methyl-4-(4,4,5,5-tetramethyl-1,3,2-dioxaborolan-2-yl)pyridine A solution of (4-bromo-6-methyl-2-pyridyl)methoxy-tert-butyl-dimethyl-silane (Intermediate ZD1)(2.96 g, 9.35 mmol), bis(pinacolato)diboron (3.56 g, 14.02 mmol), potassium acetate (5.16 g, 37.39 mmol) and Pd(dppf)$Cl_2$ (889 mg, 1.22 mmol) in 1,4-dioxane (45 mL) was heated to 80° C. overnight. The resulting mixture was concentrated in vacuo, redissolved in DCM/hexane and filtered through Celite® (filter material), eluting with hexane. The filtrate was concentrated in vacuo to afford the title compound as a brown solid.

1H NMR (500 MHz, DMSO-d6) δ 7.46 (s, 1H), 7.31 (s, 1H), 4.71 (s, 2H), 2.44 (s, 3H), 1.30 (s, 12H), 0.91 (s, 9H), 0.09 (s, 6H).

Intermediate ZE -3-Fluoro-2,6-dimethyl-4-(4,4,5,5-tetramethyl-1,3,2-dioxaborolan-2-yl)pyridine

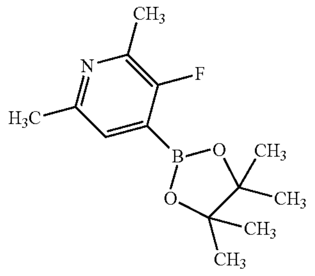

A mixture of 4-bromo-3-fluoro-2,6-dimethyl-pyridine (350 mg, 1.72 mmol), 4,4,5,5-tetramethyl-2-(4,4,5,5-tetramethyl-1,3,2-dioxaborolan-2-yl)-1,3,2-dioxaborolane (523 mg, 2.06 mmol) and potassium acetate (505 mg, 5.15 mmol) in 1,4-dioxane (6 mL) was degassed under a flow of nitrogen. Pd(dpp)$Cl_2$ (126 mg, 0.17 mmol) was added and the reaction mixture was heated to 100° C. overnight. After cooling to room temperature, the resulting mixture was filtered through Celite® (filter material), eluting with EtOAc (2×30 mL).

The filtrate was concentrated in vacuo to afford the title compound as a brown oil.

1H NMR (500 MHz, DMSO-d6) δ 7.20 (d, J=3.8 Hz, 1H), 2.40-2.32 (m, 6H), 1.23 (s, 12H).

Intermediate ZF -(2S)-3,3,3-Trifluoro-2-hydroxy-2-methyl-propanamide

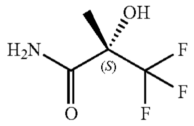

Intermediate ZF1: (2S)-2-Acetoxy-3,3,3-trifluoro-2-methyl-propanoic acid

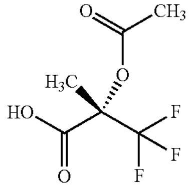

Acetyl chloride (90 μL, 1.27 mmol) was added dropwise to a stirred solution of (2S)-3,3,3-trifluoro-2-hydroxy-2-methyl-propanoicacid (100 mg, 0.63 mmol) in anhydrous THF (6 mL) at 0° C. under nitrogen. The ice bath was removed and the mixture was stirred at room temperature for 1 h. The resulting mixture was concentrated in vacuo to afford the title compound as a colourless solid.

1H NMR (500 MHz, CDCl3) δ 3.87-3.81 (m, 3H), 1.95-1.89 (m, 3H). Carboxylic acid proton not observed.

Intermediate ZF2: [(1R)-1-Chlorocarbonyl-2,2,2-trifluoro-1-methyl-ethyl]acetate

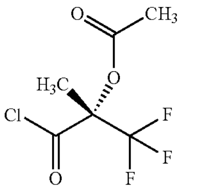

Oxalyl chloride (60 μL, 0.71 mmol) was added dropwise to a stirred solution of (2S)-2-acetoxy-3,3,3-trifluoro-2-methyl-propanoic acid (Intermediate ZF1)(121 mg, 0.6 mmol) and DMF (1 drop) in anhydrous THF (5 mL) at 0° C. under nitrogen. The mixture was stirred and allowed to warm to 5° C. over the course of 1 h. The resulting mixture was concentrated in vacuo to afford the title compound as a colourless oil.

1H NMR (500 MHz, CDCl3) δ 3.78-3.71 (m, 3H), 1.89-1.82 (m, 3H).

Intermediate ZF: (2S)-3,3,3-Trifluoro-2-hydroxy-2-methyl-propanamide 0.4M Ammonia solution in THF (7.44 mL, 2.97 mmol) was added via syringe to a cooled (0° C.), stirred solution of [(1R)-1-chlorocarbonyl-2,2,2-trifluoro-1-methyl-ethyl]acetate (Intermediate ZF2) (130 mg, 0.59 mmol) in anhydrous THF (3 mL) under nitrogen. The reaction mixture was allowed to warm to room temperature, stirring for 30 mins. The resulting mixture was concentrated in vacuo and purification by chromatography on silica eluting with 5% MeOH in DCM to afforded the title compound as a white solid.

1H NMR (500 MHz, CDCl3) δ 6.14 (br s, 1H), 5.69 (br s, 1H), 3.95 (s, 1H), 1.63 (s, 3H).

Intermediate ZG -3-(2-cyanoacetyl)-2-methyl-benzonitrile

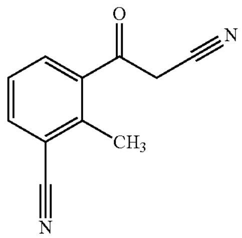

Intermediate ZG1- methyl 3-cyano-2-methyl-benzoate

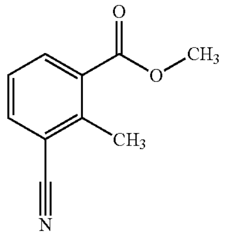

To a flask was added methyl 3-bromo-2-methylbenzoate (21 g, 91.7 mmol), potassium hexacyanoferrate (II) trihydrate (9.7 g, 22.9 mmol), $Na_2CO_3$ (9.7 g, 91.7 mmol) and $Pd(OAc)_2$ (102 mg) in N,N-dimethylacetamide (100 mL). The mixture was degassed under nitrogen, and the reaction mixture heated at 120° C. for 16h. Additional $Pd(OAc)_2$ (205.82 mg, 0.9200 mmol) and Potassium hexacyanoferrate (II) trihydrate (2. g, 4.73 mmol) were added to the reaction mixture and the mixture was stirred at 120° C., After a further 4.5 h, additional $Pd(OAc)_2$ (205.82 mg, 0.9200 mmol) and Potassium hexacyanoferrate(II) trihydrate (2. g, 4.73 mmol) were added and the reaction was stirred at 120° C. for a further 16 h. The mixture was cooled to room temperature and ethyl acetate (150 mL) was added. The slurry was filtered, washing the collected solid with ethyl acetate (2×50 mL). The filtrate was washed with 50% brine (3×100 mL) before being dried over magnesium sulfate, filtered and concentrated in vacuo. Fine needles formed from the crude mixture which were collected by filtration, washed with diethyl ether (3×5 mL) and dried to afford the title compound as an off-white solid. Additional material could be obtained by concentrating the combined filtrates and collecting the formed solids by filtration.

LC-MS (Method 5B): Rt 2.36 mins; no ionization observed.

$^1H$ NMR (500 MHz, DMSO-$d_6$) δ 8.07 (d, J=7.8 Hz, 1H), 8.01 (d, J=7.8 Hz, 1H), 7.52 (t, J=7.8 Hz, 1H), 3.87 (s, 3H), 2.68 (s, 3H).

Intermediate ZG—3-(2-cyanoacetyl)-2-methyl-benzonitrile

To a solution of acetonitrile (2.97 mL, 56.86 mmol) in THF (50 mL) was added sodium hydride (60% in mineral oil) (2.08 g, 52.12 mmol) and the mixture was stirred at room temperature for 15 min. A solution of methyl 3-cyano-2-methyl-benzoate (Intermediate ZG1) (8.3 g, 47.38 mmol) in THE (20 mL) was then added dropwise and the reaction mixture was stirred at room temperature overnight. The formed precipitate was collected by filtration and washed with THE (2×10 mL). The solid was added to water (75 mL) before 2M aq. HCl was added to acidify the solution. The cream precipitate was then collected by filtration, washed with water (2×20 mL) and concentrated in vacuo from MeOH to afford the title compound as a cream solid.

LC-MS (Method 3A): Rt 1.40 mins; MS m/z 183.1=[M−H]−

Intermediate ZH—2-[(2R)-piperazin-2-yl]propan-2-ol dihydrochloride

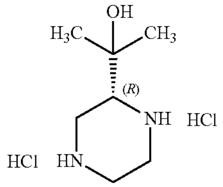

Intermediate ZH1-1,4-di-tert-butyl 2-methyl(2R)-piperazine-1,2,4-tricarboxylate

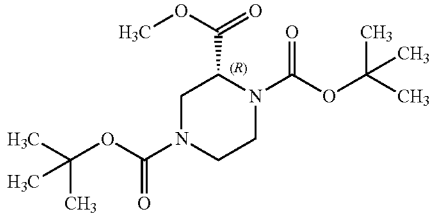

A mixture of di-tert-butyl dicarbonate (982.75 mg, 4.5 mmol), 1-tert-butyl 2-methyl(2R)-piperazine-1,2-dicarboxylate (1.0 g, 4.09 mmol) and triethylamine (0.8 mL, 5.73 mmol) in DCM (25 mL) was stirred at room temperature for 2 h. The reaction mixture was diluted with DCM (50 mL) and washed with $NaHCO_3$ (40 mL). The organic phase was dried over $MgSO_4$ and concentrated in vacuo to afford the title compound as a clear oil which solidified on standing.

1H NMR (500 MHz, DMSO-d6) δ 4.62-4.50 (m, 1H), 4.28 (dd, J=31.6, 13.8 Hz, 1H), 3.83 (s, 1H), 3.68 (s, 3H), 3.22-2.67 (m, 4H), 1.42-1.33 (m, 18H).

Intermediate ZH2- di-tert-butyl(2R)-2-(1-hydroxy-1-methyl-ethyl)piperazine-1,4-dicarboxylate

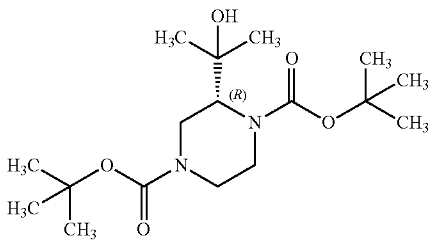

To a solution of 1,4-di-tert-butyl 2-methyl(2R)-piperazine-1,2,4-tricarboxylate (Intermediate ZH1)(1.65 g, 4.79 mmol) in THF (40 mL) at 0° C. was added MeMgCl (3 M in THF) (3.99 mL, 11.98 mmol) dropwise. The reaction was allowed to warm to room temperature and was stirred at this temperature for 3 h. $NH_4Cl$ (30 mL) was added cautiously and the THF was removed in vacuo. The aq. fraction was extracted with DCM (3×50 mL) and the combined organic extracts were dried over $MgSO_4$ and concentrated in vacuo. Purification by chromatography on silica eluting with a gradient of 1 to 2% MeOH in DCM afforded the title compound as a clear oil.

1H NMR (500 MHz, DMSO-d6) δ 4.40 (s, 1H), 3.98-3.51 (m, 4H), 3.17-3.12 (m, 2H), 2.99-2.84 (m, 1H), 1,39 (m, 18H), 1.20-0.94 (m, 6H).

Intermediate ZH—2-[(2R)-piperazin-2-yl]propan-2-ol dihydrochloride

To a solution of di-tert-butyl(2R)-2-(1-hydroxy-1-methyl-ethyl)piperazine-1,4-dicarboxylate (Intermediate ZH2)(795, mg, 2.31 mmol) in MeOH (15 mL) was added HCl (4 N in dioxane) (3.46 mL, 17.31 mmol) and the reaction mixture was stirred at room temperature for 3 h. Additional HCl (4 N in dioxane) (3.46 mL, 17.31 mmol) was added and the reaction was stirred at room temperature for a further 2 h before being concentrated in vacuo to afford the title compound as a white solid.

1H NMR (500 MHz, DMSO-d6) δ 10.04-8.95 (m, 4H), 5.57 (s, 1H), 3.60-3.53 (m, 1H), 3.42 (m, 3H), 3.49-3.38 (m, 2H), 2.99 (t, J=12.8 Hz, 1H), 1.26 (s, 3H), 1.20 (s, 3H).

Intermediate ZI—2-[(2S)-piperazin-2-yl]propan-2-ol dihydrochloride

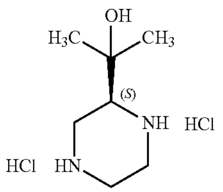

Intermediate ZI1-1,4-di-tert-butyl 2-methyl(2S)-piperazine-1,2,4-tricarboxylate

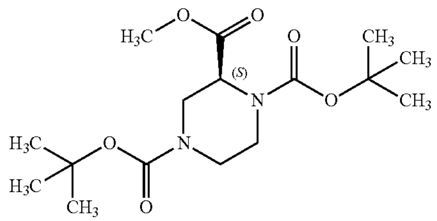

The title compound was prepared analogously to 1,4-di-tert-butyl 2-methyl(2R)-piperazine-1,2,4-tricarboxylate (Intermediate ZH1) using 1-tert-butyl 2-methyl(2S)-piperazine-1,2-dicarboxylate and di-tert-butyl dicarbonate.

1H NMR (500 MHz, DMSO-d6) δ 4.56 (d, J=37.3 Hz, 1H), 4.28 (dd, J=31.7, 13.8 Hz, 1H), 3.83 (s, 1H), 3.68 (s, 3H), 3.23-2.72 (m, 4H), 1.44-1.31 (m, 18H).

Intermediate ZI2- di-tert-butyl(2S)-2-(1-hydroxy-1-methyl-ethyl)piperazine-1,4-dicarboxylate

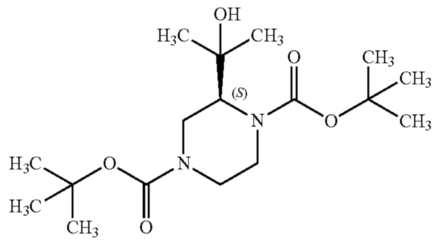

The title compound was prepared analogously to di-tert-butyl(2R)-2-(1-hydroxy-1-methyl-ethyl)piperazine-1,4-dicarboxylate (Intermediate ZH2) using 1,4-di-tert-butyl 2-methyl(2S)-piperazine-1,2,4-tricarboxylate (Intermediate ZI1) and MeMgBr.

1H NMR (500 MHz, DMSO-d6) δ 4.39 (s, 1H), 4.03-3.43 (m, 4H), 3.17-3.04 (m, 2H), 3.01-2.82 (m, 1H), 1.39 (s, 18H), 1.17-1.01 (m, 6H) Intermediate ZI—2-[(2S)-piperazin-2-yl]propan-2-ol dihydrochloride The title compound was prepared analogously to 2-[(2R)-piperazin-2-yl]propan-2-ol dihydrochloride (Example ZH) using di-tert-butyl(2S)-2-(1-hydroxy-1-methyl-ethyl)piperazine-1,4-dicarboxylate (Intermediate ZI2) and 4M HCl in dioxane.

1H NMR (500 MHz, DMSO-d6) δ 9.67 (s, 2H), 9.41 (s, 1H), 9.07 (s, 1H), 5.57 (s, 1H), 3.62-3.53 (m, 1FH), 3.49-3.38 (m, 3H), 3.29-3.21 (m, 2H), 2.98 (t, J=12.8 Hz, 1H), 1.26 (s, 3H), 1.19 (s, 3H).

BIOLOGICAL EXAMPLES

Biological Example 1—Adenosine receptor time-resolved fluorescence resonance energy transfer (TRFRET) binding assay All FRET binding experiments were conducted at room temperature in white 384-well plates, in assay binding buffer containing 1× LabMed (Cisbio, France), 100μg/mL saponin, 1% DMSO and 0.02% pluronic acid. Binding of the fluorescently labelled Adenosine receptor antagonist XAC (CA200645, FRET acceptor) to terbium-labelled A1, A2a, A2b and A3 adenosine receptors (FRET donors) was detected by time-resolved FRET due to the close proximity of the donor and acceptor in a binding event. To investigate the ability of unlabelled test compounds to bind to Adenosine A1, A2a, A2b and A3 receptors, dose response curves were constructed that determined the ability of a range of concentrations to inhibit the binding of 30 nM CA200645 to the A2b receptor and 100 nM CA200645 to the A1, A2a, and A3 receptor.

Serial dilution (1:3 dilutions) of test compounds in neat DMSO and transfer of a 400 nL sample of test compound into the assay plate was carried out using the Mosquito (TTP Labtech, UK). The compound samples were incubated for 2 hours at room temperature with a fixed concentration of CA200645 defined for each receptor (see above) and CHO cell membranes containing the human Adenosine A1 (0.5 µg/well), A2a (0.3 µg/well), A2b (1 µg/well) or A3 (1 µg/well) receptor in 40 µL of assay buffer. Total and non-specific binding of CA200645 was determined in the absence and presence of 10 µM XAC, respectively. Following 2 hours incubation, the level of CA200645 binding was detected on a Pherastar FSX (BMG Labtech, Germany) using standard TR-FRET settings. The terbium donor was excited with three laser flashes at a wavelength of 337 nm, and donor and acceptor emission was detected at 620 nm and 665 nm wavelengths, respectively. FRET ratios were obtained by multiplying the acceptor/donor ratio value by 10,000. Specific binding was determined by subtracting the non-specific binding FRET ratio from the total binding FRET ratio. Compound IC50 curves were analysed using GraphPad Prism 7.0 (GraphPad, USA) and Ki affinity values were determined from the obtained IC50 values using the method of Cheng and Prusoff. The results are presented in Table 1.

TABLE 1

| Example Number | A2a Ki (nM) | A2b Ki (nM) | A1 Ki (nM) | A3 Ki (nM) |
|---|---|---|---|---|
| 1 | 2.1 | 2 | 3 | 147 |
| 1.1 | 146.8 | 239 | 95 | 613 |
| 1.2 | 13.9 | 29 | 20 | 646 |
| 1.3 | 74.8 | 16 | 197 | >1000 |
| 1.4 | 2.6 | 4 | 66 | >1000 |
| 1.6 | 2.2 | 9 | 37 | >1000 |
| 2 | 3.9 | 67 | 366 | >1000 |
| 2.1 | 0.4 | 3 | 21 | >1000 |
| 2.2 | 0.5 | 45 | 5 | >1000 |
| 2.3 | 0.6 | 4 | 21 | 1279 |
| 2.4 | 0.7 | 2 | 53 | >1000 |
| 2.5 | 0.9 | 1 | 24 | >1000 |
| 2.6 | 1.0 | 12 | 87 | >1000 |
| 2.7 | 1.3 | 57 | 76 | >1000 |
| 2.8 | 1.3 | 3 | 62 | >1000 |
| 2.9 | 1.4 | 19 | 31 | >1000 |
| 2.10 | 1.4 | 10 | 119 | 1550 |
| 2.11 | 1.5 | 34 | 176 | >1000 |
| 2.12 | 1.5 | 22 | 87 | 2326 |
| 2.13 | 71.4 | 1309 | 1393 | >1000 |
| 2.14 | 1.5 | 8 | 29 | >1000 |
| 2.15 | 2.0 | 239 | 896 | >1000 |
| 2.16 | 2.1 | 4 | 232 | >1000 |
| 2.17 | 2.4 | 6 | 45 | >1000 |
| 2.18 | 2.6 | 10 | 192 | 2434 |
| 2.19 | 2.8 | 21 | 32 | >1000 |
| 2.20 | 3.4 | 18 | 263 | >1000 |
| 2.21 | 4.6 | 19 | 178 | >1000 |
| 2.22 | 6.2 | 48 | 109 | >1000 |
| 2.23 | 6.4 | 3 | 55 | >1000 |
| 2.24 | 6.9 | 58 | 255 | 2559 |

TABLE 1-continued

| Example Number | A2a Ki (nM) | A2b Ki (nM) | A1 Ki (nM) | A3 Ki (nM) |
|---|---|---|---|---|
| 2.25 | 7.5 | 27 | 674 | >1000 |
| 2.26 | 7.7 | 23 | 366 | >1000 |
| 2.27 | 10.7 | 43 | 317 | >1000 |
| 2.28 | 11.6 | 2 | 81 | >1000 |
| 2.29 | 11.8 | 21 | 124 | >1000 |
| 2.30 | 15.8 | 55 | 450 | >1000 |
| 2.31 | 15.8 | 70 | 551 | >1000 |
| 2.32 | 17.1 | 102 | 593 | >1000 |
| 2.33 | 22.5 | 212 | | 1996 |
| 2.34 | 22.5 | 163 | 234 | >1000 |
| 2.35 | 23.3 | 259 | 305 | 2528 |
| 2.36 | 25.1 | 430 | 179 | >1000 |
| 2.37 | 26.5 | 9 | 1415 | >1000 |
| 2.38 | 45.3 | 346 | 837 | >1000 |
| 2.39 | 1.4 | 2 | 241 | >1000 |
| 2.40 | 5.7 | 23 | 145 | >1000 |
| 2.41 | 1.7 | 2 | 82 | >1000 |
| 2.42 | 0.5 | 4 | 149 | >1000 |
| 3 | 0.6 | 1 | 74 | >1000 |
| 3.1 | 2.2 | 5 | 58 | 2595 |
| 3.2 | 12.0 | 113 | | >1000 |
| 3.3 | 0.3 | 2 | 6 | >1000 |
| 3.4 | 0.4 | 2 | 56 | 2451 |
| 4 | 0.1 | 3 | 15 | >1000 |
| 4.1 | 38.5 | 163 | 522 | >1000 |
| 4.2 | 1.2 | 34 | 32 | >1000 |
| 4.3 | 1.2 | 3 | 8 | >1000 |
| 4.4 | 3.2 | 149 | 1102 | >1000 |
| 4.5 | 4.2 | 25 | 189 | >1000 |
| 4.6 | 5.1 | 4 | 230 | >1000 |
| 4.7 | 13.9 | 6 | 213 | >1000 |
| 4.8 | 0.5 | 6 | 7 | >1000 |
| 4.9 | 1.1 | 12 | 5 | >1000 |
| 4.10 | 3.3 | 12 | 43 | >1000 |
| 4.11 | 6.8 | 1 | 53 | >1000 |
| 5 | 0.8 | 9 | 296 | >1000 |
| 5.1 | 0.1 | 16 | 477 | >1000 |
| 5.2 | 0.2 | 24 | 294 | >1000 |
| 5.3 | 0.3 | 20 | 224 | >1000 |
| 5.4 | 1.3 | 19 | 107 | >1000 |
| 5.5 | 1.7 | 55 | 200 | >1000 |
| 5.6 | 4.6 | 16 | 303 | >1000 |
| 5.7 | 14.8 | 10 | 135 | >1000 |
| 5.8 | 5.7 | 41 | 418 | >1000 |
| 6 | 0.1 | 6 | 57 | 945 |
| 6.1 | 11.7 | 53 | 664 | >1000 |
| 6.2 | 0.3 | 10 | 122 | 2308 |
| 6.3 | 0.3 | 3 | 127 | >1000 |
| 6.4 | 0.6 | 30 | 402 | 1825 |
| 6.5 | 0.9 | 7 | 361 | >1000 |
| 6.6 | 0.9 | :35 | 390 | >1000 |
| 6.7 | 1.4 | 5 | 174 | >1000 |
| 6.8 | 8.3 | 39 | 522 | 2551 |
| 6.9 | 0.9 | 2 | 232 | >1000 |
| 6.10 | 2.5 | 24 | 581 | >1000 |
| 6.11 | 0.1 | 3 | 32 | 379 |
| 6.12 | 3.7 | 6 | 105 | >1000 |
| 6.13 | 1.7 | 17 | 424 | >1000 |
| 6.14 | 1.1 | 60 | 231 | >1000 |
| 6.15 | 0.7 | 3 | 115 | >1000 |
| 6.16 | 5.9 | 54 | 346 | >1000 |
| 6.17 | 0.5 | 3 | 110 | >1000 |
| 6.18 | 4.2 | 13 | 125 | >1000 |
| 6.19 | 0.3 | 22 | 456 | >1000 |
| 6.20 | 0.7 | 19 | 204 | >1000 |
| 6.21 | 0.1 | 17 | 252 | >1000 |
| 6.22 | 0.1 | 5 | 61 | 1907 |
| 6.23 | 0.4 | 74 | 223 | >1000 |
| 7 | 0.4 | 5 | 143 | >1000 |
| 7.1 | 2.0 | 17 | 245 | >1000 |
| 7.2 | 2.6 | 3 | 458 | >1000 |
| 7.3 | 2.9 | 15 | 44 | >1000 |
| 7.4 | 4.1 | 119 | 833 | >1000 |
| 7.5 | 5.5 | 5 | 612 | >1000 |
| 7.6 | 6.8 | 13 | 672 | >1000 |
| 7.7 | 14.9 | 12 | 413 | >1000 |
| 7.8 | 2.4 | 10 | 160 | >1000 |

TABLE 1-continued

| Example Number | A2a Ki (nM) | A2b Ki (nM) | A1 Ki (nM) | A3 Ki (nM) |
|---|---|---|---|---|
| 7.9 | 0.6 | 2 | 160 | >1000 |
| 7.10 | 4.3 | 19 | 181 | >1000 |
| 7.11 | 4.9 | 3 | 137 | >1000 |
| 7.12 | 44.3 | 20 | 459 | >1000 |
| 7.13 | 6.3 | 28 | 160 | >1000 |
| 7.14 | 2.8 | 32 | 249 | >1000 |
| 7.15 | 22.1 | 25 | 703 | >1000 |
| 7.16 | 17.7 | 54 | 418 | >1000 |
| 7.17 | 16.4 | 68 | 279 | >1000 |
| 7.18 | 1.0 | 14 | 20 | >1000 |
| 7.19 | 0.1 | 4 | 20 | 1415 |
| 8 | 9.9 | 41 | 291 | >1000 |
| 9 | 94.0 | 426 | | >1000 |
| 10 | 0.4 | 19 | 236 | >1000 |
| 12 | 144.6 | 240 | | >1000 |
| 12.1 | | 1575 | | 1740 |
| 12.2 | 2.9 | 21 | 5 | 56 |
| 12.3 | | 2307 | | >1000 |
| 12.4 | 0.1 | 12 | 148 | 1555 |
| 12.5 | | 1510 | 2384 | 1577 |
| 12.6 | 1.0 | 75 | 251 | 690 |
| 12.7 | 27.4 | 792 | 725 | 154 |
| 12.8 | 3.4 | 177 | 575 | >1000 |
| 12.9 | 0.1 | 6 | 47 | 860 |
| 13 | 67.1 | | | >1000 |
| 14 | 218.0 | | | >1000 |
| 15 | 1.2 | 9 | 46 | 1917 |
| 16 | 13.7 | 1 | 303 | 1178 |
| 16.1 | 1.4 | 8 | 116 | 2595 |
| 17 | 17.9 | 10 | 136 | >1000 |
| 18 | 9.7 | 16 | 54 | >1000 |
| 19 | 0.3 | 4 | 16 | 2605 |
| 20 | 11.6 | 22 | 573 | >1000 |
| 20.1 | 116.0 | 626 | 2526 | >1000 |
| 21 | 81.5 | 102 | 2442 | >1000 |
| 22 | 1.0 | 34 | 141 | >1000 |
| 23 | 0.6 | 53 | 42 | >1000 |
| 23.1 | 1.3 | 143 | 147 | >1000 |
| 23.2 | 1.9 | 168 | 280 | >1000 |
| 23.3 | 10.1 | 29 | 394 | >1000 |
| 23.4 | 10.2 | 90 | 163 | 1976 |
| 24 | 0.6 | 16 | 216 | >1000 |
| 24.1 | 3.3 | 29 | 9 | 1653 |
| 24.2 | 12.5 | 25 | | >1000 |
| 24.3 | 50.8 | 91 | | >1000 |
| 26 | 146.7 | 409 | 6 | 2431 |
| 26.1 | 1.5 | 2 | 17 | 2358 |
| 26.2 | 6.2 | 18 | 123 | 2520 |
| 26.3 | 7.2 | 12 | 44 | 2600 |
| 26.4 | 10.1 | 16 | 6 | 578 |
| 26.5 | 105.5 | 1200 | 89 | 749 |
| 27 | 1.8 | 2 | 4 | >1000 |
| 27.1 | 9.2 | 43 | 62 | >1000 |
| 27.2 | 13.3 | 39 | 17 | >1000 |
| 27.4 | 54.1 | 519 | 583 | >1000 |
| 27.5 | 359.6 | 108 | 46 | >1000 |
| 28 | 359.2 | 2458 | 1124 | >1000 |
| 29 | 15.2 | 56 | 144 | >1000 |
| 30 | 0.8 | 5 | 57 | >1000 |
| 30.1 | 1.3 | 5 | 26 | >1000 |
| 30.2 | 31.5 | 49 | 130 | >1000 |
| 30.3 | 1.8 | 14 | 47 | >1000 |
| 30.4 | 7.8 | 73 | 103 | >1000 |
| 30.5 | 8.4 | 28 | 262 | >1000 |
| 31 | 10.4 | 2 | 96 | >1000 |
| 31.1 | 10.8 | 15 | 200 | >1000 |
| 31.2 | 4.6 | 6 | 238 | >1000 |
| 31.3 | 4.6 | 5 | 151 | >1000 |
| 31.4 | 9.8 | 13 | 112 | >1000 |
| 32 | 17.4 | 53 | 800 | >1000 |
| 32.1 | 0.2 | 1 | 10 | 115 |
| 32.2 | 0.8 | 5 | 29 | >1000 |
| 33 | 13.1 | 28 | 118 | >1000 |
| 33.1 | 14.9 | 62 | 184 | >1000 |
| 33.2 | 15.2 | 159 | 126 | >1000 |
| 33.3 | 28.6 | 710 | 67 | >1000 |
| 33.4 | 48.6 | 120 | 254 | >1000 |

TABLE 1-continued

| Example Number | A2a Ki (nM) | A2b Ki (nM) | A1 Ki (nM) | A3 Ki (nM) |
|---|---|---|---|---|
| 33.5 | 91.9 | 17 | 124 | >1000 |
| 33.6 | 134.0 | 61 | 898 | >1000 |
| 33.7 | 439.7 | 416 | 1796 | >1000 |
| 35 | 4.5 | 122 | 4 | 5 |
| 36 | 175.1 | 1784 | | >1000 |
| 37 | 0.3 | 22 | 5 | 186 |
| 37.1 | 13.3 | 46 | 45 | 2093 |
| 37.2 | 19.2 | | 103 | 1934 |
| 37.3 | 22.6 | | 262 | >1000 |
| 37.4 | 29.8 | 1752 | 38 | 771 |
| 37.5 | 33.2 | 1097 | 133 | 1738 |
| 37.6 | 45.4 | | 363 | >1000 |
| 37.7 | 49.3 | | 154 | 7849 |
| 37.8 | 62.4 | | 426 | >1000 |
| 37.9 | 69.5 | 36 | 398 | >1000 |
| 37.10 | 76.0 | 5043 | 1762 | 2881 |
| 37.11 | 171.4 | | 2167 | 2722 |
| 37.12 | 309.6 | 1322 | 319 | 923 |
| 38 | 10.5 | 971 | 158 | 1012 |
| 39 | 38.9 | | 2578 | >1000 |
| 39.1 | 126.6 | | 1345 | >1000 |
| 40 | 93.6 | 5499 | 1947 | 1767 |
| 41 | 237.3 | 2230 | 1568 | 5141 |
| 42 | 344.5 | 3062 | 313 | >1000 |
| 42.1 | 410.1 | 4447 | 680 | >1000 |
| 43 | 16.4 | 1863 | 278 | >1000 |
| 44 | 3.4 | 2846 | 141 | 25 |
| 45 | 0.5 | 74 | 6 | 73 |
| 46 | 2.7 | 257 | 146 | 1274 |
| 47 | 5.2 | 483 | 174 | 510 |
| 48 | 16.6 | 1175 | 137 | 41 |
| 49 | 147.4 | 2224 | 172 | 3957 |
| 50 | 150.9 | | 459 | 3071 |
| 51 | 24.1 | 2552 | 125 | 2117 |
| 51.1 | 26.5 | 1422 | 322 | >1000 |
| 51.2 | 54.9 | | 104 | >1000 |
| 52 | 114.4 | | 1149 | >1000 |
| 53 | 27.7 | | 214 | 618 |
| 53.1 | 48.6 | 129 | 34 | 174 |
| 54 | 34.7 | | 18 | 68 |
| 54.1 | 102.3 | | 856 | 6180 |
| 55 | 43.1 | 2370 | | >1000 |
| 55.1 | 103.0 | 1744 | 355 | 8464 |
| 55.2 | 243.6 | 1705 | 284 | 4181 |
| 56 | 140.6 | 2696 | 521 | >1000 |
| 57 | 24.7 | 1490 | 236 | 1872 |
| 58 | 2.0 | | 83 | >1000 |
| 59 | 17.5 | | 1034 | 3677 |
| 60 | 33.9 | 4600 | 27 | 1001 |
| 61 | 37.9 | | 42 | 4923 |
| 62 | 365.1 | | | >1000 |
| 63 | 49.1 | | 24 | 65 |
| 64 | 7.5 | 508 | 16 | 41 |
| 65 | 407.2 | | 2481 | >1000 |
| 66 | 44.7 | 384 | 59 | >1000 |
| 66.1 | 72.0 | 1201 | | >1000 |
| 66.2 | 283.8 | 2158 | | 25 |
| 66.3 | 491.9 | 2426 | 102 | 191 |
| 66.4 | 705.8 | | 803 | 2899 |
| 67 | 120.4 | 7472 | | >1000 |
| 68 | 572.2 | | | >1000 |
| 69 | 141.2 | 10000 | | >1000 |
| 70 | 2.2 | 181 | 2 | 5 |
| 71 | 197.5 | 3862 | | >1000 |
| 72 | 30.9 | 116 | 0.3 | 92 |
| 74 | 586.9 | 6243 | 649 | 160 |
| 75 | 153.3 | 1455 | 1142 | 1741 |
| 76 | 116.4 | 2430 | 2538 | 3391 |
| 77 | 46.4 | | 1434 | 135 |
| 79 | 145.9 | 34 | 14 | 2075 |
| 80 | 155.0 | 4463 | 988 | >1000 |
| 81 | 201.8 | | 1259 | >1000 |
| 82 | 665.4 | | 4327 | >1000 |
| 83 | 694.2 | | | >1000 |
| 84 | 160.1 | | 389 | 231 |
| 85 | 493.4 | | 366 | >1000 |
| 87 | 23.6 | | 2282 | >1000 |

TABLE 1-continued

| Example Number | A2a Ki (nM) | A2b Ki (nM) | A1 Ki (nM) | A3 Ki (nM) |
|---|---|---|---|---|
| 87.1 | 16.3 | | 213 | >1000 |
| 88 | 35.7 | 63 | 29 | 536 |
| 90 | 12.3 | 80 | 1842 | >1000 |
| 91 | 0.2 | 71 | 102 | 1040 |
| 92 | 0.4 | 37 | 107 | 1467 |
| 92.1 | 0.5 | 4 | 222 | >1000 |
| 92.2 | 1.6 | 25 | 324 | >1000 |
| 92.3 | 2.0 | 7 | 212 | >1000 |
| 92.4 | 4.4 | 23 | 362 | >1000 |
| 92.5 | 9.2 | 17 | 438 | >1000 |
| 92.6 | 0.7 | 22 | 167 | >1000 |
| 92.7 | 27.6 | 3 | 158 | >1000 |
| 92.8 | 0.6 | 14 | 70 | >1000 |
| 92.9 | 1.0 | 26 | 150 | >1000 |
| 92.10 | 0.5 | 117 | 591 | >1000 |
| 92.11 | 1.5 | 21 | 217 | >1000 |
| 92.12 | 0.8 | 44 | 274 | >1000 |
| 92.13 | 1.0 | 101 | 282 | >1000 |
| 92.14 | 0.4 | 10 | 79 | >1000 |
| 92.15 | 0.3 | 19 | 150 | 599 |
| 92.16 | 0.7 | 59 | 232 | >1000 |
| 92.17 | 1.1 | 28 | 246 | >1000 |
| 92.18 | 0.7 | 51 | 28 | >1000 |
| 92.19 | 19.2 | 115 | 179 | >1000 |
| 92.20 | 1.2 | 37 | 301 | >1000 |
| 92.21 | 0.7 | 17 | 288 | >1000 |
| 92.22 | 0.6 | 29 | 204 | >1000 |
| 92.23 | 3.4 | 35 | 1119 | >1000 |
| 92.24 | 1.3 | 23 | 347 | >1000 |
| 92.25 | 5.4 | 69 | 634 | >1000 |
| 92.26 | 5.8 | 22 | 175 | >1000 |
| 92.27 | 6.6 | 16 | 210 | >1000 |
| 92.28 | 3.2 | 64 | 345 | >1000 |
| 92.29 | 1.9 | 34 | 412 | >1000 |
| 92.30 | 0.8 | 36 | 361 | >1000 |
| 92.31 | 2.1 | 57 | 333 | >1000 |
| 92.32 | 2.9 | 24 | 459 | >1000 |
| 92.33 | 13.0 | 57 | 652 | >1000 |
| 92.34 | 1.5 | 32 | 428 | >1000 |
| 93 | 11.1 | 1 | 307 | 1787 |
| 94 | 1.0 | 3 | 124 | >1000 |
| 94.1 | 1.8 | 14 | 99 | >1000 |
| 94.2 | 1.2 | 7 | 81 | 2049 |
| 94.3 | 2.0 | 15 | 184 | >1000 |
| 94.4 | 1.7 | 13 | 79 | >1000 |
| 94.5 | 3.7 | 20 | 145 | >1000 |
| 95 | 2.7 | 31 | 146 | >1000 |
| 96 | 0.5 | 7 | 143 | >1000 |
| 97 | 1.5 | 21 | 260 | >1000 |
| 98 | 0.4 | 9 | 87 | 655 |
| 99 | 0.4 | 35 | 99 | >1000 |
| 100 | 0.4 | 28 | 64 | >1000 |
| 101 | 5.0 | 13 | 1514 | >1000 |
| 101.1 | 4.3 | 38 | 1238 | >1000 |
| 102 | 0.5 | 32 | 233 | >1000 |
| 103 | 0.3 | 22 | 298 | >1000 |
| 104 | 0.9 | 330 | 735 | >1000 |
| 104.1 | 1.2 | 111 | 398 | >1000 |
| 105 | 127.3 | 378 | 776 | >1000 |
| 105.1 | 8.0 | 50 | 692 | >1000 |
| 105.2 | 1.7 | 18 | 35 | >1000 |

Biological Example 2- CD3/CD28 stimulated IL-2 release NECA reversal assay in human PBMCs Blood is drawn from healthy volunteers using sodium citrate as the anticoagulant (0.3% final concentration). After centrifugation of the blood over Histopaque-1077, PBMCs are collected from the Histopaque/plasma interface and washed twice in PBS (300g for 10 mins at room temp). Cells are plated at 50,000 cells/well in 150 μl RPMI/10% FCS in 96-well cell culture plates that have been precoated with 1 μg/ml CD3 antibody. 50μl diluted compound mix is added to the cells, to obtain final concentrations of 1 μg/ml CD28 antibody, 1 μM NECA and 0.003-10 μM adenosine receptor antagonist. Assay plates are incubated for 24 hours at 370C in a humidified incubator. Culture supernatant is tested for IL-2 levels using the human IL-2 Tissue Culture Kit (Meso Scale Discovery). Data for dose-response curves is calculated as % inhibition with 100% inhibition defined from no agonist control wells (+CD3/28-NECA). The results are shown in table 2.

TABLE 2

| Example | IL-2 IC50 (μM) |
|---|---|
| 1 | 0.305 |
| 1.4 | 0.037 |
| 1.6 | 0.057 |
| 2 | 0.084 |
| 2.1 | 0.012 |
| 2.3 | 0.012 |
| 2.4 | 0.032 |
| 2.8 | 0.041 |
| 2.9 | 0.019 |
| 2.10 | 0.048 |
| 2.11 | 0.005 |
| 2.12 | 0.032 |
| 2.15 | 0.059 |
| 2.16 | 0.007 |
| 2.18 | 0.046 |
| 2.20 | 0.068 |
| 2.21 | 0.031 |
| 2.23 | 0.024 |
| 2.24 | 0.092 |
| 3 | 0.017 |
| 3.1 | 0.023 |
| 3.3 | 0.001 |
| 3.4 | 0.100 |
| 4 | 0.008 |
| 4.2 | 0.054 |
| 4.5 | 0.012 |
| 5 | 0.023 |
| 5.1 | 0.020 |
| 5.2 | 0.004 |
| 5.5 | 0.021 |
| 5.6 | 0.016 |
| 6 | 0.002 |
| 6.2 | 0.008 |
| 6.4 | 0.006 |
| 6.9 | 0.010 |
| 6.13 | 0.032 |
| 6.14 | 0.018 |
| 6.15 | 0.014 |
| 6.18 | 0.093 |
| 6.19 | 0.026 |
| 6.20 | 0.0363 |
| 6.21 | 0.0013 |
| 6.22 | 0.0025 |
| 6.23 | 0.0057 |
| 7 | 0.034 |
| 7.2 | 0.070 |
| 7.3 | 0.172 |
| 7.9 | 0.004 |
| 7.14 | 0.142 |
| 7.18 | 0.019 |
| 7.19 | 0.004 |
| 10 | 0.006 |
| 12.2 | 0.022 |
| 12.4 | 0.004 |
| 12.6 | 0.009 |
| 12.8 | 0.035 |
| 12.9 | 0.002 |
| 15 | 0.002 |
| 16.1 | 0.077 |
| 23 | 0.020 |
| 23.1 | 0.083 |
| 23.2 | 0.025 |
| 24 | 0.051 |
| 26.1 | 0.032 |
| 26.2 | 0.069 |
| 27.1 | 0.036 |

TABLE 2-continued

| Example | IL-2 IC50 (μM) |
|---|---|
| 30 | 0.021 |
| 30.3 | 0.050 |
| 32.1 | 0.009 |
| 32.2 | 0.016 |
| 35 | 0.408 |
| 37 | 0.013 |
| 37.1 | 0.477 |
| 44 | 0.501 |
| 45 | 0.107 |
| 46 | 0.060 |
| 47 | 0.140 |
| 48 | 1.886 |
| 51 | 0.073 |
| 51.1 | 0.016 |
| 53 | 0.128 |
| 58 | 0.118 |
| 64 | 0.146 |
| 66 | 0.869 |
| 70 | 0.177 |
| 72 | 0.565 |
| 87 | 0.057 |
| 92 | 0.004 |
| 92.1 | 0.014 |
| 92.2 | 0.017 |
| 92.3 | 0.011 |
| 92.4 | 0.033 |
| 94 | 0.027 |
| 94.1 | 0.026 |
| 94.2 | 0.020 |
| 94.4 | 0.014 |
| 94.5 | 0.016 |
| 96 | 0.010 |
| 97 | 0.038 |
| 98 | 0.003 |
| 102 | 0.016 |
| 103 | 0.024 |
| 104 | 0.010 |
| 104.1 | 0.004 |
| 105.1 | 0.033 |

Biological Example 3—Measurement of pCREB in CD8+ T cells in human whole blood Heparinised human whole blood was pre-incubated at 37° C. with serial dilutions of A2a antagonists for 20 min. and the phosphodiesterase inhibitor rolipram to amplify the pCREB response. The adenosine receptor agonist NECA is then added at a final concentration of 3 μM and following a 60 min incubation the blood is fixed and red blood cells lysed. White blood cells are isolated, permeabilized and stained with directly conjugated fluorescent antibodies to phospho-CREB (Alexa Fluor 488) and CD8 (Alexa Fluor 647) and the level of phospho-CREB in CD8+ T cells is measured by FACS using a BD Accuri C6 Flow Cytometer. The results are shown in table 3.

TABLE 3

| Example | pCREB IC50 (μM) |
|---|---|
| 1 | 2.01 |
| 1.4 | 0.59 |
| 1.6 | 0.25 |
| 2 | 0.42 |
| 2.1 | 1.44 |
| 2.3 | 1.25 |
| 2.4 | 2.82 |
| 2.8 | 0.61 |
| 2.9 | 0.07 |
| 2.10 | 1.19 |

TABLE 3-continued

| Example | pCREB IC50 (μM) |
|---|---|
| 2.11 | 1.33 |
| 2.12 | 4.19 |
| 2.15 | 0.92 |
| 2.16 | 0.39 |
| 2.18 | 1.87 |
| 2.20 | 0.66 |
| 2.21 | 1.24 |
| 2.23 | 0.57 |
| 2.24 | 2.76 |
| 3 | 0.75 |
| 3.1 | 0.56 |
| 3.3 | 0.21 |
| 3.4 | 0.26 |
| 4 | 1.57 |
| 4.2 | 2.03 |
| 4.5 | 1.06 |
| 5 | 1.82 |
| 5.1 | 2.86 |
| 5.2 | 0.28 |
| 5.6 | 8.54 |
| 6 | 0.03 |
| 6.2 | 0.83 |
| 6.4 | 0.43 |
| 6.9 | 0.16 |
| 6.11 | 0.02 |
| 6.13 | 0.39 |
| 6.14 | 0.37 |
| 6.15 | 0.24 |
| 6.18 | 1.69 |
| 6.19 | 0.47 |
| 6.20 | 0.56 |
| 6.21 | 0.43 |
| 6.22 | 0.10 |
| 6.23 | 0.33 |
| 7 | 0.28 |
| 7.2 | 1.07 |
| 7.3 | 1.80 |
| 7.9 | 0.07 |
| 7.14 | 1.93 |
| 7.18 | 0.47 |
| 7.19 | 0.10 |
| 10 | 0.08 |
| 12.2 | 0.52 |
| 12.4 | 0.15 |
| 12.6 | 0.37 |
| 12.8 | 0.35 |
| 12.9 | 0.08 |
| 15 | 0.38 |
| 16.1 | 1.05 |
| 23 | 0.39 |
| 23.1 | 1.01 |
| 23.2 | 0.26 |
| 24 | 3.63 |
| 26.1 | 0.46 |
| 26.2 | 2.54 |
| 27.1 | 0.74 |
| 30 | 0.64 |
| 30.3 | 0.12 |
| 32.1 | 1.18 |
| 32.2 | 0.49 |
| 37 | 1.46 |
| 91 | 0.34 |
| 92 | 0.02 |
| 92.1 | 0.11 |
| 92.2 | 0.35 |
| 92.3 | 0.26 |
| 92.4 | 0.83 |
| 92.10 | 0.15 |
| 92.11 | 2.10 |
| 92.12 | 0.15 |
| 92.13 | 0.10 |
| 92.14 | 0.06 |
| 92.21 | 0.11 |
| 92.22 | 0.37 |
| 92.24 | 0.33 |
| 92.34 | 0.14 |
| 94 | 1.72 |

TABLE 3-continued

| Example | pCREB IC50 (μM) |
|---|---|
| 94.1 | 0.75 |
| 94.2 | 0.53 |
| 94.4 | 0.15 |
| 94.5 | 0.59 |
| 96 | 0.36 |
| 97 | 0.58 |
| 98 | 0.36 |
| 102 | 0.14 |
| 103 | 0.03 |
| 104 | 0.19 |
| 104.1 | 0.03 |
| 105.1 | 0.89 |

REFERENCES

1. Sukari A Nagasaka MAI-Hadidi Aand Lum LG (2016). Anticancer Res. 36(11):5593-5606.
2. Vijayan D, Young A, Teng MWL, and Smyth M J (2017), Nat Rev Cancer. 17(12):709-724.
3. Houthuys, E, Marillier R, Deregnaucourt,T, Brouwer, M, Pirson, R, Marchante, J, et al (2016). SITC 2017 Conference, Maryland.
4. Gao Z W, Dong K, Zhang H Z (2014). "The roles of CD73 in cancer". Biomed Res/nt 2014:460654.
5. Loi S, Pommey S, Haibe-Kains B, Beavis P A, Darcy P K, Smyth M J, et al. (2013), "CD73 promotes anthracycline resistance and poor prognosis in triple negative breast cancer" Proc Nat/Acad Sci USA.;110(27):11091-6.
6. Deaglio S, Dwyer K M, Gao W, Friedman D, Usheva A, Erat A et al (2007). J. Exp Med.. 204, No. 6, Jun. 11, 2007 1257-1265

The invention claimed is:

1. A compound, or pharmaceutically acceptable salt thereof, having the structural formula Ii3 shown below:

Ii3

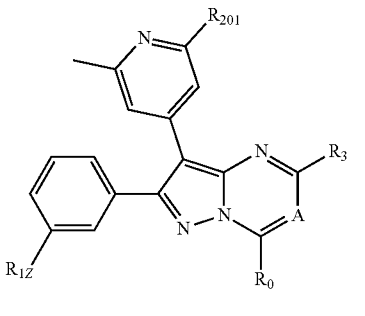

wherein $R_0$ is hydrogen $R_{1z}$ is cyano $R_3$ is a group of the formula:

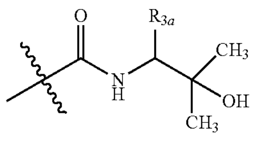

wherein $R_{3a}$ is hydrogen or methyl;

A is CH or N; and $R_{201}$ is methyl or chloro.

2. A compound, or a pharmaceutically acceptable salt thereof, wherein the compound is:

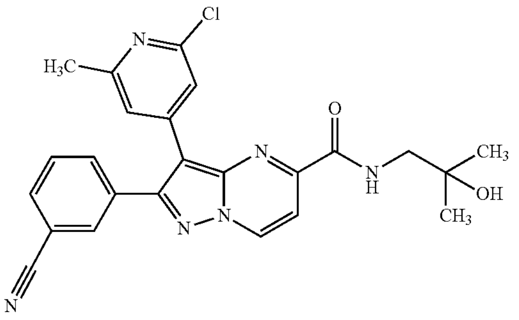 [SMILES: Cc1cc(-c2c(-c3cccc(C#N)c3)nn3ccc(C(=O)NCC(C)(C)O)nc23)cc(Cl)n1]

3-(2-Chloro-6-methyl-4-pyridyl)-2-(3-cyanophenyl)-N-(2-hydroxy-2-methyl-propyl)pyrazolo[1,5-a]pyrimidine-5-carboxamide.

3. A compound, or a pharmaceutically acceptable salt thereof, wherein the compound is:

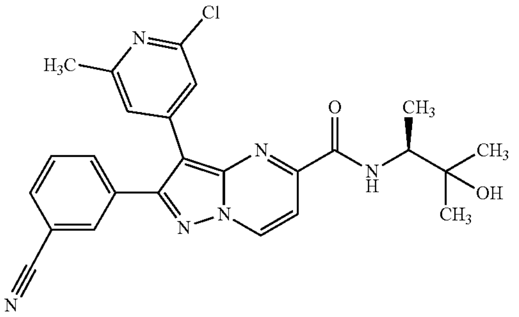 [SMILES: Cc1cc(-c2c(-c3cccc(C#N)c3)nn3ccc(C(=O)N[C@@H](C)C(C)(C)O)nc23)cc(Cl)n1]

3-(2-Chloro-6-methyl-4-pyridyl)-2-(3-cyanophenyl)-N-[(1S)-2-hydroxy-1,2-dimethyl-propyl]pyrazolo[1,5-a]pyrimidine-5-carboxamide.

4. A compound, or a pharmaceutically acceptable salt thereof, wherein the compound is:

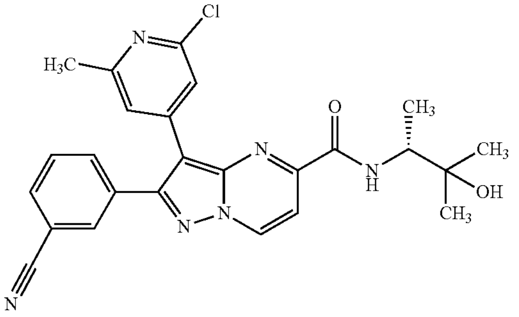 [SMILES: Cc1cc(-c2c(-c3cccc(C#N)c3)nn3ccc(C(=O)N[C@H](C)C(C)(C)O)nc23)cc(Cl)n1]

3-(2-Chloro-6-methyl-4-pyridyl)-2-(3-cyanophenyl)-N-[(1R)-2-hydroxy-1,2-dimethyl-propyl]pyrazolo[1,5-a]pyrimidine-5-carboxamide.

5. A compound, or a pharmaceutically acceptable salt thereof, wherein the compound is:

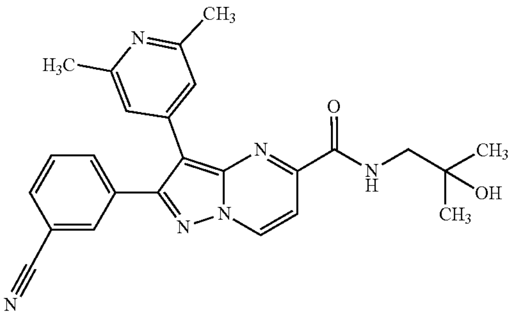 [SMILES: Cc1cc(-c2c(-c3cccc(C#N)c3)nn3ccc(C(=O)NCC(C)(C)O)nc23)cc(C)n1]

2-(3-Cyanophenyl)-3-(2,6-dimethyl-4-pyridyl)-N-(2-hydroxy-2-methyl-propyl)pyrazolo[1,5-a]pyrimidine-5-carboxamide.

6. A compound, or a pharmaceutically acceptable salt thereof, wherein the compound is:

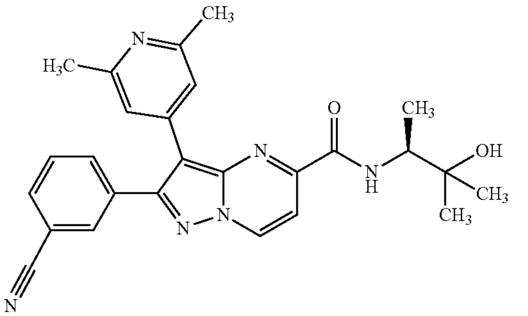 [SMILES: Cc1cc(-c2c(-c3cccc(C#N)c3)nn3ccc(C(=O)N[C@@H](C)C(C)(C)O)nc23)cc(C)n1]

2-(3-Cyanophenyl)-3-(2,6-dimethyl-4-pyridyl)-N-[(1S)-2-hydroxy-1,2-dimethyl-propyl]pyrazolo[1,5-a]pyrimidine-5-carboxamide.

7. A compound, or a pharmaceutically acceptable salt thereof, wherein the compound is:

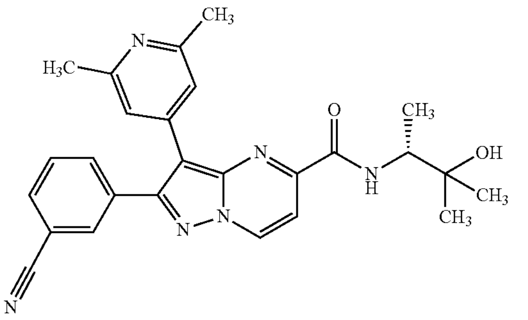 [SMILES: Cc1cc(-c2c(-c3cccc(C#N)c3)nn3ccc(C(=O)N[C@H](C)C(C)(C)O)nc23)cc(C)n1]

2-(3-cyanophenyl)-3-(2,6-dimethyl-4-pyridyl)-N-[(1R)-2-hydroxy-1,2-dimethyl-propyl]pyrazolo[1,5-a]pyrimidine-5-carboxamide.

8. A pharmaceutical composition comprising 3-(2-chloro-6-methyl-4-pyridyl)-2-(3-cyanophenyl)-N-[(1S)-2-hydroxy-1,2-dimethyl-propyl]pyrazolo[1,5-a]pyrimidine-5-carboxamide:

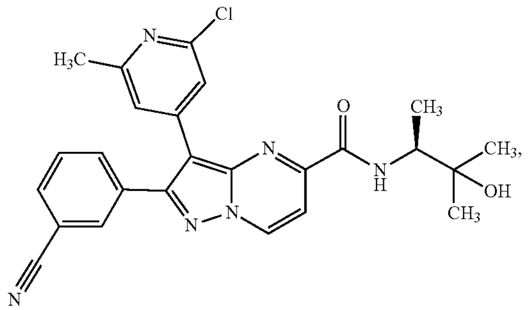 [SMILES: Cc1cc(-c2c(-c3cccc(C#N)c3)nn3ccc(C(=O)N[C@@H](C)C(C)(C)O)nc23)cc(Cl)n1]

or a pharmaceutically acceptable salt thereof, in admixture with a pharmaceutically acceptable diluent or carrier.

9. A pharmaceutical composition comprising 3-(2-chloro-6-methyl-4-pyridyl)-2-(3-cyanophenyl)-N-[(1R)-2-hydroxy-1,2-dimethyl-propyl]pyrazolo[1,5-a]pyrimidine-5-carboxamide

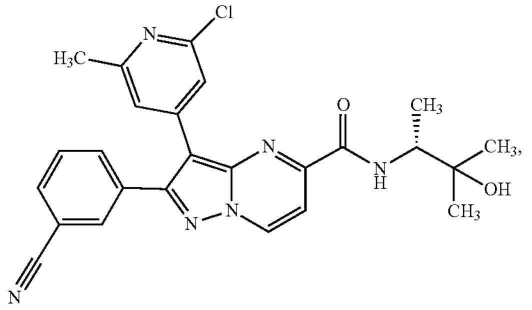 [SMILES: Cc1cc(-c2c(-c3cccc(C#N)c3)nn3ccc(C(=O)N[C@H](C)C(C)(C)O)nc23)cc(Cl)n1]

or a pharmaceutically acceptable salt thereof, in admixture with a pharmaceutically acceptable diluent or carrier.

10. A pharmaceutical composition comprising 2-(3-cyanophenyl)-3-(2,6-dimethyl-4-pyridyl)-N-(2-hydroxy-2-methyl-propyl)pyrazolo[1,5-a]pyrimidine-5-carboxamide:

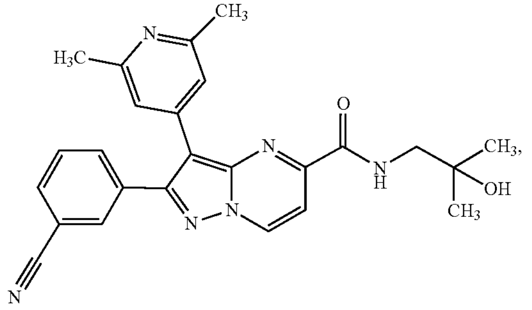 [SMILES: Cc1cc(-c2c(-c3cccc(C#N)c3)nn3ccc(C(=O)NCC(C)(C)O)nc23)cc(C)n1]

or a pharmaceutically acceptable salt thereof, in admixture with a pharmaceutically acceptable diluent or carrier.

11. A pharmaceutical composition comprising 2-(3-cyanophenyl)-3-(2,6-dimethyl-4-pyridyl)-N-[(1S)-2-hydroxy-1,2-dimethyl-propyl]pyrazolo[1,5-a]pyrimidine-5-carboxamide:

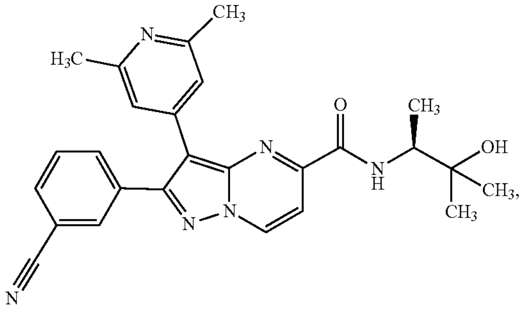 [SMILES: Cc1cc(-c2c(-c3cccc(C#N)c3)nn3ccc(C(=O)N[C@@H](C)C(C)(C)O)nc23)cc(C)n1]

or a pharmaceutically acceptable salt thereof, in admixture with a pharmaceutically acceptable diluent or carrier.

12. A pharmaceutical composition comprising 2-(3-cyanophenyl)-3-(2,6-dimethyl-4-pyridyl)-N-[(1R)-2-hydroxy-1,2-dimethyl-propyl]pyrazolo[1,5-a]pyrimidine-5-carboxamide:

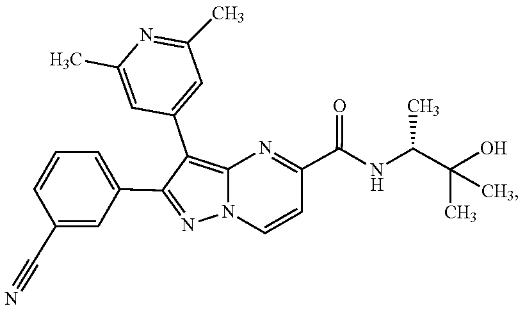 [SMILES: Cc1cc(-c2c(-c3cccc(C#N)c3)nn3ccc(C(=O)N[C@H](C)C(C)(C)O)nc23)cc(C)n1]

or a pharmaceutically acceptable salt thereof, in admixture with a pharmaceutically acceptable diluent or carrier.

* * * * *